US012195446B2

(12) United States Patent
Kim et al.

(10) Patent No.: US 12,195,446 B2
(45) Date of Patent: *Jan. 14, 2025

(54) HETEROARYL COMPOUNDS AND THEIR USE AS THERAPEUTIC DRUGS

(71) Applicant: Dong-A Socio Holdings Co., Ltd., Seoul (KR)

(72) Inventors: Myeong-Seop Kim, Gyeonggi-do (KR); Sumin Kim, Seoul (KR); Jin Kwan Kim, Gyeonggi-do (KR); Hadong Kim, Seoul (KR); Ki Moon Ryu, Gyeonggi-do (KR); Seong Jin Park, Seoul (KR); Taesun Park, Gyeonggi-do (KR); Joon-Ho Sheen, Seoul (KR); Taeyoung Yoon, Seoul (KR); Mi Yeon Jang, Gyeonggi-do (KR)

(73) Assignee: DONG-A SOCIO HOLDINGS CO., LTD., Seoul (KR)

( * ) Notice: Subject to any disclaimer, the term of this patent is extended or adjusted under 35 U.S.C. 154(b) by 212 days.

This patent is subject to a terminal disclaimer.

(21) Appl. No.: 17/138,309

(22) Filed: Dec. 30, 2020

(65) Prior Publication Data
US 2023/0002353 A1    Jan. 5, 2023

Related U.S. Application Data

(60) Continuation of application No. 16/141,044, filed on Sep. 25, 2018, now Pat. No. 10,947,215, which is a division of application No. 15/253,773, filed on Aug. 31, 2016, now Pat. No. 10,125,118.

(60) Provisional application No. 62/212,520, filed on Aug. 31, 2015.

(51) Int. Cl.
C07D 401/14    (2006.01)
C07D 213/82    (2006.01)
C07D 401/04    (2006.01)
C07D 401/10    (2006.01)
C07D 401/12    (2006.01)
C07D 403/04    (2006.01)
C07D 405/14    (2006.01)
C07D 409/14    (2006.01)
C07D 417/04    (2006.01)
C07D 417/14    (2006.01)

(52) U.S. Cl.
CPC ......... C07D 401/14 (2013.01); C07D 213/82 (2013.01); C07D 401/04 (2013.01); C07D 401/10 (2013.01); C07D 401/12 (2013.01); C07D 403/04 (2013.01); C07D 405/14 (2013.01); C07D 409/14 (2013.01); C07D 417/04 (2013.01); C07D 417/14 (2013.01)

(58) Field of Classification Search
CPC .. C07D 401/14; C07D 213/82; C07D 401/04; C07D 401/10; C07D 401/12; C07D 403/04; C07D 405/14; C07D 409/14; C07D 417/04; C07D 417/14; C07D 409/04; A61P 31/04; A61P 35/00; A61P 35/02; A61P 35/04; A61P 37/02; A61P 43/00; A61K 31/4439; A61K 31/497; A61K 31/4545; A61K 31/4709; A61K 31/496; A61K 31/5377
See application file for complete search history.

(56) References Cited

U.S. PATENT DOCUMENTS

| 2002/0151712 A1 | 10/2002 | Lin et al. |
| 2004/0180905 A1 | 9/2004 | Munchhof |
| 2007/0043068 A1 | 2/2007 | Arnold et al. |
| 2007/0060619 A1 | 3/2007 | Burns et al. |
| 2013/0072679 A1 | 3/2013 | Aebi et al. |
| 2013/0209422 A1 | 8/2013 | Kang et al. |
| 2014/0249135 A1 | 9/2014 | Burger et al. |
| 2017/0066742 A1 | 3/2017 | Kim et al. |

FOREIGN PATENT DOCUMENTS

| JP | 2006510737 A | 3/2006 |
| WO | 2001055114 A1 | 8/2001 |
| WO | 2002066463 A1 | 8/2002 |
| WO | 2003093297 A2 | 11/2003 |
| WO | 2004054977 A1 | 7/2004 |
| WO | 2004080982 A1 | 9/2004 |
| WO | 2007011760 A2 | 1/2007 |

(Continued)

OTHER PUBLICATIONS

Simone, Oncology (Introduction), 1997, Textbook of Medicine, 20(1), pp. 1004-1010 (Year: 1997).*

(Continued)

Primary Examiner — Savitha M Rao
Assistant Examiner — Andrew P Lee
(74) Attorney, Agent, or Firm — LEX IP MEISTER, PLLC

(57) ABSTRACT

The present invention provides heterocyclic compounds, the stereoisomer thereof, the enantiomer thereof, or the pharmaceutically acceptable salt, which are capable of modulating the activity of Mer receptor tyrosine kinase (MERTK). This invention also provides pharmaceutical compositions thereof, methods to prepare the said compounds, and the use of such compounds as a medicament.

The present invention is directed to MERTK inhibitory compounds with marked potency, thereby having an outstanding potential for a pharmaceutical intervention of cancer and any other diseases related to MERTK dysregulation.

4 Claims, No Drawings

(56) References Cited

FOREIGN PATENT DOCUMENTS

| WO | 2008009122 A1 | 1/2008 |
| WO | 2017039331 A1 | 3/2017 |

OTHER PUBLICATIONS

Danziger, Automated site-directed drug design: a general algorithm for knowledge acquisition about hydrogen-bonding regioins at protein surfaces, 1989, Proc. R. Soc. Lond., 236, pp. 101-113 (Year: 1989).*
CAS Registry No. 1570411-62-9, entered STN Mar. 20, 2014.
CAS Registry No. 1457824-45-1, entered STN Oct. 13, 2013.
CAS Registry No. 1457319-01-5, entered STN Oct. 13, 2013.
CAS Registry No. 1456391-79-9, entered STN Oct. 6, 2013.
CAS Registry No. 1283306-48-8, entered STN Apr. 21, 2011.
CAS Registry No. 1274823-26-5, entered STN Apr. 4, 2011.
CAS Registry No. 1274529-78-0, entered STN Apr. 4, 2011.
CAS Registry No. 1272204-91-7, entered STN Mar. 30, 2011.
CAS Registry No. 1271632-12-2, entered STN Mar. 29, 2011.
CAS Registry No. 1386934-67-3, entered STN Aug. 6, 2012.
CAS Registry No. 1456224-53-5, entered STN Oct. 6, 2013.
CAS Registry No. 1457048-36-0, entered STN Oct. 13, 2013.
Database Caplus Chemical Abstracts Service, Columbus, Ohio, US; Database Accession No. 1935: 19785, Abstract of Gryszkiewicz-Trochimowski, Archiwum Chemji I Farmacji, 1, 65-71 (1934).
Database Caplus Chemical Abstracts Service, Columbus, Ohio, US; Database Accession No. 1949: 13185, Abstract of Charonnat et al., Bulletin de la societe Chimique de France, 1014-1017 (1948).
Database PubChem Compound [Online] XP002787138, Database accession No. 55069206, Compound 55069206, retrieved from NCBI (3 pages), Jan. 24, 2012 (Jan. 24, 2012).
Database PubChem Compound [Online] XP002787139, Database accession No. 60315064, Compound 60315064, retrieved from NCBI (3 pages), Oct. 18, 2012 (Oct. 18, 2012).
Database PubChem Compound [Online] XP002787140, Database accession No. 60315178, Compound 60315178, retrieved from NCBI (3 pages), Oct. 18, 2012 (Oct. 18, 2012).
Database PubChem Compound [Online] XP002787141, Database accession No. 62160816, Compound 62160816, retrieved from NCBI (3 pages), Oct. 22, 2012 (Oct. 22, 2012).
Database PubChem Compound [Online] XP002787142, Database accession No. 63279265, Compound 63279265, retrieved from NCBI (3 pages), Oct. 22, 2012 (Oct. 22, 2012).
Database PubChem Compound [Online] XP002787143, Database accession No. 64915258, Compound 64915258, retrieved from NCBI (3 pages), Oct. 23, 2012 (Oct. 23, 2012).
CAS registry No. 1571516-18-1, Mar. 22, 2014; 1568656-19-8, Mar. 15, 2014; 1562088-75-8, Mar. 5, 2014; 1562085-51-1, Mar. 5, 2014; 1561812-16-5, Mar. 5, 2014; 1561439-83-5, Mar. 5, 2014; 1560995-67-6, Mar. 4, 2014; 1560710-73-7, Mar. 4, 2014; 1559172-16-5, Mar. 5, 2014; 1532476-59-7, Jan. 29, 2014; 1530787-79-1, Jan. 28, 2014; 1455489-09-4, Oct. 5, 2013; 1390139-22-6, Aug. 15, 2012; 1389443-99-5, Aug. 12, 2012; 1282597-07-2, Apr. 19, 2011; 1281884-56-7, Apr. 18, 2011; 1274587-99-3, Apr. 4, 2011.
Huang, et al., "Structural insights into the inhibited states of the Mer receptor tyrosine kinase," J. Struc. Biol. 165(2): 88-96 (2009).
International Search Report and Written Opinion issued for International Application No. PCT/US2017/055793 dated Dec. 1, 2017.
International Search Report and Written Opinion issued for International Application No. PCT/KR2016/009743 dated Dec. 9, 2016.
Liu et al., "Discovery of Novel Small Molecule Mer Kinase Inhibitors for the Treatment of Pediatric Acute Lymphoblastic Leukemia," ACS Med. Chem. Lett., 3(2): 129-134 (2012).
Liu et al., "UNC1062, a new and potent Mer inhibitor," Eur. J. Med. Chem., 65: 83-93 (2013).
Rahmani, R. et al., "6-Arylpyrazine-2-carboxamides: A New Core for Trypanosoma brucei Inhibitors," J. Med. Chem., 58(17): 6753-6765 (2015).
Zhang et al., "UNC2025, a potent and orally bioavailable MER/FLT3 dual inhibitor," J. Med. Chem., 57(16): 7031-7041 (2014).
Zhang, W. et al., "Pseudo-Cyclization through Intramolecular Hydrogen Bond Enables Discovery of Pyridine Substituted Pyrimidines as New Mer Kinase Inhibitors," J. Med. Chem., 56(23): 9683-9692 (2013).

* cited by examiner

HETEROARYL COMPOUNDS AND THEIR USE AS THERAPEUTIC DRUGS

RELATED APPLICATION

This application is a continuation of U.S. patent application Ser. No. 16/141,044, filed Sep. 25, 2018, which is herein incorporated by reference, and which is a divisional application of U.S. patent application Ser. No. 15/253,773, filed Aug. 31, 2016, which has issued as U.S. Pat. No. 10,125,118, which is herein incorporated by reference, and which claims the benefit of priority under U.S.C. § 119 (e) to U.S. Provisional Patent Application Ser. No. 62/212,520 filed Aug. 31, 2015, which is herein incorporated by reference.

TECHNICAL FIELD

The present invention relates to novel heterocyclic compounds having Mer kinase inhibitory activity, a stereoisomer thereof, an enantiomer thereof, or a pharmaceutically acceptable salt thereof, the use for preparing pharmaceutical compositions, pharmaceutical compositions comprising the same, methods of treating diseases using these compositions.

BACKGROUND ART

Transmembrane receptor tyrosine kinases (RTKs) comprise an evolutionarily conserved family of structurally related proteins. The gene Mer is a member of the Tyro3/Axl/Mer (TAM) receptor kinase family and a proto-oncogene. Its abnormal expression and activation is found in conjunction with human cancers such as pituitary adenomas, mantle cell lymphomas, and T-cell acute lymphoblastic leukemia.

The ATP-binding site is similar for all protein kinases. For this reason, it is challenging to find an inhibitor that is specific for the Mer. Compound-52, a 2,6,9-trisubstituted purine that occupies the ATP-binding site, was actually the first molecule that was found to be successful in inhibiting Mer (J Struct Biol. 2009 February; 165(2): 88-96). This inhibitor has, however, limited potency and lack of selectivity. Lately, several compounds have been unveiled mostly by modifying Compound-52 including UNC-569, UNC-1062, and UNC-2025 (ACS Med Chem Lett. 2012 Feb. 9; 3(2):129-134, Eur J Med Chem. 2013 July; 65:83-93, J Med Chem. 2014 Aug. 28; 57(16):7031-41).

It is an object of the invention to provide reagents and methods of regulating a receptor tyrosine kinase Mer. This and other objects of the invention are provided by one or more of the embodiments described below.

DISCLOSURE

Technical Problem

Several Mer kinase inhibitors have been previously described, but they have different moieties onto the scaffold from the present invention. Highly potent and selective Mer kinase inhibitors based on aminopyridine or aminopyrimidine scaffolds are described.

The present invention relates to compounds capable of inhibiting the activity of Mer, which compounds are useful for the prevention and/or the treatment of cancer and other immune-related diseases such as infection and sepsis.

Technical Solution

Novel Mer Kinase Inhibitors

The present invention relates to a heterocyclic compound represented by the following Formula I, a stereoisomer thereof, an enantiomer thereof, or a pharmaceutically acceptable salt thereof:

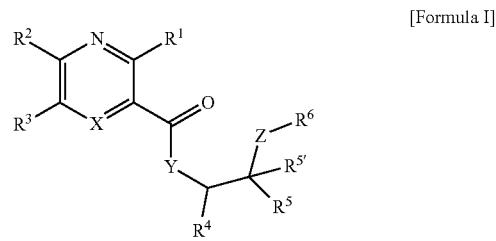

[Formula I]

wherein:
X is $CR^7$, or N;
Y is $CHR^8$, $NR^8$, or O;
Z is $CH_2$, $CH_2O$, $C(=O)$, $C(=O)O$, $C(=O)NH$, $NR^8$, $NHC(=O)$, O or $O(C=O)$;
$R^1$ is H, halogen, $C_{1-3}$ alkyl, $NHR^8$ or $OR^8$;
$R^2$ is H, halogen, $C_{1-4}$ alkyl, $C_{1-2}$ alkylaryl, $C_{1-2}$ alkylheteroaryl, $C_{1-2}$ alkylheterocyclyl or -L-aryl, which $C_{1-2}$ alkylaryl, $C_{1-2}$ alkylheteroaryl, $C_{1-2}$ alkylheterocyclyl or -L-aryl may optionally be substituted with one or more $R^9$;
$R^3$ is H, halogen, CN, $C_{1-3}$ alkyl, cycloalkenyl, $C_{2-6}$ alkenyl, aryl, biaryl, heteroaryl, heterobiaryl, heterocyclyl, $C_{1-2}$ alkylaryl, $C_{1-2}$ alkylheteroaryl, or $C_{1-2}$ alkylheterocyclyl which aryl, biaryl, heteroaryl, heterobiaryl, heterocyclyl, $C_{1-2}$ alkylaryl, $C_{1-2}$ alkylheteroaryl, or $C_{1-2}$ alkylheterocyclyl may optionally be substituted with one or more $R^9$;
$R^4$ and $R^5$ each independently is H, $C_{1-6}$ alkyl, $C_{1-6}$ alkoxy, $C_{3-10}$ cycloalkyl, $C(=O)$ $R^6$, $C_{1-2}$ alkylaryl, aryl; or
$R^4$ and $R^5$ may be combined with each other to form a 3-7 membered cyclic ring or heterocyclic ring containing 1 or 2 of $NR^8$, O or S, and the cyclic or heterocyclic ring may optionally be substituted with 1 or 2 halogen(s), $C_{1-4}$ alkyl or $C_{1-4}$ alkoxy;
$R^{5'}$ is H or $R^5$ and $R^{5'}$ may be combined with each other to form carbonyl;
$R^6$ is H, $C_{1-4}$ alkyl, $C_{1-6}$ alkoxy, $-NR^{15}R^{16}$, aryl, biaryl, heteroaryl, heterobiaryl, heterocyclyl, $C_{1-2}$ alkylaryl, $C_{1-2}$ alkylheteroaryl, $C_{1-2}$ alkylheterocyclyl, $C_{1-2}$ alkylbiaryl, -L-aryl or -L-biaryl, which $C_{1-4}$ alkyl, aryl, biaryl, heteroaryl, heterobiaryl, heterocyclyl, $C_{1-2}$ alkylaryl, $C_{1-2}$ alkylheteroaryl, $C_{1-2}$ alkylheterocyclyl, $C_{1-2}$ alkylbiaryl, -L-aryl or -L-biaryl, may optionally be substituted with one or more $R^9$;
$R^7$ is H, halogen or $C_{1-3}$ alkyl;
$R^8$ is H, $C_{1-6}$ alkyl, $C_{1-4}$ fluoroalkyl, $C_{1-4}$ hydroxyalkyl, $C_{1-3}$ alkylaryl or $C(=O)R^{10}$ which $C_{1-6}$ alkyl or $C_{1-3}$ alkylaryl may optionally be substituted with one or more $R^9$;
when Z is $NR^8$, $R^8$ and $R^6$ may be combined with each other to form a 3-7 membered heterocyclic ring comprising 1 to 2 N or 0 to 2 O heteroatoms;
$R^9$ is halogen, hydroxyl, —CN, —$NO_2$, —COOH, —(C=O)H, $C_{1-6}$ alkyl, $C_{2-6}$ alkenyl, $C_{2-6}$ alkynyl, $C_{3-10}$ cycloalkyl, $C_{1-4}$ hydroxyalkyl, $C_{1-6}$ alkoxy, cycloalkenyl, aryl, heterocyclyl, heteroaryl, —NR$^{15}$R$^{16}$, -L-NR$^{15}$R$^{16}$, -L-COOR$^{17}$, -L-alkyl, -L-C$_{3-10}$ cycloalkyl, -L-heterocyclyl, -L-heteroaryl, or -L-aryl which C$_{1-6}$ alkyl, C$_{2-6}$ alkenyl, C$_{2-6}$ alkynyl, C$_{3-10}$ cycloalkyl, C$_{1-4}$ hydroxyalkyl, C$_{1-6}$ alkoxy, cycloalkenyl, aryl, heterocyclyl, heteroaryl, -L-alkyl, -L-C$_{3-10}$ cycloalkyl, -L-heterocyclyl, -L-heteroaryl, or -L-aryl may substituted with halogen, hydroxyl, —CN, —NR$^{15}$R$^{16}$, C$_{1-6}$ alkyl, C$_{3-10}$ cycloalkyl, C$_{1-4}$ hydroxyalkyl, C$_{2-6}$ alkenyl, aryl, heterocyclyl, -L-heterocyclyl, or —(CH$_2$)—C(=O)—NR$^{15}$R$^{16}$;

R$^{10}$ is C$_{1-3}$ alkyl or C$_{1-3}$ alkylaryl;

R$^{15}$ and R$^{16}$ each independently is H, C$_{1-6}$ alkyl, C$_{3-10}$ cycloalkyl or SO$_2$R$^{17}$;

R$^{17}$ is H, C$_{1-3}$alkyl or C$_{1-3}$ alkylaryl;

L is C$_{1-3}$ alkyl, C$_{1-3}$ alkylO, C$_{2-6}$ alkynyl, C$_{3-10}$ cycloalkyl, —(CH$_2$)$_l$—C(=O)—(CH$_2$)$_m$—, C(=O)O, —(CH$_2$)$_l$—C(=O)NH—(CH$_2$)$_m$—, —(CH$_2$)$_l$—NHC(=O)—(CH$_2$)$_m$—, —(CH$_2$)$_l$—NH—(CH$_2$)$_m$—, NR$^8$, —NH—C(=O)—CR$^{15}$R$^{16}$—NH—C(=O)—, NHC(=O), O, O(C=O) S, S(=O), or SO$_2$; and l and m each independently is an integer of 0 to 2.

In accordance with a second embodiment of the present invention, there are provided the heterocyclic compound represented formula I is represented by the following Formula Ia:

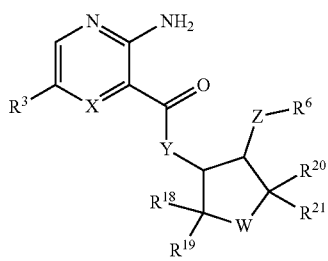

[Formula Ia]

wherein:
X is CH, or N;
Y is NR$^8$, or O;
W is CH$_2$, (CH$_2$)$_2$, NR$^{11}$, or O;
Z is CH$_2$, CH$_2$O, C(=O), C(=O)O, C(=O)NH, NR$^8$, NHC(=O), O or O(C=O);

R$^3$ is H, halogen, CN, C$_{1-3}$ alkyl, cycloalkenyl, C$_{2-6}$ alkenyl, aryl, biaryl, heteroaryl, heterobiaryl, heterocyclyl, C$_{1-2}$ alkylaryl, C$_{1-2}$ alkylheteroaryl, or C$_{1-2}$ alkylheterocyclyl which aryl, biaryl, heteroaryl, heterobiaryl, heterocyclyl, C$_{1-2}$ alkylaryl, C$_{1-2}$ alkylheteroaryl, or C$_{1-2}$ alkylheterocyclyl may optionally be substituted with one or more R$^9$;

R$^6$ is H, C$_{1-4}$ alkyl, C$_{1-6}$ alkoxy, —NR$^{15}$R$^{16}$, aryl, biaryl, heteroaryl, heterobiaryl, heterocyclyl, C$_{1-2}$ alkylaryl, C$_{1-2}$ alkylheteroaryl, C$_{1-2}$ alkylheterocyclyl, C$_{1-2}$ alkylbiaryl, -L-aryl or -L-biaryl, which C$_{1-4}$ alkyl, aryl, biaryl, heteroaryl, heterobiaryl, heterocyclyl, C$_{1-2}$ alkylaryl, C$_{1-2}$ alkylheteroaryl, C$_{1-2}$ alkylheterocyclyl, C$_{1-2}$ alkylbiaryl, -L-aryl or -L-biaryl, may optionally be substituted with one or more R$^9$;

R$^8$ is H, C$_{1-6}$ alkyl, C$_{1-4}$ fluoroalkyl, C$_{1-4}$ hydroxyalkyl, C$_{1-3}$ alkylaryl or C(=O)R$^{10}$ which C$_{1-6}$ alkyl or C$_{1-3}$ alkylaryl may optionally be substituted with one or more R$^9$;

when Z is NR$^8$, R$^8$ and R$^6$ may be combined with each other to form a 3-7 membered heterocyclic ring comprising 1 to 2 N or 0 to 2 O heteroatoms;

R$^9$ is halogen, hydroxyl, —CN, —NO$_2$, —COOH, —(C=O)H, C$_{1-6}$ alkyl, C$_{2-6}$ alkenyl, C$_{2-6}$ alkynyl, C$_{3-10}$ cycloalkyl, C$_{1-4}$ hydroxyalkyl, C$_{1-6}$ alkoxy, cycloalkenyl, aryl, heterocyclyl, heteroaryl, —NR$^{15}$R$^{16}$, -L-NR$^{15}$R$^{16}$, -L-COOR$^{17}$, -L-alkyl, -L-C$_{3-10}$ cycloalkyl, -L-heterocyclyl, -L-heteroaryl, or -L-aryl which C$_{1-6}$ alkyl, C$_{2-6}$ alkenyl, C$_{2-6}$ alkynyl, C$_{3-10}$ cycloalkyl, C$_{1-4}$ hydroxyalkyl, C$_{1-6}$ alkoxy, cycloalkenyl, aryl, heterocyclyl, heteroaryl, -L-alkyl, -L-C$_{3-10}$ cycloalkyl, -L-heterocyclyl, -L-heteroaryl, or -L-aryl may substituted with halogen, hydroxyl, —CN, —NR$^{15}$R$^{16}$, C$_{1-6}$ alkyl, C$_{3-10}$ cycloalkyl, C$_{1-4}$ hydroxyalkyl, C$_{2-6}$ alkenyl, aryl, heterocyclyl, -L-heterocyclyl, or —(CH$_2$)$_l$—C(=O)—NR$^{15}$R$^{16}$;

R$^{10}$ is C$_{1-3}$ alkyl or C$_{1-3}$ alkylaryl;

R$^{11}$ is H, C$_{1-6}$ alkyl, C$_{1-4}$ fluoroalkyl, C$_{1-4}$ hydroxyalkyl, C$_{1-3}$ alkylaryl or C(=O)R$^{10}$ which C$_{1-6}$ alkyl or C$_{1-3}$ alkylaryl may optionally be substituted with one or more R$^9$;

R$^{15}$ and R$^{16}$ each independently is H, C$_{1-6}$ alkyl, C$_{3-10}$ cycloalkyl or SO$_2$R$^{17}$;

R$^{17}$ is H, C$_{1-3}$ alkyl or C$_{1-3}$ alkylaryl;

R$^{18}$ to R$^{21}$ are the same as or different from each other, and are each independently H or halogen; or R$^{18}$ and R$^{19}$; or R$^{20}$ and R$^{21}$ may be combined with each other to form a 3-7 membered cyclic ring or heterocyclic ring containing 1 or 2 of NR$^8$, O or S, and the cyclic or heterocyclic ring may optionally be substituted with 1 or 2 halogen(s), C$_{1-4}$ alkyl or C$_{1-4}$ alkoxy;

L is C$_{1-3}$ alkyl, C$_{1-3}$ alkylO, C$_{2-6}$ alkynyl, C$_{3-10}$ cycloalkyl, —(CH$_2$)$_l$—C(=O)—(CH$_2$)$_m$—, C(=O)O, —(CH$_2$)$_l$—C(=O)NH—(CH$_2$)$_m$—, —(CH$_2$)$_l$—NHC(=O)—(CH$_2$)$_m$—, —(CH$_2$)$_l$—NH—(CH$_2$)$_m$—, NR$^8$, —NH—C(=O)—CR$^{15}$R$^{16}$—NH—C(=O)—NHC(=O), O, O(C=O) S, S, S(=O), or SO$_2$; and l and m each independently is an integer of 0 to 2.

In accordance with a third embodiment of the present invention, there are provided the heterocyclic compound represented formula I is represented by the following Formula Ib:

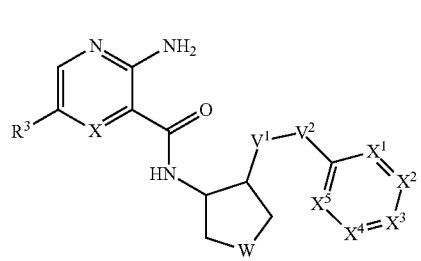

[Formula Ib]

wherein:
X is CH, or N;
W is CH$_2$, NR$^{11}$, or O;
V$^1$ and V$^2$ each independently is CR$^{13}$R$^{13'}$, NR$^{13}$, or O;
at least one of V$_1$ and V$_2$ is CR$^{13}$R$^{13'}$;
X$^1$ to X$^5$ are the same as or different from each other, and are each independently CR$^{14}$ or N;
at least one of X$^1$ to X$^5$ is CR$^{14}$;
R$^3$ is H, halogen, CN, C$_{1-3}$ alkyl, cycloalkenyl, C$_{2-6}$ alkenyl, aryl, biaryl, heteroaryl, heterobiaryl, heterocyclyl, $C_{1-2}$ alkylaryl, $C_{1-2}$ alkylheteroaryl, or $C_{1-2}$ alkylheterocyclyl which aryl, biaryl, heteroaryl, heterobiaryl, heterocyclyl, $C_{1-2}$ alkylaryl, $C_{1-2}$ alkylheteroaryl, or $C_{1-2}$ alkylheterocyclyl may optionally be substituted with one or more $R^9$;

$R^9$ is halogen, hydroxyl, —CN, —NO$_2$, —COOH, —(C=O)H, $C_{1-6}$ alkyl, $C_{2-6}$ alkenyl, $C_{2-6}$ alkynyl, $C_{3-10}$ cycloalkyl, $C_{1-4}$ hydroxyalkyl, $C_{1-6}$ alkoxy, cycloalkenyl, aryl, heterocyclyl, heteroaryl, —NR$^{15}$R$^{16}$, -L-NR$^{15}$R$^{16}$, -L-COOR$^{17}$, -L-alkyl, -L-$C_{3-10}$ cycloalkyl, -L-heterocyclyl, -L-heteroaryl, or -L-aryl which $C_{1-6}$ alkyl, $C_{2-6}$ alkenyl, $C_{2-6}$ alkynyl, $C_{3-10}$ cycloalkyl, $C_{1-4}$ hydroxyalkyl, $C_{1-6}$ alkoxy, cycloalkenyl, aryl, heterocyclyl, heteroaryl, -L-alkyl, -L-$C_{3-10}$cycloalkyl, -L-heterocyclyl, -L-heteroaryl, or -L-aryl may substituted with halogen, hydroxyl, —CN, —NR$^{15}$R$^{16}$, $C_{1-6}$ alkyl, $C_{3-10}$ cycloalkyl, $C_{1-4}$ hydroxyalkyl, $C_{2-6}$ alkenyl, aryl, heterocyclyl, -L-heterocyclyl, or —(CH$_2$)$_l$—C(=O)—NR$^{15}$R$^{16}$;

$R^{10}$ is $C_{1-3}$ alkyl or $C_{1-3}$ alkylaryl;

$R^{11}$ is H, $C_{1-6}$ alkyl, $C_{1-4}$ fluoroalkyl, $C_{1-4}$ hydroxyalkyl, $C_{1-3}$ alkylaryl or C(=O)R$^{10}$ which $C_{1-6}$ alkyl or $C_{1-3}$ alkylaryl may optionally be substituted with one or more $R^9$;

$R^{13}$ and $R^{13'}$ each independently is H, $C_{1-3}$ alkyl, $C_{2-3}$ hydroxyalkyl;

each $R^{14}$ is independently selected from H, halogen, hydroxyl, —CN, —NO$_2$, $C_{1-6}$ alkyl, $C_{2-6}$ alkenyl, $C_{2-6}$ alkynyl, $C_{3-10}$ cycloalkyl, cycloalkenyl, aryl, heterocyclyl, heteroaryl, —NR$^{15}$R$^{16}$, -L-alkyl, -L-heterocyclyl, -L-heteroaryl, or -L-aryl which $C_{1-6}$ alkyl, aryl, heteroaryl, heterocyyl may optionally be substituted with one or more $R^9$; or adjacent groups among a plurality of $R^{14}$s are bonded to each other to form a 3-7 membered cyclic ring or heterocyclic ring containing 1 or 2 of NR$^{11}$ O or S, and the cyclic or heterocyclic ring may optionally be substituted with 1 or 2 halogen(s), $C_{1-4}$ alkyl or $C_{1-4}$ alkoxy;

$R^{15}$ and $R^{16}$ each independently is H, $C_{1-6}$ alkyl, $C_{3-10}$ cycloalkyl or SO$_2$R$^{17}$;

$R^{17}$ is H, $C_{1-3}$ alkyl or $C_{1-3}$ alkylaryl;

L is $C_{1-3}$ alkyl, $C_{1-3}$ alkylO, $C_{2-6}$ alkynyl, $C_{3-10}$ cycloalkyl, —(CH$_2$)$_l$—C(=O)—(CH$_2$)$_m$—, C(=O)O, —(CH$_2$)$_l$—C(=O)NH—(CH$_2$)$_m$—, —(CH$_2$)$_l$—NHC(=O)—(CH$_2$)$_m$—, —(CH$_2$)$_l$—NH—(CH$_2$)$_m$—, NR$^8$, —NH—C(=O)—CR$^{15}$R$^{16}$—NH—C(=O)—, NHC(=O), O, O(C=O) S, S, S(=O), or SO$_2$; and l and m each independently is an integer of 0 to 2.

In the present disclosure, a halogen may be fluorine, chlorine, bromine or iodine.

In the present disclosure, the alkyl may be straight or branched, and the number of carbon atoms thereof is not particularly limited, but is preferably 1 to 6. Specific examples thereof include a methyl group, an ethyl group, a propyl group, an isopropyl group, a butyl group, a pentyl group, a hexyl group, and the like, or a branched chain thereof, but are not limited thereto.

In the present disclosure, the cycloalkyl is not particularly limited, but has preferably 3 to 10 carbon atoms. Specific examples thereof include cyclopropyl, cyclobutyl, cyclopentyl, cyclohexyl, cycloheptyl, cyclooctyl, a norbornyl group, an adamantly group, and the like, but are not limited thereto.

In the present disclosure, the alkoxy may be straight, branched, or cyclic. The number of carbon atoms of the alkoxy group is not particularly limited, but is preferably 1 to 6. Specific examples thereof include methoxy, ethoxy, n-propoxy, isopropoxy, n-butoxy, isobutoxy, and the like, but are not limited thereto.

In the present disclosure, the alkenyl may be straight or branched, and the number of carbon atoms thereof is not particularly limited, but is preferably 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, and the like, but are not limited thereto.

In the present disclosure, the aryl may be monocyclic, or polycyclic and the number of carbon atoms is not particularly limited, but is preferably 6 to 60. Specific examples of the aryl group include a monocyclic aromatic group, such as a phenyl group and a polycyclic aromatic group, such as a naphthyl group, an anthracenyl group, a phenanthrenyl group, a pyrenyl group, a perylenyl group, a tetracenyl group, a chrysenyl group, a fluorenyl group, an acenaphthacenyl group, a triphenylene group, and a fluoranthene group, and the like, but are not limited thereto.

In the present disclosure, the biaryl may two or more monocyclics and/or polycyclics linked each other.

In the present disclosure, the aryl in the alkylaryl and biaryl is the same as the above-described examples of the aryl group.

In the present disclosure, a heterocyclic or a heteroaryl including one or more hetero atom, for example, a heterocyclic group including one or more of O, N, S, Si, Se and the like. Examples of the heterocyclic group include a thiophene group, a furan group, a pyrrole group, an, imidazole group, a thiazole group, an oxazole group, an oxadiazole group, a triazole group, a pyridyl group, a bipyridyl group, a triazine group, an acridyl group, a pyridazine group, a pyrrolidine group, a morpholine group, a piperazin group, a piperidine group, a tetrahydrofuran group, a pyrazole group, a quinolinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a dibenzofuranyl group, and the like, but are not limited thereto.

In the present disclosure, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups "adjacent" to each other.

In the present disclosure, the cyclic ring or heterocyclic ring formed by binding two or more $R^{14}$s comprises cycloalkyl, cycloalkenyl, aryl, heterocycle, heteroaryl. In accordance with a forth embodiment of the present invention, there are provided the heterocyclic compound represented formula I is represented by any one of the following compounds.

| | |
|---|---|
| Example 1 | 2-amino-N-((1S,2S)-2-(benzyloxy)cyclopentyl)-5-(1-methyl-1H-pyrazol-4-yl)nicotinamide |
| Example 2 | 2-amino-N-((1R,2R)-2-(benzyloxy)cyclopentyl)-5-(1-methyl-1H-pyrazol-4-yl)nicotinamide |

-continued

| | |
|---|---|
| Example 3 | 2-amino-N-(trans-2-(benzyloxy)cyclopentyl)-5-(1-methyl-1H-pyrazol-4-yl)nicotinamide |
| Example 4 | 2-amino-N-((1R,2S)-2-(benzyloxy)cyclopentyl)-5-(1-methyl-1H-pyrazol-4-yl)nicotinamide |
| Example 5 | 2-amino-N-(cis-2-(benzyloxy)cyclopentyl)-5-(1-methyl-1H-pyrazol-4-yl)nicotinamide |
| Example 6 | 2-amino-5-(1-methyl-1H-pyrazol-4-yl)-N-((1S,2S)-2-((2-methylbenzyl)oxy)cyclopentyl)nicotinamide |
| Example 7 | 2-amino-N-((1S,2S)-2-((3-ethylbenzyl)oxy)cyclopentyl)-5-(1-methyl-1H-pyrazol-4-yl)nicotinamide |
| Example 8 | 2-amino-N-((1S,2S)-2-((4-ethylbenzyl)oxy)cyclopentyl)-5-(1-methyl-1H-pyrazol-4-yl)nicotinamide |
| Example 9 | 2-amino-N-(trans-2-((4-ethylbenzyl)oxy)cyclopentyl)-5-(1-methyl-1H-pyrazol-4-yl)nicotinamide |
| Example 10 | 2-amino-N-((1S,2S)-2-((4-isopropylbenzyl)oxy)cyclopentyl)-5-(1-methyl-1H-pyrazol-4-yl)nicotinamide |
| Example 11 | 2-amino-N-((1S,2S)-2-((3,4-dimethylbenzyl)oxy)cyclopentyl)-5-(1-methyl-1H-pyrazol-4-yl)nicotinamide |
| Example 12 | 2-amino-N-((1R,2R)-2-((3,4-dimethylbenzyl)oxy)cyclopentyl)-5-(1-methyl-1H-pyrazol-4-yl)nicotinamide |
| Example 13 | 2-amino-N-(trans-2-((3,4-dimethylbenzyl)oxy)cyclopentyl)-5-(1-methyl-1H-pyrazol-4-yl)nicotinamide |
| Example 14 | 2-amino-N-((1S,2S)-2-((2,3-dimethylbenzyl)oxy)cyclopentyl)-5-(1-methyl-1H-pyrazol-4-yl)nicotinamide |
| Example 15 | 2-amino-N-((1S,2S)-2-((2,6-dimethylbenzyl)oxy)cyclopentyl)-5-(1-methyl-1H-pyrazol-4-yl)nicotinamide |
| Example 16 | 2-amino-N-((1S,2S)-2-((2,5-dimethylbenzyl)oxy)cyclopentyl)-5-(1-methyl-1H-pyrazol-4-yl)nicotinamide |
| Example 17 | 2-amino-N-((1S,2S)-2-((3,5-dimethylbenzyl)oxy)cyclopentyl)-5-(1-methyl-1H-pyrazol-4-yl)nicotinamide |
| Example 18 | 2-amino-N-((1S,2S)-2-((2,4-dimethylbenzyl)oxy)cyclopentyl)-5-(1-methyl-1H-pyrazol-4-yl)nicotinamide |
| Example 19 | 2-amino-N-((1S,2S)-2-((4-ethyl-3-methylbenzyl)oxy)cyclopentyl)-5-(1-methyl-1H-pyrazol-4-yl)nicotinamide |
| Example 20 | 2-amino-N-((1S,2S)-2-((3,4-diethylbenzyl)oxy)cyclopentyl)-5-(1-methyl-1H-pyrazol-4-yl)nicotinamide |
| Example 21 | 2-amino-N-((1S,2S)-2-((3-ethyl-4-methylbenzyl)oxy)cyclopentyl)-5-(1-methyl-1H-pyrazol-4-yl)nicotinamide |
| Example 22 | 2-amino-5-(1-methyl-1H-pyrazol-4-yl)-N-((1S,2S)-2-((3-propylbenzyl)oxy)cyclopentyl)nicotinamide |
| Example 23 | 2-amino-N-((1S,2S)-2-((3-cyclopentylbenzyl)oxy)cyclopentyl)-5-(1-methyl-1H-pyrazol-4-yl)nicotinamide |
| Example 24 | 2-amino-N-((1S,2S)-2-((3-isopropylbenzyl)oxy)cyclopentyl)-5-(1-methyl-1H-pyrazol-4-yl)nicotinamide |
| Example 25 | 2-amino-5-(1-methyl-1H-pyrazol-4-yl)-N-((1S,2S)-2-((3-(prop-1-en-2-yl)benzyl)oxy)cyclopentyl)nicotinamide |
| Example 26 | 2-amino-N-((1S,2S)-2-((3-cyclopropylbenzyl)oxy)cyclopentyl)-5-(1-methyl-1H-pyrazol-4-yl)nicotinamide |
| Example 27 | 2-amino-N-((1S,2S)-2-((3-cyclobutylbenzyl)oxy)cyclopentyl)-5-(1-methyl-1H-pyrazol-4-yl)nicotinamide |
| Example 28 | 2-amino-N-((1S,2S)-2-((3-ethynylbenzyl)oxy)cyclopentyl)-5-(1-methyl-1H-pyrazol-4-yl)nicotinamide |
| Example 29 | 2-amino-5-(1-methyl-1H-pyrazol-4-yl)-N-((1S,2S)-2-((4-(trifluoromethyl)benzyl)oxy)cyclopentyl)nicotinamide |
| Example 30 | 2-amino-5-(1-methyl-1H-pyrazol-4-yl)-N-((1S,2S)-2-((3-nitrobenzyl)oxy)cyclopentyl)nicotinamide |
| Example 31 | 2-amino-N-((1S,2S)-2-((3-cyanobenzyl)oxy)cyclopentyl)-5-(1-methyl-1H-pyrazol-4-yl)nicotinamide |
| Example 32 | 2-amino-N-((1S,2S)-2-((3-hydroxybenzyl)oxy)cyclopentyl)-5-(1-methyl-1H-pyrazol-4-yl)nicotinamide |
| Example 33 | 2-amino-N-((1S,2S)-2-((3-methyloxybenzyl)oxy)cyclopentyl)-5-(1-methyl-1H-pyrazol-4-yl)nicotinamide |
| Example 34 | 2-amino-N-((1R,2R)-2-((3-methoxybenzyl)oxy)cyclopentyl)-5-(1-methyl-1H-pyrazol-4-yl)nicotinamide |
| Example 35 | 2-amino-N-((1S,2S)-2-((4-methoxybenzyl)oxy)cyclopentyl)-5-(1-methyl-1H-pyrazol-4-yl)nicotinamide |
| Example 36 | 2-amino-N-((1R,2R)-2-((4-methoxybenzyl)oxy)cyclopentyl)-5-(1-methyl-1H-pyrazol-4-yl)nicotinamide |
| Example 37 | 2-amino-N-(trans-2-((3,5-dimethoxybenzyl)oxy)cyclopentyl)-5-(1-methyl-1H-pyrazol-4-yl)nicotinamide |
| Example 38 | 2-amino-N-((1S,2S)-2-((2,3-dimethoxybenzyl)oxy)cyclopentyl)-5-(1-methyl-1H-pyrazol-4-yl)nicotinamide |
| Example 39 | 2-amino-5-(1-methyl-1H-pyrazol-4-yl)-N-((1S,2S)-2-((3-phenoxybenzyl)oxy)cyclopentyl)nicotinamide |
| Example 40 | 2-amino-N-((1S,2S)-2-(benzo[d][1,3]dioxol-5-ylmethoxy)cyclopentyl)-5-(1-methyl-1H-pyrazol-4-yl)nicotinamide |
| Example 41 | 2-amino-5-(1-methyl-1H-pyrazol-4-yl)-N-((1S,2S)-2-((4-(methylthio)benzyl)oxy)cyclopentyl)nicotinamide |

| | -continued |
|---|---|
| Example 42 | methyl 3-(((((1S,2S)-2-(2-amino-5-(1-methyl-1H-pyrazol-4-yl)nicotinamido)cyclopentyl)oxy)methyl)benzoate |
| Example 43 | 2-amino-N-((1S,2S)-2-((3-chlorobenzyl)oxy)cyclopentyl)-5-(1-methyl-1H-pyrazol-4-yl)nicotinamide |
| Example 44 | 2-amino-N-(trans-2-((3-chlorobenzyl)oxy)cyclopentyl)-5-(1-methyl-1H-pyrazol-4-yl)nicotinamide |
| Example 45 | 2-amino-N-(trans-2-((4-chlorobenzyl)oxy)cyclopentyl)-5-(1-methyl-1H-pyrazol-4-yl)nicotinamide |
| Example 46 | 2-amino-N-(trans-2-((3,4-dichlorobenzyl)oxy)cyclopentyl)-5-(1-methyl-1H-pyrazol-4-yl)nicotinamid |
| Example 47 | 2-amino-N-(trans-2-((2-fluorobenzyl)oxy)cyclopentyl)-5-(1-methyl-1H-pyrazol-4-yl)nicotinamide |
| Example 48 | 2-amino-N-((1S,2S)-2-((3-fluorobenzyl)oxy)cyclopentyl)-5-(1-methyl-1H-pyrazol-4-yl)nicotinamide |
| Example 49 | 2-amino-N-(trans-2-((4-bromo-2-fluorobenzyl)oxy)cyclopentyl)-5-(1-methyl-1H-pyrazol-4-yl)nicotinamide |
| Example 50 | 2-amino-5-(1-methyl-1H-pyrazol-4-yl)-N-(trans-2-((2,4,5-trifluorobenzyl)oxy)cyclopentyl)nicotinamide |
| Example 51 | 2-amino-N-((1S,2S)-2-((3-bromobenzyl)oxy)cyclopentyl)-5-(1-methyl-1H-pyrazol-4-yl)nicotinamide |
| Example 52 | 2-amino-N-(trans-2-((3-bromo-4-fluorobenzyl)oxy)cyclopentyl)-5-(1-methyl-1H-pyrazol-4-yl)nicotinamide |
| Example 53 | 2-amino-N-((1R,2R)-2-((3-bromo-4-fluorobenzyl)oxy)cyclopentyl)-5-(1-methyl-1H-pyrazol-4-yl)nicotinamide |
| Example 54 | 2-amino-N-((1S,2S)-2-(1-(4-bromophenyl)ethoxy)cyclopentyl)-5-(1-methyl-1H-pyrazol-4-yl)nicotinamide |
| Example 55 | methyl (3-(((((1S,2S)-2-(2-amino-5-(1-methyl-1H-pyrazol-4-yl)nicotinamido)cyclopentyl)oxy)methyl)benzoyl)glycinate |
| Example 56 | 2-amino-N-((1S,2S)-2-((3-((2-hydroxyethyl)carbamoyl)benzyl)oxy)cyclopentyl)-5-(1-methyl-1H-pyrazol-4-yl)nicotinamide |
| Example 57 | 2-amino-5-(1-methyl-1H-pyrazol-4-yl)-N-((1S,2S)-2-((3-(piperidine-4-carboxamido)benzyl)oxy)cyclopentyl)nicotinamide |
| Example 58 | 2-amino-N-((1S,2S)-2-((3-((S)-2-aminopropanamido)benzyl)oxy)cyclopentyl)-5-(1-methyl-1H-pyrazol-4-yl)nicotinamide |
| Example 59 | N-((1S,2S)-2-((3-((S)-2-acetamidopropanamido)benzyl)oxy)cyclopentyl)-2-amino-5-(1-methyl-1H-pyrazol-4-yl)nicotinamide |
| Example 60 | 2-amino-N-((1S,2S)-2-((3-(3-aminopropanamido)benzyl)oxy)-cyclopentyl)-5-(1-methyl-1H-pyrazol-4-yl)nicotinamide |
| Example 61 | N-((1S,2S)-2-((3-(2H-1,2,3-triazol-2-yl)benzyl)oxy)cyclopentyl)-2-amino-5-(1-methyl-1H-pyrazol-4-yl)nicotinamide |
| Example 62 | N-((1S,2S)-2-((4-(2H-1,2,3-triazol-2-yl)benzyl)oxy)cyclopentyl)-2-amino-5-(1-methyl-1H-pyrazol-4-yl)nicotinamide |
| Example 63 | 2-amino-5-(1-methyl-1H-pyrazol-4-yl)-N-((1S,2S)-2-(naphthalen-2-ylmethoxy)cyclopentyl)nicotinamide |
| Example 64 | 2-amino-5-(1-methyl-1H-pyrazol-4-yl)-N-((1S,2S)-2-(quinolin-8-ylmethoxy)cyclopentyl)nicotinamide |
| Example 65 | 2-amino-5-(1-methyl-1H-pyrazol-4-yl)-N-((1S,2S)-2-((2',3',4',5'-tetrahydro-[1,1'-biphenyl]-4-yl)methoxy)cyclopentyl)nicotinamide |
| Example 66 | N-(trans-2-([1,1'-biphenyl]-2-ylmethoxy)cyclopentyl)-2-amino-5-(1-methyl-1H-pyrazol-4-yl)nicotinamide |
| Example 67 | N-((1S,2S)-2-([1,1'-biphenyl]-3-ylmethoxy)cyclopentyl)-2-amino-5-(1-methyl-1H-pyrazol-4-yl)nicotinamide |
| Example 68 | N-((1S,2S)-2-([1,1'-biphenyl]-4-ylmethoxy)cyclopentyl)-2-amino-5-(1-methyl-1H-pyrazol-4-yl)nicotinamide |
| Example 69 | 2-amino-N-((1S,2S)-2-hydroxycyclopentyl)-5-(1-methyl-1H-pyrazol-4-yl)nicotinamide |
| Example 70 | 2-amino-N-(cis-2-hydroxycyclopentyl)-5-(1-methyl-1H-pyrazol-4-yl)nicotinamide |
| Example 71 | N-((1S,2S)-2-(benzyloxy)cyclopentyl)-2-(ethylamino)-5-(1-methyl-1H-pyrazol-4-yl)nicotinamide |
| Example 72 | N-((1S,2S)-2-(benzyloxy)cyclopentyl)-2-((3,4-dimethylbenzyl)amino)-5-(1-methyl-1H-pyrazol-4-yl)nicotinamide |
| Example 73 | 2-amino-N-((6R,7S)-6-(benzyloxy)-1,4-dioxaspiro[4.4]nonan-7-yl)-5-(1-methyl-1H-pyrazol-4-yl)nicotinamide |
| Example 74 | 2-amino-N-(trans-2-(benzyloxy)cyclohexyl)-5-(1-methyl-1H-pyrazol-4-yl)nicotinamide |
| Example 75 | 2-amino-N-((1S,2S)-2-(benzyloxy)cyclohexyl)-5-(1-methyl-1H-pyrazol-4-yl)nicotinamide |
| Example 76 | 2-amino-N-(trans-2-(benzyl(methyl)amino)cyclopentyl)-5-(1-methyl-1H-pyrazol-4-yl)nicotinamide |
| Example 77 | 2-amino-5-(1-methyl-1H-pyrazol-4-yl)-N-((1S,2S)-2-(phenoxymethyl)cyclopentyl)nicotinamide |
| Example 78 | 2-amino-N-((1S,2S)-2-((3,4-dimethylphenoxy)methyl)cyclopentyl)-5-(1-methyl-1H-pyrazol-4-yl)nicotinamide |
| Example 79 | 2-amino-N-(trans-2,2-difluoro-5-(phenoxymethyl)cyclopentyl)-5-(1-methyl-1H-pyrazol-4-yl)nicotinamide |

| | |
|---|---|
| Example 80 | 2-amino-N-((1S,2S)-2-(((2,3-dihydro-1H-inden-5-yl)oxy)methyl)cyclopentyl)-5-(1-methyl-1H-pyrazol-4-yl)nicotinamide |
| Example 81 | 2-amino-5-(1-methyl-1H-pyrazol-4-yl)-N-((1S,2S)-2-((3,4,5-trimethylphenoxy)methyl)cyclopentyl)nicotinamide |
| Example 82 | 2-amino-N-((1S,2S)-2-((3-(dimethylamino)phenoxy)methyl)-cyclopentyl)-5-(1-methyl-1H-pyrazol-4-yl)nicotinamide |
| Example 83 | 2-amino-5-(1-methyl-1H-pyrazol-4-yl)-N-((1S,2S)-2-((3-(piperidine-1-carbonyl)phenoxy)methyl)cyclopentyl)nicotinamide |
| Example 84 | 2-amino-5-(1-methyl-1H-pyrazol-4-yl)-N-((1S,2S)-2-((4-phenoxyphenoxy)methyl)cyclopentyl)nicotinamide |
| Example 85 | 2-amino-N-((1S,2S)-2-((benzyloxy)methyl)cyclopentyl)-5-(1-methyl-1H-pyrazol-4-yl)nicotinamide |
| Example 86 | 2-amino-5-(1-methyl-1H-pyrazol-4-yl)-N-((1S,2S)-2-(((4'-((4-methylpiperazin-1-yl)methyl)-[1,1'-biphenyl]-4-yl)oxy)methyl)cyclopentyl)nicotinamide |
| Example 87 | (1S,2S)-2-(benzyloxy)cyclopentyl 2-amino-5-(1-methyl-1H-pyrazol-4-yl)nicotinate |
| Example 88 | 2-amino-5-(1-methyl-1H-pyrazol-4-yl)-N-((1S,2R)-2-phenethylcyclopentyl)nicotinamide |
| Example 89 | 2-amino-N-(trans-4-(benzyloxy)tetrahydrofuran-3-yl)-5-(1-methyl-1H-pyrazol-4-yl)nicotinamide |
| Example 90 | 2-amino-5-(1-methyl-1H-pyrazol-4-yl)-N-(trans-4-morpholinotetrahydrofuran-3-yl)nicotinamide |
| Example 91 | 2-amino-5-(1-methyl-1H-pyrazol-4-yl)-N-(trans-4-(pyrrolidin-1-yl)tetrahydrofuran-3-yl)nicotinamide |
| Example 92 | 2-amino-N-(cis-4-hydroxytetrahydrofuran-3-yl)-5-(1-methyl-1H-pyrazol-4-yl)nicotinamide |
| Example 93 | 2-amino-N-(4-(benzyloxy)-1-methylpyrrolidin-3-yl)-5-(1-methyl-1H-pyrazol-4-yl)nicotinamide |
| Example 94 | 2-amino-N-(trans-4-(benzyloxy)-1-isopropylpyrrolidin-3-yl)-5-(1-methyl-1H-pyrazol-4-yl)nicotinamide |
| Example 95 | (R)-2-amino-N-(2-(benzyloxy)propyl)-5-(1-methyl-1H-pyrazol-4-yl)nicotinamide |
| Example 96 | (S)-2-amino-N-(2-(benzyloxy)propyl)-5-(1-methyl-1H-pyrazol-4-yl)nicotinamide |
| Example 97 | (S)-2-amino-N-(1-(benzyloxy)propan-2-yl)-5-(1-methyl-1H-pyrazol-4-yl)nicotinamide |
| Example 98 | (R)-2-amino-N-(1-(benzyloxy)propan-2-yl)-5-(1-methyl-1H-pyrazol-4-yl)nicotinamide |
| Example 99 | 2-amino-N-(1-(benzyloxy)-2-methylpropan-2-yl)-5-(1-methyl-1H-pyrazol-4-yl)nicotinamide |
| Example 100 | (R)-2-amino-N-(1-((3,4-dimethylbenzyl)oxy)propan-2-yl)-5-(1-methyl-1H-pyrazol-4-yl)nicotinamide |
| Example 101 | (S)-2-amino-N-(2-((3,4-dimethylbenzyl)oxy)propyl)-5-(1-methyl-1H-pyrazol-4-yl)nicotinamide |
| Example 102 | (R)-2-amino-N-(1-((4-chlorobenzyl)oxy)propan-2-yl)-5-(1-methyl-1H-pyrazol-4-yl)nicotinamide |
| Example 103 | (S)-2-amino-N-(2-((4-chlorobenzyl)oxy)propyl)-5-(1-methyl-1H-pyrazol-4-yl)nicotinamide |
| Example 104 | (R)-2-amino-N-(1-((3,4-dichlorobenzyl)oxy)propan-2-yl)-5-(1-methyl-1H-pyrazol-4-yl)nicotinamide |
| Example 105 | (S)-2-amino-N-(2-((3,4-dichlorobenzyl)oxy)propyl)-5-(1-methyl-1H-pyrazol-4-yl)nicotinamide |
| Example 106 | (R)-2-amino-N-(1-((3-methoxybenzyl)oxy)propan-2-yl)-5-(1-methyl-1H-pyrazol-4-yl)nicotinamide |
| Example 107 | (S)-2-amino-N-(2-((3-methoxybenzyl)oxy)propyl)-5-(1-methyl-1H-pyrazol-4-yl)nicotinamide |
| Example 108 | (R)-2-amino-N-(1-(benzyloxy)butan-2-yl)-5-(1-methyl-1H-pyrazol-4-yl)nicotinamide |
| Example 109 | (S)-2-amino-N-(1-(benzyloxy)-3-methylbutan-2-yl)-5-(1-methyl-1H-pyrazol-4-yl)nicotinamide |
| Example 110 | (R)-2-amino-N-(1-(benzyloxy)-3-methylbutan-2-yl)-5-(1-methyl-1H-pyrazol-4-yl)nicotinamide |
| Example 111 | (S)-2-amino-N-(1-(benzyloxy)-4-methylpentan-2-yl)-5-(1-methyl-1H-pyrazol-4-yl)nicotinamide |
| Example 112 | (R)-2-amino-N-(1-(benzyloxy)-4-methylpentan-2-yl)-5-(1-methyl-1H-pyrazol-4-yl)nicotinamide |
| Example 113 | (R)-2-amino-N-(2-(benzyloxy)-1-cyclohexylethyl)-5-(1-methyl-1H-pyrazol-4-yl)nicotinamide |
| Example 114 | (R)-2-amino-N-(1-cyclohexyl-2-hydroxyethyl)-5-(1-methyl-1H-pyrazol-4-yl)nicotinamide |
| Example 115 | (S)-2-amino-N-(2-(benzyloxy)-1-phenylethyl)-5-(1-methyl-1H-pyrazol-4-yl)nicotinamide |
| Example 116 | (R)-2-amino-N-(2-(benzyloxy)-1-phenylethyl)-5-(1-methyl-1H-pyrazol-4-yl)nicotinamide |
| Example 117 | (S)-2-amino-N-(1-(benzyloxy)-3-phenylpropan-2-yl)-5-(1-methyl-1H-pyrazol-4-yl)nicotinamide |
| Example 118 | (R)-2-amino-N-(1-(benzyloxy)-3-phenylpropan-2-yl)-5-(1-methyl-1H-pyrazol-4-yl)nicotinamide |

-continued

| | |
|---|---|
| Example 119 | (R)-2-amino-N-(1-(cyclobutylmethoxy)propan-2-yl)-5-(1-methyl-1H-pyrazol-4-yl)nicotinamide |
| Example 120 | methyl N-(2-amino-5-(1-methyl-1H-pyrazol-4-yl)nicotinoyl)-O-benzyl-L-serinate |
| Example 121 | methyl N-(2-amino-5-(1-methyl-1H-pyrazol-4-yl)nicotinoyl)-O-benzyl-L-threoninate |
| Example 122 | 2-amino-N-((2S,3R)-3-(benzyloxy)-1-(methylamino)-1-oxobutan-2-yl)-5-(1-methyl-1H-pyrazol-4-yl)nicotinamide |
| Example 123 | 2-amino-N-((2S,3R)-3-(benzyloxy)-1-oxo-1-(propylamino)butan-2-yl)-5-(1-methyl-1H-pyrazol-4-yl)nicotinamide |
| Example 124 | 2-amino-N-((2S,3R)-3-(benzyloxy)-1-(cyclopentylamino)-1-oxobutan-2-yl)-5-(1-methyl-1H-pyrazol-4-yl)nicotinamide |
| Example 125 | 2-amino-N-((2S,3R)-3-(benzyloxy)-1-oxo-1-(pyrrolidin-1-yl)butan-2-yl)-5-(1-methyl-1H-pyrazol-4-yl)nicotinamide |
| Example 126 | benzyl (2-amino-5-(1-methyl-1H-pyrazol-4-yl)nicotinoyl)-L-alaninate |
| Example 127 | benzyl (2-amino-5-(1-methyl-1H-pyrazol-4-yl)nicotinoyl)-L-valinate |
| Example 128 | benzyl (2-amino-5-(1-methyl-1H-pyrazol-4-yl)nicotinoyl)-L-serinate |
| Example 129 | 3-amino-N-((1S,2S)-2-(benzyloxy)cyclopentyl)-6-(1-methyl-1H-pyrazol-4-yl)pyrazine-2-carboxamide |
| Example 130 | 3-amino-N-((1S,2S)-2-((3,4-dimethylbenzyl)oxy)cyclopentyl)-6-(1-methyl-1H-pyrazol-4-yl)pyrazine-2-carboxamide |
| Example 131 | (S)-3-amino-6-(1-methyl-1H-pyrazol-4-yl)-N-(1,2,3,4-tetrahydronaphthalen-1-yl)pyrazine-2-carboxamide |
| Example 132 | 3-amino-N-(trans-4-(benzyloxy)tetrahydrofuran-3-yl)-6-(1-methyl-1H-pyrazol-4-yl)pyrazine-2-carboxamide |
| Example 133 | 3-amino-N-(cis-4-(benzyloxy)tetrahydrofuran-3-yl)-6-(1-methyl-1H-pyrazol-4-yl)pyrazine-2-carboxamide |
| Example 134 | 2-amino-N-((1S,2S)-2-((3'-amino-[1,1'-biphenyl]-4-yl)methoxy)cyclopentyl)-5-(1-methyl-1H-pyrazol-4-yl)nicotinamide |
| Example 135 | 2-amino-N-((1S,2S)-2-((4'-amino-[1,1'-biphenyl]-4-yl)methoxy)cyclopentyl)-5-(1-methyl-1H-pyrazol-4-yl)nicotinamide |
| Example 136 | 2-amino-5-(1-methyl-1H-pyrazol-4-yl)-N-((1S,2S)-2-((4'-(methylamino)-[1,1'-biphenyl]-4-yl)methoxy)cyclopentyl)nicotinamide |
| Example 137 | 2-amino-N-((1S,2S)-2-((4'-(dimethylamino)-[1,1'-biphenyl]-4-yl)methoxy)cyclopentyl)-5-(1-methyl-1H-pyrazol-4-yl)nicotinamide |
| Example 138 | 2-amino-N-((1S,2S)-2-((4'-((dimethylamino)methyl)-[1,1'-biphenyl]-4-yl)methoxy)cyclopentyl)-5-(1-methyl-1H-pyrazol-4-yl)nicotinamide |
| Example 139 | 2-amino-N-((1S,2S)-2-((3'-amino-2'-methyl-[1,1'-biphenyl]-4-yl)methoxy)cyclopentyl)-5-(1-methyl-1H-pyrazol-4-yl)nicotinamide |
| Example 140 | 2-amino-N-((1S,2S)-2-((3'-hydroxy-[1,1'-biphenyl]-4-yl)methoxy)cyclopentyl)-5-(1-methyl-1H-pyrazol-4-yl)nicotinamide |
| Example 141 | 2-amino-N-((1S,2S)-2-((3'-(hydroxymethyl)-[1,1'-biphenyl]-4-yl)methoxy)cyclopentyl)-5-(1-methyl-1H-pyrazol-4-yl)nicotinamide |
| Example 142 | 2-amino-N-((1S,2S)-2-((4'-(hydroxymethyl)-[1,1'-biphenyl]-4-yl)methoxy)cyclopentyl)-5-(1-methyl-1H-pyrazol-4-yl)nicotinamide |
| Example 143 | 2-amino-N-((1S,2S)-2-((3'-(aminomethyl)-[1,1'-biphenyl]-4-yl)methoxy)cyclopentyl)-5-(1-methyl-1H-pyrazol-4-yl)nicotinamide |
| Example 144 | 2-amino-N-((1S,2S)-2-((4'-(aminomethyl)-[1,1'-biphenyl]-4-yl)methoxy)cyclopentyl)-5-(1-methyl-1H-pyrazol-4-yl)nicotinamide |
| Example 145 | 2-amino-N-((1S,2S)-2-((4'-(2-aminoethyl)-[1,1'-biphenyl]-4-yl)methoxy)cyclopentyl)-5-(1-methyl-1H-pyrazol-4-yl)nicotinamide |
| Example 146 | 2-amino-5-(1-methyl-1H-pyrazol-4-yl)-N-((1S,2S)-2-((4'-(4-methylpiperazin-1-yl)-[1,1'-biphenyl]-4-yl)methoxy)-cyclopentyl)nicotinamide |
| Example 147 | 2-amino-5-(1-methyl-1H-pyrazol-4-yl)-N-((1S,2S)-2-((4-(6-(piperazin-1-yl)pyridin-3-yl)benzyl)oxy)cyclopentyl)nicotinamide |
| Example 148 | 2-amino-5-(1-methyl-1H-pyrazol-4-yl)-N-((1S,2S)-2-((4-(6-(4-methylpiperazin-1-yl)pyridin-3-yl)benzyl)oxy)cyclopentyl)nicotinamide |
| Example 149 | 2-amino-5-(1-methyl-1H-pyrazol-4-yl)-N-((1S,2S)-2-((3'-(piperazin-1-yl)-[1,1'-biphenyl]-4-yl)methoxy)cyclopentyl)nicotinainide |
| Example 150 | 2-amino-5-(1-methyl-1H-pyrazol-4-yl)-N-((1S,2S)-2-((3'-(4-methyl-piperazin-1-yl)-[1,1'-biphenyl]-4-yl)methoxy)cyclopentyl)nicotinamide |
| Example 151 | 2-amino-5-(1-methyl-1H-pyrazol-4-yl)-N-((1S,2S)-2-((3'-((4-methyl-piperazin-1-yl)methyl)-[1,1'-biphenyl]-4-yl)methoxy)cyclopentyl)-nicotinamide |
| Example 152 | 2-amino-5-(1-methyl-1H-pyrazol-4-yl)-N-((1S,2S)-2-((4'-(morpholine-4-carbonyl)-[1,1'-biphenyl]-4-yl)methoxy)cyclopentyl)nicotinamide |
| Example 153 | 2-amino-N-((1S,2S)-2-((4'-ethyl-[1,1'-biphenyl]-4-yl)methoxy)cyclopentyl)-5-(1-methyl-1H-pyrazol-4-yl)nicotinamide |
| Example 154 | 2-amino-N-((1S,2S)-2-((4'-(cyanomethyl)-[1,1'-biphenyl]-4-yl)methoxy)cyclopentyl)-5-(1-methyl-1H-pyrazol-4-yl)nicotinamide |
| Example 155 | 2-amino-N-((1S,2S)-2-((4'-carbamoyl-[1,1'-biphenyl]-4-yl)methoxy)cyclopentyl)-5-(1-methyl-1H-pyrazol-4-yl)nicotinamide |
| Example 156 | 2-amino-N-((1S,2S)-2-((3-fluoro-4'-((4-methylpiperazin-1-yl)methyl)-[1,1'-biphenyl]-4-yl)methoxy)cyclopentyl)-5-(1-methyl-1H-pyrazol-4-yl)nicotinamide |
| Example 157 | 2-amino-N-((1S,2S)-2-((3-fluoro-4'-((cis-3,4,5-trimethylpiperazin-1-yl)methyl)-[1,1'-biphenyl]-4-yl)methoxy)cyclopentyl)-5-(1-methyl-1H-pyrazol-4-yl)nicotinamide |

-continued

| | |
|---|---|
| Example 158 | 2-amino-5-(1-methyl-1H-pyrazol-4-yl)-N-((1S,2S)-2-((4'-((4-methylpiperazin-1-yl)methyl)-3-(trifluoromethyl)-[1,1'-biphenyl]-4-yl)methoxy)cyclopentyl)nicotinamide |
| Example 159 | 2-amino-N-((1S,2S)-2-((2-chloro-4'-((4-methylpiperazin-1-yl)methyl)-[1,1'-biphenyl]-4-yl)methoxy)cyclopentyl)-5-(1-methyl-1H-pyrazol-4-yl)nicotinamide |
| Example 160 | 2-amino-N-((1S,2S)-2-((3-fluoro-4'-((cis-4-(2-hydroxyethyl)-3,5-dimethylpiperazin-1-yl)methyl)-[1,1'-biphenyl]-4-yl)methoxy)cyclopentyl)-5-(1-methyl-1H-pyrazol-4-yl)nicotinamide |
| Example 161 | 2-amino-5-(1-methyl-1H-pyrazol-4-yl)-N-((1S,2S)-2-((4'-(2-(4-methylpiperazin-1-yl)ethyl)-[1,1'-biphenyl]-4-yl)methoxy)cyclopentyl)nicotinamide |
| Example 162 | 2-amino-5-(1-methyl-1H-pyrazol-4-yl)-N-((1S,2S)-2-((4-(1-(piperidin-4-yl)-1H-pyrazol-4-yl)benzyl)oxy)cyclopentyl)nicotinamide |
| Example 163 | 2-amino-5-(1-methyl-1H-pyrazol-4-yl)-N-((1S,2S)-2-((4-(1-(1-methylpiperidin-4-yl)-1H-pyrazol-4-yl)benzyl)oxy)cyclopentyl)nicotinamide |
| Example 164 | 2-amino-5-(1-methyl-1H-pyrazol-4-yl)-N-((1S,2R)-2-((4'-((4-methylpiperazin-1-yl)methyl)-[1,1'-biphenyl]-4-yl)methoxy)cyclopentyl)nicotinamide |
| Example 165 | 2-amino-5-(1-methyl-1H-pyrazol-4-yl)-N-((1R,2S)-2-((4'-((4-methylpiperazin-1-yl)methyl)-[1,1'-biphenyl]-4-yl)methoxy)cyclopentyl)nicotinamide |
| Example 166 | 2-amino-5-(1-methyl-1H-pyrazol-4-yl)-N-((1S,2S)-2-((4'-((4-methylpiperazin-1-yl)methyl)-[1,1'-biphenyl]-4-yl)methoxy)cyclohexyl)nicotinamide |
| Example 167 | 2-amino-N-((1S,2S)-2-((4'-(2-(4-methylpiperazin-1-yl)propan-2-yl)-[1,1'-biphenyl]-4-yl)methoxy)cyclopentyl)nicotinamide |
| Example 168 | 2-amino-N-((1S,2S)-2-((4'-((4-methylpiperazin-1-yl)methyl)-3-(trifluoromethyl)-[1,1'-biphenyl]-4-yl)methoxy)cyclopentyl)nicotinamide |
| Example 169 | 2-amino-N-((1S,2S)-2-((3'-hydroxy-[1,1'-biphenyl]-3-yl)methoxy)cyclopentyl)-5-(1-methyl-1H-pyrazol-4-yl)nicotinamide |
| Example 170 | 2-amino-N-((1S,2S)-2-((3'-amino-[1,1'-biphenyl]-3-yl)methoxy)cyclopentyl)-5-(1-methyl-1H-pyrazol-4-yl)nicotinamide |
| Example 171 | 2-amino-N-((1S,2S)-2-((3'-(hydroxymethyl)-[1,1'-biphenyl]-3-yl)methoxy)cyclopentyl)-5-(1-methyl-1H-pyrazol-4-yl)nicotinamide |
| Example 172 | 2-amino-5-(1-methyl-1H-pyrazol-4-yl)-N-((1S,2S)-2-((4'-((4-methylpiperazin-1-yl)methyl)-[1,1'-biphenyl]-4-yl)methoxy)cyclopentyl)nicotinamide |
| Example 173 | 2-amino-N-((1S,2S)-2-((4'-(((2-hydroxyethyl)amino)methyl)-[1,1'-biphenyl]-4-yl)methoxy)cyclopentyl)-5-(1-methyl-1H-pyrazol-4-yl)nicotinamide |
| Example 174 | 2-amino-5-(1-methyl-1H-pyrazol-4-yl)-N-((1S,2S)-2-((4'-(morpholinomethyl)-[1,1'-biphenyl]-4-yl)methoxy)cyclopentyl)nicotinamide |
| Example 175 | 2-amino-N-((1S,2S)-2-((4'-((3,3-difluoropiperidin-1-yl)methyl)-[1,1'-biphenyl]-4-yl)methoxy)cyclopentyl)-5-(1-methyl-1H-pyrazol-4-yl)nicotinamide |
| Example 176 | 2-amino-5-(1-methyl-1H-pyrazol-4-yl)-N-((1S,2S)-2-((4'-((4-methylpiperidin-1-yl)methyl)-[1,1'-biphenyl]-4-yl)methoxy)cyclopentyl)nicotinamide |
| Example 177 | 2-amino-5-(1-methyl-1H-pyrazol-4-yl)-N-((1S,2S)-2-((4'-(piperazin-1-ylmethyl)-[1,1'-biphenyl]-4-yl)methoxy)cyclopentyl)nicotinamide |
| Example 178 | 2-amino-5-(1-methyl-1H-pyrazol-4-yl)-N-((1S,2S)-2-((4'-((4-phenylpiperazin-1-yl)methyl)-[1,1'-biphenyl]-4-yl)methoxy)cyclopentyl)nicotinamide |
| Example 179 | 2-amino-5-(1-methyl-1H-pyrazol-4-yl)-N-((1S,2S)-2-((4'-((4-(pyrrolidin-1-yl)piperidin-1-yl)methyl)-[1,1'-biphenyl]-4-yl)methoxy)cyclopentyl)nicotinamide |
| Example 180 | 2-amino-N-((1S,2S)-2-((4'-((4-hydroxypiperidin-1-yl)methyl)-[1,1'-biphenyl]-4-yl)methoxy)cyclopentyl)-5-(1-methyl-1H-pyrazol-4-yl)nicotinamide |
| Example 181 | 2-amino-N-((1S,2S)-2-((4'-((4-(2-hydroxyethyl)piperazin-1-yl)methyl)-[1,1'-biphenyl]-4-yl)methoxy)cyclopentyl)-5-(1-methyl-1H-pyrazol-4-yl)nicotinamide |
| Example 182 | 2-amino-N-((1S,2S)-2-((4'-((4-(2-hydroxy-2-methylpropyl)piperazin-1-yl)methyl)-[1,1'-biphenyl]-4-yl)methoxy)cyclopentyl)-5-(1-methyl-1H-pyrazol-4-yl)nicotinamide |
| Example 183 | 2-amino-N-((1S,2S)-2-((4'-((4-ethylpiperazin-1-yl)methyl)-[1,1'-biphenyl]-4-yl)methoxy)cyclopentyl)-5-(1-methyl-1H-pyrazol-4-yl)nicotinamide |
| Example 184 | 2-amino-N-((1S,2S)-2-((4'-((4-cyclopropylpiperazin-1-yl)methyl)-[1,1'-biphenyl]-4-yl)methoxy)cyclopentyl)-5-(1-methyl-1H-pyrazol-4-yl)nicotinamide |
| Example 185 | 2-amino-5-(1-methyl-1H-pyrazol-4-yl)-N-((1S,2S)-2-((4'-(((R)-3-methylpiperazin-1-yl)methyl)-[1,1'-biphenyl]-4-yl)methoxy)cyclopentyl)nicotinamide |

-continued

| | |
|---|---|
| Example 186 | 2-amino-N-((1S,2S)-2-((4'-(((R)-3,4-dimethylpiperazin-1-yl)methyl)-[1,1'-biphenyl]-4-yl)methoxy)cyclopentyl)-5-(1-methyl-1H-pyrazol-4-yl)nicotinamide |
| Example 187 | 2-amino-N-((1S,2S)-2-((4'-(((R)-2,4-dimethylpiperazin-1-yl)methyl)-[1,1'-biphenyl]-4-yl)methoxy)cyclopentyl)-5-(1-methyl-1H-pyrazol-4-yl)nicotinamide |
| Example 188 | 2-amino-N-((1S,2S)-2-((4'-((3-ethyl-4-methylpiperazin-1-yl)methyl)-[1,1'-biphenyl]-4-yl)methoxy)cyclopentyl)-5-(1-methyl-1H-pyrazol-4-yl)nicotinamide |
| Example 189 | 2-amino-N-((1S,2S)-2-((4'-((cis-3,5-dimethylpiperazin-1-yl)methyl)-[1,1'-biphenyl]-4-yl)methoxy)cyclopentyl)-5-(1-methyl-1H-pyrazol-4-yl)nicotinamide |
| Example 190 | 2-amino-5-(1-methyl-1H-pyrazol-4-yl)-N-((1S,2S)-2-((4'-((cis-3,4,5-trimethylpiperazin-1-yl)methyl)-[1,1'-biphenyl]-4-yl)methoxy)cyclopentyl)nicotinamide |
| Example 191 | 2-amino-N-((1S,2S)-2-((4'-((trans-2,5-dimethylpiperazin-1-yl)methyl)-[1,1'-biphenyl]-4-yl)methoxy)cyclopentyl)-5-(1-methyl-1H-pyrazol-4-yl)nicotinamide |
| Example 192 | 2-amino-5-(1-methyl-1H-pyrazol-4-yl)-N-((1S,2S)-2-((4'-(((2R,5S)-2,4,5-trimethylpiperazin-1-yl)methyl)-[1,1'-biphenyl]-4-yl)methoxy)cyclopentyl)nicotinamide |
| Example 193 | 2-amino-N-((1S,2S)-2-((4'-((3-(dimethylamino)pyrrolidin-1-yl)methyl)-[1,1'-biphenyl]-4-yl)methoxy)cyclopentyl)-5-(1-methyl-1H-pyrazol-4-yl)nicotinamide |
| Example 194 | 3-amino-6-(1-methyl-1H-pyrazol-4-yl)-N-((1S,2S)-2-((4'-((4-methylpiperazin-1-yl)methyl)-[1,1'-biphenyl]-4-yl)methoxy)cyclopentyl)pyrazine-2-carboxamide |
| Example 195 | 2-amino-N-((1S,2S)-2-((3'-fluoro-4'-((4-methylpiperazin-1-yl)methyl)-[1,1'-biphenyl]-4-yl)methoxy)cyclopentyl)-5-(1-methyl-1H-pyrazol-4-yl)nicotinamide |
| Example 196 | 2-amino-N-((1S,2S)-2-((3',5'-difluoro-4'-((4-methylpiperazin-1-yl)methyl)-[1,1'-biphenyl]-4-yl)methoxy)cyclopentyl)-5-(1-methyl-1H-pyrazol-4-yl)nicotinamide |
| Example 197 | 2-amino-5-(1-methyl-1H-pyrazol-4-yl)-N-((1S,2S)-2-((4'-((4-methylpiperazin-1-yl)methyl)-3'-(trifluoromethyl)-[1,1'-biphenyl]-4-yl)methoxy)cyclopentyl)nicotinamide |
| Example 198 | 2-amino-5-(1-methyl-1H-pyrazol-4-yl)-N-((1S,2S)-2-((3'-methyl-4'-((4-methylpiperazin-1-yl)methyl)-[1,1'-biphenyl]-4-yl)methoxy)cyclopentyl)nicotinamide |
| Example 199 | 2-amino-N-((1S,2S)-2-((3'-hydroxy-4'-((4-methylpiperazin-1-yl)methyl)-[1,1'-biphenyl]-4-yl)methoxy)cyclopentyl)-5-(1-methyl-1H-pyrazol-4-yl)nicotinamide |
| Example 200 | 2-amino-5-(1-methyl-1H-pyrazol-4-yl)-N-((1S,2S)-2-((4'-((4-methylpiperazin-1-yl)methyl)-3'-nitro-[1,1'-biphenyl]-4-yl)methoxy)cyclopentyl)nicotinamide |
| Example 201 | 2-amino-N-((1S,2S)-2-((3'-methoxy-4'-((4-methylpiperazin-1-yl)methyl)-[1,1'-biphenyl]-4-yl)methoxy)cyclopentyl)-5-(1-methyl-1H-pyrazol-4-yl)nicotinamide |
| Example 202 | 2-amino-N-((1S,2S)-2-((2'-chloro-4'-((4-methylpiperazin-1-yl)methyl)-[1,1'-biphenyl]-4-yl)methoxy)cyclopentyl)-5-(1-methyl-1H-pyrazol-4-yl)nicotinamide |
| Example 203 | 2-amino-5-(1-methyl-1H-pyrazol-4-yl)-N-((1S,2S)-2-((4-(6-((4-methylpiperazin-1-yl)methyl)pyridin-3-yl)benzyl)oxy)cyclopentyl)nicotinamide |
| Example 204 | 2-amino-5-(1-methyl-1H-pyrazol-4-yl)-N-((1S,2S)-2-((4-(5-((4-methylpiperazin-1-yl)methyl)pyridin-2-yl)benzyl)oxy)cyclopentyl)nicotinamide |
| Example 205 | 2-amino-N-((1S,2S)-2-((4'-((4-(2-hydroxyethyl)piperazin-1-yl)methyl)-3'-(trifluoromethyl)-[1,1'-biphenyl]-4-yl)methoxy)cyclopentyl)-5-(1-methyl-1H-pyrazol-4-yl)nicotinamide |
| Example 206 | 2-amino-N-((1S,2S)-2-((2'-chloro-4'-((4-(2-hydroxyethyl)piperazin-1-yl)methyl)-[1,1'-biphenyl]-4-yl)methoxy)cyclopentyl)-5-(1-methyl-1H-pyrazol-4-yl)nicotinamide |
| Example 207 | 2-amino-N-((1S,2S)-2-((4'-((4-methylpiperazin-1-yl)methyl)-3'-(trifluoromethyl)-[1,1'-biphenyl]-4-yl)methoxy)cyclopentyl)nicotinamide |
| Example 208 | 2-amino-5-(1-methyl-1H-pyrazol-4-yl)-N-((1S,2S)-2-((4'-(1-(4-methylpiperazin-1-yl)ethyl)-[1,1'-biphenyl]-4-yl)methoxy)cyclopentyl)nicotinamide |
| Example 209 | 2-amino-5-(1-methyl-1H-pyrazol-4-yl)-N-((1S,2S)-2-((4'-(1-((3S,5R)-3,4,5-trimethylpiperazin-1-yl)ethyl)-[1,1'-biphenyl]-4-yl)methoxy)cyclopentyl)nicotinamide |
| Example 210 | 2-amino-N-((1S,2S)-2-((4'-(1-(4-(2-hydroxyethyl)piperazin-1-yl)ethyl)-[1,1'-biphenyl]-4-yl)methoxy)cyclopentyl)-5-(1-methyl-1H-pyrazol-4-yl)nicotinamide |
| Example 211 | 2-amino-N-((1S,2S)-2-((4'-(1-((3S,5R)-4-(2-hydroxyethyl)-3,5-dimethylpiperazin-1-yl)ethyl)-[1,1'-biphenyl]-4-yl)methoxy)cyclopentyl)-5-(1-methyl-1H-pyrazol-4-yl)nicotinamide |

| | |
|---|---|
| Example 212 | 2-amino-N-((1S,2S)-2-((3',5'-difluoro-4'-(1-(4-(2-hydroxyethyl)piperazin-1-yl)ethyl)-[1,1'-biphenyl]-4-yl)methoxy)cyclopentyl)-5-(1-methyl-1H-pyrazol-4-yl)nicotinamide |
| Example 213 | 2-amino-5-(1-methyl-1H-pyrazol-4-yl)-N-((1S,2S)-2-((4'-((R)-1-(piperazin-1-yl)ethyl)-[1,1'-biphenyl]-4-yl)methoxy)cyclopentyl)nicotinamide |
| Example 214 | 2-amino-5-(1-methyl-1H-pyrazol-4-yl)-N-((1S,2S)-2-((4'-((R)-1-(4-methylpiperazin-1-yl)ethyl)-[1,1'-biphenyl]-4-yl)methoxy)cyclopentyl)nicotinamide |
| Example 215 | 2-amino-5-(1-methyl-1H-pyrazol-4-yl)-N-((1S,2S)-2-((4'-((S)-1-(4-methylpiperazin-1-yl)ethyl)-[1,1'-biphenyl]-4-yl)methoxy)cyclopentyl)nicotinamide |
| Example 216 | 2-amino-5-(1-methyl-1H-pyrazol-4-yl)-N-((1S,2S)-2-((4'-(1-(4-methylpiperazin-1-yl)cyclopropyl)-[1,1'-biphenyl]-4-yl)methoxy)cyclopentyl)nicotinamide |
| Example 217 | 2-amino-5-(1-methyl-1H-pyrazol-4-yl)-N-((1S,2S)-2-((4'-(2-(4-methylpiperazin-1-yl)propan-2-yl)-[1,1'-biphenyl]-4-yl)methoxy)cyclopentyl)nicotinamide |
| Example 218 | 2-amino-N-((1S,2S)-2-((4'-((R)-1-(4-(2-hydroxyethyl)piperazin-1-yl)ethyl)-[1,1'-biphenyl]-4-yl)methoxy)cyclopentyl)-5-(1-methyl-1H-pyrazol-4-yl)nicotinamide |
| Example 219 | 2-amino-N-((1S,2S)-2-((4'-((S)-1-(4-(2-hydroxyethyl)piperazin-1-yl)ethyl)-[1,1'-biphenyl]-4-yl)methoxy)cyclopentyl)-5-(1-methyl-1H-pyrazol-4-yl)nicotinamide |
| Example 220 | 2-amino-N-((1S,2S)-2-((4'-(1-(4-(2-hydroxyethyl)piperazin-1-yl)cyclopropyl)-[1,1'-biphenyl]-4-yl)methoxy)cyclopentyl)-5-(1-methyl-1H-pyrazol-4-yl)nicotinamide |
| Example 221 | 2-amino-N-((1S,2S)-2-((4'-(2-(4-(2-hydroxyethyl)piperazin-1-yl)propan-2-yl)-[1,1'-biphenyl]-4-yl)methoxy)cyclopentyl)-5-(1-methyl-1H-pyrazol-4-yl)nicotinamide |
| Example 222 | 6-amino-6'-fluoro-N-((1S,2S)-2-((4'-((S)-1-(4-methylpiperazin-1-yl)ethyl)-[1,1'-biphenyl]-4-yl)methoxy)cyclopentyl)-[3,3'-bipyridine]-5-carboxamide |
| Example 223 | 6-amino-6'-fluoro-N-((1S,2S)-2-((4'-((R)-1-(4-methylpiperazin-1-yl)ethyl)-[1,1'-biphenyl]-4-yl)methoxy)cyclopentyl)-[3,3'-bipyridine]-5-carboxamide |
| Example 224 | 6-amino-6'-fluoro-N-((1S,2S)-2-((4'-(1-(4-methylpiperazin-1-yl)cyclopropyl)-[1,1'-biphenyl]-4-yl)methoxy)cyclopentyl)-[3,3'-bipyridine]-5-carboxamide |
| Example 225 | 6-amino-6'-fluoro-N-((1S,2S)-2-((4'-(2-(4-methylpiperazin-1-yl)propan-2-yl)-[1,1'-biphenyl]-4-yl)methoxy)cyclopentyl)-[3,3'-bipyridine]-5-carboxamide |
| Example 226 | 6-amino-6'-fluoro-N-((1S,2S)-2-((4'-((S)-1-(4-(2-hydroxyethyl)piperazin-1-yl)ethyl)-[1,1'-biphenyl]-4-yl)methoxy)cyclopentyl)-[3,3'-bipyridine]-5-carboxamide |
| Example 227 | 6-amino-6'-fluoro-N-((1S,2S)-2-((4'-((R)-1-(4-(2-hydroxyethyl)piperazin-1-yl)ethyl)-[1,1'-biphenyl]-4-yl)methoxy)cyclopentyl)-[3,3'-bipyridine]-5-carboxamide |
| Example 228 | 6-amino-6'-fluoro-N-((1S,2S)-2-((4'-(1-(4-(2-hydroxyethyl)piperazin-1-yl)cyclopropyl)-[1,1'-biphenyl]-4-yl)methoxy)cyclopentyl)-[3,3'-bipyridine]-5-carboxamide |
| Example 229 | 6-amino-6'-fluoro-N-((1S,2S)-2-((4'-(2-(4-(2-hydroxyethyl)piperazin-1-yl)propan-2-yl)-[1,1'-biphenyl]-4-yl)methoxy)cyclopenty])-[3,3'-bipyridine]-5-carboxamide |
| Example 230 | 6-amino-5'-fluoro-N-((1S,2S)-2-((4'-(1-(4-methylpiperazin-1-yl)ethyl)-[1,1'-biphenyl]-4-yl)methoxy)cyclopentyl)-[3,3'-bipyridine]-5-carboxamide |
| Example 231 | 2-amino-5-chloro-N-((1S,2S)-2-((4'-(1-(4-methylpiperazin-1-yl)ethyl)-[1,1'-biphenyl]-4-yl)methoxy)cyclopentyl)nicotinamide |
| Example 232 | 2-amino-5-fluoro-N-((1S,2S)-2-((4'-(1-(4-methylpiperazin-1-yl)ethyl)-[1,1'-biphenyl]-4-yl)methoxy)cyclopentyl)nicotinamide |
| Example 233 | 2-amino-5-cyano-N-((1S,2S)-2-((4'-(1-(4-methylpiperazin-1-yl)ethyl)-[1,1'-biphenyl]-4-yl)methoxy)cyclopentyl)nicotinamide |
| Example 234 | 2-amino-6-chloro-N-((1S,2S)-2-((4'-(1-(4-methylpiperazin-1-yl)ethyl)-[1,1'-biphenyl]-4-yl)methoxy)cyclopentyl)nicotinamide |
| Example 235 | 2-amino-N-((1S,2S)-2-((4'-(1-(4-methylpiperazin-1-yl)ethyl)-[1,1'-biphenyl]-4-yl)methoxy)cyclopentyl)nicotinamide |
| Example 236 | 6-amino-5'-fluoro-N-((1S,2S)-2-((4'-(1-(4-(2-hydroxyethyl)piperazin-1-yl)ethyl)-[1,1'-biphenyl]-4-yl)methoxy)cyclopentyl)-[3,3'-bipyridine]-5-carboxamide |
| Example 237 | 6-amino-6'-fluoro-N-((1S,2S)-2-((4'-(1-(4-(2-hydroxyethyl)piperazin-1-yl)ethyl)-[1,1'-biphenyl]-4-yl)methoxy)cyclopentyl)-[3,3'-bipyridine]-5-carboxamide |
| Example 238 | 6-amino-2'-fluoro-N-((1S,2S)-2-((4'-(1-(4-(2-hydroxyethyl)piperazin-1-yl)ethyl)-[1,1'-biphenyl]-4-yl)methoxy)cyclopentyl)-[3,3'-bipyridine]-5-carboxamide |
| Example 239 | 2-amino-5-(1-methyl-1H-pyrazol-4-yl)-N-((1S,2S)-2-((4'-((1-methylpiperidin-4-yl)methyl)-[1,1'-biphenyl]-4-yl)methoxy)cyclopentyl)nicotinamide |

-continued

| | |
|---|---|
| Example 240 | 2-amino-N-((1S,2S)-2-((4'-((1-(2-hydroxyethyl)piperidin-4-yl)methyl)-[1,1'-biphenyl]-4-yl)methoxy)cyclopentyl)-5-(1-methyl-1H-pyrazol-4-yl)nicotinamide |
| Example 241 | methyl 2-(4-((4'-(((((1S,2S)-2-(2-amino-5-(1-methyl-1H-pyrazol-4-yl)nicotinamido)cyclopentyl)oxy)methyl)-[1,1'-biphenyl]-4-yl)methyl)piperidin-1-yl)acetate |
| Example 242 | 2-amino-N-((1S,2S)-2-((4'-((1-(2-amino-2-oxoethyl)piperidin-4-yl)methyl)-[1,1'-biphenyl]-4-yl)methoxy)cyclopentyl)-5-(1-methyl-1H-pyrazol-4-yl)nicotinamide |
| Example 243 | 2-amino-5-(1-methyl-1H-pyrazol-4-yl)-N-((1S,2S)-2-((4-(3-(4-methylpiperazin-1-yl)propyl)benzyl)oxy)cyclopentyl)nicotinamide |
| Example 244 | 2-amino-N-((1S,2S)-2-((4-(3-(dimethylamino)propyl)benzyl)oxy)-cyclopentyl)-5-(1-methyl-1H-pyrazol-4-yl)nicotinamide |
| Example 245 | 2-amino-N-((1S,2S)-2-((4'-(2-(dimethylamino)ethoxy)-[1,1'-biphenyl]-4-yl)methoxy)cyclopentyl)-5-(1-methyl-1H-pyrazol-4-yl)nicotinamide |
| Example 246 | 2-amino-N-((1S,2S)-2-((4'-(3-(dimethylamino)propoxy)-[1,1'-biphenyl]-4-yl)methoxy)cyclopentyl)-5-(1-methyl-1H-pyrazol-4-yl)nicotinamide |
| Example 247 | 2-amino-5-(1-methyl-1H-pyrazol-4-yl)-N-((1S,2S)-2-((4'-((1-methylpiperidin-4-yl)oxy)-[1,1'-biphenyl]-4-yl)methoxy)cyclopentyl)nicotinamide |
| Example 248 | 2-amino-N-((1S,2S)-2-((4-(3-(dimethylamino)prop-1-yn-1-yl)benzyl)oxy)cyclopentyl)-5-(1-methyl-1H-pyrazol-4-yl)nicotinamide |
| Example 249 | 2-amino-N-((1S,2S)-2-((4-(4-hydroxybut-1-yn-1-yl)benzyl)oxy)cyclopentyl)-5-(1-methyl-1H-pyrazol-4-yl)nicotinamide |
| Example 250 | 2-amino-N-((1S,2S)-2-((4-(5-hydroxypent-1-yn-1-yl)benzyl)oxy)cyclopentyl)-5-(1-methyl-1H-pyrazol-4-yl)nicotinamide |
| Example 251 | 2-amino-N-((1S,2S)-2-((4-(6-hydroxyhex-1-yn-1-yl)benzyl)oxy)cyclopentyl)-5-(1-methy1-1H-pyrazol-4-yl)nicotinamide |
| Example 252 | 2-amino-5-(1-methyl-1H-pyrazol-4-yl)-N-((1S,2S)-2-((4-(4-(4-methylpiperazin-1-yl)but-1-yn-1-yl)benzyl)oxy)cyclopentyl)nicotinamide |
| Example 253 | 2-amino-N-((1S,2S)-2-(benzyloxy)cyclopentyl)-5-(4-((4-methylpiperazin-1-yl)methyl)phenyl)nicotinamide |
| Example 254 | 2-amino-N-((1S,2S)-2-(benzyloxy)cyclopentyl)-5-(1-(piperidin-4-yl)-1H-pyrazol-4-yl)nicotinamide |
| Example 255 | 2-amino-N-((1S,2S)-2-(benzyloxy)cyclopentyl)-5-(1-(1-methylpiperidin-4-yl)-1H-pyrazol-4-yl)nicotinamide |
| Example 256 | 2-amino-N-((1S,2S)-2-(benzyloxy)cyclopentyl)-5-(1-(1-ethylpiperidin-4-yl)-1H-pyrazol-4-yl)nicotinamide |
| Example 257 | 2-amino-N-((1S,2S)-2-(benzyloxy)cyclopentyl)-5-(1-(1-isopropylpiperidin-4-yl)-1H-pyrazol-4-yl)nicotinamide |
| Example 258 | 2-amino-N-((1S,2S)-2-(benzyloxy)cyclopentyl)-5-(1-(1-(pyrrolidin-3-ylmethyl)piperidin-4-yl)-1H-pyrazol-4-yl)nicotinamide |
| Example 259 | 2-amino-N-((1R,2R)-2-(benzyloxy)cyclopentyl)-5-(1-(piperidin-4-yl)-1H-pyrazol-4-yl)nicotinamide |
| Example 260 | 2-amino-N-((1S,2S)-2-((3,4-dichlorobenzyl)oxy)cyclopentyl)-5-(1-(piperidin-4-yl)-1H-pyrazol-4-yl)nicotinamide |
| Example 261 | 2-amino-N-((1S,2S)-2-(benzyloxy)cyclopentyl)-5-(3-(hydroxymethyl)-1-methyl-1H-pyrazol-4-yl)nicotinamide |
| Example 262 | 2-amino-N-((1S,2S)-2-(benzyloxy)cyclopentyl)-5-(3-(((2-hydroxyethyl)amino)methyl)-1-methyl-1H-pyrazol-4-yl)nicotinamide |
| Example 263 | 2-amino-N-((1S,2S)-2-(benzyloxy)cyclopentyl)-5-(3-((3-hydroxypiperidin-1-yl)methyl)-1-methyl-1H-pyrazol-4-yl)nicotinamide |
| Example 264 | 2-amino-N-((1S,2S)-2-(benzyloxy)cyclopentyl)-5-(4-cyanophenyl)nicotinamide |
| Example 265 | 2-amino-N-((1S,2S)-2-(benzyloxy)cyclopentyl)-5-(3-cyanophenyl)nicotinamide |
| Example 266 | 2-amino-N-((1S,2S)-2-(benzyloxy)cyclopentyl)-5-(4-(cyanomethyl)phenyl)nicotinamide |
| Example 267 | 2-amino-N-((1S,2S)-2-(benzyloxy)cyclopentyl)-5-(4-phenoxyphenyl)nicotinamide |
| Example 268 | 2-amino-N-((1S,2S)-2-(benzyloxy)cyclopentyl)-5-(3-((1-methylpiperidin-4-yl)carbamoyl)phenyl)nicotinamide |
| Example 269 | 6-amino-N-((1S,2S)-2-(benzyloxy)cyclopentyl)-6'-(hydroxymethyl)-[3,3-bipyridine]-5-carboxamide |
| Example 270 | 2-amino-N-((1S,2S)-2-((3-methylbenzyl)oxy)cyclopentyl)-5-(4-((4-methylpiperazin-1-yl)methyl)phenyl)nicotinamide |
| Example 271 | 2-amino-N-((1S,2S)-2-((3-methylbenzyl)oxy)cyclopentyl)-5-(3-(4-methylpiperazine-1-carbonyl)phenyl)nicotinamide |
| Example 272 | 2-amino-N-((1S,2S)-2-((3-methylbenzyl)oxy)cyclopentyl)-5-(3-(4-(pyrrolidin-1-yl)piperidine-1-carbonyl)phenyl)nicotinamide |
| Example 273 | 2-amino-N-((1S,2S)-2-((3-methylbenzyl)oxy)cyclopentyl)-5-(3-((4-methylpiperazin-1-yl)methyl)phenyl)nicotinamide |
| Example 274 | 2-amino-5-(3-fluoro-4-((4-methylpiperazin-1-yl)methyl)phenyl)-N-((1S,2S)-2-((3-methylbenzyl)oxy)cyclopentyl)nicotinamide |
| Example 275 | 2-amino-N-((1S,2S)-2-((3-methylbenzyl)oxy)cyclopentyl)-5-(4-((4-(pyrrolidin-1-yl)piperidin-1-yl)methyl)phenyl)nicotinamide |
| Example 276 | 2-amino-N-((1S,2S)-2-((3-methylbenzyl)oxy)cyclopentyl)-5-(4-(4-methylpiperazine-1-carbonyl)phenyl)nicotinamide |

| | |
|---|---|
| Example 277 | 2-amino-N-((1S,2S)-2-((3-methylbenzyl)oxy)cyclopentyl)-5-(4-(4-(pyrrolidin-1-yl)piperidine-1-carbonyl)phenyl)nicotinamide |
| Example 278 | 2-amino-N-((1S,2S)-2-((3-methylbenzyl)oxy)cyclopentyl)-5-(4-(2-((1-methylpiperidin-4-yl)amino)-2-oxoethyl)phenyl)nicotinamide |
| Example 279 | 2-amino-N-((1S,2S)-2-((3-methylbenzyl)oxy)cyclopentyl)-5-(4-(2-(4-methylpiperazin-1-yl)acetyl)phenyl)nicotinamide |
| Example 280 | 2-amino-5-(3-fluoro-4-((4-(pyrrolidin-1-yl)piperidin-1-yl)methyl)-phenyl)-N-((1S,2S)-2-((3-methylbenzyl)oxy)cyclopentyl)nicotinamide |
| Example 281 | 2-amino-N-((1S,2S)-2-((3-methylbenzyl)oxy)cyclopentyl)-5-(4-(4-(4-methylpiperazin-1-yl)piperidine-1-carbonyl)phenyl)nicotinamide |
| Example 282 | 2-amino-N-((1S,2S)-2-((3-methylbenzyl)oxy)cyclopentyl)-5-(4-(piperazin-1-ylmethyl)phenyl)nicotinamide |
| Example 283 | 2-amino-N-((1S,2S)-2-((4-methylbenzyl)oxy)cyclopentyl)-5-(4-(4-methylpiperazine-1-carbonyl)phenyl)nicotinamide |
| Example 284 | 2-amino-N-((1S,2S)-2-((4-methylbenzyl)oxy)cyclopentyl)-5-(4-(4-(pyrrolidin-1-yl)piperidine-1-carbonyl)phenyl)nicotinamide |
| Example 285 | 2-amino-5-(1,5-dimethyl-1H-pyrazol-4-yl)-N-((1S,2S)-2-((3,4-dimethylbenzyl)oxy)cyclopentyl)nicotinamide |
| Example 286 | 2-amino-5-(1,3-dimethyl-1H-pyrazol-4-yl)-N-((1S,2S)-2-((3,4-dimethylbenzyl)oxy)cyclopentyl)nicotinamide |
| Example 287 | 2-amino-N-((1S,2S)-2-((3,4-dimethylbenzyl)oxy)cyclopentyl)-5-(2-(2-hydroxypropan-2-yl)-4-methylthiazol-5-yl)nicotinamide |
| Example 288 | 2-amino-N-((1S,2S)-2-((3,4-dimethylbenzyl)oxy)cyclopentyl)-5-(2-(3-hydroxytetrahydrofuran-3-yl)-4-methylthiazol-5-yl)nicotinamide |
| Example 289 | 2-amino-N-((1S,2S)-2-((3,4-dimethylbenzyl)oxy)cyclopentyl)-5-(4-((4-methylpiperazin-1-yl)methyl)phenyl)nicotinamide |
| Example 290 | 2-amino-N-((1S,2S)-2-((3,4-dimethylbenzyl)oxy)cyclopentyl)-5-(4-(2-(4-methylpiperazin-1-yl)-2-oxoethyl)phenyl)nicotinamide |
| Example 291 | 2-amino-N-((1S,2S)-2-((3,4-dimethylbenzyl)oxy)cyclopentyl)-5-(4-(morpholinomethyl)phenyl)nicotinamide |
| Example 292 | 2-amino-5-(4-((dimethylamino)methyl)phenyl)-N-((1S,2S)-2-((3,4-dimethylbenzyl)oxy)cyclopentyl)nicotinamide |
| Example 293 | 2-amino-N-((1S,2S)-2-((3,4-dimethylbenzyl)oxy)cyclopentyl)-5-(4-((4-(2-hydroxyethyl)piperazin-1-yl)methyl)phenyl)nicotinamide |
| Example 294 | 6-amino-N-((1S,2S)-2-((3,4-dimethylbenzyl)oxy)cyclopentyl)-2'-methoxy-[3,3'-bipyridine]-5-carboxamide |
| Example 295 | 2-amino-5-(4-(dimethylamino)phenyl)-N-((1S,2S)-2-((3,4-dimethylbenzyl)oxy)cyclopentyl)nicotinamide |
| Example 296 | 2-amino-N-((1S,2S)-2-((3,4-dimethylbenzyl)oxy)cyclopentyl)-5-(3-hydroxyphenyl)nicotinamide |
| Example 297 | 2-amino-5-(3-aminophenyl)-N-((1S,2S)-2-((3,4-dimethylbenzyl)oxy)cyclopentyl)nicotinamide |
| Example 298 | 2-amino-N-((1S,2S)-2-((3,4-dimethylbenzyl)oxy)cyclopentyl)-5-(3-(methylsulfonamido)phenyl)nicotinamide |
| Example 299 | 2-amino-N-((1S,2S)-2-((3,4-dimethylbenzyl)oxy)cyclopentyl)-5-(3-(hydroxymethyl)phenyl)nicotinamide |
| Example 300 | 2-amino-5-(3-(aminomethyl)phenyl)-N-((1S,2S)-2-((3,4-dimethylbenzyl)oxy)cyclopentyl)nicotinamide |
| Example 301 | 2-amino-N-((1S,2S)-2-((3,4-dimethylbenzyl)oxy)cyclopentyl)-5-(3-(3-hydroxypropyl)phenyl)nicotinamide |
| Example 302 | 2-amino-N-((1S,2S)-2-((3,4-dimethylbenzyl)oxy)cyclopentyl)-5-(3-((((1r,4S)-4-hydroxycyclohexyl)amino)methyl)phenyl)nicotinamide |
| Example 303 | 2-amino-N-((1S,2S)-2-((3,4-dimethylbenzyl)oxy)cyclopentyl)-5-(3-(((1-methylpiperidin-4-yl)amino)methyl)phenyl)nicotinamide |
| Example 304 | 2-amino-N-((1S,2S)-2-((3,4-dimethylbenzyl)oxy)cyclopentyl)-5-(3-((((S)-piperidin-3-yl)amino)methyl)phenyl)nicotinamide |
| Example 305 | 3-(6-amino-5-(((1S,2S)-2-((3,4-dimethylbenzyl)oxy)cyclopentyl)-carbamoyl)pyridin-3-yl)-5-hydroxybenzoic acid |
| Example 306 | 4-(6-amino-5-(((1S,2S)-2-((3,4-dimethylbenzyl)oxy)cyclopentyl)-carbamoyl)pyridin-3-yl)-2-methylbenzoic acid |
| Example 307 | 2-amino-5-(4-aminophenyl)-N-((1S,2S)-2-((3,4-dimethylbenzyl)oxy)-cyclopentyl)nicotinamide |
| Example 308 | 3-(6-amino-5-(((1S,2S)-2-((3,4-dimethylbenzyl)oxy)cyclopentyl)carbamoyl)pyridin-3-yl)benzoic acid |
| Example 309 | 3-amino-5-(6-amino-5-(((1S,2S)-2-((3,4-dimethylbenzyl)oxy)cyclopentyl)carbamoyl)pyridin-3-yl)benzoic acid |
| Example 310 | 2-amino-N-((1S,2S)-2-((3,4-dimethylbenzyl)oxy)cyclopentyl)-5-(2-methyl-5-(4-(pyrrolidin-1-yl)piperidine-1-carbonyl)phenyl)nicotinamide |
| Example 311 | 2-amino-N-((1S,2S)-2-((3,4-dimethylbenzyl)oxy)cyclopentyl)-5-(3-methyl-4-(4-methylpiperazine-1-carbonyl)phenyl)nicotinamide |
| Example 312 | 2-amino-5-(3-amino-5-(4-(pyrrolidin-1-yl)piperidine-1-carbonyl)-phenyl)-N-((1S,2S)-2-((3,4-dimethylbenzyl)oxy)cyclopentyl)-nicotinamide |
| Example 313 | 2-amino-N-((1S,2S)-2-((3,4-dimethylbenzyl)oxy)cyclopentyl)-5-(4-(hydroxymethyl)phenyl)nicotinamide |
| Example 314 | 2-amino-N-((1S,2S)-2-((3,4-dimethylbenzyl)oxy)cyclopentyl)-5-(4-formylphenyl)nicotinamide |
| Example 315 | 4-(6-amino-5-(((1S,2S)-2-((3,4-dimethylbenzyl)oxy)cyclopentyl)carbamoyl)pyridin-3-yl)benzoic acid |

| | -continued |
|---|---|
| Example 316 | 3-(4-(6-amino-5-(((1S,2S)-2-((3,4-dimethylbenzyl)oxy)cyclopentyl)carbamoyl)pyridin-3-yl)phenyl)propanoic acid |
| Example 317 | 2-amino-N-((1S,2S)-2-((3,4-dimethylbenzyl)oxy)cyclopentyl)-5-(2-hydroxyphenyl)nicotinamide |
| Example 318 | 2-amino-N-((1S,2S)-2-((3,4-dimethylbenzyl)oxy)cyclopentyl)-5-(4-((1-methylpiperidin-4-yl)carbamoyl)phenyl)nicotinamide |
| Example 319 | 2-amino-N-((1S,2S)-2-((3,4-dimethylbenzyl)oxy)cyclopentyl)-5-(4-(dimethylcarbamoyl)phenyl)nicotinamide |
| Example 320 | 2-amino-N-((1S,2S)-2-((3,4-dimethylbenzyl)oxy)cyclopentyl)-5-(4-(((1-methylpiperidin-4-yl)amino)methyl)phenyl)nicotinamide |
| Example 321 | 6-amino-N-((1S,2S)-2-((3,4-dimethylbenzyl)oxy)cyclopentyl)-6'-(hydroxymethyl)-[3,3'-bipyridine]-5-carboxamide |
| Example 322 | 2-amino-4-(6-amino-5-(((1S,2S)-2-((3,4-dimethylbenzyl)oxy)cyclopentyl)carbamoyl)pyridin-3-yl)benzoic acid |
| Example 323 | 2-amino-N-((1S,2S)-2-((3,4-dimethylbenzyl)oxy)cyclopentyl)-5-(4-(hydroxymethyl)-3-methoxyphenyl)nicotinamide |
| Example 324 | 2-amino-N-((1S,2S)-2-((3,4-dimethylbenzyl)oxy)cyclopentyl)-5-(3-fluoro-4-(hydroxymethyl)phenyl)nicotinamide |
| Example 325 | 2-amino-N-((1S,2S)-2-((3,4-dimethylbenzyl)oxy)cyclopentyl)-5-(3-fluoro-4-((4-(pyrrolidin-1-yl)piperidin-1-yl)methyl)phenyl)nicotinamide |
| Example 326 | 2-amino-N-((1S,2S)-2-((3,4-dimethylbenzyl)oxy)cyclopentyl)-5-(4-(1-hydroxyethyl)phenyl)nicotinamide |
| Example 327 | 2-amino-5-(4-((3-(dimethylamino)pyrrolidin-1-yl)methyl)phenyl)-N-((1S,2S)-2-((3,4-dimethylbenzyl)oxy)cyclopentyl)nicotinamide |
| Example 328 | 2-amino-N-((1S,2S)-2-((3,4-dimethylbenzyl)oxy)cyclopentyl)-5-(4-((4-hydroxypiperidin-1-yl)methyl)phenyl)nicotinamide |
| Example 329 | 2-amino-N-((1S,2S)-2-((3,4-dimethylbenzyl)oxy)cyclopentyl)-5-(4-((((1-methylpiperidin-4-yl)methyl)amino)methyl)phenyl)nicotinamide |
| Example 330 | 2-amino-N-((1S,2S)-2-((3,4-dimethylbenzyl)oxy)cyclopentyl)-5-(3-methyl-4-(4-(pyrrolidin-1-yl)piperidine-1-carbonyl)phenyl)nicotinamide |
| Example 331 | 2-amino-5-(3-amino-4-(4-(pyrrolidin-1-yl)piperidine-1-carbonyl)phenyl)-N-((1S,2S)-2-((3,4-dimethylbenzyl)oxy)cyclopentyl)nicotinamide |
| Example 332 | 2-amino-5-(3-amino-4-((4-(pyrrolidin-1-yl)piperidin-1-yl)methyl)phenyl)-N-((1S,2S)-2-((3,4-dimethylbenzyl)oxy)cyclopentyl)nicotinamide |
| Example 333 | 2-amino-N-((1S,2S)-2-((3,4-dimethylbenzyl)oxy)cyclopentyl)-5-(4-(hydroxymethyl)-3-methylphenyl)nicotinamide |
| Example 334 | 2-amino-5-(3-chlorophenyl)-N-((1S,2S)-2-((3,4-dimethylbenzyl)oxy)cyclopentyl)nicotinamide |
| Example 335 | 2-amino-N-((1S,2S)-2-((3,4-dimethylbenzyl)oxy)cyclopentyl)-5-(m-tolyl)nicotinamide |
| Example 336 | 2-amino-N-((1S,2S)-2-((3,4-dimethylbenzyl)oxy)cyclopentyl)-5-(3,5-dimethylphenyl)nicotinamide |
| Example 337 | 2-amino-N-((1S,2S)-2-((3,4-dimethylbenzyl)oxy)cyclopentyl)-5-(4-((3-morpholinopyrrolidin-1-yl)methyl)phenyl)nicotinamide |
| Example 338 | 2-amino-5-(4-((4-aminopiperidin-1-yl)methyl)phenyl)-N-((1S,2S)-2-((3,4-dimethylbenzyl)oxy)cyclopentyl)nicotinamide |
| Example 339 | 2-amino-5-(4-((3-aminopiperidin-1-yl)methyl)phenyl)-N-((1S,2S)-2-((3,4-dimethylbenzyl)oxy)cyclopentyl)nicotinamide |
| Example 340 | 2-amino-5-(4-((3-aminopyrrolidin-1-yl)methyl)phenyl)-N-((1S,2S)-2-((3,4-dimethylbenzyl)oxy)cyclopentyl)nicotinamide |
| Example 341 | 2-amino-5-(4-((3-aminopyrrolidin-1-yl)methyl)-3-fluorophenyl)-N-((1S,2S)-2-((3,4-dimethylbenzyl)oxy)cyclopentyl)nicotinamide |
| Example 342 | 2-amino-5-(4-((3-aminopyrrolidin-1-yl)methyl)-3-fluorophenyl)-N-((1S,2S)-2-((3,4-dimethylbenzyl)oxy)cyclopentyl)nicotinamide |
| Example 343 | 2-amino-5-(3-((3-(dimethylamino)pyrrolidin-1-yl)methyl)phenyl)-N-((1S,2S)-2-((3,4-dimethylbenzyl)oxy)cyclopentyl)nicotinamide |
| Example 344 | 2-amino-5-(3-((3-(dimethylamino)pyrrolidin-1-yl)methyl)-4-methoxyphenyl)-N-((1S,2S)-2-((3,4-dimethylbenzyl)oxy)cyclopentyl)nicotinamide |
| Example 345 | 2-amino-N-((1S,2S)-2-((3,4-dimethylbenzyl)oxy)cyclopentyl)-5-(4-((3-hydroxyazetidin-1-yl)methyl)phenyl)nicotinamide |
| Example 346 | 2-amino-5-(4-(((R)-3-(dimethylamino)pyrrolidin-1-yl)methyl)phenyl)-N-((1S,2S)-2-((3,4-dimethylbenzyl)oxy)cyclopentyl)nicotinamide |
| Example 347 | 2-amino-5-(4-(((S)-3-(dimethylamino)pyrrolidin-1-yl)methyl)phenyl)-N-((1S,2S)-2-((3,4-dimethylbenzyl)oxy)cyclopentyl)nicotinamide |
| Example 348 | 2-amino-N-((1S,2S)-2-((3,4-dimethylbenzyl)oxy)cyclopentyl)-5-(4-(((R)-3-hydroxypyrrolidin-1-yl)methyl)phenyl)nicotinamide |
| Example 349 | 2-amino-N-((1S,2S)-2-((3,4-dimethylbenzyl)oxy)cyclopentyl)-5-(4-(((S)-3-hydroxypyrrolidin-1-yl)methyl)phenyl)nicotinamide |
| Example 350 | 2-amino-N-((1S,2S)-2-((3,4-dimethylbenzyl)oxy)cyclopentyl)-5-(4-((3-hydroxypiperidin-1-yl)methyl)phenyl)nicotinamide |
| Example 351 | 2-amino-N-((1S,2S)-2-((3,4-dimethylbenzyl)oxy)cyclopentyl)-5-(4-hydroxyphenyl)nicotinamide |
| Example 352 | 2-amino-N-((1S,2S)-2-((3,4-dimethylbenzyl)oxy)cyclopentyl)-5-(4-hydroxy-3-methoxyphenyl)nicotinamide |

| | |
|---|---|
| Example 353 | 2-amino-5-(3,4-dimethoxyphenyl)-N-((1S,2S)-2-((3,4-dimethylbenzyl)oxy)cyclopentyl)nicotinamide |
| Example 354 | amino-N-((1S,2S)-2-((3,4-dimethylbenzyl)oxy)cyclopentyl)-5-(3-(pyrrolidin-1-yl)phenyl)nicotinamide |
| Example 355 | 2-amino-5-(5-amino-1-methyl-1H-pyrazol-4-yl)-N-((1S,2S)-2-((3,4-dimethylbenzyl)oxy)cyclopentyl)nicotinamide |
| Example 356 | 2-amino-N-((1S,2S)-2-((3-ethyl-4-methylbenzyl)oxy)cyclopentyl)-5-(4-(hydroxymethyl)phenyl)nicotinamide |
| Example 357 | 2-amino-5-(4-((3-(dimethylamino)pyrrolidin-1-yl)methyl)phenyl)-N-((1S,2S)-2-((3-ethyl-4-methylbenzyl)oxy)cyclopentyl)nicotinamide |
| Example 358 | 2-amino-N-((1S,2S)-2-((3-ethyl-4-methylbenzyl)oxy)cyclopentyl)-5-(4-((3-hydroxypyrrolidin-1-yl)methyl)phenyl)nicotinamide |
| Example 359 | 2-amino-N-((1S,2S)-2-((3-ethyl-4-methylbenzyl)oxy)cyclopentyl)-5-(4-(2-(piperazin-1-yl)propan-2-yl)phenyl)nicotinamide |
| Example 360 | 2-amino-N-((1S,2S)-2-((3-ethyl-4-methylbenzyl)oxy)cyclopentyl)-5-(4-(2-(4-(2-hydroxyethyl)piperazin-1-yl)propan-2-yl)phenyl)nicotinamide |
| Example 361 | 3-amino-N-((1S,2S)-2-(benzyloxy)cyclopentyl)-6-(1-(piperidin-4-yl)-1H-pyrazol-4-yl)pyrazine-2-carboxamide |
| Example 362 | (S)-3-amino-6-(1-(piperidin-4-yl)-1H-pyrazol-4-yl)-N-(1,2,3,4-tetrahydronaphthalen-1-yl)pyrazine-2-carboxamide |
| Example 363 | 2-amino-5-(4-fluorophenyl)-N-((1S,2S)-2-((4'-((4-methylpiperazin-1-yl)methyl)-[1,1'-biphenyl]-4-yl)methoxy)cyclopentyl)nicotinamide |
| Example 364 | 2-amino-5-(3,4-difluorophenyl)-N-((1S,2S)-2-((4'-((4-methylpiperazin-1-yl)methyl)-[1,1'-biphenyl]-4-yl)methoxy)cyclopentyl)nicotinamide |
| Example 365 | 2-amino-N-((1S,2S)-2-((4'-((4-methylpiperazin-1-yl)methyl)-[1,1'-biphenyl]-4-yl)methoxy)cyclopentyl)-5-(4-(trifluoromethyl)phenyl)nicotinamide |
| Example 366 | 2-amino-N-((1S,2S)-2-((4'-((4-methylpiperazin-1-yl)methyl)-[1,1'-biphenyl]-4-yl)methoxy)cyclopentyl)-5-(1-(1-methylpiperidin-4-yl)-1H-pyrazol-4-yl)nicotinamide |
| Example 367 | 2-amino-N-((1S,2S)-2-((4'-((4-methylpiperazin-1-yl)methyl)-[1,1'-biphenyl]-4-yl)methoxy)cyclopentyl)-5-(4-(4-methylpiperazin-1-yl)phenyl)nicotinamide |
| Example 368 | 2-amino-N-((1S,2S)-2-((4'-((4-methylpiperazin-1-yl)methyl)-[1,1'-biphenyl]-4-yl)methoxy)cyclopentyl)-5-(4-((4-methylpiperazin-1-yl)methyl)phenyl)nicotinamide |
| Example 369 | 2-amino-5-(4-(hydroxymethyl)phenyl)-N-((1S,2S)-2-((4'-((4-methylpiperazin-1-yl)methyl)-[1,1'-biphenyl]-4-yl)methoxy)cyclopentyl)nicotinamide |
| Example 370 | 2-amino-N-((1S,2S)-2-((4'-((4-methylpiperazin-1-yl)methyl)-[1,1'-biphenyl]-4-yl)methoxy)cyclopentyl)-5-(m-tolyl)nicotinamide |
| Example 371 | 2-amino-N-((1S,2S)-2-((4'-((4-methylpiperazin-1-yl)methyl)-[1,1'-biphenyl]-4-yl)methoxy)cyclopentyl)-5-phenylnicotinamide |
| Example 372 | 2-amino-5-(4-hydroxyphenyl)-N-((1S,2S)-2-((4'-((4-methylpiperazin-1-yl)methyl)-[1,1'-biphenyl]-4-yl)methoxy)cyclopentyl)nicotinamide |
| Example 373 | 2-amino-5-(4-chloro-3-fluorophenyl)-N-((1S,2S)-2-((4'-((4-methylpiperazin-1-yl)methyl)-[1,1'-biphenyl]-4-yl)methoxy)cyclopentyl)nicotinamide |
| Example 374 | 2-amino-5-methyl-N-((1S,2S)-2-((4'-((4-methylpiperazin-1-yl)methyl)-[1,1'-biphenyl]-4-yl)methoxy)cyclopentyl)nicotinamide |
| Example 375 | 6-amino-N-((1S,2S)-2-((4'-((4-methylpiperazin-1-yl)methyl)-[1,1'-biphenyl]-4-yl)methoxy)cyclopentyl)-[3,3'-bipyridine]-5-carboxamide |
| Example 376 | 2-amino-5-(4-methoxyphenyl)-N-((1S,2S)-2-((4'-((4-methylpiperazin-1-yl)methyl)-[1,1'-biphenyl]-4-yl)methoxy)cyclopentyl)nicotinamide |
| Example 377 | 6-amino-N-((1S,2S)-2-((4'-((4-methylpiperazin-1-yl)methyl)-[1,1'-biphenyl]-4-yl)methoxy)cyclopentyl)-[3,4'-bipyridine]-5-carboxamide |
| Example 378 | 2-amino-N-((1S,2S)-2-((4'-((4-methylpiperazin-1-yl)methyl)-[1,1'-biphenyl]-4-yl)methoxy)cyclopentyl)-5-(4-((4-methylpiperidin-1-yl)methyl)phenyl)nicotinamide |
| Example 379 | 2-amino-N-((1S,2S)-2-((4'-((4-methylpiperazin-1-yl)methyl)-[1,1'-biphenyl]-4-yl)methoxy)cyclopentyl)-5-(4-(morpholinomethyl)phenyl)nicotinamide |
| Example 380 | 2-amino-N-((1S,2S)-2-((4'-((4-methylpiperazin-1-yl)methyl)-[1,1'-biphenyl]-4-yl)methoxy)cyclopentyl)-5-(1-(tetrahydro-2H-pyran-4-yl)-1H-pyrazol-4-yl)nicotinamide |
| Example 381 | 2-amino-N-((1S,2S)-2-((4'-((4-methylpiperazin-1-yl)methyl)-[1,1'-biphenyl]-4-yl)methoxy)cyclopentyl)-5-(4-morpholinophenyl)nicotinamide |
| Example 382 | 2-amino-5-(cyclohex-1-en-1-yl)-N-((1S,2S)-2-((4'-((4-methylpiperazin-1-yl)methyl)-[1,1'-biphenyl]-4-yl)methoxy)cyclopentyl)nicotinamide |
| Example 383 | 2-amino-5-(3,4-dimethoxyphenyl)-N-((1S,2S)-2-((4'-((4-methylpiperazin-1-yl)methyl)-[1,1'-biphenyl]-4-yl)methoxy)cyclopentyl)nicotinamide |
| Example 384 | 6-amino-2',6'-difluoro-N-((1S,2S)-2-((4'-((4-methylpiperazin-1-yl)methyl)-[1,1'-biphenyl]-4-yl)methoxy)cyclopentyl)-[3,4'-bipyridine]-5-carboxamide |
| Example 385 | 2-amino-N-((1S,2S)-2-((4'-((4-methylpiperazin-1-yl)methyl)-[1,1'-biphenyl]-4-yl)methoxy)cyclopentyl)-5-(4-methylthiophen-3-yl)nicotinamide |

| | -continued |
|---|---|
| Example 386 | 6-amino-6'-fluoro-N-((1S,2S)-2-((4'-((4-methylpiperazin-1-yl)methyl)-[1,1'-biphenyl]-4-yl)methoxy)cyclopentyl)-[3,3'-bipyridine]-5-carboxamide |
| Example 387 | 2-amino-N-((1S,2S)-2-((4'-((4-methylpiperazin-1-yl)methyl)-[1,1'-biphenyl]-4-yl)methoxy)cyclopentyl)-5-(1-(1,1,2,2-tetrafluoroethyl)-1H-pyrazol-4-yl)nicotinamide |
| Example 388 | 2-amino-N-((3S,4S)-4-((3-ethyl-4-methylbenzyl)oxy)pyrrolidin-3-yl)-5-(1-methyl-1H-pyrazol-4-yl)nicotinamide |
| Example 389 | 2-amino-N-((3S,4S)-4-((3-ethyl-4-methylbenzyl)oxy)pyrrolidin-3-yl)-5-(4-(hydroxymethyl)phenyl)nicotinamide |
| Example 390 | 2-amino-N-((3S,4S)-4-((3-ethyl-4-methylbenzyl)oxy)pyrrolidin-3-yl)-5-(4-((4-methylpiperazin-1-yl)methyl)phenyl)nicotinamide |
| Example 391 | 2-amino-5-(4-carbamoylphenyl)-N-((3S,4S)-4-((3-ethyl-4-methylbenzyl)oxy)pyrrolidin-3-yl)nicotinamide |
| Example 392 | 2-amino-N-((3S,4S)-4-((3-ethyl-4-methylbenzyl)oxy)pyrrolidin-3-yl)-5-(m-tolyl)nicotinamide |
| Example 393 | 4-(6-amino-5-(((3S,4S)-4-((3-ethyl-4-methylbenzyl)oxy)pyrrolidin-3-yl)carbamoyl)pyridin-3-yl)benzoic acid |
| Example 394 | 2-amino-N-((3S,4S)-4-((3-ethyl-4-methylbenzyl)oxy)pyrrolidin-3-yl)-5-phenylnicotinamide |
| Example 395 | 6-amino-N-((3S,4S)-4-((3-ethyl-4-methylbenzyl)oxy)pyrrolidin-3-yl)-[3,4'-bipyridine]-5-carboxamide |
| Example 396 | 6-amino-N-((3S,4S)-4-((3-ethyl-4-methylbenzyl)oxy)pyrrolidin-3-yl)-[3,3'-bipyridine]-5-carboxamide |
| Example 397 | 2-amino-N-((3S,4S)-4-((3-ethyl-4-methylbenzyl)oxy)pyrrolidin-3-yl)-5-vinylnicotinamide |
| Example 398 | 2-amino-N-((3S,4S)-4-((3-ethyl-4-methylbenzyl)oxy)pyrrolidin-3-yl)-5-(4-fluorophenyl)nicotinamide |
| Example 399 | 2-amino-N-((3S,4S)-4-((3-ethyl-4-methylbenzyl)oxy)pyrrolidin-3-yl)-5-(4-formylphenyl)nicotinamide |
| Example 400 | 2-amino-5-(4-cyanophenyl)-N-((3S,4S)-4-((3-ethyl-4-methylbenzyl)oxy)pyrrolidin-3-yl)nicotinamide |
| Example 401 | 2-amino-N-((3S,4S)-4-((3-ethyl-4-methylbenzyl)oxy)pyrrolidin-3-yl)-5-(4-(methylsulfonamido)phenyl)nicotinamide |
| Example 402 | 2-amino-N-((3S,4S)-4-((3-ethyl-4-methylbenzyl)oxy)pyrrolidin-3-yl)-5-(4-phenoxyphenyl)nicotinamide |
| Example 403 | 5-([1,1'-biphenyl]-4-yl)-2-amino-N-((3S,4S)-4-((3-ethyl-4-methylbenzyl)oxy)pyrrolidin-3-yl)nicotinamide |
| Example 404 | 2-amino-5-(4-(benzyloxy)phenyl)-N-((3S,4S)-4-((3-ethyl-4-methylbenzyl)oxy)pyrrolidin-3-yl)nicotinamide |
| Example 405 | 2-amino-5-(4-(dimethylamino)phenyl)-N-((3S,4S)-4-((3-ethyl-4-methylbenzyl)oxy)pyrrolidin-3-yl)nicotinamide |
| Example 406 | 2-amino-N-((3S,4S)-4-((3-ethyl-4-methylbenzyl)oxy)pyrrolidin-3-yl)-5-(quinolin-3-yl)nicotinamide |
| Example 407 | 2-amino-5-(benzofuran-2-yl)-N-((3S,4S)-4-((3-ethyl-4-methylbenzyl)oxy)pyrrolidin-3-yl)nicotinamide |
| Example 408 | 2-amino-N-((3S,4S)-4-((3-ethyl-4-methylbenzyl)oxy)pyrrolidin-3-yl)-5-(naphthalen-1-yl)nicotinamide |
| Example 409 | 2-amino-N-((3S,4S)-4-((3-ethyl-4-methylbenzyl)oxy)pyrrolidin-3-yl)-5-(4-(trifluoromethyl)phenyl)nicotinamide |
| Example 410 | 2-amino-N-((3S,4S)-4-((3-ethyl-4-methylbenzyl)oxy)pyrrolidin-3-yl)-5-(2,4,5-trifluorophenyl)nicotinamide |
| Example 411 | 2-amino-5-(4-(cyanomethyl)phenyl)-N-((3S,4S)-4-((3-ethyl-4-methylbenzyl)oxy)pyrrolidin-3-yl)nicotinamide |
| Example 412 | 2-amino-N-((3S,4S)-4-((3-ethyl-4-methylbenzyl)oxy)pyrrolidin-3-yl)-5-(1-(piperidin-4-yl)-1H-pyrazol-4-yl)nicotinamide |
| Example 413 | 2-amino-N-((3S,4S)-4-((3-ethyl-4-methylbenzyl)oxy)pyrrolidin-3-yl)-5-(1-(1-methylpiperidin-4-yl)-1H-pyrazol-4-yl)nicotinamide |
| Example 414 | 2-amino-N-((3S,4S)-4-(benzyloxy)pyrrolidin-3-yl)-5-(1-methyl-1H-pyrazol-4-yl)nicotinamide |
| Example 415 | 2-amino-5-(1-methyl-1H-pyrazol-4-yl)-N-((3S,4S)-4-((4-methylbenzyl)oxy)pyrrolidin-3-yl)nicotinamide |
| Example 416 | 2-amino-N-((3S,4S)-4-((3-ethylbenzyl)oxy)pyrrolidin-3-yl)-5-(1-methyl-1H-pyrazol-4-yl)nicotinamide |
| Example 417 | 2-amino-N-((3S,4S)-4-((3-ethyl-4-fluorobenzyl)oxy)pyrrolidin-3-yl)-5-(1-methyl-1H-pyrazol-4-yl)nicotinamide |
| Example 418 | 2-amino-N-((3S,4S)-4-((4-chloro-3-ethylbenzyl)oxy)pyrrolidin-3-yl)-5-(1-methyl-1H-pyrazol-4-yl)nicotinamide |
| Example 419 | 2-amino-N-((3S,4S)-4-((3-ethyl-4-methylbenzyl)oxy)pyrrolidin-3-yl)-5-(4-((1-methylpiperidin-4-yl)carbamoyl)phenyl)nicotinamide |
| Example 420 | 2-amino-N-((3S,4S)-4-((3-ethyl-4-methylbenzyl)oxy)pyrrolidin-3-yl)-5-(4-((4-methylcyclohexyl)carbamoyl)phenyl)nicotinamide |
| Example 421 | 2-amino-N-((3S,4S)-4-((3-ethyl-4-methylbenzyl)oxy)pyrrolidin-3-yl)-5-(4-(4-methylpiperidine-1-carbonyl)phenyl)nicotinamide |
| Example 422 | 2-amino-5-(4-(dimethylcarbamoyl)phenyl)-N-((3S,4S)-4-((3-ethyl-4-methylbenzyl)oxy)pyrrolidin-3-yl)nicotinamide |
| Example 423 | 2-amino-N-((3S,4S)-4-((3-ethyl-4-methylbenzyl)oxy)pyrrolidin-3-yl)-5-(4-((4-methylpiperidin-1-yl)methyl)phenyl)nicotinamide |

| | -continued |
|---|---|
| Example 424 | 2-amino-N-((3S,4S)-4-((3-ethyl-4-methylbenzyl)oxy)pyrrolidin-3-yl)-5-(4-(morpholinomethyl)phenyl)nicotinamide |
| Example 425 | 2-amino-5-(4-((3,3-difluoropiperidin-1-yl)methyl)phenyl)-N-((3S,4S)-4-((3-ethyl-4-methylbenzyl)oxy)pyrrolidin-3-yl)nicotinamide |
| Example 426 | 2-amino-N-((3S,4S)-4-((3-ethyl-4-methylbenzyl)oxy)-1-methylpyrrolidin-3-yl)-5-(1-methyl-1H-pyrazol-4-yl)nicotinamide |
| Example 427 | 2-amino-N-((3S,4S)-1-benzyl-4-((3-ethyl-4-methylbenzyl)oxy)pyrrolidin-3-yl)-5-(1-methyl-1H-pyrazol-4-yl)nicotinamide |
| Example 428 | 2-amino-N-((3S,4S)-4-((3-ethyl-4-methylbenzyl)oxy)-1-(3-phenylpropyl)pyrrolidin-3-yl)-5-(1-methyl-1H-pyrazol-4-yl)nicotinamide |
| Example 429 | 2-amino-N-((3S,4S)-4-((3-ethyl-4-methylbenzyl)oxy)-1-phenethylpyrrolidin-3-yl)-5-(1-methyl-1H-pyrazol-4-yl)nicotinamide |
| Example 430 | 2-amino-N-((3S,4S)-4-((3-ethyl-4-methylbenzyl)oxy)-1-isobutylpyrrolidin-3-yl)-5-(1-methyl-1H-pyrazol-4-yl)nicotinamide |
| Example 431 | 2-amino-N-((3S,4S)-1-butyl-4-((3-ethyl-4-methylbenzyl)oxy)pyrrolidin-3-yl)-5-(1-methyl-1H-pyrazol-4-yl)nicotinamide |
| Example 432 | 2-amino-N-((3S,4S)-1-ethyl-4-((3-ethyl-4-methylbenzyl)oxy)pyrrolidin-3-yl)-5-(1-methyl-1H-pyrazol-4-yl)nicotinamide |
| Example 433 | 2-amino-N-((3S,4S)-4-((3-ethyl-4-methylbenzyl)oxy)-1-methylpyrrolidin-3-yl)-5-(1-(1-methylpiperidin-4-yl)-1H-pyrazol-4-yl)nicotinamide |
| Example 434 | 2-amino-5-(1-methyl-1H-pyrazol-4-yl)-N-((3S,4S)-4-((4'-((4-methylpiperazin-1-yl)methyl)-[1,1'-biphenyl]-4-yl)methoxy)pyrrolidin-3-yl)nicotinamide |
| Example 435 | 2-amino-5-(1-methyl-1H-pyrazol-4-yl)-N-((3S,4S)-1-methyl-4-((4'-((4-methylpiperazin-1-yl)methyl)-[1,1'-biphenyl]-4-yl)methoxy)pyrrolidin-3-yl)nicotinamide |
| Example 436 | 2-amino-5-(1-methyl-1H-pyrazol-4-yl)-N-((3S,4S)-4-((4'-((4-methylpiperazin-1-yl)methyl)-3'-(trifluoromethyl)-[1,1'-biphenyl]-4-yl)methoxy)pyrrolidin-3-yl)nicotinamid |
| Example 437 | 2-amino-5-(1-methyl-1H-pyrazol-4-yl)-N-((3S,4S)-1-methyl-4-((4'-((4-methylpiperazin-1-yl)methyl)-3'-(trifluoromethyl)-[1,1'-biphenyl]-4-yl)methoxy)pyrrolidin-3-yl)nicotinamide |
| Example 438 | 2-amino-5-(1-methyl-1H-pyrazol-4-yl)-N-((3S,4S)-4-((4'-(1-(4-methylpiperazin-1-yl)ethyl)-[1,1'-biphenyl]-4-yl)methoxy)pyrrolidin-3-yl)nicotinamide |
| Example 439 | 2-amino-5-(1-methyl-1H-pyrazol-4-yl)-N-((3S,4S)-1-methyl-4-((4'-(1-(4-methylpiperazin-1-yl)ethyl)-[1,1'-biphenyl]-4-yl)methoxy)pyrrolidin-3-yl)nicotinamide |
| Example 440 | 2-amino-N-((3S,4S)-4-((4'-(2-(4-(2-hydroxyethyl)piperazin-1-yl)propan-2-yl)-[1,1'-biphenyl]-4-yl)methoxy)pyrrolidin-3-yl)-5-(1-methyl-1H-pyrazol-4-yl)nicotinamide |
| Example 441 | 2-amino-N-((3S,4S)-4-((4'-(2-(4-(2-hydroxyethyl)piperazin-1-yl)propan-2-yl)-[1,1'-biphenyl]-4-yl)methoxy)-1-methylpyrrolidin-3-yl)-5-(1-methyl-1H-pyrazol-4-yl)nicotinamide |
| Example 442 | 2-amino-N-((3S,4S)-4-((4'-(1-(4-(2-hydroxyethyl)piperazin-1-yl)ethyl)-[1,1'-biphenyl]-4-yl)methoxy)pyrrolidin-3-yl)-5-(1-methyl-1H-pyrazol-4-yl)nicotinamide |
| Example 443 | 2-amino-N-((3S,4S)-4-((4'-(1-(4-(2-hydroxyethyl)piperazin-1-yl)ethyl)-[1,1'-biphenyl]-4-yl)methoxy)-1-methylpyirolidin-3-yl)-5-(1-methyl-1H-pyrazol-4-yl)nicotinamide |
| Example 444 | 2-amino-N-((3S,4S)-4-((4'-((4-(2-hydroxyethyl)piperazin-1-yl)methyl)-3'-(trifluoromethyl)-[1,1'-biphenyl]-4-yl)methoxy)pyrrolidin-3-yl)-5-(1-methyl-1H-pyrazol-4-yl)nicotinamide |
| Example 445 | 2-amino-N-((3S,4S)-4-((4'-((4-(2-hydroxyethyl)piperazin-1-yl)methyl)-3'-(trifluoromethyl)-[1,1'-biphenyl]-4-yl)methoxy)-1-methylpyrrolidin-3-yl)-5-(1-methyl-1H-pyrazol-4-yl)nicotinamide |
| Example 446 | 2-amino-N-((3S,4S)-4-((4'-((4-(2-hydroxyethyl)piperazin-1-yl)methyl)-[1,1'-biphenyl]-4-yl)methoxy)pyrrolidin-3-yl)-5-(1-methyl-1H-pyrazol-4-yl)nicotinamide |
| Example 447 | 2-amino-N-((3S,4S)-4-((4'-((4-(2-hydroxyethyl)piperazin-1-yl)methyl)-[1,1'-biphenyl]-4-yl)methoxy)-1-methylpyrrolidin-3-yl)-5-(1-methyl-1H-pyrazol-4-yl)nicotinamide |
| Example 448 | 2-amino-5-(1-methyl-1H-pyrazol-4-yl)-N-((3S,4R)-4-((4'-((4-methylpiperazin-1-yl)methyl)-[1,1'-biphenyl]-4-yl)methoxy)tetrahydrofuran-3-yl)nicotinamide |
| Example 449 | 2-amino-5-(1-methyl-1H-pyrazol-4-yl)-N-((3S,4R)-4-((4'-((4-methylpiperazin-1-yl)methyl)-3'-(trifluoromethyl)-[1,1'-biphenyl]-4-yl)methoxy)tetrahydrofuran-3-yl)nicotinamide |
| Example 450 | 2-amino-5-(1-methyl-1H-pyrazol-4-yl)-N-((3S,4R)-4-((4'-(2-(4-methylpiperazin-1-yl)propan-2-yl)-[1,1'-biphenyl]-4-yl)methoxy)tetrahydrofuran-3-yl)nicotinamide |
| Example 451 | 2-amino-N-((3S,4R)-4-((4'-((4-(2-hydroxyethyl)piperazin-1-yl)methyl)-[1,1'-biphenyl]-4-yl)methoxy)tetrahydrofuran-3-yl)-5-(1-methyl-1H-pyrazol-4-yl)nicotinamide |

| | -continued |
|---|---|
| Example 452 | 2-amino-N-((3S,4R)-4-((4'-((4-(2-hydroxyethyl)piperazin-1-yl)methyl)-3'-(trifluoromethyl)-[1,1'-biphenyl]-4-yl)methoxy)tetrahydrofuran-3-yl)-5-(1-methyl-1H-pyrazol-4-yl)nicotinamide |
| Example 453 | 2-amino-N-((3S,4R)-4-((4'-(2-(4-(2-hydroxyethyl)piperazin-1-yl)propan-2-yl)-[1,1'-biphenyl]-4-yl)methoxy)tetrahydrofuran-3-yl)-5-(1-methyl-1H-pyrazol-4-yl)nicotinamide |
| Example 454 | 2-amino-5-(1-methyl-1H-pyrazol-4-yl)-N-(trans-4-((4'-((4-methylpiperazin-1-yl)methyl)-[1,1'-biphenyl]-4-yl)methoxy)tetrahydrofuran-3-yl)nicotinamide |
| Example 455 | 2-amino-N-(trans-4-((4'-((4-methylpiperazin-1-yl)methyl)-[1,1'-biphenyl]-4-yl)methoxy)tetrahydrofuran-3-yl)nicotinamide |
| Example 456 | 2-amino-N-((1S,2S)-2-(benzyloxy)cyclopentyl)-6-((4-((4-methylpiperazin-1-yl)methyl)phenyl)amino)nicotinamide |
| Example 457 | 2-amino-N-((1S,2S)-2-(benzyloxy)cyclopentyl)-6-(phenylamino)nicotinamide |
| Example 458 | 2-amino-N-((1S,2S)-2-(benzyloxy)cyclopentyl)-6-((4-(4-methylpiperazin-1-yl)phenyl)amino)nicotinamide |

Pharmaceutical Compositions Comprising of Novel Mer Kinase Inhibitors

The present invention provides pharmaceutical compositions comprising the heterocyclic compounds, the stereoisomer thereof, the enantiomer thereof, or the pharmaceutically acceptable salt thereof together with pharmaceutically acceptable carriers.

The carriers that are used in the present invention may be those that are conventionally used in the art, and examples thereof include, but are not limited to, sugar, starch, microcrystalline cellulose, lactose (lactose hydrate), glucose, di-mannitol, alginate, alkaline earth metal salts, clay, polyethylene glycol, anhydrous dibasic calcium phosphate, or mixtures thereof.

Further, according to another embodiment of the present invention, the pharmaceutical compositions may contain additives such as binders, disintegrants, lubricants, pH-adjusting agents, antioxidants, and the like.

Examples of the binders that may be used in the present invention include, but are not limited to, starch, microcrystalline cellulose, highly dispersed silica, mannitol, di-mannitol, sucrose, lactose hydrate, polyethylene glycol, polyvinylpyrrolidone (povidone), polyvinylpyrrolidone copolymer (copovidone), hypromellose, hydroxypropyl cellulose, natural gum, synthetic gum, copovidone, gelatin, or mixtures thereof.

Examples of the disintegrants that may be used in the present invention include, but are not limited to, starches or modified starches such as sodium starch glyconate, maize starch, potato starch or pregelatinized starch; clays such as bentonite, montmorillonite, or veegum; celluloses such as microcrystalline cellulose, hydroxypropylcellulose or carboxymethylcellulose; algins such as sodium alginate or alginic acid; crosslinked celluloses such as croscarmellose sodium; gums such as guar gum or xanthan gum; crosslinked polymers such as crosslinked polyvinylpyrrolidone (crospovidone); effervescent formulations such as sodium bicarbonate or citric acid; or mixtures thereof.

Examples of the lubricants that may be used in the present invention include, but are not limited to, talc, stearic acid, magnesium stearate, calcium stearate, sodium lauryl sulfate, hydrogenated vegetable oil, sodium benzoate, sodium stearyl fumarate, glyceryl behenate, glyceryl monooleate, glyceryl monostearate, glyceryl palmitostearate, colloidal silicon dioxide, or mixtures thereof.

Examples of the pH-adjusting agents that may be used in the present invention include, but are not limited to, acidifying agents such as acetic acid, adipic acid, ascorbic acid, sodium ascorbate, sodium etherate, malic acid, succinic acid, tartaric acid, fumaric acid or citric acid, and basifying agents such as precipitated calcium carbonate, ammonia water, meglumine, sodium carbonate, magnesium oxide, magnesium carbonate, sodium citrate, or tribasic calcium phosphate.

Examples of the antioxidants that may be used in the present invention include, but are not limited to, dibutyl hydroxytoluene, butylated hydroxyanisole, tocopherol acetate, tocopherol, propyl gallate, sodium hydrogen sulfite, sodium pyrosulfite, and the like.

The present invention provides the pharmaceutical compositions comprise, as active ingredients, the heterocyclic compounds, the stereoisomer thereof, the enantiomer thereof, or the pharmaceutically acceptable salt thereof and are used for prevention or treatment of a disease which is influenced by inhibition of Mer kinase.

The present invention provides the disease which is influenced by inhibition of Mer kinase is cancer or immune-related diseases.

The cancer is selected from the group consisting of: glioma, gliosarcoma, anaplastic astrocytoma, medulloblastoma, lung cancer, small cell lung carcinoma, cervical carcinoma, colon cancer, rectal cancer, chordoma, throat cancer, Kaposi's sarcoma, lymphangiosarcoma, lymphangioendotheliosarcoma, colorectal cancer, endometrium cancer, ovarian cancer, breast cancer, pancreatic cancer, prostate cancer, renal cell carcinoma, hepatic carcinoma, bile duct carcinoma, choriocarcinoma, seminoma, testicular tumor, Wilms' tumor, Ewing's tumor, bladder carcinoma, angiosarcoma, endotheliosarcoma, adenocarcinoma, sweat gland carcinoma, sebaceous gland sarcoma, papillary sarcoma, papillary adenosarcoma, cystadenosarcoma, bronchogenic carcinoma, medullary carcinoma, mastocytoma, mesotheliorma, synovioma, melanoma, leiomyosarcoma, rhabdomyosarcoma, neuroblastoma, retinoblastoma, oligodentroglioma, acoustic neuroma, hemangioblastoma, meningioma, pinealoma, ependymoma, craniopharyngioma, epithelial carcinoma, embryonal carcinoma, squamous cell carcinoma, base cell carcinoma, fibrosarcoma, myxoma, myxosarcoma, liposarcorna, chondrosarcoma, osteogenic sarcoma, leukemia and metastatic lesions secondary to these primary tumors.

The immune-related disease is selected from the group consisting of infection and sepsis.

The term "treatment" is used to refer to both prevention of diseases and treatment of pre-existing conditions.

The therapeutic amount varies according to the specific disease and can be determined by the person skilled in the art without undue effort.

In addition, the subject in the prevention or treatment method of the present invention includes mammals, particularly humans.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

Method for Prevention or Treatment of Immune-Related Diseases or Cancer

The present invention provides a method of treating or preventing immune-related diseases or cancer, the method comprising administering to a mammals including humans in need thereof compositions comprising, as active ingredients, the heterocyclic compounds, isomers thereof or pharmaceutically acceptable salts thereof.

The composition that is used in the inventive method for preventing or treating immune-related diseases or cancer includes the pharmaceutical composition described in the specification The present invention provides use of compositions comprising, as active ingredients, the heterocyclic compounds, the stereoisomer thereof, the enantiomer thereof, or the pharmaceutically acceptable salt thereof for preparation of medicaments for preventing or treating cancer or immune-related diseases.

Methods for Preparing of Novel Mer Kinase Inhibitors

The compounds of this invention can be prepared in accordance with one or more of schemes discussed below.

These methods can be used either directly or with obvious variations to trained chemists to prepare key intermediates and certain compounds of this invention.

Suitable synthetic sequences are readily selected per specific structures of this invention, but within the art known to individuals practicing organic synthesis, such as methods summarized in available chemistry data bases, as in CAS Scifinder and Elesevier Reaxys. Based on these general methods, the enablement for making the compounds of this invention is straightforward and can be practiced within a common professional knowledge. Some general synthetic methods to prepare the compounds of this invention are illustrated below in Schemes 1-2 (non-limiting, for illustration only).

One general approach to the compounds of this invention is illustrated in general Scheme 1.

Scheme 1. General procedure A

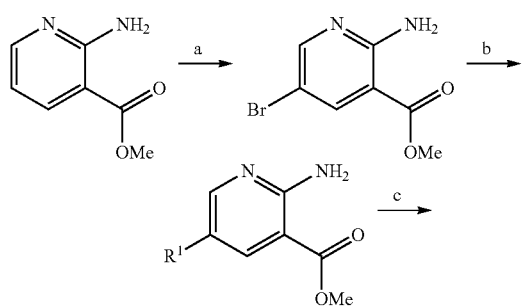

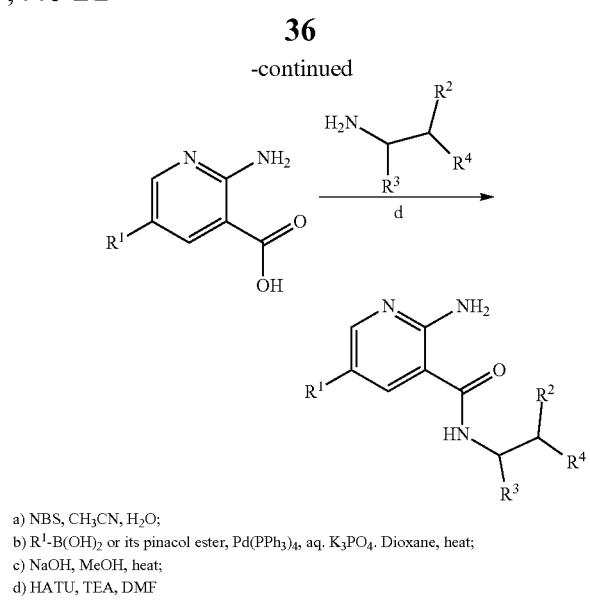

a) NBS, CH$_3$CN, H$_2$O;
b) R$^1$-B(OH)$_2$ or its pinacol ester, Pd(PPh$_3$)$_4$, aq. K$_3$PO$_4$, Dioxane, heat;
c) NaOH, MeOH, heat;
d) HATU, TEA, DMF Another general approach to the compounds of this invention is illustrated in general Scheme 2.

Scheme 2. General procedure B

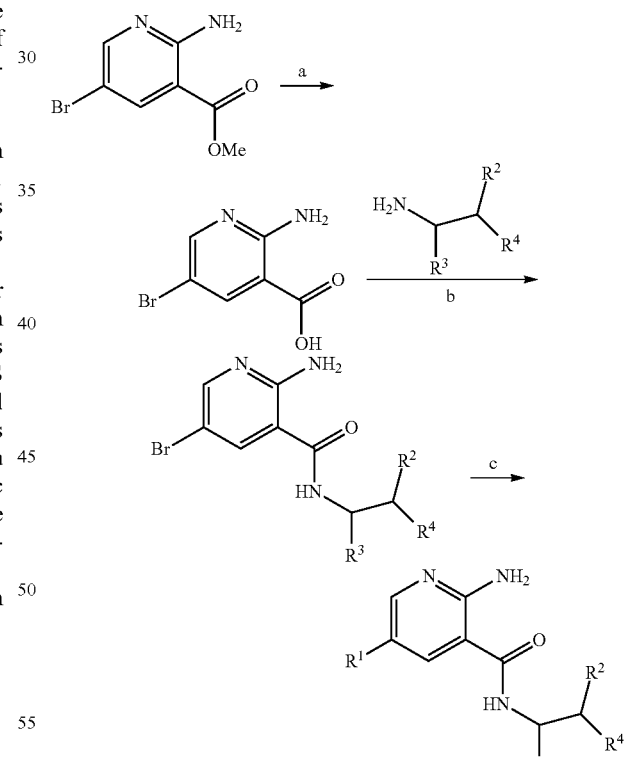

a) NaOH, MeOH, heat; b) HATU, TEA, DMF; c) R$^1$—B(OH)$_2$ or ots pinacol ester, Pd(PPh$_3$)$_4$, aq. K$_3$PO$_4$, Dioxane, heat Advantageous Effects Novel heterocyclic compounds according to the present invention, a stereoisomer thereof, an enantiomer thereof, or a pharmaceutically acceptable salt thereof exhibit the effect of effectively inhibiting Mer kinase.

Novel heterocyclic compounds according to the present invention, a stereoisomer thereof, an enantiomer thereof, or a pharmaceutically acceptable salt can be used for the prevention or treatment of cancer or immune-related disease.

MODE FOR INVENTION

Based on the studies conducted and the results obtained so far, it is believed that the following compounds (numbered 1 to 458), including isomers, mixtures of isomer as well as pharmaceutically acceptable salts and solvates thereof, are particularly interesting.

General Synthetic Methods

EXAMPLES

Embodiments of the present invention are described in the following examples, which are meant to illustrate and not limit the scope of this invention. Common abbreviations well known to those with ordinary skills in the synthetic art used throughout.

All chemical reagents were commercially available. Flash column chromatography means silica gel chromatography unless specified otherwise, which was performed on Teledyne Combiflash-RF200 System. $^1$H NMR spectra (δ, ppm) are recorded on 400 MHz or 600 MHz instrument. Mass spectroscopy data for a positive ionization method are provided. Preparative HPLC was performed on Agilent technologies G1361A.

Example 1. 2-amino-N-((1S,2S)-2-(benzyloxy)cyclopentyl)-5-(1-methyl-1H-pyrazol-4-yl)nicotinamide Scheme for the Preparation of the Compound of Example 1:

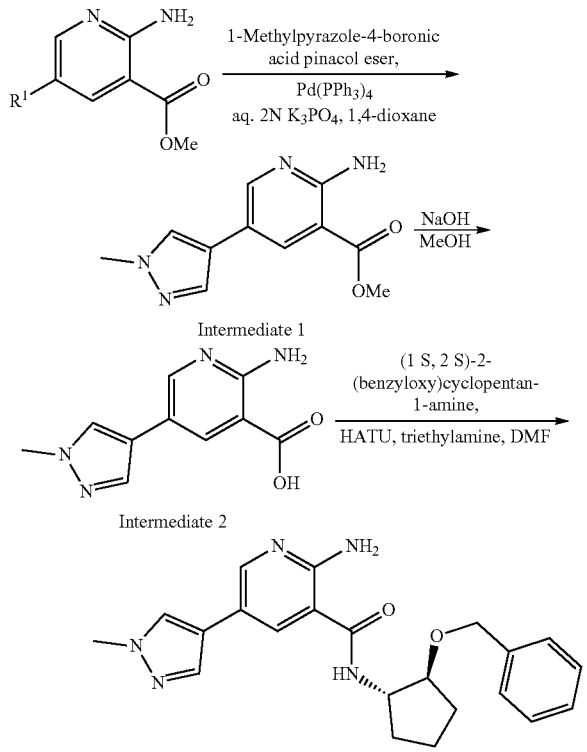

Intermediate 1

To a mixture of methyl 2-amino-5-bromonicotinate (1.5 g, 6.5 mmol) and 1-Methylpyrazole-4-boronic acid pinacol ester (1.76 g, 8.5 mmol) in 24 ml of 1,4-dioxane was added 8 ml of aq. 2N $K_3PO_4$ followed by $Pd(PPh_3)_4$ (370 mg, 0.32 mmol). The reaction mixture was heated at 100° C. for 3 hrs, cooled to room temperature, and extracted with EtOAc, dried over anhydrous $MgSO_4$ and concentrated under vacuum. The crude product was purified by silicagel column chromatography to give 1.25 g of off-white solid.

$^1$H NMR (400 MHz, $CD_3OD$) δ 3.90 (s, 3H), 3.91 (s, 3H), 7.74 (s, 1H), 7.91 (s, 1H), 8.29 (d, J=2.4 Hz, 1H), 8.35 (d, J=2.4 Hz, 1H);

MS (ESI, m/z): 233.1 [M+H]$^+$

Intermediate 2

To a suspension of intermediate 1 (1.2 g, 5.17 mmol) in 26 ml of MeOH was added 2N NaOH (4.3 ml, 8.63 mmol) and the mixture was heated at 65° C. for 1 hr, cooled to room temperature, neutralized (4.3 ml of 2N HCl), and the resulting precipitate was filtered, washed with MeOH, and dried to give 0.97 g of off-white solid.

$^1$H NMR (600 MHz, DMSO-d$_6$) δ ppm 3.82 (s, 3H), 5.73 (s, 2H), 7.77 (s, 1H), 8.05 (s, 1H), 8.13 (d, J=2.4 Hz, 1H), 8.42 (d, J=2.4 Hz, 1H);

MS (ESI, m/z): 219.1 [M+H]$^+$

Example 1. 2-amino-N-((1S,2S)-2-(benzyloxy)cyclopentyl)-5-(1-methyl-1H-pyrazol-4-yl)nicotinamide To a mixture of intermediate 2 (43 mg, 0.2 mmol) and triethylamine (24 mg, 0.24 mmol) in 2 ml of DMF was added HATU (91 mg, 0.24 mmol) followed by (1S,2S)-2-(benzyloxy)cyclopentan-1-amine (38 mg, 0.2 mmol). The mixture was stirred at room temperature for 1 hr and then saturated sodium bicarbonate solution was added. The mixture was extracted with EtOAc, washed with brine, dried over $MgSO_4$, and concentrated in vacuo. The crude residue was purified by preparative HPLC to afford 46 mg of the title compound.

$^1$H NMR (600 MHz, $CD_3OD$) δ ppm 1.57-1.69 (m, 1H) 1.72-1.86 (m, 3H) 1.90-2.08 (m, 1H) 2.11-2.21 (m, 1H) 3.93 (s, 3H) 3.96 (dt, J=6.75, 4.26 Hz, t H) 4.39 (td, J=7.34, 4.11 Hz, 1H) 4.61 (s, 2H) 7.13-7.24 (m, 1H) 7.27 (t, J=7.46 Hz, 2H) 7.32 (d, J=7.04 Hz, 2H) 7.79-7.90 (m, 1H) 8.00 (s, 1H) 8.23 (d, J=1.76 Hz, 1H) 8.46 (d, J=2.35 Hz, 1H);

MS (ESI, m/z): 392.2 [M+H]$^+$

Example 2. 2-amino-N-((1R,2R)-2-(benzyloxy)cyclopentyl)-5-(1-methyl-1H-pyrazol-4-yl)nicotinamide Using (1R,2R)-2-(benzyloxy)cyclopentan-1-amine, the title compound was obtained as described for the example 1.

MS (ESI, m/z): 392.2 [M+H]$^+$

Example 3. 2-amino-N-(trans-2-(benzyloxy)cyclopentyl)-5-(1-methyl-1H-pyrazol-4-yl)nicotinamide Using trans-2-(benzyloxy)cyclopentan-1-amine, the title compound was obtained as described for the example 1.

MS (ESI, m/z): 392.2 [M+H]$^+$

Example 4. 2-amino-N-((1R,2S)-2-(benzyloxy)cyclopentyl)-5-(1-methyl-1H-pyrazol-4-yl)nicotinamide Using (1R,2S)-2-(benzyloxy)cyclopentan-1-amine, the title compound was obtained as described for the example 1.

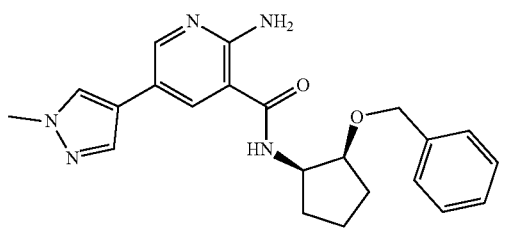 [SMILES: Cn1cc(-c2cnc(N)c(C(=O)N[C@@H]3CCC[C@@H]3OCc3ccccc3)c2)cn1]

MS (ESI, m/z): 392.2 [M+H]$^+$

Example 5. 2-amino-N-(cis-2-(benzyloxy)cyclopentyl)-5-(1-methyl-1H-pyrazol-4-yl)nicotinamide Using cis-2-(benzyloxy)cyclopentan-1-amine, the title compound was obtained as described for the example 1.

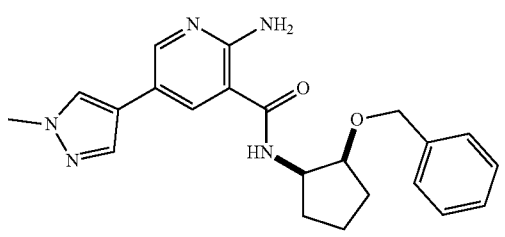

MS (ESI, m/z): 392.2 [M+H]$^+$

Example 6. 2-amino-5-(1-methyl-1H-pyrazol-4-yl)-N-((1S,2S)-2-((2-methylbenzyl)oxy)cyclopentyl)nicotinamide Using (1S,2S)-2-((2-methylbenzyl)oxy)cyclopentan-1-amine, the title compound was obtained as described for the example 1.

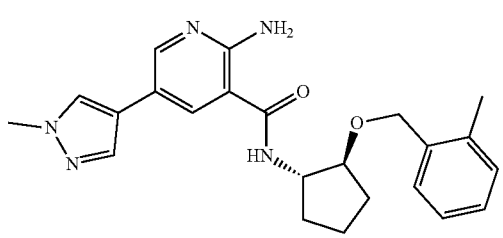 [SMILES: Cc1ccccc1CO[C@H]1CCC[C@@H]1NC(=O)c1cc(-c2cnn(C)c2)cnc1N]

MS (ESI, m/z): 406.2 [M+H]$^+$

Example 7. 2-amino-N-((1S,2S)-2-((3-ethylbenzyl)oxy)cyclopentyl)-5-(1-methyl-1H-pyrazol-4-yl)nicotinamide Using (1S,2S)-2-((3-ethylbenzyl)oxy)cyclopentan-1-amine, the title compound was obtained as described for the example 1.

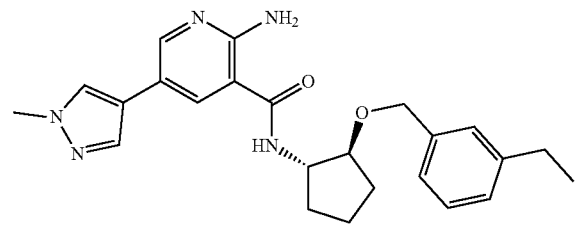 [SMILES: CCc1cccc(CO[C@H]2CCC[C@@H]2NC(=O)c2cc(-c3cnn(C)c3)cnc2N)c1]

MS (ESI, m/z): 420.2 [M+H]$^+$

Example 8. 2-amino-N-((1S,2S)-2-((4-ethylbenzyl)oxy)cyclopentyl)-5-(1-methyl-1H-pyrazol-4-yl)nicotinamide Using (1S,2S)-2-((4-ethylbenzyl)oxy)cyclopentan-1-amine, the title compound was obtained as described for the example 1.

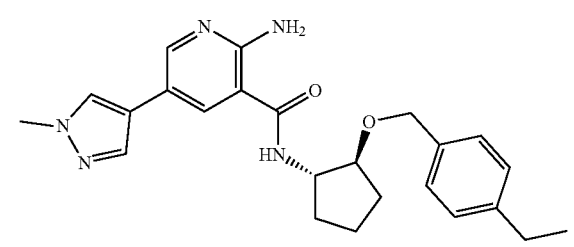 [SMILES: CCc1ccc(CO[C@H]2CCC[C@@H]2NC(=O)c2cc(-c3cnn(C)c3)cnc2N)cc1]

MS (ESI, m/z): 420.2 [M+H]$^+$

Example 9. 2-amino-N-(trans-2-((4-ethylbenzyl)oxy)cyclopentyl)-5-(1-methyl-1H-pyrazol-4-yl)nicotinamide Using trans-2-((4-ethylbenzyl)oxy)cyclopentan-1-amine, the title compound was obtained as described for the example 1.

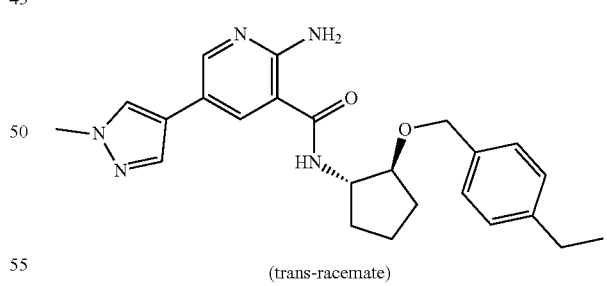

(trans-racemate)

MS (ESI, m/z): 420.2 [M+H]$^+$

Example 10. 2-amino-N-((1S,2S)-2-((4-isopropylbenzyl)oxy)cyclopentyl)-5-(1-methyl-1H-pyrazol-4-yl)nicotinamide Using (1S,2S)-2-((4-isopropylbenzyl)oxy)cyclopentan-1-amine, the title compound was obtained as described for the example 1.

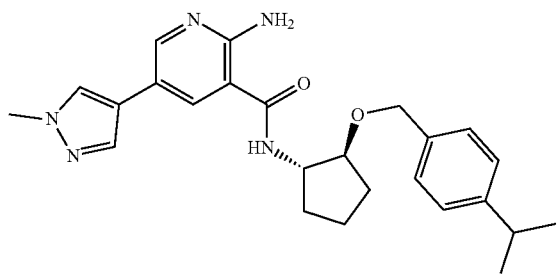 [SMILES: CC(C)c1ccc(CO[C@H]2CCC[C@@H]2NC(=O)c2cc(-c3cnn(C)c3)cnc2N)cc1]

MS (ESI, m/z): 434.3 [M+H]⁺

Example 11. 2-amino-N-((1S,2S)-2-((3,4-dimethylbenzyl)oxy)cyclopentyl)-5-(1-methyl-1H-pyrazol-4-yl)nicotinamide Using (1S,2S)-2-((2,3-dimethylbenzyl)oxy)cyclopentan-1-amine, the title compound was obtained as described for the example 1.

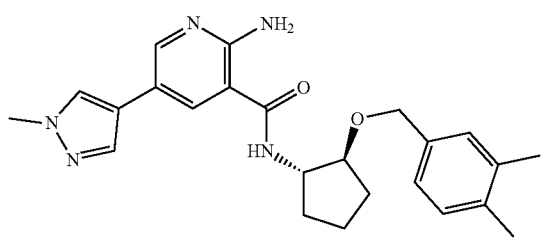

MS (ESI, m/z): 420.2 [M+H]⁺

Example 12. 2-amino-N-((1R,2R)-2-((3,4-dimethylbenzyl)oxy)cyclopentyl)-5-(1-methyl-1H-pyrazol-4-yl)nicotinamide Using (1R,2R)-2-((3,4-dimethylbenzyl)oxy)cyclopentan-1-amine, the title compound was obtained as described for the example 1.

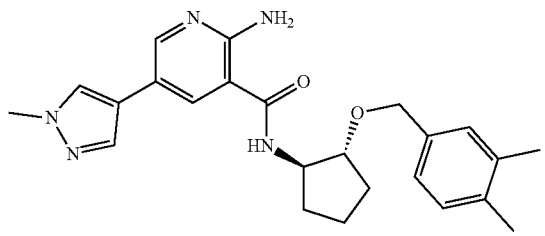

MS (ESI, m/z): 420.2 [M+H]⁺

Example 13. 2-amino-N-(trans-2-((3,4-dimethylbenzyl)oxy)cyclopentyl)-5-(1-methyl-1H-pyrazol-4-yl)nicotinamide Using trans-2-((3,4-dimethylbenzyl)oxy)cyclopentan-1-amine, the title compound was obtained as described for the example 1.

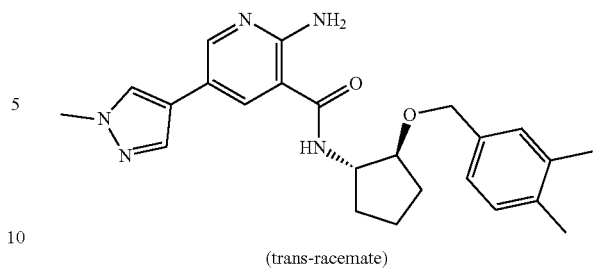

(trans-racemate)

MS (ESI, m/z): 420.2 [M+H]⁺

Example 14. 2-amino-N-((1S,2S)-2-((2,3-dimethylbenzyl)oxy)cyclopentyl)-5-(1-methyl-1H-pyrazol-4-yl)nicotinamide Using (1S,2S)-2-((2,3-dimethylbenzyl)oxy)cyclopentan-1-amine, the title compound was obtained as described for the example 1.

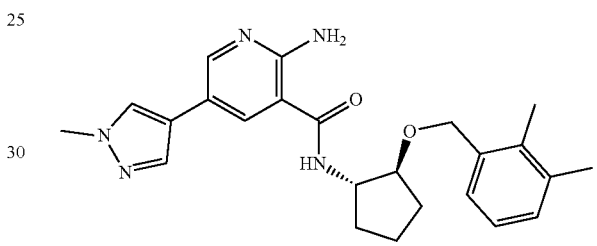

MS (ESI, m/z): 420.2 [M+H]⁺

Example 15. 2-amino-N-((1S,2S)-2-((2,6-dimethylbenzyl)oxy)cyclopentyl)-5-(1-methyl-1H-pyrazol-4-yl)nicotinamide Using (1S,2S)-2-((2,6-dimethylbenzyl)oxy)cyclopentan-1-amine, the title compound was obtained as described for the example 1.

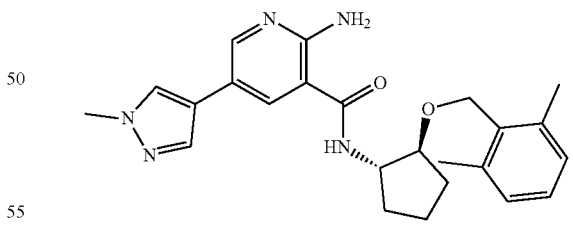

MS (ESI, m/z): 420.2 [M+H]⁺

Example 16. 2-amino-N-((1S,2S)-2-((2,5-dimethylbenzyl)oxy)cyclopentyl)-5-(1-methyl-1H-pyrazol-4-yl)nicotinamide Using (1S,2S)-2-((2,5-dimethylbenzyl)oxy)cyclopentan-1-amine, the title compound was obtained as described for the example 1.

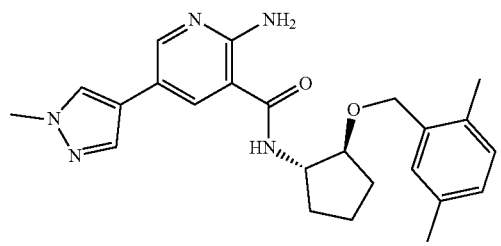 [SMILES: Cc1ccc(C)c(CO[C@H]2CCC[C@@H]2NC(=O)c2cc(-c3cnn(C)c3)cnc2N)c1]

MS (ESI, m/z): 420.2 [M+H]+

Example 17. 2-amino-N-((1S,2S)-2-((3,5-dimethyl-benzyl)oxy)cyclopentyl)-5-(1-methyl-1H-pyrazol-4-yl)nicotinamide Using (1S,2S)-2-((3,5-dimethylbenzyl)oxy)cyclopentan-1-amine, the title compound was obtained as described for the example 1.

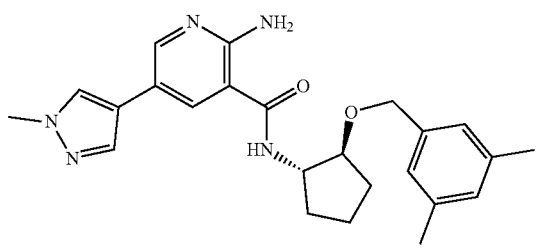

MS (ESI, m/z): 420.2 [M+H]+

Example 18. 2-amino-N-((1S,2S)-2-((2,4-dimethyl-benzyl)oxy)cyclopentyl)-5-(1-methyl-1H-pyrazol-4-yl)nicotinamide Using (1S,2S)-2-((2,4-dimethylbenzyl)oxy)cyclopentan-1-amine, the title compound was obtained as described for the example 1.

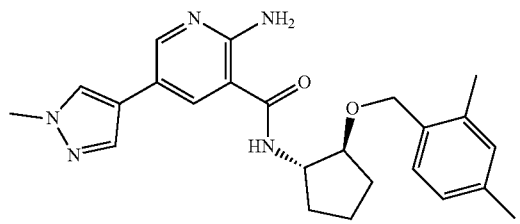

MS (ESI, m/z): 420.2 [M+H]+

Example 19. 2-amino-N-((1S,2S)-2-((4-ethyl-3-methylbenzyl)oxy)cyclopentyl)-5-(1-methyl-1H-pyrazol-4-yl)nicotinamide Using (1S,2S)-2-((4-ethyl-3-methylbenzyl)oxy)cyclopentan-1-amine, the title compound was obtained as described for the example 1.

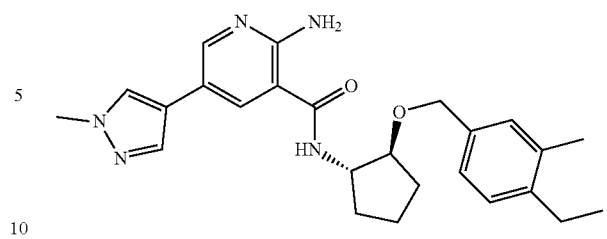

MS (ESI, m/z): 434.3 [M+H]+

Example 20. 2-amino-N-((1S,2S)-2-((3,4-diethyl-benzyl)oxy)cyclopentyl)-5-(1-methyl-1H-pyrazol-4-yl)nicotinamide Using (1S,2S)-2-((3,4-diethylbenzyl)oxy)cyclopentan-1-amine, the title compound was obtained as described for the example 1.

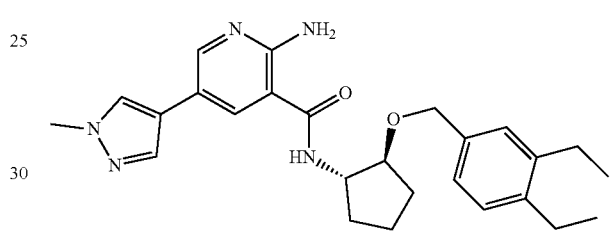

MS (ESI, m/z): 448.3 [M+H]+

Example 21. 2-amino-N-((1S,2S)-2-((3-ethyl-4-methylbenzyl)oxy)cyclopentyl)-5-(1-methyl-1H-pyrazol-4-yl)nicotinamide Using (1S,2S)-2-((3-ethyl-4-methylbenzyl)oxy)cyclopentan-1-amine, the title compound was obtained as described for the example 1.

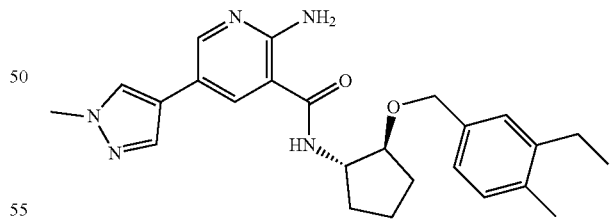

MS (ESI, m/z): 434.3 [M+H]+

Example 22. 2-amino-5-(1-methyl-1H-pyrazol-4-yl)-N-((1S,2S)-2-((3-propylbenzyl)oxy)cyclopentyl)nicotinamide Using (1S,2S)-2-((3-propylbenzyl)oxy)cyclopentan-1-amine, the title compound was obtained as described for the example 1.

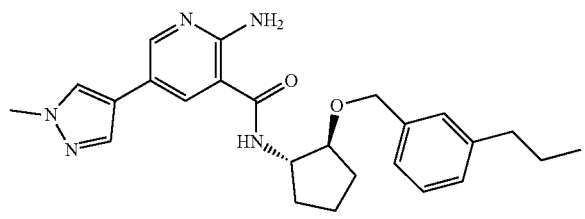 [SMILES: CCCc1cccc(CO[C@H]2CCC[C@@H]2NC(=O)c2cc(-c3cnn(C)c3)cnc2N)c1]

MS (ESI, m/z): 434.3 [M+H]+

Example 23. 2-amino-N-((1S,2S)-2-((3-cyclopentyl-benzyl)oxy)cyclopentyl)-5-(1-methyl-1H-pyrazol-4-yl)nicotinamide Using (1S,2S)-2-((3-cyclopentylbenzyl)oxy)cyclopentan-1-amine, the title compound was obtained as described for the example 1.

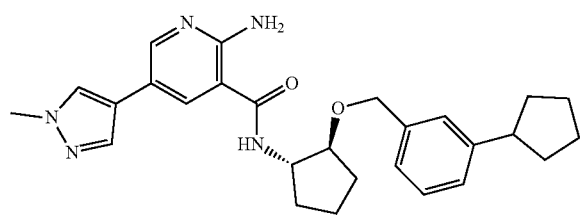 [SMILES: Cn1cc(-c2cnc(N)c(C(=O)N[C@H]3CCC[C@@H]3OCc3cccc(C4CCCC4)c3)c2)cn1]

MS (ESI, m/z): 460.3 [M+H]+

Example 24. 2-amino-N-((1S,2S)-2-((3-isopropyl-benzyl)oxy)cyclopentyl)-5-(1-methyl-1H-pyrazol-4-yl)nicotinamide Using (1S,2S)-2-((3-isopropylbenzyl)oxy)cyclopentan-1-amine, the title compound was obtained as described for the example 1.

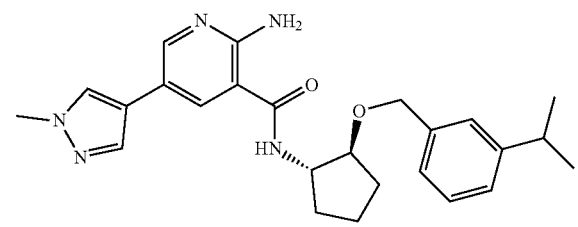 [SMILES: CC(C)c1cccc(CO[C@H]2CCC[C@@H]2NC(=O)c2cc(-c3cnn(C)c3)cnc2N)c1]

MS (ESI, m/z): 434.3 [M+H]+

Example 25. 2-amino-5-(1-methyl-1H-pyrazol-4-yl)-N-((1S,2S)-2-((3-(prop-1-en-2-yl)benzyl)oxy)cyclopentyl)nicotinamide Using (1S,2S)-2-((3-(prop-1-en-2-yl)benzyl)oxy)cyclopentan-1-amine, the title compound was obtained as described for the example 1.

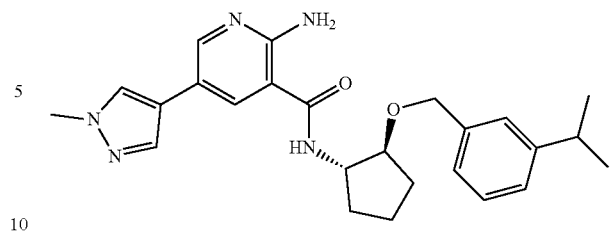

MS (ESI, m/z): 432.2 [M+H]+

Example 26. 2-amino-N-((1S,2S)-2-((3-cyclopropyl-benzyl)oxy)cyclopentyl)-5-(1-methyl-1H-pyrazol-4-yl)nicotinamide Using (1S,2S)-2-((3-cyclopropylbenzyl)oxy)cyclopentan-1-amine, the title compound was obtained as described for the example 1.

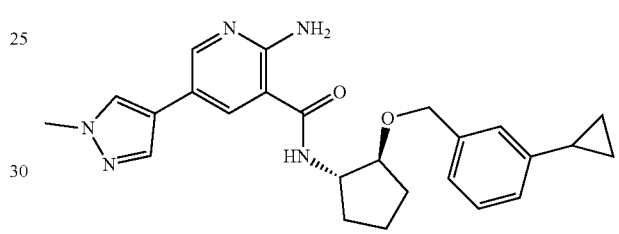

MS (ESI, m/z): 432.2 [M+H]+

Example 27. 2-amino-N-((1S,2S)-2-((3-cyclobutyl-benzyl)oxy)cyclopentyl)-5-(1-methyl-1H-pyrazol-4-yl)nicotinamide Using (1S,2S)-2-((3-cyclobutylbenzyl)oxy)cyclopentan-1-amine, the title compound was obtained as described for the example 1.

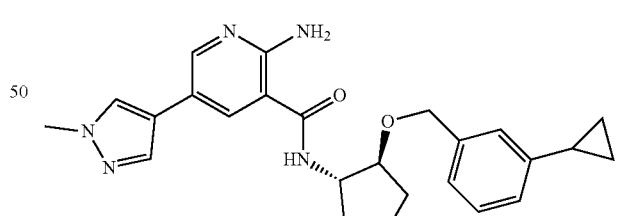

MS (ESI, m/z): 446.3 [M+H]+

Example 28. 2-amino-N-((1S,2S)-2-((3-ethynylben-zyl)oxy)cyclopentyl)-5-(1-methyl-1H-pyrazol-4-yl)nicotinamide Using (1S,2S)-2-((3-ethynylbenzyl)oxy)cyclopentan-1-amine, the title compound was obtained as described for the example 1.

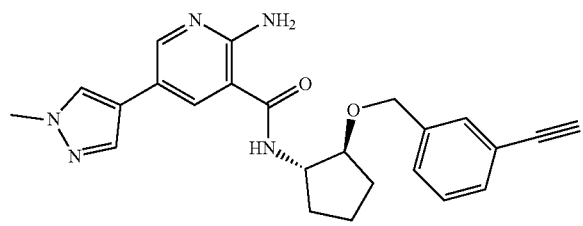 [SMILES: C#Cc1cccc(CO[C@H]2CCC[C@@H]2NC(=O)c2cc(-c3cnn(C)c3)cnc2N)c1]

MS (ESI, m/z): 416.2 [M+H]+

Example 29. 2-amino-5-(1-methyl-1H-pyrazol-4-yl)-N-((1S,2S)-2-((4-(trifluoromethyl)benzyl)oxy)cyclopentyl)nicotinamide Using (1S,2S)-2-((4-(trifluoromethyl)benzyl)oxy)cyclopentan-1-amine, the title compound was obtained as described for the example 1.

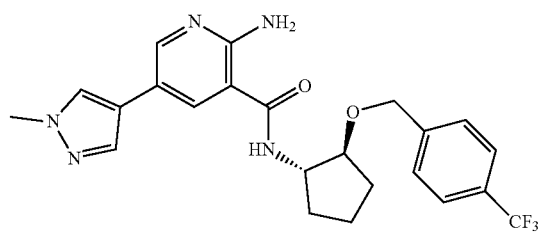 [SMILES: Cn1cc(-c2cnc(N)c(C(=O)N[C@H]3CCC[C@@H]3OCc3ccc(C(F)(F)F)cc3)c2)cn1]

MS (ESI, m/z): 460.2 [M+H]+

Example 30. 2-amino-5-(1-methyl-1H-pyrazol-4-yl)-N-((1S,2S)-2-((3-nitrobenzyl)oxy)cyclopentyl)nicotinamide Using (1S,2S)-2-((3-nitrobenzyl)oxy)cyclopentan-1-amine, the title compound was obtained as described for the example 1.

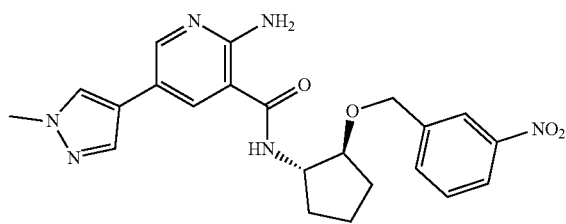 [SMILES: Cn1cc(-c2cnc(N)c(C(=O)N[C@H]3CCC[C@@H]3OCc3cccc([N+](=O)[O-])c3)c2)cn1]

MS (ESI, m/z): 437.2 [M+H]+

Example 31. 2-amino-N-((1S,2S)-2-((3-cyanobenzyl)oxy)cyclopentyl)-5-(1-methyl-1H-pyrazol-4-yl)nicotinamide Using 3-((((1S,2S)-2-aminocyclopentyl)oxy)methyl)benzonitrile, the title compound was obtained as described for the example 1.

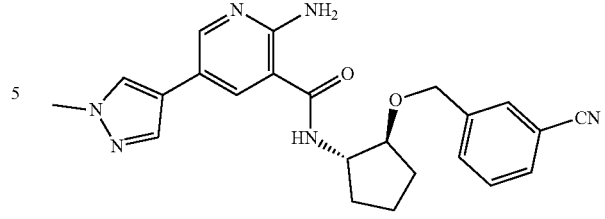

$^1$H NMR (400 MHz, CD$_3$OD) δ ppm 1.58-1.70 (m, 1H) 1.73-1.90 (m, 3H) 1.95-2.07 (m, 1H) 2.11-2.22 (m, 1H) 3.88-3.98 (m, 4H) 4.36-4.44 (m, 1H) 4.61-4.72 (m, 2H) 7.43-7.51 (m, 1H) 7.57 (br d, J=7.43 Hz, 1H) 7.63 (br d, J=7.43 Hz, 1H) 7.70 (s, 1H) 7.85 (s, 1H) 7.99 (s, 1H) 8.23 (d, J=1.96 Hz, 1H) 8.45 (d, J=1.96 Hz, 1H);

MS (ESI, m/z): 417.2 [M+H]+

Example 32. 2-amino-N-((1S,2S)-2-(3-hydroxybenzyl)oxy)cyclopentyl)-5-(1-methyl-1H-pyrazol-4-yl)nicotinamide Using (1S,2S)-2-((3-hydroxybenzyl)oxy)cyclopentan-1-amine, the title compound was obtained as described for the example 1.

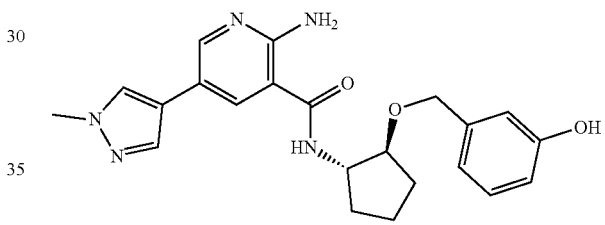

MS (ESI, m/z): 408.2 [M+H]+

Example 33. 2-amino-N-((1S,2S)-2-((3-methyloxybenzyl)oxy)cyclopentyl)-5-(1-methyl-1H-pyrazol-4-yl)nicotinamide Using (1S,2S)-2-((3-methyloxybenzyl)oxy)cyclopentan-1-amine, the title compound was obtained as described for the example 1.

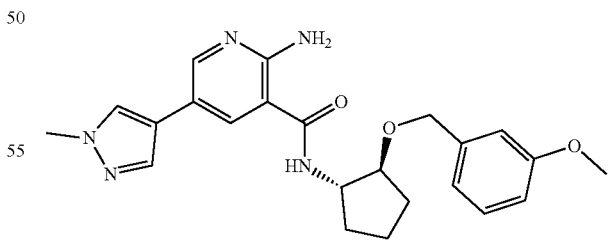

$^1$H NMR (400 MHz, CD$_3$OD) δ ppm 1.54-1.65 (m, 1H) 1.68-1.88 (m, 3H) 1.95-2.07 (m, 1H) 2.09-2.22 (m, 1H) 3.65-3.74 (m, 3H) 3.88-3.98 (m, 4H) 4.33-4.43 (m, 1H) 4.51-4.66 (m, 2H) 6.74 (dd, J=8.41, 1.76 Hz, 1H) 6.83-6.93 (m, 2H) 7.12-7.22 (m, 1H) 7.85 (s, 1H) 7.99 (s, 1H) 8.22 (d, J=1.96 Hz, 1H) 8.45 (d, J=1.96 Hz, 1H);

MS (ESI, m/z): 422.2 [M+H]+

Example 34. 2-amino-N-((1R,2R)-2-((3-methoxybenzyl)oxy)cyclopentyl)-5-(1-methyl-1H-pyrazol-4-yl)nicotinamide Using (1R,2R)-2-((3-methoxybenzyl)oxy)cyclopentan-1-amine, the title compound was obtained as described for the example 1.

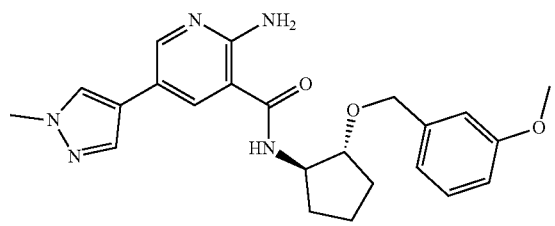

MS (ESI, m/z): 422.2 [M+H]$^+$

Example 35. 2-amino-N-((1S,2S)-2-((4-methoxybenzyl)oxy)cyclopentyl)-5-(1-methyl-1H-pyrazol-4-yl)nicotinamide Using (1S,2S)-2-((4-methoxybenzyl)oxy)cyclopentan-1-amine, the title compound was obtained as described for the example 1.

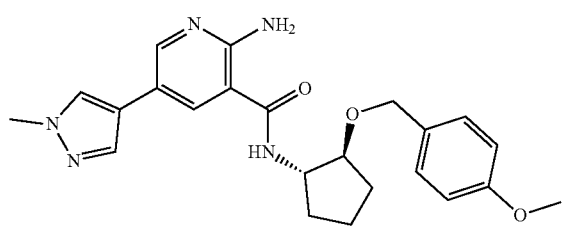

MS (ESI, m/z): 422.2 [M+H]$^+$

Example 36. 2-amino-N-((1R,2R)-2-((4-methoxybenzyl)oxy)cyclopentyl)-5-(1-methyl-1H-pyrazol-4-yl)nicotinamide Using (1R,2R)-2-((4-methoxybenzyl)oxy)cyclopentan-1-amine, the title compound was obtained as described for the example 1.

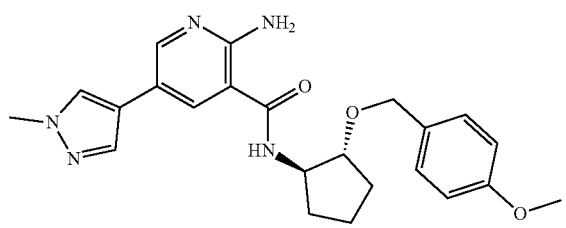

MS (ESI, m/z): 422.2 [M+H]$^+$

Example 37. 2-amino-N-(trans-2-((3,5-dimethoxybenzyl)oxy)cyclopentyl)-5-(1-methyl-1H-pyrazol-4-yl)nicotinamide Using trans-2-((3,5-dimethoxybenzyl)oxy)cyclopentan-1-amine, the title compound was obtained as described for the example 1.

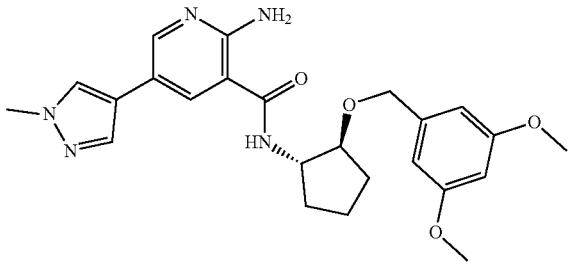

(trans-racemate)

MS (ESI, m/z): 452.2 [M+H]$^+$

Example 38. 2-amino-N-((1S,2S)-2-((2,3-dimethoxybenzyl)oxy)cyclopentyl)-5-(1-methyl-1H-pyrazol-4-yl)nicotinamide Using (1S,2S)-2-((2,3-dimethoxybenzyl)oxy)cyclopentan-1-amine, the title compound was obtained as described for the example 1.

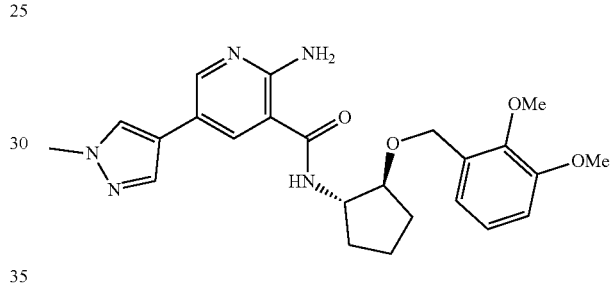

MS (ESI, m/z): 452.2 [M+H]$^+$

Example 39. 2-amino-5-(1-methyl-1H-pyrazol-4-yl)-N-((1S,2S)-2-((3-phenoxybenzyl)oxy)cyclopentyl)nicotinamide Using (1S,2S)-2-((3-phenoxybenzyl)oxy)cyclopentan-1-amine, the title compound was obtained as described for the example 1.

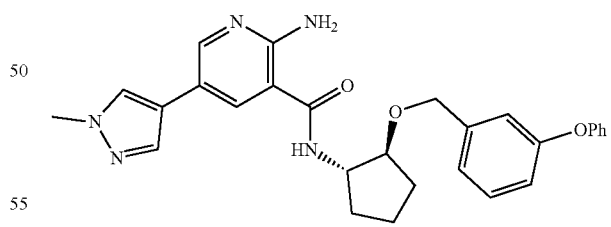

MS (ESI, m/z): 484.2 [M+H]$^+$

Example 40. 2-amino-N-((1S,2S)-2-(benzo[d][1,3]dioxol-5-yl-methoxy)-cyclopentyl)-5-(1-methyl-1H-pyrazol-4-yl)nicotinamide Using (1S,2S)-2-(benzo[d][1,3]dioxol-5-ylmethoxy)cyclopentan-1-amine, the title compound was obtained as described for the example 1.

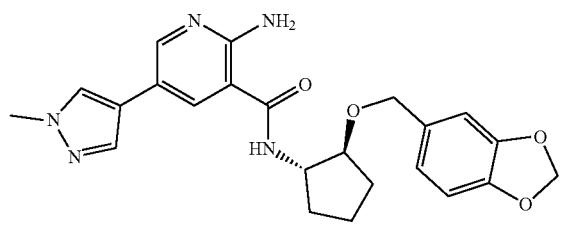 [SMILES: Cn1cc(-c2cnc(N)c(C(=O)N[C@H]3CCC[C@@H]3OCc3ccc4c(c3)OCO4)c2)cn1]

MS (ESI, m/z): 436.2 [M+H]+

Example 41. 2-amino-5-(1-methyl-1H-pyrazol-4-yl)-N-((1S,2S)-2-((4-(methylthio)benzyl)oxy)cyclopentyl)nicotinamide Using (1S,2S)-2-((4-(methylthio)benzyl)oxy)cyclopentan-1-amine, the title compound was obtained as described for the example 1.

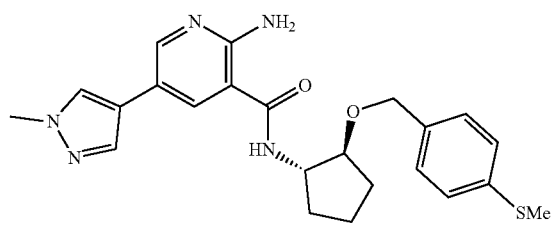 [SMILES: CSc1ccc(CO[C@H]2CCC[C@@H]2NC(=O)c2cc(-c3cnn(C)c3)cnc2N)cc1]

MS (ESI, m/z): 438.2 [M+H]+

Example 42. methyl 3-(((((1S,2S)-2-(2-amino-5-(1-methyl-1H-pyrazol-4-yl)nicotinamido)cyclopentyl)oxy)methyl)benzoate Using methyl 3-((((1S,2S)-2-aminocyclopentyl)oxy)methyl)benzoate, the title compound was obtained as described for the example 1.

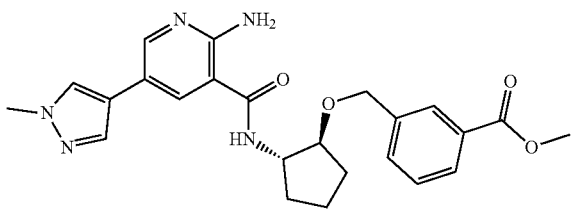

MS (ESI, m/z): 450.2 [M+H]+

Example 43. 2-amino-N-((1S,2S)-2-((3-chlorobenzyl)oxy)cyclopentyl)-5-(1-methyl-1H-pyrazol-4-yl)nicotinamide Using (1S,2S)-2-((3-chlorobenzyl)oxy)cyclopentan-1-amine, the title compound was obtained as described for the example 1.

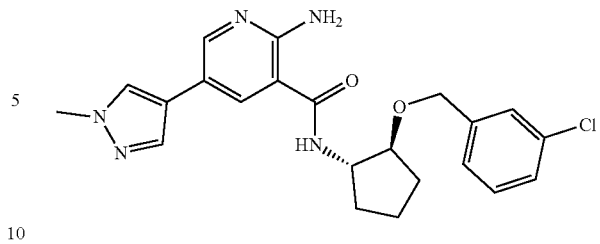

$^{1}$H NMR (400 MHz, CD$_3$OD) δ ppm 1.62 (br dd, J=13.50, 6.46 Hz, 1H) 1.72-1.87 (m, 3H) 1.94-2.05 (m, 1H) 2.16 (br d, J=6.65 Hz, 1H) 3.89-3.97 (m, 4H) 4.38 (br d, J=4.70 Hz, 1H) 4.55-4.66 (m, 2H) 7.20 (br s, 1H) 7.22-7.28 (m, 2H) 7.34 (s, 1H) 7.85 (s, 1H) 7.99 (s, 1H) 8.22 (d, J=2.35 Hz, 1H) 8.44 (br d, J=2.35 Hz, 1H);
MS (ESI, m/z): 426.2 [M+H]+

Example 44. 2-amino-N-(trans-2-((3-chlorobenzyl)oxy)cyclopentyl)-5-(1-methyl-1H-pyrazol-4-yl)nicotinamide Using trans-2-((3-chlorobenzyl)oxy)cyclopentan-1-amine, the title compound was obtained as described for the example 1.

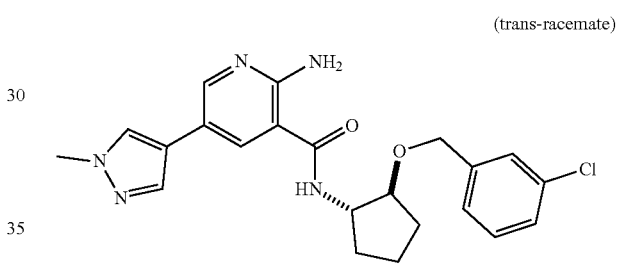

(trans-racemate)

MS (ESI, m/z): 426.2 [M+H]+

Example 45. 2-amino-N-(trans-2-((4-chlorobenzyl)oxy)cyclopentyl)-5-(1-methyl-1H-pyrazol-4-yl)nicotinamide Using trans-2-((4-chlorobenzyl)oxy)cyclopentan-1-amine, the title compound was obtained as described for the example 1.

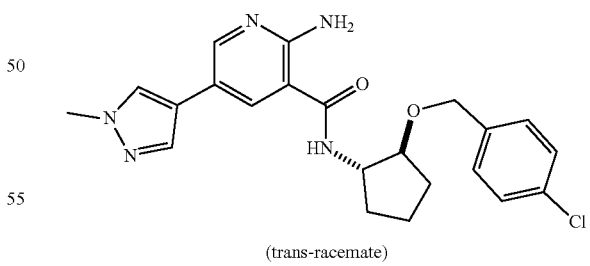

(trans-racemate)

MS (ESI, m/z): 426.2 [M+H]+

Example 46. 2-amino-N-(trans-2-((3,4-dichlorobenzyl)oxy)cyclopentyl)-5-(1-methyl-1H-pyrazol-4-yl)nicotinamide Using trans-2-((3,4-dichlorobenzyl)oxy)cyclopentan-1-amine, the title compound was obtained as described for the example 1.

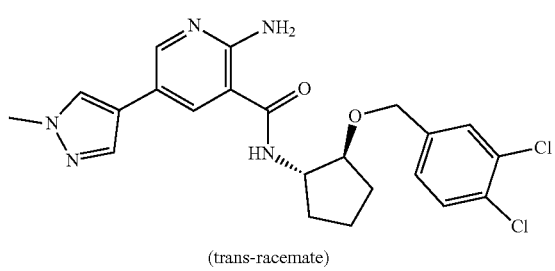 [SMILES: Cn1cc(-c2cnc(N)c(C(=O)N[C@H]3CCC[C@@H]3OCc3ccc(Cl)c(Cl)c3)c2)cn1]

(trans-racemate)

MS (ESI, m/z): 460.1 [M+H]$^+$

Example 47. 2-amino-N-(trans-2-((2-fluorobenzyl)oxy)cyclopentyl)-5-(1-methyl-1H-pyrazol-4-yl)nicotinamide Using trans-2-((2-fluorobenzyl)oxy)cyclopentan-1-amine, the title compound was obtained as described for the example 1.

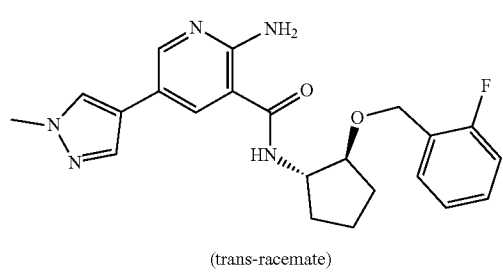 [SMILES: Cn1cc(-c2cnc(N)c(C(=O)N[C@H]3CCC[C@@H]3OCc3ccccc3F)c2)cn1]

(trans-racemate)

MS (ESI, m/z): 410.2 [M+H]$^+$

Example 48. 2-amino-N-((1S,2S)-2-((3-fluorobenzyl)oxy)cyclopentyl)-5-(1-methyl-1H-pyrazol-4-yl)nicotinamide Using (1S,2S)-2-((3-fluorobenzyl)oxy)cyclopentan-1-amine, the title compound was obtained as described for the example 1.

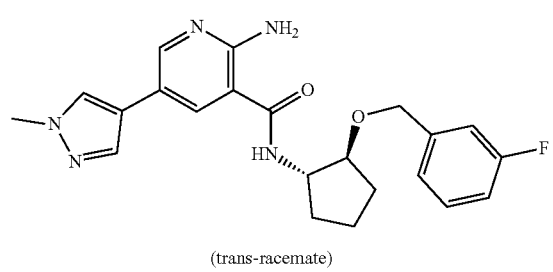 [SMILES: Cn1cc(-c2cnc(N)c(C(=O)N[C@H]3CCC[C@@H]3OCc3cccc(F)c3)c2)cn1]

(trans-racemate)

$^1$H NMR (400 MHz, CD$_3$OD) δ ppm 1.63 (dq, J=13.69, 7.17 Hz, 1H) 1.70-1.88 (m, 3H) 1.93-2.06 (m, 1H) 2.15 (dt, J=13.69, 6.85 Hz, 1H) 3.87-4.00 (m, 4H) 4.34-4.42 (m, 1H) 4.62 (s, 2H) 6.92 (td, J=8.61, 1.96 Hz, 1H) 7.03-7.16 (m, 2H) 7.27 (dd, J=8.02, 6.06 Hz, 1H) 7.85 (s, 1H) 8.00 (s, 1H) 8.22 (d, J=1.96 Hz, 1H) 8.49 (d, J=1.96 Hz, 1H); MS (ESI, m/z): 410.2 [M+H]$^+$ Example 49. 2-amino-N-(trans-2-((4-bromo-2-fluorobenzyl)oxy)cyclopentyl)-5-(1-methyl-1H-pyrazol-4-yl)nicotinamide Using trans-2-((4-bromo-2-fluorobenzyl)oxy)cyclopentan-1-amine, the title compound was obtained as described for the example 1.

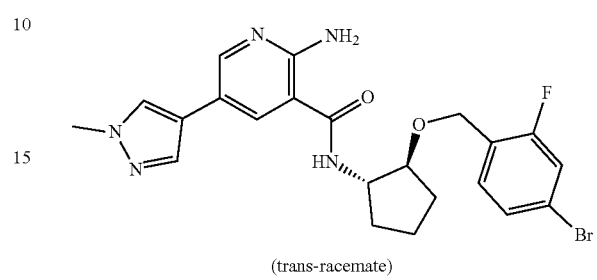

(trans-racemate)

MS (ESI m/z): 488.1/490.1 [M+H]$^+$

Example 50. 2-amino-5-(1-methyl-1H-pyrazol-4-yl)-N-(trans-2-((2,4,5-trifluorobenzyl)oxy)cyclopentyl)nicotinamide Using trans-2-((2,4,5-trifluorobenzyl)oxy)cyclopentan-1-amine, the title compound was obtained as described for the example 1.

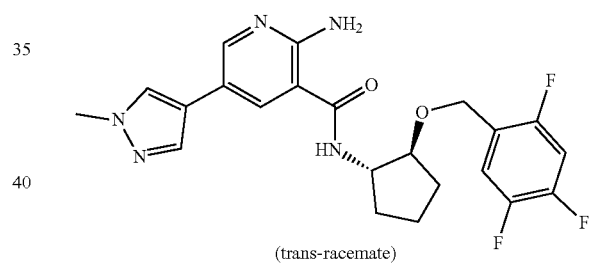

(trans-racemate)

MS (ESI, m/z): 446.2 [M+H]$^+$

Example 51. 2-amino-N-((1S,2S)-2-((3-bromobenzyl)oxy)cyclopentyl)-5-(1-methyl-1H-pyrazol-4-yl)nicotinamide Using (1S,2S)-2-((3-bromobenzyl)oxy)cyclopentan-1-amine, the title compound was obtained as described for the example 1.

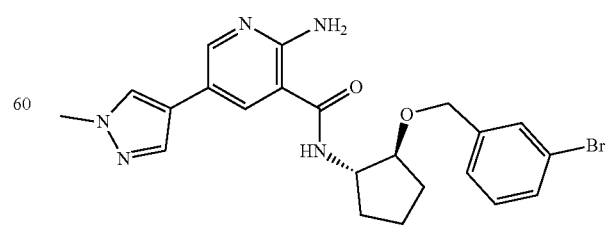

MS (ESI, m/z): 470.1/472.1 [M+H]$^+$

Example 52. 2-amino-N-(trans-2-((3-bromo-4-fluorobenzyl)oxy)cyclopentyl)-5-(1-methyl-1H-pyrazol-4-yl)nicotinamide Using trans-2-((3-bromo-4-fluorobenzyl)oxy)cyclopentan-1-amine, the title compound was obtained as described for the example 1.

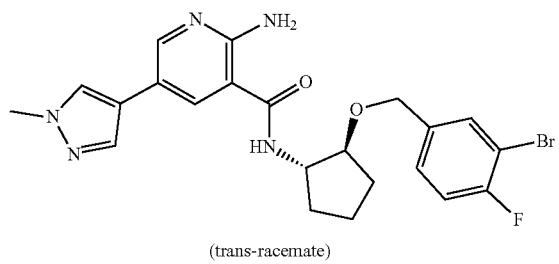 [SMILES: Cn1cc(-c2cnc(N)c(C(=O)N[C@H]3CCC[C@@H]3OCc3ccc(F)c(Br)c3)c2)cn1]

(trans-racemate)

MS (ESI, m/z): 488.1/490.1 [M+H]$^+$

Example 53. 2-amino-N-((1R,2R)-2-((3-bromo-4-fluorobenzyl)oxy)cyclopentyl)-5-(1-methyl-1H-pyrazol-4-yl)nicotinamide Using (1R,2R)-2-((3-bromo-4-fluorobenzyl)oxy)cyclopentan-1-amine, the title compound was obtained as described for the example 1.

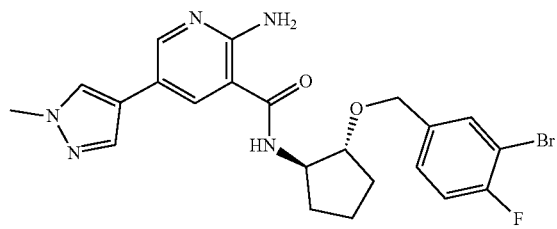 [SMILES: Cn1cc(-c2cnc(N)c(C(=O)N[C@@H]3CCC[C@H]3OCc3ccc(F)c(Br)c3)c2)cn1]

MS (ESI, m/z): 488.1/490.1 [M+H]$^+$

Example 54. 2-amino-N-((1S,2S)-2-(1-(4-bromophenyl)ethoxy)cyclopentyl)-5-(1-methyl-1H-pyrazol-4-yl)nicotinamide Using (1S,2S)-2-(1-(4-bromophenyl)ethoxy)cyclopentan-1-amine, the title compound was obtained as described for the example 1.

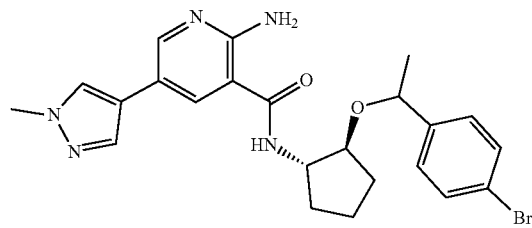 [SMILES: CC(O[C@H]1CCC[C@@H]1NC(=O)c1cc(-c2cnn(C)c2)cnc1N)c1ccc(Br)cc1]

MS (ESI, m/z): 484.1/486.1 [M+H]$^+$

Example 55. methyl (3-((((1S,2S)-2-(2-amino-5-(1-methyl-1H-pyrazol-4-yl)nicotinamido)cyclopentyl)oxy)methyl)benzoyl)glycinate Using methyl (3-((((1S,2S)-2-aminocyclopentyl)oxy)methyl)benzoyl)glycinate, the title compound was obtained as described for the example 1.

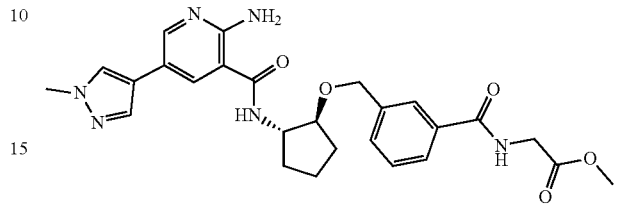

$^1$H NMR (400 MHz, CD$_3$OD) δ ppm 1.58-1.70 (m, 1H) 1.73-1.90 (m, 3H) 1.95-2.07 (m, 1H) 2.11-2.22 (m, 1H) 3.88-3.98 (m, 4H) 4.36-4.44 (m, 1H) 4.61-4.72 (m, 2H) 7.43-7.51 (m, 1H) 7.57 (br d, J=7.43 Hz, 1H) 7.63 (br d, J=7.43 Hz, 1H) 7.70 (s, 1H) 7.85 (s, 1H) 7.99 (s, 1H) 8.23 (d, J=1.96 Hz, 1H) 8.45 (d, J=1.96 Hz, 1H);

MS (ESI, m/z): 507.2[M+H]$^+$

Example 56. 2-amino-N-((1S,2S)-2-((3-((2-hydroxyethyl)carbamoyl)benzyl)-oxy)cyclopentyl)-5-(1-methyl-1H-pyrazol-4-yl)nicotinamide Using methyl (3-((((1S,2S)-2-aminocyclopentyl)oxy)methyl)-N-(2-hydroxyethyl)-benzamide, the title compound was obtained as described for the example 1.

MS (ESI, m/z): 479.2[M+H]$^+$

Example 57. 2-amino-5-(1-methyl-1H-pyrazol-4-yl)-N-((1S,2S)-2-((3-(piperidine-4-carboxamido)benzyl)oxy)cyclopentyl)nicotinamide Using tert-butyl 4-((3-((((1S,2S)-2-aminocyclopentyl)oxy)methyl)phenyl)carbamoyl)-piperidine-1-carboxylate, the title compound was obtained as described for the example 1 and following deprotection with TFA.

MS (ESI, m/z): 518.3[M+H]$^+$

Example 58. 2-amino-N-((1S,2S)-2-((3-((S)-2-aminopropanamido)benzyl)oxy)-cyclopentyl)-5-(1-methyl-1H-pyrazol-4-yl)nicotinamide Using tert-butyl ((S)-1-((3-(((((1S,2S)-2-aminocyclopentyl)oxy)methyl)phenyl)amino)-1-oxopropan-2-yl)carbamate, the title compound was obtained as described for the example 1 and following deprotection with TFA.

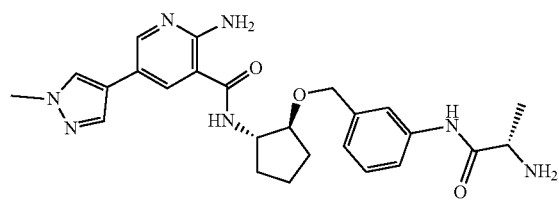 [SMILES: C[C@H](N)C(=O)Nc1cccc(CO[C@H]2CCC[C@@H]2NC(=O)c2cc(-c3cnn(C)c3)cnc2N)c1]

MS (EST, m/z): 478.3 [M+H]+

Example 59. N-((1S,2S)-2-((3-((S)-2-acetamidopropanamido)benzyl)oxy)-cyclopentyl)-2-amino-5-(1-methyl-1H-pyrazol-4-yl)nicotinamide Using (S)-2-acetamido-N-(3-(((((1S,2S)-2-aminocyclopentyl)oxy)methyl)phenyl)-propanamide, the title compound was obtained as described for the example 1.

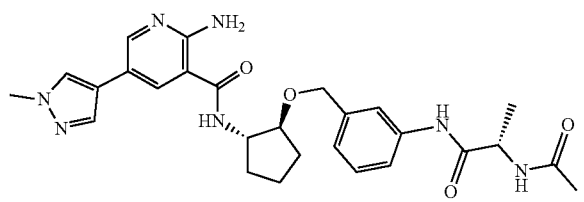 [SMILES: CC(=O)N[C@@H](C)C(=O)Nc1cccc(CO[C@H]2CCC[C@@H]2NC(=O)c2cc(-c3cnn(C)c3)cnc2N)c1]

MS (ESI, m/z): 520.3[M+H]+

Example 60. 2-amino-N-((1S,2S)-2-((3-(3-aminopropanamido)benzyl)oxy)-cyclopentyl)-5-(1-methyl-1H-pyrazol-4-yl)nicotinamide Using tert-butyl (3-((3-(((((1S,2S)-2-aminocyclopentyl)oxy)methyl)phenyl)amino)-3-oxopropyl)carbamate, the title compound was obtained as described for the example 1 and following deprotection with TFA.

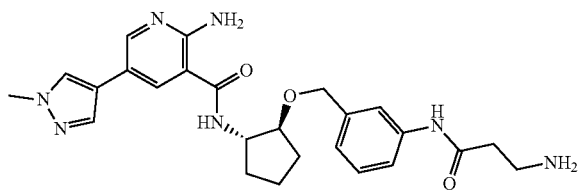

MS (ESI, m/z): 478.3[M+H]+

Example 61. N-((1S,2S)-2-((3-(2H-1,2,3-triazol-2-yl)benzyl)oxy)cyclopentyl)-2-amino-5-(1-methyl-1H-pyrazol-4-yl)nicotinamide Using (1S,2S)-2-((3-(2H-1,2,3-triazol-2-yl)benzyl)oxy)cyclopentan-1-amine, the title compound was obtained as described for the example 1.

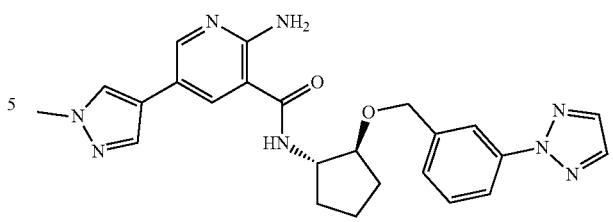

MS (ESI, m/z): 459.2 [M+H]+

Example 62. N-(1S,2S)-2-((4-(2H-1,2,3-triazol-2-yl)benzyl)oxy)cyclopentyl)-2-amino-5-(1-methyl-1H-pyrazol-4-yl)nicotinamide Using (1S,2S)-2-((4-(2H-1,2,3-triazol-2-yl)benzyl)oxy)cyclopentan-1-amine, the title compound was obtained as described for the example 1.

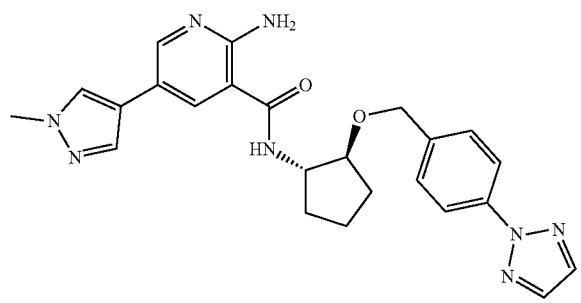

MS (ESI, m/z): 459.2 [M+H]+

Example 63. 2-amino-5-(1-methyl-1H-pyrazol-4-yl)-N-((1S,2S)-2-(naphthalen-2-ylmethoxy)cyclopentyl)nicotinamide Using (1S,2S)-2-(naphthalen-2-ylmethoxy)cyclopentan-1-amine, the title compound was obtained as described for the example 1.

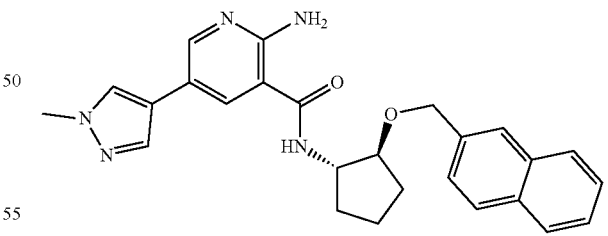

MS (ESI, m/z): 442.2 [M+H]+

Example 64. 2-amino-5-(1-methyl-1H-pyrazol-4-yl)-N-((1S,2S)-2-(quinolin-8-ylmethoxy)cyclopentyl)nicotinamide Using (1S,2S)-2-(quinolin-8-ylmethoxy)cyclopentan-1-amine, the title compound was obtained as described for the example 1.

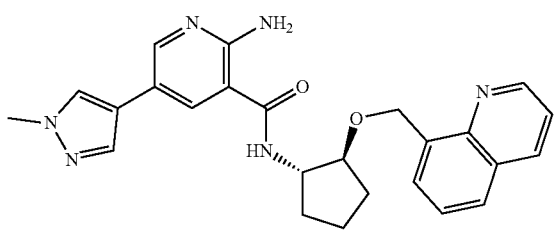

MS (ESI, m/z): 443.2 [M+H]+

Example 65. 2-amino-5-(1-methyl-1H-pyrazol-4-yl)-N-((1S,2S)-2-((2',3',4',5'-tetrahydro-[1,1'-biphenyl]-4-yl)methoxy)cyclopentyl)nicotinamide Using (1S,2S)-2-((2',3',4',5'-tetrahydro-[1,1'-biphenyl]-4-yl)methoxy)cyclopentan-1-amine, the title compound was obtained as described for the example 1.

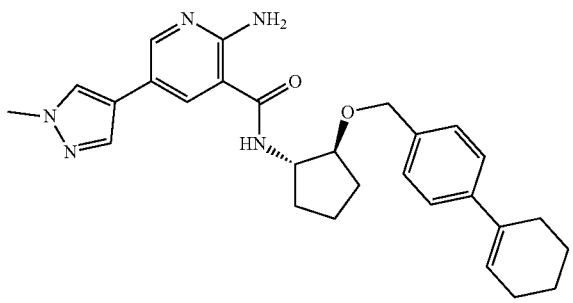

$^1$H NMR (400 MHz, CD$_3$OD) δ ppm 1.62 (br d, J=5.87 Hz, 2H) 1.67-1.87 (m, 5H) 1.93-2.09 (m, 2H) 2.14 (br s, 3H) 2.28 (br s, 2H) 3.92 (s, 3H) 4.37 (br d, J=5.48 Hz, 1H) 4.49-4.65 (m, 2H) 6.00 (br s, 1H) 7.18-7.30 (m, 2H) 7.54 (br s, 1H) 7.59-7.69 (m, 1H) 7.84 (s, 1H) 7.98 (s, 1H) 8.23 (s, 1H) 8.38 (s, 1H);

MS (ESI, m/z): 472.3 [M+H]+

Example 66. N-(trans-2-([1,1'-biphenyl]-2-ylmethoxy)cyclopentyl)-2-amino-5-(1-methyl-1H-pyrazol-4-yl)nicotinamide Using trans-2-([1,1'-biphenyl]-2-ylmethoxy)cyclopentan-1-amine, the title compound was obtained as described for the example 1.

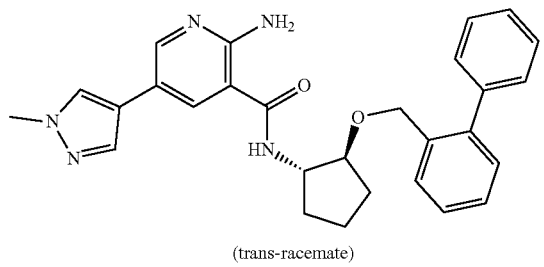

(trans-racemate)

MS (ESI, m/z): 468.2 [M+H]+

Example 67. N-((1S,2S)-2-([1,1'-biphenyl]-3-ylmethoxy)cyclopentyl)-2-amino-5-(1-methyl-1H-pyrazol-4-yl)nicotinamide Using (1S,2S)-2-([1,1'-biphenyl]-3-ylmethoxy)cyclopentan-1-amine, the title compound was obtained as described for the example 1.

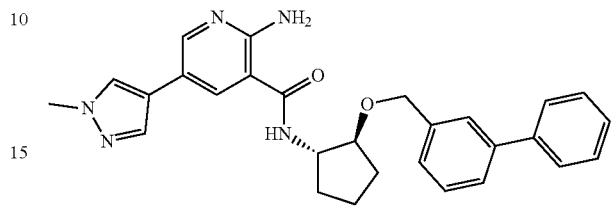

MS (ESI, m/z): 468.2 [M+H]+

Example 68. N-((1S,2S)-2-([1,1'-biphenyl]-4-ylmethoxy)cyclopentyl)-2-amino-5-(1-methyl-1H-pyrazol-4-yl)nicotinamide Using (1S,2S)-3-([1,1'-biphenyl]-4-ylmethoxy)cyclopentan-1-amine, the title compound was obtained as described for the example 1.

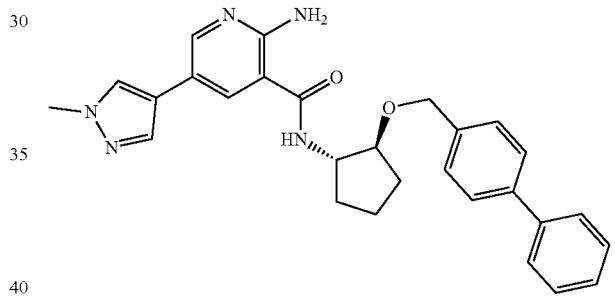

$^1$H NMR (400 MHz, CD$_3$OD) δ ppm 1.59 (br d, J=1.17 Hz, 1H) 1.79 (br s, 3H) 1.97 (br s, 1H) 2.11-2.21 (m, 1H) 3.62 (s, 2H) 3.87 (s, 3H) 3.97 (br s, 1H) 4.39 (br s, 1H) 4.65 (br d, J=13.69 Hz, 2H) 7.34-7.42 (m, 2H) 7.50 (br t, J=7.43 Hz, 2H) 7.80 (s, 1H) 7.90 (s, 1H) 8.17 (br s, 1H) 8.29-8.34 (m, 1H);

MS (ESI, m/z): 468.2 [M+H]+

Example 69. 2-amino-N-((1S,2S)-2-hydroxycyclopentyl)-5-(1-methyl-1H-pyrazol-4-yl)nicotinamide Using (1S,2S)-2-aminocyclopentan-1-ol, the title compound was obtained as described for the example 1.

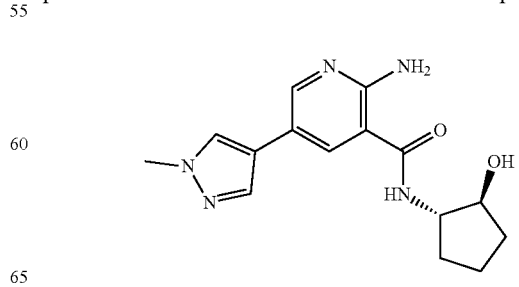

MS (ESI, m/z): 302.2 [M+H]+

Example 70. 2-amino-N-(cis-2-hydroxycyclopentyl)-5-(1-methyl-1H-pyrazol-4-yl)nicotinamide Using cis-2-aminocyclopentan-1-ol, the title compound was obtained as described for the example 1.

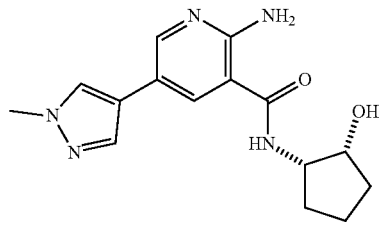

MS (ESI, m/z): 302.2 [M+H]+

Example 71. N-((1S,2S)-2-(benzyloxy)cyclopentyl)-2-(ethylamino)-5-(1-methyl-1H-pyrazol-4-yl)nicotinamide Using 2-(ethylamino)-5-(1-methyl-1H-pyrazol-4-yl)nicotinic acid, the title compound was obtained as described for the example 1.

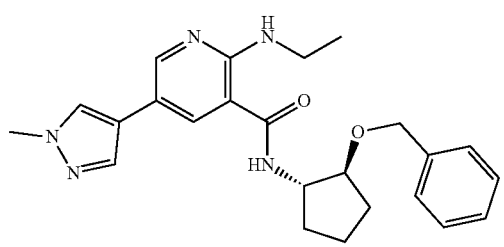

MS (ESI, m/z): 420.2 [M+H]+

Example 72. N-((1S,2S)-2-(benzyloxy)cyclopentyl)-2-((3,4-dimethylbenzyl-)amino)-5-(1-methyl-1H-pyrazol-4-yl)nicotinamide Using 2-((3,4-dimethylbenzyl)amino)-5-(1-methyl-1H-pyrazol-4-yl)nicotinic acid, the title compound was obtained as described for the example 1.

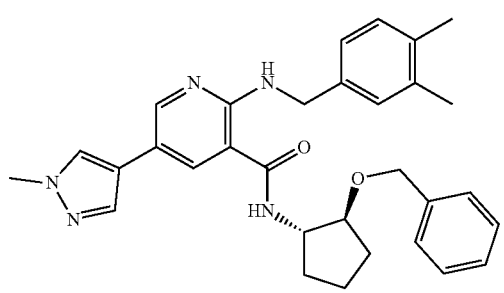

MS (ESI, m/z): 510.3 [M+H]+

Example 73. 2-amino-N-((6R,7S)-6-(benzyloxy)-1,4-dioxaspiro[4.4]nonan-7-yl)-5-(1-methyl-1H-pyrazol-4-yl)nicotinamide Using (6R,7S)-6-(benzyloxy)-1,4-dioxaspiro[4.4]nonan-7-amine, the title compound was obtained as described for the example 1.

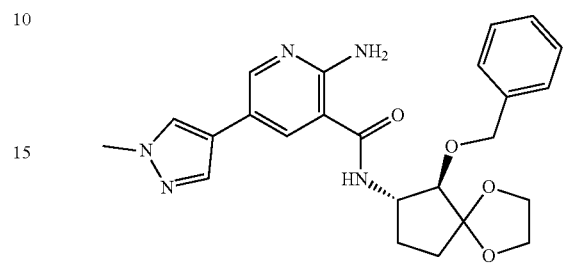

MS (ESI, m/z): 450.2 [M+H]+

Example 74. 2-amino-N-(trans-2-(benzyloxy)cyclohexyl)-5-(1-methyl-1H-pyrazol-4-yl)nicotinamide Using trans-2-(benzyloxy)cyclohexan-1-amine, the title compound was obtained as described for the example 1.

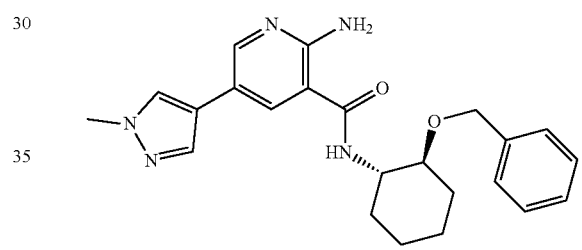

MS (ESI, m/z): 406.2 [M+H]+

Example 75. 2-amino-N-((1S,2S)-2-(benzyloxy)cyclohexyl)-5-(1-methyl-1H-pyrazol-4-yl)nicotinamide Using (1S,2S)-2-(benzyloxy)cyclohexan-1-amine, the title compound was obtained as described for the example 1.

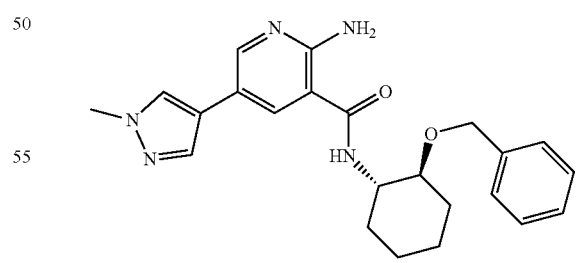

$^1$H NMR (400 MHz, CD$_3$OD) δ ppm 1.28-1.47 (m, 4H) 1.77 (br s, 1H) 1.83 (br s, 1H) 1.97 (s, 1H) 2.29 (br s, 1H) 3.38 (br d, J=9.39 Hz, 1H) 3.92 (s, 3H) 3.99 (br d, J=10.17 Hz, 1H) 4.41-4.47 (m, 1H) 4.68 (br d, J=12.13 Hz, 1H) 7.13 (dt, J=14.57, 6.99 Hz, 3H) 7.25 (br d, J=7.43 Hz, 2H) 7.77 (s, 1H) 7.89 (s, 1H) 8.21 (s, 1H) 8.25 (br s, 1H);
MS (ESI, m/z): 406.2 [M+H]+

Example 76. 2-amino-N-(trans-2-(benzyl(methyl)amino)cyclopentyl)-5-(1-methyl-1H-pyrazol-4-yl)nicotinamide Using trans-N1-benzyl-N1-methylcyclopentane-1,2-diamine, the title compound was obtained as described for the example 1.

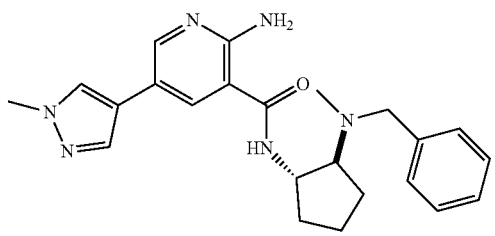

MS (ESI, m/z): 405.2 [M+H]$^+$

Example 77. 2-amino-5-(1-methyl-1H-pyrazol-4-yl)-N-((1S,2S)-2-(phenoxymethyl)cyclopentyl)nicotinamide Using (1S,2S)-2-(phenoxymethyl)cyclopentan-1-amine, the title compound was obtained as described for the example 1.

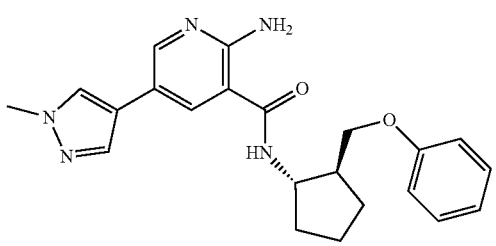 [SMILES: Cn1cc(-c2cnc(N)c(C(=O)N[C@H]3CCC[C@@H]3COc3ccccc3)c2)cn1]

MS (ESI, m/z): 392.2 [M+H]$^+$

Example 78. 2-amino-N-((1S,2S)-2-((3,4-dimethylphenoxy)methyl)cyclopentyl)-5-(1-methyl-1H-pyrazol-4-yl)nicotinamide Using (1S,2S)-2-((3,4-dimethylphenoxy)methyl)cyclopentan-1-amine, the title compound was obtained as described for the example 1.

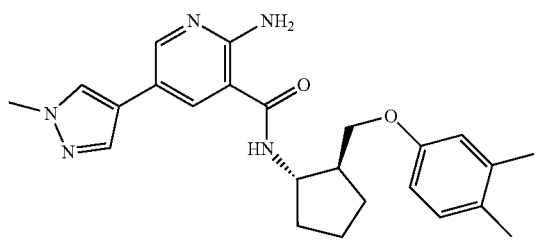

MS (ESI, m/z): 420.2 [M+H]$^+$

Example 79. 2-amino-N-(trans-2,2-difluoro-5-(phenoxymethyl)cyclopentyl)-5-(1-methyl-1H-pyrazol-4-yl)nicotinamide Using (trans-2,2-difluoro-5-(phenoxymethyl)cyclopentan-1-amine, the title compound was obtained as described for the example 1.

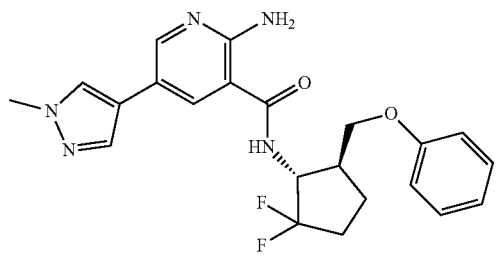 [SMILES: Cn1cc(-c2cnc(N)c(C(=O)N[C@@H]3[C@@H](COc4ccccc4)CCC3(F)F)c2)cn1]

MS (ESI, m/z): 428.2 [M+H]$^+$

Example 80. 2-amino-N-((1S,2S)-2-(((2,3-dihydro-1H-inden-5-yl)oxy)-methyl)cyclopentyl)-5-(1-methyl-1H-pyrazol-4-yl)nicotinamide Using (1S,2S)-2-(((2,3-dihydro-1H-inden-5-yl)oxy)methyl)cyclopentan-1-amine, the title compound was obtained as described for the example 1.

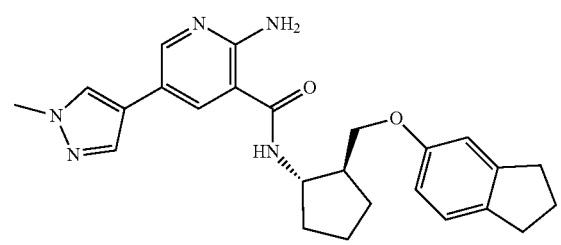 [SMILES: Cn1cc(-c2cnc(N)c(C(=O)N[C@H]3CCC[C@@H]3COc3ccc4c(c3)CCC4)c2)cn1]

MS (ESI, m/z): 432.2 [M+H]$^+$

Example 81. 2-amino-5-(1-methyl-1H-pyrazol-4-yl)-N-((1S,2S)-2-((3,4,5-trimethylphenoxy)methyl)cyclopentyl)nicotinamide Using (1S,2S)-2-((3,4,5-trimethylphenoxy)methyl)cyclopentan-1-amine, the title compound was obtained as described for the example 1.

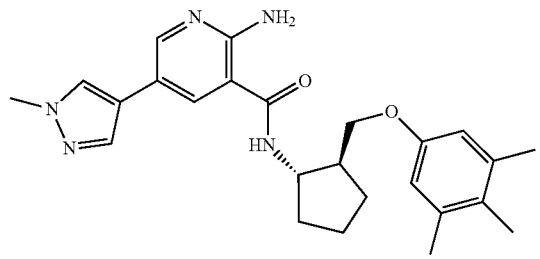

MS (ESI, m/z): 434.3 [M+H]$^+$

Example 82. 2-amino-N-((1S,2S)-2-((3-(dimethylamino)phenoxy)-methyl)cyclopentyl)-5-(1-methyl-1H-pyrazol-4-yl)nicotinamide Using 3-(((1S,2S)-2-aminocyclopentyl)methoxy)-N,N-dimethylaniline, the title compound was obtained as described for the example 1.

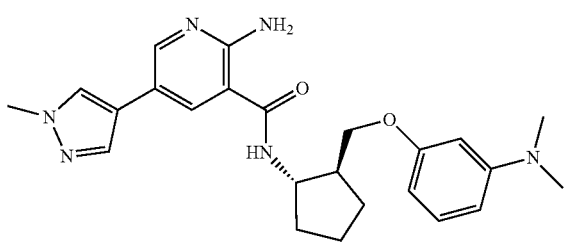

MS (ESI, m/z): 435.2 [M+H]+

Example 83. 2-amino-5-(1-methyl-1H-pyrazol-4-yl)-N-((1S,2S)-2-((3-(piperidine-1-carbonyl)phenoxy)methyl)cyclopentyl)nicotinamide Using (3-(((1S,2S)-2-aminocyclopentyl)methoxy)phenyl)(piperidin-1-yl)methanone, the title compound was obtained as described for the example 1.

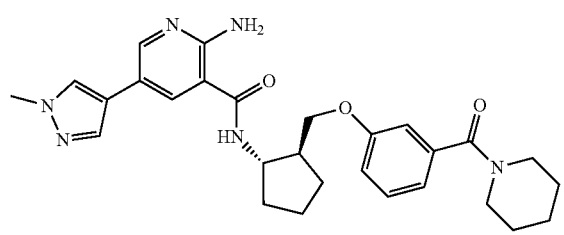 [SMILES: Cn1cc(-c2cnc(N)c(C(=O)N[C@H]3CCC[C@@H]3COc3cccc(C(=O)N4CCCCC4)c3)c2)cn1]

MS (ESI, m/z): 503.3 [M+H]+

Example 84. 2-amino-5-(1-methyl-1H-pyrazol-4-yl)-N-((1S,2S)-2-((4-phenoxyphenoxy)methyl)cyclopentyl)nicotinamide Using (1S,2S)-2-((4-phenoxyphenoxy)methyl)cyclopentan-1-amine, the title compound was obtained as described for the example 1.

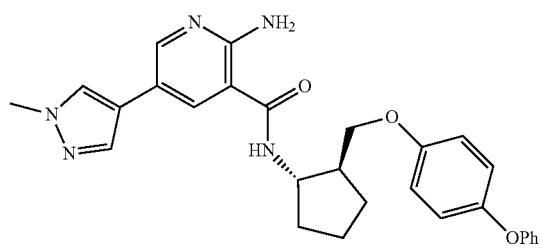 [SMILES: Cn1cc(-c2cnc(N)c(C(=O)N[C@H]3CCC[C@@H]3COc3ccc(Oc4ccccc4)cc3)c2)cn1]

MS (ESI, m/z): 484.2 [M+H]+

Example 85. 2-amino-N-((1S,2S)-2-((benzyloxy)methyl)cyclopentyl)-5-(1-methyl-1H-pyrazol-4-yl)nicotinamide Using (1S,2S)-2-((benzyloxy)methyl)cyclopentan-1-amine, the title compound was obtained as described for the example 1.

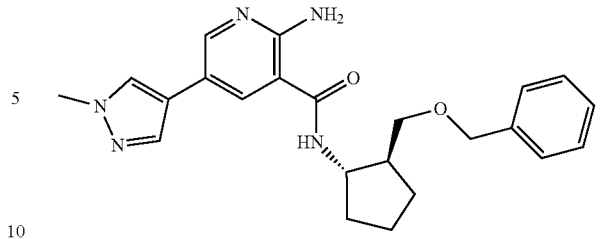

MS (ESI, m/z): 406.2 [M+H]+

Example 86. 2-amino-5-(1-methyl-1H-pyrazol-4-yl)-N-((1S,2S)-2-(((4'-((4-methylpiperazin-1-yl)methyl)-[1,1'-biphenyl]-4-yl)oxy)methyl)cyclopentyl)nicotinamide Using (1S,2S)-2-(((4'-((4-methylpiperazin-1-yl)methyl)-[1,1'-biphenyl]-4-yl)oxy)methyl)cyclopentan-1-amine, the title compound was obtained as described for the example 1.

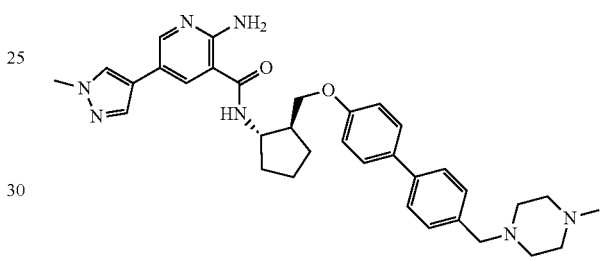

$^1$H NMR (600 MHz, CD$_3$OD) δ ppm 1.56-1.65 (m, 1H) 1.67-1.75 (m, 1H) 1.79 (br d, J=6.46 Hz, 1H) 1.85 (br d, J=8.80 Hz, 1H) 2.03-2.12 (m, 1H) 2.16 (br dd, J=12.91, 5.87 Hz, 1H) 2.43-2.51 (m, 1H) 2.84 (s, 3H) 3.75 (s, 2H) 3.89 (s, 3H) 4.10 (d, J=5.87 Hz, 2H) 4.30-4.38 (m, 1H) 6.96 (d, J=8.80 Hz, 2H) 7.38 (br d, J=8.22 Hz, 2H) 7.50 (dd, J=16.43, 8.22 Hz, 4H) 7.86 (s, 1H) 7.98 (s, 1H) 8.21 (d, J=2.35 Hz, 1H) 8.51 (d, J=2.35 Hz, 1H);
MS (ESI m/z): 580.3 [M+H]+

Example 87. (1S,2S)-2-(benzyloxyl)cyclopentyl 2-amino-5-(1-methyl-1H-pyrazol-4-yl)nicotinate Using (1S,2S)-2-(benzyloxy)cyclopentan-1-ol, the title compound was obtained as described for the example 1.

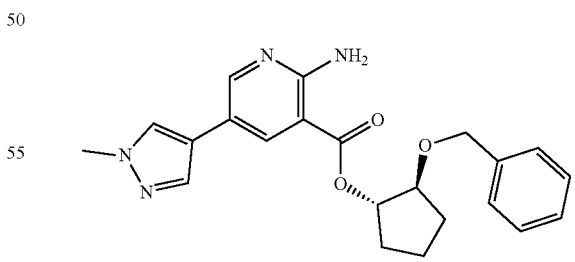

MS (ESI, m/z): 393.2 [M+H]+

Example 88. 2-amino-5-(1-methyl-1H-pyrazol-4-yl)-N-((1S,2R)-2-phenethylcyclopentyl)nicotinamide Using (1S,2R)-2-phenethylcyclopentan-1-amine, the title compound was obtained as described for the example 1.

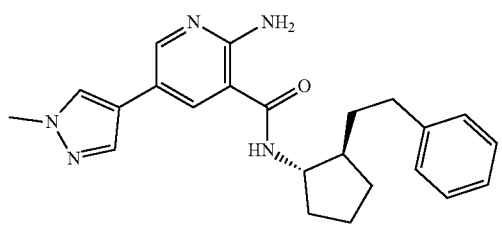 [SMILES: Cn1cc(-c2cnc(N)c(C(=O)N[C@H]3CCC[C@@H]3CCc3ccccc3)c2)cn1]

MS (ESI, m/z): 390.2 [M+H]+

Example 89. 2-amino-N-(trans-4-(benzyloxy)tetrahydrofuran-3-yl)-5-(1-methyl-1H-pyrazol-4-yl)nicotinamide Using trans-4-(benzyloxy)tetrahydrofuran-3-amine, the title compound was obtained as described for the example 1.

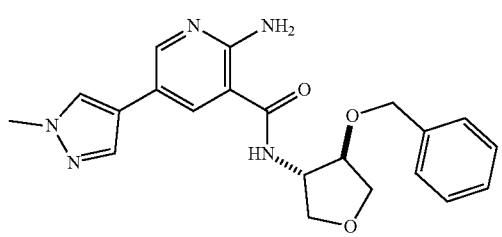

MS (ESI, m/z): 394.2 [M+H]+

Example 90. 2-amino-5-(1-methyl-1H-pyrazol-4-yl)-N-(trans-4-morpholino-tetrahydrofuran-3-yl)nicotinamide Using trans-4-morpholinotetrahydrofuran-3-amine, the title compound was obtained as described for the example 1.

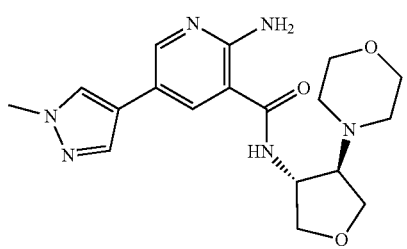 [SMILES: Cn1cc(-c2cnc(N)c(C(=O)N[C@H]3COC[C@@H]3N3CCOCC3)c2)cn1]

MS (ESI, m/z): 373.2 [M+H]+

Example 91. 2-amino-5-(1-methyl-1H-pyrazol-4-yl)-N-(trans-4-(pyrrolidin-1-yl)tetrahydrofuran-3-yl)nicotinamide Using trans-4-(pyrrolidin-1-yl)tetrahydrofuran-3-amine, the title compound was obtained as described for the example 1.

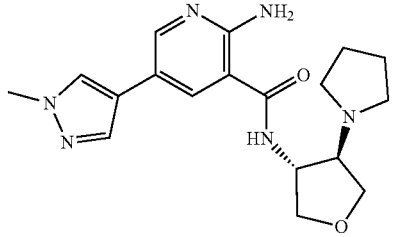 [SMILES: Cn1cc(-c2cnc(N)c(C(=O)N[C@H]3COC[C@@H]3N3CCCC3)c2)cn1]

MS (ESI, m/z): 357.2 [M+H]+

Example 92. 2-amino-N-(cis-4-hydroxytetrahydrofuran-3-yl)-5-(1-methyl-1H-pyrazol-4-yl)nicotinamide Using cis-4-aminotetrahydrofuran-3-ol, the title compound was obtained as described for the example 1.

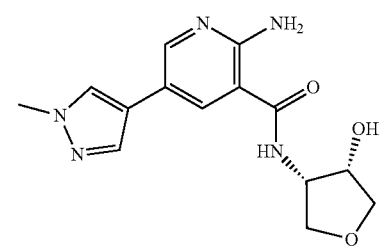 [SMILES: Cn1cc(-c2cnc(N)c(C(=O)N[C@H]3COC[C@H]3O)c2)cn1]

MS (ESI, m/z): 304.1 [M+H]+

Example 93. 2-amino-N-(4-(benzyloxy)-1-methylpyrrolidin-3-yl)-5-(1-methyl-1H-pyrazol-4-yl)nicotinamide Using trans-4-(benzyloxy)-1-methylpyrrolidin-3-amine, the title compound was obtained as described for the example 1.

(trans-racemate)

MS (ESI, m/z): 407.2 [M+H]+

Example 94. 2-amino-N-(trans-4-(benzyloxy)-1-isopropylpyrrolidin-3-yl)-5-(1-methyl-1H-pyrazol-4-yl)nicotinamide Using trans-4-(benzyloxy)-1-isopropylpyrrolidin-3-amine, the title compound was obtained as described for the example 1.

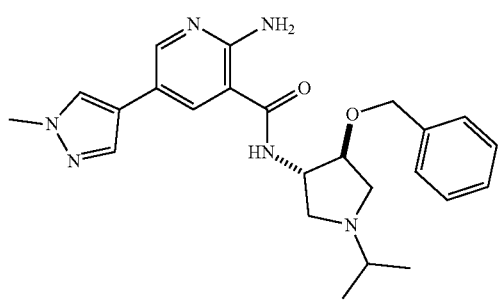

MS (ESI, m/z): 435.2 [M+H]$^+$

Example 95. (R)-2-amino-N-(2-(benzyloxy)propyl)-5-(1-methyl-1H-pyrazol-4-yl)nicotinamide Using (R)-2-(benzyloxy)propan-1-amine, the title compound was obtained as described for the example 1.

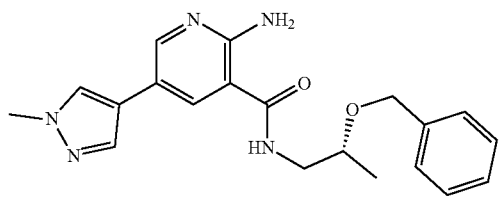 [SMILES: C[C@H](CNC(=O)c1cc(-c2cnn(C)c2)cnc1N)OCc1ccccc1]

MS (ESI, m/z): 366.2 [M+H]$^+$

Example 96. (S)-2-amino-N-(2-(benzyloxy)propyl)-5-(1-methyl-1H-pyrazol-4-yl)nicotinamide Using (S)-2-(benzyloxy)propan-1-amine, the title compound was obtained as described for the example 1.

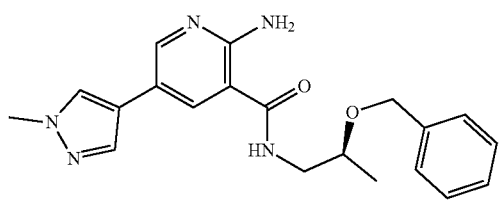 [SMILES: C[C@@H](CNC(=O)c1cc(-c2cnn(C)c2)cnc1N)OCc1ccccc1]

MS (ESI, m/z): 366.2 [M+H]$^+$

Example 97. (S)-2-amino-N-(1-(benzyloxy)propan-2-yl)-5-(1-methyl-1H-pyrazol-4-yl)nicotinamide Using (S)-1-(benzyloxy)propan-2-amine, the title compound was obtained as described for the example 1.

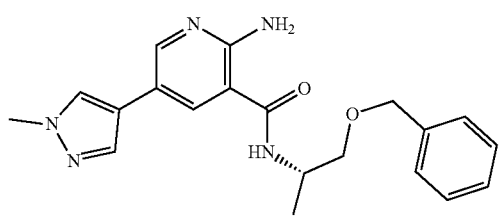 [SMILES: C[C@@H](COCc1ccccc1)NC(=O)c1cc(-c2cnn(C)c2)cnc1N]

MS (ESI, m/z): 366.2 [M+H]$^+$

Example 98. (R)-2-amino-N-(1-(benzyloxy)propan-2-yl)-5-(1-methyl-1H-pyrazol-4-yl)nicotinamide Using (R)-1-(benzyloxy)propan-2-amine, the title compound was obtained as described for the example 1.

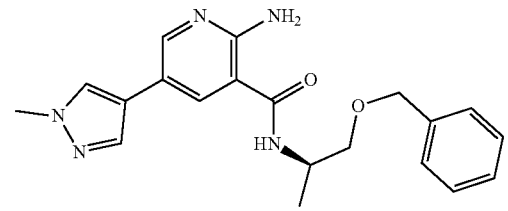 [SMILES: C[C@H](COCc1ccccc1)NC(=O)c1cc(-c2cnn(C)c2)cnc1N]

MS (ESI, m/z): 366.2 [M+H]$^+$

Example 99. 2-amino-N-(1-(benzyloxy)-2-methylpropan-2-yl)-5-(1-methyl-1H-pyrazol-4-yl)nicotinamide Using 1-(benzyloxy)-2-methylpropan-2-amine, the title compound was obtained as described for the example 1.

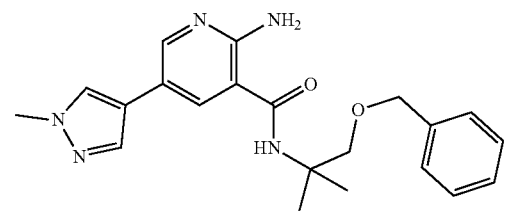 [SMILES: Cn1cc(-c2cnc(N)c(C(=O)NC(C)(C)COCc3ccccc3)c2)cn1]

MS (ESI, m/z): 380.2 [M+H]$^+$

Example 100. (R)-2-amino-N-(1-((3,4-dimethylbenzyl)oxy)propan-2-yl)-5-(1-methyl-1H-pyrazol-4-yl)nicotinamide Using (R)-1-((3,4-dimethylbenzyl)oxy)propan-2-amine, the title compound was obtained as described for the example 1.

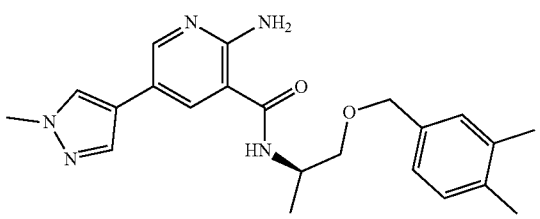

MS (ESI, m/z): 394.2 [M+H]$^+$

Example 101. (S)-2-amino-N-(2-((3,4-dimethylbenzyl)oxy)propyl)-5-(1-methyl-1H-pyrazol-4-yl)nicotinamide Using (S)-2-((3,4-dimethylbenzyl)oxy)propan-1-amine, the title compound was obtained as described for the example 1.

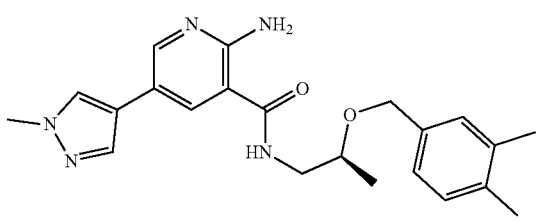

MS (ESI, m/z): 394.2 [M+H]+

Example 102. (R)-2-amino-N-(1-((4-chlorobenzyl)oxy)propan-2-yl)-5-(1-methyl-1H-pyrazol-4-yl)nicotinamide Using (R)-1-((4-chlorobenzyl)oxy)propan-2-amine, the title compound was obtained as described for the example 1.

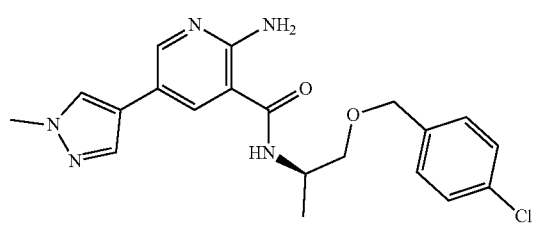 [SMILES: C[C@H](COCc1ccc(Cl)cc1)NC(=O)c1cc(-c2cnn(C)c2)cnc1N]

MS (ESI, m/z): 400.2 [M+H]+

Example 103. (S)-2-amino-N-(2-((4-chlorobenzyl)oxy)propyl)-5-(1-methyl-1H-pyrazol-4-yl)nicotinamide Using (S)-2-((4-chlorobenzyl)oxy)propan-1-amine, the title compound was obtained as described for the example 1.

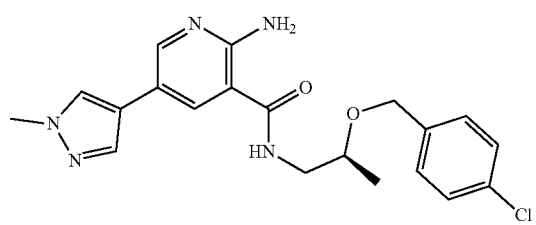 [SMILES: C[C@@H](CNC(=O)c1cc(-c2cnn(C)c2)cnc1N)OCc1ccc(Cl)cc1]

MS (ESI, m/z): 400.2 [M+H]+

Example 104. (R)-2-amino-N-(1-((3,4-dichlorobenzyl)oxy)propan-2-yl)-5-(1-methyl-1H-pyrazol-4-yl)nicotinamide Using (R)-1-((3,4-dichlorobenzyl)oxy)propan-2-amine, the title compound was obtained as described for the example 1.

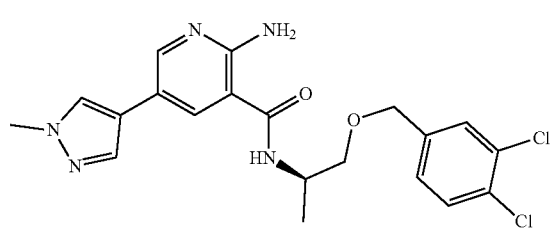 [SMILES: C[C@H](COCc1ccc(Cl)c(Cl)c1)NC(=O)c1cc(-c2cnn(C)c2)cnc1N]

MS (ESI, m/z): 434.1 [M+H]+

Example 105. (S)-2-amino-N-(2-((3,4-dichlorobenzyl)oxy)propyl)-5-(1-methyl-1H-pyrazol-4-yl)nicotinamide Using (S)-2-((3,4-dichlorobenzyl)oxy)propan-1-amine, the title compound was obtained as described for the example 1.

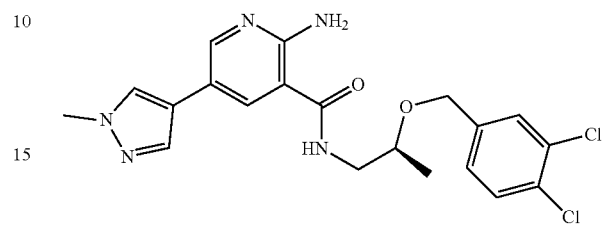

MS (ESI, m/z): 419.1 [M+H]+

Example 106. (R)-2-amino-N-(1-((3-methoxybenzyl)oxy)propan-2-yl)-5-(1-methyl-1H-pyrazol-4-yl)nicotinamide Using (R)-1-((3-methoxybenzyl)oxy)propan-2-amine, the title compound was obtained as described for the example 1.

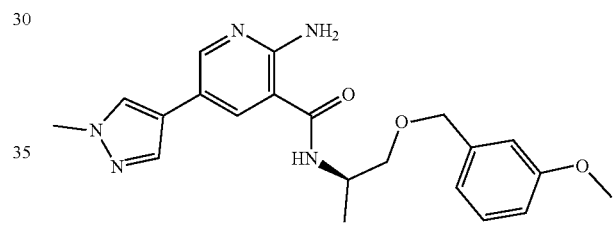

MS (ESI, m/z): 396.2 [M+H]+

Example 107. (S)-2-amino-N-(2-((3-methoxybenzyl)oxy)propyl)-5-(1-methyl-1H-pyrazol-4-yl)nicotinamide Using (S)-2-((3-methoxybenzyl)oxy)propan-1-amine, the title compound was obtained as described for the example 1.

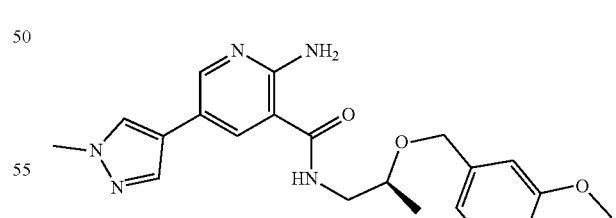

MS (ESI, m/z): 396.2 [M+H]+

Example 108. (R)-2-amino-N-(1-(benzyloxy)butan-2-yl)-5-(1-methyl-1H-pyrazol-4-yl)nicotinamide Using (R)-1-(benzyloxy)butan-2-amine, the title compound was obtained as described for the example 1.

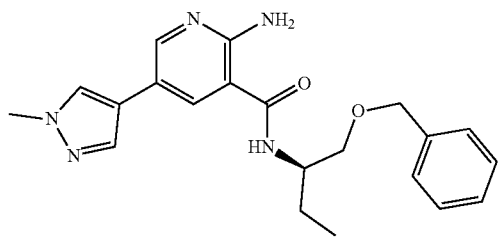 [SMILES: CC[C@H](COCc1ccccc1)NC(=O)c1cc(-c2cnn(C)c2)cnc1N]

MS (ESI, m/z): 380.2 [M+H]+

Example 109. (S)-2-amino-N-(1-(benzyloxy)-3-methylbutan-2-yl)-5-(1-methyl-1H-pyrazol-4-yl)nicotinamide Using (S)-1-(benzyloxy)-3-methylbutan-2-amine, the title compound was obtained as described for the example 1.

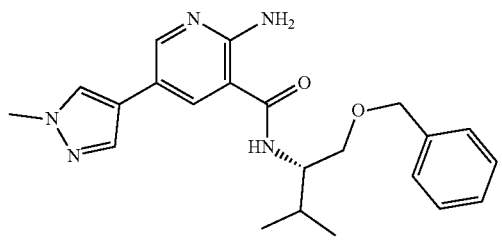 [SMILES: CC(C)[C@@H](COCc1ccccc1)NC(=O)c1cc(-c2cnn(C)c2)cnc1N]

MS (ESI, m/z): 394.2 [M+H]+

Example 110. (R)-2-amino-N-(1-(benzyloxy)-3-methylbutan-2-yl)-5-(1-methyl-1H-pyrazol-4-yl)nicotinamide Using (R)-1-(benzyloxy)-3-methylbutan-2-amine, the title compound was obtained as described for the example 1.

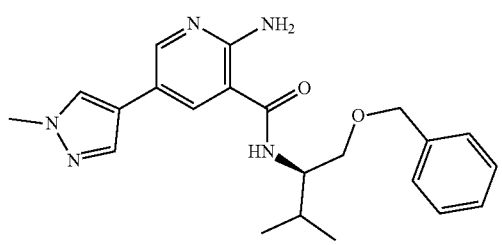 [SMILES: CC(C)[C@H](COCc1ccccc1)NC(=O)c1cc(-c2cnn(C)c2)cnc1N]

MS (ESI, m/z): 394.2 [M+H]+

Example 111. (S)-2-amino-N-(1-(benzyloxy)-4-methylpentan-2-yl)-5-(1-methyl-1H-pyrazol-4-yl)nicotinamide Using (S)-1-(benzyloxy)-4-methylpentan-2-amine, the title compound was obtained as described for the example 1.

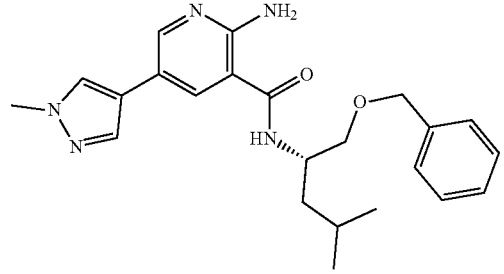 [SMILES: CC(C)C[C@@H](COCc1ccccc1)NC(=O)c1cc(-c2cnn(C)c2)cnc1N]

MS (ESI, m/z): 408.2 [M+H]+

Example 112. (R)-2-amino-N-(1-(benzyloxy)-4-methylpentan-2-yl)-5-(1-methyl-1H-pyrazol-4-yl)nicotinamide Using (R)-1-(benzyloxy)-4-methylpentan-2-amine, the title compound was obtained as described for the example 1.

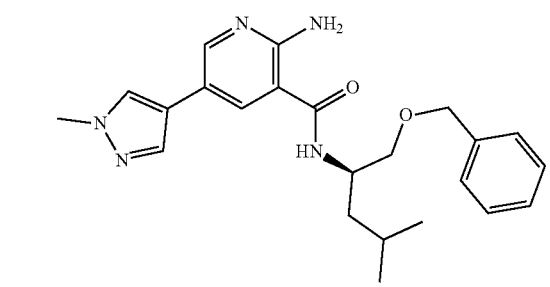 [SMILES: CC(C)C[C@H](COCc1ccccc1)NC(=O)c1cc(-c2cnn(C)c2)cnc1N]

MS (ESI, m/z): 408.2 [M+H]+

Example 113. (R)-2-amino-N-(2-(benzyloxy)-1-cyclohexylethyl)-5-(1-methyl-1H-pyrazol-4-yl)nicotinamide Using (R)-2-(benzyloxy)-1-cyclohexylethan-1-amine, the title compound was obtained as described for the example 1.

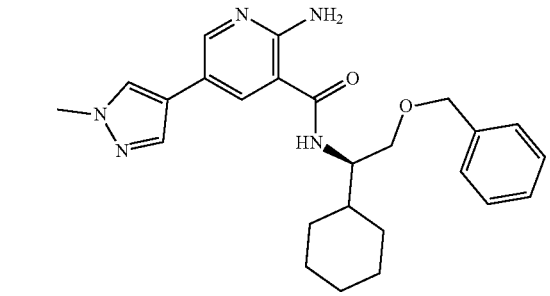 [SMILES: Cn1cc(-c2cnc(N)c(C(=O)N[C@@H](COCc3ccccc3)C3CCCCC3)c2)cn1]

MS (ESI, m/z): 434.3 [M+H]+

Example 114. (R)-2-amino-N-(1-cyclohexyl-2-hydroxyethyl)-5-(1-methyl-1H-pyrazol-4-yl)nicotinamide Using (R)-2-amino-2-cyclohexylethan-1-ol, the title compound was obtained as described for the example 1.

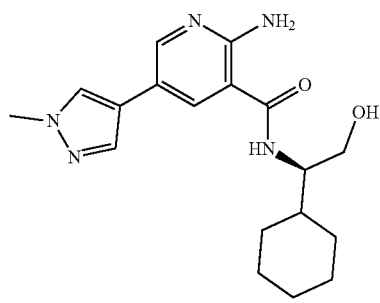 [SMILES: Cn1cc(-c2cnc(N)c(C(=O)N[C@@H](CO)C3CCCCC3)c2)cn1]

MS (ESI, m/z): 344.3 [M+H]+

Example 115. (S)-2-amino-N-(2-(benzyloxy)-1-phenylethyl)-5-(1-methyl-1H-pyrazol-4-yl)nicotinamide Using (S)-2-(benzyloxy)-1-phenylethan-1-amine, the title compound was obtained as described for the example 1.

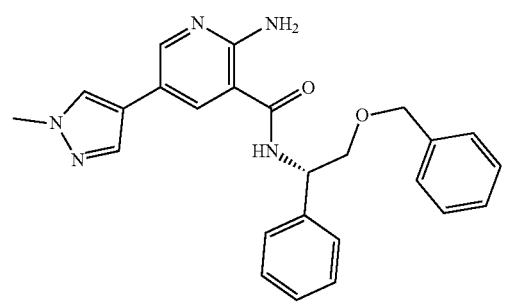 [SMILES: Cn1cc(-c2cnc(N)c(C(=O)N[C@H](COCc3ccccc3)c3ccccc3)c2)cn1]

MS (ESI, m/z): 428.2 [M+H]+

Example 116. (R)-2-amino-N-(2-(benzyloxy)-1-phenylethyl)-5-(1-methyl-1H-pyrazol-4-yl)nicotinamide Using (R)-2-(benzyloxy)-1-phenylethan-1-amine, the title compound was obtained as described for the example 1.

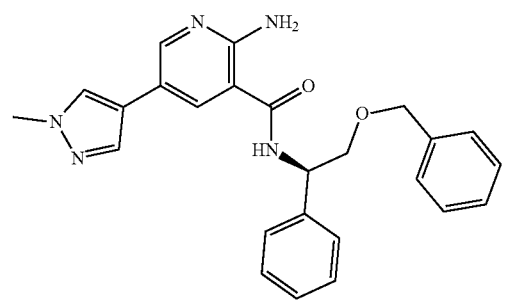 [SMILES: Cn1cc(-c2cnc(N)c(C(=O)N[C@@H](COCc3ccccc3)c3ccccc3)c2)cn1]

MS (ESI, m/z): 428.2 [M+H]+

Example 117. (S)-2-amino-N-(1-(benzyloxy)-3-phenylpropan-2-yl)-5-(1-methyl-1H-pyrazol-4-yl)nicotinamide Using (S)-1-(benzyloxy)-3-phenylpropan-2-amine, the title compound was obtained as described for the example 1.

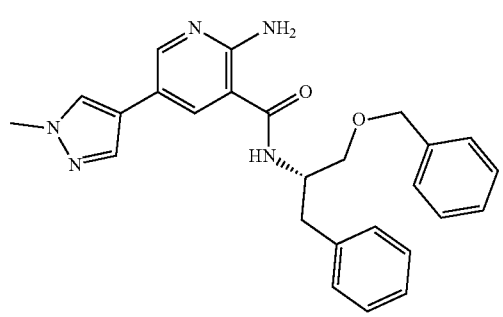 [SMILES: Cn1cc(-c2cnc(N)c(C(=O)N[C@H](COCc3ccccc3)Cc3ccccc3)c2)cn1]

MS (ESI m/z): 442.2 [M+H]+

Example 118. (R)-2-amino-N-(1-(benzyloxy)-3-phenylpropan-2-yl)-5-(1-methyl-1H-pyrazol-4-yl)nicotinamide Using (R)-1-(benzyloxy)-3-phenylpropan-2-amine, the title compound was obtained as described for the example 1.

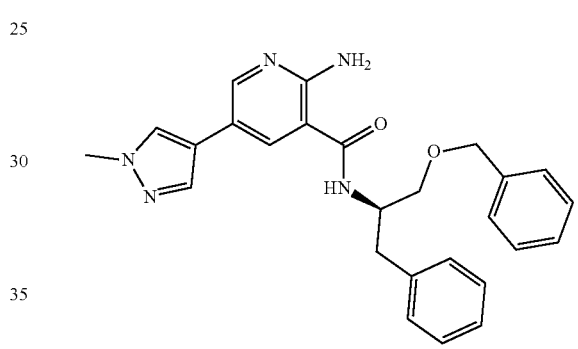

MS (ESI, m/z): 442.2 [M+H]+

Example 119. (R)-2-amino-N-(1-(cyclobutylmethoxy)propan-2-yl)-5-(1-methyl-1H-pyrazol-4-yl)nicotinamide Using (R)-1-(cyclobutylmethoxy)propan-2-amine, the title compound was obtained as described for the example 1.

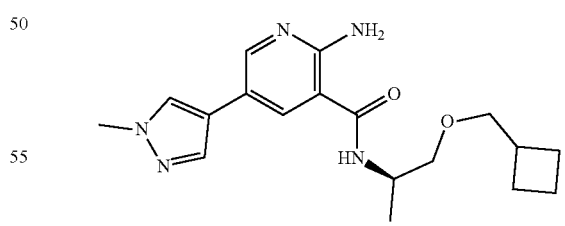

MS (ESI, m/z): 344.2 [M+H]+

Example 120. methyl N-(2-amino-5-(1-methyl-1H-pyrazol-4-yl)nicotinoyl)-O-benzyl-L-serinate Using methyl O-benzyl-L-serinate, the title compound was obtained as described for the example 1.

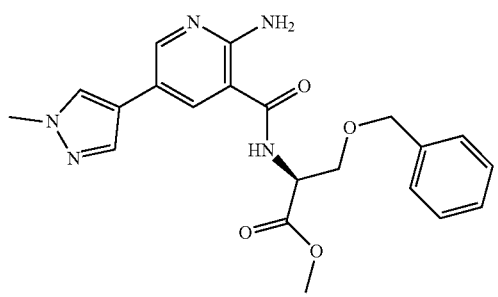 [SMILES: COC(=O)[C@H](COCc1ccccc1)NC(=O)c1cc(-c2cnn(C)c2)cnc1N]

MS (ESI, m/z): 410.2 [M+H]+

Example 121. methyl N-(2-amino-5-(1-methyl-1H-pyrazol-4-yl)nicotinoyl)-O-benzyl-L-threoninate Using methyl O-benzyl-L-threoninate, the title compound was obtained as described for the example 1.

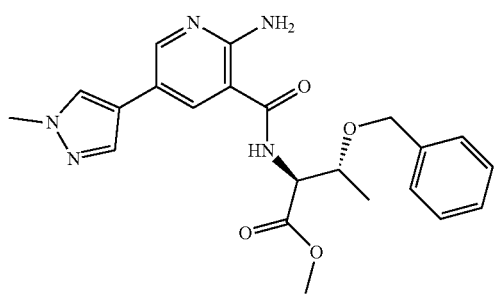 [SMILES: COC(=O)[C@@H](NC(=O)c1cc(-c2cnn(C)c2)cnc1N)[C@@H](C)OCc1ccccc1]

MS (ESI, m/z): 424.2 [M+H]+

Example 122 2-amino-N-((2S,3R)-3-(benzyloxy)-1-(methylamino)-1-oxobutan-2-yl)-5-(1-methyl-1H-pyrazol-4-yl)nicotinamide Using (2S,3R)-2-amino-3-(benzyloxy)-N-methylbutanamide, the title compound was obtained as described for the example 1.

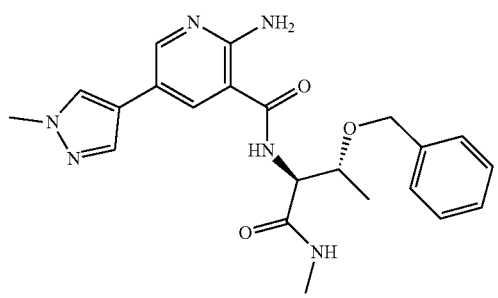 [SMILES: CNC(=O)[C@@H](NC(=O)c1cc(-c2cnn(C)c2)cnc1N)[C@@H](C)OCc1ccccc1]

MS (ESI m/z): 423.2 [M+H]+

Example 123. 2-amino-N-((2S,3R)-3-(benzyloxy)-1-oxo-1-(propylamino)butan-2-yl)-5-(1-methyl-1H-pyrazol-4-yl)nicotinamide Using (2S,3R)-2-amino-3-(benzyloxy)-N-propylbutanamide, the title compound was obtained as described for the example 1.

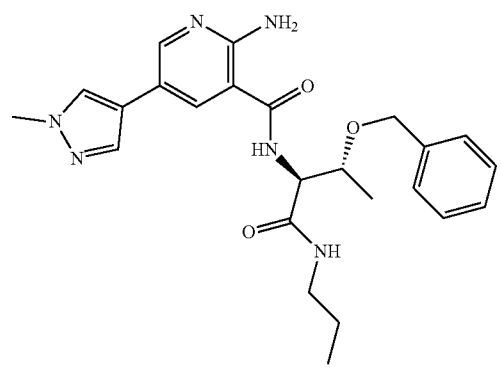 [SMILES: CCCNC(=O)[C@@H](NC(=O)c1cc(-c2cnn(C)c2)cnc1N)[C@@H](C)OCc1ccccc1]

MS (ESI, m/z): 451.2 [M+H]+

Example 124. 2-amino-N-((2S,3R)-3-(benzyloxy)-1-(cyclopentylamino)-1-oxobutan-2-yl)-5-(1-methyl-1H-pyrazol-4-yl)nicotinamide Using (2S,3R)-2-amino-3-(benzyloxy)-N-cyclopentylbutanamide, the title compound was obtained as described for the example 1.

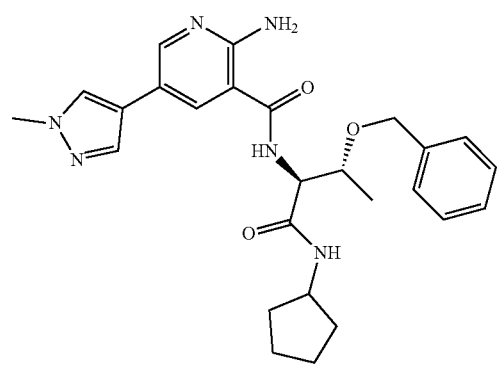 [SMILES: C[C@@H](OCc1ccccc1)[C@H](NC(=O)c1cc(-c2cnn(C)c2)cnc1N)C(=O)NC1CCCC1]

MS (ESI, m/z): 477.3 [M+H]+

Example 125. 2-amino-N-((2S,3R)-3-(benzyloxy)-1-oxo-1-(pyrrolidin-1-yl)butan-2-yl)-5-(1-methyl-1H-pyrazol-4-yl)nicotinamide Using (2S,3R)-2-amino-3-(benzyloxy)-1-(pyrrolidin-1-yl)butan-1-one, the title compound was obtained as described for the example 1.

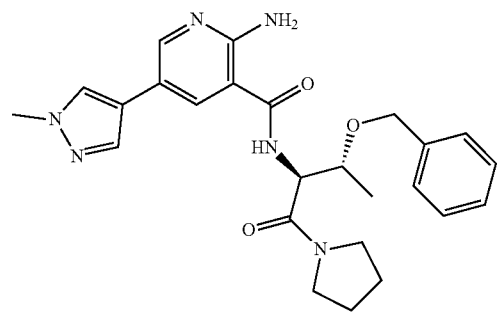 [SMILES: C[C@@H](OCc1ccccc1)[C@H](NC(=O)c1cc(-c2cnn(C)c2)cnc1N)C(=O)N1CCCC1]

MS (ESI, m/z): 463.2 [M+H]+

Example 126. benzyl (2-amino-5-(1-methyl-1H-pyrazol-4-yl)nicotinoyl)-L-alaninate Using benzyl L-alaninate, the title compound was obtained as described for the example 1.

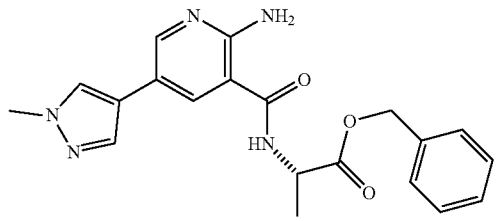

$^1$H NMR (400 MHz, CD$_3$OD) δ ppm 1.51 (d, J=7.43 Hz, 3H) 3.92 (s, 3H) 4.64 (d, J=7.43 Hz, 1H) 5.12-5.25 (m, 2H) 7.21-7.42 (m, 5H) 7.84 (s, 1H) 7.96-8.00 (m, 1H) 8.21-8.27 (m, 1H) 8.54 (d, J=2.35 Hz, 1H);
MS (ESI, m/z): 380.2 [M+H]$^+$ Example 127. benzyl (2-amino-5-(1-methyl-1H-pyrazol-4-yl)nicotinoyl)-L-valinate Using benzyl L-valinate, the title compound was obtained as described for the example 1.

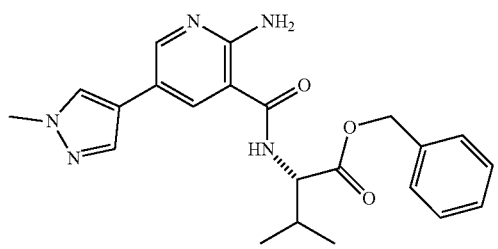

$^1$H NMR (400 MHz, CD$_3$OD) δ ppm 1.00 (dd, J=9.19, 6.85 Hz, 6H) 2.16-2.36 (m, 1H) 4.46-4.55 (m, 1H) 5.10-5.30 (m, 2H) 7.22-7.41 (m, 5H) 7.84 (d, J=0.78 Hz, 1H) 7.98 (s, 1H) 8.24 (d, J=1.96 Hz, 1H) 8.48 (d, J=2.35 Hz, 1H);
MS (ESI, m/z): 408.2 [M+H]$^+$ Example 128. benzyl (2-amino-5-(1-methyl-1H-pyrazol-4-yl)nicotinoyl)-L-serinate Using benzyl L-serinate, the title compound was obtained as described for the example 1.

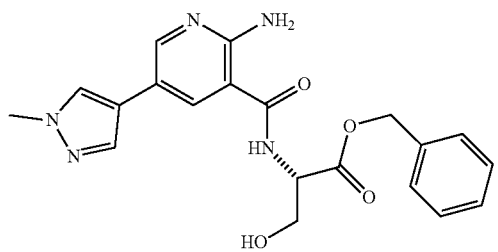

$^1$H NMR (400 MHz, CD$_3$OD) δ ppm 3.94-4.07 (m, 2H) 4.78 (dd, J=5.48, 4.30 Hz, 1H) 5.21 (s, 2H) 7.23-7.43 (m, 5H) 7.86 (d, J=0.78 Hz, 1H) 8.01 (s, 1H) 8.24 (d, J=1.96 Hz, 1H) 8.64 (d, J=1.96 Hz, 1H);
MS (ESI, m/z): 396.2 [M+H]$^+$ Example 129. 3-amino-N-((1S,2S)-2-(benzyloxy)cyclopentyl)-6-(1-methyl-1H-pyrazol-4-yl)pyrazine-2-carboxamide Using 3-amino-6-(1-methyl-1H-pyrazol-4-yl)pyrazine-2-carboxylic acid and (1S,2S)-2-(benzyloxy)cyclopentan-1-amine, the title compound was obtained as described for the example 1.

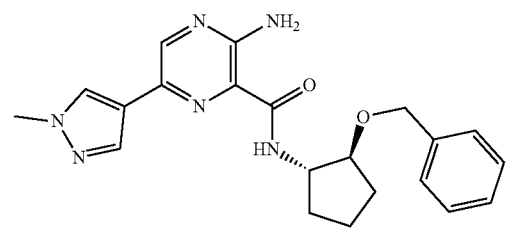 [SMILES: Cn1cc(-c2cnc(N)c(C(=O)N[C@H]3CCC[C@@H]3OCc3ccccc3)n2)cn1]

MS (ESI, m/z): 393.2 [M+H]$^+$

Example 130. 3-amino-N-((1S,2S)-2-((3,4-dimethylbenzyl)oxy)cyclopentyl)-6-(1-methyl-1H-pyrazol-4-yl)pyrazine-2-carboxamide Using 3-amino-6-(1-methyl-1H-pyrazol-4-yl)pyrazine-2-carboxylic acid and (1S,2S)-2-((3,4-dimethylbenzyl)oxy)cyclopentan-1-amine, the title compound was obtained as described for the example 1.

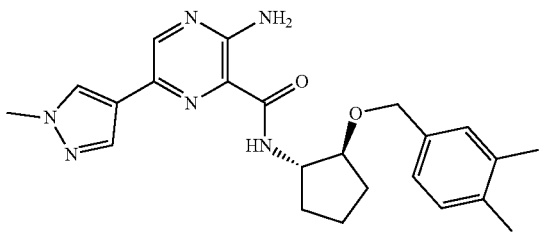

MS (ESL, m/z): 421.2 [M+H]$^+$

Example 131. (S)-3-amino-6-(1-methyl-1H-pyrazol-4-yl)-N-(1,2,3,4-tetrahydronaphthalen-1-yl)pyrazine-2-carboxamide Using 3-amino-6-(1-methyl-1H-pyrazol-4-yl)pyrazine-2-carboxylic acid and (S)-1,2,3,4-tetrahydronaphthalen-1-amine, the title compound was obtained as described for the example 1.

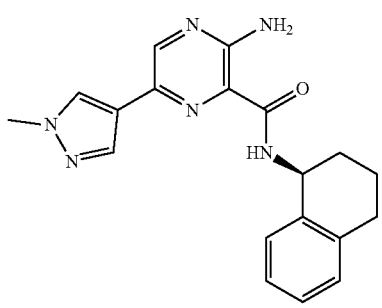 [SMILES: Cn1cc(-c2cnc(N)c(C(=O)N[C@H]3CCCc4ccccc43)n2)cn1]

MS (ESI, m/z): 349.2 [M+H]$^+$

Example 132. 3-amino-N-(trans-4-(benzyloxy)tetrahydrofuran-3-yl)-6-(1-methyl-1H-pyrazol-4-yl)pyrazine-2-carboxamide Using 3-amino-6-(1-methyl-1H-pyrazol-4-yl)pyrazine-2-carboxylic acid and trans-4-(benzyloxy)tetrahydrofuran-3-amine, the title compound was obtained as described for the example 1.

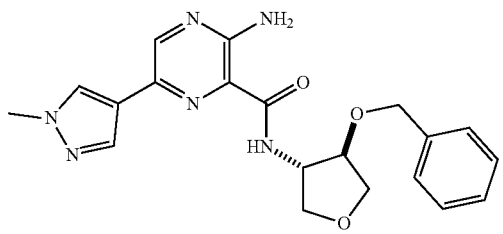

MS (ESI, m/z): 395.2 [M+H]$^+$

Example 133. 3-amino-N-(cis-4-(benzyloxy)tetrahydrofuran-3-yl)-6-(1-methyl-1H-pyrazol-4-yl)pyrazine-2-carboxamide Using 3-amino-6-(1-methyl-1H-pyrazol-4-yl)pyrazine-2-carboxylic acid and cis-4-(benzyloxy)tetrahydrofuran-3-amine, the title compound was obtained as described for the example 1.

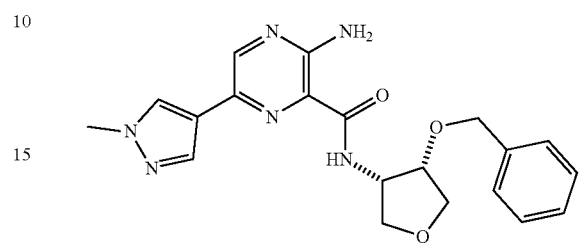

MS (ESI, m/z): 395.2 [M+H]$^+$

Example 134. 2-amino-N-((1S,2S)-2-((3'-amino-[1,1'-biphenyl]-4-yl)methoxy)cyclopentyl)-5-(1-methyl-1H-pyrazol-4-yl)nicotinamide Scheme for the Preparation of the Compound of Example 134:

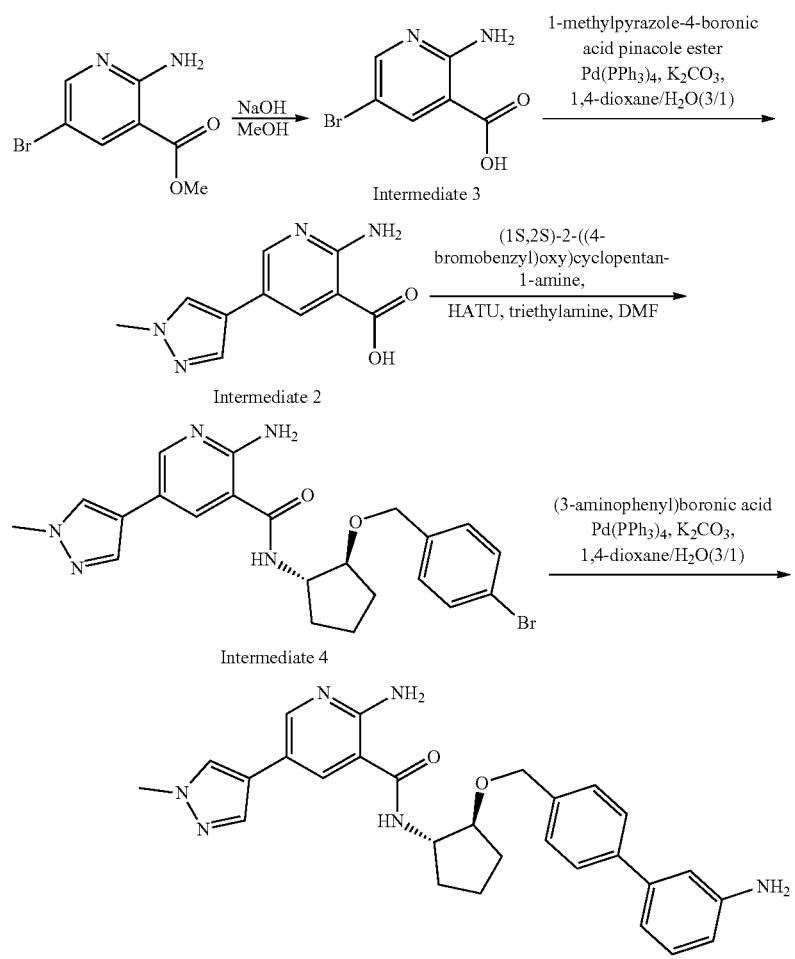

Intermediate 3

To a solution of methyl 2-amino-5-bromonicotinate (560 mg, 2.42 mmol) in 10 ml of MeOH was added 2N NaOH (2 ml, 4 mmol) and the mixture was heated at 65° C. for 1 hr, cooled to room temperature, neutralized (2 ml of 2N HCl), and the resulting precipitate was filtered, washed with MeOH, and dried to give 0.35 g of white solid.

$^1$H NMR (400 MHz, CD$_3$OD) δ ppm 8.17 (d, J=2.4 Hz, 1H), 8.23 (d, J=2.4 Hz, 1H);
MS (ESI, m/z): 217.0 [M+H]$^+$

Intermediate 2

To a mixture of intermediate 3 (4.48 g, 20.6 mmol) and 1-methylpyrazole-4-boronic acid pinacol ester (5.5 g, 26.8 mmol) in 100 ml of 1,4-dioxane/water (3/1) was added K$_2$CO$_3$ (8.5 g, 61.9 mmol) followed by Pd(PPh$_3$)$_4$ (1.19 g, 1.03 mmol). The reaction mixture was heated at 100° C. for 3 hrs, cooled to room temperature, and partitioned between water and EtOAc. Water layer was separated and adjusted to pH value between 4 and 5. The precipitate was collected by filtration and dried to afford 4 g of the title compound. The crude product was used for the next step without further purification.

$^1$H NMR (600 MHz, DMSO-d$_6$) δ ppm 3.82 (s, 3H), 5.73 (s, 2H), 7.77 (s, 1H), 8.05 (s, 1H), 8.13 (d, J=2.4 Hz, 1H), 8.42 (d, J=2.4 Hz, 1H);
MS (ESI, m/z): 219.1 [M+H]$^+$

Intermediate 4

To a mixture of intermediate 2 (350 mg, 1.60 mmol) and triethylamine (0.34 ml, 2.41 mmol) in 4 ml of DMF was added HATU (732 mg, 1.92 mmol) followed by (1S,2S)-2-((4-bromobenzyl)oxy)cyclopentan-1-amine (475 mg, 1.76 mmol). The mixture was stirred at room temperature for 1 hr and then saturated sodium bicarbonate solution was added. The mixture was extracted with EtOAc, washed with brine, dried over MgSO$_4$, and concentrated in vacuo. The crude product was purified through silicagel column chromatography to give 650 mg of off-white solid.

$^1$H NMR (600 MHz, CD$_3$OD) δ ppm 1.59-1.69 (m, 1H) 1.72-1.78 (m, 1H) 1.78-1.86 (m, 2H) 1.96-2.07 (m, 1H) 2.16 (dq, J=13.50, 6.85 Hz, 1H) 3.94 (s, 3H) 3.95 (br d, J=1.76 Hz, 1H) 4.33-4.42 (m, 1H) 4.53-4.62 (m, 2H) 7.25 (m, J=8.22 Hz, 2H) 7.41 (m, J=8.22 Hz, 2H) 7.87 (s, 1H) 8.01 (s, 1H) 8.22 (d, J=1.76 Hz, 1H) 8.52 (d, J=1.76 Hz, 1H);
MS (ESI, m/z): 470.1/472.1 [M+H]$^+$

Example 134. 2-amino-N-(1S,2S)-2-((3'-amino-[1,1'-biphenyl]-4-yl)-methoxy)cyclopentyl)-5-(1-methyl-1H-pyrazol-4-yl)nicotinamide To a mixture of intermediate 4 (33 mg, 0.07 mmol) and (3-aminophenyl)boronic acid (11 mg, 0.08 mmol) in 0.4 ml of 1,4-dioxane/water (3/1) was added K$_2$CO$_3$ (29 mg, 0.21 mmol) followed by Pd(PPh$_3$)$_4$ (4 mg, 0.003 mmol). The reaction mixture was heated at 100° C. for 3 hrs, cooled to room temperature, and extracted with EtOAc, dried over anhydrous MgSO$_4$ and concentrated under vacuum. After concentration under vacuum, the crude residue was purified by preparative HPLC to afford 30 mg of the title compound.

$^1$H NMR (400 MHz, CD$_3$OD) δ ppm 1.60-1.69 (m, 1H) 1.73-1.90 (m, 3H) 2.05 (br d, J=7.04 Hz, 1H) 2.17 (s, 1H) 3.89 (s, 3H) 4.00 (br d, J=4.30 Hz, 1H) 4.36-4.46 (m, 2H) 4.67 (s, 2H) 7.24 (br d, J=7.43 Hz, 1H) 7.42-7.59 (m, 7H) 7.84 (s, 1H) 7.97 (s, 1H) 8.20 (d, J=2.35 Hz, 1H) 8.48 (d, J=2.35 Hz, 1H);
MS (ESI, m/z): 483.2 [M+H]$^+$

Example 135. 2-amino-N-((1S,2S)-2-((4'-amino-[1,1'-biphenyl]-4-yl)methoxy)cyclopentyl)-5-(1-methyl-1H-pyrazol-4-yl)nicotinamide Using (4-aminophenyl)boronic acid, the title compound was obtained as described for the example 134.

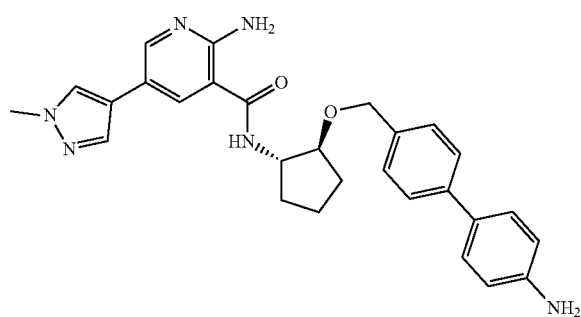 [SMILES: Cn1cc(-c2cnc(N)c(C(=O)N[C@H]3CCC[C@@H]3OCc3ccc(-c4ccc(N)cc4)cc3)c2)cn1]

MS (ESI, m/z): 483.2 [M+H]$^+$

Example 136. 2-amino-5-(1-methyl-1H-pyrazol-4-yl)-N-((1S,2S)-2-((4'-(methylamino)-[1,1'-biphenyl]-4-yl)methoxy)cyclopentyl)nicotinamide Using (4-(methylamino)phenyl)boronic acid, the title compound was obtained as described for the example 134.

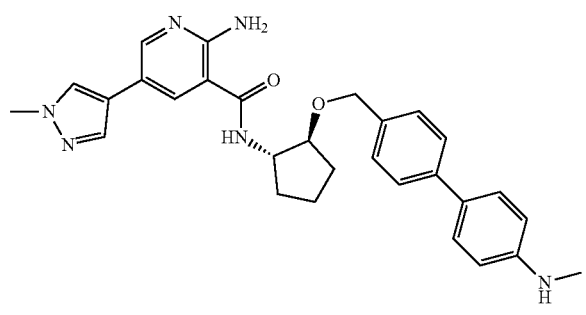

$^1$H NMR (400 MHz, CD$_3$OD) δ ppm 1.64 (br d, J=5.87 Hz, 1H) 1.73-1.94 (m, 3H) 2.05 (br s, 1H) 2.17 (br s, 1H) 3.55 (br t, J=11.15 Hz, 3H) 3.90 (s, 3H) 4.00 (br s, 1H) 4.43 (s, 4H) 4.67 (s, 2H) 7.45 (br d, J=8.22 Hz, 2H) 7.55 (br d, J=7.83 Hz, 2H) 7.60 (br d, J=7.83 Hz, 2H) 7.71 (br d, J=7.83 Hz, 2H) 7.85 (s, 1H) 7.98 (s, 1H) 8.21 (s, 1H) 8.52 (s, 1H);
MS (ESI, m/z): 497.3 [M+H]$^+$

Example 137. 2-amino-N-((1S,2S)-2-((4'-(dimethylamino)-[1,1'-biphenyl]-4-yl)methoxy)cyclopentyl)-5-(1-methyl-1H-pyrazol-4-yl)nicotinamide Using (4-(dimethylamino)phenyl)boronic acid, the title compound was obtained as described for the example 134.

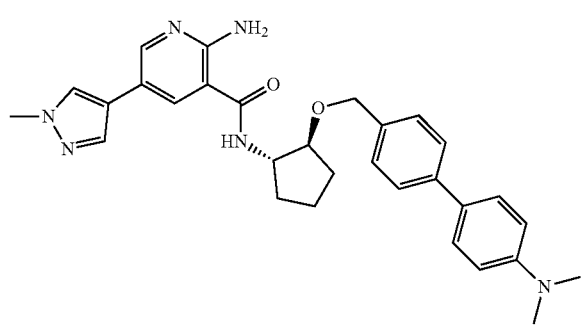

MS (ESI, m/z): 511.3 [M+H]⁺

Example 138. 2-amino-N-((1S,2S)-2-((4'-((dimethylamino)methyl)-[1,1'-biphenyl]-4-yl)methoxy)cyclopentyl)-5-(1-methyl-1H-pyrazol-4-yl)nicotinamide Using ((4-((dimethylamino)methyl)phenyl)boronic acid, the title compound was obtained as described for the example 134.

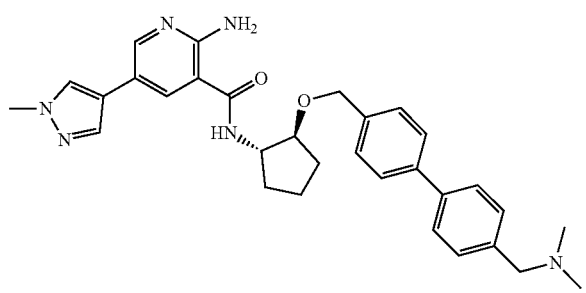

$^1$H NMR (400 MHz, CD$_3$OD) δ ppm 1.55-1.68 (m, 1H) 1.80 (br s, 3H) 2.04 (br d, J=7.43 Hz, 1H) 2.15 (br s, 1H) 3.49 (br s, 3H) 3.62 (br s, 3H) 3.75 (br s, 2H) 3.89 (s, 3H) 3.97 (br s, 1H) 4.39 (br s, 1H) 4.62 (br d, J=12.91 Hz, 1H) 4.66-4.73 (m, 1H) 7.44 (br t, J=9.19 Hz, 4H) 7.56 (br d, J=8.22 Hz, 2H) 7.62 (br d, J=7.83 Hz, 2H) 7.82 (s, 1H) 7.94 (s, 1H) 8.16 (s, 1H) 8.42 (s, 1H);
MS (ESI, m/z): 525.3 [M+H]⁺

Example 139. 2-amino-N-((1S,2S)-2-((3'-amino-2'-methyl-[1,1'-biphenyl]-4-yl)methoxy)cyclopentyl)-5-(1-methyl-1H-pyrazol-4-yl)nicotinamide Using (3-amino-2-methylphenyl)boronic acid, the title compound was obtained as described for the example 134.

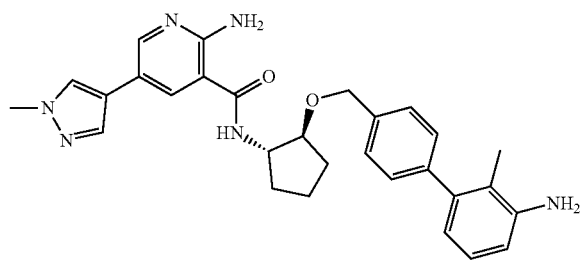 [SMILES: Cc1c(N)cccc1-c1ccc(CO[C@H]2CCC[C@@H]2NC(=O)c2cc(-c3cnn(C)c3)cnc2N)cc1]

MS (ESI, m/z): 497.2 [M+H]⁺

Example 140. 2-amino-N-((1S,2S)-2-((3'-hydroxy-[1,1'-biphenyl]-4-yl)-methoxy)cyclopentyl)-5-(1-methyl-1H-pyrazol-4-yl)nicotinamide Using (3-hydroxyphenyl)boronic acid, the title compound was obtained as described for the example 134.

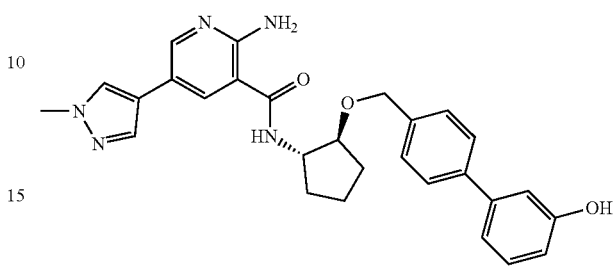

$^1$H NMR (400 MHz, CD$_3$OD) δ ppm 1.61 (br d, J=7.43 Hz, 1H) 1.72-1.86 (m, 3H) 1.95-2.08 (m, 1H) 2.09-2.20 (m, 1H) 3.87 (s, 3H) 3.97 (br s, 1H) 4.40 (br d, J=18.00 Hz, 1H) 4.56-4.71 (m, 2H) 6.70-6.75 (m, 1H) 6.90 (br s, 1H) 6.95 (br d, J=7.83 Hz, 1H) 7.14-7.21 (m, 1H) 7.32-7.41 (m, 2H) 7.42-7.50 (m, 2H) 7.78-7.83 (m, 1H) 7.88-7.93 (m, 1H) 8.16 (br d, J=1.96 Hz, 1H) 8.36 (br d, J=2.35 Hz, 1H);
MS (ESI, m/z): 484.2 [M+H]⁺

Example 141. 2-amino-N-((1S,2S)-2-((3'-(hydroxymethyl)-[1,1'-biphenyl]-4-yl)methoxy)cyclopentyl)-5-(1-methyl-1H-pyrazol-4-yl)nicotinamide Using (3-(hydroxymethyl)phenyl)boronic acid, the title compound was obtained as described for the example 134.

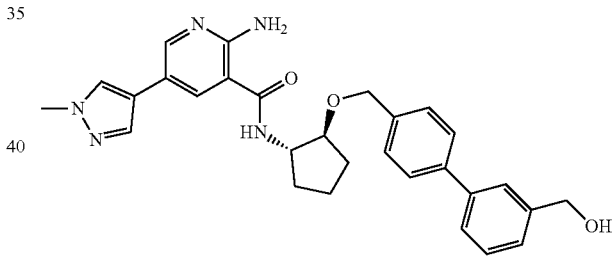

MS (ESI, m/z): 498.2 [M+H]⁺

Example 142. 2-amino-N-((1S,2S)-2-(4'-(hydroxymethyl)-[1,1'-biphenyl]-4-yl)methoxy)cyclopentyl)-5-(1-methyl-1H-pyrazol-4-yl)nicotinamide Using ((4-(hydroxymethyl)phenyl)boronic acid, the title compound was obtained as described for the example 134.

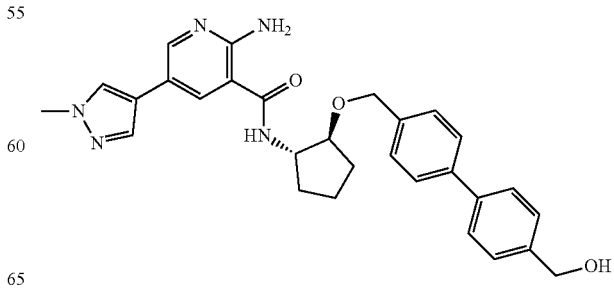

MS (ESI, m/z): 498.2 [M+H]⁺

Example 143. 2-amino-N-((1S,2S)-2-((3'-(aminomethyl)-[1,1'-biphenyl]-4-yl)methoxy)cyclopentyl)-5-(1-methyl-1H-pyrazol-4-yl)nicotinamide Using (3-(aminomethyl)phenyl)boronic acid, the title compound was obtained as described for the example 134.

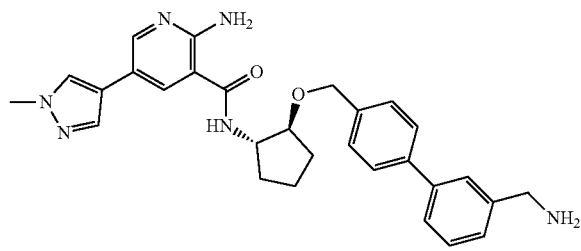 [SMILES: Cn1cc(-c2cnc(N)c(C(=O)N[C@H]3CCC[C@@H]3OCc3ccc(-c4cccc(CN)c4)cc3)c2)cn1]

¹H NMR (600 MHz, CD₃OD) δ ppm 1.54-1.67 (m, 1H) 1.71-1.90 (m, 3H) 2.03 (br dd, J=12.33, 7.04 Hz, 1H) 2.11-2.21 (m, 1H) 3.88 (s, 3H) 3.96-4.03 (m, 1H) 4.16 (s, 2H) 4.35-4.47 (m, 1H) 4.67 (s, 2H) 7.40 (br d, J=7.63 Hz, 1H) 7.44 (d, J=8.22 Hz, 1H) 7.49 (br t, J=7.63 Hz, 2H) 7.58 (d, J=7.63 Hz, 1H) 7.59-7.62 (m, 2H) 7.61 (br d, J=7.63 Hz, 1H) 7.66 (s, 1H) 7.80 (s, 1H) 7.92 (s, 1H) 8.21 (d, J=2.35 Hz, 1H) 8.29 (br s, 1H);

MS (ESI, m/z): 497.3 [M+H]⁺

Example 144. 2-amino-N-((1S,2S)-2-((4'-(aminomethyl)-[1,1'-biphenyl]-4-yl)methoxy)cyclopentyl)-5-(1-methyl-1H-pyrazol-4-yl)nicotinamide Using (4-(aminomethyl)phenyl)boronic acid, the title compound was obtained as described for the example 134.

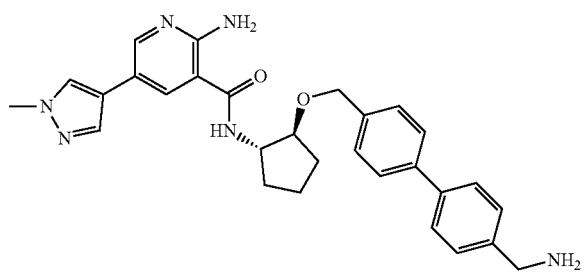 [SMILES: Cn1cc(-c2cnc(N)c(C(=O)N[C@H]3CCC[C@@H]3OCc3ccc(-c4ccc(CN)cc4)cc3)c2)cn1]

¹H NMR (600 MHz, CD₃OD) δ ppm 1.64 (br dd, J=14.09, 7.04 Hz, 1H) 1.72-1.90 (m, 3H) 2.03 (br dd, J=13.21, 6.16 Hz, 1H) 2.14-2.23 (m, 1H) 3.90 (s, 3H) 4.01 (br d, J=7.04 Hz, 1H) 4.14 (s, 2H) 4.40-4.45 (m, 1H) 4.63-4.70 (m, 2H) 7.43 (d, J=8.22 Hz, 2H) 7.49 (d, J=7.63 Hz, 2H) 7.57 (d, J=7.63 Hz, 2H) 7.65 (d, J=8.22 Hz, 2H) 7.85 (s, 1H) 7.97 (s, 1H) 8.21 (d, J=1.76 Hz, 1H) 8.49 (br s, 1H);

MS (ESI, m/z): 497.3 [M+H]⁺

Example 145. 2-amino-N-((1S,2S)-2-((4'-(2-aminoethyl)-[1,1'-biphenyl]-4-yl)methoxy)cyclopentyl)-5-(1-methyl-1H-pyrazol-4-yl)nicotinamide Using (4-(2-aminoethyl)phenyl)boronic acid, the title compound was obtained as described for the example 134.

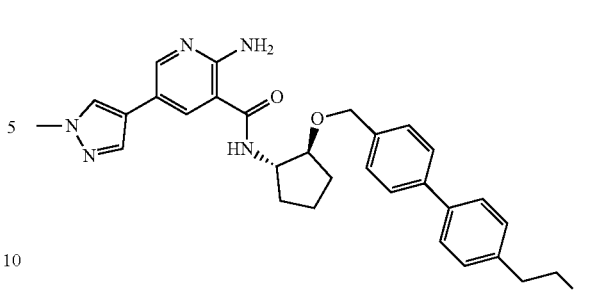

MS (ESI, m/z): 511.3 [M+H]⁺

Example 146. 2-amino-5-(1-methyl-1H-pyrazol-4-yl)-N-((1S,2S)-2-((4'-(4-methylpiperazin-1-yl)-[1,1'-biphenyl]-4-yl)methoxy)cyclopentyl)nicotinamide Using (4-(4-methylpiperazin-1-yl)phenyl)boronic acid, the title compound was obtained as described for the example 134.

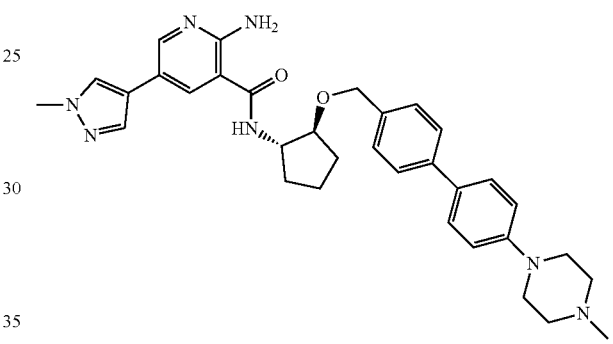

MS (ESI, m/z): 566.3 [M+H]⁺

Example 147. 2-amino-5-(1-methyl-1H-pyrazol-4-yl)-N-((1S,2S)-2-((4-(6-(piperazin-1-yl)pyridin-3-yl)benzyl)oxy)cyclopentyl)nicotinamide Using (6-(piperazin-1-yl)pyridin-3-yl)boronic acid, the title compound was obtained as described for the example 134.

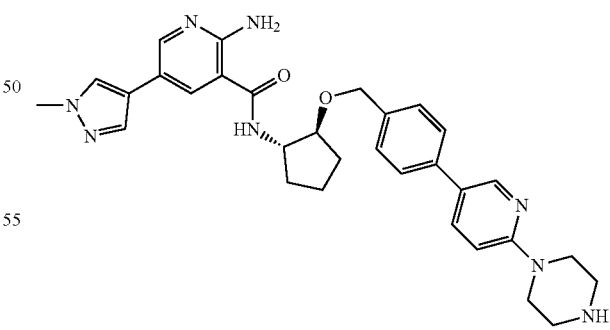

¹H NMR (400 MHz, CD₃OD) δ ppm 1.64 (br d, J=7.83 Hz, 1H) 1.81 (br d, J=7.83 Hz, 3H) 2.04 (br s, 1H) 2.18 (br s, 1H) 3.32-3.40 (m, 4H) 3.84 (br s, 4H) 3.90 (s, 3H) 3.98 (br s, 1H) 4.40 (br s, 1H) 4.65 (s, 2H) 6.98-7.02 (m, 1H) 7.41 (br d, J=7.04 Hz, 2H) 7.50 (d, J=7.83 Hz, 2H) 7.83-7.89 (m, 2H) 7.96 (s, 1H) 8.20 (s, 1H) 8.35 (s, 1H) 8.48 (s, 1H);

MS (ESI, m/z): 553.3 [M+H]⁺

Example 148. 2-amino-5-(1-methyl-1H-pyrazol-4-yl)-N-((1S,2S)-2-((4-(6-(4-methylpiperazin-1-yl)pyridin-3-yl)benzyl)oxy)cyclopentyl)nicotinamide Using (6-(4-methylpiperazin-1-yl)pyridin-3-yl)boronic acid, the title compound was obtained as described for the example 134.

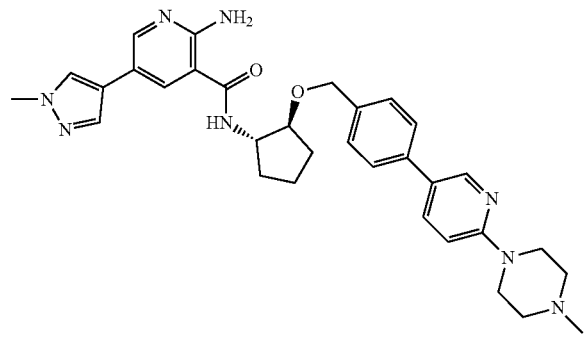

$^1$H NMR (600 MHz, CD$_3$OD) δ ppm 1.58-1.66 (m, 1H) 1.73-1.87 (m, 3H) 2.04 (dq, J=13.72, 6.77 Hz, 1H) 2.16 (dt, J=13.35, 6.53 Hz, 1H) 2.96 (s, 3H) 3.90 (s, 3H) 3.96-4.01 (m, 1H) 4.37-4.45 (m, 1H) 4.60-4.69 (m, 2H) 6.99 (d, J=8.80 Hz, 1H) 7.41 (d, J=8.22 Hz, 2H) 7.50 (d, J=8.22 Hz, 2H) 7.83 (s, 1H) 7.85 (d, J=2.35 Hz, 1H) 7.96 (s, 1H) 8.20 (d, J=2.35 Hz, 1H) 8.36 (d, J=2.35 Hz, 1H) 8.45 (s, 1H);
MS (ESI, m/z): 567.3 [M+H]$^+$ Example 149. 2-amino-5-(1-methyl-1H-pyrazol-4-yl)-N-((1S,2S)-2-((3'-(piperazin-1-yl)-[1,1'-biphenyl]-4-yl)methoxy)cyclopentyl)nicotinamide Using (3-(piperazin-1-yl)phenyl)boronic acid, the title compound was obtained as described for the example 134.

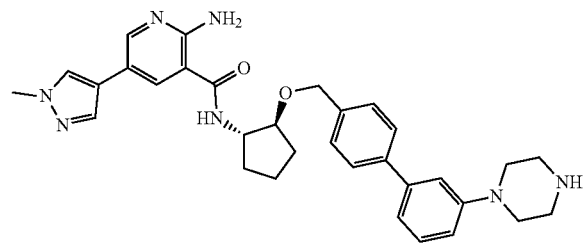 [SMILES: Cn1cc(-c2cnc(N)c(C(=O)N[C@H]3CCC[C@@H]3OCc3ccc(-c4cccc(N5CCNCC5)c4)cc3)c2)cn1]

$^1$H NMR (400 MHz, CD$_3$OD) δ ppm 1.62 (br d, J=5.87 Hz, 2H) 1.81 (br d, J=6.65 Hz, 3H) 1.96-2.07 (m, 1H) 2.17 (br s, 1H) 3.40 (br dd, J=19.95, 5.87 Hz, 8H) 3.88 (s, 3H) 4.00 (br s, 1H) 4.40 (br s, 1H) 4.65 (s, 2H) 6.99 (br d, J=7.43 Hz, 1H) 7.10 (br d, J=6.65 Hz, 1H) 7.16 (s, 1H) 7.32 (t, J=7.60 Hz, 1H) 7.40 (d, J=7.83 Hz, 2H) 7.53 (d, J=8.61 Hz, 2H) 7.84 (s, 1H) 7.95 (s, 1H) 8.19 (s, 1H) 8.46 (s, 1H);
MS (ESI, m/z): 552.3 [M+H]$^+$ Example 150. 2-amino-5-(1-methyl-1H-pyrazol-4-yl)-N-(1S,2S)-2-((3'-(4-methylpiperazin-1-yl)-[1,1'-biphenyl]-4-yl)methoxy)cyclopentyl)nicotinamide Using (3-(4-methylpiperazin-1-yl)phenyl)boronic acid, the title compound was obtained as described for the example 134.

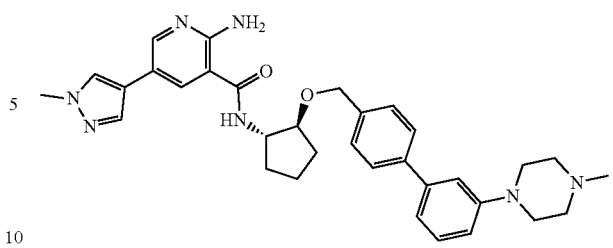

$^1$H NMR (600 MHz, CD$_3$OD) δ ppm 1.66 (s, 1H) 1.73-1.88 (m, 3H) 1.99-2.08 (m, 1H) 2.17 (br dd, J=13.50, 5.87 Hz, 1H) 2.97 (s, 3H) 3.06 (br s, 2H) 3.60 (br s, 2H) 3.88 (s, 3H) 3.96-4.03 (m, 1H) 4.41 (br d, J=4.70 Hz, 1H) 4.61-4.70 (m, 2H) 6.99 (br d, J=8.80 Hz, 1H) 7.10 (br d, J=7.63 Hz, 1H) 7.16 (s, 1H) 7.32 (t, J=7.92 Hz, 1H) 7.41 (d, J=8.22 Hz, 2H) 7.53 (d, J=8.22 Hz, 2H) 7.82 (s, 1H) 7.93 (s, 1H) 8.19 (d, J=1.76 Hz, 1H) 8.35-8.41 (m, 1H);

MS (ESI, m/z): 566.3 [M+H]$^+$

Example 151. 2-amino-5-(1-methyl-1H-pyrazol-4-yl)-N-((1S,2S)-2-((3'-((4-methylpiperazin-1-yl)methyl)-[1,1'-biphenyl]-4-yl)methoxy)cyclopentyl)nicotinamide Using (3-((4-methylpiperazin-1-yl)methyl)phenyl)boronic acid pinacol ester, the title compound was obtained as described for the example 134.

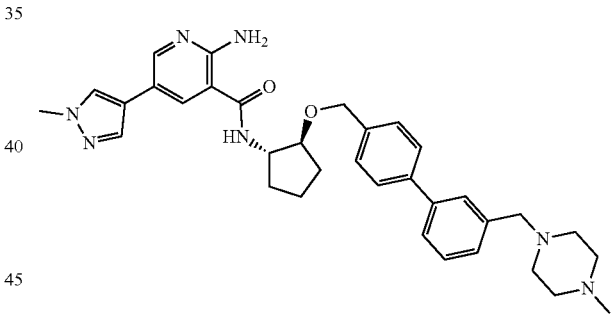

$^1$H NMR (400 MHz, CD$_3$OD) δ ppm 1.65 (br dd, J=13.30, 6.26 Hz, 1H) 1.76-1.90 (m, 3H) 1.99-2.10 (m, 1H) 2.18 (br dd, J=14.09, 6.65 Hz, 1H) 2.85 (s, 3H) 3.78 (s, 2H) 3.91 (s, 3H) 4.02 (br s, 1H) 4.43 (br dd, J=10.96, 7.83 Hz, 1H) 4.68 (s, 2H) 7.34 (br d, J=7.43 Hz, 1H) 7.38-7.45 (m, 3H) 7.51 (br d, J=7.83 Hz, 1H) 7.54-7.60 (m, 3H) 7.86 (s, 1H) 7.99 (s, 1H) 8.21 (d, J=1.96 Hz, 1H) 8.51 (d, J=1.96 Hz, 1H);

MS (ESI, m/z): 579.3 [M+H]$^+$

Example 152. 2-amino-5-(1-methyl-1-pyrazol-4-yl)-N-((1S,2S)-2-((4'-(morpholine-4-carbonyl)-[1,1'-biphenyl]-4-yl)methoxy)cyclopentyl)nicotinamide Using (4-(morpholine-4-carbonyl)phenyl)boronic acid, the title compound was obtained as described for the example 134.

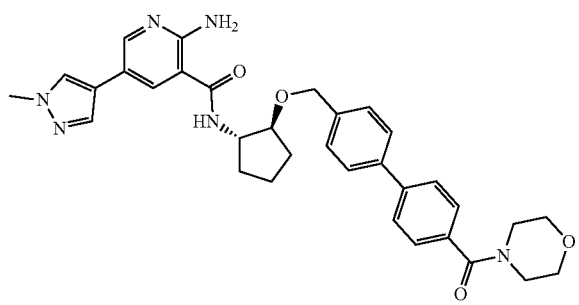 [SMILES: Cn1cc(-c2cnc(N)c(C(=O)N[C@H]3CCC[C@@H]3OCc3ccc(-c4ccc(C(=O)N5CCOCC5)cc4)cc3)c2)cn1]

MS (ESI, m/z): 581.3 [M+H]⁺

Example 153. 2-amino-N-((1S,2S)-2-((4'-ethyl-[1,1'-biphenyl]-4-yl)-methoxy)cyclopentyl)-5-(1-methyl-1H-pyrazol-4-yl)nicotinamide Using (4-ethylphenyl)boronic acid, the title compound was obtained as described for the example 134.

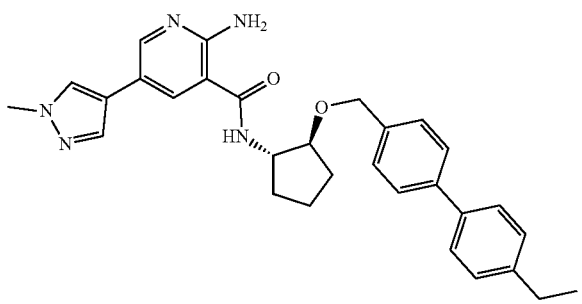 [SMILES: CCc1ccc(-c2ccc(CO[C@H]3CCC[C@@H]3NC(=O)c3cc(-c4cnn(C)c4)cnc3N)cc2)cc1]

$^1$H NMR (600 MHz, CD$_3$OD) δ ppm 1.24 (t, J=7.63 Hz, 3H) 1.55-1.67 (m, 1H) 1.73-1.86 (m, 3H) 2.01-2.08 (m, 1H) 2.16 (br dd, J=13.21, 5.58 Hz, 1H) 2.66 (q, J=7.63 Hz, 2H) 3.87 (s, 3H) 3.93-3.99 (m, 1H) 4.38-4.42 (m, 1H) 4.61 (d, J=12.91 Hz, 1H) 4.65-4.71 (m, 1H) 7.21 (d, J=7.63 Hz, 2H) 7.38 (d, J=8.22 Hz, 2H) 7.41 (d, J=8.22 Hz, 2H) 7.50 (d, J=8.22 Hz, 2H) 7.82 (s, 1H) 7.91 (s, 1H) 8.16 (d, J=1.76 Hz, 1H) 8.42 (d, J=2.35 Hz, 1H);
MS (ESI, m/z): 496.3 [M+H]⁺

Example 154. 2-amino-N-((1S,2S)-2-((4'-(cyanomethyl)-[1,1'-biphenyl]-4-yl)-methoxy)cyclopentyl)-5-(1-methyl-1H-pyrazol-4-yl)nicotinamide Using (4-(cyanomethyl)phenyl)boronic acid, the title compound was obtained as described for the example 134.

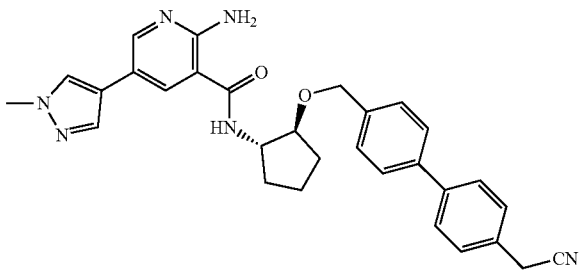 [SMILES: Cn1cc(-c2cnc(N)c(C(=O)N[C@H]3CCC[C@@H]3OCc3ccc(-c4ccc(CC#N)cc4)cc3)c2)cn1]

MS (ESI, m/z): 507.2 [M+H]⁺

Example 155. 2-amino-N-((1S,2S)-2-((4'-carbamoyl-[1,1'-biphenyl]-4-yl)-methoxy)cyclopentyl)-5-(1-methyl-1H-pyrazol-4-yl)nicotinamide Using (4-carbamoylphenyl)boronic acid, the title compound was obtained as described for the example 134.

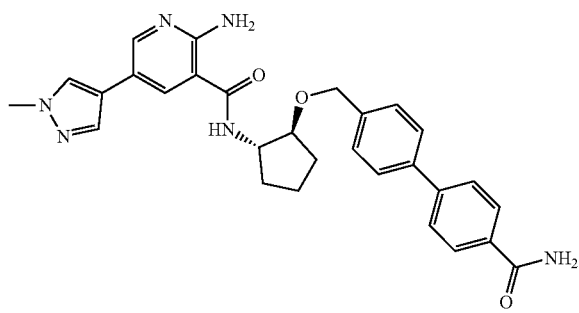 [SMILES: Cn1cc(-c2cnc(N)c(C(=O)N[C@H]3CCC[C@@H]3OCc3ccc(-c4ccc(C(N)=O)cc4)cc3)c2)cn1]

$^1$H NMR (600 MHz, CD$_3$OD) δ ppm 1.62 (s, 1H) 1.70-1.88 (m, 3H) 2.05 (s, 1H) 2.16 (td, J=13.06, 7.92 Hz, 1H) 3.88 (s, 3H) 3.98 (br d, J=6.46 Hz, 1H) 4.40 (br d, J=4.70 Hz, 1H) 4.63 (d, J=12.33 Hz, 1H) 4.70 (d, J=12.91 Hz, 1H) 7.44 (d, J=8.22 Hz, 2H) 7.58 (d, J=8.22 Hz, 2H) 7.61 (d, J=8.80 Hz, 2H) 7.81 (s, 1H) 7.89 (d, J=8.22 Hz, 2H) 7.92 (s, 1H) 8.17 (d, J=2.35 Hz, 1H) 8.38 (d, J=1.76 Hz, 1H);
MS (ESI, m/z): 511.2 [M+H]⁺

Example 156. 2-amino-N-((1S,2S)-2-((3-fluoro-4'-((4-methylpiperazin-1-yl)-methyl)-[1,1'-biphenyl]-4-yl)methoxy)cyclopentyl)-5-(1-methyl-1H-pyrazol-4-yl)-nicotinamide Using (1S,2S)-2-((4-bromo-2-fluorobenzyl)oxy)cyclopentan-1-amine and 4-(4-methylpiperazino)methylphenylboronic acid pinacol ester, the title compound was obtained as described for the example 134.

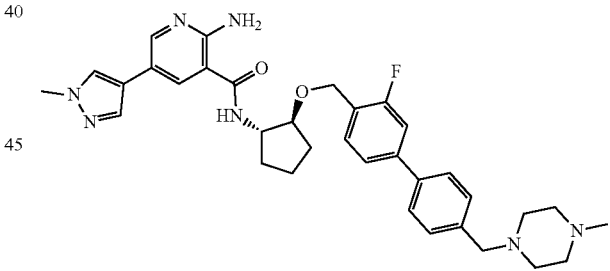

$^1$H NMR (400 MHz, CD$_3$OD) δ ppm 1.64 (br dd, J=13.30, 7.04 Hz, 1H) 1.74-1.92 (m, 3H) 2.04 (br dd, J=12.72, 6.06 Hz, 1H) 2.17 (br dd, J=13.50, 6.46 Hz, 1H) 2.91 (s, 3H) 3.25 (br s, 4H) 3.47 (br s, 4H) 3.90 (s, 3H) 3.96-4.08 (m, 1H) 4.12 (s, 2H) 4.34-4.45 (m, 1H) 4.64-4.78 (m, 2H) 5.47 (s, 1H) 7.32 (br d, J=11.35 Hz, 1H) 7.40 (br d, J=7.83 Hz, 1H) 7.47-7.57 (m, 3H) 7.62 (br d, J=7.83 Hz, 2H) 7.85 (s, 1H) 7.99 (s, 1H) 8.18 (s, 1H) 8.55 (s, 1H);
MS (ESI, m/z): 598.4 [M+H]⁺

Example 157. 2-amino-N-((1S,2S)-2-((3-fluoro-4'-((cis-3,4,5-trimethylpiperazin-1-yl)methyl)-[1,1'-biphenyl]-4-yl)methoxy)cyclopentyl)-5-(1-methyl-1H-pyrazol-4-yl)-nicotinamide Using (1S,2S)-2-((4-bromo-2-fluorobenzyl)oxy)cyclopentan-1-amine and (4-((cis-3,4,5-trimethylpiperazin-1-yl)

methyl)phenyl)boronic acid pinacol ester, the title compound was obtained as described for the example 134.

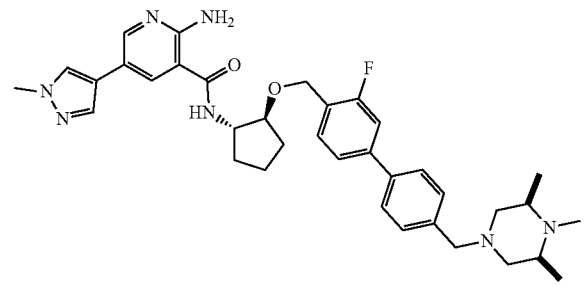

MS (ESI, m/z): 626.4 [M+H]⁺

Example 158. 2-amino-5-(1-methyl-1H-pyrazol-4-yl)-N-((1S,2S)-2-((4'-((4-methylpiperazin-1-yl)methyl)-3-(trifluoromethyl)-[1,1'-biphenyl]-4-yl)-methoxy)cyclopentyl)nicotinamide Using (1S,2S)-2-((4-bromo-2-(trifluoromethyl)benzyl)oxy)cyclopentan-1-amine and 4-(4-methylpiperazino)methylphenylboronic acid pinacol ester, the title compound was obtained as described for the example 134.

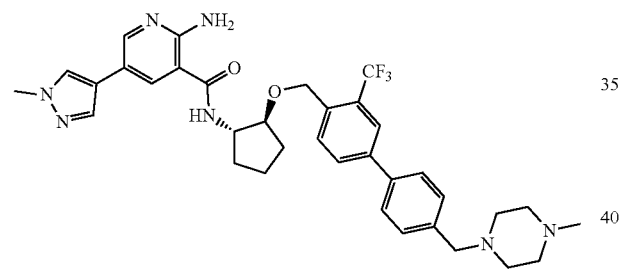

$^1$H NMR (400 MHz, CD$_3$OD) δ ppm 1.69 (dt, J=13.89, 6.75 Hz, 1H) 1.77-1.93 (m, 3H) 2.01-2.12 (m, 1H) 2.13-2.30 (m, 1H) 2.87 (s, 3H) 3.75 (s, 2H) 3.92 (s, 3H) 4.00-4.08 (m, 1H) 4.45 (br dd, J=11.54, 7.24 Hz, 1H) 7.47 (d, J=8.22 Hz, 2H) 7.62 (m, J=8.22 Hz, 2H) 7.81-7.84 (m, 2H) 7.86 (d, J=5.09 Hz, 2H) 8.00 (s, 1H) 8.23 (d, J=1.96 Hz, 1H) 8.56 (d, J=2.35 Hz, 1H);
MS (ESI, m/z): 648.3[M+H]⁺

Example 159. 2-amino-N-((1S,2S)-2-((2-chloro-4'-((4-methylpiperazin-1-yl)-methyl)-[1,1'-biphenyl]-4-yl)methoxy)cyclopentyl)-5-(1-methyl-1H-pyrazol-4-yl)-nicotinamide Using (1S,2S)-2-((4-bromo-3-chlorobenzyl)oxy)cyclopentan-1-amine and 4-(4-methylpiperazino)methylphenylboronic acid pinacol ester, the title compound was obtained as described for the example 134.

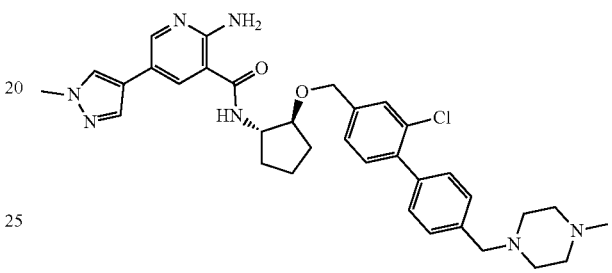

$^1$H NMR (600 MHz, CD$_3$OD) δ ppm 1.65 (br dd, J=13.50, 7.04 Hz, 1H) 1.74-1.89 (m, 3H) 1.97-2.11 (m, 1H) 2.15-2.22 (m, 1H) 2.85 (s, 3H) 3.72 (s, 2H) 3.92 (s, 3H) 3.98 (dt, J=6.46, 4.11 Hz, 1H) 4.42 (td, J=7.34, 4.11 Hz, 1H) 4.66 (d, J=2.35 Hz, 2H) 7.27 (d, J=7.63 Hz, 1H) 7.30-7.37 (m, 3H) 7.40 (d, J=8.22 Hz, 2H) 7.47 (d, J=1.17 Hz, 1H) 7.86 (s, 1H) 7.99 (s, 1H) 8.22 (d, J=2.35 Hz, 1H) 8.49 (d, J=2.35 Hz, 1H);
MS (ESI, m/z): 614.3[M+H]⁺

Example 160. 2-amino-N-((1S,2S)-2-((3-fluoro-4'-((cis-4-(2-hydroxyethyl)-3,5-dimethylpiperazin-1-yl)methyl)-[1,1'-biphenyl]-4-yl)methoxy)cyclopentyl)-5-(1-methyl-1H-pyrazol-4-yl)nicotinamide Using (1S,2S)-2-((4-bromo-2-fluorobenzyl)oxy)cyclopentan-1-amine and (4-((cis-4-(2-hydroxyethyl)-3,5-dimethylpiperazin-1-yl)methyl)phenyl)boronic acid pinacol ester, the title compound was obtained as described for the example 134.

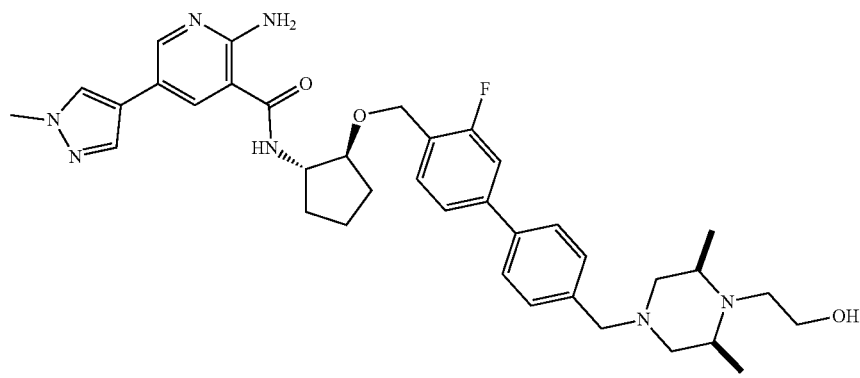 [SMILES: C[C@@H]1CN(Cc2ccc(-c3ccc(CO[C@H]4CCC[C@@H]4NC(=O)c4cc(-c5cnn(C)c5)cnc4N)c(F)c3)cc2)C[C@H](C)N1CCO]

MS (ESI, m/z): 656.4 [M+H]⁺

Example 161. 2-amino-5-(1-methyl-1H-pyrazol-4-yl)-N-((1S,2S)-2-((4'-(2-(4-methylpiperazin-1-yl)ethyl)-[1,1'-biphenyl]-4-yl)methoxy)cyclopentyl)nicotinamide Using 4-(2-(4-methylpiperazino)ethyl)phenylboronic acid pinacol ester, the title compound was obtained as described for the example 134.

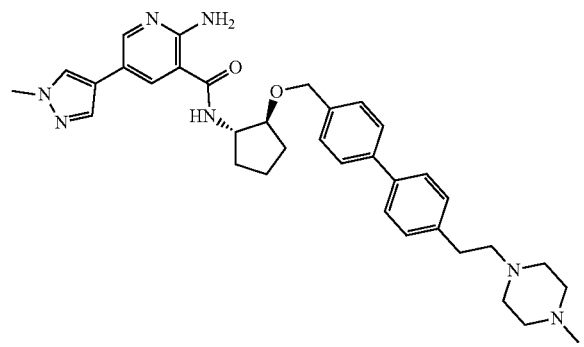

$^1$H NMR (600 MHz, CD$_3$OD) δ ppm 1.63 (br dd, J=13.79, 6.75 Hz, 1H) 1.74-1.87 (m, 3H) 2.00-2.11 (m, 1H) 2.11-2.23 (m, 1H) 2.79-2.96 (m, 2H) 3.02 (br s, 2H) 3.24 (s, 2H) 3.41 (br s, 4H) 3.89 (s, 3H) 3.97-4.03 (m, 1H) 4.41 (br s, 1H) 4.61-4.71 (m, 2H) 7.31 (br d, J=8.22 Hz, 2H) 7.40 (d, J=7.63 Hz, 2H) 7.50 (br d, J=8.22 Hz, 2H) 7.51-7.57 (m, 2H) 7.84 (br d, J=2.93 Hz, 1H) 7.96 (s, 1H) 8.16-8.21 (m, 1H) 8.50 (br d, J=4.70 Hz, 1H);
MS (ESI, m/z): 594.4 [M+H]$^+$

Example 162. 2-amino-5-(1-methyl-1H-pyrazol-4-yl)-N-((1S,2S)-2-((4-(1-(piperidin-4-yl)-1H-pyrazol-4-yl)benzyl)oxy)cyclopentyl)nicotinamide Using tert-butyl 4-(4-(4,4,5,5-tetramethyl-1,3,2-dioxaborolan-2-yl)-1H-pyrazol-1-yl)piperidine-1-carboxylate, the title compound was obtained as described for the example 134 and following deprotection with TFA.

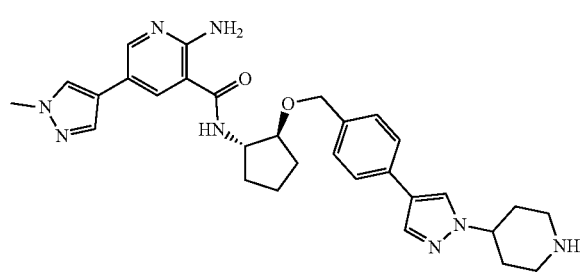 [SMILES: Cn1cc(-c2cnc(N)c(C(=O)N[C@H]3CCC[C@@H]3OCc3ccc(-c4cnn(C5CCNCC5)c4)cc3)c2)cn1]

$^1$H NMR (400 MHz, CD$_3$OD) δ ppm 1.62 (br s, 1H) 1.80 (br d, J=6.65 Hz, 3H) 2.03 (br s, 1H) 2.15 (br s, 1H) 2.28 (br d, J=13.69 Hz, 4H) 3.14-3.25 (m, 2H) 3.56 (br d, J=11.35 Hz, 2H) 3.90 (s, 3H) 3.97 (br s, 1H) 4.39 (br s, 1H) 4.53 (br s, 1H) 4.60 (s, 2H) 7.32 (br d, J=7.83 Hz, 2H) 7.47 (br d, J=7.83 Hz, 2H) 7.79 (s, 1H) 7.85 (s, 1H) 7.97 (br s, 2H) 8.20 (br s, 1H) 8.48 (s, 1H);
MS (ESI, m/z): 541.3 [M+H]$^+$

Example 163. 2-amino-5-(1-methyl-1H-pyrazol-4-yl)-N-((1S,2S)-2-((4-(1-(1-methylpiperidin-4-yl)-1H-pyrazol-4-yl)benzyl)oxy)cyclopentyl)nicotinamide Using (1-methyl-4-(4-(4,4,5,5-tetramethyl-1,3,2-dioxaborolan-2-yl)-1H-pyrazol-1-yl)-piperidine, the title compound was obtained as described for the example 134.

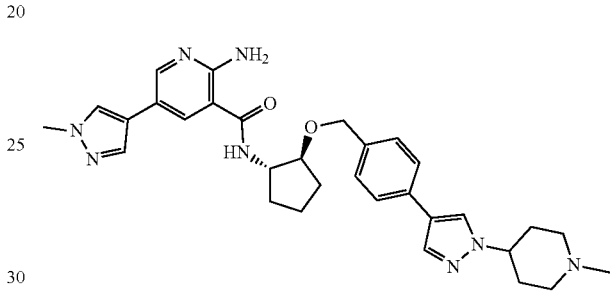

$^1$H NMR (600 MHz, CD$_3$OD) δ ppm 1.57-1.66 (m, 1H) 1.72-1.87 (m, 3H) 2.03 (br dd, J=12.62, 6.75 Hz, 1H) 2.17 (br s, 1H) 2.24-2.42 (m, 4H) 2.94 (s, 3H) 3.19-3.27 (m, 2H) 3.48 (br s, 1H) 3.90 (s, 3H) 3.98 (br d, J=6.46 Hz, 1H) 4.36-4.45 (m, 1H) 4.46-4.55 (m, 1H) 4.57-4.64 (m, 2H) 7.33 (br d, J=8.22 Hz, 2H) 7.47 (br d, J=8.22 Hz, 2H) 7.79 (br s, 1H) 7.84 (s, 1H) 7.97 (d, J=5.87 Hz, 2H) 8.20 (br d, J=1.76 Hz, 1H) 8.47 (s, 1H);
MS (ESI, m/z): 555.3 [M+H]$^+$

Example 164. 2-amino-5-(1-methyl-1H-pyrazol-4-yl)-N-((1S,2R)-2-((4'-((4-methylpiperazin-1-yl)methyl)-[1,1'-biphenyl]-4-yl)methoxy)cyclopentyl)nicotinamide Using (1S,2R)-2-((4-bromobenzyl)oxy)cyclopentan-1-amine and (4-((4-methylpiperazin-1-yl)methyl)phenyl)boronic acid pinacol ester, the title compound was obtained as described for the example 134.

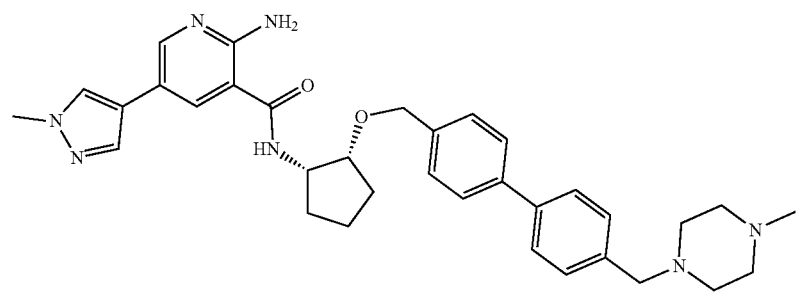

$^1$H NMR (600 MHz, CD$_3$OD) δ ppm 1.58-1.69 (m, 1H) 1.82-1.97 (m, 4H) 2.00-2.07 (m, 1H) 2.83-2.90 (m, 3H) 3.79 (s, 3H) 3.80-3.87 (m, 2H) 4.11-4.18 (m, 1H) 4.36-4.43 (m, 1H) 4.45 (d, J=11.74 Hz, 1H) 4.67 (d, J=11.74 Hz, 1H) 7.38 (d, J=8.22 Hz, 2H) 7.40-7.44 (m, 2H) 7.46 (d, J=8.22 Hz, 2H) 7.49 (d, J=8.22 Hz, 2H) 7.78 (s, 1H) 7.83 (s, 1H) 8.12-8.19 (m, 1H) 8.44 (s, 1H);

MS (ESI, m/z): 580.3 [M+H]$^+$

Example 165. 2-amino-5-(1-methyl-1H-pyrazol-4-yl)-N-((1R,2S)-2-((4'-((4-methylpiperazin-1-yl)methyl)-[1,1'-biphenyl]-4-yl)methoxy)cyclopentyl)nicotinamide Using (1R,2S)-2-((4-bromobenzyl)oxy)cyclopentan-1-amine and (4-((4-methylpiperazin-1-yl)methyl)phenyl)boronic acid pinacol ester, the title compound was obtained as described for the example 134.

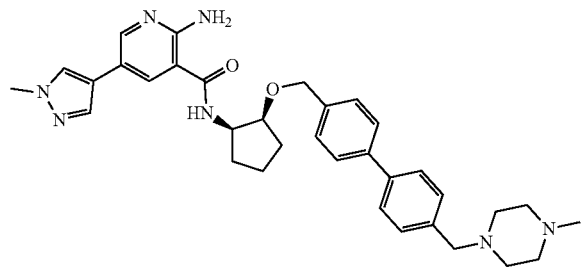

$^1$H NMR (600 MHz, CD$_3$OD) δ ppm 1.60-1.70 (m, 1H) 1.81-1.98 (m, 4H) 2.00-2.09 (m, 1H) 2.87 (s, 3H) 3.79 (s, 3H) 3.80-3.85 (m, 2H) 4.15 (d, J=4.70 Hz, 1H) 4.36-4.42 (m, 1H) 4.45 (d, J=11.74 Hz, 1H) 4.67 (d, J=12.33 Hz, 1H) 7.38 (d, J=8.22 Hz, 2H) 7.42 (d, J=7.04 Hz, 2H) 7.46 (d, J=8.22 Hz, 2H) 7.48-7.50 (m, 2H) 7.78 (s, 1H) 7.83 (s, 1H) 8.15 (d, J=1.76 Hz, 1H) 8.44 (d, J=2.35 Hz, 1H);

MS (ESI, m/z): 580.3 [M+H]$^+$

Example 166. 2-amino-5-(1-methyl-1H-pyrazol-4-yl)-N-((1S,2S)-2-((4'-((4-methylpiperazin-1-yl)methyl)-[1,1'-biphenyl]-4-yl)methoxy)cyclohexyl)nicotinamide Using (1S,2S)-2-((4-bromobenzyl)oxy)cyclohexan-1-amine and (4-((4-methylpiperazin-1-yl)methyl)phenyl)boronic acid pinacol ester, the title compound was obtained as described for the example 134.

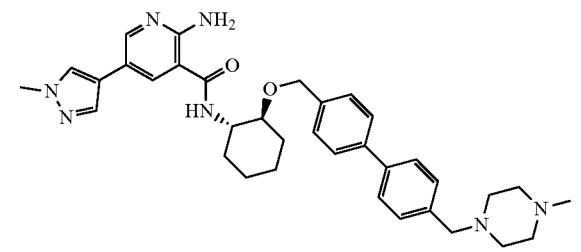

$^1$H NMR (600 MHz, CD$_3$OD) δ ppm 1.43 (br s, 4H) 1.97-2.07 (m, 2H) 2.18 (br s, 2H) 2.32 (s, 3H) 3.40-3.48 (m, 1H) 3.58 (s, 2H) 3.80-3.89 (m, 1H) 3.90 (s, 3H) 4.61 (s, 2H) 7.41 (dd, J=14.09, 8.22 Hz, 4H) 7.55-7.62 (m, 4H) 7.78 (s, 1H) 7.89 (s, 1H) 8.03 (d, J=1.76 Hz, 1H) 8.23 (br s, 1H);

MS (ESI m/z): 594.4 [M+H]$^+$

Example 167. 2-amino-N-((1S,2S)-2-((4'-(2-(4-methylpiperazin-1-yl)propan-2-yl)-[1,1'-biphenyl]-4-yl)methoxy)cyclopentyl)nicotinamide Using 2-aminonicotinic acid and (4-(2-(4-methylpiperazin-1-yl)propan-2-yl)phenyl)boronic acid pinacol ester, the title compound was obtained as described for the example 134.

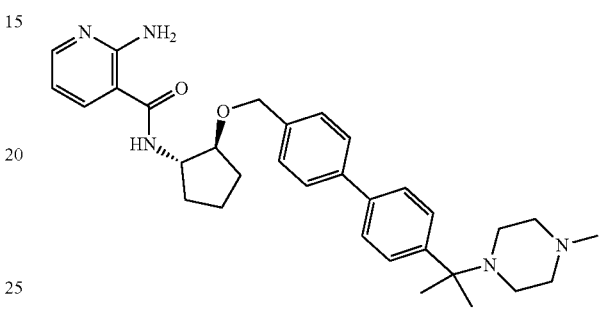

$^1$H NMR (400 MHz, CD$_3$OD) δ ppm 1.47 (s, 6H) 1.55-1.70 (m, 1H) 1.82 (br d, J=7.04 Hz, 3H) 2.03 (br s, 1H) 2.12-2.25 (m, 1H) 2.86 (s, 3H) 4.00 (br s, 1H) 4.40 (br s, 1H) 4.66 (s, 2H) 6.90-6.99 (m, 1H) 7.38-7.46 (m, 2H) 7.59 (br dd, J=10.96, 7.83 Hz, 6H) 8.01 (d, J=5.09 Hz, 1H) 8.33 (d, J=7.83 Hz, 1H);

MS (ESI, m/z): 528.3 [M+H]$^+$

Example 168. 2-amino-N-((1S,2S)-2-((4'-((4-methylpiperazin-1-yl)methyl)-3-(trifluoromethyl)-[1,1'-biphenyl]-4-yl)methoxy)cyclopentyl)nicotinamide Using 2-aminonicotinic acid, (1S,2S)-2-((4-bromo-2-(trifluoromethyl)benzyl)oxy)cyclopentan-1-amine and 4-(4-methylpiperazino)methylphenylboronic acid pinacol ester, the title compound was obtained as described for the example 134.

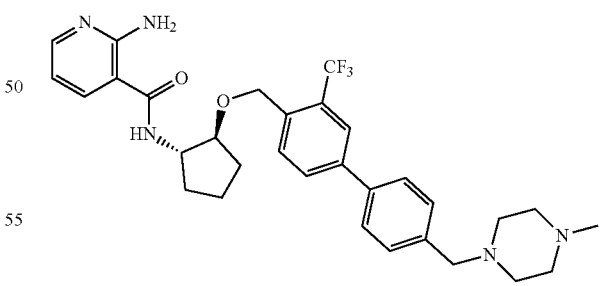

$^1$H NMR (400 MHz, CD$_3$OD) δ ppm 1.66 (dt, J=13.60, 6.70 Hz, 1H) 1.78-1.93 (m, 3H) 1.97-2.12 (m, 1H) 2.13-2.26 (m, 1H) 2.87 (s, 3H) 3.77 (s, 2H) 4.00-4.05 (m, 1H) 4.43 (br dd, J=10.76, 7.63 Hz, 1H) 6.98 (dd, J=7.43, 6.26 Hz, 1H) 7.48 (d, J=8.22 Hz, 2H) 7.65 (d, J=8.22 Hz, 2H) 7.77-7.93 (m, 3H) 8.02 (br dd, J=6.26, 1.57 Hz, 1H) 8.37 (dd, J7.43, 1.57 Hz, 1H);

MS (ESI, m/z): 568.3[M+H]$^+$

Example 169. amino-N-((1S,2S)-2-((3'-hydroxy-[1,1'-biphenyl]-3-yl)methoxy)-cyclopentyl)-5-(1-methyl-1H-pyrazol-4-yl)nicotinamide Scheme for the Preparation of the Compound of Example 169:

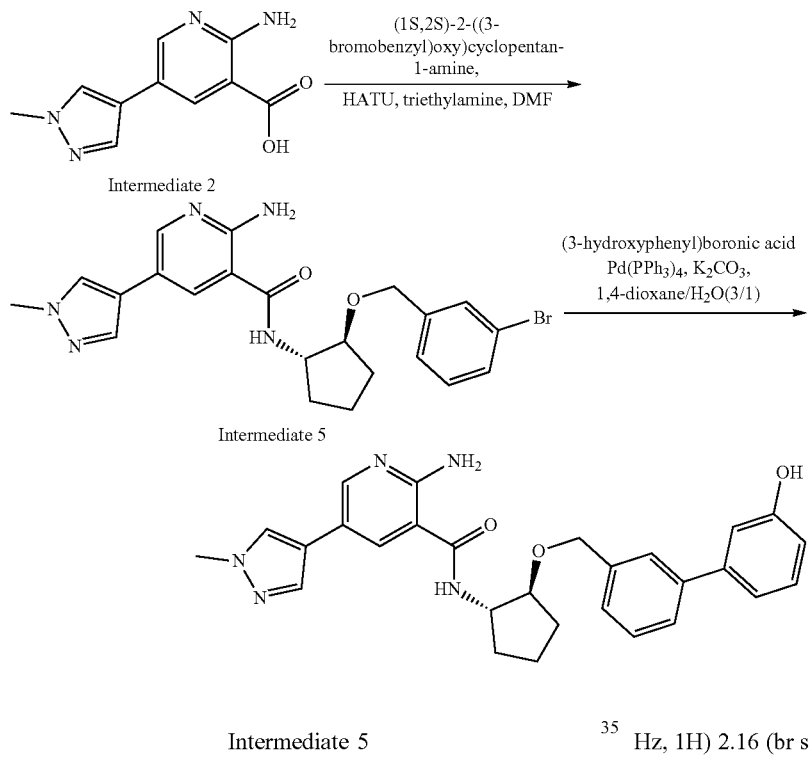

Intermediate 5

To a mixture of intermediate 2 (350 mg, 1.60 mmol) and triethylamine (0.34 ml, 2.41 mmol) in 4 ml of DMF was added HATU (732 mg, 1.92 mmol) followed by (1S,2S)-2-((3-bromobenzyl)oxy)cyclopentan-1-amine (475 mg, 1.76 mmol). The mixture was stirred at room temperature for 1 hr and then saturated sodium bicarbonate solution was added. The mixture was extracted with EtOAc, washed with brine, dried over MgSO$_4$, and concentrated in vacuo. The crude product was purified through silicagel column chromatography to give 680 mg of off-white solid.

$^1$H NMR (400 MHz, CD$_3$OD) δ ppm 1.58-1.69 (m, 1H) 1.72-1.88 (m, 3H) 1.96-2.08 (m, 1H) 2.16 (td, J=13.35, 7.92 Hz, 1H) 3.86-4.00 (m, 3H) 4.39 (td, J=7.48, 4.40 Hz, 1H) 4.60 (q, J=12.72 Hz, 2H) 7.20 (t, J=7.92 Hz, 1H) 7.29 (d, J=7.63 Hz, 1H) 7.35 (d, J=7.63 Hz, 1H) 7.50 (s, 1H) 7.45-7.53 (m, 1H) 7.86 (s, 1H) 8.00 (s, 1H) 8.23 (d, J=2.35 Hz, 1H) 8.46 (d, J=1.76 Hz, 1H):
MS (ESI, m/z): 470.1/472.1 [M+H]$^+$

Example 169. 2-amino-N-((1S,2S)-2-((3'-hydroxy-[1,1'-biphenyl]-3-yl)-methoxy)cyclopentyl)-5-(1-methyl-1H-pyrazol-4-yl)nicotinamide To a mixture of intermediate 5 (33 mg, 0.07 mmol) and (3-hydroxyphenyl)boronic acid (11 mg, 0.08 mmol) in 0.4 ml of 1,4-dioxane/water (3/1) was added K$_2$CO$_3$ (29 mg, 0.21 mmol) followed by Pd(PPh$_3$)$_4$ (4 mg, 0.003 mmol). The reaction mixture was heated at 100° C. for 3 hrs, cooled to room temperature, and extracted with EtOAc, dried over anhydrous MgSO$_4$ and concentrated under vacuum. The crude residue was dissolved with 0.5 ml of CH$_2$Cl$_2$/TFA (10/1) and the mixture was stirred for 2 hrs. After concentration under vacuum, the crude residue was purified by preparative HPLC to afford 27 mg of the title compound.

$^1$H NMR (600 MHz, CD$_3$OD) δ ppm 1.62 (br dd, J=12.62, 6.75 Hz, 1H) 1.81 (br d, J=4.70 Hz, 3H) 2.03 (br d, J=11.74 Hz, 1H) 2.16 (br s, 1H) 3.92 (s, 3H) 3.94-4.01 (m, 1H) 4.43 (br s, 1H) 4.64-4.74 (m, 2H) 7.13 (br d, J=6.46 Hz, 2H) 7.34-7.43 (m, 3H) 7.47 (br d, J=7.63 Hz, 2H) 7.58-7.62 (m, 1H) 7.81 (s, 1H) 7.96 (s, 1H) 8.17 (br d, J=1.76 Hz, 1H) 8.36 (br d, J=2.35 Hz, 1H);
MS (ESI, m/z): 484.2 [M+H]$^+$

Example 170. 2-amino-N-((1S,2S)-2-((3'-amino-[1,1'-biphenyl]-3-yl)methoxy)-cyclopentyl)-5-(1-methyl-1H-pyrazol-4-yl)nicotinamide Using (3-aminophenyl)boronic acid, the title compound was obtained as described for the example 169.

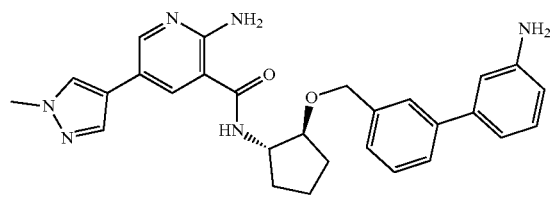 [SMILES: Cn1cc(-c2cnc(N)c(C(=O)N[C@H]3CCC[C@@H]3OCc3cccc(-c4cccc(N)c4)c3)c2)cn1]

MS (ESI, m/z): 483.2 [M+H]$^+$

Example 171. 2-amino-N-((1S,2S)-2-((3'-(hydroxymethyl)-[1,1'-biphenyl]-3-yl)-methoxy)cyclopentyl)-5-(1-methyl-1H-pyrazol-4-yl)nicotinamide Using (3-(hydroxymethyl)phenyl)boronic acid, the title compound was obtained as described for the example 169.

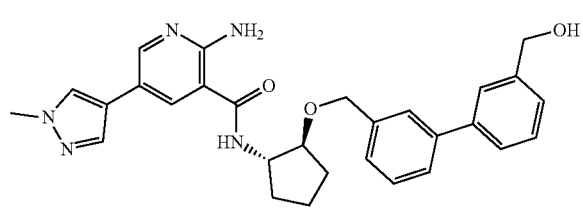 [SMILES: Cn1cc(-c2cnc(N)c(C(=O)N[C@H]3CCC[C@@H]3OCc3cccc(-c4cccc(CO)c4)c3)c2)cn1]

MS (ESI, m/z): 498.2 [M+H]+

Example 172. 2-amino-5-(1-methyl-1H-pyrazol-4-yl)-N-((1S,2S)-2-((4'-((4-methylpiperazin-1-yl)methyl)-[1,1'-biphenyl]-4-yl)methoxy)cyclopentyl)nicotinamide Scheme for the Preparation of the Compound of Example 172:

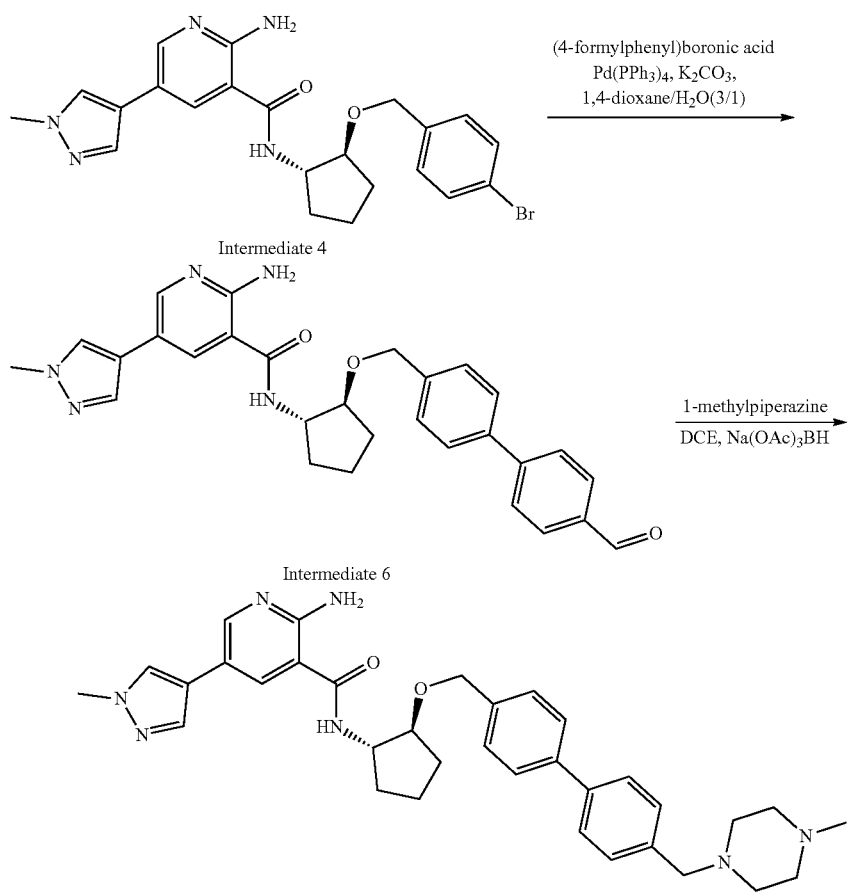

Intermediate 6

To a mixture of intermediate 4 (33 mg, 0.07 mmol) and (4-formylphenyl)boronic acid (12 mg, 0.08 mmol) in 0.4 ml of 1,4-dioxane/water (3/1) was added $K_2CO_3$ (29 mg, 0.21 mmol) followed by Pd(PPh$_3$)$_4$ (4 mg, 0.003 mmol). The reaction mixture was heated at 100° C. for 3 hrs, cooled to room temperature, and extracted with EtOAc, dried over anhydrous MgSO$_4$. After concentration under vacuum, the crude residue was purified by preparative HPLC to afford 30 mg of the title compound.

$^1$H NMR (400 MHz, CDCl$_3$) δ ppm 1.52-1.62 (m, 1H) 1.74-1.85 (m, 3H) 1.85-1.93 (m, 1H) 1.97-2.06 (m, 1H) 2.27 (br dd, J=13.30, 5.48 Hz, 1H) 3.87 (s, 3H) 3.97-4.03 (m, 1H) 4.36-4.46 (m, 1H) 4.69 (s, 2H) 6.90 (br s, 1H) 7.12 (br s, 1H) 7.16-7.19 (m, 1H) 7.43-7.48 (m, 2H) 7.50 (s, 1H) 7.54-7.60 (m, 2H) 7.68 (m, J=8.22 Hz, 2H) 7.79 (s, 1H) 7.90 (m, J=8.22 Hz, 2H) 7.98 (s, 1H) 10.02 (s, 1H); MS (ESI, m/z): 496.2 [M+H]+

Example 172. 2-amino-5-(1-methyl-1H-pyrazol-4-yl)-N-((1S,2S)-2-((4'-((4-methylpiperazin-1-yl)methyl)-[1,1'-biphenyl]-4-yl)methoxy)cyclopentyl)nicotinamide To intermediate 6 (30 mg, 0.06 mmol) in 0.4 ml of dichloroethane was added 1-methylpiperazine (12 mg, 0.12 mmol) followed by NaBH(OAc)$_3$ (26 mg, 0.18 mmol). The mixture was stirred at room temperature for 4 hr and then water was added. The mixture was extracted with EtOAc, washed with brine, dried over MgSO$_4$. After concentration under vacuum, the crude residue was purified by preparative HPLC to afford 27 mg of the title compound.

$^1$H NMR (400 MHz, CD$_3$OD) δ ppm 1.52-1.67 (m, 1H) 1.69-1.86 (m, 3H) 2.01 (br dd, J=12.52, 5.87 Hz, 1H) 2.08-2.21 (m, 1H) 2.28 (s, 3H) 2.51 (br s, 8H) 3.54 (s, 2H) 3.84 (s, 3H) 3.91-3.99 (m, 1H) 4.40 (br d, J=4.70 Hz, 1H) 4.64 (br d, J=3.13 Hz, 2H) 7.34 (br d, J=7.83 Hz, 2H) 7.39

(br d, J=8.22 Hz, 2H) 7.47 (br d, J=7.83 Hz, 1H) 7.50 (br d, J=7.83 Hz, 2H) 7.73 (s, 1H) 7.81 (s, 1H) 7.96 (s, 1H) 8.23 (s, 1H);
MS (ESI, m/z): 580.3 [M+H]+

Example 173. 2-amino-N-((1S,2S)-2-((4'-(((2-hydroxyethyl)amino)methyl)-[1,1'-biphenyl]-4-yl)methoxy)cyclopentyl)-5-(1-methyl-1H-pyrazol-4-yl)nicotinamide Using 2-aminoethan-1-ol, the title compound was obtained as described for the example 172.

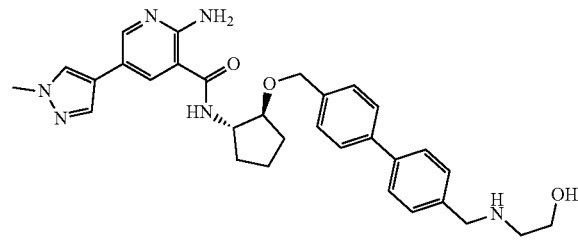 [SMILES: Cn1cc(-c2cnc(N)c(C(=O)N[C@H]3CCC[C@@H]3OCc3ccc(-c4ccc(CNCCO)cc4)cc3)c2)cn1]

1H NMR (600 MHz, CD3OD) δ ppm 1.59-1.69 (m, 1H) 1.74-1.88 (m, 3H) 1.99-2.11 (m, 1H) 2.18 (td, J=12.91, 7.04 Hz, 1H) 3.11-3.12 (m, 1H) 3.11-3.16 (m, 1H) 3.77-3.86 (m, 2H) 3.90 (s, 3H) 3.93 (br d, J=5.87 Hz, 1H) 3.97-4.05 (m, 1H) 4.26 (s, 2H) 4.39-4.48 (m, 1H) 4.67 (s, 2H) 7.44 (d, J=8.22 Hz, 2H) 7.53 (m, J=8.22 Hz, 2H) 7.55-7.62 (m, 2H) 7.66 (d, J=8.22 Hz, 2H) 7.85 (s, 1H) 7.97 (s, 1H) 8.20 (s, 1H) 8.49 (br s, 1H);
MS (ESI, m/z): 541.3 [M+H]+

Example 174. 2-amino-5-(1-methyl-1H-pyrazol-4-yl)-N-((1S,2S)-2-((4'-(morpholinomethyl)-[1,1'-biphenyl]-4-yl)methoxy)cyclopentyl)nicotinamide Using morpholine, the title compound was obtained as described for the example 172.

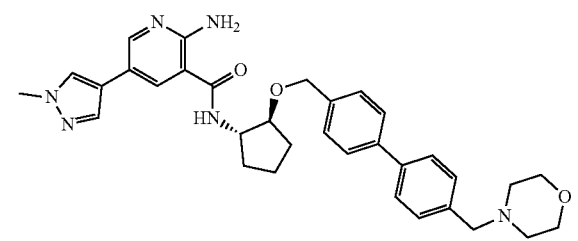 [SMILES: Cn1cc(-c2cnc(N)c(C(=O)N[C@H]3CCC[C@@H]3OCc3ccc(-c4ccc(CN5CCOCC5)cc4)cc3)c2)cn1]

1H NMR (600 MHz, CD3OD) δ ppm 1.57-1.69 (m, 1H) 1.74-1.90 (m, 3H) 2.04 (s, 1H) 2.14-2.23 (m, 1H) 2.19 (br d, J=7.63 Hz, 1H) 3.31-3.46 (m, 2H) 3.90 (s, 3H) 3.99-4.03 (m, 1H) 4.39 (s, 2H) 4.42 (br d, J=5.28 Hz, 1H) 4.67 (d, J=3.52 Hz, 2H) 7.45 (d, J=8.22 Hz, 2H) 7.56 (d, J=8.22 Hz, 2H) 7.59 (d, J=8.22 Hz, 2H) 7.71 (d, J=7.63 Hz, 2H) 7.85 (s, 1H) 7.98 (s, 1H) 8.21 (d, J=1.76 Hz, 1H) 8.49 (br s, 1H);
MS (ESI, m/z): 567.3 [M+H]+

Example 175. 2-amino-N-((1S,2S)-2-((4'-((3,3-difluoropiperidin-1-yl)methyl)-[1,1'-biphenyl]-4-yl)methoxy)cyclopentyl)-5-(1-methyl-1H-pyrazol-4-yl)nicotinamide Using 3,3-difluoropiperidine, the title compound was obtained as described for the example 172.

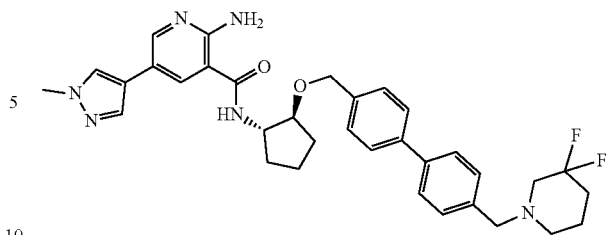

MS (ESI, m/z): 601.3 [M+H]+

Example 176. 2-amino-5-(1-methyl-1H-pyrazol-4-yl)-N-((1S,2S)-2-((4'-((4-methylpiperidin-1-yl)methyl)-[1,1'-biphenyl]-4-yl)methoxy)cyclopentyl)nicotinamide Using 4-methylpiperidine, the title compound was obtained as described for the example 172.

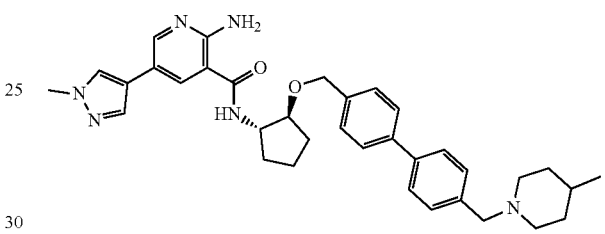

MS (ESI, m/z): 579.3 [M+H]+

Example 177. 2-amino-5-(1-methyl-1H-pyrazol-4-yl)-N-((1S,2S)-2-((4'-(piperazin-1-ylmethyl)-[1,1'-biphenyl]-4-yl)methoxy)cyclopentyl)nicotinamide Using piperazine, the title compound was obtained as described for the example 172.

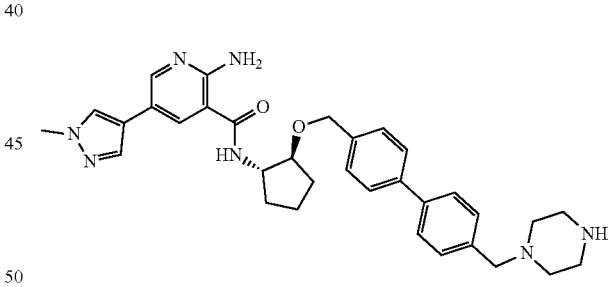

1H NMR (600 MHz, CD3OD) δ ppm 1.63 (br dd, J=13.50, 7.04 Hz, 1H) 1.73-1.88 (m, 3H) 2.00-2.08 (m, 1H) 2.13-2.22 (m, 1H) 2.96 (br s, 4H) 3.32 (br d, J=9.98 Hz, 4H) 3.50 (s, 1H) 3.84-3.89 (m, 2H) 3.90 (s, 3H) 4.00 (br s, 1H) 4.38-4.44 (m, 1H) 4.66 (d, J=2.93 Hz, 2H) 7.38-7.47 (m, 4H) 7.52-7.60 (m, 4H) 7.85 (s, 1H) 7.97 (s, 1H) 8.19 (d, J=2.35 Hz, 1H) 8.50 (d, J=2.35 Hz, 1H);
MS (ESI, m/z): 566.3 [M+H]+

Example 178. 2-amino-5-(1-methyl-1H-pyrazol-4-yl)-N-((1S,2S)-2-((4'-((4-phenylpiperazin-1-yl)methyl)-[1,1'-biphenyl]-4-yl)methoxy)cyclopentyl)nicotinamide Using 1-phenylpiperazine, the title compound was obtained as described for the example 172.

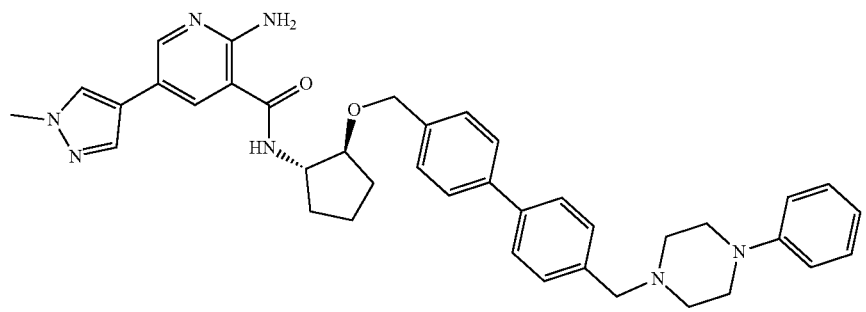 [SMILES: Cn1cc(-c2cnc(N)c(C(=O)N[C@H]3CCC[C@@H]3OCc3ccc(-c4ccc(CN5CCN(c6ccccc6)CC5)cc4)cc3)c2)cn1]

¹H NMR (600 MHz, CD₃OD) δ ppm 1.61-1.69 (m, 1H) 1.76-1.87 (m, 3H) 2.00-2.07 (m, 1H) 2.15-2.23 (m, 1H) 3.90 (s, 3H) 3.98-4.04 (m, 1H) 4.39-4.44 (m, 1H) 4.45 (s, 2H) 4.68 (s, 2H) 6.92 (t, J=7.34 Hz, 1H) 7.00 (d, J=8.22 Hz, 2H) 7.27 (t, J=7.92 Hz, 2H) 7.45 (d, J=8.22 Hz, 2H) 7.60 (dd, J=9.68, 8.51 Hz, 4H) 7.72 (br d, J=8.22 Hz, 2H) 7.85 (s, 1H) 7.98 (s, 1H) 8.21 (d, J=1.76 Hz, 1H) 8.51 (d, J=1.76 Hz, 1H);
MS (ESI, m/z): 642.4 [M+H]⁺

Example 179. 2-amino-5-(1-methyl-1H-pyrazol-4-yl)-N-((1S,2S)-2-((4'-((4-(pyrrolidin-1-yl)piperidin-1-yl)methyl)-[1,1'-biphenyl]-4-yl)methoxy)cyclopentyl)-nicotinamide Using 4-(pyrrolidin-1-yl)piperidine, the title compound was obtained as described for the example 172.

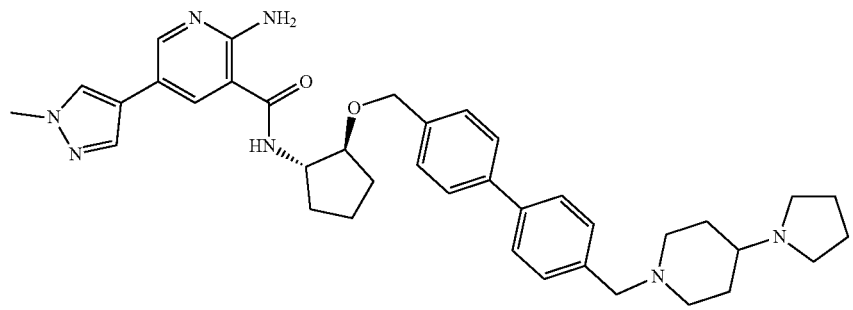 [SMILES: Cn1cc(-c2cnc(N)c(C(=O)N[C@H]3CCC[C@@H]3OCc3ccc(-c4ccc(CN5CCC(N6CCCC6)CC5)cc4)cc3)c2)cn1]

¹H NMR (600 MHz, CD₃OD) δ ppm 1.60-1.69 (m, 1H) 1.74-1.88 (m, 3H) 1.96-2.23 (m, 8H) 2.43 (br d, J=13.50 Hz, 2H) 3.06-3.21 (m, 4H) 3.44 (br s, 2H) 3.66 (br d, J=12.91 Hz, 4H) 3.90 (s, 3H) 3.99-4.03 (m, 1H) 4.37 (s, 2H) 4.39-4.45 (m, 1H) 4.67 (s, 2H) 7.41-7.48 (m, 2H) 7.51-7.57 (m, 2H) 7.58 (d, J=8.22 Hz, 2H) 7.68 (br d, J=8.22 Hz, 2H) 7.85 (s, 1H) 7.98 (s, 1H) 8.20 (d, J=2.35 Hz, 1H) 8.50 (d, J=1.76 Hz, 1H);
MS (ESI, m/z): 634.4 [M+H]⁺

Example 180. 2-amino-N-((1S,2S)-2-((4'-((4-hydroxypiperidin-1-yl)methyl)-[1,1'-biphenyl]-4-yl)methoxy)cyclopentyl)-5-(1-methyl-1H-pyrazol-4-yl)nicotinamide Using piperidin-4-ol, the title compound was obtained as described for the example 172.

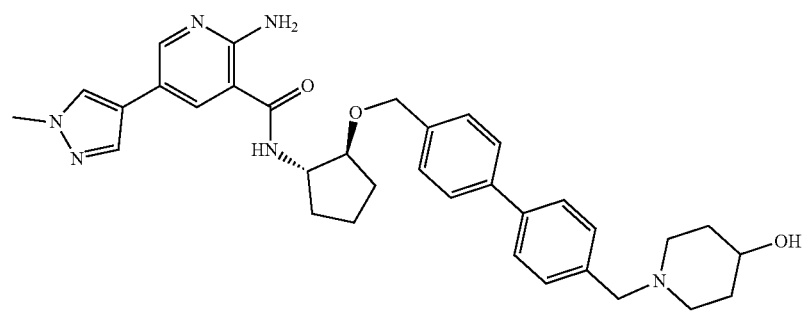 [SMILES: Cn1cc(-c2cnc(N)c(C(=O)N[C@H]3CCC[C@@H]3OCc3ccc(-c4ccc(CN5CCC(O)CC5)cc4)cc3)c2)cn1]

¹H NMR (600 MHz, CD₃OD) δ ppm 1.59-1.68 (m, 1H) 1.74-1.87 (m, 3H) 1.92 (br s, 1H) 2.03 (dt, J=13.35, 6.53 Hz, 1H) 2.10-2.23 (m, 1H) 3.07 (br s, 1H) 3.51 (br d, J=10.56 Hz, 1H) 3.82 (br s, 1H) 3.89-3.92 (m, 3H) 3.98-4.03 (m, 1H) 4.08 (br s, 1H) 4.34 (br s, 2H) 4.39-4.45 (m, 1H) 4.67 (s, 2H) 7.45 (d, J=8.22 Hz, 2H) 7.54 (br s, 2H) 7.57-7.61 (m, 2H) 7.59 (d, J=8.22 Hz, 2H) 7.69 (br d, J=8.22 Hz, 2H) 7.85 (s, 1H) 7.99 (s, 1H) 8.21 (s, 1H) 8.52 (d, J=1.76 Hz, 1H);

MS (ESI, m/z): 581.3 [M+H]⁺

Example 181. 2-amino-N-((1S,2S)-2-((4'-((4-(2-hydroxyethyl)piperazin-1-yl)-methyl)-[1,1'-biphenyl]-4-yl)methoxy)cyclopentyl)-5-(1-methyl-1H-pyrazol-4-yl)-nicotinamide Using 2-(piperazin-1-yl)ethan-1-ol, the title compound was obtained as described for the example 172.

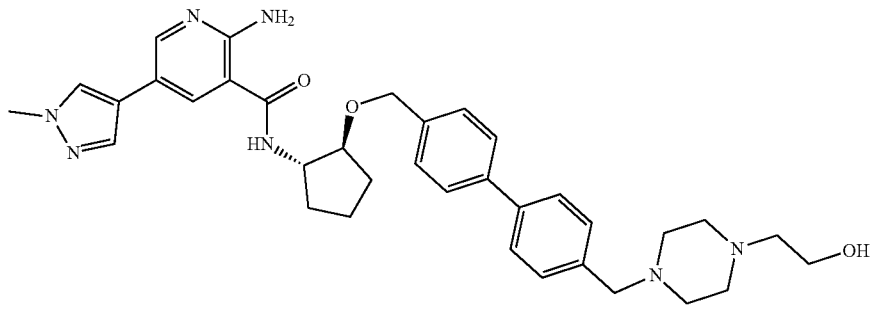 [SMILES: Cn1cc(-c2cnc(N)c(C(=O)N[C@H]3CCC[C@@H]3OCc3ccc(-c4ccc(CN5CCN(CCO)CC5)cc4)cc3)c2)cn1]

¹H NMR (600 MHz, CD₃OD) δ ppm 1.64 (br dd, J=13.50, 7.04 Hz, 1H) 1.76-1.86 (m, 3H) 2.00-2.08 (m, 1H) 2.14-2.22 (m, 1H) 3.19 (br s, 2H) 3.82-3.85 (m, 2H) 3.90 (s, 3H) 3.98-4.02 (m, 1H) 4.39-4.44 (m, 1H) 4.66 (s, 2H) 7.40-7.47 (m, 4H) 7.53-7.61 (m, 4H) 7.85 (s, 1H) 7.97 (s, 1H) 8.20 (d, J=2.35 Hz, 1H) 8.52 (d, J=2.35 Hz, 1H);

MS (ESI, m/z): 610.3 [M+H]⁺

Example 182. 2-amino-N-((1S,2S)-2-((4'-((4-(2-hydroxy-2-methylpropyl)-piperazin-1-yl)methyl)-[1,1'-biphenyl]-4-yl)methoxy)cyclopentyl)-5-(1-methyl-1H-pyrazol-4-yl)nicotinamide Using 2-methyl-1-(piperazin-1-yl)propan-2-ol, the title compound was obtained as described for the example 172.

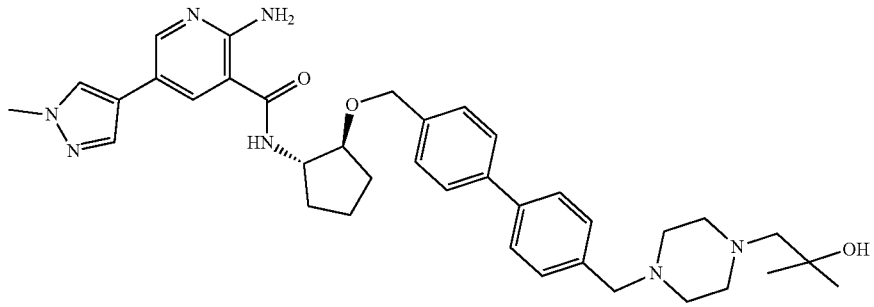 [SMILES: Cn1cc(-c2cnc(N)c(C(=O)N[C@H]3CCC[C@@H]3OCc3ccc(-c4ccc(CN5CCN(CC(C)(C)O)CC5)cc4)cc3)c2)cn1]

MS (ESI, m/z): 638.4 [M+H]⁺

Example 183. 2-amino-N-((1S,2S)-2-((4'-((4-eth-ylpiperazin-1-yl)methyl)-[1,1'-biphenyl]-4-yl)methoxy)cyclopentyl)-5-(1-methyl-1H-pyrazol-4-yl)nicotinamide Using 1-ethylpiperazine, the title compound was obtained as described for the example 172.

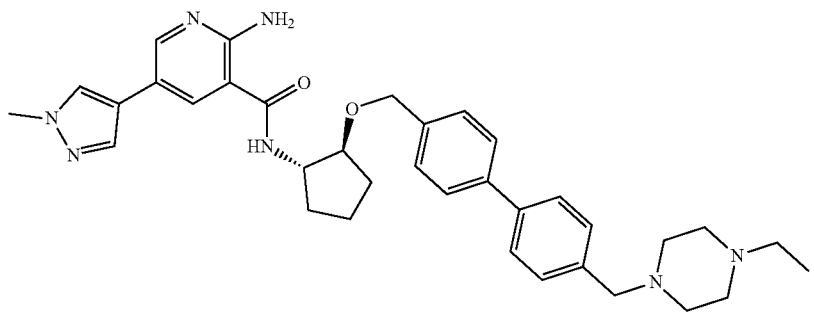 [SMILES: CCN1CCN(Cc2ccc(-c3ccc(CO[C@H]4CCC[C@@H]4NC(=O)c4cc(-c5cnn(C)c5)cnc4N)cc3)cc2)CC1]

¹H NMR (600 MHz, CD₃OD) δ ppm 1.32 (t, J=7.34 Hz, 3H) 1.59-1.68 (m, 1H) 1.74-1.88 (m, 3H) 2.04 (dq, J=13.50, 6.85 Hz, 1H) 2.13-2.21 (m, 1H) 3.18 (br d, J=7.63 Hz, 2H) 3.78-3.87 (m, 2H) 3.90 (s, 3H) 3.98-4.02 (m, 1H) 4.38-4.44 (m, 1H) 4.66 (d, =1.76 Hz, 2H) 7.38-7.46 (m, 4H) 7.51-7.60 (m, 4H) 7.85 (s, 1H) 7.97 (s, 1H) 8.19 (d, J=2.35 Hz, 1H) 8.51 (d, J=2.35 Hz, 1H); MS (ESI, m/z): 594.4 [M+H]⁺

Example 184. 2-amino-N-((1S,2S)-2-((4'-((4-cyclo-pronylpiperazin-1-yl)methyl)-[1,1'-biphenyl]-4-yl)methoxy)cyclopentyl)-5-(1-methyl-1H-pyrazol-4-yl)nicotinamide Using 1-cyclopropylpiperazine, the title compound was obtained as described for the example 172.

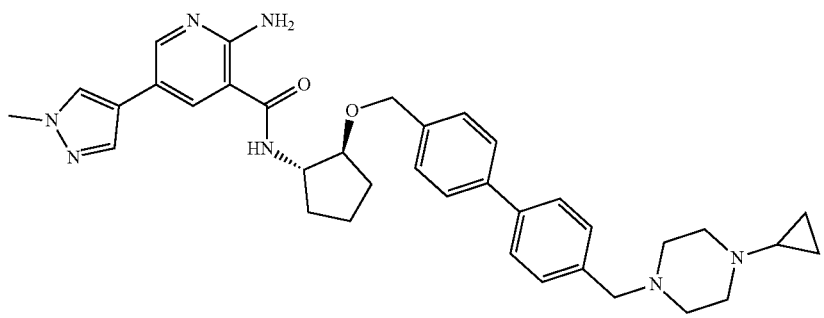 [SMILES: Cn1cc(-c2cnc(N)c(C(=O)N[C@H]3CCC[C@@H]3OCc3ccc(-c4ccc(CN5CCN(C6CC6)CC5)cc4)cc3)c2)cn1]

MS (ESI, m/z): 606.4 [M+H]⁺

Example 185. 2-amino-5-(1-methyl-1H-pyrazol-4-yl)-N-((1S,2S)-2-((4'-(((R)-3-methylpiperazin-1-yl)methyl)-[1,1'-biphenyl]-4-yl)methoxy)cyclopentyl)nicotinamide Using tert-butyl(R)-2-methylpiperazine-1-carboxylate, the title compound was obtained as described for the example 172 and following deprotection with TFA.

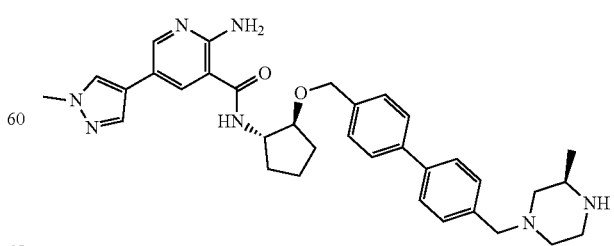

MS (ESI, m/z): 580.3 [M+H]⁺

Example 186. 2-amino-N-((1S,2S)-2-((4'-(((R)-3,4-dimethylpiperazin-1-yl)-methyl)-[1,1'-biphenyl]-4-yl)methoxy)cyclopentyl)-5-(1-methyl-1H-pyrazol-4-yl)-nicotinamide Using (R)-1,2-dimethylpiperazine, the title compound was obtained as described for the example 172.

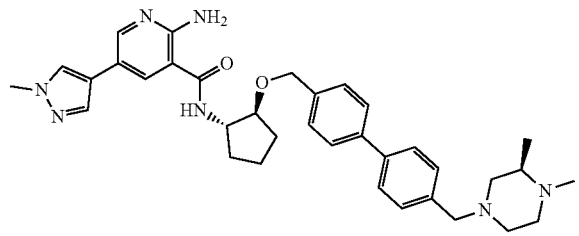

MS (ESI, m/z): 594.4 [M+H]+

Example 187. 2-amino-N-((1S,2S)-2-((4'-(((R)-2,4-dimethylpiperazin-1-yl)-methyl)-[1,1'-biphenyl]-4-yl)methoxy)cyclopentyl)-5-(1-methyl-1l-pyrazol-4-yl)-nicotinamide Using (R)-1,3-dimethylpiperazine, the title compound was obtained as described for the example 172.

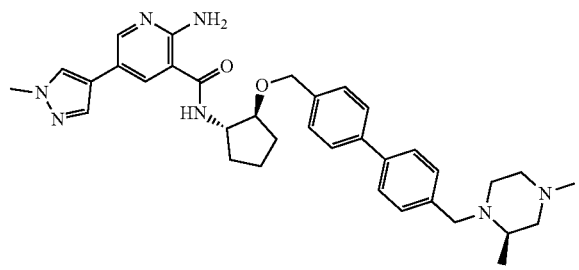

$^1$H NMR (400 MHz, CD$_3$OD) δ ppm 1.34 (br d, J=5.09 Hz, 3H) 1.63 (br dd, J=15.06, 6.46 Hz, 1H) 1.81 (br d, J=7.43 Hz, 3H) 2.03 (br d, J=6.26 Hz, 1H) 2.18 (s, 1H) 2.55 (br s, 1H) 2.82 (s, 3H) 2.92 (br s, 1H) 3.02 (br d, J=12.52 Hz, 1H) 3.89 (s, 3H) 4.00 (br s, 1H) 4.30 (br d, J=11.35 Hz, 1H) 4.42 (br s, 1H) 4.65 (s, 2H) 7.41 (br d, J=7.43 Hz, 4H) 7.54 (br dd, J=7.63, 3.33 Hz, 4H) 7.84 (s, 1H) 7.96 (s, 1H) 8.19 (s, 1H) 8.50 (s, 1H);
MS (ESI, m/z): 594.4 [M+H]+

Example 188. 2-amino-N-((1S,2S)-2-((4'-((3-ethyl-4-methylpiperazin-1-yl)-methyl)-[1,1'-biphenyl]-4-yl)methoxy)cyclopentyl)-5-(1-methyl-1H-pyrazol-4-yl)-nicotinamide Using 2-ethyl-1-methylpiperazine, the title compound was obtained as described for the example 172.

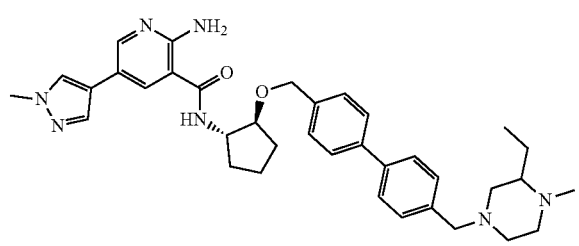

$^1$H NMR (400 MHz, CD$_3$OD) δ ppm 0.96 (br t, J=7.24 Hz, 3H) 1.62 (br d, J=14.48 Hz, 3H) 1.81 (br d, J=7.43 Hz, 3H) 1.92 (br s, 1H) 2.04 (br s, 1H) 2.16 (br d, J=7.04 Hz, 1H) 2.87 (s, 3H) 3.20 (br d, J=14.09 Hz, 1H) 3.45 (br d, J=13.30 Hz, 1H) 3.70 (br d, J=13.30 Hz, 1H) 3.81 (br d, J=12.91 Hz, 1H) 3.89 (s, 3H) 3.99 (br s, 1H) 4.42 (br s, 1H) 4.65 (s, 2H) 7.41 (br d, J=8.22 Hz, 4H) 7.55 (br d, J=7.43 Hz, 4H) 7.85 (s, 1H) 7.97 (s, 1H) 8.19 (s, 1H) 8.51 (s, 1H);
MS (ESI, m/z): 608.4 [M+H]+

Example 189. 2-amino-N-((1S,2S)-2-((4'-((cis-3,5-dimethylpiperazin-1-yl)-methyl)-[1,1'-biphenyl]-4-yl)methoxy)cyclopentyl)-5-(1-methyl-1H-pyrazol-4-yl)-nicotinamide Using tert-butyl cis-2,6-dimethylpiperazine-1-carboxylate, the title compound was obtained as described for the example 172 and following deprotection with TFA.

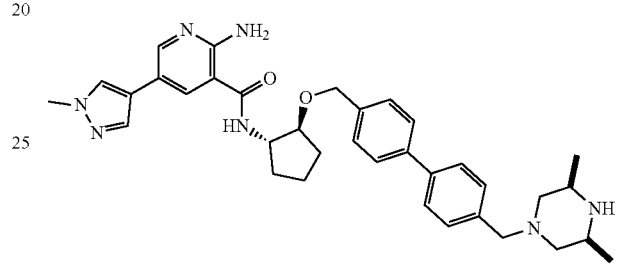

$^1$H NMR (400 MHz, CD$_3$OD) δ ppm 1.27 (br d, J=6.26 Hz, 6H) 1.64 (br d, J=5.87 Hz, 1H) 1.81 (br d, J=7.04 Hz, 3H) 1.96-2.24 (m, 3H) 3.09 (d, J=12.91 Hz, 2H) 3.62 (br s, 5H) 3.68 (s, 3H) 3.89 (s, 3H) 4.00 (br s, 1H) 4.37-4.45 (m, 1H) 4.65 (s, 2H) 7.34-7.46 (m, 4H) 7.53 (br d, J=7.43 Hz, 4H) 7.83 (s, 1H) 7.95 (s, 1H) 8.20 (s, 1H) 8.45 (s, 1H);
MS (ESI, m/z): 594.4 [M+H]+

Example 190. 2-amino-5-(1-methyl-1H-pyrazol-4-yl)-N-((1S,2S)-2-((4'-((cis-3,4,5-trimethylpiperazin-1-yl)methyl)-[1,1'-biphenyl]-4-yl)methoxy)cyclopentyl)-nicotinamide Using cis-1,2,6-trimethylpiperazine, the title compound was obtained as described for the example 172.

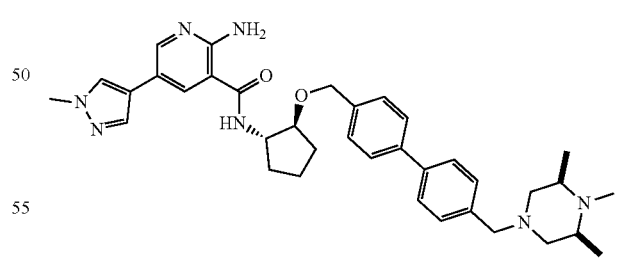

$^1$H NMR (600 MHz, CD$_3$OD) δ ppm 1.30 (br d, J=6.46 Hz, 6H) 1.64 (br dd, J=13.50, 7.04 Hz, 1H) 1.74-1.90 (m, 3H) 2.00-2.09 (m, 1H) 2.18 (br dd, J=12.91, 5.87 Hz, 1H) 2.30 (br d, J=12.91 Hz, 3H) 3.22 (br s, 3H) 3.45 (br s, 2H) 3.84 (br d, J=19.37 Hz, 2H) 3.90 (s, 3H) 3.97-4.03 (m, 1H) 4.38-4.45 (m, 1H) 4.66 (s, 2H) 4.69 (s, 1H) 7.42 (br d, J=7.63 Hz, 4H) 7.49-7.62 (m, 4H) 7.85 (s, 1H) 7.97 (s, 1H) 8.20 (d, J=2.35 Hz, 1H) 8.52 (d, J=1.76 Hz, 1H);
MS (ESI, m/z): 608.4 [M+H]+

Example 191. 2-amino-N-((1S,2S)-2-((4'-((trans-2,5-dimethylpiperazin-1-yl)methyl)-[1,1'-biphenyl]-4-yl)methoxy)cyclopentyl)-5-(1-methyl-1H-pyrazol-4-yl)nicotinamide Using trans-2,5-dimethylpiperazine, the title compound was obtained as described for the example 172.

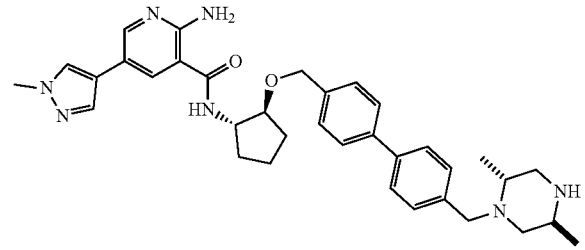

MS (ESI, m/z): 594.4 [M+H]$^+$

Example 192. 2-amino-5-(1-methyl-1H-pyrazol-4-yl)-N-((1S,2S)-2-((4'-(((2R,5S)-2,4,5-trimethylpiperazin-1-yl)methyl)-[1,1'-biphenyl]-4-yl)methoxy)cyclopentyl)nicotinamide Using trans-1,2,5-trimethylpiperazine, the title compound was obtained as described for the example 172.

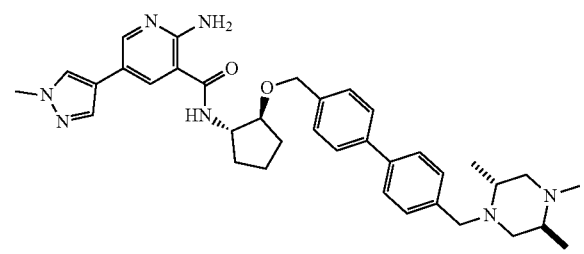

MS (ESI, m/z): 608.4 [M+H]$^+$

Example 193. 2-amino-N-((1S,2S)-2-((4'-((3-(dimethylamino)pyrrolidin-1-yl)methyl)-[1,1'-biphenyl]-4-yl)methoxy)cyclopentyl)-5-(1-methyl-1H-pyrazol-4-yl)nicotinamide Using N,N-Dimethyl-3-pyrrolidinamine, the title compound was obtained as described for the example 172.

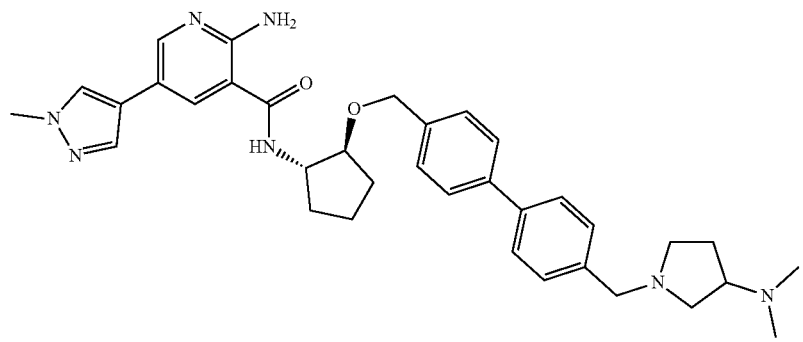

MS (ESI, m/z): 594.4 [M+H]$^+$

Example 194. 3-amino-6-(1-methyl-1H-pyrazol-4-yl)-N-((1S,2S)-2-((4'-((4-methylpiperazin-1-yl)methyl)-[1,1'-biphenyl]-4-yl)methoxy)cyclopentyl)pyrazine-2-carboxamide Using 3-amino-6-(1-methyl-1H-pyrazol-4-yl)pyrazine-2-carboxylic acid, the title compound was obtained as described for the example 172.

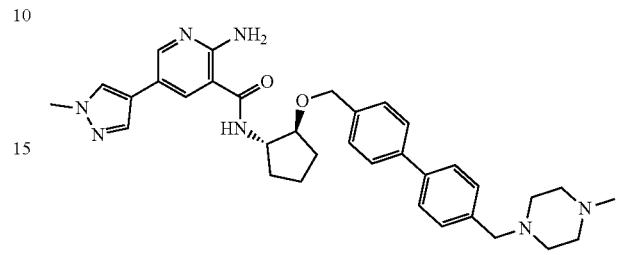

$^1$H NMR (600 MHz, CD$_3$OD) δ ppm 1.60-1.69 (m, 1H) 1.70-1.78 (m, 1H) 1.78-1.87 (m, 2H) 2.03-2.20 (m, 3H) 2.88 (d, J=1.76 Hz, 3H) 3.00 (br s, 4H) 3.34 (br d, J=11.74 Hz, 3H) 3.85 (s, 3H) 3.91 (br d, J=11.74 Hz, 2H) 3.99-4.06 (m, 1H) 4.33-4.40 (m, 1H) 4.59-4.70 (m, 2H) 7.38 (d, J=8.22 Hz, 2H) 7.42 (br d, J=8.22 Hz, 2H) 7.47 (d, J=8.22 Hz, 2H) 7.52 (br d, J=8.22 Hz, 2H) 7.99 (s, 1H) 8.12 (s, 1H) 8.41 (s, 1H); MS (ESI, m/z): 581.3 [M+H]$^+$ Example 195. 2-amino-N-((1S,2S)-2-((3'-fluoro-4'-((4-methylpiperazin-1-yl)-methyl)-[1,1'-biphenyl]-4-yl)methoxy)cyclopentyl)-5-(1-methyl-1H-pyrazol-4-yl)-nicotinamide Using (3-fluoro-4-formylphenyl)boronic acid pinacol ester, the title compound was obtained as described for the example 172.

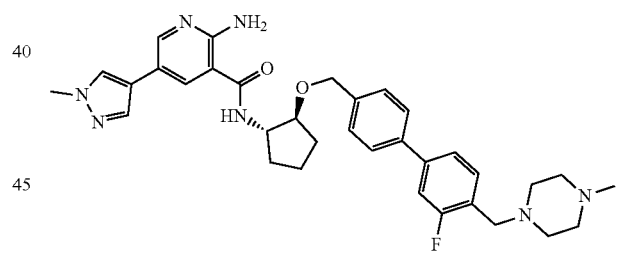

¹H NMR (400 MHz, CD₃OD) δ ppm 1.63 (br dd, J=13.69, 7.04 Hz, 1H) 1.72-1.90 (m, 3H) 1.96-2.09 (m, 1H) 2.10-2.23 (m, 1H) 2.90 (s, 3H) 3.05-3.27 (m, 4H) 3.34-3.51 (m, 4H) 3.89 (s, 3H) 3.94-4.01 (m, 1H) 4.07 (s, 2H) 4.34-4.47 (m, 1H) 4.60-4.73 (m, 2H) 5.47 (s, 1H) 7.35 (br d, J=11.35 Hz, 1H) 7.42 (br d, J=7.83 Hz, 3H) 7.50 (br t, J=7.83 Hz, 1H) 7.55 (d, J=8.22 Hz, 2H) 7.83 (s, 1H) 7.97 (s, 1H) 8.17 (d, J=1.96 Hz, 1H) 8.50 (d, J=1.96 Hz, 1H);

MS (ESI, m/z): 598.7 [M+H]⁺

Example 196. 2-amino-N-((1S,2S)-2-((3',5'-difluoro-4'-((4-methylpiperazin-1-yl)methyl)-[1,1'-biphenyl]-4-yl)methoxy)cyclopentyl)-5-(1-methyl-1H-pyrazol-4-yl)nicotinamide Using ((3,5-difluoro-4-formylphenyl)boronic acid pinacol ester, the title compound was obtained as described for the example 172.

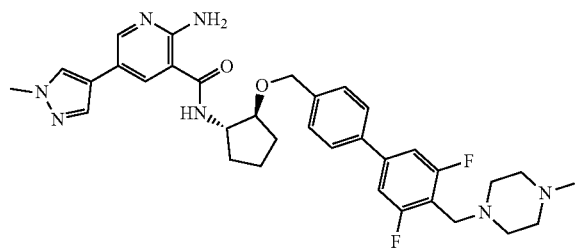

¹H NMR (400 MHz, CD₃OD) δ ppm 1.63 (br dd, J=13.30, 7.04 Hz, 1H) 1.71-1.91 (m, 3H) 2.03 (br dd, J=12.91, 5.48 Hz, 1H) 2.12-2.23 (m, 1H) 2.87 (s, 3H) 2.94 (br d, J=18.00 Hz, 3H) 3.32 (br s, 4H) 3.90 (s, 3H) 3.99 (br s, 1H) 4.40 (br d, J=3.91 Hz, 1H) 4.62-4.77 (m, 2H) 7.24 (br d, J=8.61 Hz, 2H) 7.44 (m, J=7.83 Hz, 2H) 7.57 (m, J=7.83 Hz, 2H) 7.83 (s, 1H) 7.98 (s, 1H) 8.19 (s, 1H) 8.50 (s, 1H);

MS (ESI m/z): 616.8 [M+H]⁺

Example 197. 2-amino-5-(1-methyl-1H-pyrazol-4-yl)-N-((1S,2S)-2-((4'-((4-methylpiperazin-1-yl)methyl)-3'-(trifluoromethyl)-[1,1'-biphenyl]-4-yl)methoxy)-cyclopentyl)nicotinamide Using (4-formyl-3-(trifluoromethyl)phenyl)boronic acid pinacol ester, the title compound was obtained as described for the example 172.

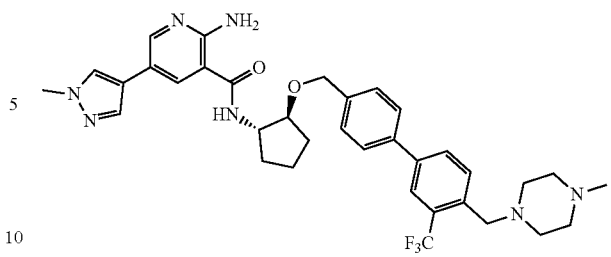

¹H NMR (400 MHz, CD₃OD) δ ppm 1.59-1.71 (m, 1H) 1.75-1.89 (m, 3H) 1.99-2.10 (m, 1H) 2.13-2.25 (m, 1H) 2.91 (s, 3H) 3.47 (br d, J=1.57 Hz, 2H) 3.81 (s, 2H) 3.91 (s, 3H) 4.02 (br d, J=4.30 Hz, 1H) 4.39-4.46 (m, 1H) 4.69 (s, 2H) 7.47 (m, J=8.22 Hz, 2H) 7.60 (m, J=8.22 Hz, 2H) 7.83 (d, J=8.22 Hz, 4H) 7.98 (s, 1H) 8.21 (d, J=1.96 Hz, 1H) 8.50 (d, J=2.35 Hz, 1H);

MS (ESI, m/z): 648.32 [M+H]⁺

Example 198. 2-amino-5-(1-methyl-1H-pyrazol-4-yl)-N-((1S,2S)-2-((3'-methyl-4'-((4-methylpiperazin-1-yl)methyl)-[1,1'-biphenyl]-4-yl)methoxy)cyclopentyl)-nicotinamide Using (4-formyl-3-methylphenyl)boronic acid pinacol ester, the title compound was obtained as described for the example 172.

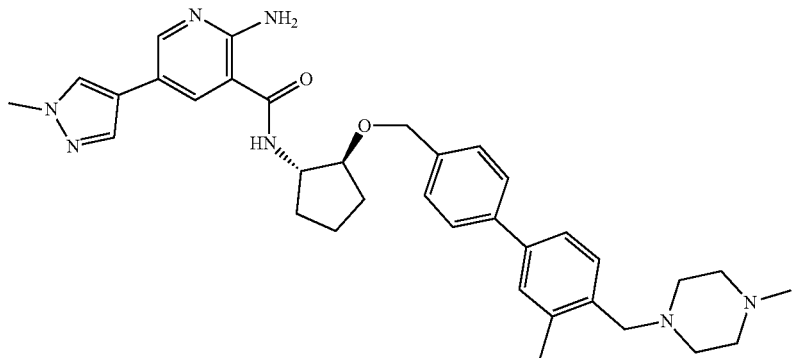

¹H NMR (400 MHz, CD₃OD) δ ppm 1.64 (br dd, J=13.11, 6.85 Hz, 2H) 1.72-1.90 (m, 3H) 1.82 (br s, 1H) 1.94-2.09 (m, 2H) 2.10-2.24 (m, 2H) 2.43 (s, 1H) 2.88 (s, 3H) 3.29-3.31 (m, 1H) 3.69 (s, 1H) 3.90 (s, 2H) 3.93-3.96 (m, 1H) 4.01 (br d, J=4.70 Hz, 1H) 4.16 (s, 1H) 4.37-4.47 (m, 1H) 4.66 (d, J=3.13 Hz, 1H) 7.37-7.43 (m, 2H) 7.51-7.55 (m, 1H) 7.52-7.59 (m, 1H) 7.85 (d, J=0.78 Hz, 1H) 7.96 (s, 1H) 8.19 (d, J=1.96 Hz, 1H) 8.49 (d, J=2.35 Hz, 1H);

MS (ESI, m/z): 594.4 [M+H]⁺

Example 199. 2-amino-N-((1S,2S)-2-((3'-hydroxy-4'-((4-methylpiperazin-1-yl)methyl)-[1,1'-biphenyl]-4-yl)methoxy)cyclopentyl)-5-(1-methyl-1H-pyrazol-4-yl)nicotinamide Using (4-formyl-3-hydroxyphenyl)boronic acid pinacol ester, the title compound was obtained as described for the example 172.

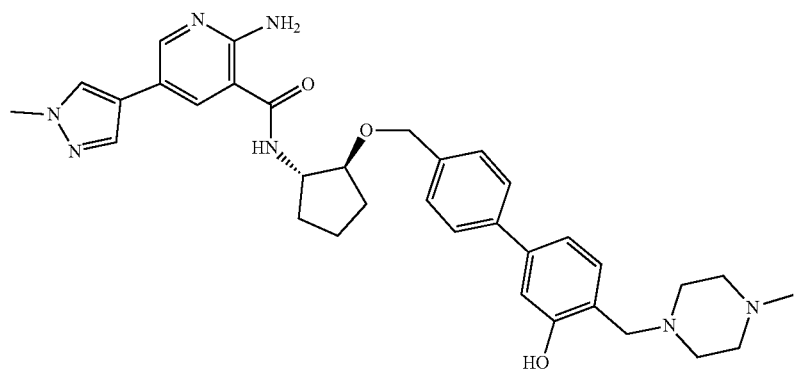

¹H NMR (400 MHz, CD₃OD) δ ppm 1.64 (br dd, J=12.72, 6.85 Hz, 1H) 1.74-1.90 (m, 3H) 2.05 (br s, 1H) 2.12-2.26 (m, 1H) 2.82 (d, J=3.13 Hz, 3H) 3.13 (br s, 5H) 3.91 (s, 3H) 4.01 (br d, J=6.26 Hz, 1H) 4.05 (s, 1H) 4.08 (s, 1H) 4.38-4.46 (m, 1H) 4.66 (s, 2H) 7.05 (s, 1H) 7.28 (br d, J=8.61 Hz, 1H) 7.25-7.34 (m, 1H) 7.32 (br d, J=7.83 Hz, 1H) 7.41 (d, J=8.22 Hz, 2H) 7.52 (d, J=8.22 Hz, 2H) 7.54-7.59 (m, 1H) 7.85 (s, 1H) 7.97 (s, 1H) 8.20 (d, J=2.35 Hz, 1H) 8.48 (d, J=2.35 Hz, 1H);
MS (ESI, m/z): 596.3 [M+H]⁺

Example 200. 2-amino-5-(1-methyl-1H-pyrazol-4-yl)-N-((1S,2S)-2-((4'-((4-methylpiperazin-1-yl)methyl)-3'-nitro-[1,1'-biphenyl]-4-yl)methoxy-cyclopentyl)nicotinamide Using (4-formyl-3-nitrophenyl)boronic acid pinacol ester, the title compound was obtained as described for the example 172.

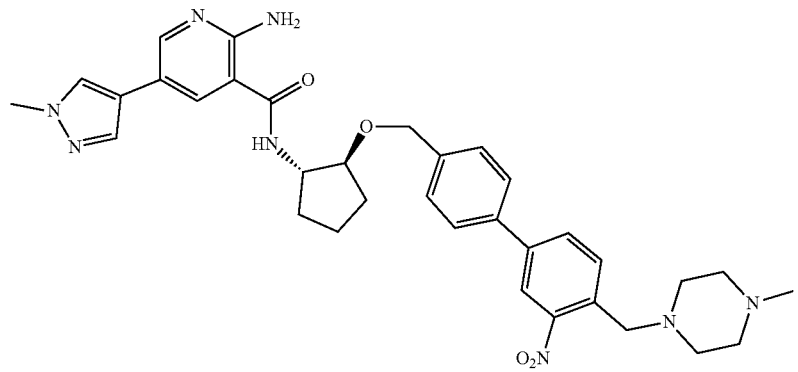

¹H NMR (400 MHz, CD₃OD) δ ppm 1.64 (dt, J=13.89, 7.14 Hz, 1H) 1.74-1.91 (m, 3H) 2.00-2.10 (m, 1H) 2.13-2.24 (m, 1H) 2.88 (s, 3H) 3.35-3.39 (m, 2H) 3.91 (s, 3H) 3.92-3.95 (m, 2H) 3.99-4.03 (m, 1H) 4.39-4.47 (m, 1H) 4.69 (d, J=3.13 Hz, 2H) 7.48 (d, J=8.22 Hz, 2H) 7.60-7.65 (m, 4H) 7.83 (s, 1H) 7.97 (s, 1H) 8.02 (d, J=1.96 Hz, 1H) 8.21 (d, J=2.35 Hz, 1H) 8.48 (d, J=2.35 Hz, 1H);
MS (ESI, m/z): 625.3 [M+H]⁺

Example 201. 2-amino-N-((1S,2S)-2-((3'-methoxy-4'-((4-methylpiperazin-1-yl)methyl)-[1,1-biphenyl]-4-yl)methoxy)cyclopentyl)-5-(1-methyl-1H-pyrazol-4-yl)nicotinamide Using (4-formyl-3-methoxyphenyl)boronic acid pinacol ester, the title compound was obtained as described for the example 172.

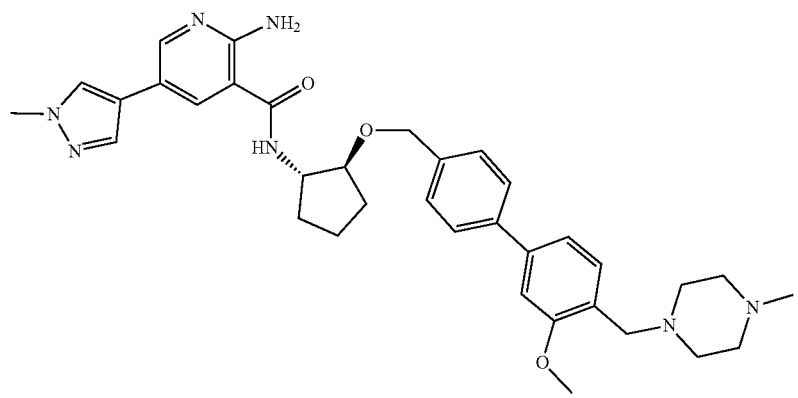

¹H NMR (400 MHz, CD₃OD) δ ppm 1.65 (br dd, J=13.50, 6.46 Hz, 1H) 1.74-1.91 (m, 3H) 1.99-2.10 (m, 1H) 2.19 (br d, J=6.65 Hz, 1H) 2.81 (s, 3H) 3.91 (s, 3H) 3.92 (s, 3H) 3.98-4.07 (m, 1H) 4.43 (br d, J=3.52 Hz, 1H) 4.68 (s, 2H) 7.15-7.24 (m, 2H) 7.37-7.47 (m, 3H) 7.59 (d, J=8.22 Hz, 2H) 7.86 (s, 1H) 7.98 (s, 1H) 8.21 (d, J=1.96 Hz, 1H) 8.51 (d, J=2.35 Hz, 1H);
MS (ESI, m/z): 610.3 [M+H]⁺

Example 202. 2-amino-N-((1S,2S)-2-((2'-chloro-4'-((4-methylpiperazin-1-yl)-methyl)-[1,1'-biphenyl]-4-yl)methoxy)cyclopentyl)-5-(1-methyl-1H-pyrazol-4-yl)-nicotinamide Using (2-chloro-4-formylphenyl)boronic acid pinacol ester, the title compound was obtained as described for the example 172.

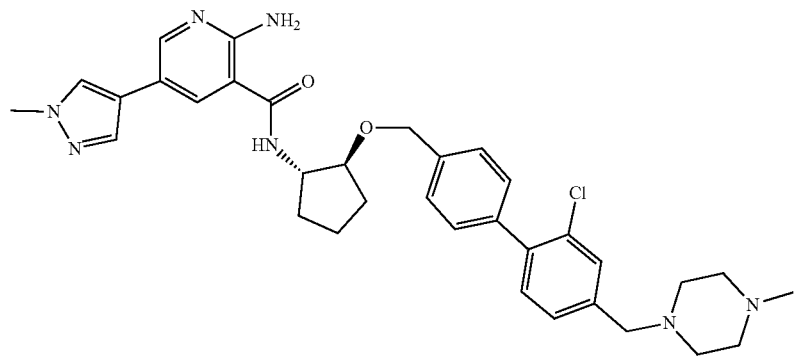

MS (ESI, m/z): 614.3 [M+H]⁺

Example 203. 2-amino-5-(1-methyl-1H-pyrazol-4-yl)-N-((1S,2S)-2-((4-(6-((4-methylpiperazin-1-yl)methyl)pyridin-3-yl)benzyl)oxy)cyclopentyl)nicotinamide Using ((6-formylpyridin-3-yl)boronic acid pinacol ester, the title compound was obtained as described for the example 172.

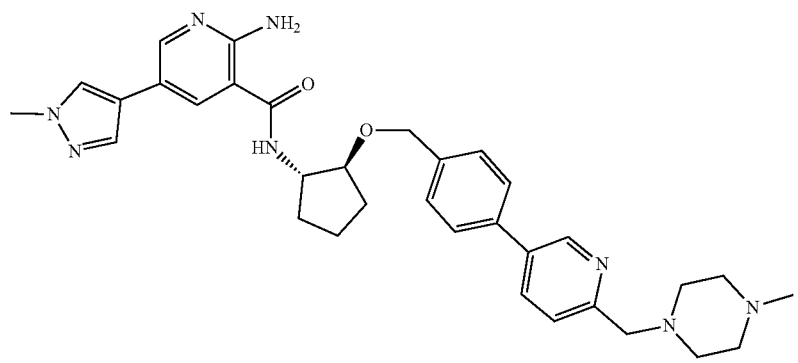

¹H NMR (400 MHz, CD₃OD) δ ppm 1.65 (dt, J=13.60, 7.09 Hz, 1H) 1.74-1.90 (m, 3H) 2.05 (br dd, J=13.11, 6.46 Hz, 1H) 2.13-2.26 (m, 1H) 2.90 (s, 3H) 3.91-3.94 (m, 3H) 3.99-4.06 (m, 1H) 4.43 (br dd, J=11.93, 6.85 Hz, 1H) 7.52 (d, J=8.22 Hz, 2H) 7.64-7.68 (m, 2H) 7.72 (br dd, J=12.33, 8.41 Hz, 2H) 7.85 (s, 1H) 7.99 (s, 1H) 8.22 (d, J=2.35 Hz, 1H) 8.51 (d, J=1.96 Hz, 1H) 8.82 (d, J=2.35 Hz, 1H);
MS (ESI, m/z): 581.3 [M+H]⁺

Example 204. 2-amino-5-(1-methyl-1H-pyrazol-4-yl)-N-((1S,2S)-2-((4-(5-((4-methylpiperazin-1-yl)methyl)pyridin-2-yl)benzyl)oxy)cyclopentyl)nicotinamide Using (5-formylpyridin-2-yl)boronic acid pinacol ester, the title compound was obtained as described for the example 172.

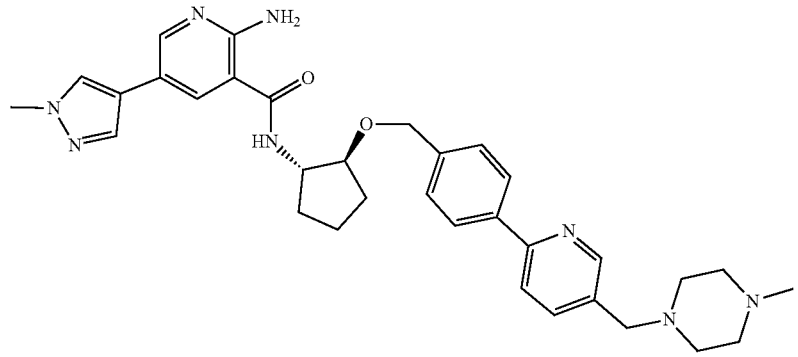

¹H NMR (400 MHz, CD₃OD) δ ppm 1.66 (td, J=14.09, 7.04 Hz, 1H) 1.76-1.92 (m, 3H) 1.98-2.11 (m, 1H) 2.19 (br s, 1H) 2.90 (s, 3H) 3.64 (s, 1H) 3.76 (s, 3H) 3.98-4.07 (m, 1H) 4.38-4.48 (m, 1H) 7.52 (d, J=8.22 Hz, 2H) 7.84 (s, 1H) 7.90 (dd, J=8.41, 1.76 Hz, 3H) 7.98 (s, 1H) 8.02 (br d, J=8.61 Hz, 1H) 8.21 (d, J=1.96 Hz, 1H) 8.50 (d, J=1.96 Hz, 1H) 8.60 (s, 1H);
MS (ESI, m/z): 581.3 [M+H]⁺

Example 205. 2-amino-N-((1S,2S)-2-((4'-((4-(2-hydroxyethyl)piperazin-1-yl)methyl)-3'-(trifluoromethyl)-[1,1'-biphenyl]-4-yl)methoxy)cyclopentyl)-5-(1-methyl-1H-pyrazol-4-yl)nicotinamide Using (4-formyl-3-(trifluoromethyl)phenyl)boronic acid pinacol ester and 2-(piperazin-1-yl)ethan-1-ol, the title compound was obtained as described for the example 172.

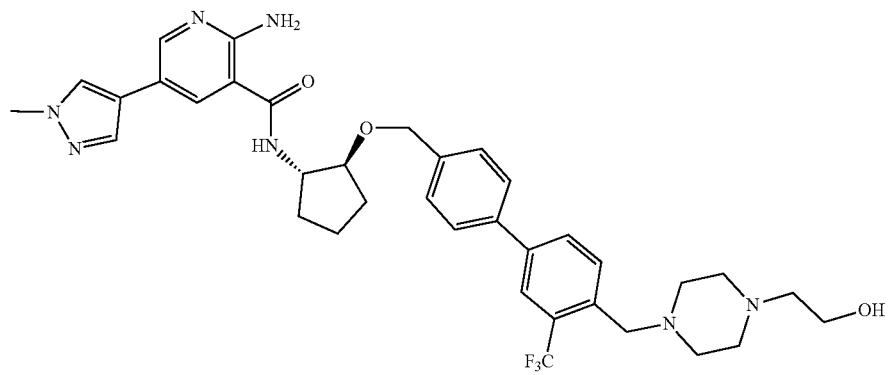 [SMILES: Cn1cc(-c2cnc(N)c(C(=O)N[C@H]3CCC[C@@H]3OCc3ccc(-c4ccc(CN5CCN(CCO)CC5)c(C(F)(F)F)c4)cc3)c2)cn1]

¹H NMR (400 MHz, CD₃OD) δ ppm 1.57-1.72 (m, 1H) 1.75-1.90 (m, 3H) 2.04 (dt, J=12.81, 6.70 Hz, 1H) 2.13-2.26 (m, 1H) 3.82 (s, 2H) 3.86-3.90 (m, 2H) 3.91 (s, 3H) 3.97-4.05 (m, 1H) 4.43 (br dd, J=11.93, 6.46 Hz, 1H) 4.69 (s, 2H) 7.48 (d, J=8.22 Hz, 2H) 7.60 (d, J=8.22 Hz, 2H) 7.81-7.87 (m, 3H) 7.99 (s, 1H) 8.22 (d, J=2.35 Hz, 1H) 8.51 (d, J=1.96 Hz, 1H);

MS (ESI, m/z): 678.3[M+H]⁺

Example 206. 2-amino-N-((1S,2S)-2-((2'-chloro-4'-((4-(2-hydroxyethyl)-piperazin-1-yl)methyl)-[1,1'-biphenyl]-4-yl)methoxy)cyclopentyl)-5-(1-methyl-1H-pyrazol-4-yl)nicotinamide Using (2-chloro-4-formylphenyl)boronic acid pinacol ester and 2-(piperazin-1-yl)ethan-1-ol, the title compound was obtained as described for the example 172.

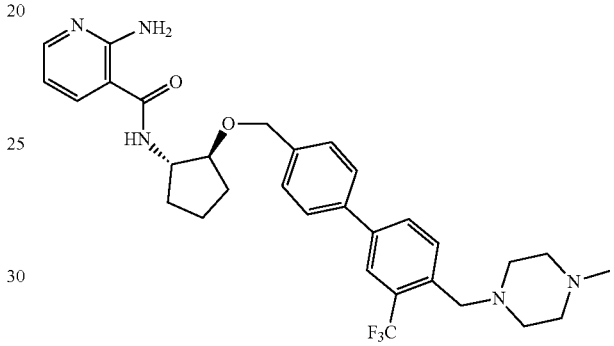

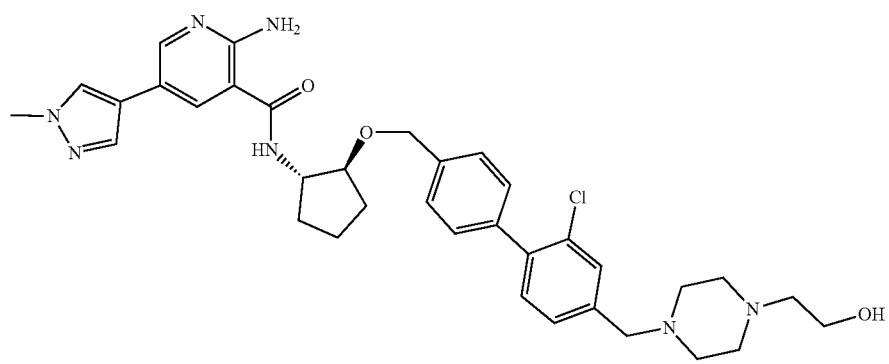 [SMILES: Cn1cc(-c2cnc(N)c(C(=O)N[C@H]3CCC[C@@H]3OCc3ccc(-c4ccc(CN5CCN(CCO)CC5)cc4Cl)cc3)c2)cn1]

MS (ESI, m/z): 644.3 [M+H]⁺

Example 207. 2-amino-N-((1S,2S)-2-((4'-((4-methylpiperazin-1-yl)methy-3'-(trifluoromethyl)-[1,1'-biphenyl]-4-yl)methoxy)cyclopentyl)nicotinamide Using 2-aminonicotinic acid and (4-formyl-3-(trifluoromethyl)phenyl)boronic acid pinacol ester, the title compound was obtained as described for the example 172.

¹H NMR (400 MHz, CD₃OD) δ ppm 1.53-1.69 (m, 1H) 1.76-1.89 (m, 3H) 2.01 (s, 1H) 2.18 (br dd, J=13.30, 5.87 Hz, 1H) 2.48 (br s, 2H) 2.91 (s, 3H) 3.82 (s, 2H) 3.99 (br d, J=4.30 Hz, 1H) 4.40 (br d, J=5.09 Hz, 1H) 4.68 (d, J=4.30 Hz, 2H) 6.95 (dd, J=7.43, 6.26 Hz, 1H) 7.47 (d, J=8.22 Hz, 2H) 7.62 (d, J=8.22 Hz, 2H) 7.84-7.92 (m, 3H) 7.98-8.05 (m, 1H) 8.32 (dd, J=7.43, 1.56 Hz, 1H);

MS (ESI, m/z): 568.3 [M+H]⁺

Example 208. 2-amino-5-(1-methyl-1H-pyrazol-4-yl)-N-((1S,2S)-2-((4'-(1-(4-methylpiperazin-1-yl)ethyl)-[1,1'-biphenyl]-4-yl)methoxy)cyclopentyl)nicotinamide Scheme for the Preparation of the Compound of Example 208:

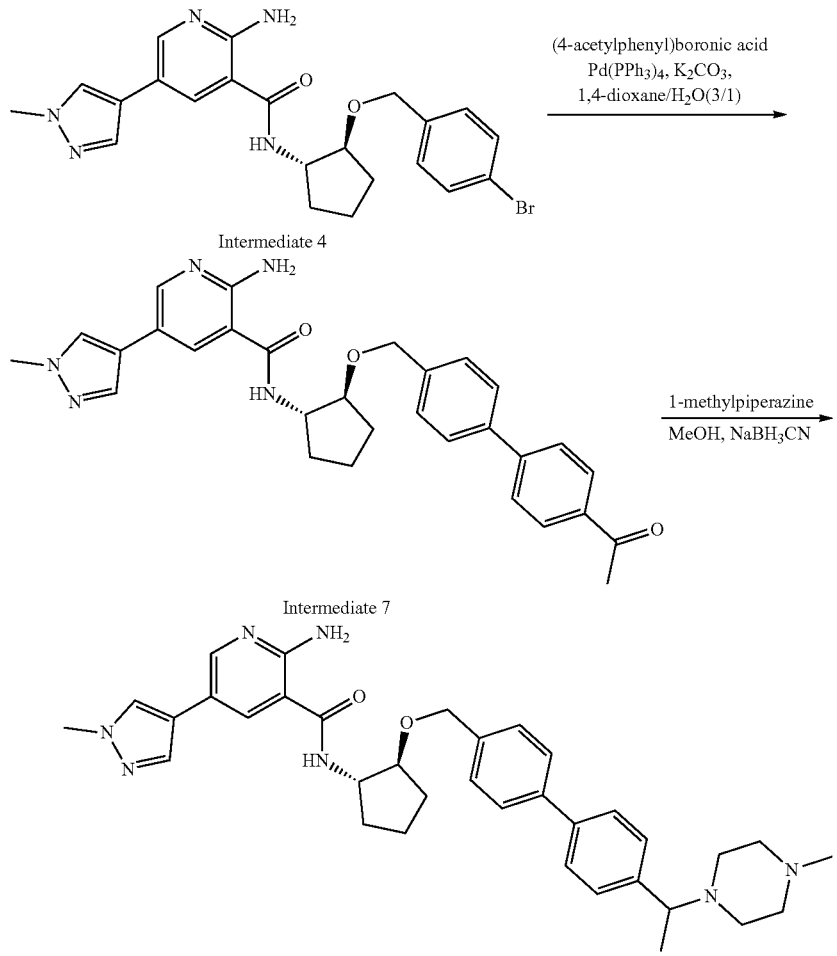

Intermediate 7

To a mixture of intermediate 4 (100 mg, 0.21 mmol) and (4-acetylphenyl)boronic acid (52 mg, 0.32 mmol) in 1.2 ml of 1,4-dioxane/water (3/1) was added K₂CO₃ (88 mg, 0.64 mmol) followed by Pd(PPh₃)₄ (12 mg, 0.01 mmol). The reaction mixture was heated at 100° C. for 3 hrs, cooled to room temperature, and extracted with EtOAc, dried over anhydrous MgSO₄. After concentration under vacuum, the crude product was purified by silicagel column chromatography to give 80 mg of off-white solid ¹H NMR (600 MHz, CD₃OD) δ ppm 1.62 (br dd, J=13.21, 7.34 Hz, 1H) 1.74-1.88 (m, 3H) 2.05 (br dd, J=12.62, 7.34 Hz, 1H) 2.17 (br dd, J=13.21, 5.58 Hz, 1H) 2.62 (s, 3H) 3.89 (s, 3H) 3.96-4.01 (m, 1H) 4.38-4.45 (m, 1H) 4.61-4.73 (m, 2H) 7.45 (d, J=8.22 Hz, 2H) 7.60 (d, J=8.22 Hz, 2H) 7.66 (d, J=8.22 Hz, 2H) 7.82 (s, 1H) 7.94 (s, 1H) 8.01 (d, J=8.22 Hz, 2H) 8.18 (d, J=1.76 Hz, 1H) 8.44 (d, J=1.76 Hz, 1H);

MS (ESI, m/z): 510.8[M+H]⁺

Example 208. 2-amino-5-(1-methyl-1H-pyrazol-4-yl)-N-((1S,2S)-2-((4'-(1-(4-methylpiperazin-1-yl)ethyl)-[1,1'-biphenyl]-4-yl)methoxy)cyclopentyl)nicotinamide To a mixture of intermediate 7 (30 mg, 0.06 mmol) in 0.4 ml of methanol was added 1-methylpiperazine (14 μl, 0.12 mmol) followed by NaBH₃CN (11 mg, 0.18 mmol). The mixture was stirred at room temperature for 4 hr and then water was added. The mixture was extracted with EtOAc, washed with brine, dried over MgSO₄. After concentration under vacuum, the crude residue was purified by preparative HPLC to afford 17 mg of the title compound.

¹H NMR (600 MHz, CD₃OD) δ ppm 1.40 (d, J=6.46 Hz, 3H) 1.59 (br dd, J=13.21, 7.34 Hz, 1H) 1.73-1.85 (m, 3H) 1.98-2.05 (m, 1H) 2.15 (br dd, J=13.21, 5.58 Hz, 1H) 2.31 (s, 3H) 2.35-2.77 (m, 8H) 3.41-3.48 (m, 1H) 3.86 (s, 3H) 3.90-3.99 (m, 1H) 4.37-4.44 (m, 1H) 4.61-4.70 (m, 2H) 7.34 (d, J=7.63 Hz, 2H) 7.39 (br d, J=7.63 Hz, 2H) 7.48 (br d, J=7.63 Hz, 2H) 7.50 (br d, J=8.22 Hz, 2H) 7.74 (s, 1H) 7.82 (d, J=2.93 Hz, 1H) 7.96 (s, 1H) 8.22-8.26 (m, 1H);

MS (ESI, m/z): 594.7 [M+H]⁺

Example 209. 2-amino-5-(1-methyl-1H-pyrazol-4-yl)-N-((1S,2S)-2-((4'-(1-((3S,5R)-3,4,5-trimethylpiperazin-1-yl)ethyl)-[1,1'-biphenyl]-4-yl)methoxy)-cyclopentyl)nicotinamide Using (2S,6R)-1,2,6-trimethylpiperazine, title compound was obtained as described for the example 208.

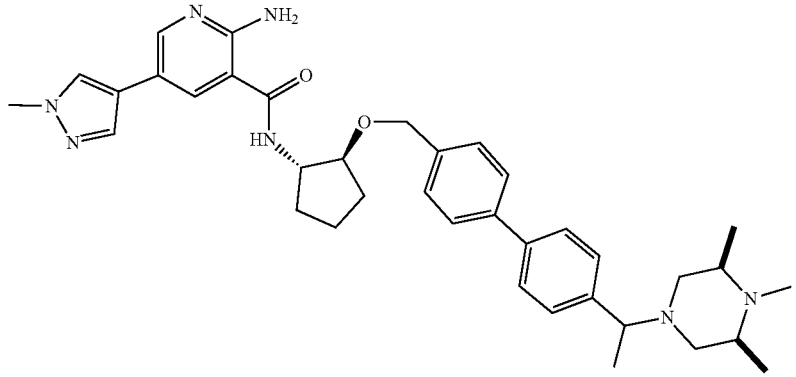

MS (ESI, m/z): 622.4 [M+H]$^+$

Example 210. 2-amino-N-((1S,2S)-2-((4'-(1-(4-(2-hydroxyethyl)piperazin-1-yl)-ethyl)-[1,1'-biphenyl]-4-yl)methoxy)cyclopentyl)-5-(1-methyl-1H-pyrazol-4-yl)-nicotinamide Using 1-(2-hydroxyethyl)piperazine, title compound was obtained as described for the example 208.

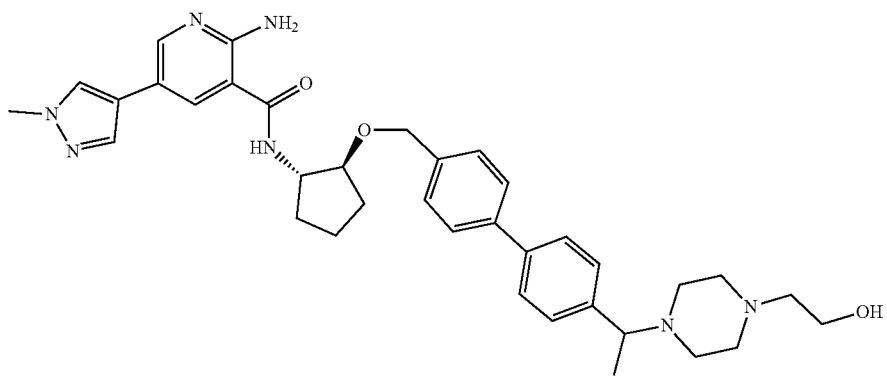 [SMILES: CC(c1ccc(-c2ccc(CO[C@H]3CCC[C@@H]3NC(=O)c3cc(-c4cnn(C)c4)cnc3N)cc2)cc1)N1CCN(CCO)CC1]

$^1$H NMR (600 MHz, CD$_3$OD) δ ppm 1.64 (br dd, J=13.50, 7.04 Hz, 1H) 1.69 (d, J=7.04 Hz, 3H) 1.75-1.88 (m, 3H) 2.00-2.08 (m, 1H) 2.18 (br dd, J=13.50, 5.87 Hz, 1H) 3.16-3.23 (m, 2H) 3.23-3.27 (m, 2H) 3.53 (br s, 4H) 3.84 (br t, J=4.99 Hz, 2H) 3.90 (s, 3H) 3.98-4.03 (m, 1H) 4.25 (br d, J=7.04 Hz, 1H) 4.38-4.45 (m, 1H) 4.64-4.70 (m, 2H) 7.43 (d, J=7.63 Hz, 2H) 7.51 (m, J=8.22 Hz, 2H) 7.56 (m, J=8.22 Hz, 2H) 7.64 (d, J=8.22 Hz, 2H) 7.85 (s, 1H) 7.98 (s, 1H) 8.19 (s, 1H) 8.53 (s, 1H);

MS (ESI, m/z): 624.4 [M+H]$^+$

Example 211. 2-amino-N-((1S,2S)-2-((4'-(1-((3S,5R)-4-(2-hydroxyethyl)-3,5-dimethylpiperazin-1-yl)ethyl)-[1,1'-biphenyl]-4-yl)methoxy)cyclopentyl)-5-(1-methyl-1H-pyrazol-4-yl)nicotinamide Using 2-(cis-2,6-dimethylpiperazin-1-yl)ethan-1-ol, title compound was obtained as described for the example 208.

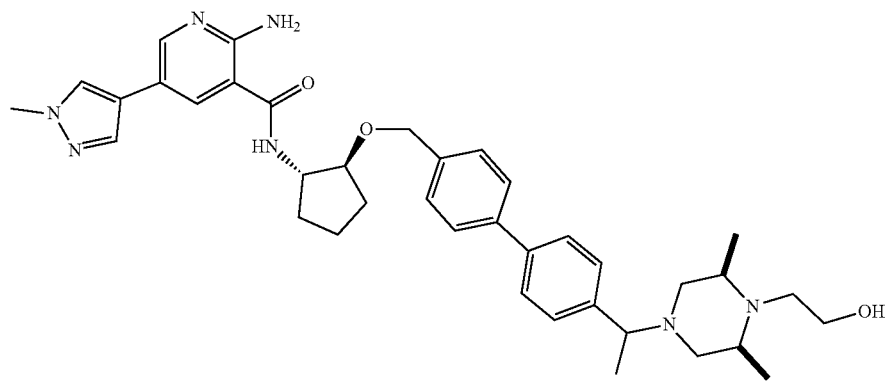 [SMILES: CC(c1ccc(-c2ccc(CO[C@H]3CCC[C@@H]3NC(=O)c3cc(-c4cnn(C)c4)cnc3N)cc2)cc1)N1C[C@@H](C)N(CCO)[C@@H](C)C1]

MS (ESI, m/z): 652.4 [M+H]⁺

Example 212. 2-amino-N-((1S,2S)-2-((3',5'-difluoro-4'-(1-(4-(2-hydroxyethyl)-piperazin-1-yl)ethyl)-[1,1'-biphenyl]-4-yl)methoxy)cyclopentyl)-5-(1-methyl-1H-pyrazol-4-yl)nicotinamide Using (4-acetyl-3,5-difluorophenyl)boronic acid pinacol ester and 2-(piperazin-1-yl)ethan-1-ol, the title compound was obtained as described for the example 208.

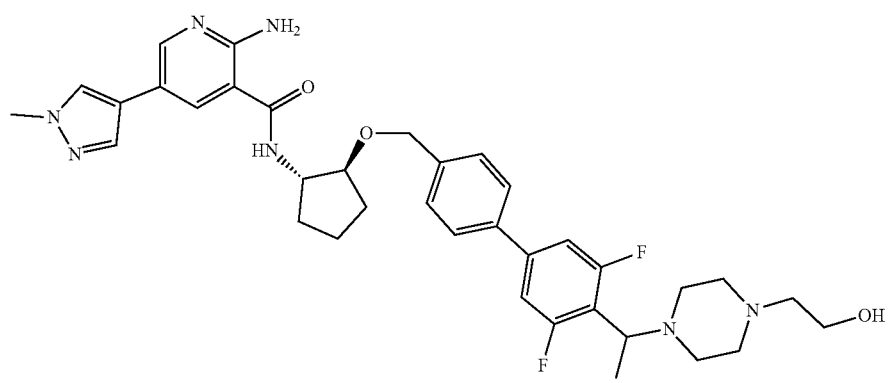 [SMILES: CC(c1c(F)cc(-c2ccc(CO[C@H]3CCC[C@@H]3NC(=O)c3cc(-c4cnn(C)c4)cnc3N)cc2)cc1F)N1CCN(CCO)CC1]

MS (ESI, m/z): 660.32 [M+H]⁺

Scheme for the Preparation of the Intermediate 9:

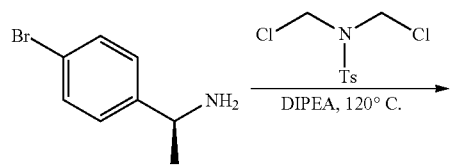

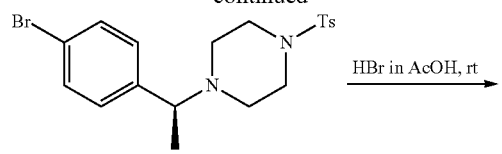

Intermediate 8

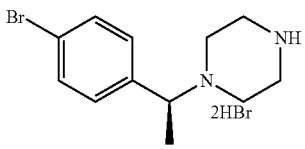

Intermediate 9

Intermediate 8

A mixture of (S)-1-(4-Bromophenyl)ethylamine (300 mg, 1.50 mmol) and (N,N-bis(2-chloroethyl)-4-methylbenzenesulfonamide (533 mg, 1.80 mmol) in 3 ml of DIPEA was heated at 120° C. for 24 hrs, cooled to room temperature, and extracted with EtOAc, dried over anhydrous MgSO₄. After concentration under vacuum, the crude product was purified by silicagel column chromatography to give 500 mg of off-white solid ¹H NMR (600 MHz, DMSO-d₆) δ ppm 1.16 (d, J=6.46 Hz, 3H) 2.27-2.33 (m, 2H) 2.39 (s, 5H) 2.78 (br s, 4H) 3.37-3.44 (m, 1H) 7.16 (d, J=7.87 Hz, 2H) 7.43 (t, J=7.59 Hz, 4H) 7.55-7.60 (m, 2H):
MS (ESI, m/z): 423.1/425.2[M+H]⁺

Intermediate 9.
(S)-1-(1-(4-bromophenyl)ethyl)piperazine

Intermediate 8 (0.5 g, 1.1 mmol) in 5 ml of HBr in AcOH was stirred at room temperature for 24 hrs. After concentration under vacuum, the crude product was diluted with EtOAC and the solid was collected by filtration to give 0.5 g of off-white solid
¹H NMR (600 MHz, DMSO-d₆) δ ppm 1.63 (br s, 3H) 3.40 (br s, 1H) 3.47-3.72 (br s, 8H) 7.54 (br s, 2H) 7.69 (br d, J=7.63 Hz, 2H);
MS (ESI, m/z): 269.1/271.4 [M+H]⁺

Intermediate 10.
(R)-1-(1-(4-bromophenyl)ethyl)piperazine

Using (R)-1-(4-Bromophenyl)ethylamine, the title compound was obtained as described for the intermediate 9.

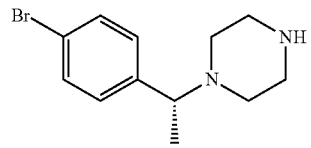

MS (ESI, m/z): 269.1/271.4 [M+H]⁺

Intermediate 11.
1-(1-(4-bromophenyl)cyclopropyl)piperazine

Using 1-(4-Bromophenyl)cyclopropan-1-amine, the title compound was obtained as described for the intermediate 9.

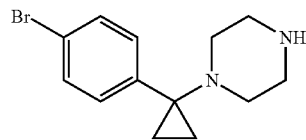 [SMILES: Brc1ccc(C2(N3CCNCC3)CC2)cc1]

MS (ESI, m/z): 281.1/283.4 [M+H]⁺

Intermediate 12.
1-(2-(4-bromophenyl)propan-2-yl)piperazine

Using 2-(4-Bromophenyl)propan-2-amine, the title compound was obtained as described for the intermediate 9.

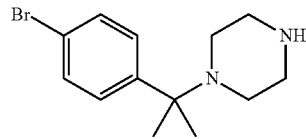

MS (ESI, m/z): 283.1/285.4 [M+H]⁺

Example 213 and 214

Scheme for the Preparation of the Compounds of Example 213 and 214;

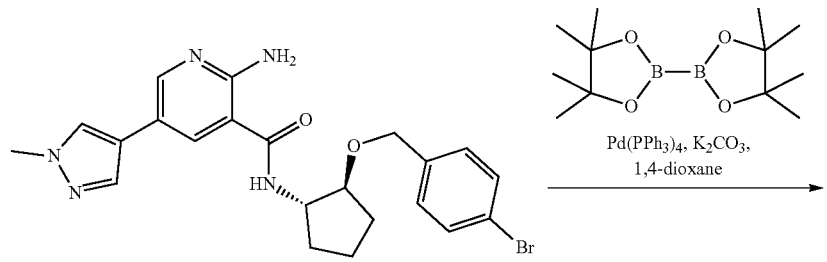

Intermediate 4

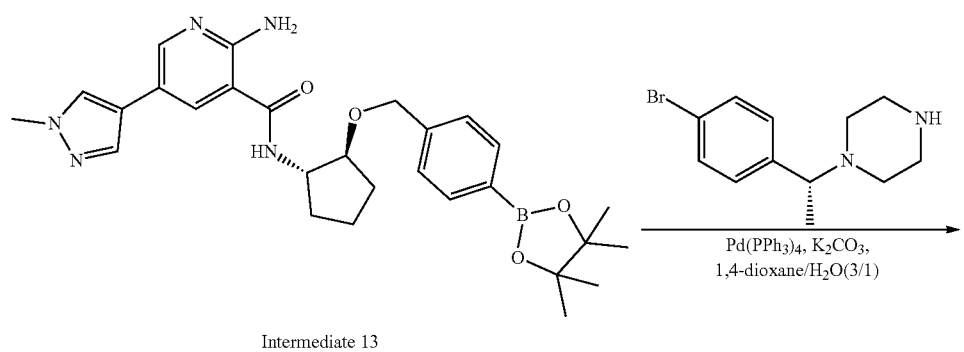

Intermediate 13

-continued

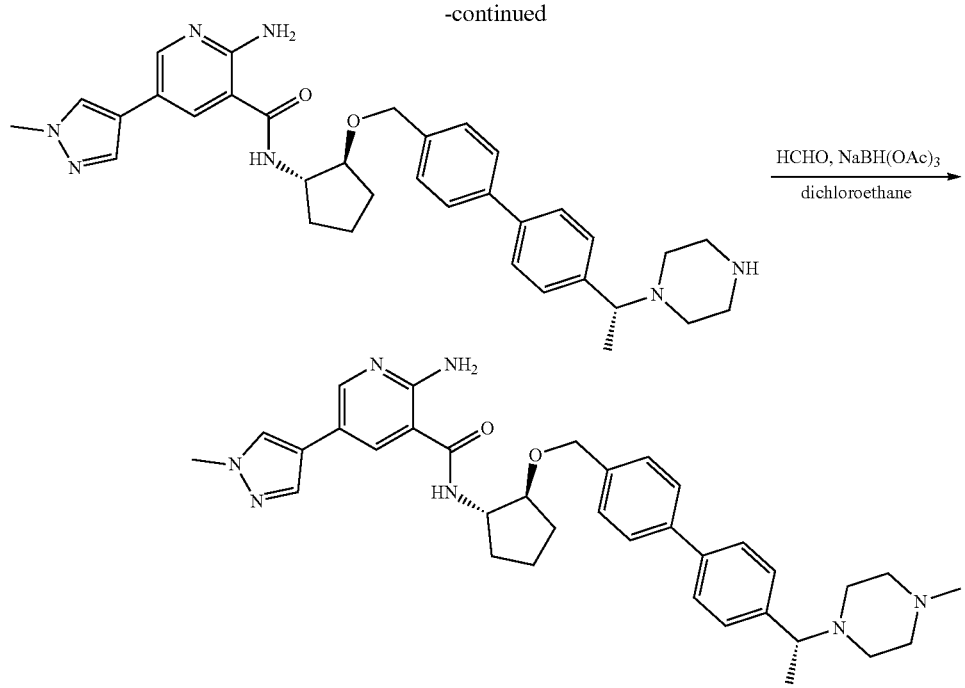

Intermediate 13

To a mixture of intermediate 4 (0.56 g, 1.19 mmol) and bis(pinacalato)diboron (0.6 g, 2.38 mmol) in 6 ml of 1,4-dioxane was added KOAc (0.35 g, 3.51 mmol) followed by Pd(PPh$_3$)$_4$ (69 mg, 0.06 mmol). The reaction mixture was heated at 110° C. for 5 hrs, cooled to room temperature, and partitioned between water and EtOAc, dried over anhydrous MgSO$_4$. After concentration under vacuum, the crude product was purified by silicagel column chromatography to give 0.5 g of light yellow solid $^1$H NMR (400 MHz, CD$_3$OD) δ ppm 1.19 (s, 6H) 1.30 (s, 6H) 1.60 (br dd, J=13.30, 7.04 Hz, 1H) 1.68-1.88 (m, 3H) 1.93-2.06 (m, 1H) 2.15 (br dd, J=13.11, 6.06 Hz, 1H) 3.90 (s, 3H) 3.92-3.99 (m, 1H) 4.32-4.44 (m, 1H) 4.64 (s, 2H) 7.33 (m, J=7.83 Hz, 2H) 7.66 (m, J=7.83 Hz, 2H) 7.75 (s, 1H) 7.85 (s, 1H) 7.97 (d, J=1.96 Hz, 1H) 8.20-8.30 (m, 1H); MS (ESI, m/z): 518.3 [M+H]$^+$

Example 213. 2-amino-5-(1-methyl-1H-pyrazol-4-yl)-N-((1S,2S)-2-((4'-((R)-1-(piperazin-1-yl)ethyl)-[1,1'-biphenyl]-4-yl)methoxy)cyclopentyl)nicotinamide To a mixture of intermediate 13 (150 mg, 0.29 mmol) and intermediate 10 (100 mg, 0.29 mmol) in 1.5 ml of 1,4-dioxane/water (3/1) was added K$_2$CO$_3$ (120 mg, 0.87 mmol) followed by Pd(PPh$_3$)$_4$ (17 mg, 0.01 mmol). The reaction mixture was heated at 100° C. for 3 hrs, cooled to room temperature, and extracted with EtOAc, dried over anhydrous MgSO$_4$. After concentration under vacuum, the crude product was purified by silicagel column chromatography to give 130 mg of off-white solid $^1$H NMR (600 MHz, CD$_3$OD) δ ppm 1.40 (d, J=6.46 Hz, 3H) 1.54-1.63 (m, 1H) 1.73-1.86 (m, 3H) 1.98-2.05 (m, 1H) 2.12-2.19 (m, 1H) 2.40 (br s, 2H) 2.82 (t, J=4.99 Hz, 4H) 3.40 (q, J=6.46 Hz, 1H) 3.86 (s, 3H) 3.95 (dt, J=6.90, 4.48 Hz, 1H) 4.41 (td, J=7.63, 4.70 Hz, 1H) 4.61-4.70 (m, 2H) 5.48 (s, 1H) 7.33 (d, J=8.22 Hz, 2H) 7.39 (d, J=8.22 Hz, 2H) 7.44-7.49 (m, 2H) 7.49-7.55 (m, 2H) 7.74 (s, 1H) 7.83 (s, 1H) 7.97 (d, J=2.35 Hz, 1H) 8.23 (d, J=2.35 Hz, 1H); MS (ESI, m/z): 580.6[M+H]$^+$

Example 214. 2-amino-5-(1-methyl-1H-pyrazol-4-yl)-N-((1S,2S)-2-((4'-((R)-1-(4-methylpiperazin-1-yl)ethyl)-[1,1'-biphenyl]-4-yl)methoxy)cyclopentyl)nicotinamide

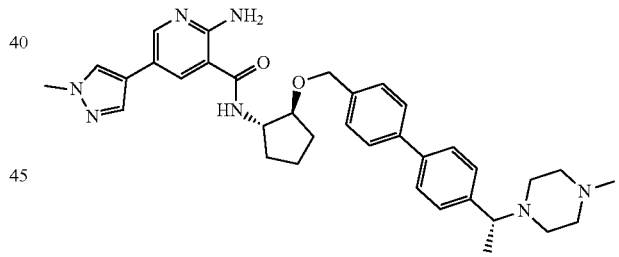

To compound 213 (20 mg, 0.03 mmol) in 0.2 ml of 1,2-dichloroethane was added formaldehyde (0.005 ml, 0.06 mmol) followed by NaBH(OAc)$_3$ (13 mg, 0.09 mmol). The mixture was stirred at room temperature for 1 hr and then water was added. The mixture was extracted with EtOAc, washed with brine, dried over MgSO$_4$, and concentrated in vacuo. The crude residue was purified by preparative HPLC to afford 15 mg of the title compound.

$^1$H NMR (600 MHz, CD$_3$OD) δ ppm 1.64 (dd, J=13.50, 7.04 Hz, 1H) 1.71 (d, J=7.04 Hz, 3H) 1.75-1.88 (m, 3H) 2.00-2.10 (m, 1H) 2.12-2.23 (m, 1H) 2.91 (s, 3H) 3.20-3.28 (m, 2H) 3.52 (br s, 4H) 3.90 (s, 3H) 4.00 (dt, J=6.46, 4.40 Hz, 1H) 4.32 (q, J=6.65 Hz, 1H) 4.42 (td, J=7.34, 4.11 Hz, 1H) 4.63-4.71 (m, 2H) 7.43 (d, J=8.22 Hz, 2H) 7.52 (d, J=8.22 Hz, 2H) 7.56 (d, J=8.22 Hz, 2H) 7.64 (d, J=8.22 Hz, 2H) 7.85 (s, 1H) 7.98 (s, 1H) 8.20 (d, J=1.76 Hz, 1H) 8.53 (d, J=2.35 Hz, 1H); MS (ESI, m/z): 594.8 [M+H]$^+$ Example 215. 2-amino-5-(1-methyl-1H-pyrazol-4-yl)-N-((1S,2S)-2-((4'-((S)-1-(4-methylpiperazin-1-yl)ethyl)-[1,1'-biphenyl]-4-yl)methoxy)cyclopentyl)nicotinamide Using intermediate 9, the title compound was obtained as described for the example

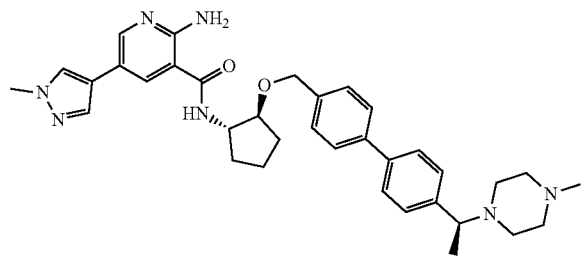

$^1$H NMR (600 MHz, CD$_3$OD) δ ppm 1.51 (d, J=7.04 Hz, 3H) 1.64 (br dd, J=13.21, 6.75 Hz, 1H) 1.76-1.85 (m, 3H) 2.01-2.06 (m, 1H) 2.14 (s, 1H) 2.15-2.20 (m, 1H) 2.84 (s, 3H) 3.82 (br d, J=6.46 Hz, 1H) 3.90 (s, 3H) 3.98-4.02 (m, 1H) 4.42 (br dd, J=6.75, 3.23 Hz, 1H) 4.66 (s, 2H) 7.42 (dd, J=8.22, 1.76 Hz, 4H) 7.54-7.59 (m, 4H) 7.86 (s, 1H) 7.98 (s, 1H) 8.20 (d, J=2.35 Hz, 1H) 8.53 (d, J=1.76 Hz, 1H);
MS (ESI, m/z): 594.8 [M+H]$^+$ Example 216. 2-amino-5-(1-methyl-1H-pyrazol-4-yl)-N-((1S,2S)-2-((4'-(1-(4-methylpiperazin-1-yl)cyclopropyl)-[1,1'-biphenyl]-4-ylmethoxy)cyclopentyl)-nicotinamide Using intermediate 11, the title compound was obtained as described for the example 214.

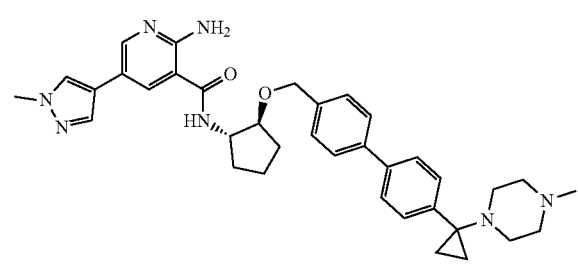

$^1$H NMR (600 MHz, CD$_3$OD) δ ppm 0.85-0.88 (m, 1H) 0.89-0.92 (m, 1H) 0.99-1.01 (m, 1H) 1.01-1.04 (m, 1H) 1.64 (br dd, J13.50, 6.46 Hz, 1H) 1.75-1.88 (m, 3H) 2.01-2.07 (m, 1H) 2.16-2.24 (m, 2H) 2.79 (d, J1.76 Hz, 3H) 3.00 (br s, 21H) 3.15-3.21 (m, 2H) 3.34-3.43 (m, 4H) 3.90 (s, 3H) 4.00 (dt, J=6.46, 4.11 Hz, 1H) 4.42 (td, J=7.34, 4.70 Hz, 1H) 4.66 (s, 2H) 7.26 (d, J=8.31 Hz, 2H) 7.37-7.40 (m, 2H) 7.40-7.43 (m, 2H) 7.49-7.52 (m, 1H) 7.86 (s, 1H) 7.98 (s, 1H) 8.20 (d, J=1.76 Hz, 1H) 8.54 (d, J=−235 Hz, 1H);
MS (ESI, m/z): 606.3 [M+H]$^+$ Example 217. 2-amino-5-(1-methyl-1H-pyrazol-4-yl)-N-((1S,2S)-2-((4'-(2-(4-methylpiperazin-1-yl)propan-2-yl)-[1,1'-biphenyl]-4-yl)methoxy)cyclopentyl)-nicotinamide Using intermediate 12, the title compound was obtained as described for the example 214.

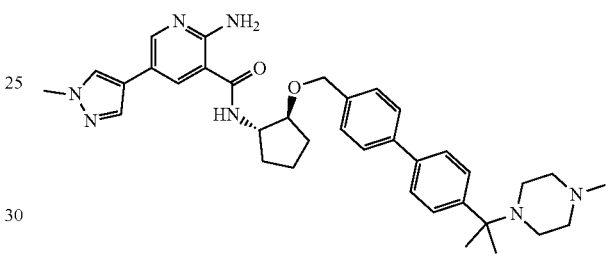

$^1$H NMR (400 MHz, CD$_3$OD) δ ppm 1.49 (s, 5H) 1.60-1.61 (m, 1H) 1.60-1.66 (m, 1H) 1.80-1.88 (m, 3H) 2.02-2.08 (m, 1H) 2.17 (br s, 1H) 2.87 (s, 3H) 3.90 (s, 3H) 4.02 (br s, 1H) 4.40-4.47 (m, 1H) 4.67 (s, 2H) 7.42 (d, J=8.22 Hz, 2H) 7.51-7.58 (m, 4H) 7.58-7.62 (m, 2H) 7.85 (d, J=0.78 Hz, 1H) 7.98 (s, 1H) 8.20 (d, J=2.35 Hz, 1H) 8.51 (d, J=1.96 Hz, 1H);
MS (ESI, m/z): 608.2 [M+H]$^+$ Example 218. 2-amino-N-((1S,2S)-2-((4'-((R)-1-(4-(2-hydroxyethyl)piperazin-1-yl)ethyl)-[1,1'-biphenyl]-4-yl)methoxy)cyclopentyl)-5-(1-methyl-1H-pyrazol-4-yl)-nicotinamide Scheme for the Preparation of the Compound of Example 218;

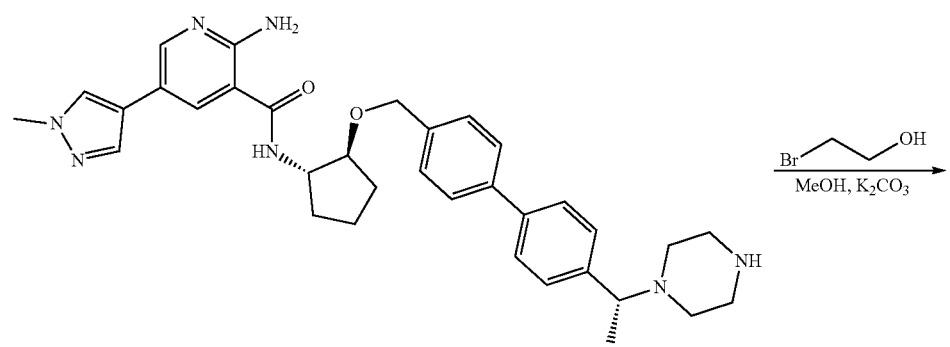

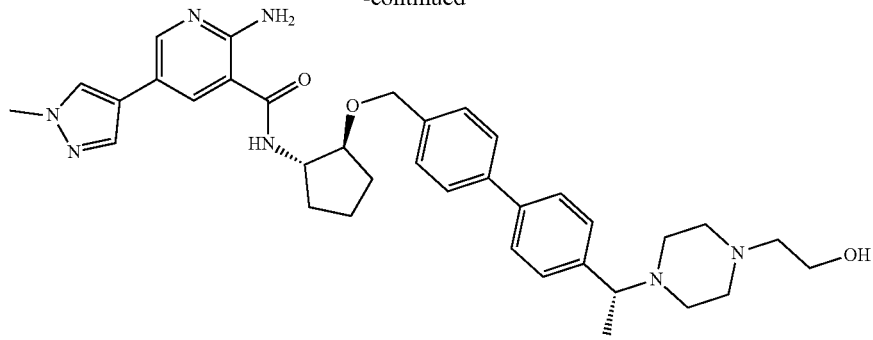

To a mixture of compound 213 (20 mg, 0.03 mmol) and $K_2CO_3$ (14 mg, 0.1 mmol) in 0.3 ml of methanol was added 2-bromothanol (4 μl, 0.05 mmol). The reaction mixture was stirred at room temperature for 3 hrs, After concentration under vacuum, the crude product was purified by HPLC to give 10 mg of off-white solid $^1$H NMR (600 MHz, $CD_3OD$) δ ppm 1.60-1.71 (m, 1H) 1.75 (d, J=7.04 Hz, 3H) 1.76-1.85 (m, 3H) 2.00-2.09 (m, 1H) 2.14-2.23 (m, 1H) 3.33-3.44 (m, 2H) 3.56-3.73 (m, 4H) 3.83-3.87 (m, 2H) 3.90 (s, 3H) 4.00 (dt, J=6.60, 4.33 Hz, 1H) 4.38-4.45 (m, 2H) 4.64-4.70 (m, 2H) 7.43 (d, J=8.22 Hz, 2H) 7.54 (d, J=8.22 Hz, 2H) 7.56-7.61 (m, 2H) 7.64-7.71 (m, 2H) 7.85 (s, 1H) 7.98 (s, 1H) 8.20 (d, J=1.76 Hz, 1H) 8.53 (s, 1H);

MS (ESI, m/z): 624.8 [M+H]$^+$

Example 219. 2-amino-N-((1S,2S)-2-((4'-((S)-1-(4-(2-hydroxyethyl)piperazin-1-yl)ethyl)-[1,1'-biphenyl]-4-yl)methoxy)cyclopentyl)-5-(1-methyl-1H-pyrazol-4-yl)-nicotinamide Using intermediate 9, the title compound was obtained as described for the example 213 and 218.

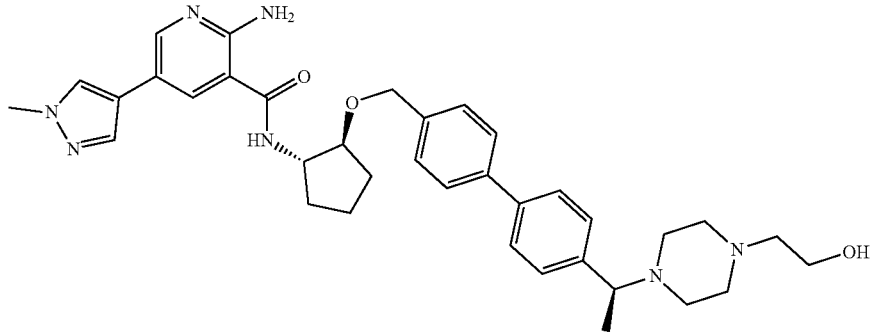 [SMILES: C[C@@H](c1ccc(-c2ccc(CO[C@H]3CCC[C@@H]3NC(=O)c3cc(-c4cnn(C)c4)cnc3N)cc2)cc1)N1CCN(CCO)CC1]

$^1$H NMR (600 MHz, $CD_3OD$) δ ppm 1.58 (d, J=7.04 Hz, 3H) 1.64 (br dd, J=13.21, 6.75 Hz, 1H) 1.72-1.87 (m, 3H) 2.00-2.07 (m, 1H) 2.15-2.23 (m, 1H) 2.99 (brs, 2H) 3.17-3.22 (m, 3H) 3.35-3.44 (m, 4H) 3.80-3.85 (m, 3H) 3.90 (s, 3H) 3.96-4.03 (m, 2H) 4.42 (td, J=7.34, 4.11 Hz, 1H) 4.66 (s, 2H) 7.42 (d, J=8.22 Hz, 2H) 7.46 (d, J=8.22 Hz, 2H) 7.55-7.57 (m, 2H) 7.60 (d, J=8.22 Hz, 2H) 7.86 (s, 1H) 7.98 (s, 1H) 8.20 (d, J=2.35 Hz, 1H) 8.52 (d, J=2.35 Hz, 1H);

MS (ESI, m/z): 624.8 [M+H]$^+$

Example 220. 2-amino-N-((1S,2S)-2-((4'-(1-(4-(2-hydroxyethyl)piperazin-1-yl)cyclopropyl)-[1,1'-biphenyl]-4-yl)methoxy)cyclopentyl)-5-(1-methyl-1H-pyrazol-4-yl)nicotinamide Using intermediate 11, the title compound was obtained as described for the example 213 and 218.

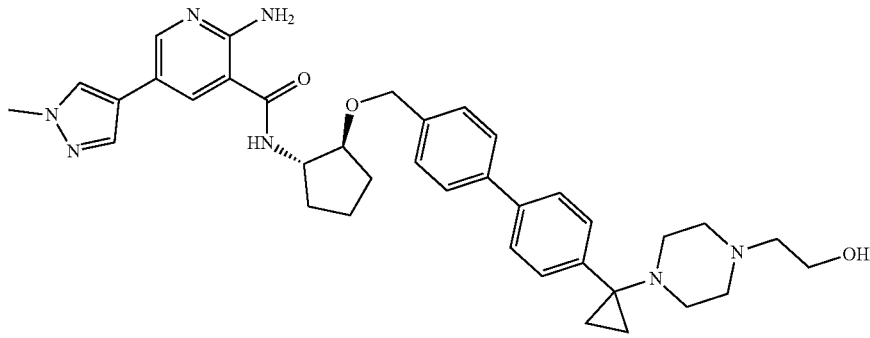 [SMILES: Cn1cc(-c2cnc(N)c(C(=O)N[C@H]3CCC[C@@H]3OCc3ccc(-c4ccc(C5(N6CCN(CCO)CC6)CC5)cc4)cc3)c2)cn1]

$^1$H NMR (600 MHz, CD$_3$OD) δ ppm 0.85-0.88 (m, 1H) 0.91-0.94 (m, 1H) 1.00-1.03 (m, 1H) 1.05-1.07 (m, 1H) 1.64 (dd, J=13.21, 6.75 Hz, 1H) 1.74-1.86 (m, 2H) 1.99-2.07 (m, 1H) 2.15-2.21 (m, 1H) 3.13-3.18 (m, 3H) 3.76-3.81 (m, 2H) 3.90 (s, 3H) 3.97-4.04 (m, 1H) 4.39-4.45 (m, 1H) 4.61-4.71 (m, 2H) 7.25-7.28 (m, 1H) 7.35-7.43 (m, 3H) 7.49-7.58 (m, 4H) 7.85 (s, 1H) 7.98 (s, 1H) 8.19 (d, J=1.76 Hz, 1H) 8.53 (d, J=1.76 Hz, 1H);
MS (ESI, m/z): 636.5 [M+H]$^+$ Example 221. 2-amino-N-((1S,2S)-2-((4'-(2-(4-(2-hydroxyethyl)piperazin-1-yl)propan-2-yl)-[1,1'-biphenyl]-4-yl)methoxy)cyclopentyl)-5-(1-methyl-1H-pyrazol-4-yl)nicotinamide Using intermediate 12, the title compound was obtained as described for the example 213 and 218.

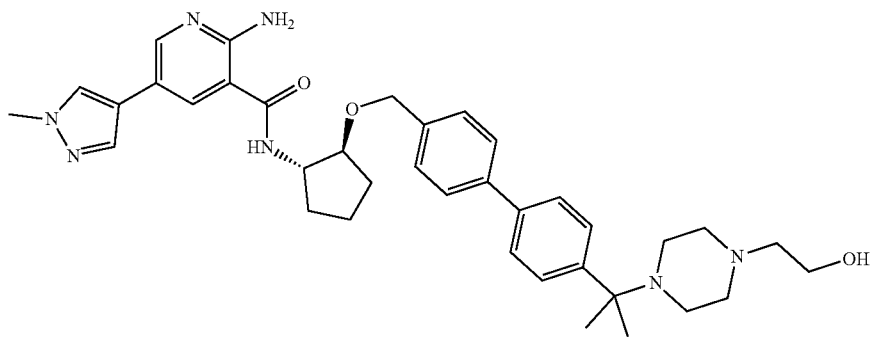 [SMILES: Cn1cc(-c2cnc(N)c(C(=O)N[C@H]3CCC[C@@H]3OCc3ccc(-c4ccc(C(C)(C)N5CCN(CCO)CC5)cc4)cc3)c2)cn1]

$^1$H NMR (400 MHz, CD$_3$OD) δ ppm 1.35-1.44 (m, 6H) 1.60 (br dd, J=12.91, 7.43 Hz, 1H) 1.73-1.89 (m, 3H) 2.03 (br dd, J=13.50, 6.46 Hz, 1H) 2.11-2.21 (m, 1H) 2.48-2.62 (m, 9H) 3.67 (t, J=6.06 Hz, 2H) 3.86 (s, 3H) 3.96 (dt, J=6.95, 4.55 Hz, 1H) 4.36-4.46 (m, 1H) 4.59-4.72 (m, 2H) 7.40 (d, J=7.83 Hz, 2H) 7.43-7.49 (m, 2H) 7.53 (dd, J=12.72, 8.41 Hz, 4H) 7.75 (s, 1H) 7.83 (s, 1H) 7.97 (d, J=2.35 Hz, 1H) 8.24 (d, J=1.96 Hz, 1H);
MS (ESI, m/z): 624.8 [M+H]$^+$ Example 222. 6-amino-6'-fluoro-N-((1S,2S)-2-((4'-((S)-1-(4-methylpiperazin-1-yl)ethyl)-[1,1'-biphenyl]-4-yl)methoxy)cyclopentyl)-[3,3'-bipyridine]-5-carboxamide
Scheme for the Preparation of the Compound of Example 222:
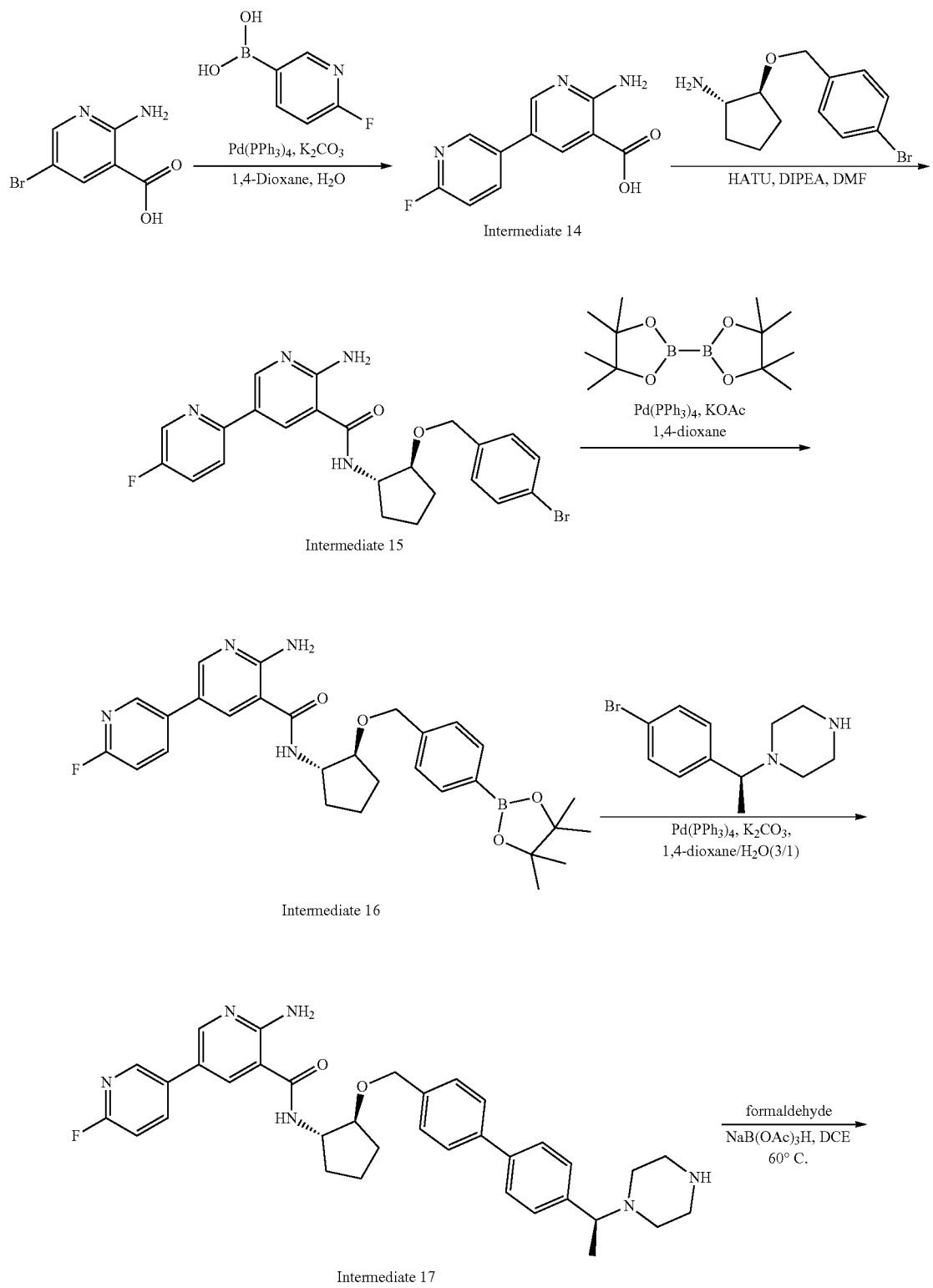

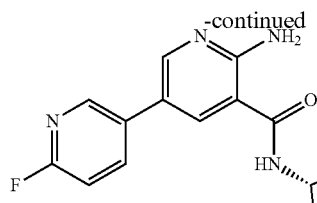

Intermediate 14

Using 6-fluoropyridine-3-boronic acid, the title compound was obtained as described for the intermediate 2.

$^1$H NMR (600 MHz, DMSO-d$_6$) δ ppm 7.20 (dd, J=8.51, 2.64 Hz, 1H) 8.20 (td, J=8.22, 2.35 Hz, 1H) 8.27 (d, J=2.93 Hz, 1H) 8.45 (d, J=2.93 Hz, 1H) 8.48 (d, J=2.35 Hz, 1H);

MS (ESI+) m/z 234.1 [M+H]$^+$

Intermediate 15

Using intermediate 14, the title compound was obtained as described for the intermediate 4.

$^1$H NMR (400 MHz, CD$_3$OD) δ ppm 1.60 (br dd, J=13.30, 7.04 Hz, 1H) 1.71-1.84 (m, 3H) 2.00 (br dd, J=13.30, 6.26 Hz, 1H) 2.10-2.21 (m, 1H) 3.92 (dt, J=6.55, 4.35 Hz, 1H) 4.39 (td, J=7.34, 4.50 Hz, 1H) 4.58 (s, 2H) 7.15 (dd, J=8.41, 2.54 Hz, 1H) 7.26 (d, J=8.22 Hz, 2H) 7.38-7.43 (m, 2H) 8.08 (d, J2.35 Hz, 1H) 8.12-8.21 (m, 1H) 8.35 (d, J=2.35 Hz, 1H) 8.43 (d, =2.35 Hz, 1H);

MS (ESI+) m/z 485.2/487.3 [M+H]$^+$

Intermediate 16

Using intermediate 15, the title compound was obtained as described for the intermediate 13.

$^1$H NMR (600 MHz, CD$_3$OD) δ ppm 1.18 (s, 12H) 1.58 (br dd, J=13.21, 7.34 Hz, 1H) 1.69-1.84 (m, 3H) 1.96-2.03 (m, 1H) 2.15 (br d, J=7.63 Hz, 1H) 3.93 (br d, J=6.46 Hz, 1H) 4.39 (br d, J=4.70 Hz, 1H) 4.63 (s, 2H) 7.13 (dd, J=8.51, 2.64 Hz, 1H) 7.32 (d, J=7.63 Hz, 2H) 7.49-7.57 (m, 1H) 7.64 (d, J=7.63 Hz, 2H) 8.07 (d, J=2.35 Hz, 1H) 8.10-8.18 (m, 1H) 8.33 (d, J=1.76 Hz, 1H) 8.41 (d, J=2.35 Hz, 1H);

MS (ESI+) m/z 533.3 [M+H]$^+$

Intermediate 17

Using intermediate 16, the title compound was obtained as described for the compound 213.

$^1$H NMR (400 MHz, CD$_3$OD) δ ppm 1.61 (d, J=6.65 Hz, 3H) 1.64 (br s, 1H) 1.77-1.86 (m, 3H) 2.02-2.08 (m, 1H) 2.16-2.22 (m, 1H) 3.02 (br s, 2H) 3.13 (br s, 2H) 3.32-3.40 (m, 4H) 3.97-4.02 (m, 2H) 4.05 (br d, J=6.26 Hz, 1H) 4.41-4.46 (m, 1H) 4.67 (d, J=3.91 Hz, 2H) 7.16 (br dd, J=8.41, 2.54 Hz, 1H) 7.43 (br d, J=8.22 Hz, 2H) 7.48 (d, J=8.22 Hz, 2H) 7.55 (d, J=7.83 Hz, 2H) 7.60 (d, J=7.83 Hz, 2H) 8.19 (td, J=8.02, 2.74 Hz, 1H) 8.35 (d, J=2.35 Hz, 1H) 8.47 (br d, J=2.74 Hz, 1H) 8.52 (d, J=2.35 Hz, 1H);

MS (ESI+) m/z 595.3 [M+H]$^+$

Example 222. 6-amino-6'-fluoro-N-((1S,2S)-2-((4'-((S)-1-(4-methylpiperazin-1-yl)ethyl)-[1,1'-biphenyl]-4-yl)methoxy)cyclopentyl)-[3,3'-bipyridine]-5-carboxamide Using intermediate 17, the title compound was obtained as described for the example 214.

$^1$H NMR (400 MHz, CD$_3$OD) δ ppm 1.57 (d, J=6.65 Hz, 3H) 1.63 (br dd, J=13.50, 6.85 Hz, 1H) 1.72-1.89 (m, 3H) 2.00-2.08 (m, 1H) 2.14-2.23 (m, 1H) 2.87 (s, 3H) 3.90-3.97 (m, 1H) 3.97-4.05 (m, 1H) 4.40-4.47 (m, 1H) 4.63-4.71 (m, 2H) 7.16 (dd, J=8.61, 2.74 Hz, 1H) 7.32-7.50 (m, 4H) 7.55 (br d, J=8.22 Hz, 2H) 7.58 (br d, J=8.22 Hz, 2H) 8.19 (ddd, J=8.61, 7.43, 2.74 Hz, 1H) 8.35 (d, J=2.35 Hz, 1H) 8.48 (d, J=2.74 Hz, 1H) 8.56 (d, J=2.35 Hz, 1H);

MS (ESI+) m/z 609.3 [M+H]$^+$

Example 223. 6-amino-6'-fluoro-N-((1S,2S)-2-((4'-((R)-1-(4-methylpiperazin-1-yl)ethyl)-[1,1'-biphenyl]-4-yl)methoxy)cyclopentyl)-[3,3'-bipyridine]-5-carboxamide Using intermediate 10, the title compound was obtained as described for the example 222.

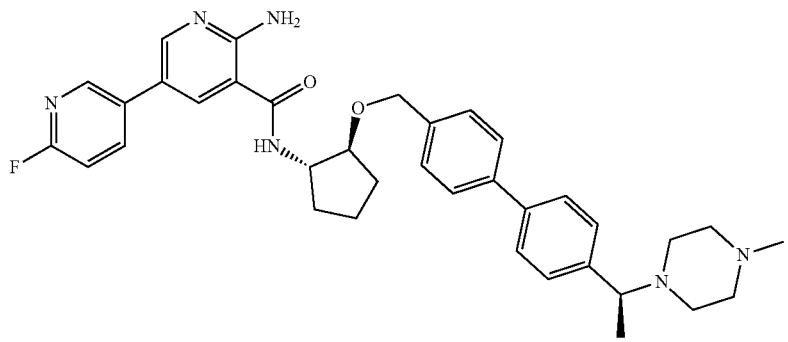 [SMILES: C[C@@H](c1ccc(-c2ccc(CO[C@H]3CCC[C@@H]3NC(=O)c3cc(-c4ccc(F)nc4)cnc3N)cc2)cc1)N1CCN(C)CC1]

¹H NMR (400 MHz, CD₃OD) δ ppm 1.49 (d, J=7.04 Hz, 3H) 1.63 (br d, J=6.65 Hz, 1H) 1.84 (br d, J=15.65 Hz, 3H) 2.06 (br s, 1H) 2.19 (br d, J=8.61 Hz, 1H) 2.84 (s, 3H) 3.74 (br d, J=6.26 Hz, 1H) 4.00 (br s, 1H) 4.43 (br s, 1H) 4.67 (d, J=3.13 Hz, 2H) 7.15 (br dd, J=9.00, 2.74 Hz, 1H) 7.42 (dd, J=7.83, 3.52 Hz, 4H) 7.54 (br dd, J=7.83, 5.09 Hz, 4H) 8.15-8.22 (m, 1H) 8.35 (br d, J=2.35 Hz, 1H) 8.46 (s, 1H) 8.50 (br d, J=1.96 Hz, 1H);

MS (ESI+) m/z 609.4 [M+H]⁺

Example 224. 6-amino-6'-fluoro-N-((1S,2S)-2-((4'-(1-(4-methylpiperazin-1-yl)cyclopropyl)-[1,1'-biphenyl]-4-yl)methoxy)cyclopentyl)-[3,3'-bipyridine]-5-carboxamide Using intermediate 11, the title compound was obtained as described for the example 222.

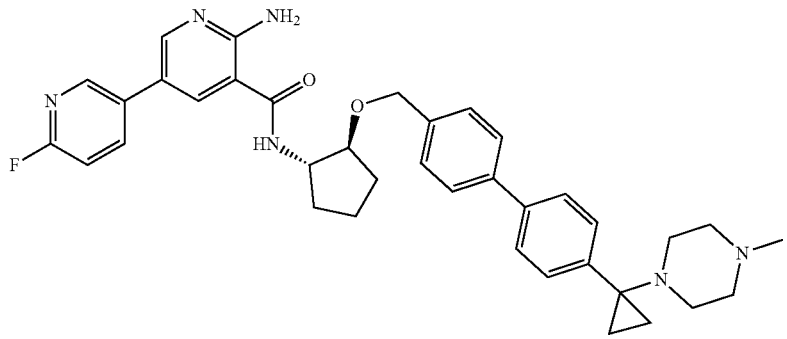 [SMILES: CN1CCN(C2(c3ccc(-c4ccc(CO[C@H]5CCC[C@@H]5NC(=O)c5cc(-c6ccc(F)nc6)cnc5N)cc4)cc3)CC2)CC1]

¹H NMR (400 MHz, CD₃OD) δ ppm 0.91-0.95 (m, 2H) 1.01-1.06 (m, 2H) 1.64 (br dd, J=13.21, 6.75 Hz, 1H) 1.76-1.85 (m, 3H) 2.01-2.06 (m, 1H) 2.14 (s, 1H) 2.15-2.20 (m, 1H) 2.80 (s, 3H) 3.34 (s, 2H) 3.99 (br d, J=4.30 Hz, 1H) 4.43 (br d, J=4.70 Hz, 1H) 4.67 (d, J=3.52 Hz, 2H) 7.12-7.16 (m, 1H) 7.40 (dd, J=14.28, 8.41 Hz, 4H) 7.52 (br dd, J=8.22, 3.91 Hz, 4H) 8.18 (s, 1H) 8.35 (d, J=2.35 Hz, 1H) 8.42 (d, J=2.35 Hz, 1H) 8.45 (s, 1H);

MS (ESI+) m/z 621.5 [M+H]⁺

Example 225. 6-amino-6'-fluoro-N-((1S,2S)-2-((4'-(2-(4-methylpiperazin-1-yl)propan-2-yl)-[1,1'-biphenyl]-4-yl)methoxy)cyclopentyl)-[3,3'-bipyridine]-5-carboxamide Using intermediate 12, the title compound was obtained as described for the example 222.

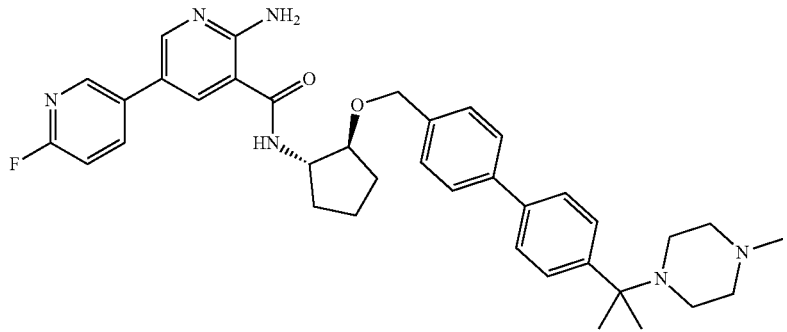 [SMILES: CN1CCN(C(C)(C)c2ccc(-c3ccc(CO[C@H]4CCC[C@@H]4NC(=O)c4cc(-c5ccc(F)nc5)cnc4N)cc3)cc2)CC1]

MS (ESI+) m/z 623.3 [M+H]⁺

Example 226. 6-amino-6'-fluoro-N-((1S,2S)-2-((4'-((S)-1-(4-(2-hydroxyethyl)piperazin-1-yl)ethyl)-[1,1'-biphenyl]-4-yl)methoxy)cyclopentyl)-[3,3'-bipyridine]-5-carboxamide Scheme for the Preparation of the Compound of Example 226:

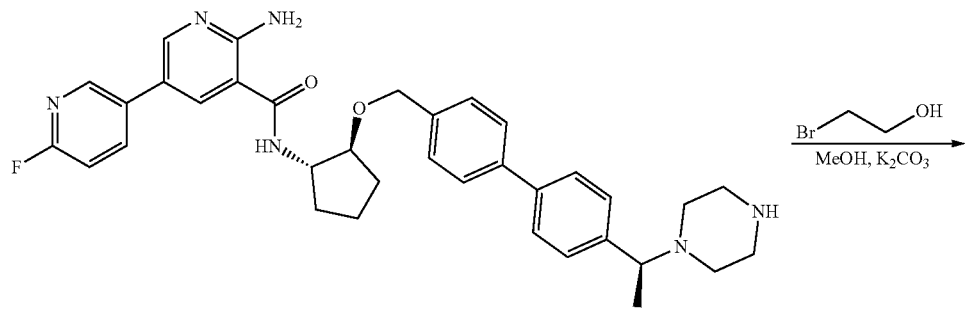

Intermediate 17

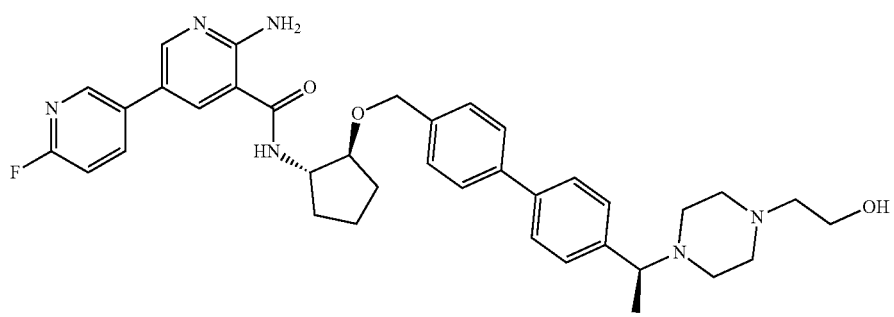

Using intermediate 17, the title compound was obtained as described for the example 218.

$^1$H NMR (400 MHz, CD$_3$OD) δ ppm 1.58-1.68 (m, 4H) 1.77-1.87 (m, 3H) 2.02-2.09 (m, 1H) 2.15-2.23 (m, 1H) 3.13 (br s, 2H) 3.17-3.26 (m, 2H) 3.46 (br s, 4H) 3.77 (br s, 1H) 3.82-3.87 (m, 2H) 4.02 (br d, J=4.70 Hz, 2H) 4.11 (br d, J=6.26 Hz, 1H) 4.44 (br dd, J=11.74, 7.43 Hz, 1H) 4.67 (d, J=2.74 Hz, 2H) 7.17 (dd, J=8.61, 2.74 Hz, 1 H) 7.43 (d, J=8.22 Hz, 2H) 7.49 (d, J=8.22 Hz, 2H) 7.56 (d, J=8.22 Hz, 2H) 7.62 (d, J=8.61 Hz, 2H) 8.20 (td, J=8.02, 2.74 Hz, 1H) 8.36 (d, J=2.35 Hz, 1H) 8.48 (br d, J=2.74 Hz, 1H) 8.57 (d, J=1.96 Hz, 1H);

MS (ESI+) m/z 639.4 [M+H]$^+$

Example 227. 6-amino-6'-fluoro-N-((1S,2S)-2-((4'-((R)-1-(4-(2-hydroxyethyl)-piperazin-1-yl)ethyl)-[1,1'-biphenyl]-4-yl)methoxy)cyclopentyl)-[3,3'-bipyridine]-5-carboxamide Using intermediate 10, the title compound was obtained as described for the example 226.

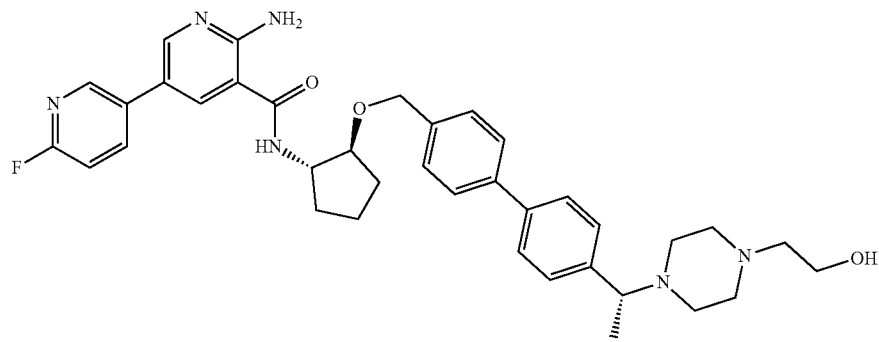 [SMILES: C[C@H](c1ccc(-c2ccc(CO[C@H]3CCC[C@@H]3NC(=O)c3cc(-c4ccc(F)nc4)cnc3N)cc2)cc1)N1CCN(CCO)CC1]

MS (ESI+) m/z 639.1 [M+H]$^+$

Example 228. 6-amino-6'-fluoro-N-((1S,2S)-2-((4'-(1-(4-(2-hydroxyethyl)-piperazin-1-yl)cyclopropyl)-[1,1'-biphenyl]-4-yl)methoxy)cyclopentyl)-[3,3'-bipyridine]-5-carboxamide Using intermediate 11, the title compound was obtained as described for the example 226.

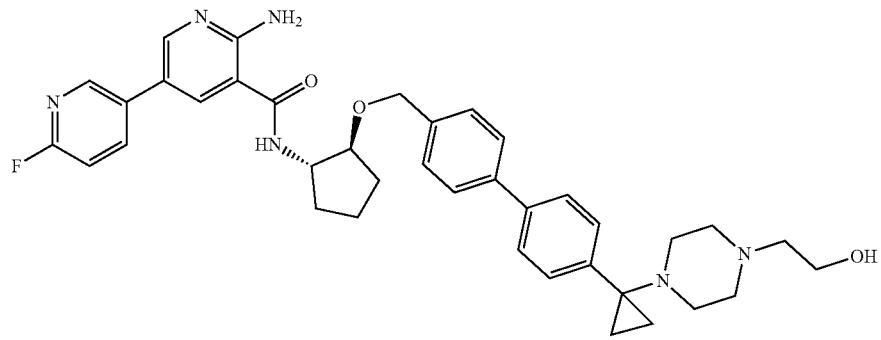 [SMILES: Nc1ncc(-c2ccc(F)nc2)cc1C(=O)N[C@H]1CCC[C@@H]1OCc1ccc(-c2ccc(C3(N4CCN(CCO)CC4)CC3)cc2)cc1]

MS (ESI+) m/z 651.6 [M+H]+

Example 229. 6-amino-6'-fluoro-N-(1S,2S)-2-((4'-(2-(4-(2-hydroxyethyl)-piperazin-1-yl)propan-2-yl)-[1,1'-biphenyl]-4-yl)methoxy)cyclopentyl)-[3,3'-bipyridine]-5-carboxamide Using intermediate 12, the title compound was obtained as described for the example 226.

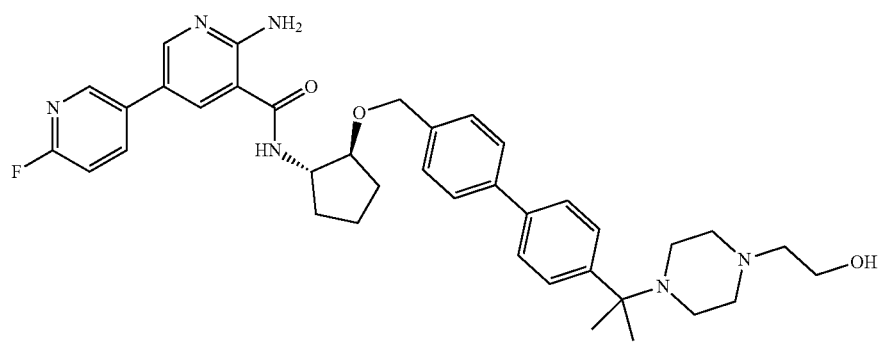 [SMILES: CC(C)(c1ccc(-c2ccc(CO[C@H]3CCC[C@@H]3NC(=O)c3cc(-c4ccc(F)nc4)cnc3N)cc2)cc1)N1CCN(CCO)CC1]

MS (ESI+) m/z 653.4 [M+H]+

Example 230. 6-amino-5'-fluoro-N-((1S,2S)-2-((4'-(1-(4-methylpiperazin-1-yl)ethyl)-[1,1'-biphenyl]-4-yl)methoxy)cyclopentyl)-[3,3'-bipyridine]-5-carboxamide
Scheme for the Preparation of the Compound of Example 230:
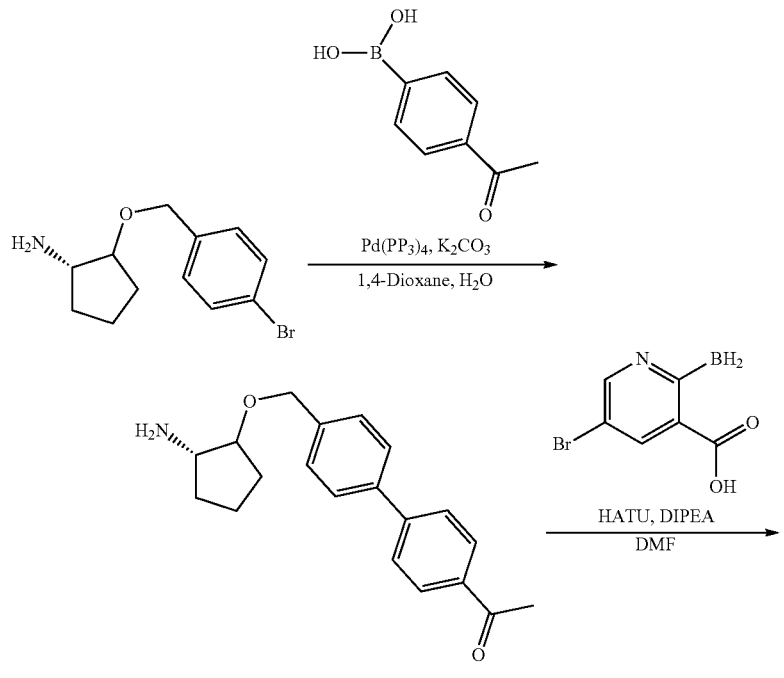
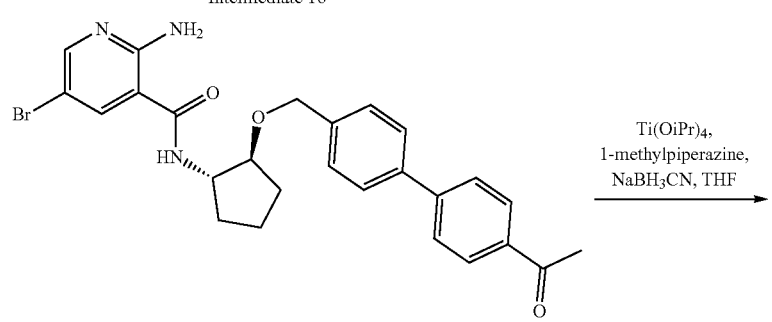
Intermediate 19
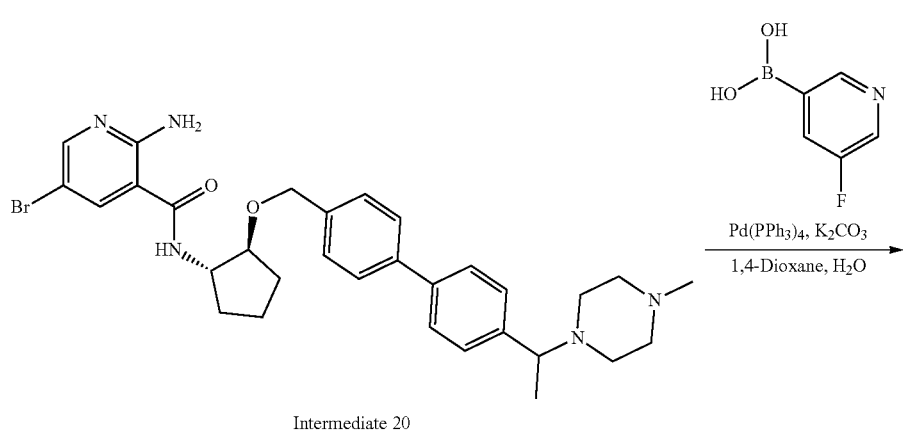
Intermediate 20

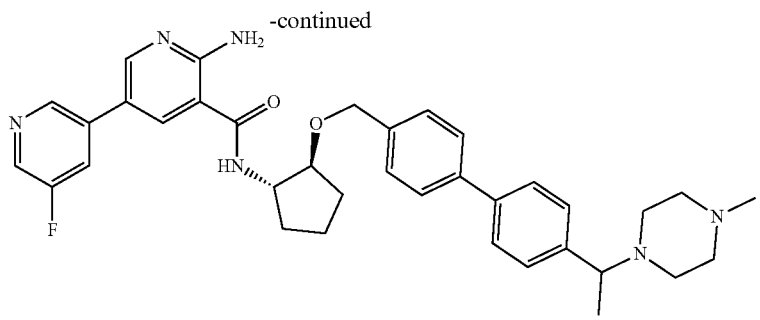

Intermediate 18

Using (1S,2S)-2-((4-bromobenzyl)oxy)cyclopentan-1-amine, the title compound was obtained as described for the intermediate 7.

¹H NMR (600 MHz, CD₃OD) δ ppm 1.58-1.65 (m, 1H) 1.74-1.85 (m, 3H) 2.01-2.08 (m, 1H) 2.12-2.18 (m, 1H) 2.60 (s, 3H) 3.41-3.48 (m, 1H) 3.92 (q, J=5.87 Hz, 1H) 4.45-4.55 (m, 2H) 7.27 (d, J=8.22 Hz, 2H) 7.43-7.50 (m, 3H) 7.65 (d, J=8.22 Hz, 1H) 7.73 (d, J=8.22 Hz, 1H) 8.03 (d, J=8.22 Hz, 1H);

MS (ESI+) m/z 310.1 [M+H]⁺

Intermediate 19

Using intermediate 18, the title compound was obtained as described for the intermediate 4.

¹H NMR (600 MHz, CDCl₃) δ ppm 1.45-1.54 (m, 1H) 1.71-1.82 (m, 2H) 1.84-1.92 (m, 1H) 1.92-2.02 (m, 1H) 2.23-2.33 (m, 1H) 2.63 (s, 3H) 3.81-3.91 (m, 1H) 4.29-4.44 (m, 1H) 4.63-4.75 (m, 2H) 5.90 (br d, J=6.46 Hz, 1H) 6.35 (br s, 2H) 7.44 (d, J=8.22 Hz, 2H) 7.56-7.62 (m, 3H) 7.66 (d, J=8.22 Hz, 2H) 8.01 (d, J=8.22 Hz, 2H) 8.15 (d, J=1.76 Hz, 1H);

MS (ESI+) m/Z 508.1/510.2 [M+H]⁺

Intermediate 20

To intermediate 19 (300 mg, 0.59 mmol) in 3 ml of THF was added 1-methylpiperazine (0.13 ml, 1.18 mmol) followed by Ti(OiPr)₄ (0.7 ml, 2.36 mmol). The mixture was stirred at 60° C. for 4 hr and then NaBH₃CN (0.11 g, 1.18 mmol) was added. The mixture was stirred for 1 h and extracted with EtOAc, washed with brine, dried over MgSO₄. After concentration under vacuum, the crude product was purified by silicagel column chromatography to give 200 mg of off-white solid.

¹H NMR (600 MHz, CD₃OD) δ ppm 1.55-1.61 (m, 1H) 1.64 (d, J=7.04 Hz, 3H) 1.72-1.84 (m, 3H) 1.97-2.05 (m, 1H) 2.09-2.17 (m, 1H) 2.88 (s, 3H) 3.11 (br s, 2H) 3.36-3.49 (m, 4H) 3.95 (dt, J=6.75, 4.26 Hz, 1H) 4.14 (br d, J=6.46 Hz, 1H) 4.35 (td, J=7.34, 4.70 Hz, 1H) 4.61-4.68 (m, 2H) 7.42 (d, J=8.22 Hz, 2H) 7.50 (d, J=8.22 Hz, 2H) 7.57 (d, J=8.22 Hz, 2H) 7.65 (d, J=8.22 Hz, 2H) 8.13 (d, J=2.35 Hz, 1H) 8.20 (d, J=2.35 Hz, 1H);

MS (ESI+) m/z 592.2/594.3 [M+H]⁺

Example 230. 6-amino-5'-fluoro-N-((1S,2S)-2-((4'-(1-(4-methylpiperazin-1-yl)ethyl)-[1,1'-biphenyl]-4-yl)methoxy)cyclopeutyl)-[3,3'-bipyridine]-5-carboxamide Using intermediate 20 and 5-fluoropyridine-3-boronic acid, the title compound was obtained as described for the intermediate 14.

¹H NMR (600 MHz, CD₃OD) δ ppm 1.54 (d, J=7.04 Hz, 3H) 1.63 (br dd, J=13.21, 6.75 Hz, 1H) 1.77-1.86 (m, 3H) 2.04 (br dd, J=12.91, 7.04 Hz, 1H) 2.16-2.23 (m, 1H) 2.85 (s, 3H) 3.88 (br d, J=7.04 Hz, 1H) 3.97-4.03 (m, 1H) 4.43 (br d, J=4.70 Hz, 1H) 4.64-4.70 (m, 2H) 7.42 (br dd, J=8.22, 4.11 Hz, 4H) 7.53 (br d, J=8.22 Hz, 2H) 7.56 (br d, J=8.22 Hz, 2H) 7.96 (br d, J=9.39 Hz, 1H) 8.42 (s, 1H) 8.50 (d, J=2.35 Hz, 1H) 8.56 (s, 1H) 8.70 (br s, 1H);

MS (ESI+) m/z 609.3 [M+H]⁺

Example 231. 2-amino-5-chloro-N-((1S,2S)-2-((4'-(1-(4-methylpiperazin-1-yl)-ethyl)-[1,1'-biphenyl]-4-yl)methoxy)cyclopentyl)nicotinamide Using 2-amino-5-chloronicotinic acid, the title compound was obtained as described for the synthesis of intermediate 20.

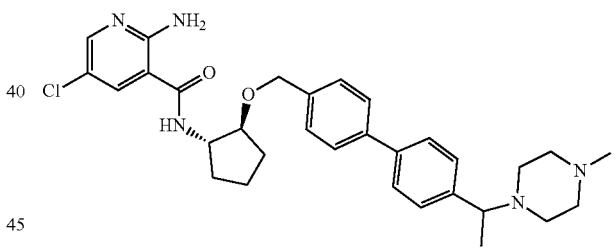

¹H NMR (400 MHz, CD₃OD) δ ppm 1.60 (dt, J=13.60, 7.09 Hz, 1H) 1.66 (d, J=6.65 Hz, 3H) 1.73-1.87 (m, 3H) 1.98-2.06 (m, 1H) 2.10-2.20 (m, 1H) 2.90 (s, 2H) 3.15 (br s, 2H) 3.45 (br s, 4H) 3.96 (dt, J=6.65, 4.30 Hz, 1H) 4.18 (q, J=6.65 Hz, 1H) 4.37 (td, J=7.24, 4.30 Hz, 1H) 4.61-4.71 (m, 2H) 7.43 (m, J=8.22 Hz, 2H) 7.52 (d, J=8.22 Hz, 2H) 7.59 (d, J=8.22 Hz, 2H) 7.67 (m, J=8.22 Hz, 2H) 8.09 (d, J=2.74 Hz, 1H) 8.14 (d, J=2.74 Hz, 1H);

MS (ESI+) m/z 548.3 [M+H]⁺

Example 232. 2-amino-5-fluoro-N-((1S,2S)-2-((4'-(1-(4-methylpiperazin-1-yl)-ethyl)-[1,1'-biphenyl]-4-yl)methoxy)cyclopentyl)nicotinamide Using 2-amino-5-fluoronicotinic acid, the title compound was obtained as described for the synthesis of intermediate 20.

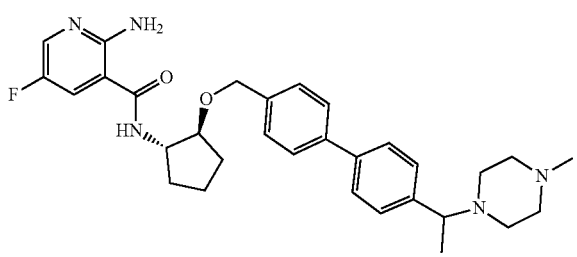 [SMILES: CC(c1ccc(-c2ccc(CO[C@H]3CCC[C@@H]3NC(=O)c3cc(F)cnc3N)cc2)cc1)N1CCN(C)CC1]

MS (ESI, m/z): 532.3 [M+H]+

Example 233. 2-amino-5-cyano-N-((1S,2S)-2-((4'-(1-(4-methylpiperazin-1-yl)-ethyl)-[1,1'-biphenyl]-4-yl)methoxy)cyclopentyl)nicotinamide Using 2-amino-5-cyanonicotinic acid, the title compound was obtained as described for the synthesis of intermediate 20.

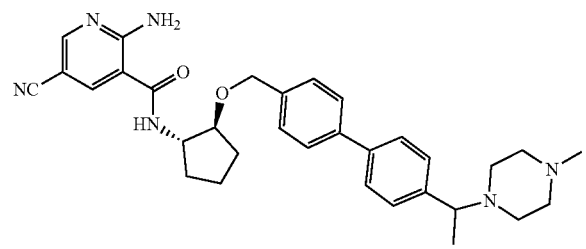 [SMILES: CC(c1ccc(-c2ccc(CO[C@H]3CCC[C@@H]3NC(=O)c3cc(C#N)cnc3N)cc2)cc1)N1CCN(C)CC1]

MS (ESI, m/z): 539.3 [M+H]+

Example 234. 2-amino-6-chloro-N-((1S,2S)-2-((4'-(1-(4-methylpiperazin-1-yl)-ethyl)-[1,1'-biphenyl]-4-yl)methoxy)cyclopentyl)nicotinamide Using 2-amino-6-chloronicotinic acid, the title compound was obtained as described for the synthesis of intermediate 20.

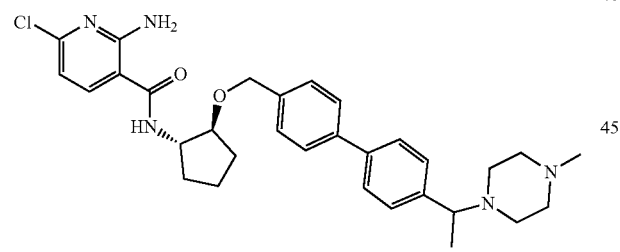

$^1$H NMR (400 MHz, CD$_3$OD) δ ppm 1.56 (br dd, J=13.11, 7.24 Hz, 1H) 1.66 (d, J=7.04 Hz, 3H) 1.70-1.85 (m, 3H) 2.01 (br dd, J=13.11, 6.46 Hz, 1H) 2.07-2.19 (m, 2H) 2.90 (s, 3H) 3.09-3.21 (m, 2H) 3.39-3.58 (m, 4H) 3.87-3.96 (m, 1H) 4.19 (br d, J=6.65 Hz, 1H) 4.35 (br d, J=4.70 Hz, 1H) 4.57-4.73 (m, 2H) 6.56 (d, J=7.83 Hz, 1H) 7.42 (m, J=8.22 Hz, 2H) 7.52 (d, J=8.22 Hz, 2H) 7.56 (d, J=8.22 Hz, 2H) 7.66 (m, J=8.22 Hz, 2H) 7.73 (d, J=8.22 Hz, 1H);

MS (ESI, m/z): 548.3 [M+H]+

Example 235. 2-amino-N-((1S,2S)-2-((4'-(1-(4-methylpiperazin-1-yl)ethyl)-[1,1'-biphenyl]-4-yl)methoxy)cyclopentyl)nicotinamide Using 2-aminonicotinic acid, the title compound was obtained as described for the synthesis of intermediate 20.

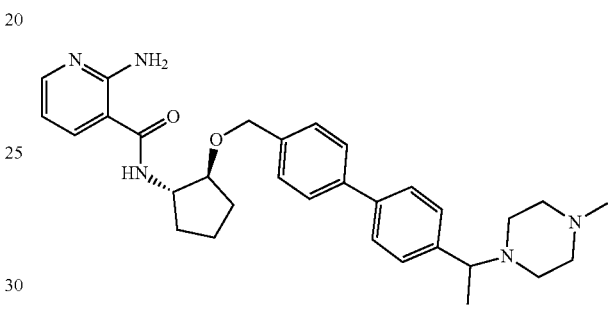

$^1$H NMR (600 MHz, CD$_3$OD) δ ppm 1.58-1.64 (m, 1H) 1.66 (d, J=7.04 Hz, 3H) 1.74-1.85 (m, 3H) 1.97-2.05 (m, 1H) 2.13-2.20 (m, 1H) 2.89 (s, 3H) 3.02-3.27 (m, 4H) 3.46 (br s, 4H) 3.93-4.00 (m, 1H) 4.20 (q, J=6.46 Hz, 1H) 4.35-4.42 (m, 1H) 4.65 (s, 2H) 6.95 (t, J=6.75 Hz, 1H) 7.43 (d, J=8.22 Hz, 2H) 7.52 (m, J=8.22 Hz, 2H) 7.58 (m, J=8.22 Hz, 2H) 7.67 (d, J=8.22 Hz, 2H) 7.99 (dd, J=6.46, 1.17 Hz, 1H) 8.33 (dd, J=7.34, 1.47 Hz, 1H);

MS (ESI, m/z): 514.3 [M+H]+

Example 236. 6-amino-5'-fluoro-N-((1S,2S)-2-((4'-(1-(4-(2-hydroxyethyl)-piperazin-1-yl)ethyl)-[1,1'-biphenyl]-4-yl)methoxy)cyclopentyl)-[3,3'-bipyridine]-5-carboxamide Scheme for the Preparation of the Compound of Example 236:

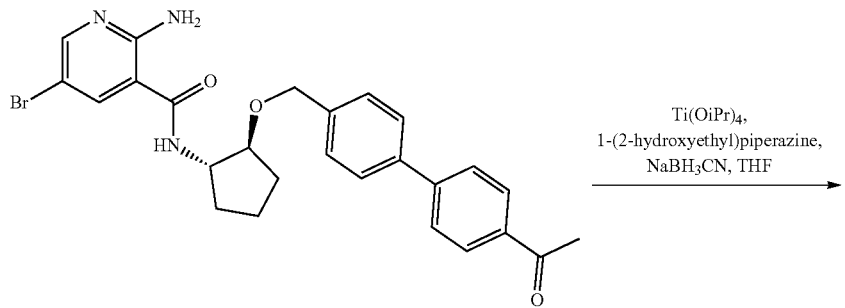

Intermediate 19

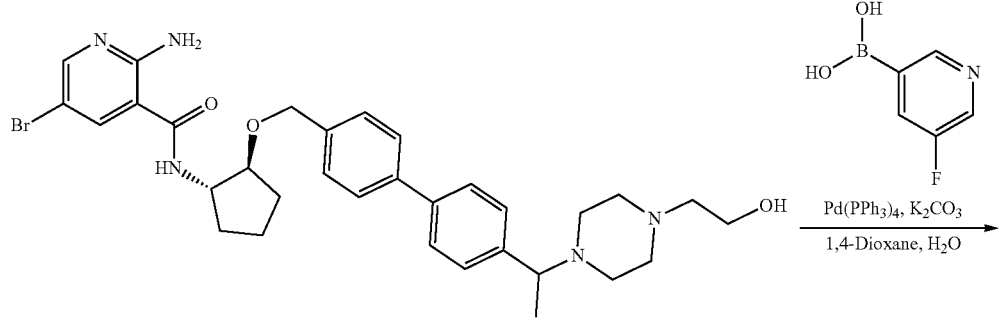

Intermediate 21

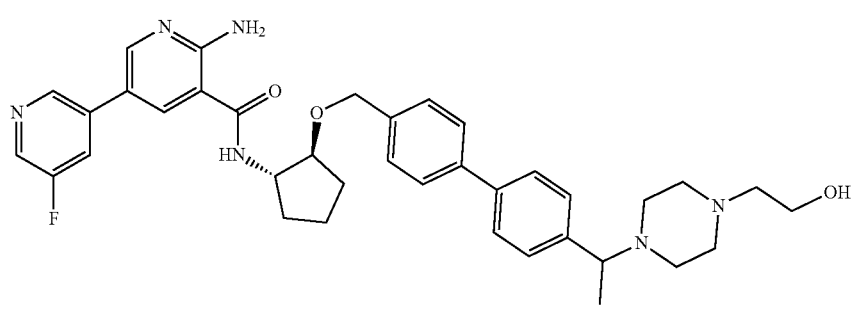

Intermediate 21. Using 1-(2-Hydroxyethyl)Piperazine, the Title Compound was Obtained as Described for the Intermediate 20

$^1$H NMR (600 MHz, CD$_3$OD) δ ppm 1.42 (d, J=6.46 Hz, 2H) 1.51-1.58 (m, 1H) 1.71-1.81 (m, 3H) 1.97-2.04 (m, 1H) 2.08-2.15 (m, 1H) 2.61 (br s, 2H) 3.47 (br d, J=5.28 Hz, 1H) 3.67 (t, J=5.87 Hz, 2H) 3.91 (dt, J=6.46, 4.70 Hz, 1H) 4.35 (td, J=7.34, 4.70 Hz, 1H) 4.59-4.67 (m, 2H) 7.37 (br d, J=8.22 Hz, 2H) 7.39 (br d, J=8.22 Hz, 2H) 7.54 (d, J=7.63 Hz, 4H) 7.90 (d, J=2.35 Hz, 1H) 8.05 (d, J=2.35 Hz, 1H); MS (ESI+) m/z 622.2/624.2 [M+H]$^+$ Example 236. 6-amino-5'-fluoro-N-((1S,2S)-2-((4'-(1-(4-(2-hydroxyethyl)piperazin-1-yl)ethyl)-[1,1'-biphenyl]-4-yl)methoxy)cyclopentyl)-[3,3'-bipyridine]-5-carboxamide Using intermediate 21, the title compound was obtained as described for the example 230.
$^1$H NMR (400 MHz, CD$_3$OD) δ ppm 1.63 (br dd, J=13.89, 6.85 Hz, 1H) 1.72 (br d, J=6.65 Hz, 3H) 1.76-1.87 (m, 3H) 2.04 (br dd, J=12.72, 6.46 Hz, 1H) 2.13-2.23 (m, 1H) 3.52-3.68 (m, 4H) 3.84 (br t, J=4.89 Hz, 2H) 4.00 (br d, J=3.91 Hz, 1H) 4.35 (br d, J=6.65 Hz, 1H) 4.39-4.49 (m, 2H) 4.61-4.73 (m, 2H) 7.43 (br d, J=7.83 Hz, 2H) 7.53 (br t, J=9.39 Hz, 4H) 7.63 (br d, J=8.22 Hz, 2H) 7.98 (br d, J=9.78 Hz, 1H) 8.43 (s, 1H) 8.52 (s, 1H) 8.61 (s, 1H) 8.71 (s, 1H); MS (ESI+) m/z 639.3 [M+H]$^+$ Example 237. 6-amino-6'-fluoro-N-((1S,2S)-2-((4'-(1-(4-(2-hydroxyethyl)-piperazin-1-yl)ethyl)-[1,1'-biphenyl]-4-yl)methoxy)cyclopentyl)-[3,3'-bipyridine]-5-carboxamide Using 6-fluoropyridine-3-boronic acid, the title compound was obtained as described for the example 236.

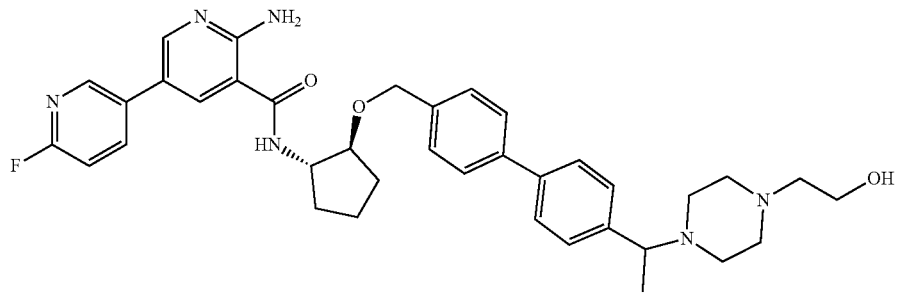 [SMILES: CC(c1ccc(-c2ccc(CO[C@H]3CCC[C@@H]3NC(=O)c3cc(-c4ccc(F)nc4)cnc3N)cc2)cc1)N1CCN(CCO)CC1]

$^1$H NMR (400 MHz, CD$_3$OD) δ ppm 1.62 (br dd, J=13.30, 6.65 Hz, 1H) 1.68 (br d, J=7.04 Hz, 3H) 1.81 (br d, J=7.43 Hz, 3H) 1.98-2.08 (m, 1H) 2.12-2.23 (m, 1H) 3.17-3.28 (m, 4H) 3.53 (br s, 4H) 3.84 (br d, J=4.30 Hz, 2H) 3.99 (br s, 1H) 4.25 (br d, J=7.04 Hz, 1H) 4.42 (br d, J=4.70 Hz, 1H) 4.62-4.72 (m, 2H) 7.16 (br d, J=7.83 Hz, 1H) 7.42 (br d, J=7.83 Hz, 2H) 7.47-7.59 (m, 4H) 7.62 (br d, J=7.83 Hz, 2H) 8.19 (br t, J=8.02 Hz, 1H) 8.34 (s, 1H) 8.47 (br s, 1H) 8.56 (s, 1H);

MS (ESI+) n/z 639.3 [M+H]$^+$

Example 238. 6-amino-2'-fluoro-N-((1S,2S)-2-((4'-(1-(4-(2-hydroxyethyl)-piperazin-1-yl)ethyl)-[1,1'-biphenyl]-4-yl)methoxy)cyclopentyl)-[3,3'-bipyridine]-5-carboxamide Using 2-fluoropyridine-3-boronic acid, the title compound was obtained as described for the example 236.

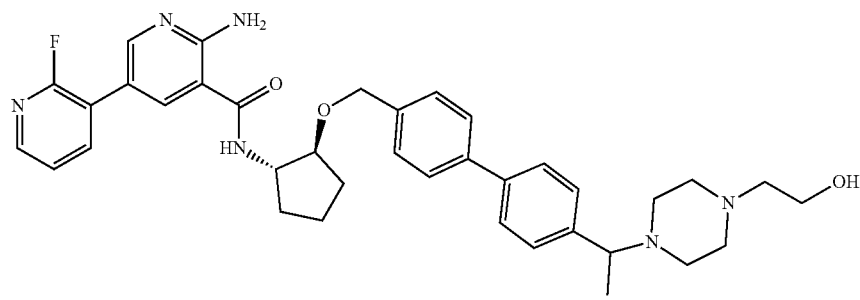 [SMILES: CC(c1ccc(-c2ccc(CO[C@H]3CCC[C@@H]3NC(=O)c3cc(-c4cccnc4F)cnc3N)cc2)cc1)N1CCN(CCO)CC1]

MS (ESI+) m/z 639.3 [M+H]$^+$

Example 239. 2-amino-5-(1-methyl-1H-pyrazol-4-yl)-N-((1S,2S)-2-((4'-((1-methylpiperidin-4-yl)methyl)-[1,1'-biphenyl]-4-yl)methoxy)cyclopentyl) nicotinamide Scheme for the Preparation of the Compound of Example 239:

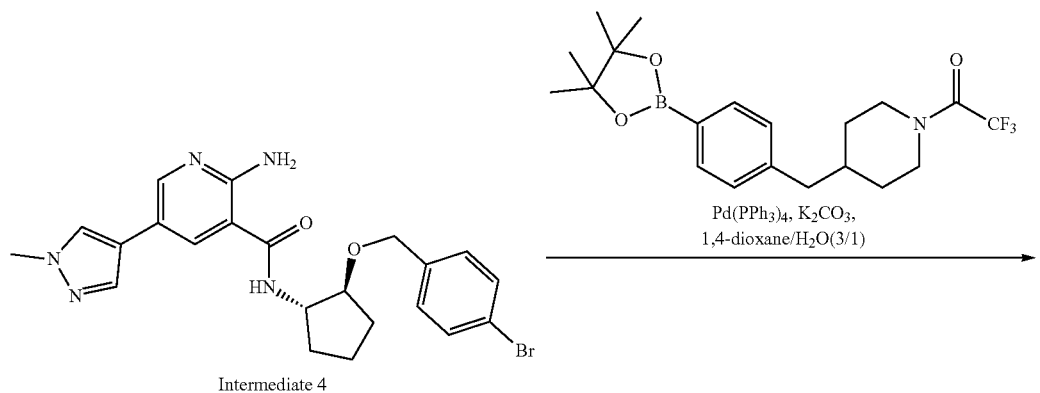

-continued

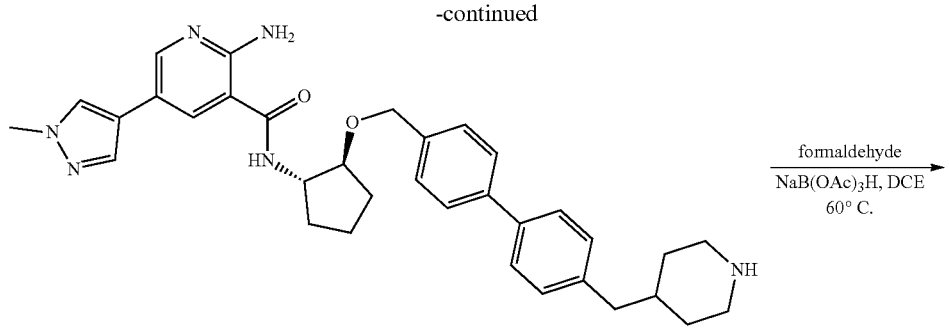

Intermediate 22

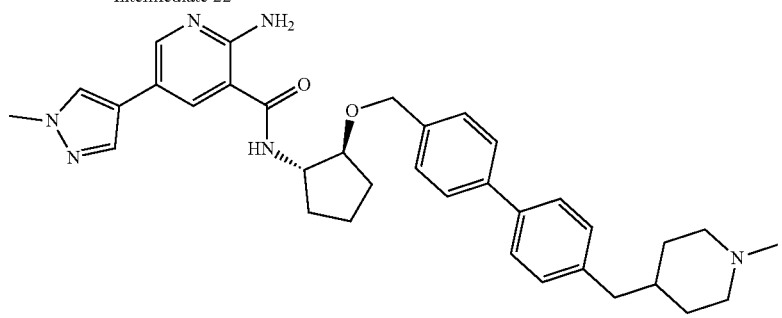

Intermediate 22

Intermediate 22

Using 4-(4-(1-trifluoroacetylpiperidino)methyl)phenylboronic acid pinacol ester, the title compound was obtained as described for the example 134.

$^1$H NMR (600 MHz, CD$_3$OD) δ ppm 1.39-1.48 (m, 2H) 1.63 (br dd, J=13.50, 7.04 Hz, 1H) 1.76-1.86 (m, 4H) 1.86-1.95 (m, 3H) 2.04 (br dd, J=13.21, 6.75 Hz, 1H) 2.18 (br dd, J=13.50, 5.87 Hz, 1H) 2.64 (br d, J=6.46 Hz, 2H) 2.90-2.98 (m, 2H) 3.33 (s, 3H) 3.36 (br d, J=12.33 Hz, 3H) 3.89 (s, 3H) 3.97-4.03 (m, 1H) 4.37-4.45 (m, 1H) 4.63-4.70 (m, 2H) 7.23 (br d, J=8.22 Hz, 2H) 7.40 (d, J=8.22 Hz, 2H) 7.48 (d, J=8.22 Hz, 2H) 7.52 (d, J=8.22 Hz, 2H) 7.85 (s, 1H) 7.97 (s, 1H) 8.19 (d, J=1.76 Hz, 1H) 8.51 (d, J=2.35 Hz, 1H);

MS (ESI, m/z): 564.8 [M+H]$^+$

Example 239. 2-amino-5-(1-methyl-1H-pyrazol-4-yl)-N-(1S,2S)-2-((4'-((1-methylpiperidin-4-yl)methyl)-[1,1'-biphenyl]-4-yl)methoxy)cyclopentyl) nicotinamide Using intermediate 22 and formaldehyde, the title compound was obtained as described for the example 214.

$^1$H NMR (600 MHz, CD$_3$OD) δ ppm 1.42-1.54 (m, 2H) 1.63 (br dd, J=13.50, 7.04 Hz, 1H) 1.75-1.88 (m, 4H) 1.92 (br d, J=14.67 Hz, 2H) 2.00-2.08 (m, 1H) 2.17 (br dd, J=13.50, 5.87 Hz, 1H) 2.64 (br d, J=7.04 Hz, 2H) 2.82 (s, 3H) 2.89-2.98 (m, 2H) 3.47 (br d, J=12.33 Hz, 2H) 3.89 (s, 3H) 3.94-4.05 (m, 1H) 4.36-4.46 (m, 1H) 4.61-4.69 (m, 2H) 7.22 (d, J=8.22 Hz, 2H) 7.39 (br d, J=8.22 Hz, 2H) 7.47 (br d, J=8.22 Hz, 2H) 7.51 (br d, J=8.22 Hz, 2H) 7.84 (s, 1H) 7.96 (s, 1H) 8.18 (d, J=1.76 Hz, 1H) 8.49 (d, J=2.35 Hz, 1H); MS (ESI, m/z): 579.8 [M+H]$^+$

Example 240. 2-amino-N-((1S,2S)-2-((4'-((1-(2-hydroxyethyl)piperidin-4-yl)-methyl)-[1,1'-biphenyl]-4-yl)methoxy)cyclopentyl)-5-(1-methyl-1H-pyrazol-4-yl)-nicotinamide Scheme for the Preparation of the Compound of Example 240:

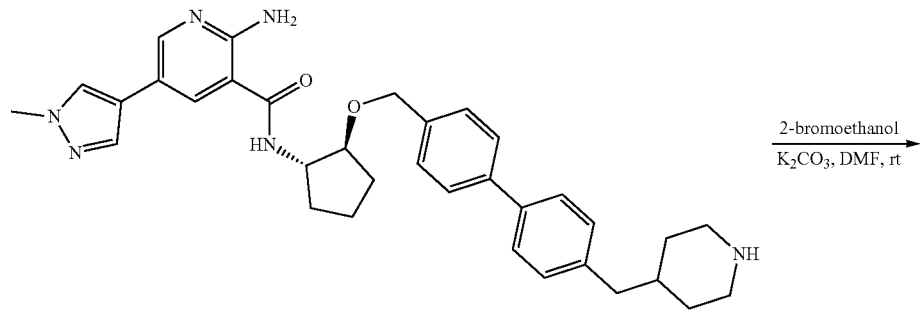

Intermediate 22

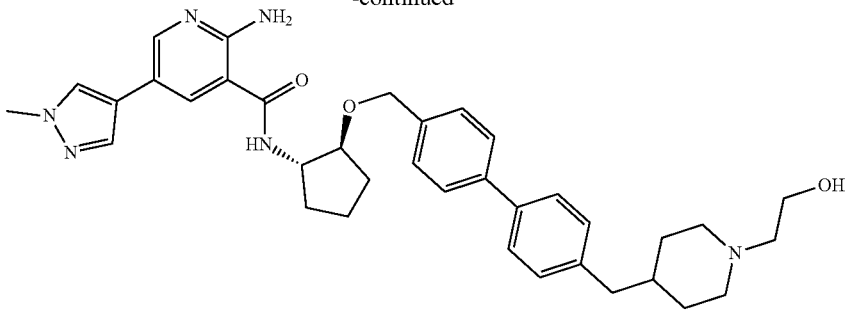

To a mixture of intermediate 22 (30 mg, 0.05 mmol) and K₂CO₃ (22 mg, 0.16 mmol) in 0.4 ml of DMF was added 2-bromoethanol (6 µl, 0.08 mmol). The mixture was stirred at room temperature for 4 hr and then water was added. The mixture was extracted with EtOAc, washed with brine, dried over MgSO₄. After concentration under vacuum, the crude residue was purified by preparative HPLC to afford 27 mg of the title compound.

¹H NMR (600 MHz, CD₃OD) δ ppm 1.26 (br d, J=13.50 Hz, 2H) 1.56-1.74 (m, 4H) 1.74-1.89 (m, 4H) 2.04 (br dd, J=13.21, 6.16 Hz, 1H) 2.20 (br dd, J=13.50, 7.04 Hz, 1H) 2.64 (br d, J=7.04 Hz, 2H) 2.77 (br t, J=12.62 Hz, 2H) 3.05-3.13 (m, 2H) 3.47 (br d, J=12.33 Hz, 2H) 3.75-3.81 (m, 2H) 3.92 (s, 3H) 4.01-4.07 (m, 1H) 4.40-4.47 (m, 1H) 4.62-4.72 (m, 2H) 7.10 (br d, J=7.63 Hz, 1H) 7.20-7.26 (m, 3H) 7.27-7.33 (m, 2H) 7.41 (br d, J=7.63 Hz, 2H) 7.87-7.90 (m, 1H) 7.88 (s, 1H) 8.03 (s, 1H) 8.23 (d, J=1.76 Hz, 1H) 8.60 (br s, 1H);

MS (ESI, m/z): 609.8 [M+H]⁺

Example 241. methyl 2-(4-((4'-(((((1S,2S)-2-(2-amino-5-(1-methyl-1H-pyrazol-4-yl)nicotinamido)cyclopentyl)oxy)methyl)-[1,1'-biphenyl]-4-yl)methyl)piperidin-1-yl)-acetate Using intermediate 22 and methyl bromoacetate, the title compound was obtained as described for the example 240.

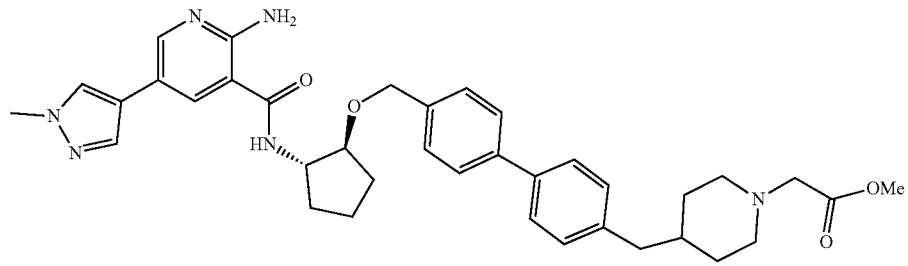 [SMILES: COC(=O)CN1CCC(Cc2ccc(-c3ccc(CO[C@H]4CCC[C@@H]4NC(=O)c4cc(-c5cnn(C)c5)cnc4N)cc3)cc2)CC1]

¹H NMR (600 MHz, CD₃OD) δ ppm 1.32 (br s, 2H) 1.61-1.71 (m, 4H) 1.79-1.89 (m, 4H) 2.01-2.06 (m, 1H) 2.20 (br dd, J=13.79, 6.75 Hz, 1H) 2.66 (br s, 2H) 2.85 (br s, 2H) 3.49 (br s, 2H) 3.79 (s, 3H) 3.92 (s, 3H) 4.01 (br s, 2H) 4.02-4.06 (m, 1H) 4.44 (br dd, J=11.15, 7.04 Hz, 1H) 4.63-4.73 (m, 2H) 7.11 (br d, J=7.63 Hz, 1H) 7.23-7.30 (m, 4H) 7.41 (br d, J=8.22 Hz, 2H) 7.88 (s, 1H) 8.02-8.04 (m, 1H) 8.23 (d, J=1.76 Hz, 1H) 8.60 (s, 1H);

MS (ESI, m/z): 637.7 [M+H]⁺

Example 242. 2-amino-N-((1S,2S)-2-((4'-((1-(2-amino-2-oxoethyl)piperidin-4-yl)methyl)-[1,1'-biphenyl]-4-yl)methoxy)cyclopentyl)-5-(1-methyl-1H-pyrazol-4-yl)-nicotinamide Using intermediate 22 and bromoacetamide, the title compound was obtained as described for the example 240.

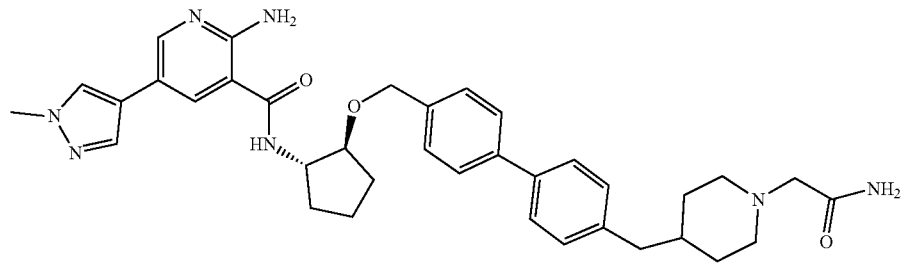 [SMILES: Cn1cc(-c2cnc(N)c(C(=O)N[C@H]3CCC[C@@H]3OCc3ccc(-c4ccc(CC5CCN(CC(N)=O)CC5)cc4)cc3)c2)cn1]

MS (ESI, m/z): 622.8 [M+H]+

Example 243. 2-amino-5-(1-methyl-1H-pyrazol-4-yl)-N-((1S,2S)-2-(4-(3-(4-methylpiperazin-1-yl)propyl)benzyl)oxy)cyclopentyl)nicotinamide Scheme for the Preparation of the Compound of Example 243

Intermediate 23

A mixture of intermediate 4 (300 mg, 0.64 mmol), Pd(dba)$_2$ (7 mg, 0.01 mmol), P(t-bu)$_3$ (8 mg, 0.04 mmol) in DMF (3 ml) was degassed with nitrogen and TEA (0.133 ml, 0.96 mmol), allyl alcohol (0.11 ml, 1.28 mmol) were added. The mixture was heated at 100° C. for 1h. After cooling, the mixture was partitioned between EA and water. The organic layer was separated and washed with water, brine dried over MgSO$_4$ and concentrated in vacuo. The crude material was purified by flash chromatography on silica gel with Et$_2$O-hexane mixtures as eluents to give 150 mg of off-white solid.

$^1$H NMR (600 MHz, CD$_3$OD) δ ppm 1.64 (br dd, J=13.21, 6.75 Hz, 1H) 1.75 (br d, J=7.63 Hz, 1H) 1.79-1.85 (m, 2H) 1.94-2.04 (m, 3H) 2.16 (br d, J=6.46 Hz, 1H) 2.64 (br t,

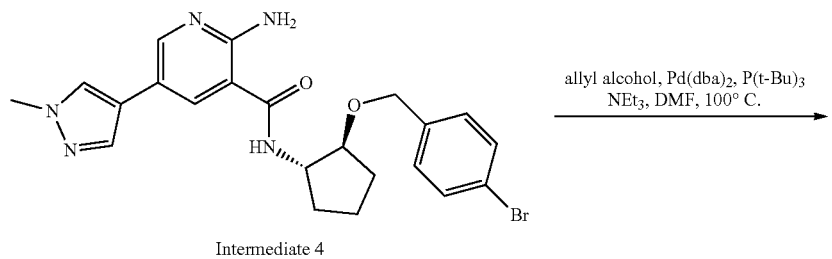

Intermediate 4

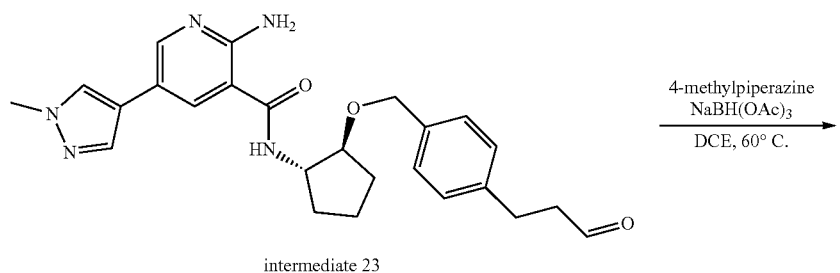

intermediate 23

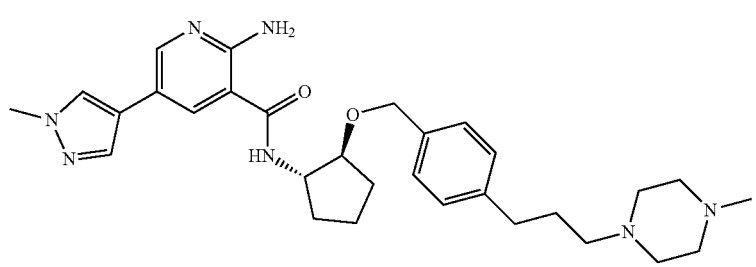

J=7.63 Hz, 2H) 2.89 (s, 3H) 3.02-3.07 (m, 2H) 3.40 (br s, 2H) 3.46 (br s, 4H) 3.93 (s, 3H) 3.96-4.00 (m, 1H) 4.36-4.42 (m, 1H) 4.54-4.65 (m, 3H) 7.16 (d, J=8.22 Hz, 2H) 7.27 (d, J=8.22 Hz, 2H) 7.84-7.89 (m, 1H) 8.03 (s, 1H) 8.23 (d, J=1.76 Hz, 1H) 8.56 (d, J=2.35 Hz, 1H);

MS (ESI, m/z): 532.5 [M+H]⁺

Example 243. 2-amino-5-(1-methyl-1H-pyrazol-4-yl)-N-((1S,2S)-2-((4-(3-(4-methylpiperazin-1-yl)propyl)benzyl)oxy)cyclopentyl)nicotinamide Using intermediate 23, the title compound was obtained as described for the example 172.

¹H NMR (600 MHz, CD₃OD) δ ppm 1.64 (br dd, J=13.21, 6.75 Hz, 1H) 1.75 (br d, J=7.63 Hz, 1H) 1.79-1.85 (m, 2H) 1.94-2.04 (m, 3H) 2.16 (br d, J=6.46 Hz, 1H) 2.64 (br t, J=7.63 Hz, 2H) 2.89 (s, 3H) 3.02-3.07 (m, 2H) 3.40 (br s, 2H) 3.46 (br s, 4H) 3.93 (s, 3H) 3.96-4.00 (m, 1H) 4.36-4.42 (m, 1H) 4.54-4.65 (m, 3H) 7.16 (d, J=8.22 Hz, 2H) 7.27 (d, J=8.22 Hz, 2H) 7.84-7.89 (m, 1H) 8.03 (s, 1H) 8.23 (d, J=1.76 Hz, 1H) 8.56 (d, J=2.35 Hz, 1H);

MS (ESI, m/z): 532.4 [M+H]⁺

Example 244. 2-amino-N-((1S,2S)-2-((4-(3-(dimethylamino)propyl)benzyl)oxy)-cyclopentyl)-5-(1-methyl-1H-pyrazol-4-yl)nicotinamide Using intermediate 23 and dimethylamine (50% in THF), the title compound was obtained as described for the example 243.

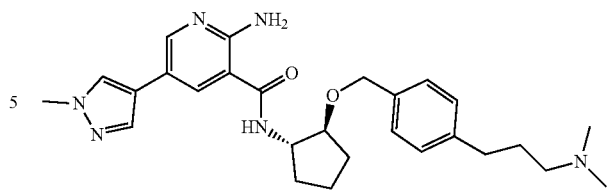

¹H NMR (600 MHz, CD₃OD) δ ppm 1.63-1.68 (m, 1H) 1.73-1.78 (m, 1H) 1.80-1.83 (m, 3H) 1.96-2.05 (m, 3H) 2.17 (br d, J=6.46 Hz, 1H) 2.65 (br t, J=7.63 Hz, 2H) 2.84 (s, 6H) 3.06-3.14 (m, 2H) 3.94 (s, 3H) 3.98 (br s, 1H) 4.39 (br s, 1H) 4.55-4.67 (m, 3H) 7.18 (br d, J=7.63 Hz, 2H) 7.29 (br d, J=7.63 Hz, 2H) 7.87-7.89 (m, 1H) 8.04 (s, 1H) 8.23 (d, J=1.76 Hz, 1H) 8.57 (d, J=2.35 Hz, 1H);

MS (ESI, m/z): 477.5 [M+H]⁺

Example 245. 2-amino-N-((1S,2S)-2-((4'-(2-(dimethylamino)ethoxy)-[1,1'-biphenyl]-4-yl)methoxy)cyclopentyl)-5-(1-methyl-1H-pyrazol-4-yl)nicotinamide Scheme for the Preparation of the Compound of Example 245

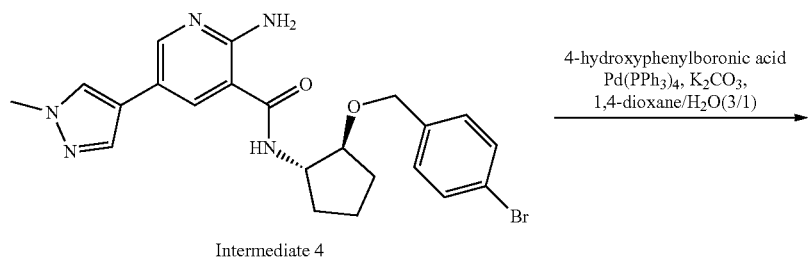

Intermediate 4

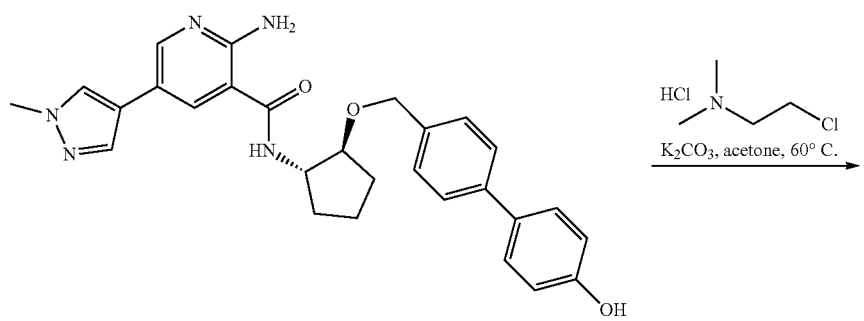

intermediate 24

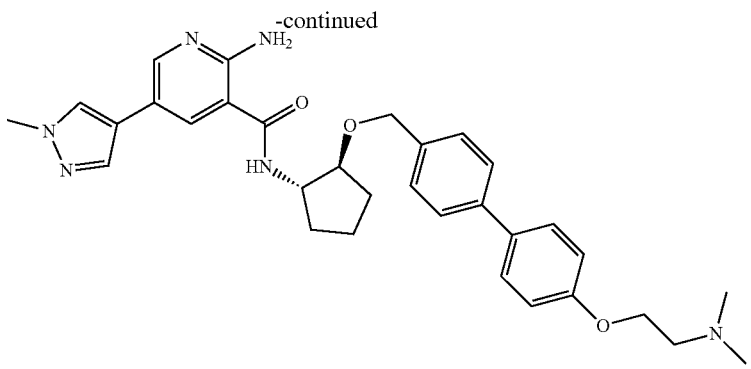

Intermediate 24

To a mixture of intermediate 4 (300 mg 0.64 mmol) and (4-hydroxyphenyl)boronic acid (132 mg, 0.96 mmol) in 4 ml of 1,4-dioxane/water (3/1) was added $K_2CO_3$ (264 mg, 1.91 mmol) followed by $Pd(PPh_3)_4$ (37 mg, 0.03 mmol). The reaction mixture was heated at 100° C. for 3 hrs, cooled to room temperature, and extracted with EtOAc, dried over anhydrous $MgSO_4$ and concentrated under vacuum. After concentration under vacuum, the crude material was purified by flash chromatography on silica gel with DCM-MeOH mixtures as eluents to give 250 mg of off-white solid.

$^1$H NMR (600 MHz, CD$_3$OD) δ ppm 1.60 (br dd, J=13.21, 7.34 Hz, 1H) 1.74-1.87 (m, 3H) 2.04 (br dd, J=12.62, 7.34 Hz, 1H) 2.10-2.20 (m, 1H) 3.88 (s, 3H) 3.92-4.00 (m, 1H) 4.35-4.44 (m, 1H) 4.57 (d, J=12.33 Hz, 1H) 4.66 (d, J=12.33 Hz, 2H) 6.78 (m, J=8.22 Hz, 2H) 7.33 (t, J=9.10 Hz, 4H) 7.43 (m, J=8.22 Hz, 2H) 7.82 (s, 1H) 7.91 (s, 1H) 8.15 (d, J=2.35 Hz, 1H) 8.43 (d, J=1.76 Hz, 1H);

MS (ESI, m/z): 484.3 [M+H]$^+$

Example 245. 2-amino-N-((1S,2S)-2-((4'-(2-(dimethylamino)ethoxy)-[1,1'-biphenyl]-4-yl)methoxy)cyclopentyl)-5-(1-methyl-1H-pyrazol-4-yl)nicotinamide A mixture of intermediate 24 (30 mg, 0.06 mmol) and $K_2CO_3$ (43 mg, 0.31 mmol) was heated at 60° C. for 12 hrs, cooled to room temperature, and extracted with EtOAc, dried over anhydrous $MgSO_4$ and concentrated under vacuum. After concentration under vacuum, the crude residue was purified by preparative HPLC to afford 30 mg of the title compound $^1$H NMR (400 MHz, CD$_3$OD) δ ppm 1.57-1.68 (m, 1H) 1.81 (br d, J=7.83 Hz, 3H) 2.01 (br d, J=19.56 Hz, 1H) 2.16 (br d, J=12.91 Hz, 1H) 2.99 (s, 6H) 3.61 (br s, 2H) 3.89 (s, 3H) 3.99 (br s, 1H) 4.37 (br d, J=3.52 Hz, 3H) 4.64 (s, 2H) 7.05 (br d, J=8.22 Hz, 2H) 7.38 (br d, J=7.83 Hz, 2H) 7.50 (br t, J=7.43 Hz, 3H) 7.84 (s, 1H) 7.96 (s, 1H) 8.19 (br s, 1H) 8.48 (s, 1H);

MS (ESI, m/z): 555.4 [M+H]$^+$

Example 246. 2-amino-N-((1S,2S)-2-((4'-(3-(dimethylamino)propoxy)-[1,1'-biphenyl]-4-yl)methoxy)cyclopentyl)-5-(1-methyl-1H-pyrazol-4-yl)nicotinamide Using (3-chloropropyl)dimethylamine, title compound was obtained as described for the example 245.

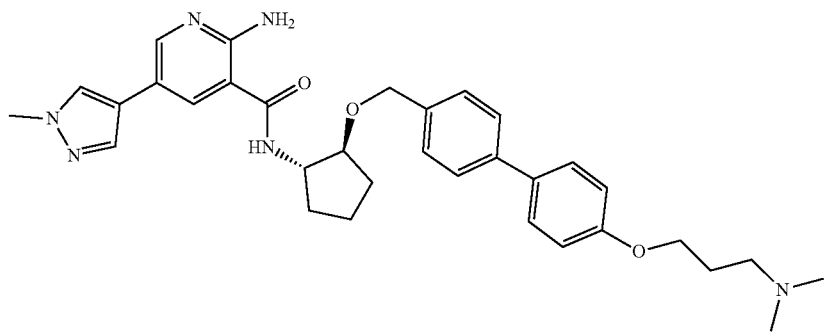

$^1$H NMR (600 MHz, CD$_3$OD) δ ppm 1.62 (br dd, J=13.21, 7.34 Hz, 1H) 1.73-1.86 (m, 3H) 2.04 (br dd, J=12.91, 7.63 Hz, 1H) 2.16 (br dd, J=13.21, 6.16 Hz, 1H) 2.19-2.28 (m, 2H) 2.94 (s, 6H) 3.32-3.41 (m, 2H) 3.88 (s, 3H) 3.93-4.05 (m, 1H) 4.13 (t, J=5.87 Hz, 2H) 4.36-4.43 (m, 1H) 4.58-4.68 (m, 2H) 6.97 (d, J=8.80 Hz, 2H) 7.37 (d, J=8.22 Hz, 2H) 7.46 (t, J=8.51 Hz, 4H) 7.82 (s, 1H) 7.93 (s, 1H) 8.17 (d, J=2.35 Hz, 1H) 8.43 (d, J=1.76 Hz, 1H);

MS (ESI, m/z): 569.4 [M+H]$^+$

Example 247. 2-amino-5-(1-methyl-1H-pyrazol-4-yl)-N-((1S,2S)-2-((4'-((1-methylpiperidin-4-yl)oxy)-[1,1'-biphenyl]-4-yl)methoxy)cyclopentyl)nicotinamide Using 4-bromo-1-methylpiperidine, title compound was obtained as described for the example 245.

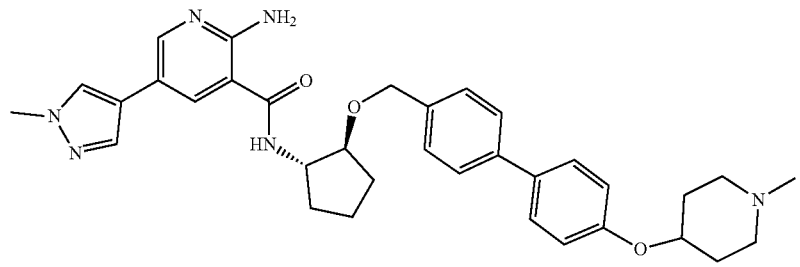

MS (ESI, m/z): 581.5 [M+H]⁺

Example 248. 2-amino-N-((1S,2S)-2-((4-(3-(dimethylamino)prop-1-yn-1-yl)benzyl)oxy)cyclopentyl)-5-(1-methyl-1H-pyrazol-4-yl)nicotinamide Scheme for the Preparation of the Compound of Example 248

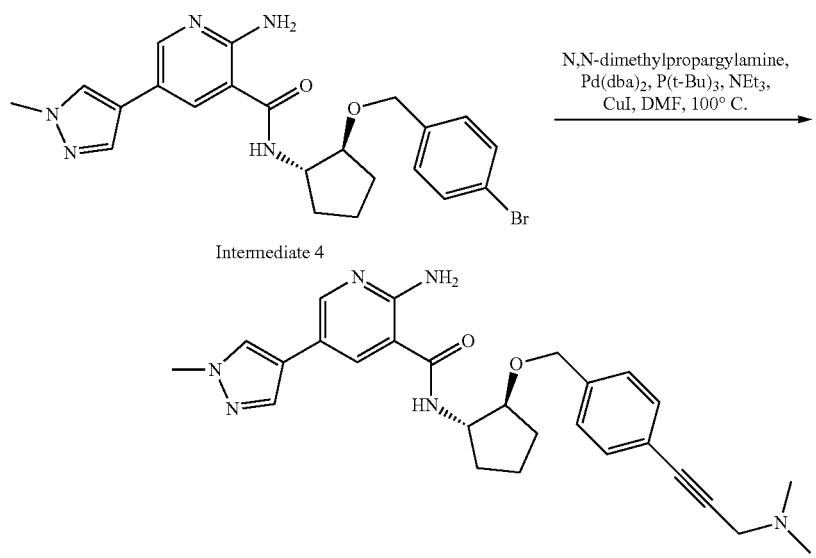

A mixture of intermediate 4 (40 mg, 0.09 mmol), Pd(dba)₂ (1 mg, 2 mol %), P(t-bu)₃ (1 mg, 6 mol %) in DMF (3 ml) was degassed with nitrogen and TEA (0.018 ml, 0.13 mmol), N,N-dimethylpropargylamine (0.016 ml, 0.17 mmol) were added. The mixture was heated at 100° C. for 12 hrs. After cooling, the mixture was partitioned between EA and water. The organic layer was separated and washed with water, brine dried over MgSO₄ and concentrated in vacuo. After concentration under vacuum, the crude residue was purified by preparative HPLC to afford 10 mg of the title compound.

¹H NMR (400 MHz, CD₃OD) δ ppm 1.63 (s, 2H) 1.78 (br dd, J=14.28, 6.85 Hz, 2H) 1.99 (br dd, J=12.91, 6.65 Hz, 1H) 2.09-2.18 (m, 1H) 2.35 (s, 3H) 3.12-3.18 (m, 1H) 3.32-3.34 (m, 4H) 3.42-3.50 (m, 2H) 3.58 (br d, J=7.04 Hz, 1H) 3.90 (s, 3H) 4.32-4.42 (m, 1H) 4.61 (s, 2H) 7.27-7.40 (m, 4H) 7.76 (s, 1H) 7.87 (s, 1H) 7.98 (s, 1H) 8.24 (s, 1H);
MS (ESI, m/z): 473.4 [M+H]⁺

Example 249. 2-amino-N-((1S,2S)-2-((4-(4-hydroxybut-1-yn-1-yl)benzyl)oxy)-cyclopentyl)-5-(1-methyl-1H-pyrazol-4-yl)nicotinamide Using 3-butyn-1-ol, title compound was obtained as described for the example 248.

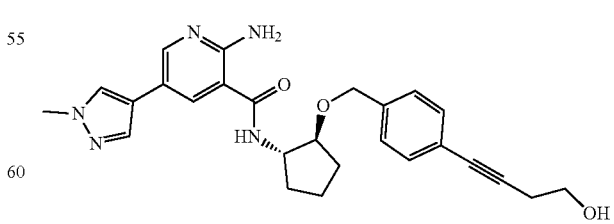

¹H NMR (600 MHz, CD₃OD) δ ppm 1.62 (br dd, J=13.21, 7.34 Hz, 1H) 1.70-1.77 (m, 1H) 1.77-1.84 (m, 3H) 2.01 (br dd, J=12.62, 7.34 Hz, 1H) 2.15 (br dd, J=13.21, 6.16 Hz, 1H) 2.57 (t, J=6.75 Hz, 2H) 3.69 (t, J=6.75 Hz, 2H) 3.94 (s, 3H)

4.32-4.40 (m, 1H) 4.54-4.63 (m, 2H) 7.23-7.31 (m, 4H) 7.87 (s, 1H) 8.01 (s, 1H) 8.23 (d, J=2.35 Hz, 1H) 8.50 (d, J=1.76 Hz, 1H);

MS (ESI, m/z): 460.6 [M+H]⁺

Example 250. 2-amino-N-((1S,2S)-2-((4-(5-hydroxypent-1-yn-1-yl)-benzyl)oxy)-cyclopentyl)-5-(1-methyl-1H-pyrazol-4-yl)nicotinamide Using 4-pentyn-1-ol, title compound was obtained as described for the example 248.

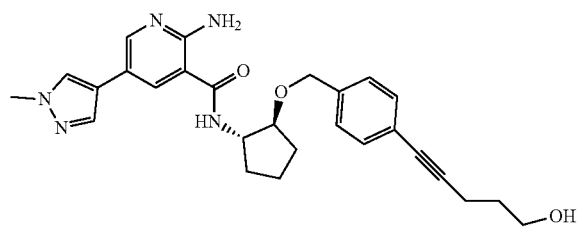 [SMILES: Cn1cc(-c2cnc(N)c(C(=O)N[C@H]3CCC[C@@H]3OCc3ccc(C#CCCCO)cc3)c2)cn1]

¹H NMR (600 MHz, CD₃OD) δ ppm 1.62 (br dd, J=12.91, 7.04 Hz, 1H) 1.69-1.78 (m, 3H) 1.78-1.86 (m, 2H) 2.01 (br dd, J=12.91, 7.63 Hz, 1H) 2.16 (br d, J=5.87 Hz, 1H) 2.45 (t, J=7.04 Hz, 2H) 3.66 (t, J=6.46 Hz, 2H) 3.88-4.00 (m, 4H) 4.31-4.41 (m, 1H) 4.51-4.65 (m, 2H) 7.26 (s, 4H) 7.87 (s, 1H) 8.01 (s, 1H) 8.23 (d, J=1.76 Hz, 1H) 8.51 (d, J=2.35 Hz, 1H);

MS (ESI, m/z): 474.2 [M+H]⁺

Example 251. 2-amino-N-((1S,2S)-2-((4-(6-hydroxyhex-1-yn-1-yl)benzyl)oxy)-cyclopentyl)-5-(1-methyl-1H-pyrazol-4-yl)nicotinamide Using 5-hexyn-1-ol, title compound was obtained as described for the example 248.

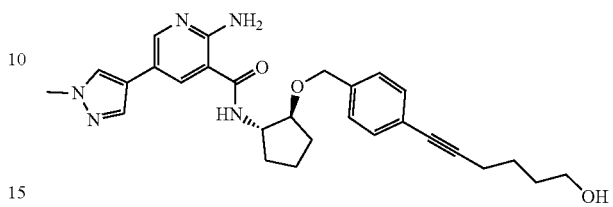

¹H NMR (600 MHz, CD₃OD) δ ppm 0.00-0.00 (m, 1H) 1.54-1.69 (m, 8H) 1.72-1.78 (m, 1H) 1.78-1.86 (m, 3H) 1.91 (br d, J=7.63 Hz, 1H) 1.97-2.05 (m, 1H) 2.12-2.20 (m, 1H) 2.24-2.30 (m, 2H) 2.32 (br d, J=3.52 Hz, 1H) 2.40 (t, J=7.04 Hz, 1H) 2.45 (t, J=6.75 Hz, 1H) 2.43-2.43 (m, 1H) 3.55 (t, J=6.46 Hz, 2H) 3.56-3.60 (m, 1H) 3.94 (d, J=1.17 Hz, 3H) 4.35-4.41 (m, 2H) 4.43 (t, J=6.46 Hz, 1H) 4.54-4.65 (m, 2H) 4.68-4.68 (m, 1H) 4.69-4.69 (m, 1H) 7.26 (d, J=7.04 Hz, 3H) 7.87 (s, 1H) 8.01 (s, 1H) 8.19-8.26 (m, 1H) 8.48-8.53 (m, 1H);

MS (ESI, m/z): 488.3 [M+H]⁺

Example 252. 2-amino-5-(1-methyl-1H-pyrazol-4-yl)-N-((1S,2S)-2-((4-(4-(4-methylpiperazin-1-yl)but-1-yn-1-yl)benzyl)oxy)cyclopentyl)nicotinamide Scheme for the Preparation of the Compound of Example 252

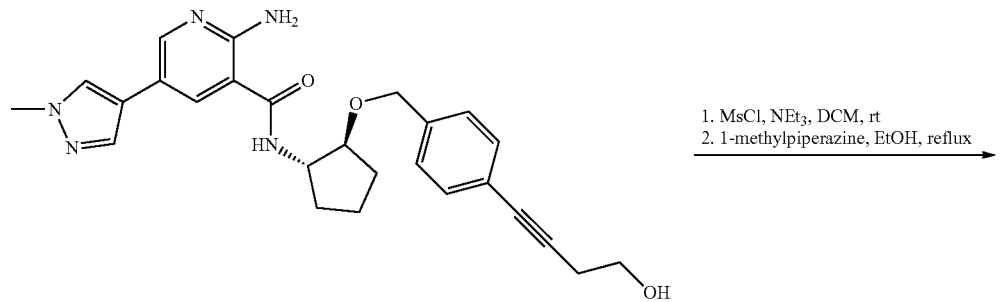

1. MsCl, NEt₃, DCM, rt
2. 1-methylpiperazine, EtOH, reflux

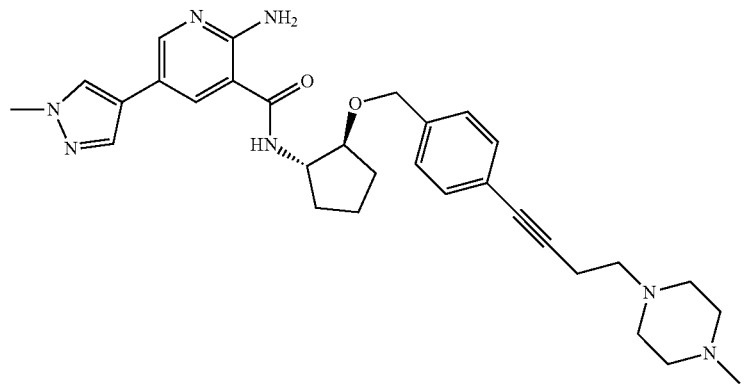

To a mixture of compound 249 (30 mg, 0.07 mmol) and triethylamine (27 µL, 0.2 mmol) in DCM (0.3 mL) was added methanesulfonyl chloride (12 µL, 0.16 mmol). The mixture was stirred at room temperature for 2 hrs. After completion of conversion, the volatile was removed under reduced pressure. The crude residue was diluted with EtOH (0.3 mL) and 1-methylpiperazine (16 µL, 0.13 mmol) was added. The mixture was refluxed for 2 hrs. After cooling, the crude residue was purified by preparative HPLC to afford 20 mg of the title compound.

$^1$H NMR (600 MHz, CD$_3$OD) δ ppm 1.63 (br dd, J=13.21, 6.75 Hz, 1H) 1.75 (br d, J=5.28 Hz, 1H) 1.80-1.84 (m, 2H) 1.98-2.02 (m, 1H) 2.16 (br dd, J=13.79, 6.75 Hz, 1H) 2.78 (brs, 2H) 2.89-2.93 (m, 3H) 3.44 (brs, 4H) 3.55 (brs, 2H) 3.94 (s, 3H) 3.95-3.99 (m, 1H) 4.38 (br dd, J=11.15, 7.04 Hz, 1H) 4.60 (s, 2H) 7.26-7.35 (m, 4H) 7.88 (s, 1H) 8.02 (s, 1H) 8.23 (d, J=2.35 Hz, 1H) 8.55 (d, J=1.76 Hz, 1H);

MS (ESI, m/z): 542.5 [M+H]$^+$

Example 253. 2-amino-N-((1S,2S)-2-(benzyloxy) cyclopentyl)-5-(4-((4-methylpiperazin-1-yl)methyl) phenyl)nicotinamide Scheme for the Preparation of the Compound of Example 253:

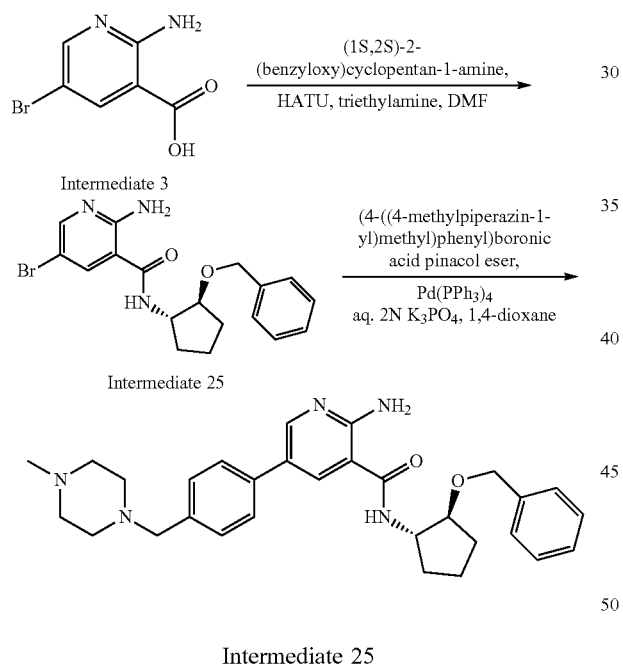

Intermediate 25

To a mixture of intermediate 3 (300 mg, 1.38 mmol) and triethylamine (168 mg, 1.66 mmol) in 7 ml of DMF was added HATU (524 mg, 1.66 mmol) followed by (1S,2S)-2-(benzyloxy)cyclopentan-1-amine (263 mg, 1.38 mmol). The mixture was stirred at room temperature for 1 hr and then saturated sodium bicarbonate solution was added. The mixture was extracted with EtOAc, washed with brine, dried over MgSO$_4$, and concentrated in vacuo. The crude product was purified through silicagel column chromatography to give 326 mg of off-white solid.

$^1$H NMR (400 MHz, CDCl$_3$) δ ppm 1.47 (dt, J=13.99, 6.90 Hz, 1H) 1.72-1.82 (m, 2H) 1.83-1.92 (m, 1H) 1.92-2.01 (m, 2H) 2.22-2.34 (m, 1H) 3.79-3.88 (m, 1H) 4.32 (dd, J=7.04, 4.70 Hz, 1H) 4.56-4.68 (m, 2H) 5.81 (br d, J=6.65 Hz, 1H) 6.35 (br s, 2H) 7.26-7.38 (m, 4H) 7.53 (d, J=2.35 Hz, 1H) 8.17 (d, J=2.35 Hz, 1H);

MS (ESI, m/z): 390.2/392.2 [M+H]$^+$

Example 253. 2-amino-N-((1S,2S)-2-(benzyloxy) cyclopentyl)-5-(4-((4-methylpiperazin-1-yl)methyl) phenyl)nicotinamide To a mixture of intermediate 25 (40 mg, 0.1 mmol) and (4-((4-methylpiperazin-1-yl)methyl)phenyl)boronic acid pinacol ester (51 mg, 0.16 mmol) in 1 ml of 1,4-dioxane was added 0.15 ml of aq. 2N K$_3$PO$_4$ followed by Pd(PPh$_3$)$_4$ (8 mg, 0.007 mmol). The reaction mixture was heated at 100° C. for 3 hrs, cooled to room temperature, and extracted with EtOAc, dried over anhydrous MgSO$_4$ and concentrated under vacuum. The crude residue was purified by preparative HPLC to afford 23 mg of the title compound.

$^1$H NMR (400 MHz, METHANOL-d$_4$) δ ppm 1.57 (br dd, J=13.30, 7.04 Hz, 1H) 1.66-1.87 (m, 3H) 1.97 (dt, J=13.01, 6.60 Hz, 1H) 2.13 (br dd, J=13.11, 6.85 Hz, 1H) 2.95 (s, 3H) 3.44-3.62 (m, 4H) 3.87-3.97 (m, 1H) 4.17 (s, 2H) 4.31-4.39 (m, 1H) 4.60 (s, 2H) 6.25 (d, J=9.00 Hz, 1H) 7.21-7.35 (m, 5H) 7.43 (d, J=8.22 Hz, 2H) 7.58 (d, J=8.61 Hz, 2H) 8.08 (d, J=9.00 Hz, 1H);

MS (ESI, m/z): 500.3 [M+H]$^+$

Example 254. 2-amino-N-((1S,2S)-2-(benzyloxy) cyclopentyl)-5-(1-(piperidin-4-yl)-1H-pyrazol-4-yl) nicotinamide Using (1-(piperidin-4-yl)-1H-pyrazol-4-yl)boronic acid pinacol ester, the title compound was obtained as described for the example 201.

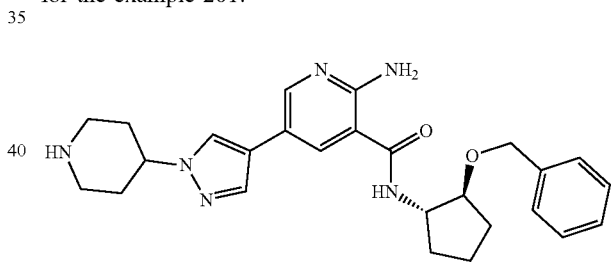

MS (ESI, m/z): 461.3 [M+H]$^+$

Example 255. 2-amino-N-((1S,2S)-2-(benzyloxy) cyclopentyl)-5-(1-(1-methylpiperidin-4-yl)-1H-pyrazol-4-yl)nicotinamide Using (1-(1-methylpiperidin-4-yl)-1H-pyrazol-4-yl)boronic acid pinacol ester, the title compound was obtained as described for the example 253.

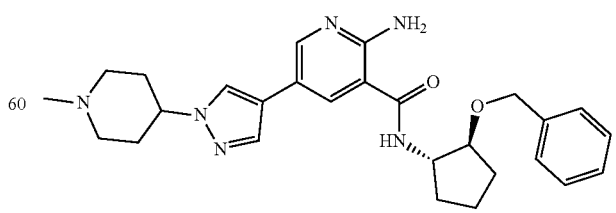

MS (ESI, m/z): 475.3 [M+H]$^+$

Example 256. 2-amino-N-((1S,2S)-2-(benzyloxy) cyclopentyl)-5-(1-(1-ethylpiperidin-4-yl)-1H-pyrazol-4-yl)nicotinamide Using (1-(1-ethylpiperidin-4-yl)-1H-pyrazol-4-yl)boronic acid pinacol ester, the title compound was obtained as described for the example 253.

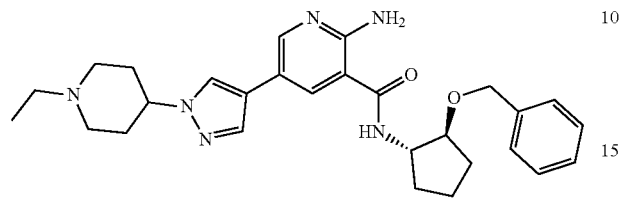

MS (ESI, m/z): 489.3 [M+H]+

Example 257. 2-amino-N-((1S,2S)-2-(benzyloxy) cyclopentyl)-5-(1-(1-isopropylpiperidin-4-yl)-1H-pyrazol-4-yl)nicotinamide Using (1-(1-isopropylpiperidin-4-yl)-1H-pyrazol-4-yl) boronic acid pinacol ester, the title compound was obtained as described for the example 253.

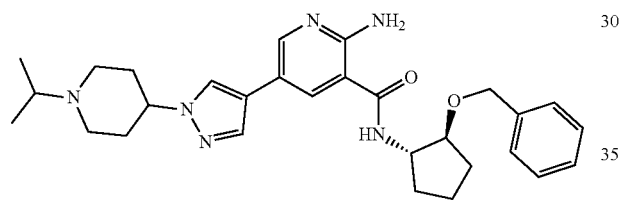

MS (ESI, m/z): 503.3 [M+H]+

Example 258. 2-amino-N-((1S,2S)-2-(benzyloxy) cyclopentyl)-5-(1-(1-(pyrrolidin-3-ylmethyl)piperidin-4-yl)-1H-pyrazol-4-yl)nicotinamide Using (1-(1-(pyrrolidin-3-ylmethyl)piperidin-4-yl)-1H-pyrazol-4-yl)boronic acid pinacol ester, the title compound was obtained as described for the example 253.

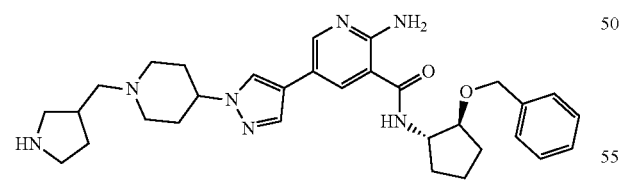

MS (ESI, m/z): 544.3 [M+H]+

Example 259. 2-amino-N-((1R,2R)-2-(benzyloxy) cyclopentyl)-5-(1-(piperidin-4-yl)-1H-pyrazol-4-yl) nicotinamide Using (1R,2R)-2-(benzyloxy)cyclopentan-1-amine and (1-(piperidin-4-yl)-1H-pyrazol-4-yl)boronic acid pinacol ester, the title compound was obtained as described for the example 253.

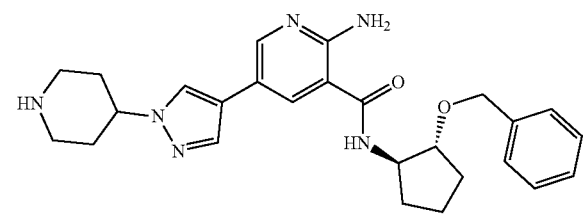 [SMILES: Nc1ncc(-c2cnn(C3CCNCC3)c2)cc1C(=O)N[C@@H]1CCC[C@H]1OCc1ccccc1]

MS (ESI, m/z): 461.3 [M+H]+

Example 260. 2-amino-N-((1S,2S)-2-((3,4-dichlorobenzyl)oxy)cyclopentyl)-5-(1-(piperidin-4-yl)-1H-pyrazol-4-yl)nicotinamide Using (1S,2S)-2-((3,4-dichlorobenzyl)oxy)cyclopentan-1-amine and (1-(piperidin-4-yl)-1H-pyrazol-4-yl)boronic acid pinacol ester, the title compound was obtained as described for the example 253.

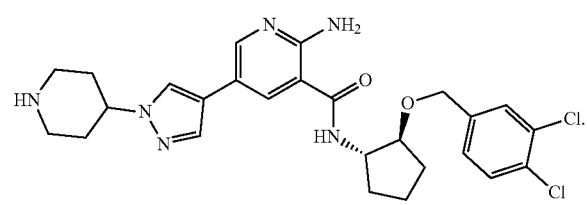 [SMILES: Nc1ncc(-c2cnn(C3CCNCC3)c2)cc1C(=O)N[C@H]1CCC[C@@H]1OCc1ccc(Cl)c(Cl)c1]

MS (ESI, m/z): 529.2 [M+H]+

Example 261. 2-amino-N-((1S,2S)-2-(benzyloxy) cyclopentyl)-5-(3-(hydroxymethyl)-1-methyl-1H-pyrazol-4-yl)nicotinamide Using (3-(hydroxymethyl)-1-methyl-1H-pyrazol-4-yl)boronic acid pinacol ester, the title compound was obtained as described for the example 253.

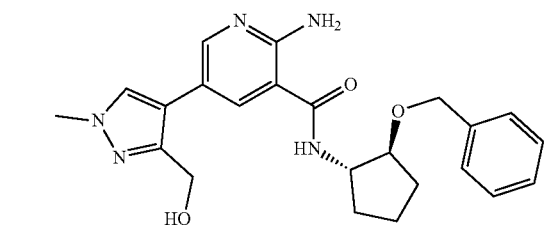 [SMILES: Cn1cc(-c2cnc(N)c(C(=O)N[C@H]3CCC[C@@H]3OCc3ccccc3)c2)c(CO)n1]

MS (ESI, m/z): 422.2 [M+H]+

Example 262. 2-amino-N-((1S,2S)-2-(benzyloxy) cyclopentyl)-5-(3-(((2-hydroxyethyl)amino)methyl)-1-methyl-1H-pyrazol-4-yl)nicotinamide Using (3-(((2-hydroxyethyl)amino)methyl)-1-methyl-1H-pyrazol-4-yl)boronic acid pinacol ester, the title compound was obtained as described for the example 253.

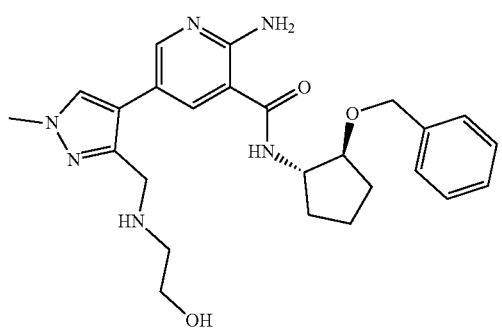 [SMILES: Cn1cc(-c2cnc(N)c(C(=O)N[C@H]3CCC[C@@H]3OCc3ccccc3)c2)c(CNCCO)n1]

MS (ESI, m/z): 465.3 [M+H]⁺

Example 263. 2-amino-N-((1S,2S)-2-(benzyloxy) cyclopentyl)-5-(3-((3-hydroxypiperidin-1-yl) methyl)-1-methyl-1H-pyrazol-4-yl)nicotinamide Using (3-((3-hydroxypiperidin-1-yl)methyl)-1-methyl-1H-pyrazol-4-yl)boronic acid pinacol ester, the title compound was obtained as described for the example 253.

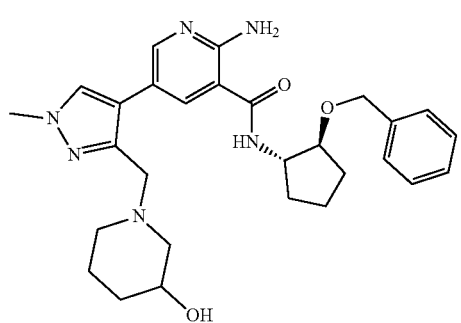 [SMILES: Cn1cc(-c2cnc(N)c(C(=O)N[C@H]3CCC[C@@H]3OCc3ccccc3)c2)c(CN2CCCC(O)C2)n1]

MS (ESI, m/z): 505.3 [M+H]⁺

Example 264. 2-amino-N-((1S,2S)-2-(benzyloxy) cyclopentyl)-5-(4-cyanophenyl)-nicotinamide Using (4-cyanophenyl)boronic acid, the title compound was obtained as described for the example 253

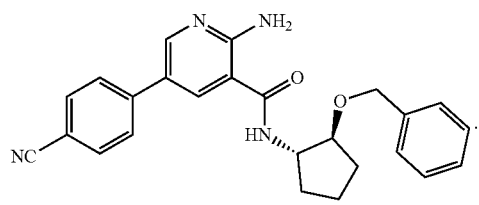 [SMILES: N#Cc1cccc(-c2cnc(N)c(C(=O)N[C@H]3CCC[C@@H]3OCc3ccccc3)c2)c1]

¹H NMR (400 MHz, CDCl₃) δ 1.59 (m, 2H) 1.85 (m, 4H) 2.10 (m, 2H) 2.24 (m, 1H) 4.17 (br d, J=7.04 Hz, 1H) 4.28 (br d, J=7.04 Hz, 1H) 4.43-4.54 (m, 1H) 4.56-4.67 (m, 2H) 7.13-7.19 (m, 1H) 7.13-7.19 (m, 1H) 7.13-7.19 (m, 2H) 7.19-7.24 (m, 2H) 7.35 (br d, J=7.43 Hz, 2H) 7.64 (m, J=8.22 Hz, 2H) 7.73 (m, J=8.22 Hz, 2H) 7.80 (s, 1H) 7.85-7.91 (m, 1H) 8.27 (s, 1H) 8.58 (br s, 2H) 11.76-11.97 (m, 2H);
MS (ESI, m/z): 413.2 [M+H]⁺

Example 265. 2-amino-N-((1S,2S)-2-(benzyloxy) cyclopentyl)-5-(3-cyanophenyl)-nicotinamide Using (3-cyanophenyl)boronic acid, the title compound was obtained as described for the example 253.

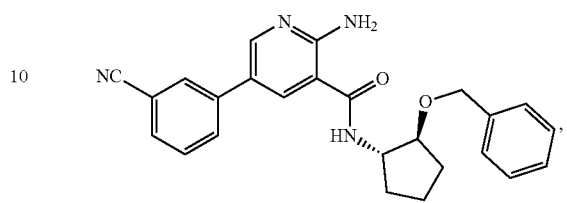

¹H NMR (400 MHz, CDCl₃) ☐☐ 1.54-1.70 (m, 2H) 1.70-1.95 (m, 4H) 2.07 (br s, 2H) 2.23 (br s, 2H) 4.08 (br d, J=5.87 Hz, 1H) 4.33 (br s, 1H) 4.61 (q, J=11.74 Hz, 2H) 7.14-7.20 (m, 1H) 7.20-7.29 (m, 2H) 7.29-7.38 (m, 2H) 7.53-7.63 (m, 1H) 7.70 (br d, J=7.43 Hz, 1H) 7.75 (br d, J=7.43 Hz, 1H) 7.87 (s, 1H) 7.91 (s, 1H) 8.26 (s, 1H) 8.87 (br s, 2H) 11.40-11.54 (m, 1H);
MS (ESI, m/z): 413.2 [M+H]⁺

Example 266. 2-amino-N-((1S,2S)-2-(benzyloxy) cyclopentyl)-5-(4-(cyanomethyl)phenyl)nicotinamide Using (4-(cyanomethyl)phenyl)boronic acid, the title compound was obtained as described for the example 253.

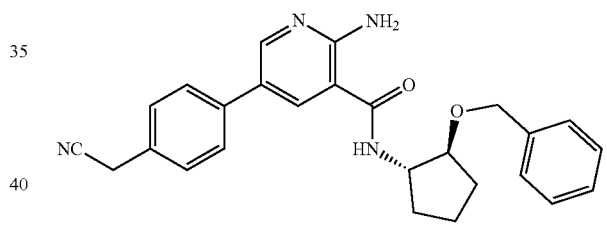

¹H NMR (400 MHz, CDCl₃) ☐☐ 1.54-1.64 (m, 1H) 1.70 (br s, 1H) 1.83 (br s, 2H) 1.97-2.05 (m, 2H) 3.11 (br s, 1H) 3.79 (s, 2H) 4.35 (br s, 1H) 4.64 (s, 2H) 7.14 (br s, 1H) 7.18-7.24 (m, 3H) 7.39 (br t, J=7.83 Hz, 2H) 7.55 (br d, J=7.83 Hz, 1H) 7.59 (s, 1H) 8.00 (br s, 1H) 8.34 (s, 1H) 8.55-8.67 (m, 1H);
MS (ESI, m/z): 427.2 [M+H]⁺

Example 267. 2-amino-N-((1S,2S)-2-(benzyloxy) cyclopentyl)-5-(4-phenoxyphenyl)nicotinamide Using (4-phenoxyphenyl)boronic acid, the title compound was obtained as described for the example 253.

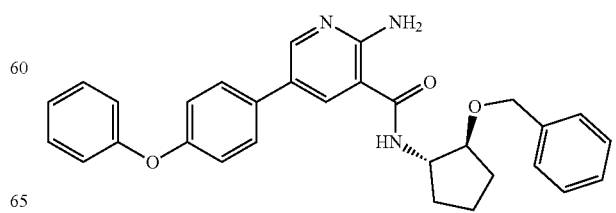

¹H NMR (400 MHz, CDCl₃) ☐ 1.23 (m, 2H) 1.56 (m, 2H) 1.75 (m, 4H) 2.07 (br s, 2H) 2.24 (br s, 2H) 4.12 (br d, J=5.87 Hz, 1H) 4.29 (br s, 1H) 4.56-4.66 (m, 2H) 7.04 (br t, J=6.85 Hz, 3H) 7.17 (br d, J=7.43 Hz, 1H) 7.22-7.26 (m, 4H) 7.30-7.39 (m, 3H) 7.39-7.44 (m, 2H) 7.50 (s, 1H) 7.74 (s, 1H) 8.18 (s, 1H) 8.45 (br s, 2H) 11.28 (br s, 1H);
MS (ESI m/z): 480.2 [M+H]⁺

Example 268. 2-amino-N-((1S,2S)-2-(benzyloxy)cyclopentyl)-5-(3-((1-methylpiperidin-4-yl)carbamoyl)phenyl)nicotinamide Using (3-((1-methylpiperidin-4-yl)carbamoyl)phenyl)boronic acid, the title compound was obtained as described for the example 253.

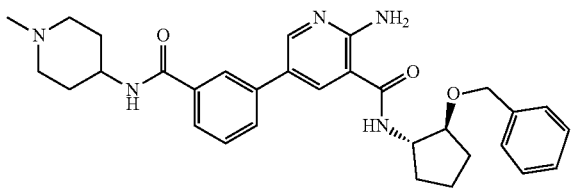 [SMILES: CN1CCC(NC(=O)c2cccc(-c3cnc(N)c(C(=O)N[C@H]4CCC[C@@H]4OCc4ccccc4)c3)c2)CC1]

MS (ESI m/z): 528.3 [M+H]⁺

Example 269. 6-amino-N-((1S,2S)-2-(benzyloxy)cyclopentyl)-6'-(hydroxymethyl)-[3,3'-bipyridine]-5-carboxamide Using (6-(hydroxymethyl)pyridin-3-yl)boronic acid, the title compound was obtained as described for the example 253.

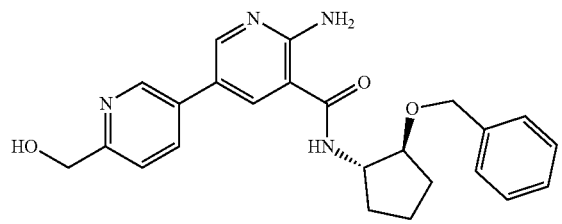 [SMILES: Nc1ncc(-c2ccc(CO)nc2)cc1C(=O)N[C@H]1CCC[C@@H]1OCc1ccccc1]

MS (ESI m/z): 420.2 [M+H]⁺

Example 270. 2-amino-N-((1S,2S)-2-((3-methylbenzyl)oxy)cyclopentyl)-5-(4-((4-methylpiperazin-1-yl)methyl)phenyl)nicotinamide Using (1S,2S)-2-((3-methylbenzyl)oxy)cyclopentan-1-amine and (4-((4-methyl-piperazin-1-yl)methyl)phenyl)boronic acid pinacol ester, the title compound was obtained as described for the example 253.

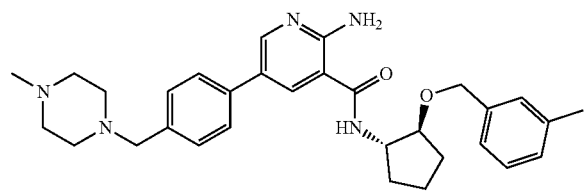

MS (ESI m/z): 514.3 [M+H]⁺

Example 271. 2-amino-N-((1S,2S)-2-((3-methylbenzyl)oxy)cyclopentyl)-5-(3-(4-methylpiperazine-1-carbonyl)phenyl)nicotinamide Using (1S,2S)-2-((3-methylbenzyl)oxy)cyclopentan-1-amine and (4-methylpiperazin-1-yl)(3-(4,4,5,5-tetramethyl-1,3,2-dioxaborolan-2-yl)phenyl)methanone, the title compound was obtained as described for the example 253.

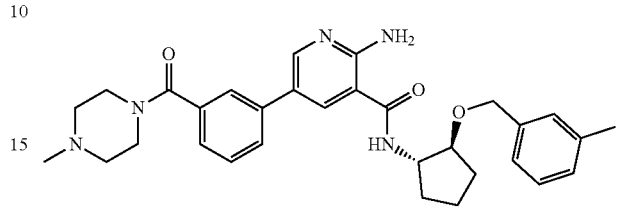

MS (ESI, m/z): 528.3 [M+H]⁺

Example 272. 2-amino-N-((1S,2S)-2-((3-methylbenzyl)oxy)cyclopentyl)-5-(3-(4-(pyrrolidin-1-yl)piperidine-1-carbonyl)phenyl)nicotinamide Using (1S,2S)-2-((3-methylbenzyl)oxy)cyclopentan-1-amine and (4-(pyrrolidin-1-yl)piperidin-1-yl)(3-(4,4,5,5-tetramethyl-1,3,2-dioxaborolan-2-yl)phenyl)methanone, the title compound was obtained as described for the example 253.

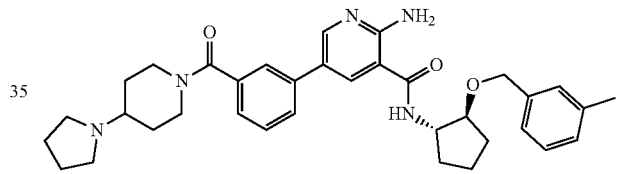

MS (ESI, m/z): 582.3 [M+H]⁺

Example 273. 2-amino-N-((1S,2S)-2-((3-methylbenzyl)oxy)cyclopentyl)-5-(3-((4-methylpiperazin-1-yl)methyl)phenyl)nicotinamide Using (1S,2S)-2-((3-methylbenzyl)oxy)cyclopentan-1-amine and 1-methyl-4-(3-(4,4,5,5-tetramethyl-1,3,2-dioxaborolan-2-yl)benzyl)piperazine, the title compound was obtained as described for the example 253.

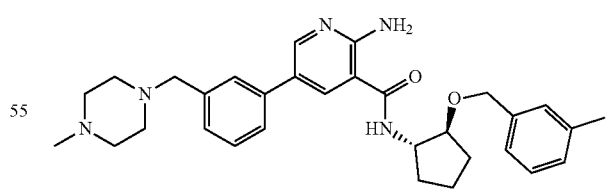

MS (ESI, m/z): 514.3 [M+H]⁺

Example 274. 2-amino-5-(3-fluoro-4-((4-methylpiperazin-1-yl)methyl)phenyl)-N-((1S,2S)-2-((3-methylbenzyl)oxy)cyclopentyl)nicotinamide Using (1S,2S)-2-((3-methylbenzyl)oxy)cyclopentan-1-amine and 1-(2-fluoro-4-(4,4,5,5-tetramethyl-1,3,2-dioxaborolan-2-yl)benzyl)-4-methylpiperazine, the title compound was obtained as described for the example 253.

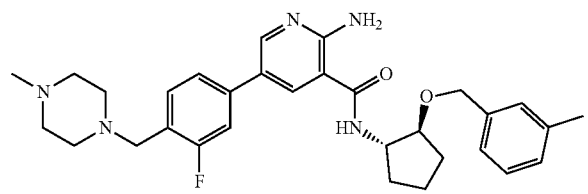

MS (ESI, m/z): 532.3 [M+H]+

Example 275. 2-amino-N-((1S,2S)-2-((3-methylbenzyl)oxy)cyclopentyl)-5-(4-((4-(pyrrolidin-1-yl)piperidin-1-yl)methyl)phenyl)nicotinamide Using (1S,2S)-2-((3-methylbenzyl)oxy)cyclopentan-1-amine and 4-(pyrrolidin-1-yl)-1-(4-(4,4,5,5-tetramethyl-1,3,2-dioxaborolan-2-yl)benzyl)piperidine, the title compound was obtained as described for the example 253.

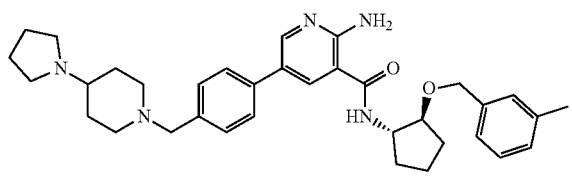 [SMILES: Cc1cccc(CO[C@H]2CCC[C@@H]2NC(=O)c2cc(-c3ccc(CN4CCC(N5CCCC5)CC4)cc3)cnc2N)c1]

MS (ESI, m/z): 568.4 [M+H]+

Example 276. 2-amino-N-((1S,2S)-2-((3-methylbenzyl)oxy)cyclopentyl)-5-(4-(4-methylpiperazine-1-carbonyl)phenyl)nicotinamide Using (1S,2S)-2-((3-methylbenzyl)oxy)cyclopentan-1-amine and (4-methylpiperazin-1-yl)(4-(4,4,5,5-tetramethyl-1,3,2-dioxaborolan-2-yl)phenyl)methanone, the title compound was obtained as described for the example 253.

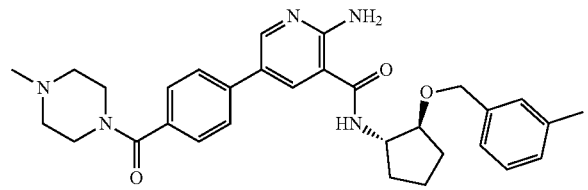

MS (ESI, m/z): 528.3 [M+H]+

Example 277. 2-amino-N-((1S,2S)-2-((3-methylbenzyl)oxy)cyclopentyl)-5-(4-(4-(pyrrolidin-1-yl)piperidine-1-carbonyl)phenyl)nicotinamide Using (1S,2S)-2-((3-methylbenzyl)oxy)cyclopentan-1-amine and (4-(pyrrolidin-1-yl)piperidin-1-yl)(4-(4,4,5,5-tetramethyl-1,3,2-dioxaborolan-2-yl)phenyl)methanone, the title compound was obtained as described for the example 253.

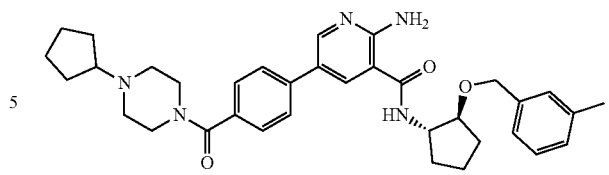

MS (ESI, m/z): 582.3 [M+H]+

Example 278. 2-amino-N-((1S,2S)-2-((3-methylbenzyl)oxy)cyclopentyl)-5-(4-(2-((1-methylpiperidin-4-yl)amino)-2-oxoethyl)phenyl)nicotinamide Using (1S,2S)-2-((3-methylbenzyl)oxy)cyclopentan-1-amine and N-(1-methylpiperidin-4-yl)-2-(4-(4,4,5,5-tetramethyl-1,3,2-dioxaborolan-2-yl)phenyl)acetamide, the title compound was obtained as described for the example 253.

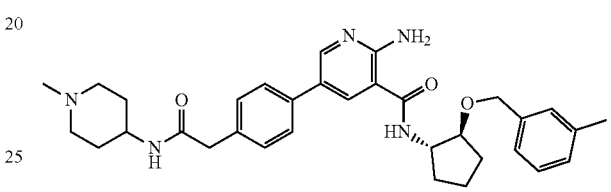

MS (ESI, m/z): 556.3 [M+H]+

Example 279. 2-amino-N-((1S,2S)-2-((3-methylbenzyl)oxy)cyclopentyl)-5-(4-(2-(4-methylpiperazin-1-yl)acetyl)phenyl)nicotinamide Using (1S,2S)-2-((3-methylbenzyl)oxy)cyclopentan-1-amine and 2-(4-methylpiperazin-1-yl)-1-(4-(4,4,5,5-tetramethyl-1,3,2-dioxaborolan-2-yl)phenyl)ethan-1-one, the title compound was obtained as described for the example 253.

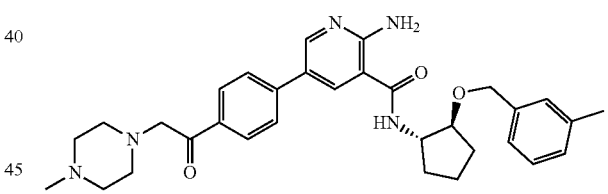

MS (ESI, m/z): 542.3 [M+H]+

Example 280. 2-amino-5-(3-fluoro-4-((4-(pyrrolidin-1-yl)piperidin-1-yl)-methyl)phenyl)-N-((1S,2S)-2-((3-methylbenzyl)oxy)cyclopentyl)nicotinamide (1S,2S)-2-((3-methylbenzyl)oxy)cyclopentan-1-amine and 1-(2-fluoro-4-(4,4,5,5-tetramethyl-1,3,2-dioxaborolan-2-yl)benzyl)-4-(pyrrolidin-1-yl)piperidine, the title compound was obtained as described for the example 253.

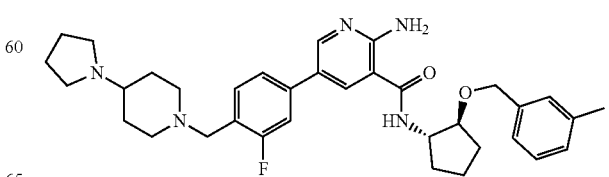

MS (ESI, m/z): 586.4 [M+H]+

Example 281. 2-amino-N-((1S,2S)-2-((3-methylbenzyl)oxy)cyclopentyl)-5-(4-(4-(4-methylpiperazin-1-yl)piperidine-1-carbonyl)phenyl)nicotinamide Using (1S,2S)-2-((3-methylbenzyl)oxy)cyclopentan-1-amine and (4-(4-methyl-piperazin-1-yl)piperidin-1-yl)(4-(4,4,5,5-tetramethyl-1,3,2-dioxaborolan-2-yl)phenyl)-methanone, the title compound was obtained as described for the example 253.

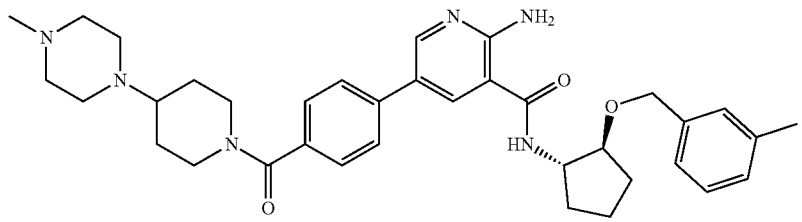

MS (ESI, m/z): 611.4 [M+H]$^+$

Example 282. 2-amino-N-((1S,2S)-2-((3-methylbenzyl)oxy)cyclopentyl)-5-(4-(piperazin-1-ylmethyl)phenyl)nicotinamide Using (1S,2S)-2-((3-methylbenzyl)oxy)cyclopentan-1-amine and 1-(4-(4,4,5,5-tetramethyl-1,3,2-dioxaborolan-2-yl)benzyl)piperazine, the title compound was obtained as described for the example 253.

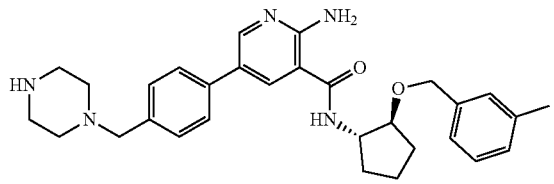 [SMILES: Cc1cccc(CO[C@H]2CCC[C@@H]2NC(=O)c2cc(-c3ccc(CN4CCNCC4)cc3)cnc2N)c1]

MS (ESI, m/z): 500.3 [M+H]$^+$

Example 283. 2-amino-N-((1S,2S)-2-((4-methylbenzyl)oxy)cyclopentyl)-5-(4-(4-methylpiperazine-1-carbonyl)phenyl)nicotinamide Using (1S,2S)-2-((4-methylbenzyl)oxy)cyclopentan-1-amine and (4-methylpiperazin-1-yl)(4-(4,4,5,5-tetramethyl-1,3,2-dioxaborolan-2-yl)phenyl)methanone, the title compound was obtained as described for the example 253.

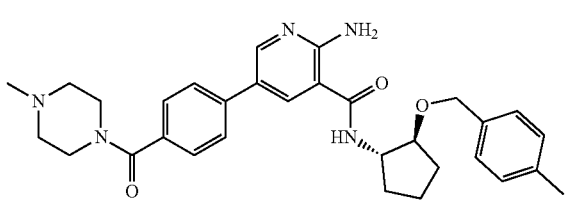

MS (ESI, m/z): 528.3 [M+H]$^+$

Example 284. 2-amino-N-((1S,2S)-2-((4-methylbenzyl)oxy)cyclopentyl)-5-(4-(4-(pyrrolidin-1-yl)piperidine-1-carbonyl)phenyl)nicotinamide Using (1S,2S)-2-((4-methylbenzyl)oxy)cyclopentan-1-amine and (4-(pyrrolidin-1-yl)piperidin-1-yl)(4-(4,4,5,5-tetramethyl-1,3,2-dioxaborolan-2-yl)phenyl)methanone, the title compound was obtained as described for the example 253.

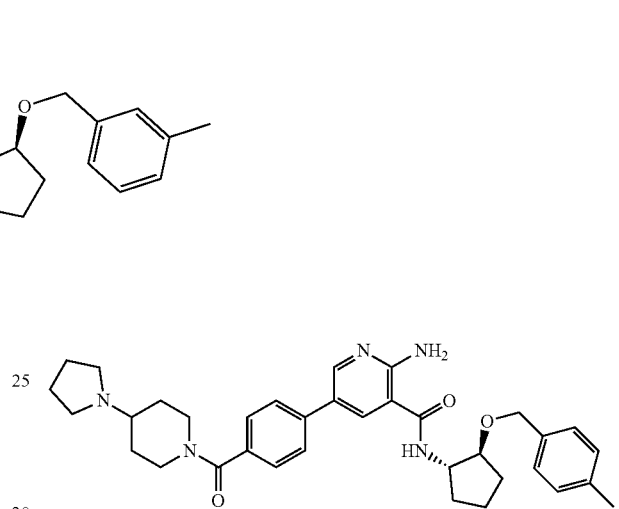

MS (ESI, m/z): 582.3 [M+H]$^+$

Example 285. 2-amino-5-(1,5-dimethyl-1H-pyrazol-4-yl)-N-((1S,2S)-2-((3,4-dimethylbenzyl)oxy)cyclopentyl)nicotinamide Using (1S,2S)-2-((3,4-dimethylbenzyl)oxy)cyclopentan-1-amine and (1,5-dimethyl-1H-pyrazol-4-yl)boronic acid pinacol ester, the title compound was obtained as described for the example 253.

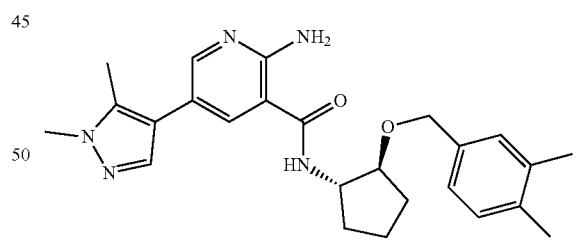

MS (ESI, m/z): 434.3 [M+H]$^+$

Example 286. 2-amino-5-(1,3-dimethyl-1H-pyrazol-4-yl)-N-((1S,2S)-2-((3,4-dimethylbenzyl)oxy)cyclopentyl)nicotinamide Using (1S,2S)-2-((3,4-dimethylbenzyl)oxy)cyclopentan-1-amine and (1,3-dimethyl-1H-pyrazol-4-yl)boronic acid pinacol ester, the title compound was obtained as described for the example 253.

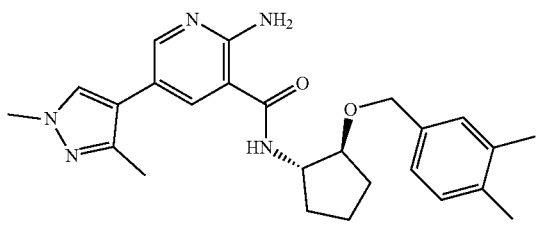

MS (ESI, m/z): 434.3 [M+H]+

Example 287. 2-amino-N-((1S,2S)-2-((3,4-dimethylbenzyl)oxy)cyclopentyl)-5-(2-(2-hydroxypropan-2-yl)-4-methylthiazol-5-yl)nicotinamide Using (1S,2S)-2-((3,4-dimethylbenzyl)oxy)cyclopentan-1-amine and (2-(2-hydroxypropan-2-yl)-4-methylthiazol-5-yl)boronic acid pinacol ester, the title compound was obtained as described for the example 253.

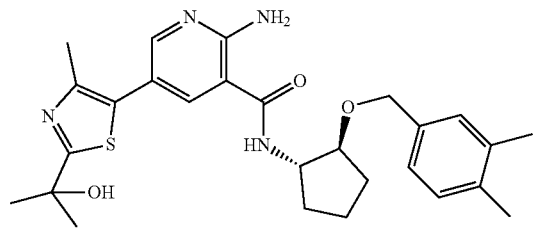 [SMILES: Cc1ccc(CO[C@H]2CCC[C@@H]2NC(=O)c2cc(-c3sc(C(C)(C)O)nc3C)cnc2N)cc1C]

MS (ESI, m/z): 495.2 [M+H]+

Example 288. 2-amino-N-((1S,2S)-2-((3,4-dimethylbenzyl)oxy)cyclopentyl)-5-(2-(3-hydroxytetrahydrofuran-3-yl)-4-methylthiazol-5-yl)nicotinamide Using (1S,2S)-2-((3,4-dimethylbenzyl)oxy)cyclopentan-1-amine and (2-(3-hydroxytetrahydrofuran-3-yl)-4-methylthiazol-5-yl)boronic acid pinacol ester, the title compound was obtained as described for the example 253.

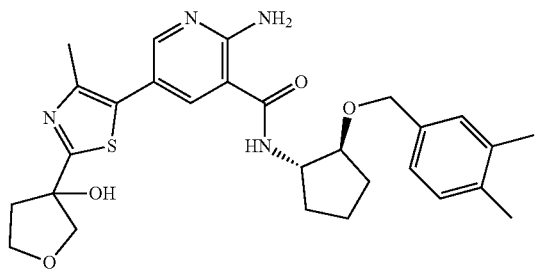 [SMILES: Cc1ccc(CO[C@H]2CCC[C@@H]2NC(=O)c2cc(-c3sc(C4(O)CCOC4)nc3C)cnc2N)cc1C]

MS (ESI, m/z): 523.2 [M+H]+

Example 289. 2-amino-N-((1S,2S)-2-((3,4-dimethylbenzyl)oxy)cyclopentyl)-5-(4-((4-methylpiperazin-1-yl)methyl)phenyl)nicotinamide Using (1S,2S)-2-((3,4-dimethylbenzyl)oxy)cyclopentan-1-amine and (4-((4-methyl-piperazin-1-yl)methyl)phenyl)boronic acid pinacol ester, the title compound was obtained as described for the example 253.

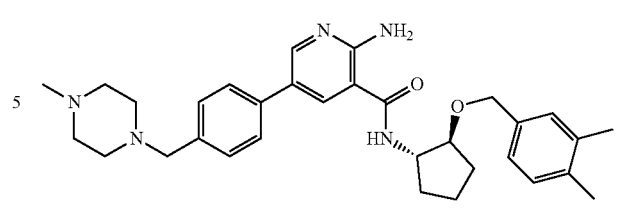

MS (ESI, m/z): 528.3 [M+H]+

Example 290. 2-amino-N-((1S,2S)-2-((3,4-dimethylbenzyl)oxy)cyclopentyl)-5-(4-(2-(4-methylpiperazin-1-yl)-2-oxoethyl)phenyl)nicotinamide Using (1S,2S)-2-((3,4-dimethylbenzyl)oxy)cyclopentan-1-amine and 1-(4-methyl-piperazin-1-yl)-2-(4-(4,4,5,5-tetramethyl-1,3,2-dioxaborolan-2-yl)phenyl)ethan-1-one, the title compound was obtained as described for the example 253.

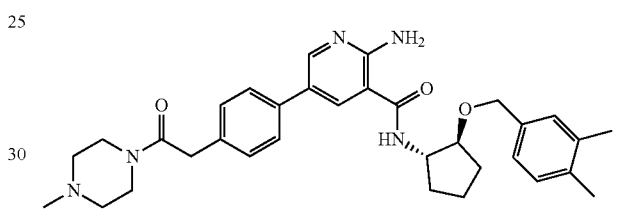

MS (ESI, m/z): 556.3 [M+H]+

Example 291. 2-amino-N-((1S,2S)-2-((3,4-dimethylbenzyl)oxy)cyclopentyl)-5-(4-(morpholinomethyl)phenyl)nicotinamide Using (1S,2S)-2-((3,4-dimethylbenzyl)oxy)cyclopentan-1-amine and 4-(4-(4,4,5,5-tetramethyl-1,3,2-dioxaborolan-2-yl)benzyl)morpholine, the title compound was obtained as described for the example 253.

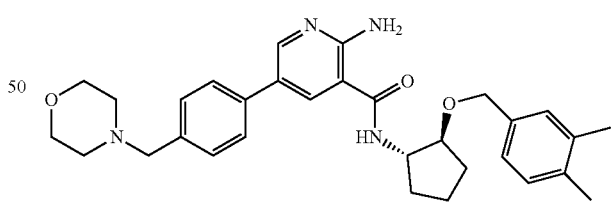

MS (ESI, m/z): 515.3 [M+H]+

Example 292. 2-amino-5-(4-((dimethylamino)methyl)phenyl)-N-((1S,2S)-2-((3,4-dimethylbenzyl)oxy)cyclopentyl)nicotinamide Using (1S,2S)-2-((3,4-dimethylbenzyl)oxy)cyclopentan-1-amine and (4-((dimethyl-amino)methyl)phenyl)boronic acid, the title compound was obtained as described for the example 253.

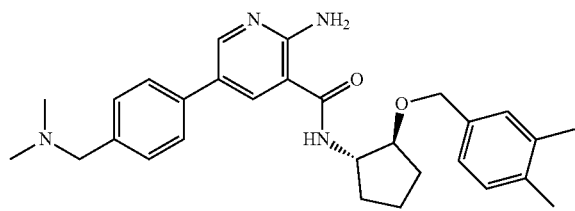

MS (ESI, m/z): 473.3 [M+H]+

Example 293. 2-amino-N-((1S,2S)-2-((3,4-dimethylbenzyl)oxy)cyclopentyl)-5-(4-((4-(2-hydroxyethyl)piperazin-1-yl)methyl)phenyl)nicotinamide Using (1S,2S)-2-((3,4-dimethylbenzyl)oxy)cyclopentan-1-amine and 2-(4-(4-(4,4,5,5-tetramethyl-1,3,2-dioxaborolan-2-yl)benzyl)piperazin-1-yl)ethan-1-ol, the title compound was obtained as described for the example 253.

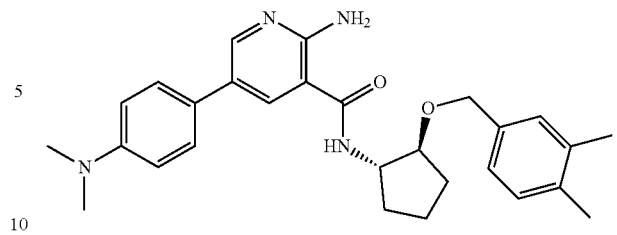

MS (ESI, m/z): 459.3 [M+H]+

Example 296. 2-amino-N-((1S,2S)-2-((3,4-dimethylbenzyl)oxy)cyclopentyl)-5-(3-hydroxyphenyl)nicotinamide Using (1S,2S)-2-((3,4-dimethylbenzyl)oxy)cyclopentan-1-amine and (3-hydroxy-phenyl)boronic acid, the title compound was obtained as described for the example 253.

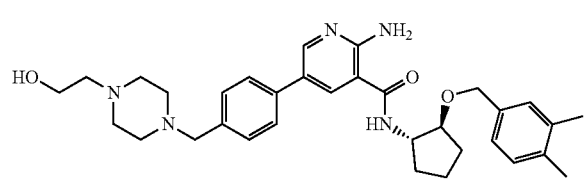 [SMILES: Cc1ccc(CO[C@H]2CCC[C@@H]2NC(=O)c2cc(-c3ccc(CN4CCN(CCO)CC4)cc3)cnc2N)cc1C]

MS (ESI, m/z): 558.3 [M+H]+

Example 294. 6-amino-N-((1S,2S)-2-((3,4-dimethylbenzyl)oxy)cyclopentyl)-2'-methoxy-[3,3'-bipyridine]-5-carboxamide Using (1S,2S)-2-((3,4-dimethylbenzyl)oxy)cyclopentan-1-amine and (2-methoxy-pyridin-3-yl)boronic acid, the title compound was obtained as described for the example 253.

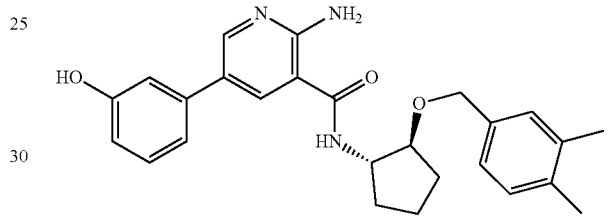

MS (ESI, m/z): 432.2 [M+H]+

Example 297. 2-amino-5-(3-aminophenyl)-N-((1S,2S)-2-((3,4-dimethylbenzyl)-oxy)cyclopentyl)nicotinamide Using (1S,2S)-2-((3,4-dimethylbenzyl)oxy)cyclopentan-1-amine and (3-amino-phenyl)boronic acid, the title compound was obtained as described for the example 253.

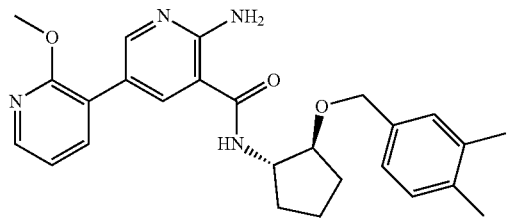 [SMILES: COc1ncccc1-c1cnc(N)c(C(=O)N[C@H]2CCC[C@@H]2OCc2ccc(C)c(C)c2)c1]

MS (ESI, m/z): 447.2 [M+H]+

Example 295. 2-amino-5-(4-(dimethylamino)phenyl)-N-((1S,2S)-2-((3,4-dimethylbenzyl)oxy)cyclopentyl)nicotinamide Using (1S,2S)-2-((3,4-dimethylbenzyl)oxy)cyclopentan-1-amine and (4-(dimethyl-amino)phenyl)boronic acid, the title compound was obtained as described for the example 253.

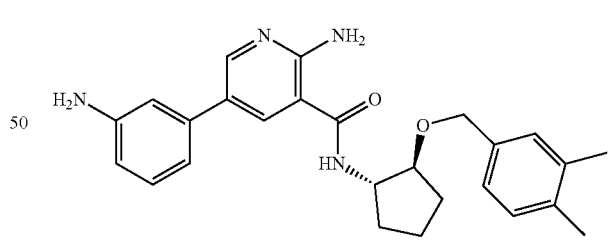

MS (ESI, m/z): 431.2 [M+H]+

Example 298. 2-amino-N-((1S,2S)-2-((3,4-dimethylbenzyl)oxy)cyclopentyl)-5-(3-(methylsulfonamido)phenyl)nicotinamide Using (1S,2S)-2-((3,4-dimethylbenzyl)oxy)cyclopentan-1-amine and (3-(methyl-sulfonamido)phenyl)boronic acid, the title compound was obtained as described for the example 253.

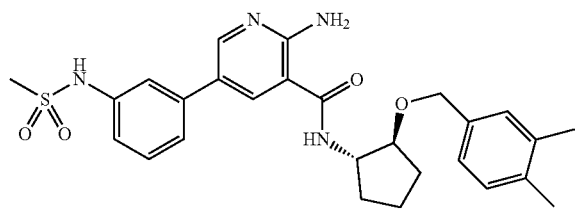

MS (ESI, m/z): 509.2 [M+H]+

Example 299. 2-amino-N-((1S,2S)-2-((3,4-dimethylbenzyl)oxy)cyclopentyl)-5-(3-(hydroxymethyl)phenyl)nicotinamide Using (1S,2S)-2-((3,4-dimethylbenzyl)oxy)cyclopentan-1-amine and (3-(hydroxy-methyl)phenyl)boronic acid, the title compound was obtained as described for the example 253.

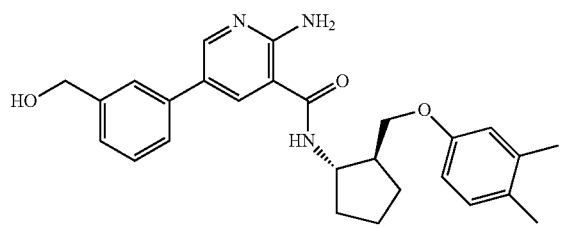 [SMILES: Cc1ccc(OC[C@H]2CCC[C@@H]2NC(=O)c2cc(-c3cccc(CO)c3)cnc2N)cc1C]

MS (ESI m/z): 446.2 [M+H]+

Example 300. 2-amino-5-(3-(aminomethyl)phenyl)-N-((1S,2S)-2-((3,4-dimethylbenzyl)oxy)cyclopentyl)nicotinamide Using (1S,2S)-2-((3,4-dimethylbenzyl)oxy)cyclopentan-1-amine and (3-(amino-methyl)phenyl)boronic acid, the title compound was obtained as described for the example 253.

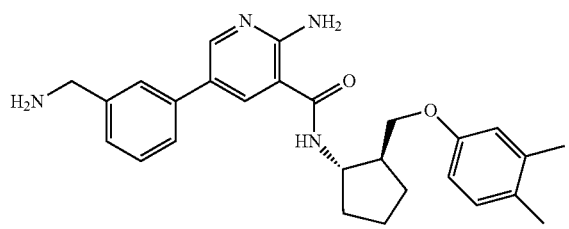 [SMILES: Cc1ccc(OC[C@H]2CCC[C@@H]2NC(=O)c2cc(-c3cccc(CN)c3)cnc2N)cc1C]

MS (ESI m/z): 445.3 [M+H]+

Example 301. 2-amino-N-((1S,2S)-2-((3,4-dimethylbenzyl)oxy)cyclopentyl)-5-(3-(3-hydroxypropyl)phenyl)nicotinamide Using (1S,2S)-2-((3,4-dimethylbenzyl)oxy)cyclopentan-1-amine and (3-(3-hydroxy-propyl)phenyl)boronic acid, the title compound was obtained as described for the example 253.

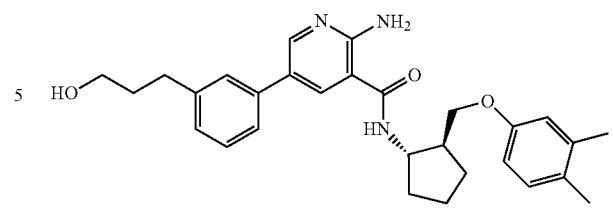

MS (ESI, m/z): 474.3 [M+H]+

Example 302. 2-amino-N-(1S,2S)-2-((3,4-dimethylbenzyl)oxy)cyclopentyl)-5-(3-((((1r,4S)-4-hydroxycyclohexyl)amino)methyl)phenyl)nicotinamide Using (1S,2S)-2-((3,4-dimethylbenzyl)oxy)cyclopentan-1-amine and (1r,4r)-4-((3-(4,4,5,5-tetramethyl-1,3,2-dioxaborolan-2-yl)benzyl)amino)cyclohexan-1-ol, the title compound was obtained as described for the example 253

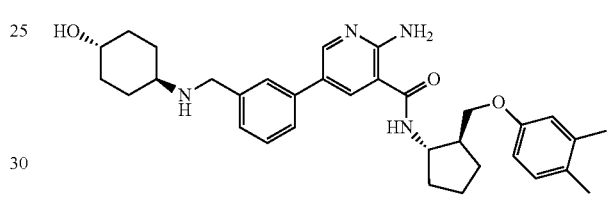

MS (ESI, m/z): 543.3 [M+H]+

Example 303. 2-amino-N-((1S,2S)-2-((3,4-dimethylbenzyl)oxy)cyclopentyl)-5-(3-(((1-methylpiperidin-4-yl)amino)methyl)phenyl)nicotinamide Using (1S,2S)-2-((3,4-dimethylbenzyl)oxy)cyclopentan-1-amine and 1-methyl-N-(3-(4,4,5,5-tetramethyl-1,3,2-dioxaborolan-2-yl)benzyl)piperidin-4-amine, the title compound was obtained as described for the example 253.

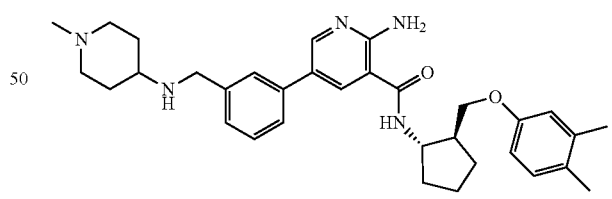

MS (ESI, m/z): 542.3 [M+H]+

Example 304. 2-amino-N-((1S,2S)-2-((3,4-dimethylbenzyl)oxy)cyclopentyl)-5-(3-((((S)-piperidin-3-yl)amino)methyl)phenyl)nicotinamide Using (1S,2S)-2-((3,4-dimethylbenzyl)oxy)cyclopentan-1-amine and (S)—N-(3-(4,4,5,5-tetramethyl-1,3,2-dioxaborolan-2-yl)benzyl)piperidin-3-amine, the title compound was obtained as described for the example 253.

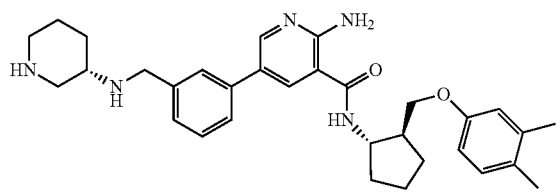 [SMILES: Cc1ccc(OC[C@H]2CCC[C@@H]2NC(=O)c2cc(-c3cccc(CN[C@H]4CCCNC4)c3)cnc2N)cc1C]

MS (ESI, m/z): 528.3 [M+H]+

Example 305. 3-(6-amino-5-(((1S,2S)-2-((3,4-dimethylbenzyl)oxy)cyclopentyl)-carbamoyl)pyridin-3-yl)-5-hydroxybenzoic Acid Using (1S,2S)-2-((3,4-dimethylbenzyl)oxy)cyclopentan-1-amine and 3-borono-5-hydroxybenzoic acid, the title compound was obtained as described for the example 253.

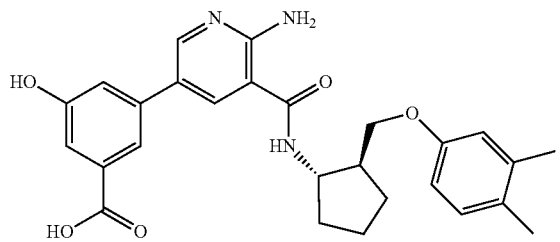 [SMILES: Cc1ccc(OC[C@H]2CCC[C@@H]2NC(=O)c2cc(-c3cc(O)cc(C(=O)O)c3)cnc2N)cc1C]

MS (ESL, m/z): 476.2 [M+H]+

Example 306. 4-(6-amino-5-(((1S,2S)-2-((3,4-dimethylbenzyl)oxy)cyclopentyl)-carbamoyl)pyridin-3-yl)-2-methylbenzoic Acid Using (1S,2S)-2-((3,4-dimethylbenzyl)oxy)cyclopentan-1-amine and 4-borono-2-methylbenzoic acid, the title compound was obtained as described for the example 253.

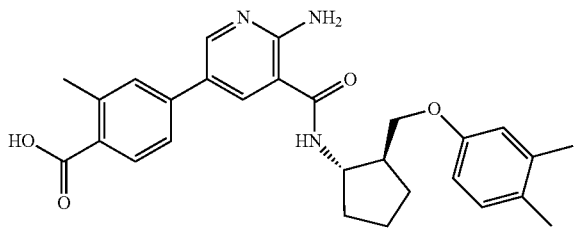 [SMILES: Cc1ccc(OC[C@H]2CCC[C@@H]2NC(=O)c2cc(-c3ccc(C(=O)O)c(C)c3)cnc2N)cc1C]

MS (ESI, m/z): 474.2 [M+H]+

Example 307. 2-amino-5-(4-aminophenyl)-N-((1S,2S)-2-((3,4-dimethylbenzyl)-oxy)cyclopentyl)nicotinamide Using (1S,2S)-2-((3,4-dimethylbenzyl)oxy)cyclopentan-1-amine and (4-amino-phenyl)boronic acid, the title compound was obtained as described for the example 253.

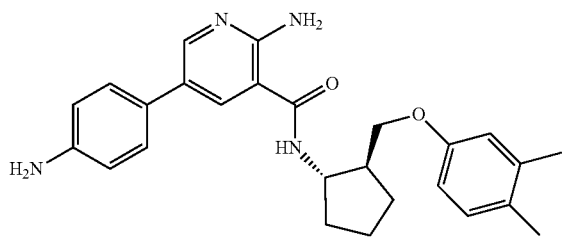 [SMILES: Cc1ccc(OC[C@H]2CCC[C@@H]2NC(=O)c2cc(-c3ccc(N)cc3)cnc2N)cc1C]

MS (ESI, m/z): 431.2 [M+H]+

Example 308. 3-(6-amino-5-(((1S,2S)-2-((3,4-dimethylbenzyl)oxy)cyclopentyl)-carbamoyl)pyridin-3-yl)benzoic Acid Using (1S,2S)-2-((3,4-dimethylbenzyl)oxy)cyclopentan-1-amine and 3-boronobenzoic acid, the title compound was obtained as described for the example 253.

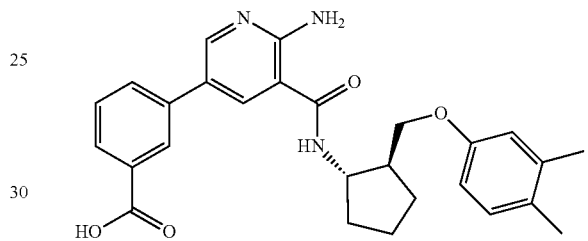

MS (ESI, m/z): 460.2 [M+H]+

Example 309. 3-amino-5-(6-amino-5-(((1S,2S)-2-((3,4-dimethylbenzyl)oxy)-cyclopentyl)carbamoyl)pyridin-3-yl)benzoic Acid Using (1S,2S)-2-((3,4-dimethylbenzyl)oxy)cyclopentan-1-amine and 3-amino-5-boronobenzoic acid, the title compound was obtained as described for the example 253.

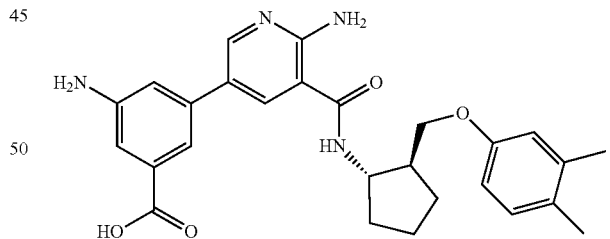

MS (ESI, m/z): 475.2 [M+H]+

Example 310. 2-amino-N-((1S,2S)-2-((3,4-dimethylbenzyl)oxy)cyclopentyl)-5-(2-methyl-5-(4-(pyrrolidin-1-yl)piperidine-1-carbonyl)phenyl)nicotinamide Using (1S,2S)-2-((3,4-dimethylbenzyl)oxy)cyclopentan-1-amine and (4-methyl-3-(4,4,5,5-tetramethyl-1,3,2-dioxaborolan-2-yl)phenyl)(4-(pyrrolidin-1-yl)piperidin-1-yl)methanone, the title compound was obtained as described for the example 253.

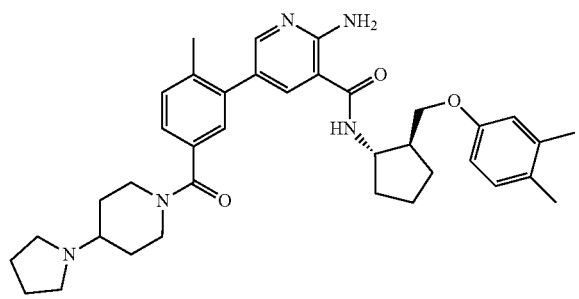 [SMILES: Cc1ccc(OC[C@H]2CCC[C@@H]2NC(=O)c2cc(-c3cc(C(=O)N4CCC(N5CCCC5)CC4)ccc3C)cnc2N)cc1C]

MS (ESI, m/z): 610.4 [M+H]⁺

Example 311. 2-amino-N-((1S,2S)-2-((3,4-dimethylbenzyl)oxy)cyclopentyl)-5-(3-methyl-4-(4-methylpiperazine-1-carbonyl)phenyl)nicotinamide Using (1S,2S)-2-((3,4-dimethylbenzyl)oxy)cyclopentan-1-amine and (2-methyl-4-(4,4,5,5-tetramethyl-1,3,2-dioxaborolan-2-yl)phenyl)(4-methylpiperazin-1-yl)methanone, the title compound was obtained as described for the example 253.

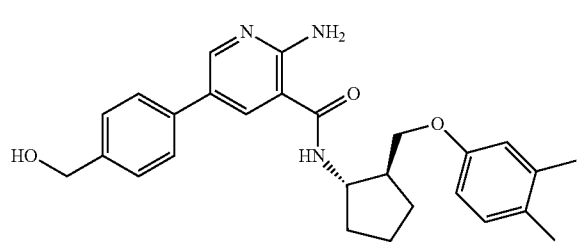

MS (ESI, m/z): 446.2 [M+H]⁺

Example 314. 2-amino-N-((1S,2S)-2-((3,4-dimethylbenzyl)oxy)cyclopentyl)-5-(4-formylphenyl)nicotinamide Using (1S,2S)-2-((3,4-dimethylbenzyl)oxy)cyclopentan-1-amine and (4-formyl-phenyl)boronic acid, the title compound was obtained as described for the example 253.

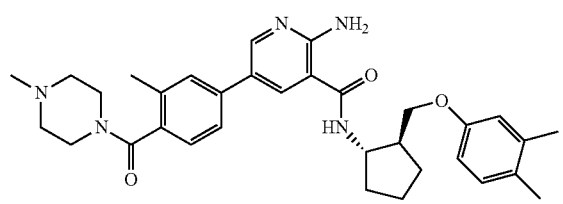

MS (ESI, m/z): 556.3 [M+H]⁺

Example 312. 2-amino-5-(3-amino-5-(4-(pyrrolidin-1-yl)piperidine-1-carbonyl)phenyl)-N-((1S,2S)-2-((3,4-dimethylbenzyl)oxy)cyclopentyl)nicotinamide Using (1S,2S)-2-((3,4-dimethylbenzyl)oxy)cyclopentan-1-amine and (3-amino-5-(4,4,5,5-tetramethyl-1,3,2-dioxaborolan-2-yl)phenyl)(4-(pyrrolidin-1-yl)piperidin-1-yl)methanone, the title compound was obtained as described for the example 253.

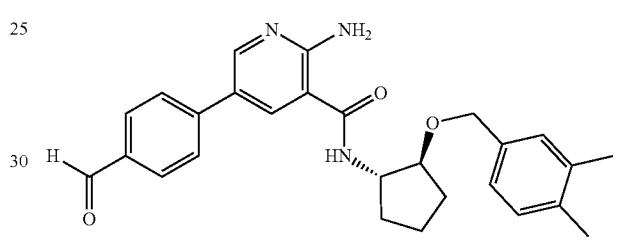

MS (ESI, m/z): 444.2 [M+H]⁺

Example 315. 4-(6-amino-5-(((1S,2S)-2-((3,4-dimethylbenzyl)oxy)cyclopentyl)-carbamoyl)pyridin-3-yl)benzoic Acid Using (1S,2S)-2-((3,4-dimethylbenzyl)oxy)cyclopentan-1-amine and 4-boronobenzoic acid, the title compound was obtained as described for the example 253.

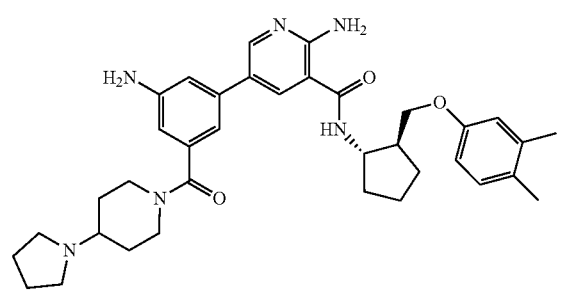 [SMILES: Cc1ccc(OC[C@H]2CCC[C@@H]2NC(=O)c2cc(-c3cc(N)cc(C(=O)N4CCC(N5CCCC5)CC4)c3)cnc2N)cc1C]

MS (ESI, m/z): 611.4 [M+H]⁺

Example 313. 2-amino-N-((1S,2S)-2-((3,4-dimethylbenzyl)oxy)cyclopentyl)-5-(4-(hydroxymethyl)phenyl)nicotinamide Using (1S,2S)-2-((3,4-dimethylbenzyl)oxy)cyclopentan-1-amine and (4-(hydroxymethyl)phenyl)boronic acid, the title compound was obtained as described for the example 253.

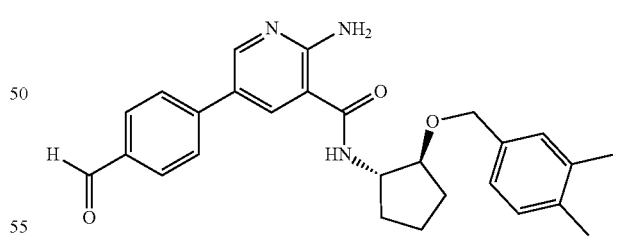

MS (ESI, m/z): 460.2 [M+H]⁺

Example 316. 3-(4-(6-amino-5-(((1S,2S)-2-((3,4-dimethylbenzyl)oxy)-cyclopentyl)carbamoyl)pyridin-3-yl)phenyl)propanoic Acid Using (1S,2S)-2-((3,4-dimethylbenzyl)oxy)cyclopentan-1-amine and 3-(4-boronophenyl)propanoic acid, the title compound was obtained as described for the example 253.

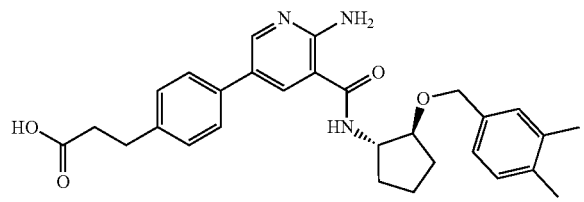 [SMILES: Cc1ccc(CO[C@H]2CCC[C@@H]2NC(=O)c2cc(-c3ccc(CCC(=O)O)cc3)cnc2N)cc1C]

MS (ESI, m/z): 488.3 [M+H]⁺

Example 317. 2-amino-N-((1S,2S)-2-((3,4-dimethylbenzyl)oxy)cyclopentyl)-5-(2-hydroxyphenyl)nicotinamide Using (1S,2S)-2-((3,4-dimethylbenzyl)oxy)cyclopentan-1-amine and (2-hydroxyphenyl)boronic acid, the title compound was obtained as described for the example 253.

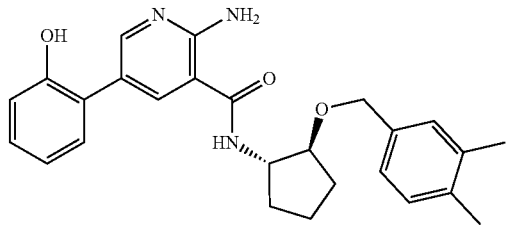 [SMILES: Cc1ccc(CO[C@H]2CCC[C@@H]2NC(=O)c2cc(-c3ccccc3O)cnc2N)cc1C]

MS (ESI, m/z): 432.22 [M+H]⁺

Example 318. 2-amino-N-((1S,2S)-2-((3,4-dimethylbenzyl)oxy)cyclopentyl)-5-(4-((1-methylpiperidin-4-yl)carbamoyl)phenyl)nicotinamide Using (1S,2S)-2-((3,4-dimethylbenzyl)oxy)cyclopentan-1-amine and N-(1-methylpiperidin-4-yl)-4-(4,4,5,5-tetramethyl-1,3,2-dioxaborolan-2-yl)benzamide, the title compound was obtained as described for the example 253.

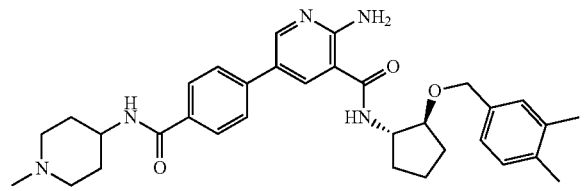

MS (ESI, m/z): 556.3 [M+H]⁺

Example 319. 2-amino-N-((1S,2S)-2-((3,4-dimethylbenzyl)oxy)cyclopentyl)-5-(4-(dimethylcarbamoyl)phenyl)nicotinamide Using (1S,2S)-2-((3,4-dimethylbenzyl)oxy)cyclopentan-1-amine and (4-(dimethyl-carbamoyl)phenyl)boronic acid, the title compound was obtained as described for the example 253.

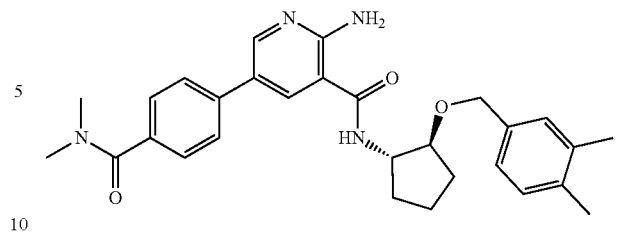

MS (ESI m/z): 487.3 [M+H]⁺

Example 320. 2-amino-N-((1S,2S)-2-((3,4-dimethylbenzyl)oxy)cyclopentyl)-5-(4-(((1-methylpiperidin-4-yl)amino)methyl)phenyl)nicotinamide Using (1S,2S)-2-((3,4-dimethylbenzyl)oxy)cyclopentan-1-amine and 1-methyl-N-(4-(4,4,5,5-tetramethyl-1,3,2-dioxaborolan-2-yl)benzyl)piperidin-4-amine, the title compound was obtained as described for the example 253.

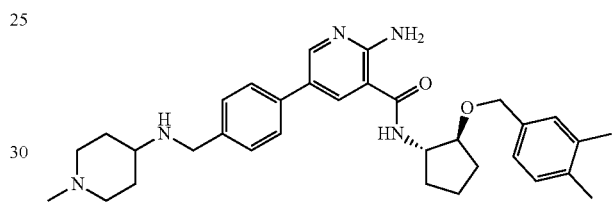

MS (ESI, m/z): 542.3 [M+H]⁺

Example 321. 6-amino-N-((1S,2S)-2-((3,4-dimethylbenzyl)oxy)cyclopentyl)-6'-(hydroxymethyl)-[3,3'-bipyridine]-5-carboxamide Using (1S,2S)-2-((3,4-dimethylbenzyl)oxy)cyclopentan-1-amine and (6-(hydroxy-methyl)pyridin-3-yl)boronic acid, the title compound was obtained as described for the example 253.

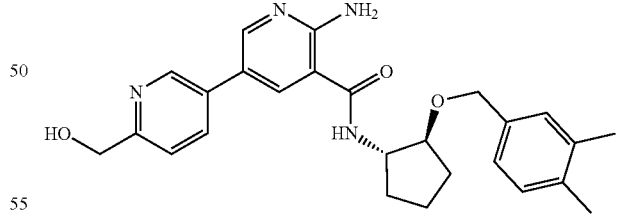

MS (ESI, m/z): 447.2 [M+H]⁺

Example 322. 2-amino-4-(6-amino-5-(((1S,2S)-2-((3,4-dimethylbenzyl)oxy)-cyclopentyl)carbamoyl)pyridin-3-yl)benzoic Acid Using (1S,2S)-2-((3,4-dimethylbenzyl)oxy)cyclopentan-1-amine and 2-amino-4-boronobenzoic acid, the title compound was obtained as described for the example 253.

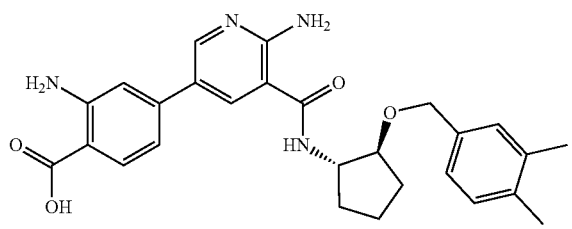 [SMILES: Cc1ccc(CO[C@H]2CCC[C@@H]2NC(=O)c2cc(-c3ccc(C(=O)O)c(N)c3)cnc2N)cc1C]

MS (ESI, m/z): 475.2 [M+H]+

Example 323. 2-amino-N-((1S,2S)-2-((3,4-dimethylbenzyl)oxy)cyclopentyl)-5-(4-(hydroxymethyl)-3-methoxyphenyl)nicotinamide Using (1S,2S)-2-((3,4-dimethylbenzyl)oxy)cyclopentan-1-amine and (2-methoxy-4-(4,4,5,5-tetramethyl-1,3,2-dioxaborolan-2-yl)phenyl)methanol, the title compound was obtained as described for the example 253.

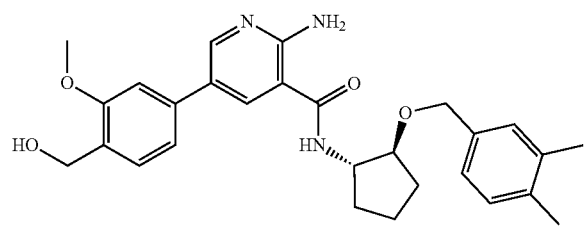 [SMILES: COc1cc(-c2cnc(N)c(C(=O)N[C@H]3CCC[C@@H]3OCc3ccc(C)c(C)c3)c2)ccc1CO]

MS (ESI, m/z): 476.3 [M+H]+

Example 324. 2-amino-N-((1S,2S)-2-((3,4-dimethylbenzyl)oxy)cyclopentyl)-5-(3-fluoro-4-(hydroxymethyl)phenyl)nicotinamide Using (1S,2S)-2-((3,4-dimethylbenzyl)oxy)cyclopentan-1-amine and (3-fluoro-4-(hydroxymethyl)phenyl)boronic acid, the title compound was obtained as described for the example 253.

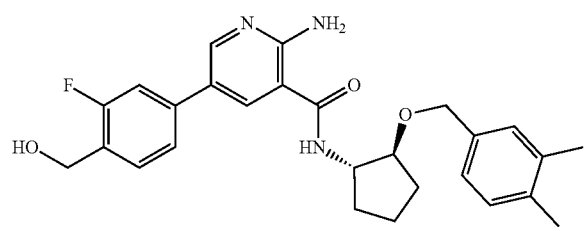 [SMILES: Cc1ccc(CO[C@H]2CCC[C@@H]2NC(=O)c2cc(-c3ccc(CO)c(F)c3)cnc2N)cc1C]

MS (ESI, m/z): 464.2 [M+H]+

Example 325. 2-amino-N-((1S,2S)-2-((3,4-dimethylbenzyl)oxy)cyclopentyl)-5-(3-fluoro-4-((4-(pyrrolidin-1-yl)piperidin-1-yl)methyl)phenyl)nicotinamide Using (1S,2S)-2-((3,4-dimethylbenzyl)oxy)cyclopentan-1-amine and 1-(2-fluoro-4-(4,4,5,5-tetramethyl-1,3,2-dioxaborolan-2-yl)benzyl)-4-(pyrrolidin-1-yl)piperidine, the title compound was obtained as described for the example 253.

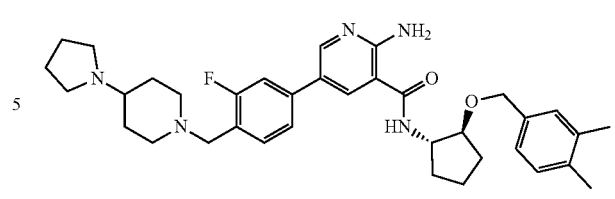

MS (ESI, m/z): 600.4 [M+H]+

Example 326. 2-amino-N-((1S,2S)-2-((3,4-dimethylbenzyl)oxy)cyclopentyl)-5-(4-(1-hydroxyethyl)phenyl)nicotinamide Using (1S,2S)-2-((3,4-dimethylbenzyl)oxy)cyclopentan-1-amine and (4-(1-hydroxyethyl)phenyl)boronic acid, the title compound was obtained as described for the example 253.

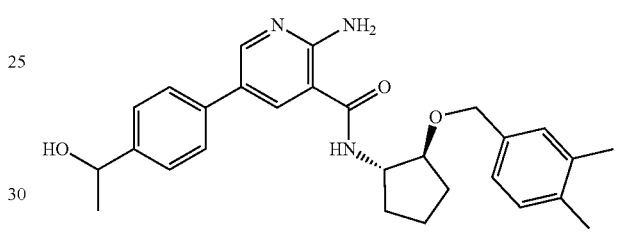

MS (ESI, m/z): 460.3 [M+H]+

Example 327. 2-amino-5-(4-((3-(dimethylamino)pyrrolidin-1-yl)methyl)phenyl)-N-((1S,2S)-2-((3,4-dimethylbenzyl)oxy)cyclopentyl)nicotinamide Using (1S,2S)-2-((3,4-dimethylbenzyl)oxy)cyclopentan-1-amine and N,N-dimethyl-1-(4-(4,4,5,5-tetramethyl-1,3,2-dioxaborolan-2-yl)benzyl)pyrrolidin-3-amine, the title compound was obtained as described for the example 253.

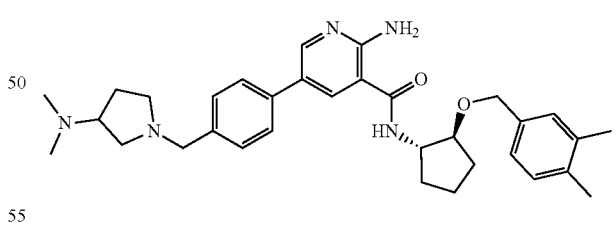

MS (ESI, m/z): 542.3 [M+H]+

Example 328. 2-amino-N-((1S,2S)-2-((3,4-dimethylbenzyl)oxy)cyclopentyl)-5-(4-((4-hydroxypiperidin-1-yl)methyl)phenyl)nicotinamide Using (1S,2S)-2-((3,4-dimethylbenzyl)oxy)cyclopentan-1-amine and 1-(4-(4,4,5,5-tetramethyl-1,3,2-dioxaborolan-2-yl)benzyl)piperidin-4-ol, the title compound was obtained as described for the example 253.

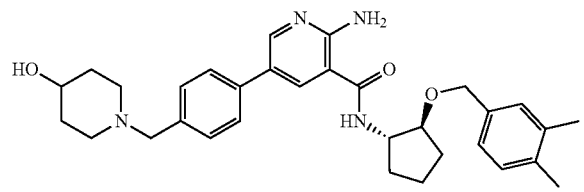 [SMILES: Cc1ccc(CO[C@H]2CCC[C@@H]2NC(=O)c2cc(-c3ccc(CN4CCC(O)CC4)cc3)cnc2N)cc1C]

MS (ESI, m/z): 529.3 [M+H]+

Example 329. 2-amino-N-((1S,2S)-2-((3,4-dimethylbenzyl)oxy)cyclopentyl)-5-(4-(((((1-methylpiperidin-4-yl)methyl)amino)methyl)phenyl)nicotinamide Using (1S,2S)-2-((3,4-dimethylbenzyl)oxy)cyclopentan-1-amine and 1-(1-methyl-piperidin-4-yl)-N-(4-(4,4,5,5-tetramethyl-1,3,2-dioxaborolan-2-yl)benzyl)methanamine, the title compound was obtained as described for the example 253.

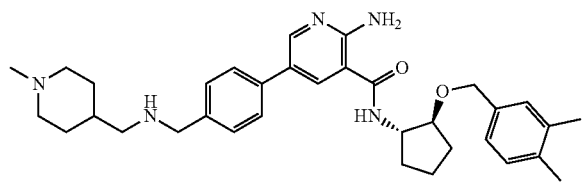

MS (ESI, m/z): 556.4 [M+H]+

Example 330. 2-amino-N-((1S,2S)-2-((3,4-dimethylbenzyl)oxy)cyclopentyl)-5-(3-methyl-4-(4-(pyrrolidin-1-yl)piperidine-1-carbonyl)phenyl)nicotinamide Using (1S,2S)-2-((3,4-dimethylbenzyl)oxy)cyclopentan-1-amine and (2-methyl-4-(4,4,5,5-tetramethyl-1,3,2-dioxaborolan-2-yl)phenyl)(4-(pyrrolidin-1-yl)piperidin-1-yl)methanone, the title compound was obtained as described for the example 253.

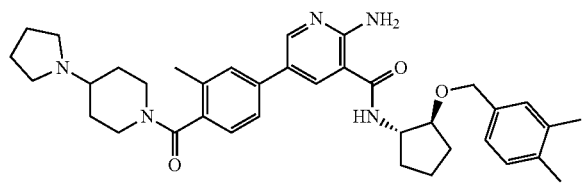 [SMILES: Cc1ccc(CO[C@H]2CCC[C@@H]2NC(=O)c2cc(-c3ccc(C(=O)N4CCC(N5CCCC5)CC4)c(C)c3)cnc2N)cc1C]

MS (ESI, m/z): 610.4 [M+H]+

Example 331. 2-amino-5-(3-amino-4-(4-(pyrrolidin-1-yl)piperidine-1-carbonyl)phenyl)-N-((1S,2S)-2-((3,4-dimethylbenzyl)oxy)cyclopentyl)nicotinamide Using (1S,2S)-2-((3,4-dimethylbenzyl)oxy)cyclopentan-1-amine and (2-amino-4-(4,4,5,5-tetramethyl-1,3,2-dioxaborolan-2-yl)phenyl)(4-(pyrrolidin-1-yl)piperidin-1-yl)methanone, the title compound was obtained as described for the example 253.

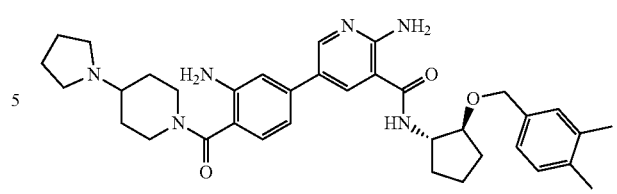

MS (ESI, m/z): 611.4 [M+H]+

Example 332. 2-amino-5-(3-amino-4-((4-(pyrrolidin-1-yl)piperidin-1-yl)methyl)phenyl)-N-((1S,2S)-2-((3,4-dimethylbenzyl)oxy)cyclopentyl)nicotinamide Using (1S,2S)-2-((3,4-dimethylbenzyl)oxy)cyclopentan-1-amine and 2-((4-(pyrrolidin-1-yl)piperidin-1-yl)methyl)-5-(4,4,5,5-tetramethyl-1,3,2-dioxaborolan-2-yl)-aniline, the title compound was obtained as described for the example 253.

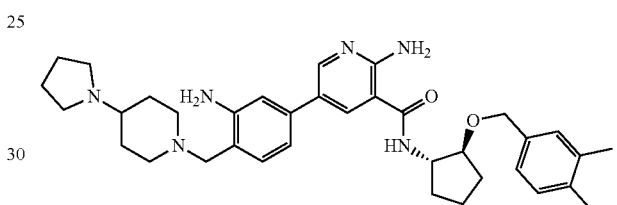

MS (ESI, m/z): 597.4 [M+H]+

Example 333. 2-amino-N-((1S,2S)-2-((3,4-dimethylbenzyl)oxy)cyclopentyl)-5-(4-(hydroxymethyl)-3-methylphenyl)nicotinamide Using (1S,2S)-2-((3,4-dimethylbenzyl)oxy)cyclopentan-1-amine and (2-methyl-4-(4,4,5,5-tetramethyl-1,3,2-dioxaborolan-2-yl)phenyl)methanol, the title compound was obtained as described for the example 253.

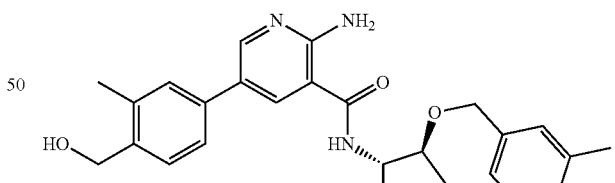

MS (ESI, m/z): 460.3 [M+H]+

Example 334. 2-amino-5-(3-chlorophenyl)-N-((1S,2S)-2-((3,4-dimethylbenzyl)-oxy)cyclopentyl)nicotinamide Using (1S,2S)-2-((3,4-dimethylbenzyl)oxy)cyclopentan-1-amine and (3-chloro-phenyl)boronic acid, the title compound was obtained as described for the example 253.

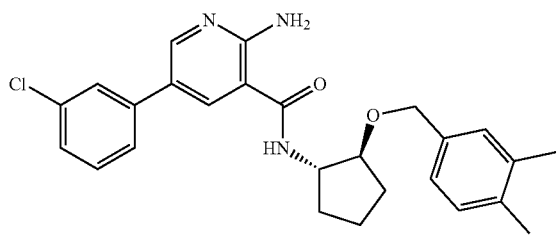 [SMILES: Cc1ccc(CO[C@H]2CCC[C@@H]2NC(=O)c2cc(-c3cccc(Cl)c3)cnc2N)cc1C]

MS (ESI, m/z): 450 [M+H]⁺

Example 335. 2-amino-N-((1S,2S)-2-((3,4-dimethylbenzyl)oxy)cyclopentyl)-5-(m-tolyl)nicotinamide Using (1S,2S)-2-((3,4-dimethylbenzyl)oxy)cyclopentan-1-amine and m-tolylboronic acid, the title compound was obtained as described for the example 253.

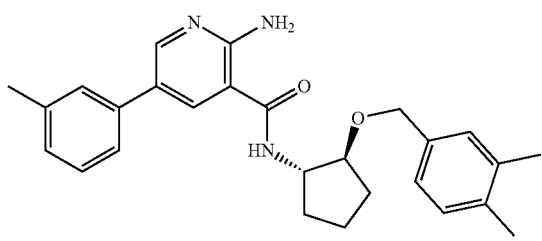

MS (ESI, m/z): 430.2 [M+H]⁺

Example 336. 2-amino-N-((1S,2S)-2-((3,4-dimethylbenzyl)oxy)cyclopentyl)-5-(3,5-dimethylphenyl)nicotinamide Using (1S,2S)-2-((3,4-dimethylbenzyl)oxy)cyclopentan-1-amine and (3,5-dimethylphenyl)boronic acid, the title compound was obtained as described for the example 253.

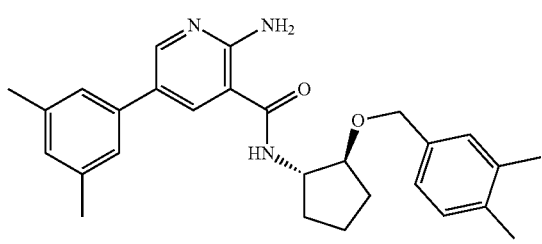

MS (ESI, m/z): 444.3 [M+H]⁺

Example 337. 2-amino-N-((1S,2S)-2-((3,4-dimethylbenzyl)oxy)cyclopentyl)-5-(4-((3-morpholinopyrrolidin-1-yl)methyl)phenyl)nicotinamide Using (1S,2S)-2-((3,4-dimethylbenzyl)oxy)cyclopentan-1-amine and 4-(1-(4-(4,4,5,5-tetramethyl-1,3,2-dioxaborolan-2-yl)benzyl)pyrrolidin-3-yl)morpholine, the title compound was obtained as described for the example 253.

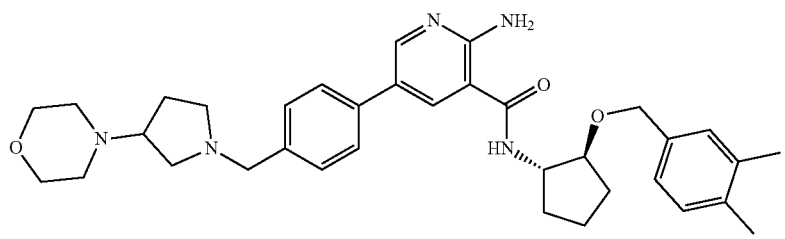 [SMILES: Cc1ccc(CO[C@H]2CCC[C@@H]2NC(=O)c2cc(-c3ccc(CN4CCC(N5CCOCC5)C4)cc3)cnc2N)cc1C]

MS (ESI, m/z): 584.4 [M+H]⁺

Example 338. 2-amino-5-(4-((4-aminopiperidin-1-yl)methyl)phenyl)-N-((1S,2S)-2-((3,4-dimethylbenzyl)oxy)cyclopentyl)nicotinamide Using (1S,2S)-2-((3,4-dimethylbenzyl)oxy)cyclopentan-1-amine and 1-(4-(4,4,5,5-tetramethyl-1,3,2-dioxaborolan-2-yl)benzyl)piperidin-4-amine, the title compound was obtained as described for the example 253.

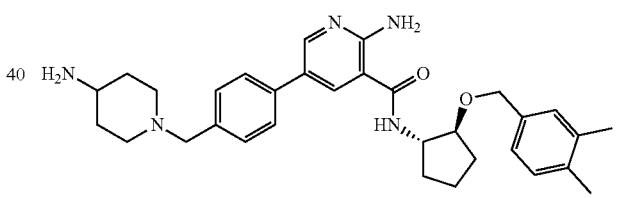

MS (ESI, m/z): 528.3 [M+H]⁺

Example 339. 2-amino-5-(4-((3-aminopiperidin-1-yl)methyl)phenyl)-N-((1S,2S)-2-((3,4-dimethylbenzyl)oxy)cyclopentyl)nicotinamide Using (1S,2S)-2-((3,4-dimethylbenzyl)oxy)cyclopentan-1-amine and 1-(4-(4,4,5,5-tetramethyl-1,3,2-dioxaborolan-2-yl)benzyl)piperidin-3-amine, the title compound was obtained as described for the example 253

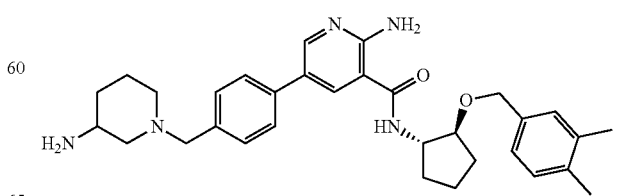

MS (ESI, m/z): 528.3 [M+H]⁺

Example 340. 2-amino-5-(4-((3-aminopyrrolidin-1-yl)methyl)phenyl)-N-((1S,2S)-2-((3,4-dimethylbenzyl)oxy)cyclopentyl)nicotinamide Using (1S,2S)-2-((3,4-dimethylbenzyl)oxy)cyclopentan-1-amine and 1-(4-(4,4,5,5-tetramethyl-1,3,2-dioxaborolan-2-yl)benzyl)pyrrolidin-3-amine, the title compound was obtained as described for the example 253.

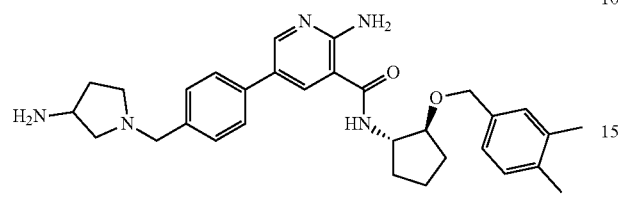

MS (ESI, m/z): 514.3 [M+H]$^+$

Example 341. 2-amino-5-(4-((3-aminopyrrolidin-1-yl)methyl)-3-fluorophenyl)-N-((1S,2S)-2-((3,4-dimethylbenzyl)oxy)cyclopentyl)nicotinamide Using (1S,2S)-2-((3,4-dimethylbenzyl)oxy)cyclopentan-1-amine and 1-(2-fluoro-4-(4,4,5,5-tetramethyl-1,3,2-dioxaborolan-2-yl)benzyl)pyrrolidin-3-amine, the title compound was obtained as described for the example 253.

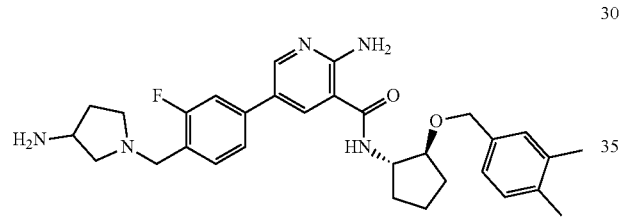

MS (ESI, m/z): 532.3 [M+H]$^+$

Example 342. 2-amino-5-(4-((3-aminopyrrolidin-1-yl)methyl)-3,5-difluorophenyl)-N-((1S,2S)-2-((3,4-dimethylbenzyl)oxy)cyclopentyl)nicotinamide Using (1S,2S)-2-((3,4-dimethylbenzyl)oxy)cyclopentan-1-amine and 1-(2,6-difluoro-4-(4,4,5,5-tetramethyl-1,3,2-dioxaborolan-2-yl)benzyl)pyrrolidin-3-amine, the title compound was obtained as described for the example 253.

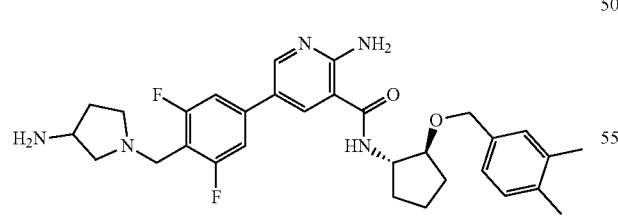

MS (ESI, m/z): 550.3 [M+H]$^+$

Example 343. 2-amino-5-(3-((3-(dimethylamino)pyrrolidin-1-yl)methyl)phenyl)-N-((1S,2S)-2-((3,4-dimethylbenzyl)oxy)cyclopentyl)nicotinamide Using (1S,2S)-2-((3,4-dimethylbenzyl)oxy)cyclopentan-1-amine and N,N-dimethyl-1-(3-(4,4,5,5-tetramethyl-1,3,2-dioxaborolan-2-yl)benzyl)pyrrolidin-3-amine, the title compound was obtained as described for the example 253.

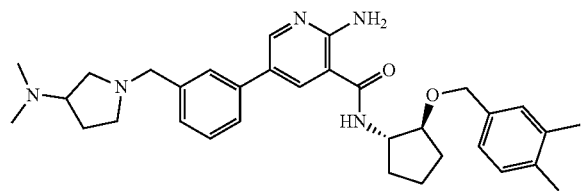

MS (ESI, m/z): 542.3 [M+H]$^+$

Example 344. 2-amino-5-(3-((3-(dimethylamino)pyrrolidin-1-yl)methyl)-4-methoxyphenyl)-N-((1S,2S)-2-((3,4-dimethylbenzyl)oxy)cyclopentyl)nicotinamide Using (1S,2S)-2-((3,4-dimethylbenzyl)oxy)cyclopentan-1-amine and 1-(2-methoxy-5-(4,4,5,5-tetramethyl-1,3,2-dioxaborolan-2-yl)benzyl)-N,N-dimethylpyrrolidin-3-amine, the title compound was obtained as described for the example 253.

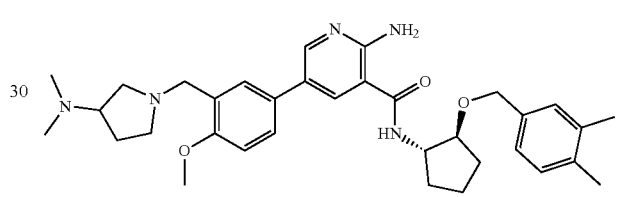

MS (ESI, m/z): 572.4 [M+H]$^+$

Example 345. 2-amino-N-((1S,2S)-2-((3,4-dimethylbenzyl)oxy)cyclopentyl)-5-(4-((3-hydroxyazetidin-1-yl)methyl)phenyl)nicotinamide Using (1S,2S)-2-((3,4-dimethylbenzyl)oxy)cyclopentan-1-amine and 1-(4-(4,4,5,5-tetramethyl-1,3,2-dioxaborolan-2-yl)benzyl)azetidin-3-ol, the title compound was obtained as described for the example 253.

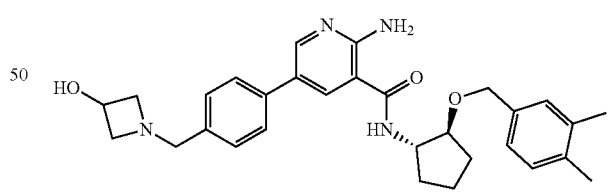

MS (ESI, m/z): 501.3 [M+H]$^+$

Example 346. 2-amino-5-(4-(((R)-3-(dimethylamino)pyrrolidin-1-yl)methyl)-phenyl)-N-((1S,2S)-2-((3,4-dimethylbenzyl)oxy)cyclopentyl)nicotinamide Using (1S,2S)-2-((3,4-dimethylbenzyl)oxy)cyclopentan-1-amine and (R)—N,N-dimethyl-1-(4-(4,4,5,5-tetramethyl-1,3,2-dioxaborolan-2-yl)benzyl)pyrrolidin-3-amine, the title compound was obtained as described for the example 253.

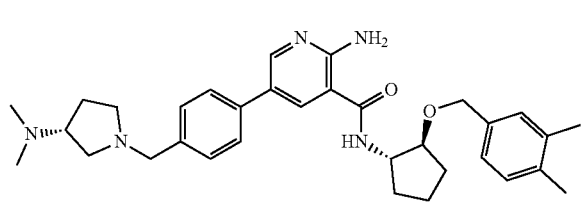

MS (ESI, m/z): 542.3 [M+H]+

Example 347. 2-amino-5-(4-(((S)-3-(dimethyl-amino)pyrrolidin-1-yl)methyl)phenyl)-N-((1S,2S)-2-((3,4-dimethylbenzyl)oxy)cyclopentyl)nicotinamide Using (1S,2S)-2-((3,4-dimethylbenzyl)oxy)cyclopentan-1-amine and (S)—N,N-dimethyl-1-(4-(4,4,5,5-tetramethyl-1,3,2-dioxaborolan-2-yl)benzyl)pyrrolidin-3-amine, the title compound was obtained as described for the example 253.

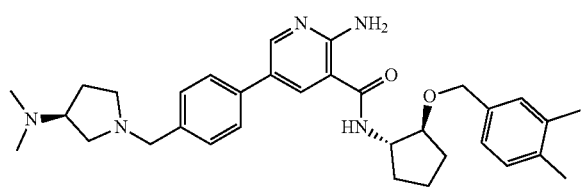

MS (ESI, m/z): 542.3 [M+H]+

Example 348. 2-amino-N-((1S,2S)-2-((3,4-dimethylbenzyl)oxy)cyclopentyl)-5-(4-(((R)-3-hydroxypyrrolidin-1-yl)methyl)phenyl)nicotinamide Using (1S,2S)-2-((3,4-dimethylbenzyl)oxy)cyclopentan-1-amine and (R)-1-(4-(4,4,5,5-tetramethyl-1,3,2-dioxaborolan-2-yl)benzyl)pyrrolidin-3-ol, the title compound was obtained as described for the example 253.

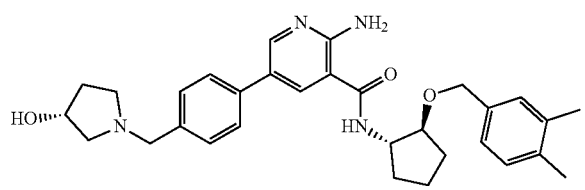 [SMILES: Cc1ccc(CO[C@H]2CCC[C@@H]2NC(=O)c2cc(-c3ccc(CN4CC[C@@H](O)C4)cc3)cnc2N)cc1C]

MS (ESI, m/z): 515.3 [M+H]+

Example 349. 2-amino-N-((1S,2S)-2-((3,4-dimethylbenzyl)oxy)cyclopentyl)-5-(4-(((S)-3-hydroxypyrrolidin-1-yl)methyl)phenyl)nicotinamide Using (1S,2S)-2-((3,4-dimethylbenzyl)oxy)cyclopentan-1-amine and (S)-1-(4-(4,4,5,5-tetramethyl-1,3,2-dioxaborolan-2-yl)benzyl)pyrrolidin-3-ol, the title compound was obtained as described for the example 253.

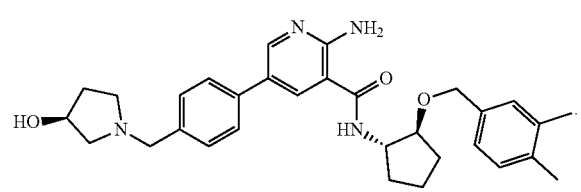 [SMILES: Cc1ccc(CO[C@H]2CCC[C@@H]2NC(=O)c2cc(-c3ccc(CN4CC[C@H](O)C4)cc3)cnc2N)cc1C]

MS (ESI, m/z): 515.3 [M+H]+

Example 350. 2-amino-N-((1S,2S)-2-((3,4-dimethylbenzyl)oxy)cyclopentyl)-5-(4-((3-hydroxypiperidin-1-yl)methyl)phenyl)nicotinamide Using (1S,2S)-2-((3,4-dimethylbenzyl)oxy)cyclopentan-1-amine and 1-(4-(4,4,5,5-tetramethyl-1,3,2-dioxaborolan-2-yl)benzyl)piperidin-3-ol, the title compound was obtained as described for the example 253.

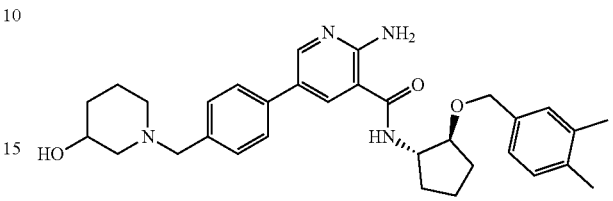

MS (ESI, m/z): 529.3 [M+H]+

Example 351. 2-amino-N-((1S,2S)-2-((3,4-dimethylbenzyl)oxy)cyclopentyl)-5-(4-hydroxyphenyl)nicotinamide Using (1S,2S)-2-((3,4-dimethylbenzyl)oxy)cyclopentan-1-amine and (4-hydroxy-phenyl)boronic acid, the title compound was obtained as described for the example 253.

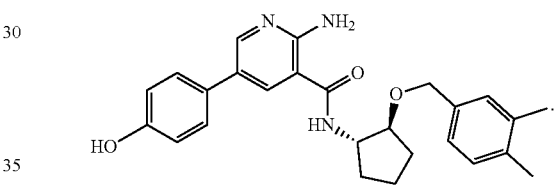

MS (ESI, m/z): 432.2 [M+H]+

Example 352. 2-amino-N-((1S,2S)-2-((3,4-dimethylbenzyl)oxy)cyclopentyl)-5-(4-hydroxy-3-methoxyphenyl)nicotinamide Using (1S,2S)-2-((3,4-dimethylbenzyl)oxy)cyclopentan-1-amine and (4-hydroxy-3-methoxyphenyl)boronic acid, the title compound was obtained as described for the example 253.

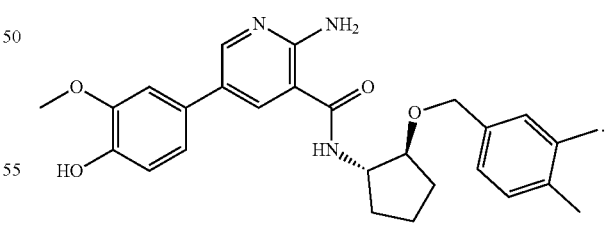

MS (ESI, m/z): 462.23 [M+H]+

Example 353. 2-amino-5-(3,4-dimethoxyphenyl)-N-((1S,2S)-2-((3,4-dimethylbenzyl)oxy)cyclopentyl)nicotinamide Using (1S,2S)-2-((3,4-dimethylbenzyl)oxy)cyclopentan-1-amine and (3,4-dimethoxy-phenyl)boronic acid, the title compound was obtained as described for the example 253.

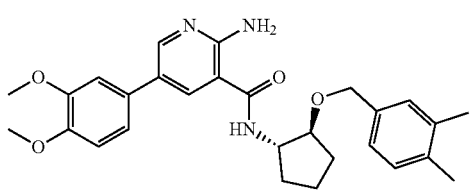

MS (ESI, m/z): 476.3 [M+H]+

Example 354. 2-amino-N-((1S,2S)-2-((3,4-dimethylbenzyl)oxy)cyclopentyl)-5-(3-(pyrrolidin-1-yl)phenyl)nicotinamide Using (1S,2S)-2-((3,4-dimethylbenzyl)oxy)cyclopentan-1-amine and (3-(pyrrolidin-1-yl)phenyl)boronic acid pinacol ester, the title compound was obtained as described for the example 253.

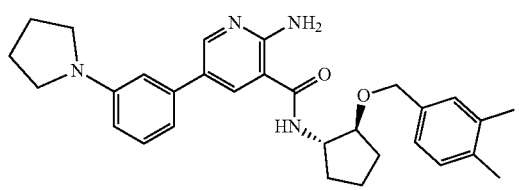 [SMILES: Cc1ccc(CO[C@H]2CCC[C@@H]2NC(=O)c2cc(-c3cccc(N4CCCC4)c3)cnc2N)cc1C]

MS (ESI, m/z): 485.3 [M+H]+

Example 355. 2-amino-5-(5-amino-1-methyl-1H-pyrazol-4-yl)-N-((1S,2S)-2-((3,4-dimethylbenzyl)oxy)cyclopentyl)nicotinamide Using (1S,2S)-2-((3,4-dimethylbenzyl)oxy)cyclopentan-1-amine and 1-methyl-4-(4,4,5,5-tetramethyl-1,3,2-dioxaborolan-2-yl)-1H-pyrazol-5-amine, the title compound was obtained as described for the example 253.

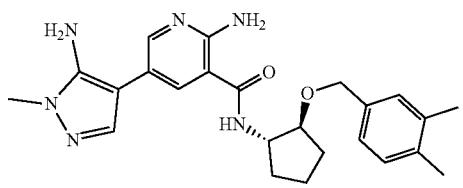

MS (ESI, m/z): 435.2 [M+H]+

Example 356. 2-amino-N-((1S,2S)-2-((3-ethyl-4-methylbenzyl)oxy)cyclopentyl)-5-(4-(hydroxymethyl)phenyl)nicotinamide Using (1S,2S)-2-((3-ethyl-4-methylbenzyl)oxy)cyclopentan-1-amine and (4-(hydroxy-methyl)phenyl)boronic acid, the title compound was obtained as described for the example 253.

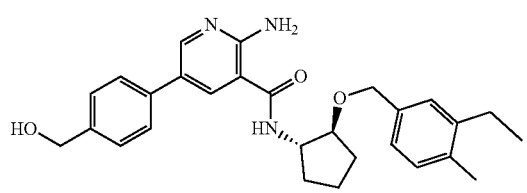 [SMILES: CCc1cc(CO[C@H]2CCC[C@@H]2NC(=O)c2cc(-c3ccc(CO)cc3)cnc2N)ccc1C]

MS (ESI, m/z): 460.3 [M+H]+

Example 357. 2-amino-5-(4-((3-(dimethylamino)pyrrolidin-1-yl)methyl)phenyl)-N-((1S,2S)-2-((3-ethyl-4-methylbenzyl)oxy)cyclopentyl)nicotinamide Using (1S,2S)-2-((3-ethyl-4-methylbenzyl)oxy)cyclopentan-1-amine and N,N-dimethyl-1-(4-(4,4,5,5-tetramethyl-1,3,2-dioxaborolan-2-yl)benzyl)pyrrolidin-3-amine, the title compound was obtained as described for the example 253.

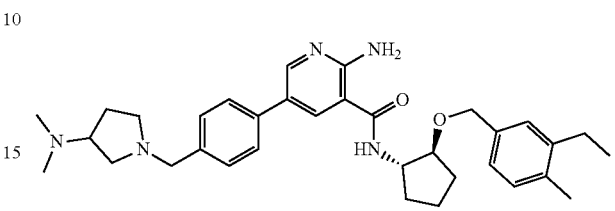

MS (ESI, m/z): 556.4 [M+H]+

Example 358. 2-amino-N-((1S,2S)-2-((3-ethyl-4-methylbenzyl)oxy)cyclopentyl)-5-(4-((3-hydroxypyrrolidin-1-yl)methyl)phenyl)nicotinamide Using (1S,2S)-2-((3-ethyl-4-methylbenzyl)oxy)cyclopentan-1-amine and 1-(4-(4,4,5,5-tetramethyl-1,3,2-dioxaborolan-2-yl)benzyl)pyrrolidin-3-ol, the title compound was obtained as described for the example 253.

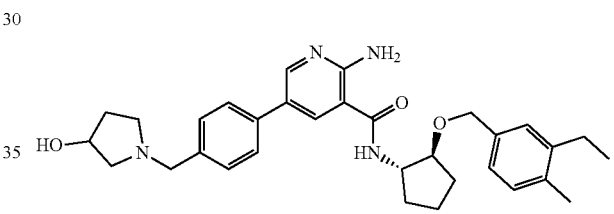

MS (ESI, m/z): 529.3 [M+H]+

Example 359. 2-amino-N-((1S,2S)-2-((3-ethyl-4-methylbenzyl)oxy)cyclopentyl)-5-(4-(2-(piperazin-1-yl)propan-2-yl)phenyl)nicotinamide Using (1S,2S)-2-((3-ethyl-4-methylbenzyl)oxy)cyclopentan-1-amine and 1-(2-(4-(4,4,5,5-tetramethyl-1,3,2-dioxaborolan-2-yl)phenyl)propan-2-yl)piperazine, the title compound was obtained as described for the example 253.

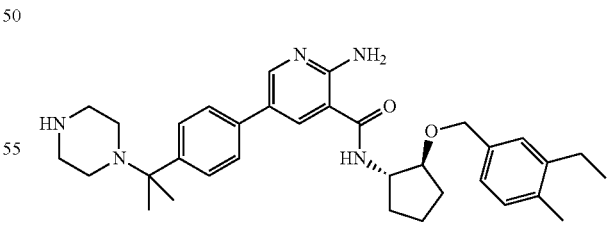

$^1$H NMR (400 MHz, CD$_3$OD) δ ppm 1.11 (t, J=7.63 Hz, 3H) 1.50 (s, 6H) 1.58-1.67 (m, 1H) 1.70-1.88 (m, 3H) 1.98-2.06 (m, 1H) 2.10-2.17 (m, 1H) 2.17 (s, 3H) 2.49-2.57 (q, J=7.63 Hz, 2H) 2.84 (br s, 4H) 3.24 (t, J=4.70 Hz, 4H) 3.91-4.00 (m, 1H) 4.40 (br d, J=4.70 Hz, 1H) 4.49-4.61 (m, 2H) 6.98-7.05 (m, 2H) 7.09 (s, 1H) 7.64-7.80 (m, 4H) 8.31 (d, J=2.35 Hz, 1H) 8.57 (d, J=1.96 Hz, 1H);

MS (ESI, m/z): 556.4 [M+H]+

Example 360. 2-amino-N-((1S,2S)-2-((3-ethyl-4-methylbenzyl)oxy)cyclopentyl)-5-(4-(2-(4-(2-hydroxyethyl)piperazin-1-yl)propan-2-yl)phenyl)nicotinamide Using (1S,2S)-2-((3-ethyl-4-methylbenzyl)oxy)cyclopentan-1-amine and 2-(4-(2-(4-(4,4,5,5-tetramethyl-1,3,2-dioxaborolan-2-yl)phenyl)propan-2-yl)piperazin-1-yl)ethan-1-ol, the title compound was obtained as described for the example 253.

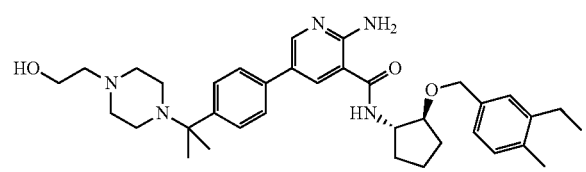 [SMILES: CCc1cc(CO[C@H]2CCC[C@@H]2NC(=O)c2cc(-c3ccc(C(C)(C)N4CCN(CCO)CC4)cc3)cnc2N)ccc1C]

$^1$H NMR (400 MHz, CD$_3$OD) δ ppm 1.11 (t, J=7.43 Hz, 3H) 1.57 (s, 3H) 1.61-1.64 (m, 1H) 1.64 (s, 3H) 1.69-1.89 (m, 3H) 2.01 (br dd, J=13.11, 6.06 Hz, 1H) 2.10-2.29 (m, 4H) 2.53 (q, J=7.56 Hz, 2H) 2.88-3.13 (m, 4H) 3.22-3.28 (m, 1H) 3.33-3.39 (m, 2H) 3.43 (br s, 2H) 3.83-3.90 (m, 1H) 3.92-4.00 (m, 1H) 4.35-4.45 (m, 1H) 4.47-4.62 (m, 2H) 6.95-7.07 (m, 2H) 7.09 (s, 1H) 7.65-7.84 (m, 4H) 8.29-8.36 (m, 1H) 8.56-8.64 (m, 1H);

MS (ESI, m/z): 600.3 [M+H]$^+$

Example 361. 3-amino-N-((1S,2S)-2-(benzyloxy)cyclopentyl)-6-(1-(piperidin-4-yl)-1H-pyrazol-4-yl)pyrazine-2-carboxamide Using 3-amino-N-((1S,2S)-2-(benzyloxy)cyclopentyl)-6-bromopyrazine-2-carboxamide and (1-(piperidin-4-yl)-1H-pyrazol-4-yl)boronic acid pinacol ester, the title compound was obtained as described for the example 253.

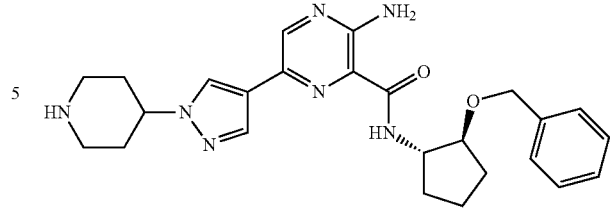

MS (ESI, m/z): 462.3 [M+H]$^+$

Example 362. (S)-3-amino-6-(1-(piperidin-4-yl)-1H-pyrazol-4-yl)-N-(1,2,3,4-tetrahydronaphthalen-1-yl)pyrazine-2-carboxamide Using (S)-3-amino-6-bromo-N-(1,2,3,4-tetrahydronaphthalen-1-yl)pyrazine-2-carboxamide and (1-(piperidin-4-yl)-1H-pyrazol-4-yl)boronic acid pinacol ester, the title compound was obtained as described for the example 253.

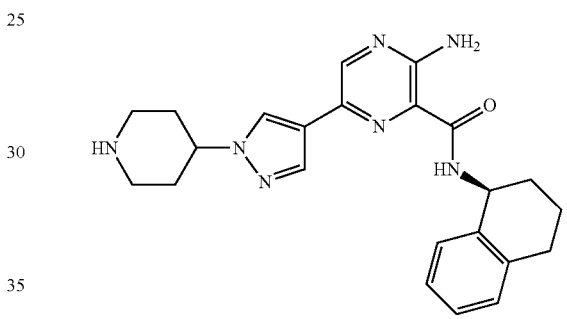

MS (ESI, m/z): 418.2 [M+H]$^+$

Example 363. 2-amino-5-(4-fluorophenyl)-N-((1S,2S)-2-((4'-((4-methylpiperazin-1-yl)methyl)-[1,1'-biphenyl]-4-yl)methoxy)cyclopentyl)nicotinamide Scheme for the Preparation of the Compound of Example 363:

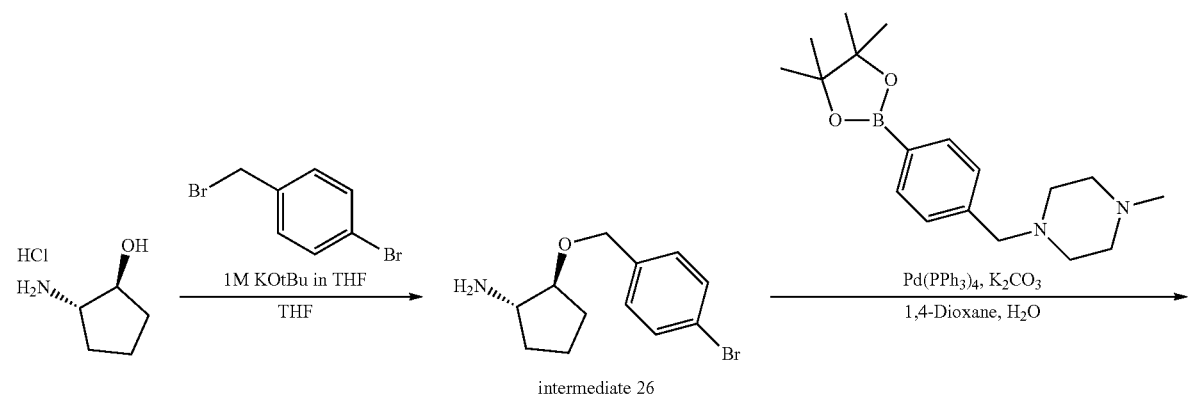

intermediate 26

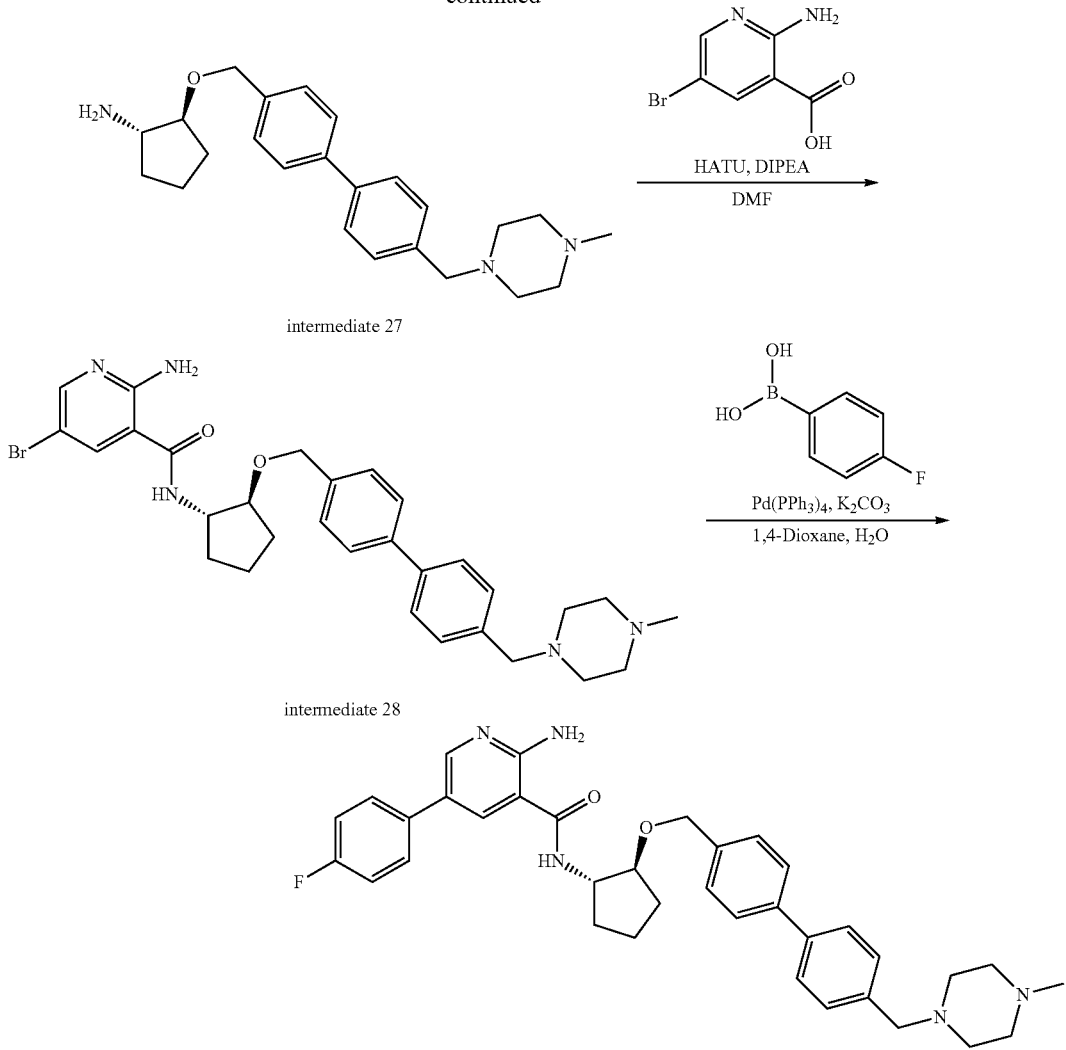

intermediate 27 intermediate 28

Intermediate 26

To a solution of trans-(1S,2S)-2-Aminocyclopentanol hydrochloride (8.0 mmol) in DMF (5 ml) was added 1M potassium tert-butoxide in THF (20 ml) at room temperature. The mixture was allowed to stir for 30 min. After being allowed to stir for 30 min, 4-bromobenzyl bromide (9.6 mmol) was added to the mixture, and then allowed to stir for additional 2 h at room temperature. The reaction mixture was then quenched with water and extracted with EtOAc. The separated organic layer was dried over MgSO$_4$, filtered and concentrated in vacuo. The concentrated residue was used in the next step without further purification.

$^1$H NMR (600 MHz, CDCl$_3$) δ ppm 1.29-1.35 (m, 1H) 1.57-1.65 (m, 1H) 1.65-1.77 (m, 2H) 1.96 (br dd, J=12.62, 6.75 Hz, 2H) 3.20-3.27 (m, 1H) 3.51 (br d, J=5.28 Hz, 1H) 4.40-4.46 (m, 1H) 4.46-4.54 (m, 1H) 7.21 (br t, J=7.63 Hz, 2H) 7.40-7.48 (m, 2H);

MS (ESI+) m/z 270 [M+H]$^+$

Intermediate 27

To a solution of intermediate 26 (0.851 mmol) in 1,4-dioxane (4 ml) and water (1 ml) was added 1-methyl-4-(4-(4,4,5,5-tetramethyl-1,3,2-dioxaborolan-2-yl)benzyl)piperazine (0.851 mmol), tetrakis(triphenylphosphine)palladium(0) (0.0851 mmol) and potassium carbonate (0.851 mmol). The mixture was heated to 100° C. and allowed to stir for overnight. After being cooled to room temperature, the reaction mixture was diluted with water (10 mL) and extracted with ethyl acetate (10 mL). The separated organic layer was dried over MgSO$_4$, filtered and concentrated in vacuo. The concentrated residue was purified by flash column chromatography to afford the desired compound (265 mg, 0.7 mmol).

$^1$H NMR (600 MHz, CD$_3$OD) δ ppm 1.36-1.45 (m, 1H) 1.63-1.78 (m, 3H) 1.97-2.07 (m, 2H) 2.26 (s, 3H) 2.30-2.71 (br s, 8H) 3.24 (td, J=7.48, 4.99 Hz, 1H) 3.55 (s, 2H) 3.67-3.74 (m, 1H) 4.53 (d, J=11.74 Hz, 1H) 4.60 (d, J=11.74 Hz, 1H) 7.38 (d, J=8.22 Hz, 2H) 7.42 (d, J=8.22 Hz, 2H) 7.55-7.58 (m, 2H) 7.58-7.61 (m, 2H);

MS (ESI+) m/z 380 [M+H]$^+$

Intermediate 28

To a solution of intermediate 27 (0.685 mmol) and 2-amino-5-bromonicotinic acid (0.685 mmol) in N,N-dimethylformamide (5 mL) was added diisopropylethylamine (3.425 mmol) and HATU (1.027 mmol) at room temperature. The reaction mixture was allowed to stir for overnight, concentrated in vacuo, diluted with EtOAc and washed with brine. The separated organic layer was dried over MgSO₄, filtered and concentrated in vacuo. The concentrated residue was purified by flash column chromatography to afford the desired compound (0.653 mmol) as a pale yellow oil.

¹H NMR (600 MHz, CD₃OD) δ ppm 1.49-1.57 (m, 1H) 1.68-1.78 (m, 3H) 1.95-2.01 (m, 1H) 2.07-2.13 (m, 1H) 2.41 (s, 3H) 2.49-2.79 (br s, 8H) 3.56 (s, 2H) 3.91 (dt, J=6.90, 4.48 Hz, 1H) 4.34 (td, J=7.48, 4.40 Hz, 1H) 4.57-4.65 (m, 2H) 7.35 (br d, J=8.22 Hz, 2H) 7.37 (br d, J=8.22 Hz, 2H) 7.52 (d, J=7.63 Hz, 4H) 7.90 (d, J=2.35 Hz, 1H) 8.04 (d, J=2.35 Hz, 1H);

MS (ESI+) m/z 579 [M+H]⁺

Example 363. 2-amino-5-(4-fluorophenyl)-N-((1S,2S)-2-((4'-((4-methylpiperazin-1-yl)methyl)-[1,1'-biphenyl]-4-yl)methoxy)cyclopentyl)nicotinamide To a solution of intermediate 28 (0.076 mmol) in 1,4-dioxane (4 ml) and water (1 ml) was added (4-fluorophenyl) boronic acid (0.076 mmol), tetrakis(triphenylphosphine)-palladium(0) (0.0076 mmol) and potassium carbonate (0.076 mmol). The mixture was heated to 100° C. and allowed to stir for overnight. After being cooled to room temperature, the reaction mixture was diluted with water (10 mL) and extracted with ethyl acetate (10 mL). The separated organic layer was dried over MgSO₄, filtered and concentrated in vacuo. The concentrated residue was purified by preparative HPLC to afford the compound of Example 363.

¹H NMR (400 MHz, CD₃OD) δ 8.57 (s, 1H), 8.23 (s, 1H), 7.64-7.47 (m, 8H), 7.42 (d, 2H), 7.17 (t, 2H), 4.66 (qd, 2H), 4.45-4.39 (m, 1H), 4.25 (s, 1H), 4.09-3.90 (m, 1H), 3.62 (s, 1H), 3.53 (br s, 2H), 3.39 (br s, 2H), 2.94 (s, 3H), 2.19-2.12 (m, 1H), 2.05-1.97 (m, 1H), 1.83-1.75 (m, 3H), 1.66-1.57 (m, 1H);

MS (ESI+) n/z 594 [M+H]⁺

Example 364. 2-amino-5-(3,4-difluorophenyl)-N-((1S,2S)-2-((4'-((4-methylpiperazin-1-yl)methyl)-[1,1'-biphenyl]-4-yl)methoxy)cyclopentyl)nicotinamide Using 3,4-difluorophenylboronic acid, the title compound was obtained as described for the example 363.

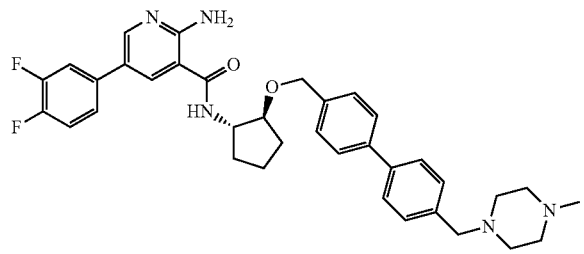 [SMILES: CN1CCN(Cc2ccc(-c3ccc(CO[C@H]4CCC[C@@H]4NC(=O)c4cc(-c5ccc(F)c(F)c5)cnc4N)cc3)cc2)CC1]

¹H NMR (400 MHz, CD₃OD) δ 8.54 (s, 1H), 8.26 (s, 1H), 7.71-7.52 (m, 8H), 7.42-7.33 (m, 3H), 4.65 (qd, 2H), 4.41 (m, 1H), 4.32 (s, 2H), 3.98 (m, 1H), 3.57 (br s, 2H), 3.48 (br s, 2H), 2.94 (s, 3H), 2.18-2.05 (m, 1H), 2.04-1.99 (m, 1H), 1.81-1.73 (m, 3H), 1.66-1.59 (m, 1H);

MS (ESI+) m/z 612 [M+H]⁺

Example 365. 2-amino-N-((1S,2S)-2-(4'-((4-methylpiperazin-1-yl)methyl)-[1,1'-biphenyl]-4-yl)methoxy)cyclopentyl)-5-(4-(trifluoromethyl)phenyl)nicotinamide Using 4-trifluoromethylphenylboronic acid, the title compound was obtained as described for the example 363.

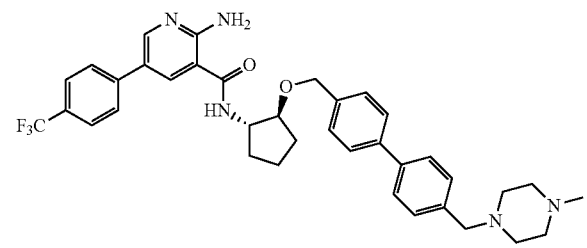 [SMILES: CN1CCN(Cc2ccc(-c3ccc(CO[C@H]4CCC[C@@H]4NC(=O)c4cc(-c5ccc(C(F)(F)F)cc5)cnc4N)cc3)cc2)CC1]

¹H NMR (400 MHz, CD₃OD) δ 8.65 (s, 1H), 8.36 (s, 1H), 7.83 (d, J=8.0 Hz, 2H), 7.75 (d, J=12.0 Hz, 2H), 7.62 (d, J=8.0 Hz, 2H), 7.54-7.50 (m, 4H), 7.42 (d, J=8.0 Hz, 2H), 4.69-4.62 (qd, 2H), 4.44-4.39 (m, 1H), 4.27 (s, 2H), 4.02-4.00 (m, 1H), 3.54 (br s, 2H), 3.42 (br s, 2H), 2.94 (s, 3H), 2.21-2.05 (m, 1H), 2.05-1.97 (m, 1H), 1.87-1.76 (m, 3H), 1.68-1.59 (m, 1H);

MS (ESI+) m/z 644 [M+H]⁺

Example 366. 2-amino-N-((1S,2S)-2-((4'-((4-methylpiperazin-1-yl)methyl)-[1,1'-biphenyl]-4-yl)methoxy)cyclopentyl)-5-(1-(1-methylpiperidin-4-yl)-1H-pyrazol-4-yl)nicotinamide Using 1-methyl-4-[4-(tetramethyl-1,3,2-dioxaborolan-2-yl)-1H-pyrazol-1-yl]-piperidine, the title compound was obtained as described for the example 363.

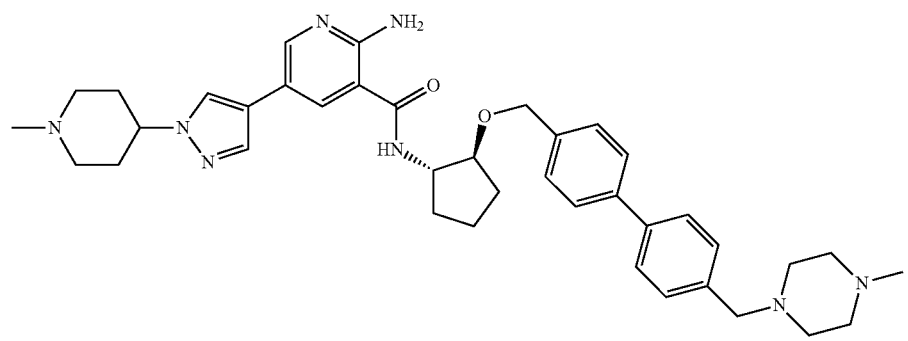

$^1$H NMR (400 MHz, CD$_3$OD) δ 8.57 (s, 1H), 8.21 (s, 1H), 8.15 (s, 1H), 7.92 (s, 1H), 7.63 (d, J=8.0 Hz, 2H), 7.57-7.50 (m, 4H), 7.42 (d, J=8.0 Hz, 2H), 4.66 (s, 2H), 4.59-4.53 (m, 1H), 4.43-4.38 (m, 1H), 4.25 (s, 2H), 4.12-4.01 (m, 2H), 3.69-3.66 (d, 2H), 3.53 (br s, 2H), 3.39 (br s, 2H), 3.25-3.20 (m, 1H), 2.93 (s, 3H), 2.92 (s, 3H), 2.41-2.33 (m, 4H), 2.19-1.97 (m, 2H), 1.84-1.76 (m, 3H), 1.69-1.60 (m, 1H);
MS (ESI+) m/z 663 [M+H]$^+$

Example 367. 2-amino-N-((1S,2S)-2-((4'-((4-methylpiperazin-1-yl)methyl)-[1,1'-biphenyl]-4-yl)methoxy)cyclopentyl)-5-(4-(4-methylpiperazin-1-yl)phenyl)-nicotinamide Using 4-(4-Methylpiperazin-1-yl)phenylboronic acid, the title compound was obtained as described for the example 363.

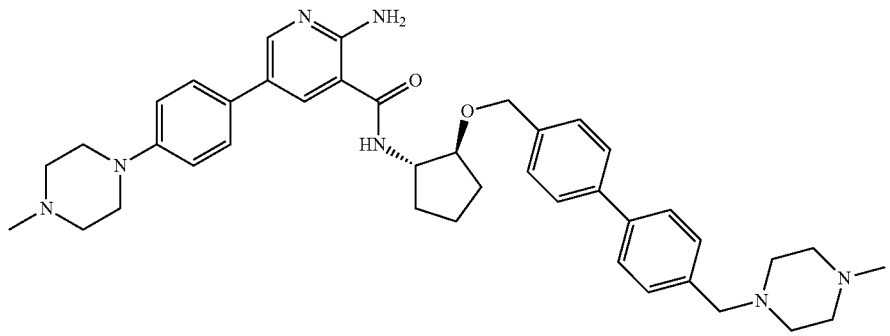

$^1$H NMR (400 MHz, CD$_3$OD) δ 8.59 (s, 1H), 8.18 (s, 1H), 7.64-7.50 (m, 8H), 7.43 (d, J=8.0 Hz, 2H), 7.11 (d, J=8.0 Hz, 2H), 4.66 (s, 2H), 4.43-4.39 (m, 1H), 4.25 (s, 2H), 4.03-4.00 (m, 1H), 3.92 (d, J=1.2 Hz, 2H), 3.62 (d, J=1.2 Hz, 2H), 3.52 (br s, 2H), 3.39 (br s, 2H), 3.26-3.20 (m, 2H), 3.12-3.06 (m, 2H), 2.96 (s, 3H), 2.93 (s, 3H), 2.18-2.13 (m, 1H), 2.05-1.92 (m, 1H), 1.83-1.76 (m, 3H), 1.66-1.59 (m, 1H);
MS (ESI+) n/z 674 [M+H]$^+$

Example 368. 2-amino-N-((1S,2S)-2-((4'-((4-methylpiperazin-1-yl)methyl)-[1,1'-biphenyl]-4-yl)methoxy)cyclopentyl)-5-(4-((4-methylpiperazin-1-yl)methyl)phenyl)nicotinamide Using 4-((4-methylpiperazin-1-yl)methyl)phenylboronic acid, the title compound was obtained as described for the example 363.

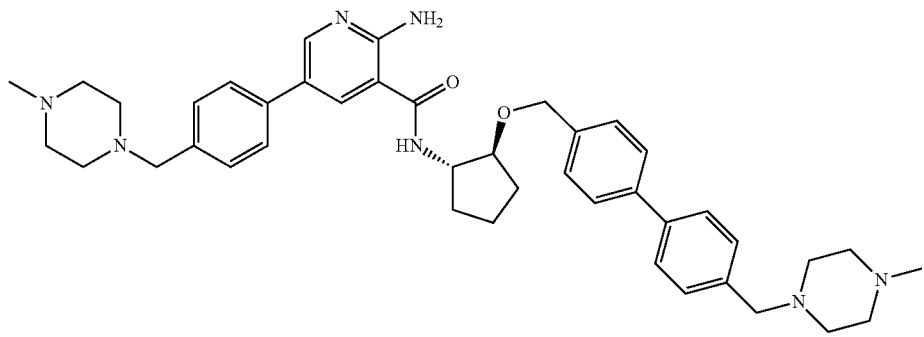

¹H NMR (400 MHz, CD₃OD) δ 8.66 (s, 1H), 8.29 (s, 1H). 7.73 (d, J=8.0 Hz, 2H), 7.65-7.52 (m, 8H), 7.43 (d, J=8.0 Hz, 2H), 4.66 (s, 2H), 4.42 (m, 1H), 4.31 (s, 2H), 4.21 (s, 2H), 4.02 (m, 1H), 3.53 (br, 8H), 3.46 (br, 4H), 3.29 (br, 4H), 2.94 (s, 3H), 2.93 (s, 3H), 2.23-2.10 (m, 1H), 2.04-1.98 (m, 1H), 1.88-1.75 (m, 3H), 1.67-1.60 (m, 1H);
MS (ESI+) m/z 688 [M+H]⁺

Example 369. 2-amino-5-(4-(hydroxymethyl)phenyl)-N-((1S,2S)-2-((4'-((4-methylpiperazin-1-yl)methyl)-[1,1'-biphenyl]-4-yl)methoxy)cyclopentyl)nicotinamide Using 4-(Hydroxymethyl)phenylboronic acid, the title compound was obtained as described for the example 363.

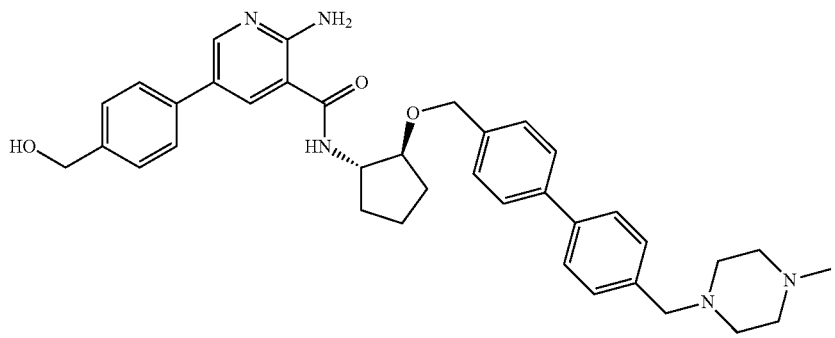 [SMILES: CN1CCN(Cc2ccc(-c3ccc(CO[C@H]4CCC[C@@H]4NC(=O)c4cc(-c5ccc(CO)cc5)cnc4N)cc3)cc2)CC1]

¹H NMR (400 MHz, CD₃OD) δ 8.63 (s, 1H), 8.26 (s, 1H), 7.70 (d, J=8.0 Hz, 1H), 7.61-7.53 (m, 5H), 7.46-7.41 (m, 6H), 4.66 (s, 2H), 4.64 (s, 2H), 4.42 (m, 1H), 3.99 (m, 1H), 3.91 (s, 2H), 3.35 (br s, 2H), 3.00 (br s, 2H), 2.88 (s, 3H), 2.22-2.10 (m, 1H), 2.04 (m, 1H), 1.85-1.74 (m, 3H), 1.63 (m, 1H);
MS (ESI+) m/z 606 [M+H]⁺

Example 370. 2-amino-N-((1S,2S)-2-((4'-((4-methylpiperazin-1-yl)methyl)-[1,1'-biphenyl]-4-yl)methoxy)cyclopentyl)-5-(m-tolyl)nicotinamide Using 3-tolylboronic acid, the title compound was obtained as described for the example 363

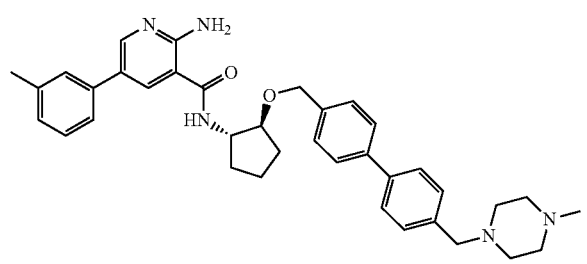

¹H NMR (400 MHz, CD₃OD) δ 8.62 (s, 1H), 8.23 (s, 1H), 7.72-7.32 (m, 1H), 7.24 (d, J=8.0 Hz, 1H), 4.66 (s, 2H), 4.41 (m, 1H), 4.06 (s, 2H), 4.00 (m, 1H), 3.43 (br s, 2H), 3.17 (br s, 2H), 2.90 (s, 3H), 2.39 (s, 3H), 2.18 (m, 1H), 2.04 (m, 1H), 1.89-1.75 (m, 3H), 1.65-1.60 (m, 1H);
MS (ESI+) m/z 590 [M+H]⁺

Example 371. 2-amino-N-((1S,2S)-2-((4'-((4-methylpiperazin-1-yl)methyl)-[1,1'-biphenyl]-4-yl)methoxy)cyclopentyl)-5-phenylnicotinamide Using phenylboronic acid, the title compound was obtained as described for the example 363.

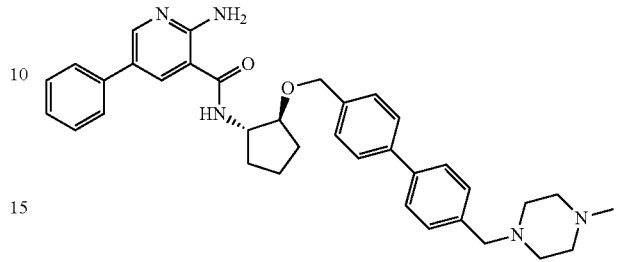

MS (ESI+) m/z 576 [M+H]⁺

Example 372. 2-amino-5-(4-hydroxyphenyl)-N-((1S,2S)-2-((4'-((4-methyl-piperazin-1-yl)methyl)-[1,1'-biphenyl]-4-yl)methoxy)cyclopentyl)nicotinamide Using 4-hydroxyphenylboronic acid, the title compound was obtained as described for the example 363.

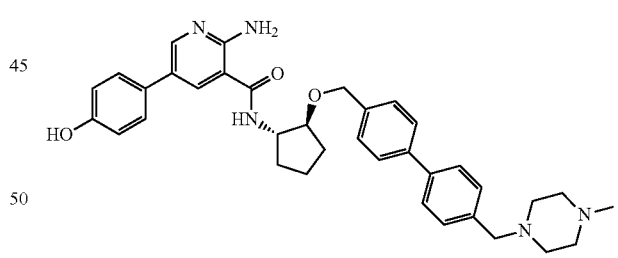

MS (ESI+) m/z 592 [M+H]⁺

Example 373. 2-amino-5-(4-chloro-3-fluorophenyl)-N-((1S,2S)-2-((4'-((4-methylpiperazin-1-yl)methyl)-[1,1'-biphenyl]-4-yl)methoxy)cyclopentyl)nicotinamide Using 4-chloro-3-fluorophenylboronic acid, the title compound was obtained as described for the example 363.

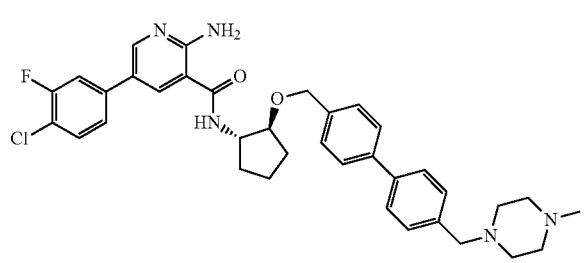 [SMILES: CN1CCN(Cc2ccc(-c3ccc(CO[C@H]4CCC[C@@H]4NC(=O)c4cc(-c5ccc(Cl)c(F)c5)cnc4N)cc3)cc2)CC1]

MS (ESI+) m/z 629 [M+H]+

Example 374. 2-amino-5-methyl-N-((1S,2S)-2-((4'-((4-methylpiperazin-1-yl)-methyl)-[1,1'-biphenyl]-4-yl)methoxy)cyclopentyl)nicotinamide Using trimethylboroxine, the title compound was obtained as described for the example 363.

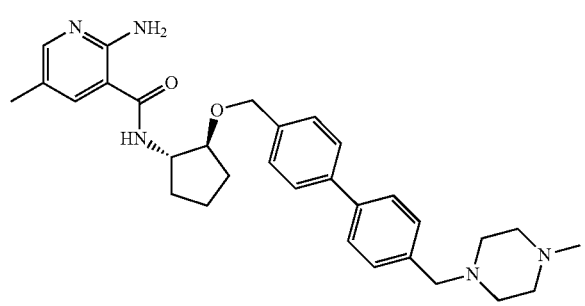

MS (ESI+) m/z 514 [M+H]+

Example 375. 6-amino-N-((1S,2S)-2-((4'-((4-methylpiperazin-1-yl)methyl)-[1,1'-biphenyl]-4-yl)methoxy)cyclopentyl)-[3,3'-bipyridine]-5-carboxamide Using 3-pyridylboronic acid, the title compound was obtained as described for the example 363.

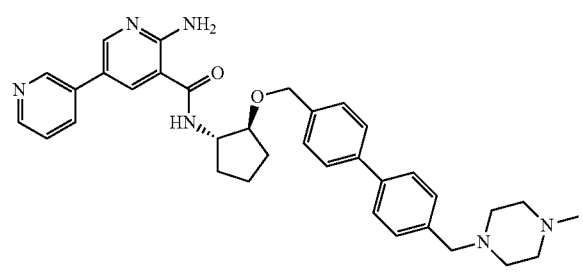 [SMILES: CN1CCN(Cc2ccc(-c3ccc(CO[C@H]4CCC[C@@H]4NC(=O)c4cc(-c5cccnc5)cnc4N)cc3)cc2)CC1]

MS (ESI+) n/z 577 [M+H]+

Example 376. 2-amino-5-(4-methoxyphenyl)-N-((1S,2S)-2-((4'-((4-methyl-piperazin-1-yl)methyl)-[1,1'-biphenyl]-4-yl)methoxy)cyclopentyl)nicotinamide Using 4-methoxyphenylboronic acid, the title compound was obtained as described for the example 363.

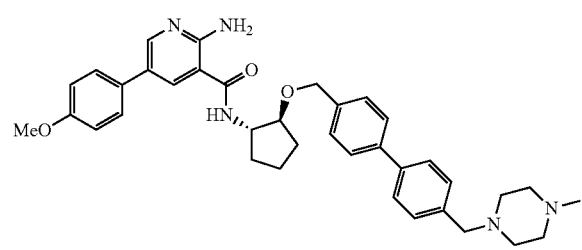 [SMILES: COc1ccc(-c2cnc(N)c(C(=O)N[C@H]3CCC[C@@H]3OCc3ccc(-c4ccc(CN5CCN(C)CC5)cc4)cc3)c2)cc1]

MS (ESI+) m/z 606 [M+H]+

Example 377. 6-amino-N-((1S,2S)-2-((4'-((4-methylpiperazin-1-yl)methyl)-[1,1'-biphenyl]-4-yl)methoxy)cyclopentyl)-[3,4'-bipyridine]-5-carboxamide Using 4-pyridylboronic acid, the title compound was obtained as described for the example 363.

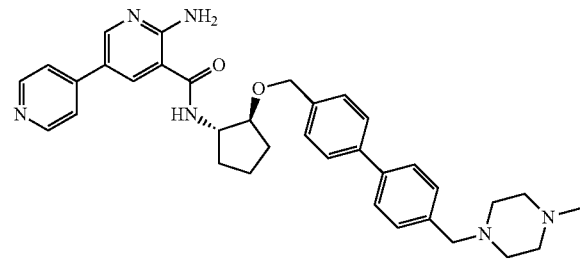 [SMILES: CN1CCN(Cc2ccc(-c3ccc(CO[C@H]4CCC[C@@H]4NC(=O)c4cc(-c5ccncc5)cnc4N)cc3)cc2)CC1]

MS (ESI+) m/z 577 [M+H]+

Example 378. 2-amino-N-((1S,2S)-2-((4'-((4-methylpiperazin-1-yl)methyl)-[1,1'-biphenyl]-4-yl)methoxy)cyclopentyl)-5-(4-((4-methylpiperidin-1-yl)methyl)phenyl)-nicotinamide Using (4-((4-methylpiperidin-1-yl)methyl)phenyl)boronic acid, the title compound was obtained as described for the example 363.

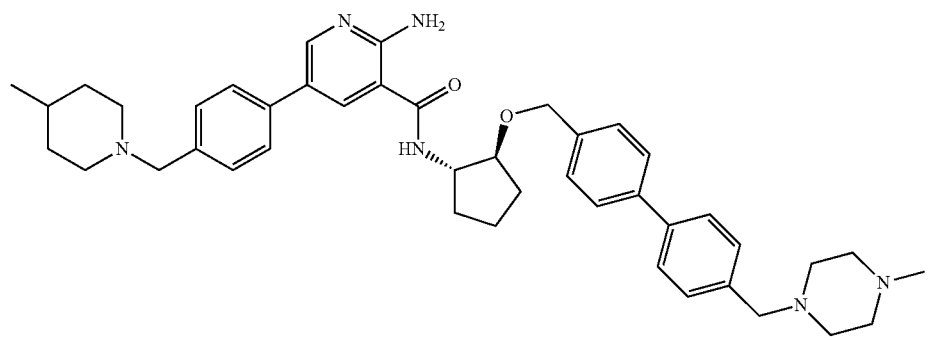

MS (ESI+) m/z 687 [M+H]$^+$

Example 379. 2-amino-N-((1S,2S)-2-((4'-((4-methylpiperazin-1-yl)methyl)-[1,1'-biphenyl]-4-yl)methoxy)cyclopentyl)-5-(4-(morpholinomethyl)phenyl)nicotinamide Using (4-(morpholinomethyl)phenyl)boronic acid, the title compound was obtained as described for the example 363.

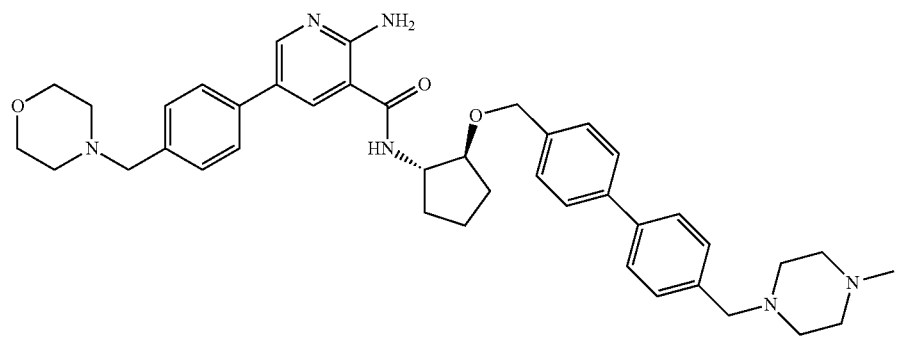 [SMILES: CN1CCN(Cc2ccc(-c3ccc(CO[C@H]4CCC[C@@H]4NC(=O)c4cc(-c5ccc(CN6CCOCC6)cc5)cnc4N)cc3)cc2)CC1]

MS (ESI+) n/z 675 [M+H]$^+$

Example 380. 2-amino-N-((1S,2S)-2-((4'-((4-methylpiperazin-1-yl)methyl)-[1,1'-biphenyl]-4-yl)methoxy)cyclopentyl)-5-(1-(tetrahydro-2H-pyran-4-yl)-1H-pyrazol-4-yl)nicotinamide Using 1-(Tetrahydro-pyran-4-yl)-1H-pyrazole-4-boronic acid pinacol ester, the title compound was obtained as described for the example 363.

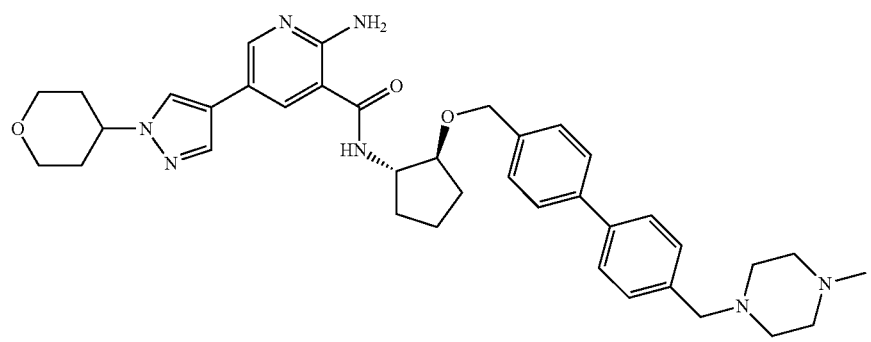 [SMILES: CN1CCN(Cc2ccc(-c3ccc(CO[C@H]4CCC[C@@H]4NC(=O)c4cc(-c5cnn(C6CCOCC6)c5)cnc4N)cc3)cc2)CC1]

MS (ESI+) m/z 650 [M+H]$^+$

Example 381. 2-amino-N-((1S,2S)-2-((4'-((4-methylpiperazin-1-yl)methyl)-[1,1'-biphenyl]-4-yl)methoxy)cyclopentyl)-5-(4-morpholinophenyl)nicotinamide Using 4-morpholinophenylboronic acid, the title compound was obtained as described for the example 363.

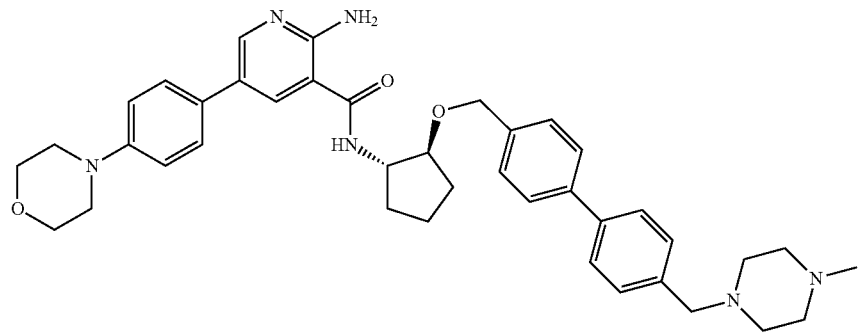 [SMILES: CN1CCN(Cc2ccc(-c3ccc(CO[C@H]4CCC[C@@H]4NC(=O)c4cc(-c5ccc(N6CCOCC6)cc5)cnc4N)cc3)cc2)CC1]

MS (ESI+) n/z 661 [M+H]+

Example 382. 2-amino-5-(cyclohex-1-en-1-yl)-N-((1S,2S)-2-((4'-((4-methyl-piperazin-1-yl)methyl)-[1,1'-biphenyl]-4-yl)methoxy)cyclopentyl)nicotinamide Using 1-cyclohexenylboronic acid, the title compound was obtained as described for the example 363.

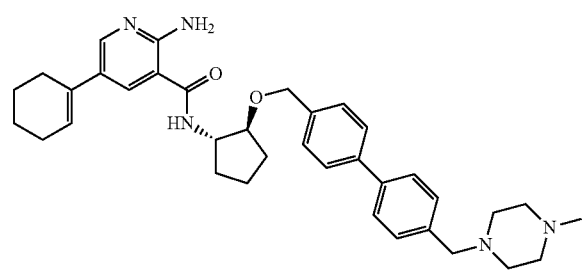 [SMILES: CN1CCN(Cc2ccc(-c3ccc(CO[C@H]4CCC[C@@H]4NC(=O)c4cc(C5=CCCCC5)cnc4N)cc3)cc2)CC1]

MS (ESI+) n/z 580 [M+H]+

Example 383. 2-amino-5-(3,4-dimethoxyphenyl)-N-((1S,2S)-2-((4'-((4-methyl-piperazin-1-yl)methyl)-[1,1'-biphenyl]-4-yl)methoxy)cyclopentyl)nicotinamide Using 3,4-dimethoxyphenylboronic acid, the title compound was obtained as described for the example 363.

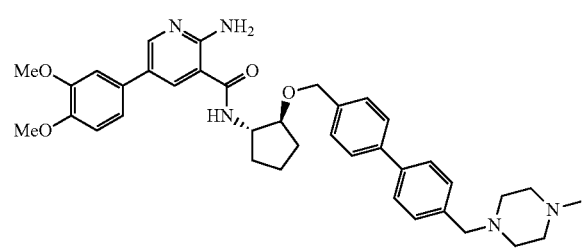 [SMILES: COc1ccc(-c2cnc(N)c(C(=O)N[C@H]3CCC[C@@H]3OCc3ccc(-c4ccc(CN5CCN(C)CC5)cc4)cc3)c2)cc1OC]

MS (ESI+) m/z 636 [M+H]+

Example 384. 6-amino-2',6'-difluoro-N-((1S,2S)-2-((4'-((4-methylpiperazin-1-yl)methyl)-[1,1'-biphenyl]-4-yl)methoxy)cyclopentyl)-[3,4'-bipyridine]-5-carboxamide Using 2,6-difluoropyridine-4-boronic acid, the title compound was obtained as described for the example 363.

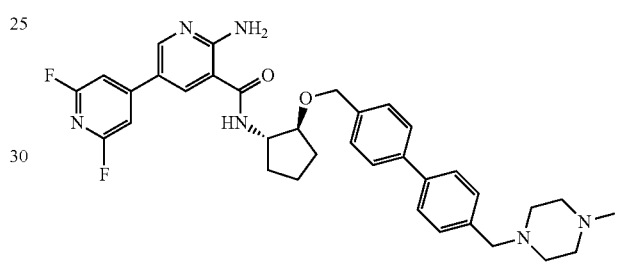

MS (ESI+) n/z 613 [M+H]+

Example 385. 2-amino-N-((1S,2S)-2-((4'-((4-methylpiperazin-1-yl)methyl)-[1,1'-biphenyl]-4-yl)methoxycyclopentyl)-5-(4-methylthiophen-3-yl)nicotinamide Using 4-Methyl-3-thienylboronic acid, the title compound was obtained as described for the example 363.

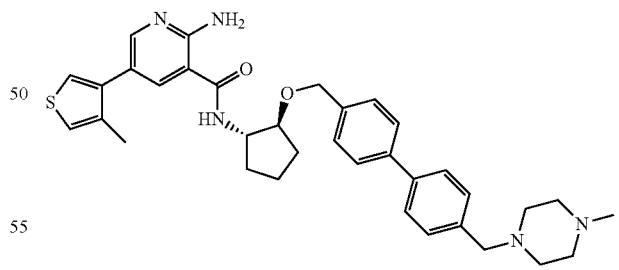

MS (ESI+) m/z 596 [M+H]+

Example 386. 6-amino-6'-fluoro-N-((1S,2S)-2-((4'-((4-methylpiperazin-1-yl)methyl)-[1,1'-biphenyl]-4-yl)methoxy)cyclopentyl)-[3,3'-bipyridine]-5-carboxamide Using 6-fluoro-3-pyridinylboronic acid, the title compound was obtained as described for the example 363.

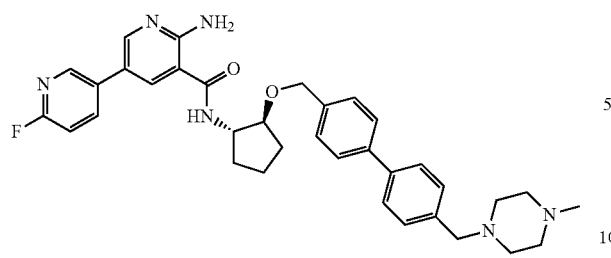

MS (ESI+) m/z 595 [M+H]+

Example 387. 2-amino-N-((1S,2S)-2-((4'-((4-methylpiperazin-1-yl)methyl)-[1,1'-biphenyl]-4-yl)methoxy)cyclopentyl)-5-(1-(1,1,2,2-tetrafluoroethyl)-1H-pyrazol-4-yl)-nicotinamide Using (1-(1,1,2,2-tetrafluoroethyl)-1H-pyrazol-4-yl)boronic acid, the title compound was obtained as described for the example 363.

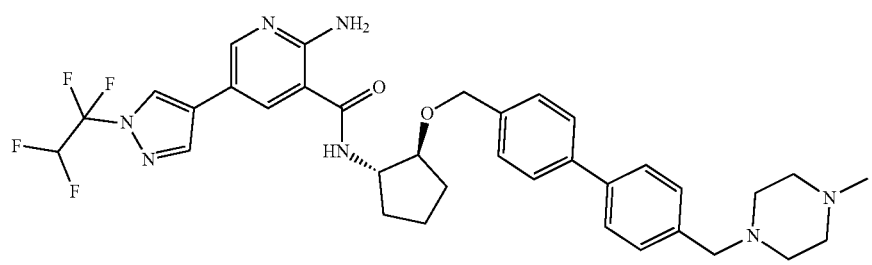 [SMILES: CN1CCN(Cc2ccc(-c3ccc(CO[C@H]4CCC[C@@H]4NC(=O)c4cc(-c5cnn(C(F)(F)C(F)F)c5)cnc4N)cc3)cc2)CC1]

$^1$H NMR (600 MHz, CD$_3$OD) δ ppm 1.64 (br dd, J=14.09, 7.04 Hz, 1H) 1.75-1.88 (m, 3H) 2.04 (br dd, J=12.33, 7.63 Hz, 1H) 2.15-2.23 (m, 1H) 2.87 (s, 3H) 2.90-3.06 (m, 4H) 3.33 (br s, 4H) 3.86 (s, 2H) 3.98-4.04 (m, 1H) 4.39-4.44 (m, 1H) 4.62-4.69 (m, 2H) 6.75-6.98 (m, 1H) 7.39-7.45 (m, 4H) 7.55 (br d, J=8.22 Hz, 2H) 7.57 (br d, J=8.22 Hz, 2H) 8.20 (s, 1H) 8.33 (d, J=1.76 Hz, 1H) 8.58 (d, J=1.76 Hz, 1H) 8.60 (s, 1H);

MS (ESI+) m/z 666.3 [M+H]+

Example 388. 2-amino-N-((3S,4S)-4-((3-ethyl-4-methylbenzyl)oxy)pyrrolidin-3-yl)-5-(1-methyl-1H-pyrazol-4-yl)nicotinamide Scheme for the Preparation of the Compound of Example 388:

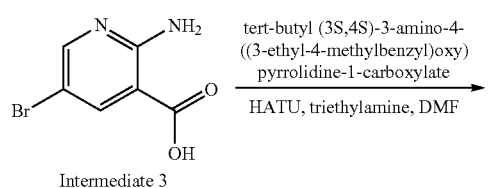

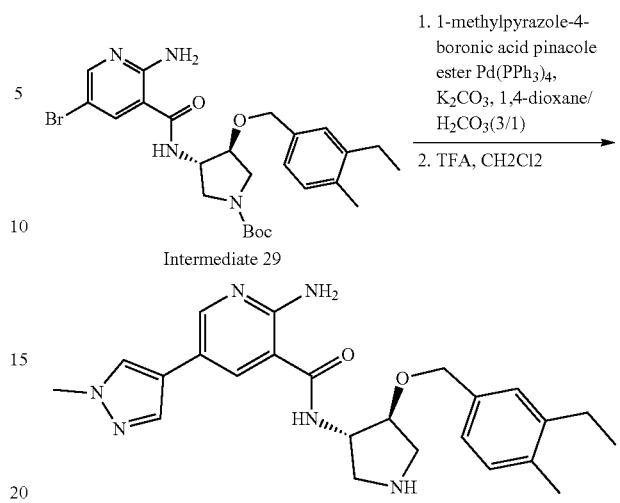

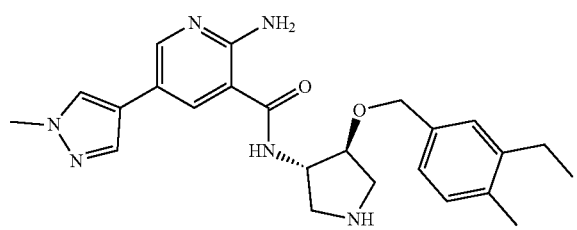

Intermediate 29

To a mixture of intermediate 3 (420 mg, 1.94 mmol) and triethylamine (0.40 ml, 2.90 mmol) in 10 ml of DMF was added HATU (884 mg, 2.32 mmol) followed by tert-butyl (3S,4S)-3-amino-4-((3-ethyl-4-methylbenzyl)oxy)pyrrolidine-1-carboxylate (647 mg, 1.94 mmol). The mixture was stirred at room temperature for 1 hr and then saturated sodium bicarbonate solution was added. The mixture was extracted with EtOAc, washed with brine, dried over MgSO$_4$, and concentrated in vacuo. The crude product was purified through silicagel column chromatography to give 800 mg of off-white solid.

$^1$H NMR (600 MHz, CDCl$_3$) δ ppm 1.14-1.22 (t, 3H) 1.41 (br s, 9H) 2.27 (s, 3H) 2.55-2.64 (q, 2H) 3.37-3.66 (m, 4H) 3.78 (dd, J=12.03, 5.58 Hz, 1H) 4.10 (br s, 1H) 4.50-4.79 (m, 2H) 6.74 (br s, 2H) 7.04-7.15 (m, 3H) 7.98 (d, J=1.76 Hz, 1H) 8.43 (br s, 1H);

MS (ESI, m/z): 534.3 [M+H]+

Example 388. 2-amino-N-((3S,4S)-4-((3-ethyl-4-methylbenzyl)oxy)pyrrolidin-3-yl)-5-(1-methyl-1H-pyrazol-4-yl)nicotinamide To a mixture of intermediate 29 (40 mg, 0.07 mmol) and 1-methylpyrazole-4-boronic acid pinacol ester (23 mg, 0.11 mmol) in 0.4 ml of 1,4-dioxane/water (3/I) was added K$_2$CO$_3$ (31 mg, 0.22 mmol) followed by Pd(PPh$_3$)$_4$ (4 mg, 0.003 mmol). The reaction mixture was heated at 100° C. for 3 hrs, cooled to room temperature, and extracted with EtOAc, dried over anhydrous MgSO$_4$ and concentrated under vacuum. The crude residue was dissolved with 0.5 ml of CH$_2$Cl$_2$/TFA (10/1) and the mixture was stirred for 2 hrs. After concentration under vacuum, the crude residue was purified by preparative HPLC to afford 23 mg of the title compound.

$^1$H NMR (600 MHz, CD$_3$OD) ppm 1.13 (t, J=7.34 Hz, 3H) 2.23 (s, 2H) 2.57 (q, J=7.24 Hz, 2H) 2.91 (dd, J=12.03, 4.40 Hz, 1H) 2.97-3.04 (m, 1H) 3.16-3.22 (m, 1H) 3.36-3.43 (m, 1H) 3.91 (s, 3H) 4.05-4.10 (m, 1H) 4.48 (br s, 1H) 4.57 (d, J=11.74 Hz, 1H) 4.65 (d, J=11.74 Hz, 1H) 7.06 (s, 2H) 7.12 (s, 1H) 7.76 (s, 1H) 7.89 (s, 1H) 8.02 (d, J=2.35 Hz, 1H) 8.26 (d, J=2.35 Hz, 1H), MS (ESI, m/z): 435.5 [M+H]$^+$ Example 389. 2-amino-N-((3S,4S)-4-((3-ethyl-4-methylbenzyl)oxy)pyrrolidin-3-yl)-5-(4-(hydroxymethyl)phenyl)nicotinamide Using 4-hydroxymethylphenylboronic acid, the title compound was obtained as described for the example 388.

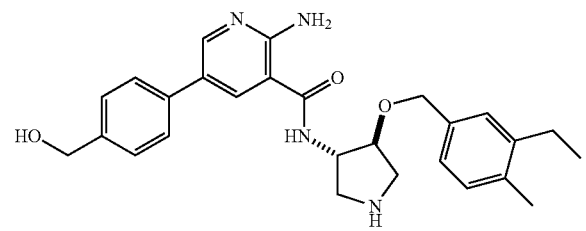

MS (ES, m/z): 461.6 [M+H]$^+$

Example 390. 2-amino-N-((3S,4S)-4-((3-ethyl-4-methylbenzyl)oxy)pyrrolidin-3-yl)-5-(4-((4-methylpiperazin-1-yl)methyl)phenyl)nicotinamide Using (4-((4-methylpiperazin-1-yl)methyl)phenyl)boronic acid, the title compound was obtained as described for the example 388.

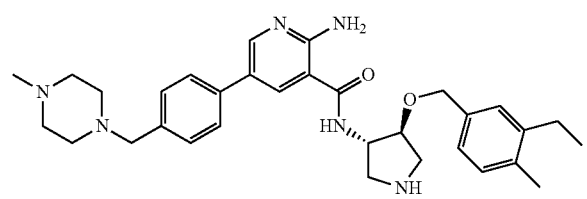 [SMILES: CCc1cc(CO[C@H]2CNC[C@@H]2NC(=O)c2cc(-c3ccc(CN4CCN(C)CC4)cc3)cnc2N)ccc1C]

MS (ESI, m/z): 543.4 [M+H]$^+$

Example 391. 2-amino-5-(4-carbamoylphenyl)-N-((3S,4S)-4-((3-ethyl-4-methylbenzyl)oxy)pyrrolidin-3-yl)nicotinamide Using (4-carbamoylphenyl)boronic acid, the title compound was obtained as described for the example 388.4

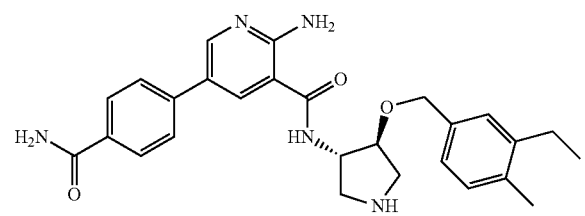 [SMILES: CCc1cc(CO[C@H]2CNC[C@@H]2NC(=O)c2cc(-c3ccc(C(N)=O)cc3)cnc2N)ccc1C]

$^1$H NMR (400 MHz, CD$_3$OD) δ ppm 1.16 (t, J=7.63 Hz, 3H) 2.25 (s, 3H) 2.19-2.19 (m, 1H) 2.60 (q, J=7.70 Hz, 2H) 3.33-3.35 (m, 1H) 3.43-3.64 (m, 2H) 3.77 (br dd, J=12.72, 7.24 Hz, 1H) 4.36 (br s, 1H) 4.55-4.73 (m, 3H) 7.10 (s, 2H) 7.17 (s, 1H) 7.78 (d, J=8.22 Hz, 2H) 7.99 (d, J=8.61 Hz, 2H) 8.44 (d, J=2.35 Hz, 1H) 8.62 (d, J=1.96 Hz, 1H);

MS (ESI, m/z): 474.5 [M+H]$^+$

Example 392. 2-amino-N-((3S,4S)-4-((3-ethyl-4-methylbenzyl)oxy)pyrrolidin-3-yl)-5-(m-tolyl)nicotinamide Using m-tolylboronic acid, the title compound was obtained as described for the example 388.

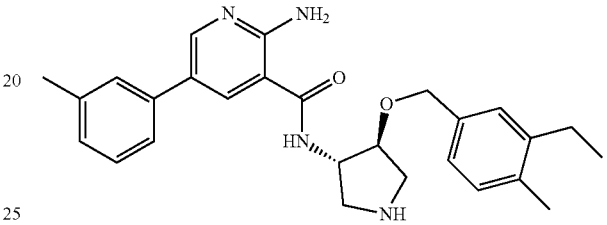

$^1$H NMR (400 MHz, CD$_3$OD) δ ppm 1.16 (t, J=7.43 Hz, 3H) 2.25 (s, 3H) 2.41 (s, 3H) 2.60 (q, J=7.56 Hz, 2H) 3.43-3.65 (m, 3H) 3.77 (dd, J=12.52, 7.04 Hz, 1H) 4.35 (br d, J=4.30 Hz, 1H) 4.62-4.74 (m, 3H) 7.09 (s, 2H) 7.16 (s, 1H) 7.25 (br d, J=7.43 Hz, 1H) 7.36 (t, J=7.63 Hz, 1H) 7.42-7.51 (m, 2H) 8.31 (d, J=1.96 Hz, 1H) 8.65 (d, J=1.96 Hz, 1H);

MS (ESI, m/z): 445.3 [M+H]$^+$

Example 393. 4-(6-amino-5-(((3S,4S)-4-((3-ethyl-4-methylbenzyl)oxy)-pyrrolidin-3-yl)carbamoyl)pyridin-3-yl)benzoic acid Using 4-carboxyphenylboronic acid, the title compound was obtained as described for the example 388.

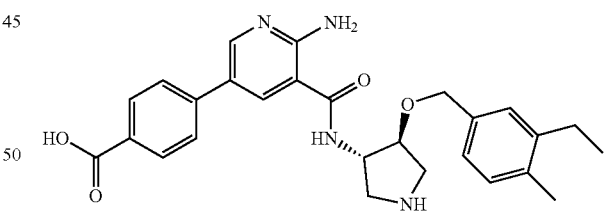

$^1$H NMR (400 MHz, CD$_3$OD) δ ppm 1.16 (t, J=7.43 Hz, 3H) 2.23 (s, 3H) 2.59 (q, J=7.56 Hz, 2H) 3.34-3.51 (m, 2H) 3.52-3.67 (m, 1H) 3.76 (br d, J=7.43 Hz, 1H) 4.13 (br s, 1H) 4.57-4.69 (m, 3H) 7.02-7.10 (m, 2H) 7.14 (s, 1H) 7.79 (br d, J=8.22 Hz, 2H) 8.13 (br d, J=8.22 Hz, 2H) 8.37-8.45 (m, 1H) 8.73 (d, J=1.56 Hz, 1H); MS (ESI, m/z): 475.4 [M+H]$^+$ Example 394. 2-amino-N-((3S,4S)-4-((3-ethyl-4-methylbenzyl)oxy)pyrrolidin-3-yl)-5-phenylnicotinamide Using phenylboronic acid, the title compound was obtained as described for the example 388.

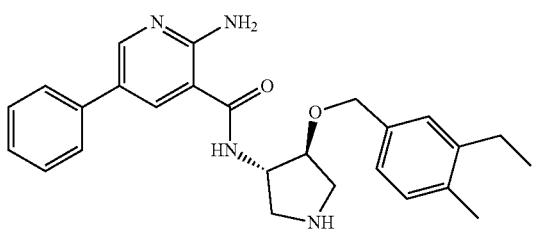 [SMILES: CCc1cc(CO[C@H]2CNC[C@@H]2NC(=O)c2cc(-c3ccccc3)cnc2N)ccc1C]

¹H NMR (400 MHz, CD₃OD) δ ppm 1.16 (t, J=7.63 Hz, 3H) 2.25 (s, 3H) 2.61 (q, J=7.43 Hz, 2H) 3.42-3.51 (m, 1H) 3.51-3.65 (m, 2H) 3.77 (dd, J=12.91, 7.04 Hz, 1H) 4.35 (br d, J=4.30 Hz, 1H) 4.57-4.76 (m, 3H) 7.06-7.13 (m, 2H) 7.17 (s, 1H) 7.35-7.58 (m, 3H) 7.68 (d, J=7.04 Hz, 2H) 8.33 (d, J=2.35 Hz, 1H) 8.74 (d, J=2.35 Hz, 1H);

MS (ESI, m/z): 431.5 [M+H]⁺

Example 395. 6-amino-N-((3S,4S)-4-((3-ethyl-4-methylbenzyl)oxy)pyrrolidin-3-yl)-[3,4'-bipyridine]-5-carboxamide Using pyridine-4-boronic acid, the title compound was obtained as described for the example 388.

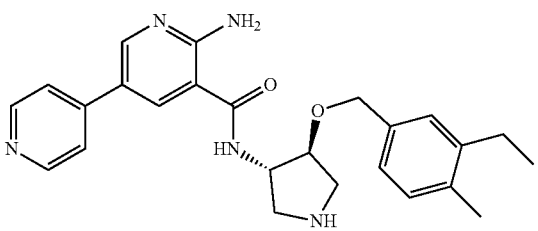 [SMILES: CCc1cc(CO[C@H]2CNC[C@@H]2NC(=O)c2cc(-c3ccncc3)cnc2N)ccc1C]

¹H NMR (400 MHz, CD₃OD) δ ppm 1.17 (t, J=7.63 Hz, 3H) 2.26 (s, 3H) 2.62 (q, J=7.56 Hz, 2H) 3.47 (br d, J=12.52 Hz, 1H) 3.52-3.67 (m, 2H) 3.77 (br dd, J=12.72, 6.85 Hz, 1H) 4.34 (br d, J=3.91 Hz, 1H) 4.61-4.78 (m, 3H) 7.07-7.13 (m, 2H) 7.13-7.19 (m, 1H) 7.99 (dd, J=8.02, 5.67 Hz, 1H) 8.56 (d, J=1.96 Hz, 1H) 8.68-8.82 (m, 3H) 9.14 (s, 1H);

MS (ESI, m/z): 432.3 [M+H]⁺

Example 396. 6-amino-N-((3S,4S)-4-((3-ethyl-4-methylbenzyl)oxy)pyrrolidin-3-yl)-[3,3'-bipyridine]-5-carboxamide Using pyridine-3-boronic acid, the title compound was obtained as described for the example 388.

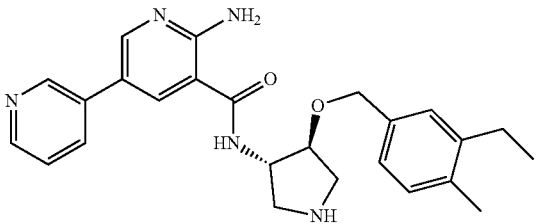 [SMILES: CCc1cc(CO[C@H]2CNC[C@@H]2NC(=O)c2cc(-c3cccnc3)cnc2N)ccc1C]

¹H NMR (400 MHz, CD₃OD) δ ppm 1.17 (t, J=7.63 Hz, 3H) 2.26 (s, 3H) 2.62 (q, J=7.56 Hz, 2H) 3.47 (br d, J=12.52 Hz, 1H) 3.52-3.67 (m, 2H) 3.77 (br dd, J=12.72, 6.85 Hz, 1H) 4.34 (br d, J=3.91 Hz, 1H) 4.60-4.78 (m, 3H) 7.07-7.13 (m, 2H) 7.17 (d, J=7.06 Hz, 1H) 7.18 (s, 1H) 7.99 (dd, J=8.02, 5.67 Hz, 1H) 8.56 (d, J=1.96 Hz, 1H) 8.67-8.83 (m, 3H) 9.14 (s, 1H);

MS (ESI, m/z): 432.3 [M+H]⁺

Example 397. 2-amino-N-((3S,4S)-4-((3-ethyl-4-methylbenzyl)oxy)pyrrolidin-3-yl)-5-vinylnicotinamide Using potassium vinyltrifluoroborate, the title compound was obtained as described for the example 388.

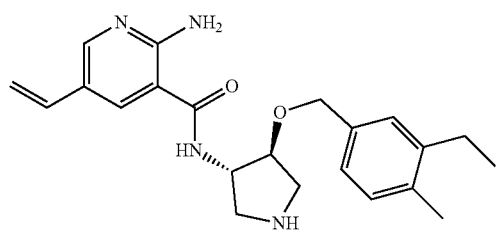 [SMILES: C=Cc1cnc(N)c(C(=O)N[C@H]2CNC[C@@H]2OCc2ccc(C)c(CC)c2)c1]

¹H NMR (400 MHz, CD₃OD) δ ppm 1.17 (t, J=7.43 Hz, 3H) 2.26 (s, 3H) 2.61 (q, J=7.56 Hz, 2H) 3.44-3.65 (m, 3H) 3.76 (br dd, J=12.91, 7.04 Hz, 1H) 4.33 (br d, J=3.91 Hz, 1H) 4.59-4.74 (m, 3H) 5.42 (d, J=10.96 Hz, 1H) 5.94 (d, J=17.61 Hz, 1H) 6.66 (dd, J=17.80, 11.15 Hz, 1H) 7.10 (s, 2H) 7.16 (s, 1H) 8.02-8.08 (m, 1H) 8.66 (d, J=1.96 Hz, 1H);

MS (ESI, m/z): 381.3 [M+H]⁺

Example 398. 2-amino-N-((3S,4S)-4-((3-ethyl-4-methylbenzyl)oxy)pyrrolidin-3-yl)-5-(4-fluorophenyl)nicotinamide Using 4-fluorophenylboronic acid, the title compound was obtained as described for the example 388.

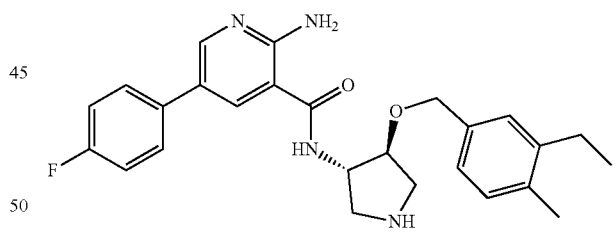

¹H NMR (600 MHz, CD₃OD) δ ppm 1.16 (t, J=7.63 Hz, 3H) 2.25 (s, 3H) 2.60 (q, J=7.63 Hz, 2H) 3.44-3.59 (m, 2H) 3.76 (dd, J=12.62, 7.34 Hz, 2H) 4.25-4.38 (m, 1H) 4.61-4.71 (m, 3H) 7.03-7.12 (m, 2H) 7.14-7.24 (m, 3H) 7.60-7.69 (m, 2H) 8.32 (d, J=2.35 Hz, 1H) 8.48 (d, J=2.35 Hz, 1H);

MS (ESI, m/z): 499.3 [M+H]⁺

Example 399. 2-amino-N-((3S,4S)-4-((3-ethyl-4-methylbenzyl)oxy)pyrrolidin-3-yl)-5-(4-formylphenyl)nicotinamide Using 4-formylphenylboronic acid, the title compound was obtained as described for the example 388.

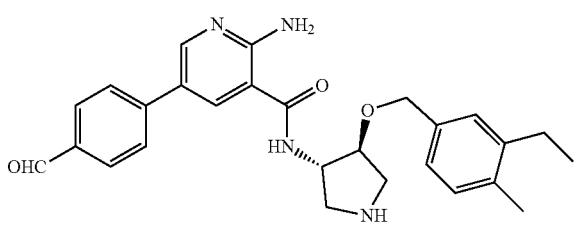 [SMILES: CCc1cc(CO[C@H]2CNC[C@@H]2NC(=O)c2cc(-c3ccc(C=O)cc3)cnc2N)ccc1C]

¹H NMR (600 MHz, CDCl₃) δ ppm 1.30 (t, J=7.63 Hz, 3H) 2.26 (br s, 3H) 2.58 (q, J=7.63 Hz, 2H), 3.43-3.49 (m, 1H) 3.50-3.65 (m, 2H) 3.77 (dd, J=12.62, 6.75 Hz, 1H), 4.17 (br s, 1H) 4.64 (br s, 2H) 4.77 (br s, 1H) 6.59 (br s, 2H) 7.05-7.20 (m, 3H) 7.55-7.73 (m, 2H) 7.86 (br d, J=5.28 Hz, 2H) 8.04 (br s, 1H) 8.46 (br s, 1H) 9.86 (br s, 1H);
MS (ESI, m/z): 459.5 [M+H]⁺

Example 400. 2-amino-5-(4-cyanophenyl)-N-((3S,4S)-4-((3-ethyl-4-methylbenzyl)oxy)pyrrolidin-3-yl)nicotinamide Using 4-cyanophenylboronic acid, the title compound was obtained as described for the example 388.

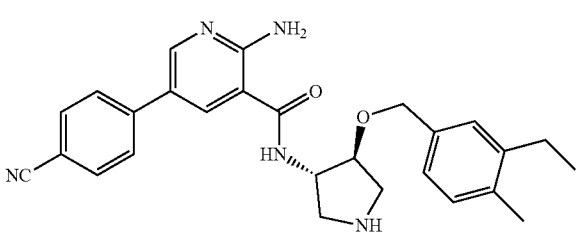 [SMILES: CCc1cc(CO[C@H]2CNC[C@@H]2NC(=O)c2cc(-c3ccc(C#N)cc3)cnc2N)ccc1C]

¹H NMR (600 MHz, CD₃OD) δ ppm 1.16 (t, J=7.34 Hz, 3H) 2.25 (s, 3H) 2.60 (q, J=7.63 Hz, 2H) 3.43-3.49 (m, 1H) 3.50-3.65 (m, 2H) 3.77 (dd, J=12.62, 6.75 Hz, 1H) 4.35 (br d, J=4.11 Hz, 1H) 4.62-4.74 (m, 3H) 7.04-7.14 (m, 2H) 7.16 (s, 1H) 7.78-7.84 (m, 2H) 7.84-7.88 (m, 2H) 8.39-8.52 (m, 1H) 8.59 (d, J=1.76 Hz, 1H);
MS (ESI, m/z): 456.3 [M+H]⁺

Example 401. 2-amino-N-((3S,4S)-4-((3-ethyl-4-methylbenzyl)oxy)pyrrolidin-3-yl)-5-(4-(methylsulfonamido)phenyl)nicotinamide Using 4-methylsulfonylphenylboronic acid, the title compound was obtained as described for the example 388.

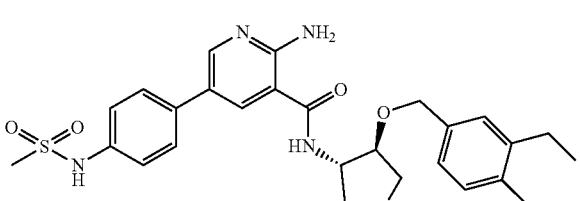

¹H NMR (600 MHz, CD₃OD) δ ppm 1.16 (t, J=7.34 Hz, 3H) 2.25 (s, 3H) 2.60 (q, J=7.63 Hz, 2H) 2.98 (s, 3H) 3.43-3.49 (m, 1H) 3.50-3.65 (m, 2H) 3.76 (dd, J=12.62, 7.34 Hz, 1H) 4.33-4.38 (m, 1H) 4.62-4.71 (m, 3H) 7.05-7.13 (m, 2H) 7.16 (s, 1H) 7.36 (d, J=8.80 Hz, 2H) 7.65 (d, J=8.22 Hz, 2H) 8.32 (d, J=1.76 Hz, 1H) 8.59 (d, J=1.76 Hz, 1H);
MS (ESI, m/z):524.6 [M+H]⁺

Example 402. 2-amino-N-((3S,4S)-4-((3-ethyl-4-methylbenzyl)oxy)pyrrolidin-3-yl)-5-(4-phenoxyphenyl)nicotinamide Using 4-phenoxyphenylboronic acid, the title compound was obtained as described for the example 388.

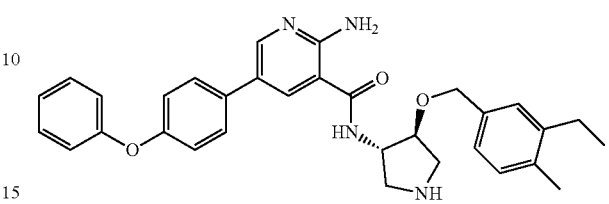

¹H NMR (600 MHz, CD₃OD) δ ppm 1.16 (t, J=7.63 Hz, 3H) 2.25 (s, 3H) 2.56-2.65 (m, 2H) 3.46 (br d, J=12.33 Hz, 1H) 3.52-3.61 (m, 2H) 3.76 (s, 1H) 4.32-4.40 (m, 1H) 4.62-4.73 (m, 3H) 7.02 (d, J=7.63 Hz, 2H) 7.04-7.12 (m, 4H) 7.13-7.19 (m, 2H) 7.38 (t, J=7.92 Hz, 2H) 7.66 (d, J=8.80 Hz, 2H) 8.29-8.34 (m, 1H) 8.68 (d, J=1.76 Hz, 1H);
MS (ESI, m/z):523.7 [M+H]⁺

Example 403. 5-([1,1'-biphenyl]-4-yl)-2-amino-N-((3S,4S)-4-((3-ethyl-4-methylbenzyl)oxy)pyrrolidin-3-yl)nicotinamide Using 4-biphenylboronic acid, the title compound was obtained as described for the example 388.

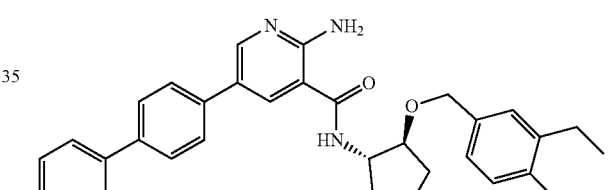

¹H NMR (600 MHz, CD₃OD) δ ppm 1.16 (t, J=7.63 Hz, 3H) 2.25 (s, 3H) 2.60 (q, J=7.63 Hz, 2H) 3.47 (br d, J=12.91 Hz, 1H) 3.51-3.62 (m, 2H) 3.77 (dd, J=12.33, 7.04 Hz, 1H) 4.31-4.40 (m, 1H) 4.63-4.73 (m, 3H) 7.05-7.14 (m, 2H) 7.17 (s, 1H) 7.34 (s, 1H) 7.36 (br d, J=7.63 Hz, 1H) 7.45 (t, J=7.63 Hz, 2H) 7.64 (d, J=7.63 Hz, 2H) 7.70-7.79 (m, 3H) 8.40 (d, J=1.76 Hz, 1H) 8.64 (d, J=2.35 Hz, 1H);
MS (ESI, m/z):507.4 [M+H]⁺

Example 404. 2-amino-5-(4-(benzyloxy)phenyl)-N-((3S,4S)-4-((3-ethyl-4-methylbenzyl)oxy)pyrrolidin-3-yl)nicotinamide Using 4-benzyloxyphenylboronic acid, the title compound was obtained as described for the example 388.

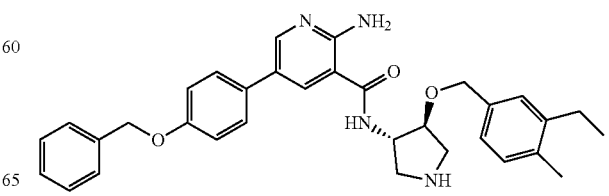

¹H NMR (600 MHz, CD₃OD) δ ppm 1.16 (t, J=7.63 Hz, 3H) 2.24 (s, 3H) 2.60 (q, J=7.63 Hz, 2H) 3.46 (br d, J=12.91 Hz, 1H) 3.49-3.60 (m, 2H) 3.76 (dd, J=12.91, 7.04 Hz, 1H) 4.28-4.36 (m, 1H) 4.60-4.73 (m, 3H) 5.13 (s, 2H) 7.03-7.13 (m, 4H) 7.16 (s, 1H) 7.23-7.32 (m, 1H) 7.36 (t, J=7.63 Hz, 2H) 7.43 (d, J=7.04 Hz, 2H) 7.59 (d, J=8.80 Hz, 2H) 8.23-8.29 (m, 1H) 8.60 (d, J=1.76 Hz, 1H);

MS (ESI, m/z): 537.8 [M+H]⁺

Example 405. 2-amino-5-(4-(dimethylamino)phenyl)-N-((3S,4S)-4-((3-ethyl-4-methylbenzyl)oxy)pyrrolidin-3-yl)nicotinamide

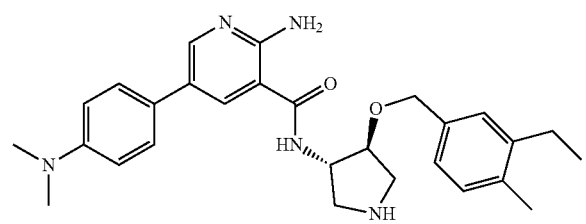 [SMILES: CCc1cc(CO[C@H]2CNC[C@@H]2NC(=O)c2cc(-c3ccc(N(C)C)cc3)cnc2N)ccc1C]

Using 4-dimethylaminophenylboronic acid, the title compound was obtained as described for the example 388.

¹H NMR (600 MHz, CD₃OD) δ ppm 1.16 (t, J=7.63 Hz, 3H) 2.25 (s, 3H) 2.60 (q, J=7.24 Hz, 2H) 3.07 (s, 6H) 3.47 (br d, J=12.91 Hz, 1H) 3.57 (ddd, J=18.78, 12.91, 3.52 Hz, 2H) 3.76 (br dd, J=12.91, 7.04 Hz, 1H) 4.32-4.37 (m, 1H) 4.61-4.72 (m, 3H) 7.02-7.12 (m, 4H) 7.16 (s, 1H) 7.62 (d, J=8.80 Hz, 2H) 8.26 (d, J=1.76 Hz, 1H) 8.69 (d, J=1.76 Hz, 1H);

MS (ESI, m/z): 474.4 [M+H]⁺

Example 406. 2-amino-N-((3S,4S)-4-((3-ethyl-4-methylbenzyl)oxy)pyrrolidin-3-yl)-5-(quinolin-3-yl)nicotinamide

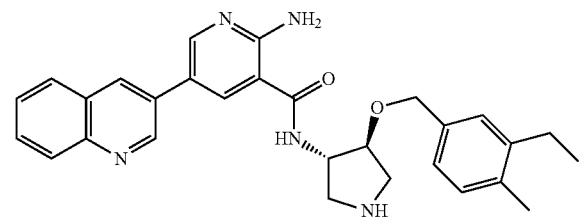 [SMILES: CCc1cc(CO[C@H]2CNC[C@@H]2NC(=O)c2cc(-c3cnc4ccccc4c3)cnc2N)ccc1C]

Using quinoline-3-boronic acid, the title compound was obtained as described for the example 388.

¹H NMR (600 MHz, CD₃OD) δ ppm 1.17 (t, J=7.34 Hz, 3H) 2.25 (s, 3H) 2.61 (q, J=7.24 Hz, 2H) 3.48 (br d, J=12.91 Hz, 1H) 3.57-3.69 (m, 2H) 3.78 (br dd, J=12.91, 7.04 Hz, 1H) 4.34-4.42 (m, 1H) 4.61-4.75 (m, 3H) 7.05-7.15 (m, 2H) 7.18 (s, 1H) 7.78-7.93 (m, 1H) 7.93-8.09 (m, 1H) 8.18 (br dd, J=8.22, 3.52 Hz, 2H) 8.63 (d, J=1.76 Hz, 1H) 8.86 (d, J=2.35 Hz, 1H) 8.99-9.07 (m, 1H) 9.37 (d, J=1.76 Hz, 1H);

MS (ESI, m/z): 482.6 [M+H]⁺

Example 407. 2-amino-5-(benzofuran-2-yl)-N-((3S,4S)-4-((3-ethyl-4-methylbenzyl)oxy)pyrrolidin-3-yl)nicotinamide

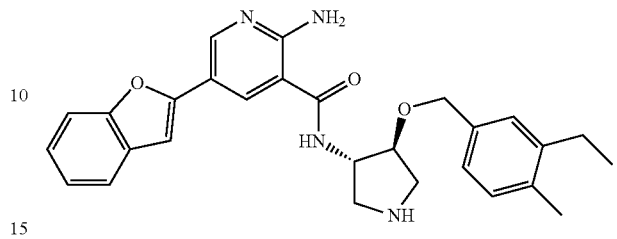

Using benzo[b]furan-2-boronic acid, the title compound was obtained as described for the example 388.

¹H NMR (600 MHz, CD₃OD) δ ppm 1.16 (t, J=7.63 Hz, 3H) 2.25 (s, 3H) 2.61 (q, J=7.63 Hz, 2H) 3.48 (br d, J=12.33 Hz, 1H) 3.53 (br dd, J=12.91, 2.93 Hz, 1H) 3.60 (br dd, J=12.91, 4.70 Hz, 1H) 3.78 (br dd, J=12.62, 7.34 Hz, 1H) 4.37 (br s, 1H) 4.63-4.72 (m, 3H) 7.04-7.14 (m, 2H) 7.15-7.20 (m, 2H) 7.20-7.26 (m, 1H) 7.29 (br t, J=7.63 Hz, 1H) 7.51 (d, J=8.22 Hz, 1H) 7.58 (br d, J=7.63 Hz, 1H) 8.57 (d, J=1.76 Hz, 1H) 8.60 (d, J=1.76 Hz, 1H);

MS (ESI, m/z): 471.5 [M+H]⁺

Example 408. 2-amino-N-((3S,4S)-4-((3-ethyl-4-methylbenzyl)oxy)pyrrolidin-3-yl)-5-(naphthalen-1-yl)nicotinamide Using 2-naphthyleneboronic acid, the title compound was obtained as described for the example 388.

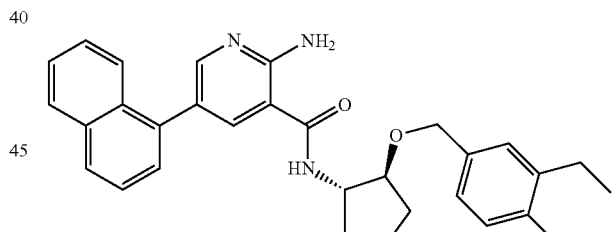

¹H NMR (600 MHz, CD₃OD) δ ppm 1.16 (t, J=7.63 Hz, 3H) 2.24 (s, 3H) 2.60 (q, J=7.43 Hz, 2H) 3.48 (br d, J=12.91 Hz, 1H) 3.53-3.69 (m, 2H) 3.78 (dd, J=12.91, 7.04 Hz, 1H) 4.31-4.46 (m, 1H) 4.55-4.72 (m, 3H) 7.05-7.14 (m, 2H) 7.17 (s, 1H) 7.47-7.58 (m, 2H) 7.79 (dd, J=8.22, 1.76 Hz, 1H) 7.85-8.02 (m, 3H) 8.16 (s, 1H) 8.47 (d, J=1.76 Hz, 1H) 8.78 (d, J=1.76 Hz, 1H);

MS (ESI, m/z): 481.4 [M+H]⁺

Example 409. 2-amino-N-((3S,4S)-4-((3-ethyl-4-methylbenzyl)oxy)pyrrolidin-3-yl)-5-(4-(trifluoromethyl)phenyl)nicotinamide Using 4-trifluoromethylbenzeneboronic acid, the title compound was obtained as described for the example 388.

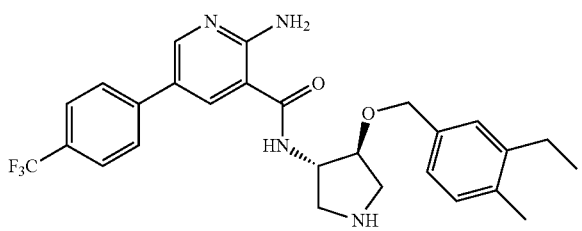 [SMILES: CCc1cc(CO[C@H]2CNC[C@@H]2NC(=O)c2cc(-c3ccc(C(F)(F)F)cc3)cnc2N)ccc1C]

¹H NMR (600 MHz, CD₃OD) δ ppm 1.16 (t, J=7.63 Hz, 3H) 2.25 (s, 3H) 2.61 (q, J=7.24 Hz, 2H) 3.45 (br d, J=12.32 Hz, 1H) 3.49-3.62 (m, 2H) 3.75 (dd, J=12.62, 6.75 Hz, 1H) 4.26-4.38 (m, 1H) 4.61-4.72 (m, 3H) 7.03-7.13 (m, 2H) 7.16 (s, 1H) 7.33 (td, J=10.12, 6.75 Hz, 2H) 7.53-7.69 (m, 2H) 8.29 (s, 1H) 8.48 (d, J=1.76 Hz, 1H);

MS (ESI, m/z): 499.6 [M+H]⁺

Example 410. 2-amino-N-((3S,4S)-4-((3-ethyl-4-methylbenzyl)oxy)pyrrolidin-3-yl)-5-(2,4,5-trifluorophenyl)nicotinamide Using 2,4,5-trifluorophenylboronic acid, the title compound was obtained as described for the example 388.

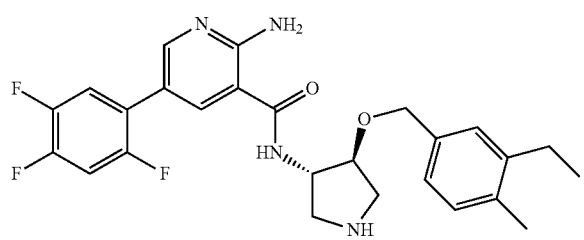 [SMILES: CCc1cc(CO[C@H]2CNC[C@@H]2NC(=O)c2cc(-c3cc(F)c(F)cc3F)cnc2N)ccc1C]

¹H NMR (600 MHz, CD₃OD) δ ppm 1.16 (t, J=7.63 Hz, 3H) 2.25 (s, 3H) 2.61 (q, J=7.24 Hz, 2H) 3.45 (br d, J=12.32 Hz, 1H) 3.49-3.62 (m, 2H) 3.75 (dd, J=12.62, 6.75 Hz, 1H) 4.26-4.38 (m, 1H) 4.61-4.72 (m, 3H) 7.03-7.13 (m, 2H) 7.16 (s, 1H) 7.33 (td, J=10.12, 6.75 Hz, 1H) 7.53-7.63 (m, 1H) 8.29 (s, 1H) 8.48 (d, J=1.76 Hz, 1H);

MS (ESI, m/z): 485.3 [M+H]⁺

Example 411. 2-amino-5-(4-(cyanomethyl)phenyl)-N-((3S,4S)-4-((3-ethyl-4-methylbenzyl)oxy)pyrrolidin-3-yl)nicotinamide Using 4-cyanomethylphenylboronic acid, the title compound was obtained as described for the example 388.

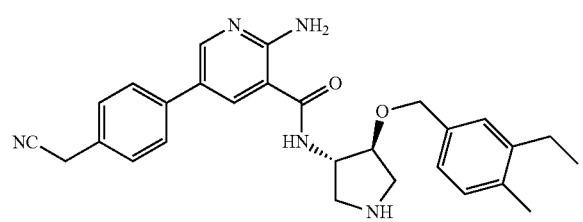 [SMILES: CCc1cc(CO[C@H]2CNC[C@@H]2NC(=O)c2cc(-c3ccc(CC#N)cc3)cnc2N)ccc1C]

¹H NMR (600 MHz, CD₃OD) δ ppm 1.16 (td, J=7.63, 2.35 Hz, 3H) 2.24 (d, J=4.11 Hz, 3H) 2.59 (qd, J=7.53, 3.23 Hz, 2H) 3.45-3.56 (m, 1H) 3.67-3.74 (m, 1H) 3.77-3.88 (m, 1H) 3.93 (s, 2H) 3.98 (br dd, J=11.44, 6.16 Hz, 1H) 4.11-4.28 (m, 1H) 4.58-4.70 (m, 3H) 7.07 (s, 2H) 7.14 (s, 1H) 7.86 (d, J=2.93 Hz, 1H) 8.02 (s, 1H) 8.19 (d, J=11.15 Hz, 1H) 8.24 (d, J=1.76 Hz, 1H) 8.59 (dd, J=7.04, 2.35 Hz, 1H);

MS (ESI, m/z): 470.8 [M+H]⁺

Example 412. 2-amino-N-((3S,4S)-4-((3-ethyl-4-methylbenzyl)oxy)pyrrolidin-3-yl)-5-(1-(piperidin-4-yl)-1H-pyrazol-4-yl)nicotinamide Using 1-(4-N-Boc-piperidine)pyrazole-4-boronic acid, the title compound was obtained as described for the example 388 and following deprotection with TFA.

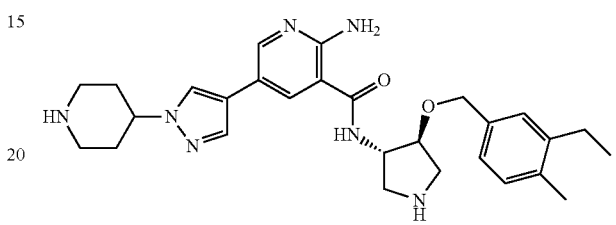

MS (ESI, m/z): 504.3 [M+H]⁺

Example 413. 2-amino-N-((3S,4S)-4-((3-ethyl-4-methylbenzyl)oxy)pyrrolidin-3-yl)-5-(1-(1-methylpiperidin-4-yl)-1H-pyrazol-4-yl)nicotinamide Using 1-(4-N-methylpiperidine)pyrazole-4-boronic acid, the title compound was obtained as described for the example 388.

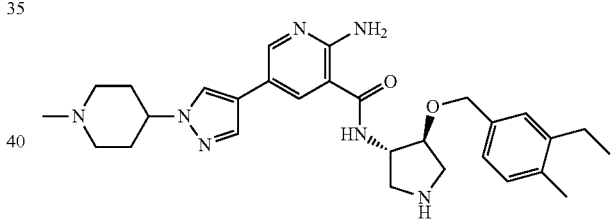

MS (ESI, m/z): 518.3 [M+H]⁺

Example 414. 2-amino-N-((3S,4S)-4-(benzyloxy)pyrrolidin-3-yl)-5-(1-methyl-1H1-pyrazol-4-yl)nicotinamide Using tert-butyl (3S,4S)-3-amino-4-(benzyloxy)pyrrolidine-1-carboxylate, the title compound was obtained as described for the example 388.

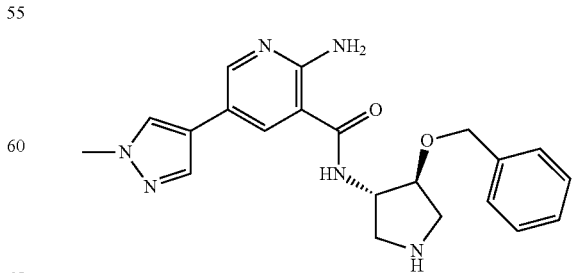

MS (ESI, m/z): 393.2 [M+H]⁺

Example 415. 2-amino-5-(1-methyl-1H-pyrazol-4-yl)-N-((3S,4S)-4-((4-methylbenzyl)oxy)pyrrolidin-3-yl)nicotinamide Using tert-butyl (3S,4S)-3-amino-4-((4-methylbenzyl)oxy)pyrolidine-1-carboxylate, the title compound was obtained as described for the example 388.

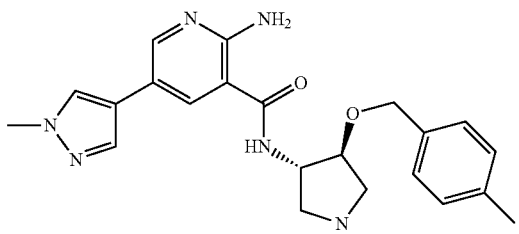

MS (ESI, m/z): 407.2 [M+H]$^+$

Example 416. 2-amino-N-((3S,4S)-4-((3-ethylbenzyl)oxy)pyrrolidin-3-yl)-5-(1-methyl-1H-pyrazol-4-yl)nicotinamide Using tert-butyl (3S,4S)-3-amino-4-((3-ethylbenzyl)oxy)pyrrolidine-1-carboxylate, the title compound was obtained as described for the example 388.

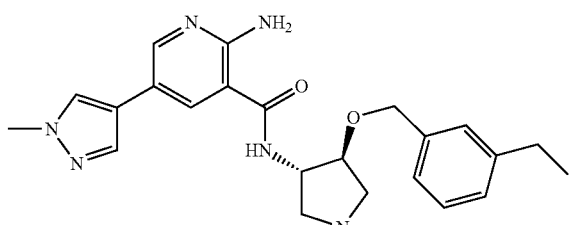

MS (ESI, m/z): 421.2 [M+H]$^+$

Example 417. 2-amino-N-((3S,4S)-4-((3-ethyl-4-fluorobenzyl)oxy)pyrrolidin-3-yl)-5-(1-methyl-1H-pyrazol-4-yl)nicotinamide Using tert-butyl (3S,4S)-3-amino-4-((3-ethyl-4-fluorobenzyl)oxy)pyrrolidine-1-carboxylate, the title compound was obtained as described for the example 388.

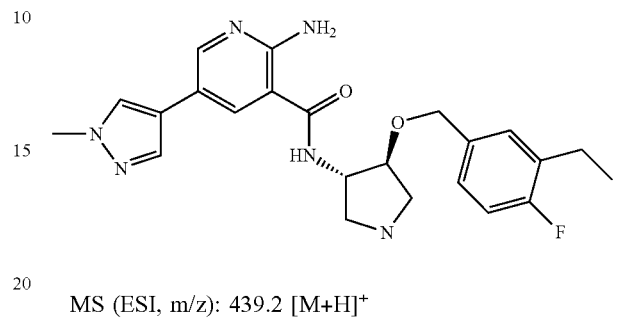

MS (ESI, m/z): 439.2 [M+H]$^+$

Example 418. 2-amino-N-(3S,4S)-4-((4-chloro-3-ethylbenzyl)oxy)pyrrolidin-3-yl)-5-(1-methyl-1H-pyrazol-4-yl)nicotinamide Using tert-butyl (3S,4S)-3-amino-4-((4-chloro-3-ethylbenzyl)oxy)pyrrolidine-1-carboxylate, the title compound was obtained as described for the example 388.

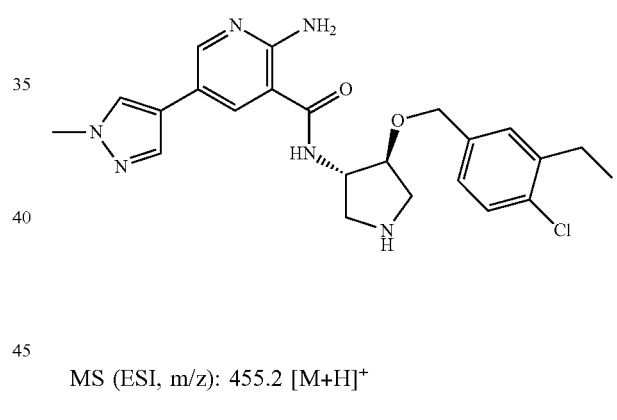

MS (ESI, m/z): 455.2 [M+H]$^+$

Example 419. 2-amino-N-((3S,4S)-4-((3-ethyl-4-methylbenzyl)oxy)pyrrolidin-3-yl)-5-(4-((1-methylpiperidin-4-yl)carbamoyl)phenyl)nicotinamide Scheme for the Preparation of the Compound of Example 419:

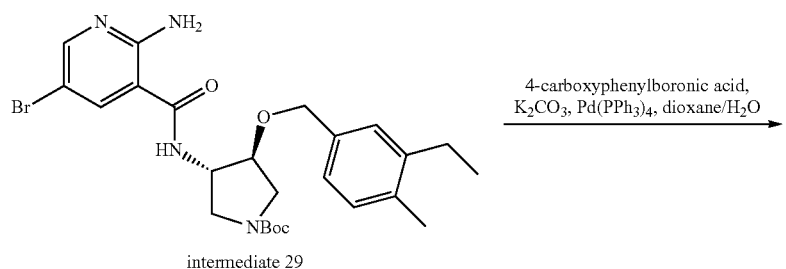

intermediate 29

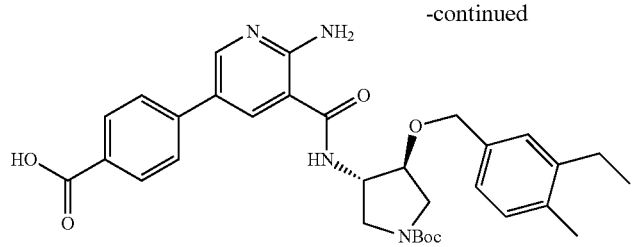

intermediate 30

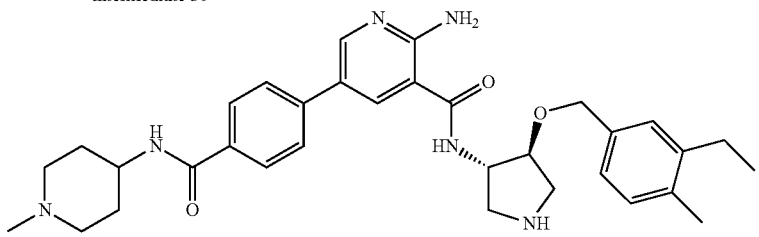

Intermediate 30

To a mixture of intermediate 29 (400 mg, 0.7 mmol) and 4-carboxyphenylboronic acid (230 mg, 1.10 mmol) in 4 ml of 1,4-dioxane/water (3/1) was added $K_2CO_3$ (310 mg, 2.2 mmol) followed by $Pd(PPh_3)_4$ (40 mg, 0.03 mmol). The reaction mixture was heated at 100° C. for 3 hrs, cooled to room temperature, and extracted with EtOAc, dried over anhydrous $MgSO_4$ and concentrated under vacuum. The crude product was purified through silicagel column chromatography to give 350 mg of off-white solid $^1$H NMR (400 MHz, $CD_3OD$) δ ppm 1.16 (t, J=7.43 Hz, 3H) 1.46 (br d, J=1.96 Hz, 9H) 2.23 (s, 3H) 2.59 (q, J=7.56 Hz, 2H) 3.40-3.51 (m, 2H) 3.52-3.65 (m, 1H) 3.76 (br d, J=7.43 Hz, 1H) 4.13 (br s, 1H) 4.57-4.74 (m, 3H) 7.06 (s, 2H) 7.14 (s, 1H) 7.79 (br d, J=8.22 Hz, 2H) 8.13 (br d, J=8.22 Hz, 2H) 8.37-8.45 (m, 1H) 8.73 (d, J=1.56 Hz, 1H); MS (ESI, m/z): 575.3 [M+H]$^+$

Example 419. 2-amino-N-((3S,4S)-4-((3-ethyl-4-methylbenzyl)oxy)pyrrolidin-3-yl)-5-(4-((1-methylpiperidin-4-yl)carbamoyl)phenyl)nicotinamide To a mixture of intermediate 30 (12 mg, 0.02 mmol) and triethylamine (0.04 ml, 0.03 mmol) in 0.2 ml of DMF was added HATU (10 mg, 0.03 mmol) followed by 4-amino-1-methylpiperidine (0.03 ml, 0.02 mmol). The mixture was stirred at room temperature for 1 hr and then saturated sodium bicarbonate solution was added. The mixture was extracted with EtOAc, washed with brine, dried over $MgSO_4$, and concentrated in vacuo. The crude residue was dissolved with 0.5 ml of $CH_2Cl_2$/TFA (10/1) and the mixture was stirred for 2 hrs. After concentration under vacuum, the crude residue was purified by preparative HPLC to afford 10 mg of the title compound.

$^1$H NMR (400 MHz, $CD_3OD$) δ ppm 1.16 (t, J=7.63 Hz, 3H) 1.86-1.98 (m, 2H) 2.23 (br s, 3H) 2.25 (s, 3H) 2.61 (q, J=7.70 Hz, 2H) 2.89 (s, 3H) 3.10-3.26 (m, 2H) 3.47 (br d, J=12.52 Hz, 1H) 3.52-3.66 (m, 3H) 3.77 (dd, J=12.72, 6.85 Hz, 1H) 4.11-4.23 (m, 1H) 4.32-4.43 (m, 1H) 4.53-4.77 (m, 3H) 7.05-7.14 (m, 2H) 7.17 (s, 1H) 7.81 (d, J=8.22 Hz, 2H) 7.88-7.99 (m, 2H) 8.42 (d, J=1.96 Hz, 1H) 8.74 (d, J=1.96 Hz, 1H);
MS (ESI, m/z): 571.4 [M+H]$^+$

Example 420. 2-amino-N-((3S,4S)-4-((3-ethyl-4-methylbenzyl)oxy)pyrrolidin-3-yl)-5-(4-((4-methylcyclohexyl)carbamoyl)phenyl)nicotinamide Using 4-methylcyclohexylamine, the title compound was obtained as described for the example 419.

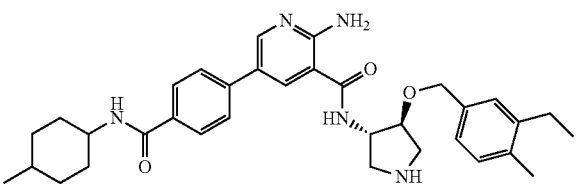 [SMILES: CCc1cc(CO[C@H]2CNC[C@@H]2NC(=O)c2cc(-c3ccc(C(=O)NC4CCC(C)CC4)cc3)cnc2N)ccc1C]

$^1$H NMR (600 MHz, $CD_3OD$) δ ppm 0.93 (d, J=6.46 Hz, 1H) 1.00 (d, J=6.46 Hz, 2H) 1.09 (br d, J=14.09 Hz, 1H) 1.16 (t, J=7.63 Hz, 3H) 1.38-1.48 (m, 2H) 1.59-1.73 (m, 3H) 1.75-1.84 (m, 2H) 1.96 (br d, J=11.15 Hz, 1H) 2.25 (s, 3H) 2.60 (q, J=7.63 Hz, 2H) 3.32-3.36 (m, 1H) 3.47 (br d, J=12.91 Hz, 1H) 3.51-3.61 (m, 3H) 3.76 (dd, J=12.91, 7.04 Hz, 2H) 3.99 (br s, 1H) 4.35 (br s, 1H) 4.62-4.72 (m, 3H) 7.03-7.14 (m, 2H) 7.16 (s, 1H) 7.76 (dd, J=8.51, 4.40 Hz, 2H) 7.91 (dd, J=8.22, 2.35 Hz, 2H) 8.42 (d, J=2.35 Hz, 1H) 8.58-8.62 (m, 1H);
MS (ESI, m/z): 570.5 [M+H]$^+$

Example 421. 2-amino-N-((3S,4S)-4-((3-ethyl-4-methylbenzyl)oxy)pyrrolidin-3-yl)-5-(4-(4-methylpiperidine-1-carbonyl)phenyl)nicotinamide Using 4-methylpiperidine, the title compound was obtained as described for the example 419.

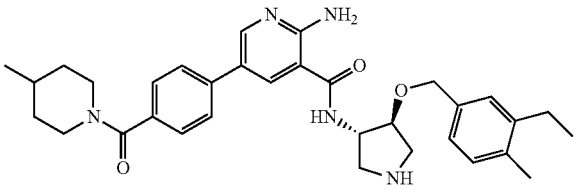 [SMILES: CCc1cc(CO[C@H]2CNC[C@@H]2NC(=O)c2cc(-c3ccc(C(=O)N4CCC(C)CC4)cc3)cnc2N)ccc1C]

¹H NMR (600 MHz, CD₃OD) δ ppm 0.98 (d, J=6.46 Hz, 3H) 1.09-1.22 (m, 3H) 1.16 (t, J=7.63, 3H) 1.62 (br d, J=11.74 Hz, 1H) 1.66-1.74 (m, 2H) 1.79 (br d, J=12.91 Hz, 1H) 2.23 (s, 3H) 2.53-2.63 (q, J=7.63 Hz, 2H) 2.85 (br t, J=12.33 Hz, 1H) 3.11 (br t, J=12.33 Hz, 1H) 3.39-3.49 (m, 2H) 3.55-3.61 (m, 1H) 3.68 (br d, J=12.91 Hz, 1H) 3.75 (td, J=11.74, 7.04 Hz, 1H) 4.12 (br s, 1H) 4.58-4.64 (m, 3H) 7.02-7.11 (m, 2H) 7.13 (s, 1H) 7.51 (d, J=8.22 Hz, 2H) 7.76 (d, J=8.80 Hz, 2H) 7.75 (d, J=8.22 Hz, 2H) 8.36 (d, J=1.76 Hz, 1H) 8.68 (d, J=2.35 Hz, 1H);

MS (ESI, m/z): 502.4 [M+H]⁺

Example 423. 2-amino-N-((3S,4S)-4-((3-ethyl-4-methylbenzyl)oxy)pyrrolidin-3-yl)-5-(4-((4-methylpiperidin-1-yl)methyl)phenyl)nicotinamide Scheme for the Preparation of the Compound of Example 423:

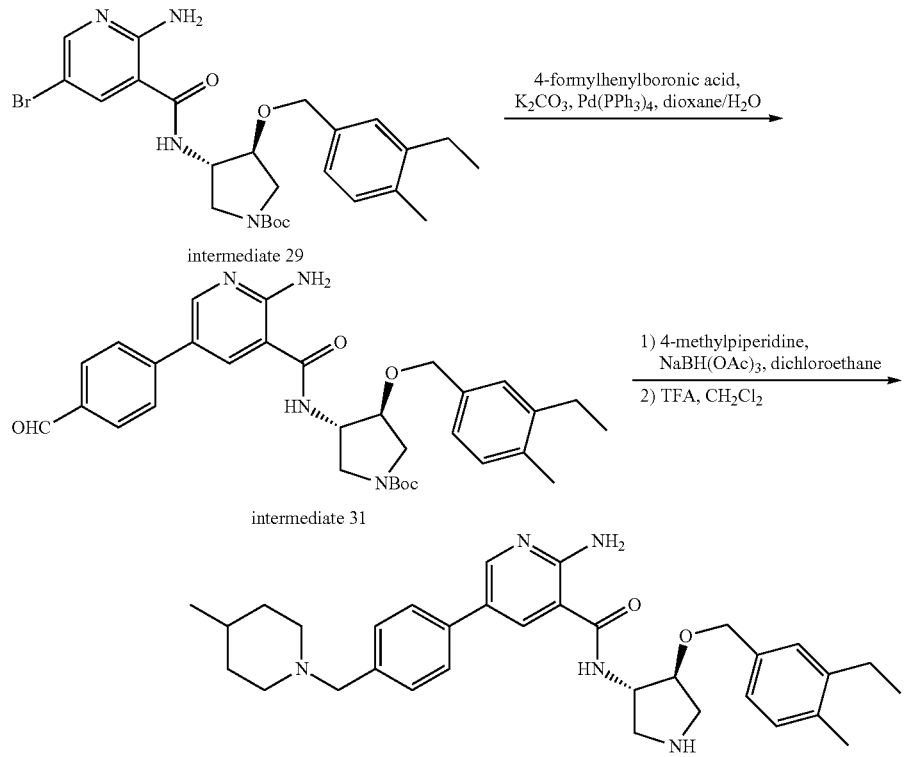

(d, J=8.22 Hz, 2H) 8.36 (d, J=1.76 Hz, 1H) 8.70 (d, J=1.76 Hz, 1H);

MS (ESI, m/z): 556.5 [M+H]⁺

Example 422. 2-amino-5-(4-(dimethylcarbamoyl)phenyl)-N-((3S,4S)-4-((3-ethyl-4-methylbenzyl)oxy)pyrrolidin-3-yl)nicotinamide Using dimethylamine, the title compound was obtained as described for the example 419.

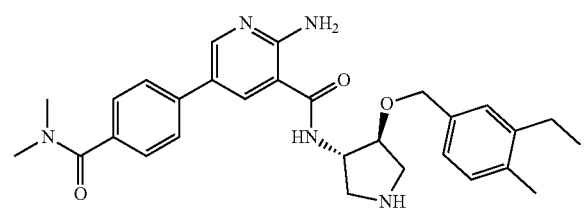 [SMILES: CCc1cc(CO[C@H]2CNC[C@@H]2NC(=O)c2cc(-c3ccc(C(=O)N(C)C)cc3)cnc2N)ccc1C]

¹H NMR (600 MHz, CD₃OD) δ ppm 1.15 (t, J=7.63 Hz, 3H) 2.22 (s, 3H) 2.58 (q, J=7.63 Hz, 2H) 3.01 (s, 3H) 3.11 (s, 3H) 3.38-3.50 (m, 2H) 3.52-3.66 (m, 1H) 3.67-3.81 (m, 1H) 4.12 (br s, 1H) 4.57-4.68 (m, 3H) 7.05 (s, 2H) 7.13 (s, Intermediate 31

Using intermediate 29 and 4-formylphenylboronic acid, the title compound was obtained as described for the synthesis of intermediate 30.

¹H NMR (600 MHz, CDCl₃) δ ppm 1.30 (t, J=7.63 Hz, 3H), 1.42 (s, 9H), 2.26 (br s, 3H) 2.58 (q, J=7.63 Hz, 2H) 3.37-3.84 (m, 4H) 4.17 (br s, 1H) 4.64 (br s, 2H) 4.77 (br s, 1H) 6.59 (br s, 2H) 7.05-7.20 (m, 3H) 7.55-7.73 (m, 2H) 7.86 (br d, J=5.28 Hz, 2H) 8.04 (br s, 1H) 8.46 (br s, 1H) 9.86 (br s, 1H);

MS (ESI, m/z): 559.4 [M+H]⁺

Example 423. 2-amino-N-((3S,4S)-4-((3-ethyl-4-methylbenzyl)oxy)pyrrolidin-3-yl)-5-(4-((4-methylpiperidin-1-yl)methyl)phenyl)nicotinamide To a mixture of intermediate 31 (40 mg, 0.07 mmol) in 0.4 ml of dichloroethane was added 4-methylpiperidine (0.017 ml, 0.14 mmol) followed by NaBH(OAc)₃ (30 mg, 0.21 mmol). The mixture was stirred at room temperature for 4 hr and then water was added. The mixture was extracted with EtOAc, washed with brine, dried over MgSO₄, and concentrated in vacuo. The crude residue was dissolved with 0.5 ml of CH₂Cl₂/TFA (10/1) and the mixture was stirred for 2 hrs. After concentration under vacuum, the crude residue was purified by preparative HPLC to afford 10 mg of the title compound.

¹H NMR (600 MHz, CD₃OD) δ ppm 0.99 (d, J=6.46 Hz, 3H) 1.16 (t, J=7.34 Hz, 3H) 1.34-1.46 (m, 2H) 1.91 (br d, J=14.09 Hz, 2H) 2.25 (s, 3H) 2.61 (q, J=7.63 Hz, 2H) 2.93-3.07 (m, 2H) 3.43-3.49 (m, 3H) 3.57 (ddd, J=16.43, 12.91, 3.52 Hz, 2H) 3.76 (dd, J=12.62, 6.75 Hz, 2H) 4.27-4.39 (m, 3H) 4.59-4.76 (m, 3H) 7.05-7.14 (m, 2H) 7.17 (s, 1H) 7.60 (d, J=8.22 Hz, 2H) 7.80 (d, J=8.22 Hz, 2H) 8.39 (d, J=1.76 Hz, 1H) 8.67 (d, J=1.76 Hz, 1H);

MS (ESI, m/z): 542.3 [M+H]⁺

Example 424. 2-amino-N-((3S,4S)-4-((3-ethyl-4-methylbenzyl)oxy)pyrrolidin-3-yl)-5-(4-(morpholinomethyl)phenyl)nicotinamide Using morpholine, the title compound was obtained as described for the example 423.

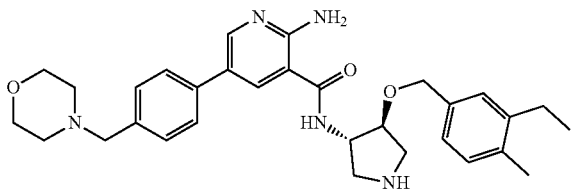 [SMILES: CCc1cc(CO[C@H]2CNC[C@@H]2NC(=O)c2cc(-c3ccc(CN4CCOCC4)cc3)cnc2N)ccc1C]

¹H NMR (600 MHz, CD₃OD) δ ppm 1.16 (t, J=7.63 Hz, 3H) 2.25 (s, 3H) 2.61 (q, J=7.63 Hz, 2H) 3.09-3.27 (m, 2H) 3.31-3.40 (m, 2H) 3.46 (d, J=12.33 Hz, 1H) 3.52-3.67 (m, 2H) 3.76 (br dd, J=12.91, 7.04 Hz, 1H) 3.77 (br s, 2H) 4.03 (br s, 2H) 4.35 (br d, J=4.11 Hz, 1H) 4.41 (s, 2H) 4.63-4.71 (m, 2H) 4.72 (br d, J=6.46 Hz, 1H) 7.06-7.12 (m, 2H) 7.17 (s, 1H) 7.63 (d, J-=8.22 Hz, 2H) 7.82 (d, J=8.22 Hz, 2H) 8.40 (d, J=2.35 Hz, 1H) 8.66-8.70 (m, 1H);

MS (ESI, m/z): 530.3 [M+H]⁺

Example 425. 2-amino-5-(4-((3,3-difluoropiperidin-1-yl)methyl)phenyl)-N-((3S,4S)-4-((3-ethyl-4-methylbenzyl)oxy)-pyrrolidin-3-yl)nicotinamide Using 3,3-difluoropiperidine, the title compound was obtained as described for the example 423.

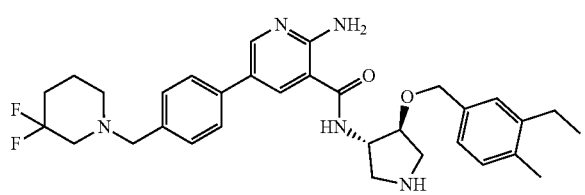 [SMILES: CCc1cc(CO[C@H]2CNC[C@@H]2NC(=O)c2cc(-c3ccc(CN4CCCC(F)(F)C4)cc3)cnc2N)ccc1C]

¹H NMR (600 MHz, CD₃OD) δ ppm 1.16 (t, J=7.63 Hz, 3H) 1.97-2.09 (m, 2H) 2.15 (br s, 2H) 2.25 (s, 3H) 2.61 (q, J=7.63 Hz, 2H) 3.22-3.28 (m, 2H) 3.38-3.49 (m, 4H) 3.50-3.66 (m, 2H) 3.76 (dd, J=12.33, 7.04 Hz, 1H) 4.35 (br d, J=4.70 Hz, 1H) 4.40 (s, 2H) 4.62-4.73 (m, 3H) 7.07-7.12 (m, 2H) 7.17 (s, 1H) 7.61 (d, J=8.22 Hz, 2H) 7.81 (d, J=8.22 Hz, 2H) 8.40 (d, J=2.35 Hz, 1H) 8.61 (d, J=1.76 Hz, 1H);

MS (ESI, m/z): 564.3 [M+H]⁺

Example 426. 2-amino-N-((3S,4S)-4-((3-ethyl-4-methylbenzyl)oxy)-1-methylpyrrolidin-3-yl)-5-(1-methyl-1H-pyrazol-4-yl)nicotinamide Scheme for the Preparation of the Compound of Example 426:

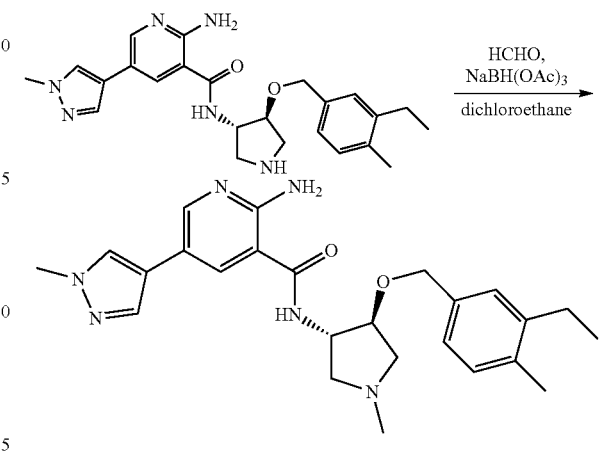

To compound 388 (40 mg, 0.09 mmol) in 0.4 ml of 1,2-dichloroethane was added formaldehyde (0.015 ml, 0.18 mmol) followed by NaBH(OAc)₃ (38 mg, 0.28 mmol). The mixture was stirred at room temperature for 1 hr and then water was added. The mixture was extracted with EtOAc, washed with brine, dried over MgSO₄, and concentrated in vacuo. The crude residue was purified by preparative HPLC to afford 30 mg of the title compound.

¹H NMR (600 MHz, CD₃OD) δ ppm 1.12-1.17 (m, 3H) 2.23 (s, 3H) 2.55-2.65 (m, 2H) 3.01 (s, 3H) 3.43-3.54 (m, 1H) 3.60-3.71 (m, 1H) 3.73-3.84 (m, 1H) 3.92 (s, 3H) 4.08-4.23 (m, 1H) 4.31-4.45 (m, 1H) 4.62-4.70 (m, 2H) 4.72 (br d, J=5.87 Hz, 1H) 7.04-7.11 (m, 2H) 7.15 (s, 1H) 7.88 (s, 1H) 8.05 (s, 1H) 8.26 (d, J=2.35 Hz, 1H) 8.66 (d, J=1.76 Hz, 1H);

MS (ESI, m/z): 449.3 [M+H]⁺

Example 427. 2-amino-N-((3S,4S)-1-benzyl-4-((3-ethyl-4-methylbenzyl)oxy)-pyrrolidin-3-yl)-5-(1-methyl-1H-pyrazol-4-yl)nicotinamide Using benzaldehyde, the title compound was obtained as described for the example 426.

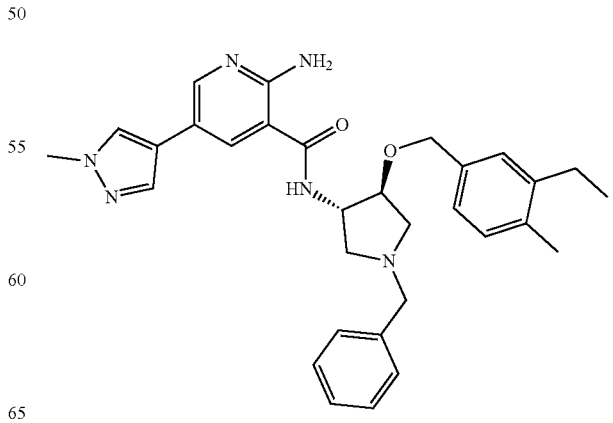

MS (ESI, m/z): 525.7 [M+H]⁺

Example 428. 2-amino-N-((3S,4S)-4-((3-ethyl-4-methylbenzyl)oxy)-1-(3-phenylpropyl)pyrrolidin-3-yl)-5-(1-methyl-1H-pyrazol-4-yl)nicotinamide Using 3-phenylpropanal, the title compound was obtained as described for the example 426.

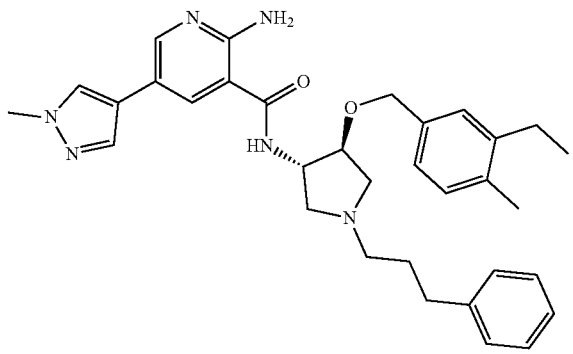 [SMILES: CCc1cc(CO[C@H]2CN(CCCc3ccccc3)C[C@@H]2NC(=O)c2cc(-c3cnn(C)c3)cnc2N)ccc1C]

$^1$H NMR (600 MHz, CD$_3$OD) δ ppm 1.14 (t, J=7.63 Hz, 3H) 1.97-2.13 (m, 2H) 2.22 (s, 3H) 2.58 (q, J=7.63 Hz, 2H) 2.70 (t, J=7.63 Hz, 2H) 3.27 (t, J=7.63 Hz, 2H) 3.43-3.54 (m, 1H) 3.60-3.71 (m, 1H) 3.73-3.84 (m, 1H) 3.92 (s, 3H) 4.08-4.23 (m, 1H) 4.36 (br s, 1H) 4.6-4.72 (m, 3H) 7.01-7.10 (m, 2H) 7.12-7.15 (m, 1H) 7.15-7.30 (m, 5H) 7.87 (s, 1H) 8.04 (s, 1H) 8.25 (d, J=1.76 Hz, 1H) 8.64 (br s, 1H);

MS (ESI, m/z): 553.3 [M+H]$^+$

Example 429. 2-amino-N-((3S,4S)-4-((3-ethyl-4-methylbenzyl)oxy)-1-phenethylpyrrolidin-3-yl)-5-(1-methyl-1H-pyrazol-4-yl)nicotinamide Using phenylacetaldehyde, the title compound was obtained as described for the example 426.

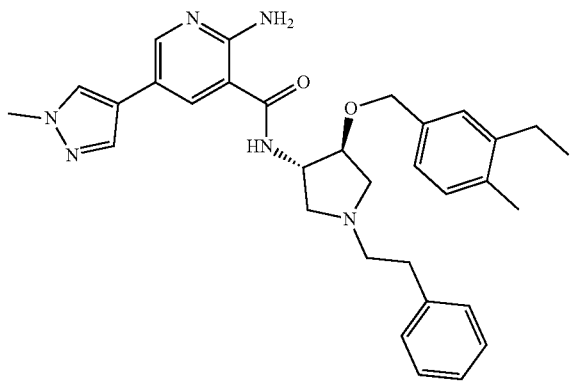 [SMILES: CCc1cc(CO[C@H]2CN(CCc3ccccc3)C[C@@H]2NC(=O)c2cc(-c3cnn(C)c3)cnc2N)ccc1C]

MS (ESI, m/z): 539.3[M+H]$^+$

Example 430. 2-amino-N-((3S,4S)-4-((3-ethyl-4-methylbenzyl)oxy)-1-isobutylpyrrolidin-3-yl)-5-(1-methyl-1H-pyrazol-4-yl)nicotinamide Using isobutyraldehyde, the title compound was obtained as described for the example 426.

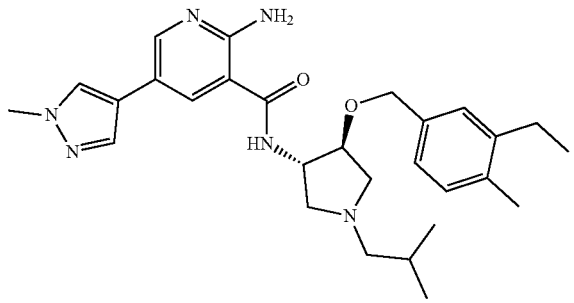 [SMILES: CCc1cc(CO[C@H]2CN(CC(C)C)C[C@@H]2NC(=O)c2cc(-c3cnn(C)c3)cnc2N)ccc1C]

$^1$H NMR (600 MHz, CD$_3$OD) δ ppm 1.04 (br d, J=3.52 Hz, 6H) 1.14 (t, J=7.63 Hz, 3H) 2.10 (dt, J=13.65, 6.97 Hz, 1H) 2.22 (s, 3H) 2.58 (q, J=7.63 Hz, 2H) 3.14 (br d, J=6.46 Hz, 2H) 3.32-3.42 (m, 1H) 3.52 (br s, 1H) 3.70-3.83 (m, 1H) 3.93 (s, 3H) 3.99-4.17 (m, 1H) 4.41 (br d, J=16.43 Hz, 1H) 4.59-4.75 (m, 3H) 7.02-7.12 (m, 2H) 7.15 (br s, 1H) 7.87 (br s, 1H) 8.05 (br d, J=11.15 Hz, 1H) 8.28 (d, J=1.76 Hz, 1H) 8.59 (br s, 1H);

MS (ESI, m/z): 491.3 [M+H]$^+$

Example 431. 2-amino-N-((3S,4S)-1-butyl-4-((3-ethyl-4-methylbenzyl)-oxy)pyrrolidin-3-yl)-5-(1-methyl-1H-pyrazol-4-yl)nicotinamide Using butyraldehyde, the title compound was obtained as described for the example 426.

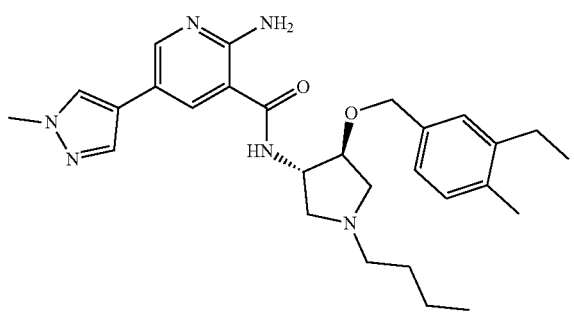 [SMILES: CCCCN1C[C@H](NC(=O)c2cc(-c3cnn(C)c3)cnc2N)[C@@H](OCc2ccc(C)c(CC)c2)C1]

MS (ESI, m/z): 491.4 [M+H]$^+$

Example 432. 2-amino-N-((3S,4S)-1-ethyl-4-((3-ethyl-4-methylbenzyl)oxy)-pyrrolidin-3-yl)-5-(1-methyl-1H-pyrazol-4-yl)nicotinamide Using acetaldehyde, the title compound was obtained as described for the example 426.

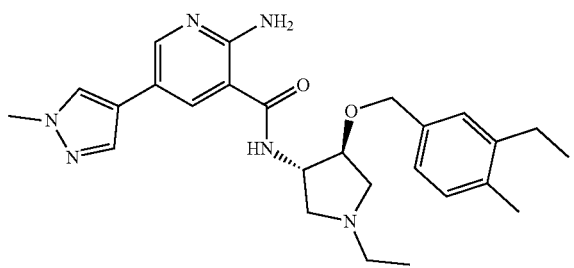 [SMILES: CCc1cc(CO[C@H]2CN(CC)C[C@@H]2NC(=O)c2cc(-c3cnn(C)c3)cnc2N)ccc1C]

MS (ESI, m/z): 463.3 [M+H]$^+$

Example 433. 2-amino-N-((3S,4S)-4-((3-ethyl-4-methylbenzyl)oxy)-1-methylpyrrolidin-3-yl)-5-(1-(1-methylpiperidin-4-yl)-1H-pyrazol-4-yl)nicotinamide From compound 359, the title compound was obtained as described for the example 426.

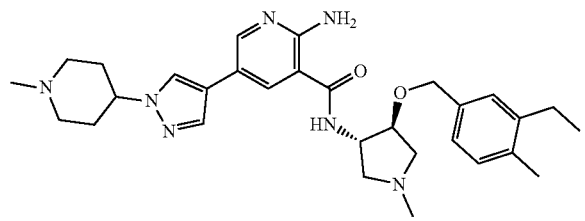 [SMILES: CCc1cc(CO[C@H]2CN(C)C[C@@H]2NC(=O)c2cc(-c3cnn(C4CCN(C)CC4)c3)cnc2N)ccc1C]

MS (ESI, m/z): 532.3 [M+H]$^+$

Example 434 and Example 435

Scheme for the Preparation of the Compounds of Example 434 and 435:

Intermediate 32

To a mixture of intermediate 2 (350 mg, 1.60 mmol) and triethylamine (0.34 ml, 2.41 mmol) in 4 ml of DMF was added HATU (732 mg, 1.92 mmol) followed by tert-butyl (3S,4S)-3-amino-4-((4-bromobenzyl)oxy)pyrrolidine-1-carboxylate (657 mg, 1.76 mmol). The mixture was stirred at room temperature for 1 hr and then saturated sodium bicarbonate solution was added. The mixture was extracted with EtOAc, washed with brine, dried over MgSO$_4$, and concentrated in vacuo. The crude product was purified through silicagel column chromatography to give 700 mg of off-white solid.

$^1$H NMR (600 MHz, CDCl$_3$) δ ppm 1.43 (br s, 9H) 3.42 (br d, J=10.56 Hz, 1H) 3.51-3.65 (m, 2H) 3.80 (dd, J=12.03, 5.58 Hz, 1H) 3.89 (s, 3H) 4.03-4.20 (m, 1H) 4.54-4.77 (m, 3H) 6.29 (br s, 2H) 7.25 (br d, J=8.22 Hz, 2H) 7.46 (br d, J=8.22 Hz, 2H) 7.53 (br s, 1H) 7.57-7.67 (m, 2H) 8.29 (d, J=1.76 Hz, 1H);

MS (ESI, m/z): 571.2 [M+H]$^+$

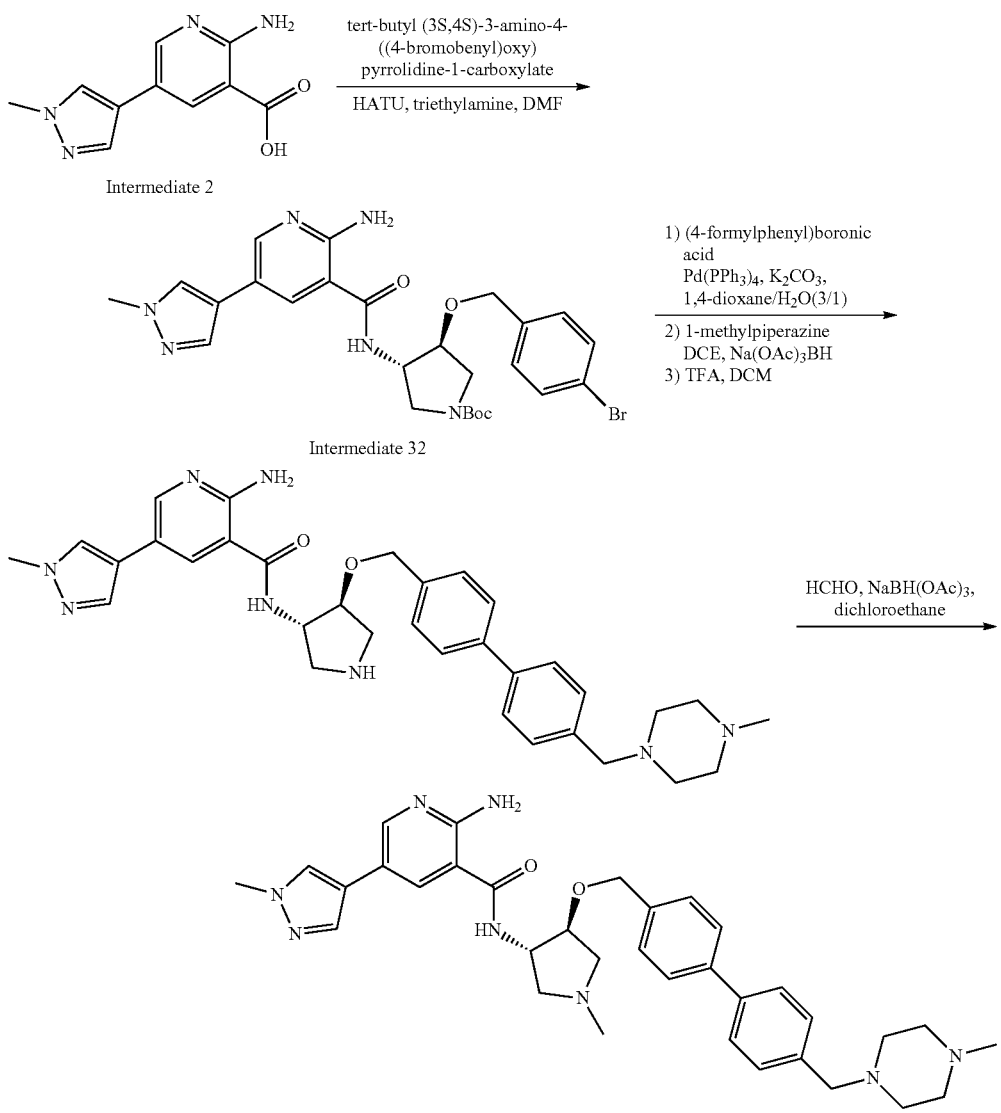

Example 434. 2-amino-5-(1-methyl-1H-pyrazol-4-yl)-N-((3S,4S)-4-((4'-((4-methylpiperazin-1-yl)methyl)-[1,1'-biphenyl]-4-yl)methoxy)pyrrolidin-3-yl)-nicotinamide To a mixture of intermediate 32 (40 mg, 0.07 mmol) and 4-((4-methylpiperazin-1-yl)-methylphenylboronic acid pinacol ester (27 mg, 0.08 mmol) in 0.4 ml of 1,4-dioxane/water (3/1) was added $K_2CO_3$ (29 mg, 0.21 mmol) followed by $Pd(PPh_3)_4$ (4 mg, 0.003 mmol) $Pd(PPh_3)_4$. The reaction mixture was heated at 100° C. for 3 hrs, cooled to room temperature, and extracted with EtOAc, dried over anhydrous $MgSO_4$ and concentrated under vacuum. The crude residue was dissolved with 0.5 ml of $CH_2Cl_2$/TFA (10/1) and the mixture was stirred for 2 hrs. After concentration under vacuum, the crude residue was purified by preparative HPLC to afford 30 mg of the title compound.

$^1$H NMR (600 MHz, $CD_3OD$) δ ppm 2.88 (s, 3H) 2.91-3.13 (m, 4H) 3.31-3.46 (m, 4H) 3.52-3.65 (m, 3H) 3.80 (dd, J=12.91, 7.04 Hz, 1H) 3.87-3.96 (m, 5H) 4.39-4.45 (m, 1H) 4.71-4.83 (m, 3H) 7.46 (br d, J=8.22 Hz, 2H) 7.49 (br d, J=8.22 Hz, 2H) 7.62 (dd, J=8.22, 2.35 Hz, 4H) 7.87 (s, 1H) 8.04 (s, 1H) 8.25 (d, J=1.76 Hz, 1H) 8.65 (d, J=1.76 Hz, 1H);

MS (ESI, m/z): 581.4 [M+H]$^+$

Example 435. 2-amino-5-(1-methyl-1H-pyrazol-4-yl)-N-((3S,4S)-1-methyl-4-((4'-((4-methylpiperazin-1-yl)methyl)-[1,1'-biphenyl]-4-yl)methoxy)pyrrolidin-3-yl)-nicotinamide To a mixture of compound 434 (52 mg, 0.09 mmol) in 0.4 ml of 1,2-dichloroethane was added formaldehyde (0.015 ml, 0.18 mmol) followed by $NaBH(OAc)_3$ (38 mg, 0.28 mmol). The mixture was stirred at room temperature for 1 hr and then water was added. The mixture was extracted with EtOAc, washed with brine, dried over $MgSO_4$, and concentrated in vacuo. The crude residue was purified by preparative HPLC to afford 35 mg of the title compound.

$^1$H NMR (600 MHz, $CD_3OD$) δ ppm 2.94 (s, 3H) 3.04 (s, 3H) 3.36-3.47 (m, 6H) 3.48-3.58 (m, 6H) 3.91 (s, 3H) 4.27 (s, 2H) 4.44 (br s, 1H) 4.72-4.83 (m, 3H) 7.49 (d, J=8.22 Hz, 2H) 7.53 (d, J=8.22 Hz, 2H) 7.61 (d, J=8.22 Hz, 2H) 7.66 (d, J=8.22 Hz, 2H) 7.86 (s, 1H) 8.03 (s, 1H) 8.22 (d, J=1.76 Hz, 1H) 8.67 (d, J=2.35 Hz, 1H);

MS (ESI, m/z): 595.3 [M+H]$^+$

Example 436. 2-amino-5-(1-methyl-1H-pyrazol-4-yl)-N-((3S,4S)-4-((4'-((4-methylpiperazin-1-yl)methyl)-3'-(trifluoromethyl)-[1,1'-biphenyl]-4-yl)methoxy)-pyrrolidin-3-yl)nicotinamide Using (4-formyl-3-(trifluoromethyl)phenyl)boronic acid pinacol ester, the title compound was obtained as described for the example 434.

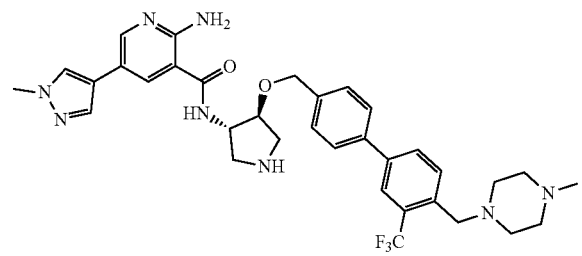

MS (ESI, m/z): 649.3 [M+H]$^+$

Example 437. 2-amino-5-(1-methyl-1H-pyrazol-4-yl)-N-((3S,4S)-1-methyl-4-((4'-((4-methylpiperazin-1-yl)methyl)-3'-(trifluoromethyl)-[1,1'-biphenyl]-4-yl)-methoxy)pyrrolidin-3-yl)nicotinamide From compound 436, the title compound was obtained as described for the example 435.

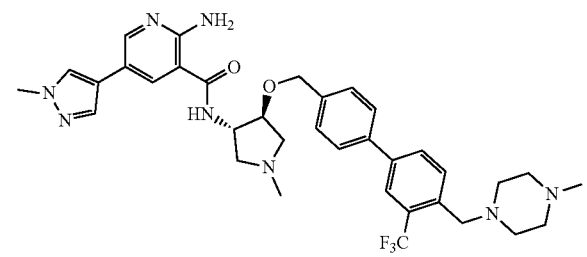

MS (ESI, m/z): 663.3 [M+H]$^+$

Example 438. 2-amino-5-(1-methyl-1H-pyrazol-4-yl)-N-((3S,4S)-4-((4'-(1-(4-methylpiperazin-1-yl)ethyl)-[1,1'-biphenyl]-4-yl)methoxy)pyrrolidin-3-yl)-nicotinamide Using (4-acetylphenyl)boronic acid, the title compound was obtained as described for the example 434.

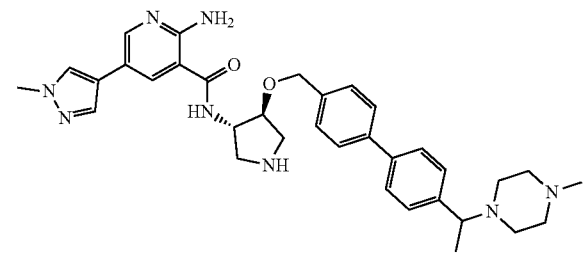

MS (ESI+) n/z 595.3 [M+H]$^+$

Example 439. 2-amino-5-(1-methyl-1H-pyrazol-4-yl)-N-((3S,4S)-1-methyl-4-((4'-(1-(4-methylpiperazin-1-yl)ethyl)-[1,1'-biphenyl]-4-yl)methoxypyrrolidin-3-yl)-nicotinamide From compound 438, the title compound was obtained as described for the example 435.

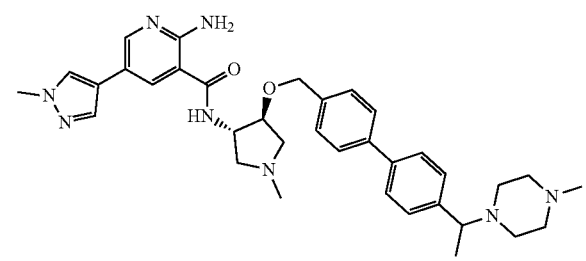

$^1$H NMR (400 MHz, $CD_3OD$) δ ppm 1.65 (d, J=7.04 Hz, 3H) 2.90 (s, 3H) 3.05 (s, 3H) 3.08-3.17 (m, 2H) 3.46 (br s, 4H) 3.93 (s, 3H) 4.16 (br d, J=6.65 Hz, 2H) 4.49 (s, 1H) 4.75-4.87 (m, 3H) 7.51 (dd, J=8.22, 4.70 Hz, 4H) 7.57-7.70 (m, 4H) 7.88 (s, 1H) 8.05 (s, 1H) 8.26 (d, J=1.96 Hz, 1H) 8.68 (d, J=1.96 Hz, 1H); MS (ESI+) n/z 609.4 [M+H]⁺

Example 440. 2-amino-N-((3S,4S)-4-((4'-(2-(4-(2-hydroxyethyl)piperazin-1-yl)propan-2-yl)-[1,1'-biphenyl]-4-yl)methoxy)pyrrolidin-3-yl)-5-(1-methyl-1H-pyrazol-4-yl)nicotinamide Using (4-(2-(4-(2-hydroxyethyl)piperazin-1-yl)propan-2-yl)phenyl)boronic acid pinacol ester, the title compound was obtained as described for the example 434.

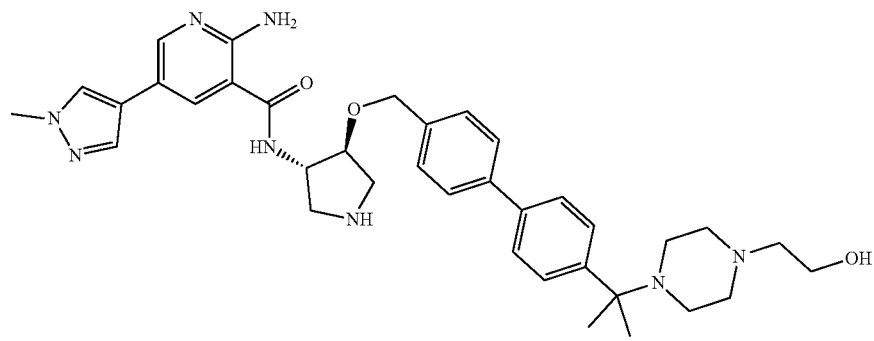 [SMILES: Cn1cc(-c2cnc(N)c(C(=O)N[C@H]3CNC[C@@H]3OCc3ccc(-c4ccc(C(C)(C)N5CCN(CCO)CC5)cc4)cc3)c2)cn1]

¹H NMR (400 MHz, CD₃OD) δ ppm 1.77 (s, 6H) 3.50-3.68 (m, 6H) 3.80 (s, 1H) 3.83-3.89 (m, 2H) 3.92 (s, 3H) 4.42 (br d, J=4.30 Hz, 1H) 4.73-4.88 (m, 3H) 7.52 (d, J=8.22 Hz, 2H) 7.65 (d, J=8.22 Hz, 2H) 7.67-7.84 (m, 3H) 7.86-7.92 (m, 1H) 8.06 (s, 1H) 8.26 (d, J=2.35 Hz, 1H) 8.70 (d, J=2.35 Hz, 1H);
MS (ESI, m/z): 639.4 [M+H]⁺

Example 441. 2-amino-N-((3S,4S)-4-((4'-(2-(4-(2-hydroxyethyl)piperazin-1-yl)-propan-2-yl)-[1,1'-biphenyl]-4-yl)methoxy)-1-methylpyrrolidin-3-yl)-5-(1-methyl-1H-pyrazol-4-yl)nicotinamide From compound 440, the title compound was obtained as described for the example 435.

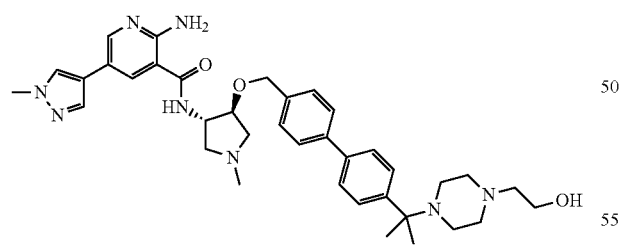

MS (ESI m/z): 653.4 [M+H]⁺

Example 442. 2-amino-N-((3S,4S)-4-((4'-(1-(4-(2-hydroxyethyl)piperazin-1-yl)ethyl)-[1,1'-biphenyl]-4-yl)methoxy)pyrrolidin-3-yl)-5-(1-methyl-1H-pyrazol-4-yl)nicotinamide Using (4-(1-(4-(2-hydroxyethyl)piperazin-1-yl)ethyl) phenyl)boronic acid pinacol ester, the title compound was obtained as described for the example 434.

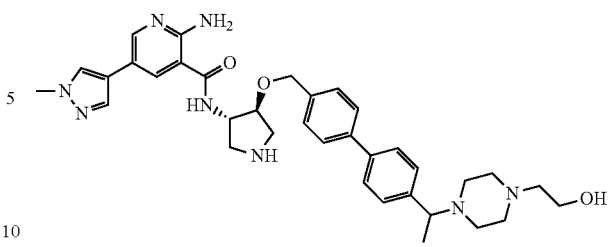

MS (ESI, m/z): 625.4 [M+H]⁺

Example 443. 2-amino-N-((3S,4S)-4-((4'-(1-(4-(2-hydroxyethyl)piperazin-1-yl)ethyl)-[1,1'-biphenyl]-4-yl)methoxy)-1-methylpyrrolidin-3-yl)-5-(1-methyl-1H-pyrazol-4-yl)nicotinamide From compound 442, the title compound was obtained as described for the example 435.

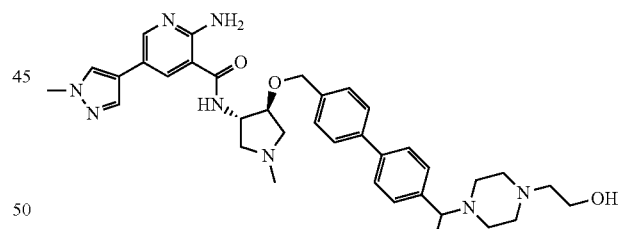

MS (ESI, m/z): 639.4 [M+H]⁺

Example 444. 2-amino-N-((3S,4S)-4-((4'-((4-(2-hydroxyethyl)piperazin-1-yl)-methyl)-3'-(trifluoromethyl)-[1,1'-biphenyl]-4-yl)methoxy)pyrrolidin-3-yl)-5-(1-methyl-1H-pyrazol-4-yl)nicotinamide Using (4-((4-(2-hydroxyethyl)piperazin-1-yl)methyl)-3-(trifluoromethyl)phenyl)-boronic acid pinacol ester, the title compound was obtained as described for the example 434.

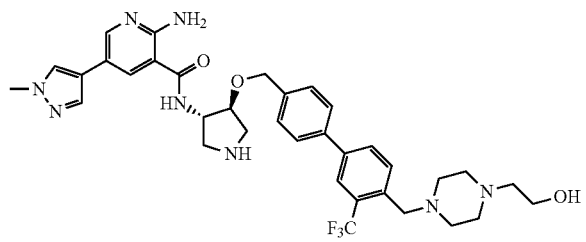 [SMILES: Cn1cc(-c2cnc(N)c(C(=O)N[C@H]3CNC[C@@H]3OCc3ccc(-c4ccc(CN5CCN(CCO)CC5)c(C(F)(F)F)c4)cc3)c2)cn1]

MS (ESI, m/z): 679.3 [M+H]+

Example 445. 2-amino-N-((3S,4S)-4-((4'-((4-(2-hydroxyethyl)piperazin-1-yl)-methyl)-3'-(trifluoromethyl)-[1,1'-biphenyl]-4-yl)methoxy)-1-methylpyrrolidin-3-yl)-5-(1-methyl-1H-pyrazol-4-yl)nicotinamide Using 1-(4-bromo-2-(trifluoromethyl)benzyl)piperazine, the title compound was obtained as described for the example 435.

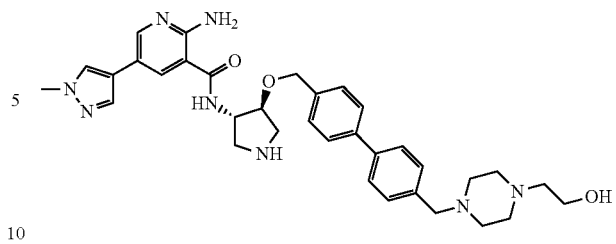

MS (ESI, m/z): 611.3 [M+H]+

Example 447. 2-amino-N-((3S,4S)-4-((4'-((4-(2-hydroxyethyl)piperazin-1-yl)-methyl)-[1,1'-biphenyl]-4-yl)methoxy)-1-methylpyrrolidin-3-yl)-5-(1-methyl-1H-pyrazol-4-yl)nicotinamide From compound 446, the title compound was obtained as described for the example 435.

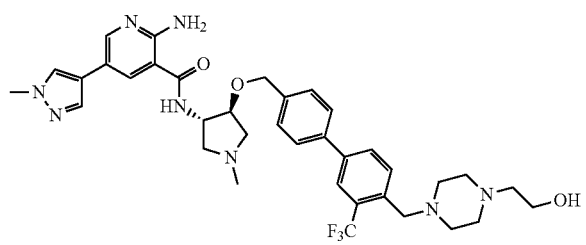 [SMILES: CN1C[C@H](NC(=O)c2cc(-c3cnn(C)c3)cnc2N)[C@@H](OCc2ccc(-c3ccc(CN4CCN(CCO)CC4)c(C(F)(F)F)c3)cc2)C1]

MS (ESI, m/z): 693.3 [M+H]+

Example 446. 2-amino-N-((3S,4S)-4-((4'-((4-(2-hydroxyethyl)piperazin-1-yl)-methyl)-[1,1'-biphenyl]-4-yl)methoxy)pyrrolidin-3-yl)-5-(1-methyl-1H-pyrazol-4-yl)-nicotinamide Using (4-((4-(2-hydroxyethyl)piperazin-1-yl)methyl)phenyl)boronic acid pinacol ester, the title compound was obtained as described for the example 434.

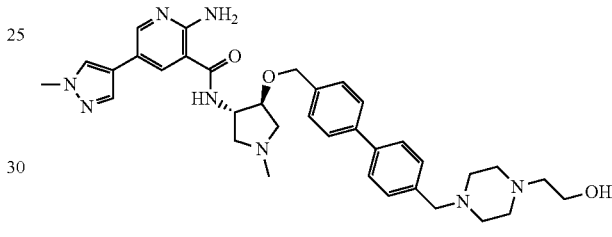

MS (ESI, m/z): 625.4 [M+H]+

Example 448. 2-amino-5-(1-methyl-1H-pyrazol-4-yl)-N-((3S,4R)-4-((4'-((4-methylpiperazin-1-yl)methyl)-[1,1'-biphenyl]-4-yl)methoxy)tetrahydrofuran-3-yl)-nicotinamide Scheme for the Preparation of the Compound of Example 448:

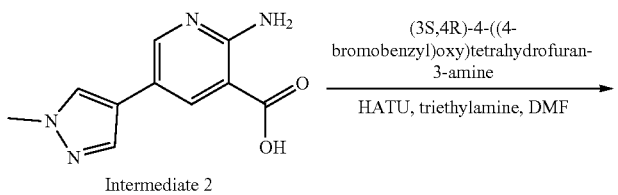

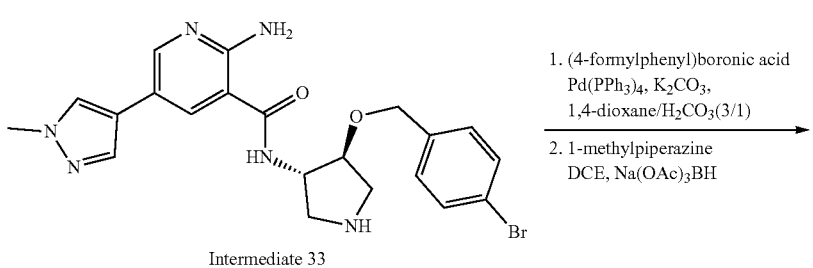

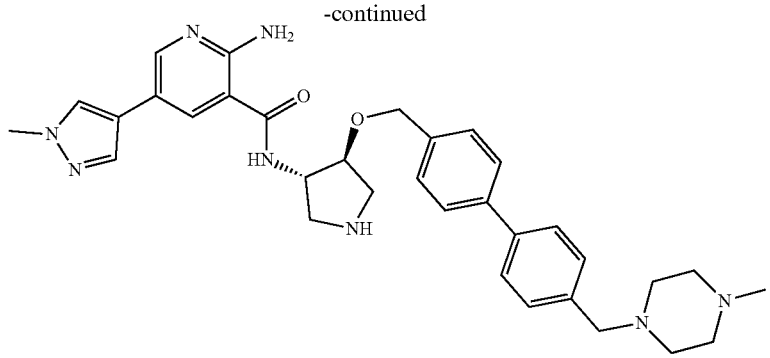

Intermediate 33

Using intermediate 2 and (3S,4R)-4-((4-bromobenzyl)oxy)tetrahydrofuran-3-amine, the title compound was obtained as described for the intermediate 4.

$^1$H NMR (600 MHz, CD$_3$OD) δ ppm 3.81 (td, J=10.27, 2.35 Hz, 2H) 3.91 (s, 3H) 4.05 (dd, J=9.98, 5.28 Hz, 1H) 4.11 (dd, J=9.39, 5.87 Hz, 1H) 4.13-4.16 (m, 1H) 4.55 (dd, J=3.81, 2.05 Hz, 1H) 4.60 (s, 2H) 4.63 (d, J=12.33 Hz, 1H) 4.74 (d, J=12.33 Hz, 1H) 7.30 (m, J=8.22 Hz, 2H) 7.45-7.49 (m, 2H) 7.78 (s, 1H) 7.90 (s, 1H) 8.07 (d, J=2.35 Hz, 1H) 8.26 (d, J=1.76 Hz, 1H);

MS (ESI, m/z): 472.1 [M+H]$^+$

Example 448. 2-amino-5-(1-methyl-1H-pyrazol-4-yl)-N-((3S,4R)-4-((4'-((4-methylpiperazin-1-yl)methyl)-[1,1'-biphenyl]-4-yl)methoxy)tetrahydrofuran-3-yl)-nicotinamide Using intermediate 33, the title compound was obtained as described for the example 172.

$^1$H NMR (600 MHz, CD$_3$OD) δ ppm 2.87 (s, 3H) 3.80-3.89 (m, 4H) 3.92 (s, 3H) 4.04-4.15 (m, 2H) 4.19-4.25 (m, 1H) 4.57-4.63 (m, 1H) 4.71 (d, J=11.74 Hz, 1H) 4.82 (d, J=11.74 Hz, 1H) 7.40-7.51 (m, 4H) 7.57-7.63 (m, 4H) 7.88 (s, 1H) 8.02 (s, 1H) 8.23 (s, 1H) 8.62 (s, 1H);

MS (ESI, m/z): 582.3 [M+H]$^+$

Example 449. 2-amino-5-(1-methyl-1_H-pyrazol-4-yl)-N-((3S,4R)-4-((4'-((4-methylpiperazin-1-yl)methyl)-3'-(trifluoromethyl)-[1,1'-biphenyl]-4-yl)methoxy)-tetrahydrofuran-3-yl)nicotinamide Using (4-formyl-3-(trifluoromethyl)phenyl)boronic acid pinacol ester pinacol ester, the title compound was obtained as described for the example 448.

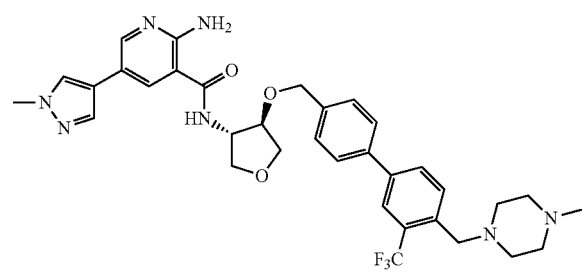

$^1$H NMR (400 MHz, CD$_3$OD) δ ppm 2.91 (s, 3H) 3.80-3.91 (m, 3H) 3.94 (s, 2H) 4.12 (td, J=9.59, 5.48 Hz, 2H) 4.23 (br s, 1H) 4.62 (br s, 1H) 4.74 (d, J=12.13 Hz, 1H) 7.52 (d, J=8.61 Hz, 2H) 7.65 (d, J=8.22 Hz, 2H) 7.88 (d, J=13.30 Hz, 4H) 8.03 (s, 1H) 8.25 (d, J=1.96 Hz, 1H) 8.63 (d, J=1.96 Hz, 1H);

MS (ESI, m/z): 650.3 [M+H]$^+$

Example 450. 2-amino-5-(1-methyl-1H-pyrazol-4-yl)-N-((3S,4R)-4-((4'-(2-(4-methylpiperazin-1-yl)propan-2-yl)-[1,1'-biphenyl]-4-yl)methoxy)tetrahydrofuran-3-yl)nicotinamide Using (4-formyl-3-(trifluoromethyl)phenyl)boronic acid pinacol ester, the title compound was obtained as described for the example 448.

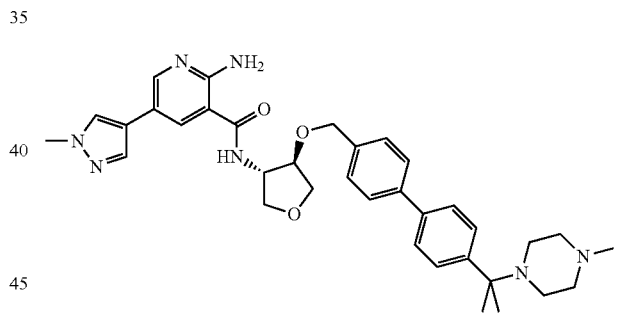

$^1$H NMR (400 MHz, CD$_3$OD) δ ppm 1.62 (s, 6H) 2.89 (s, 3H) 3.04 (br s, 2H) 3.34-3.47 (m, 4H) 3.82-3.91 (m, 2H) 3.93 (s, 3H) 4.12 (td, J=10.56, 5.48 Hz, 2H) 4.22 (br s, 1H) 4.61 (br s, 1H) 4.66-4.77 (m, 1H) 4.81-4.88 (m, 1H) 7.47 (d, J=7.83 Hz, 2H) 7.58-7.70 (m, 6H) 7.89 (s, 1H) 8.03 (s, 1H) 8.24 (d, J=1.96 Hz, 1H) 8.65 (d, J=1.96 Hz, 1H);

MS (ESI, m/z): 610.2 [M+H]$^+$

Example 451. 2-amino-N-((3S,4R)-4-((4'-((4-(2-hydroxyethyl)piperazin-1-yl)methyl)-[1,1'-biphenyl]-4-yl)methoxy)tetrahydrofuran-3-yl)-5-(1-methyl-1H-pyrazol-4-yl)nicotinamide Using (4-((4-(2-hydroxyethyl)piperazin-1-yl)methyl)phenyl)boronic acid pinacol ester, the title compound was obtained as described for the example 448.

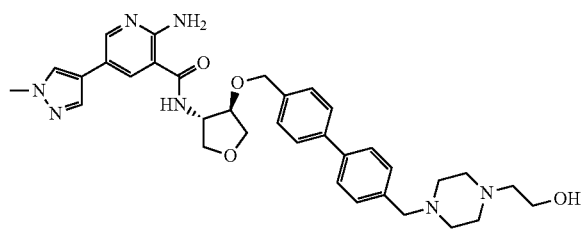 [SMILES: CN1C[C@H](NC(=O)c2cc(-c3cnn(C)c3)cnc2N)[C@@H](OCc2ccc(-c3ccc(CN4CCN(CCO)CC4)cc3)cc2)C1]

MS (ESI, m/z): 612.3 [M+H]⁺

Example 452. 2-amino-N-((3S,4R)-4-((4'-((4-(2-hydroxyethyl)piperazin-1-yl)-methyl)-3'-(trifluoromethyl)-[1,1'-biphenyl]-4-yl)methoxy)tetrahydrofuran-3-yl)-5-(1-methyl-1H-pyrazol-4-yl)nicotinamide Using (4-((4-(2-hydroxyethyl)piperazin-1-yl)methyl)-3-(trifluoromethyl)phenyl)-boronic acid pinacol ester, the title compound was obtained as described for the example 448.

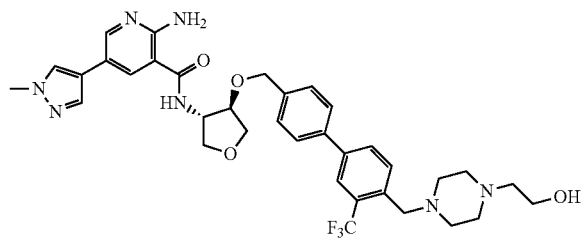 [SMILES: Cn1cc(-c2cnc(N)c(C(=O)N[C@H]3COC[C@@H]3OCc3ccc(-c4ccc(CN5CCN(CCO)CC5)c(C(F)(F)F)c4)cc3)c2)cn1]

¹H NMR (400 MHz, CD3OD) δ ppm 2.62 (br s, 4H) 3.25-3.29 (m, 2H) 3.34-3.40 (m, 2H) 3.82-3.84 (m, 2H) 3.85-3.91 (m, 2H) 3.94 (s, 2H) 4.06-4.17 (m, 2H) 4.23 (br s, 1H) 4.62 (br s, 1H) 4.74 (m, 1H) 7.52 (m, J=8.22 Hz, 2H) 7.65 (m, J=8.22 Hz, 2H) 7.86 (s, 2H) 7.89 (s, 2H) 8.03 (s, 1H) 8.25 (d, J=1.96 Hz, 1H) 8.63 (d, J=1.96 Hz, 1H);

MS (ESI, m/z): 680.3 [M+H]⁺

Example 453. 2-amino-N-((3S,4R)-4-((4'-(2-(4-(2-hydroxyethyl)piperazin-1-yl)-propan-2-yl)-[1,1'-biphenyl]-4-yl)methoxy)tetrahydrofuran-3-yl)-5-(1-methyl-1H-pyrazol-4-yl)nicotinamide Using (4-(2-(4-(2-hydroxyethyl)piperazin-1-yl)propan-2-yl)phenyl)boronic acid pinacol ester, the title compound was obtained as described for the example 448.

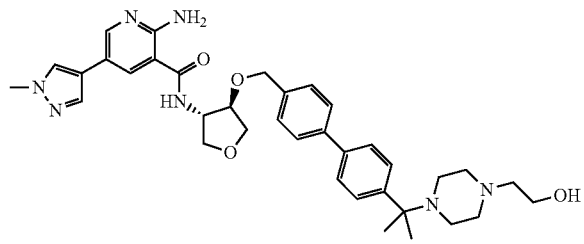 [SMILES: Cn1cc(-c2cnc(N)c(C(=O)N[C@H]3COC[C@@H]3OCc3ccc(-c4ccc(C(C)(C)N5CCN(CCO)CC5)cc4)cc3)c2)cn1]

MS (ESI, m/z): 640.2 [M+H]⁺

Example 454. 2-amino-5-(l-methyl-1H-pyrazol-4-yl)-N-(trans-4-((4'-((4-methyl-piperazin-1-yl)methyl)-[1,1'-biphenyl]-4-yl)methoxy)tetrahydrofuran-3-yl-nicotinamide Using trans-4-((4'-((4-methylpiperazin-1-yl)methyl)-[1,1'-biphenyl]-4-yl)methoxy)-tetrahydrofuran-3-amine, the title compound was obtained as described for the example 448.

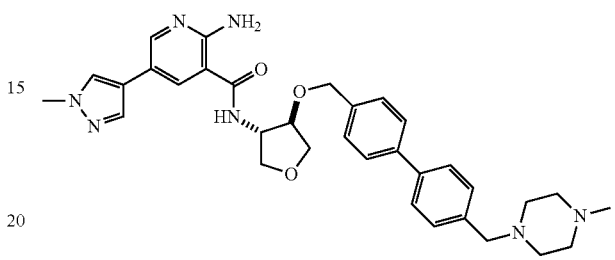

¹H NMR (400 MHz, CD₃OD) δ ppm 2.88 (s, 3H) 3.76-3.89 (m, 4H) 4.09 (ddd, J=16.92, 9.88, 5.28 Hz, 2H) 4.20 (br d, J=4.70 Hz, 1H) 4.57 (br s, 1H) 4.70 (br d, J=11.74 Hz, 1H) 6.98 (dd, J=7.43, 6.26 Hz, 1H) 7.46 (d, J=8.22 Hz, 4H) 7.56-7.67 (m, 4H) 7.99-8.06 (m, 1H) 8.40 (dd, J=7.43, 1.56 Hz, 1H);

MS (ESI, m/z): 582.3 [M+H]⁺

Example 455. 2-amino-N-(trans-4-((4'-((4-methylpiperazin-1-yl)methyl)-[1,1'-biphenyl]-4-yl)methoxy)tetrahydrofuran-3-yl)nicotinamide Using 2-aminonicotinic acid and trans-4-((4-bromobenzyl)oxy)tetrahydrofuran-3-amine, the title compound was obtained as described for the example 448.

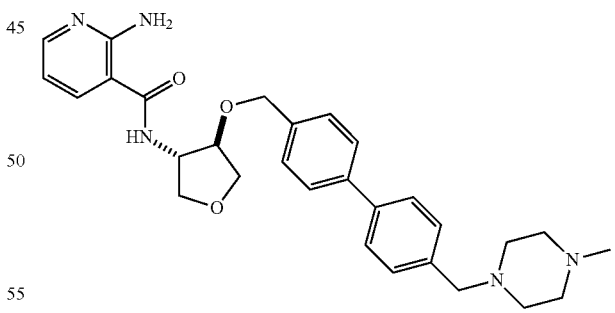

¹H NMR (400 MHz, CD₃OD) δ ppm 2.88 (s, 3H) 3.76-3.89 (m, 4H) 4.09 (ddd, J=16.92, 9.88, 5.28 Hz, 2H) 4.20 (br d, J=4.70 Hz, 1H) 4.57 (br s, 1H) 4.70 (br d, J=11.74 Hz, 1H) 6.98 (dd, J=7.43, 6.26 Hz, 1H) 7.46 (d, J=8.22 Hz, 4H) 7.56-7.67 (m, 4H) 7.99-8.06 (m, 1H) 8.40 (dd, J=7.43, 1.56 Hz, 1H);

MS (ESI m/z): 502.3 [M+H]⁺

Example 456. 2-amino-N-((1S,2S)-2-(benzyloxy)cyclopentyl-6-((4-((4-methylpiperazin-1-yl)methyl)phenyl)amino)nicotinamide Scheme for the Preparation of the Compound of Example 456:

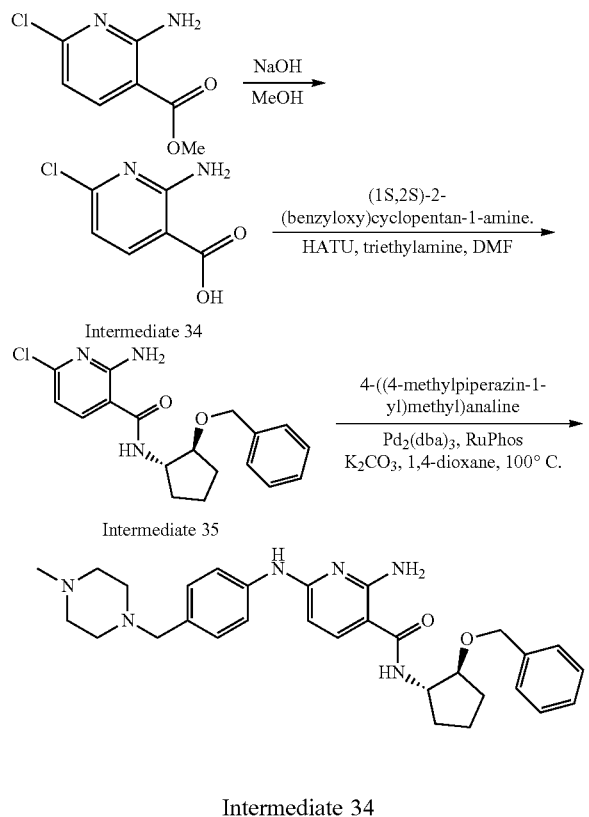

Intermediate 34

To a suspension of methyl 2-amino-6-chloronicotinate (100 mg, 0.54 mmol) in 3 ml of MeOH was added 2N NaOH (1 ml, 2 mmol) and the mixture was heated at 65° C. for 1 hr, cooled to room temperature, neutralized (1 ml of 2N HCl), and the resulting precipitate was filtered, washed with MeOH, and dried to give 80 mg of off-white solid.

$^1$H NMR (400 MHz, DMSO-$d_6$) δ ppm 6.61 (d, J=7.83 Hz, 1H) 7.53 (br s, 2H) 8.01 (d, J=8.22 Hz, 1H); MS (ESI, m/z): 173.2 [M+H]$^+$

Intermediate 35

To a mixture of intermediate 34 (50 mg, 0.29 mmol) and triethylamine (0.061 ml, 0.43 mmol) in 2 ml of DMF was added HATU (132 mg, 0.35 mmol) followed by (1S,2S)-2-(benzyloxy)cyclopentan-1-amine (55 mg, 0.29 mmol). The mixture was stirred at room temperature for 1 hr and then saturated sodium bicarbonate solution was added. The mixture was extracted with EtOAc, washed with brine, dried over MgSO$_4$, and concentrated in vacuo. The crude residue was purified by preparative HPLC to afford 80 mg of the title compound.

$^1$H NMR (400 MHz, CDCl$_3$) δ ppm 1.39-1.52 (m, 1H) 1.68-1.81 (m, 2H) 1.83-1.89 (m, 1H) 1.89-2.02 (m, 1H). 2.27 (td, J=13.69, 7.83 Hz, 1H) 3.80-3.87 (m, 1H) 4.27-4.37 (m, 1H) 4.58-4.67 (m, 2H) 5.79 (br d, J=6.26 Hz, 1H) 6.51 (br s, 2H) 6.56 (d, J=7.83 Hz, 1H) 7.25-7.37 (m, 5H) 7.39 (d, J=7.83 Hz, 1H);

MS (ESI, m/z): 345.3 [M+H]$^+$

Example 456. 2-amino-N-((1S,2S)-2-(benzyloxy)cyclopentyl)-6-((4-((4-methylpiperazin-1-yl)methyl)phenyl)amino)nicotinamide To a mixture of intermediate 35 (186 mg, 1 mmol) and 4-((4-methylpiperazine-1-yl)methyl)aniline (240 mg, 1.2 mmol) in 5 ml of 1,4-dioxane was added 480 mg of K$_2$CO$_3$ followed by Pd$_2$(dba)$_3$ (30 mg, 0.3 mmol). The reaction mixture was heated at 100° C. for 3 hrs, cooled to room temperature, and extracted with EtOAc, dried over anhydrous MgSO$_4$ and concentrated under vacuum. The crude product was purified by silicagel column chromatography to give 170 mg of off-white solid.

$^1$H NMR (400 MHz, CD$_3$OD) δ ppm 1.57 (br dd, J=13.30, 7.04 Hz, 1H) 1.66-1.87 (m, 3H) 1.97 (dt, J=13.01, 6.60 Hz, 1H) 2.13 (br dd, J=13.11, 6.85 Hz, 1H) 2.95 (s, 3H) 3.44-3.62 (m, 4H) 3.87-3.97 (m, 1H) 4.17 (s, 2H) 4.31-4.39 (m, 1H) 4.60 (s, 2H) 6.25 (d, J=9.00 Hz, 1H) 7.21-7.35 (m, 4H) 7.43 (d, J=8.22 Hz, 2H) 7.58 (d, J=8.61 Hz, 2H) 8.08 (d, J=9.00 Hz, 1H); MS (ESI, m/z): 515.3 [M+H]$^+$

Example 457. 2-amino-N-((1S,2S)-2-(benzyloxy)cyclopentyl)-6-(phenylamino)-nicotinamide Using aniline, the title compound was obtained as described for the example 456.

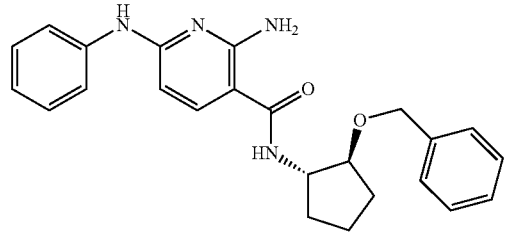 [SMILES: Nc1nc(Nc2ccccc2)ccc1C(=O)N[C@H]1CCC[C@@H]1OCc1ccccc1]

MS (ESI, m/z): 403.2 [M+H]$^+$

Example 458. 2-amino-N-((1S,2S)-2-(benzyloxy)cyclopentyl)-6-((4-(4-methylpiperazin-1-yl)phenyl)amino)nicotinamide Using 4-(4-methylpiperazin-1-yl)aniline, the title compound was obtained as described for the example 456.

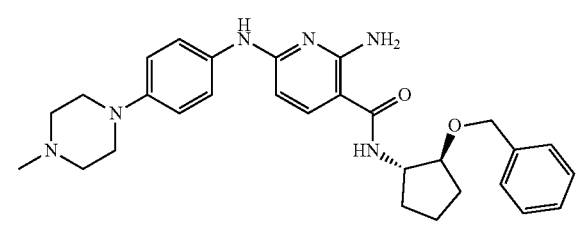 [SMILES: CN1CCN(c2ccc(Nc3ccc(C(=O)N[C@H]4CCC[C@@H]4OCc4ccccc4)c(N)n3)cc2)CC1]

MS (ESI, m/z): 501.3 [M+H]$^+$

Biochemical Assay

For the SAR (structure-activity relationship) and compound screening, LanthaScreen™ TR-FRET (Time-Resolved fluorescence energy transfer) assay was employed using the phospho-tyrosine specific Terbium (Tb)-labeled antibody with a fluorescein labeled poly-GT (glutamatetyrosine) as a substrate. Upon excitation at 340 nm by UV, the energy from Tb donor of the antibody is transferred to the fluorescein of the phosphorylated poly GT substrate, and fluorescein emits light at 520 nm. The ratio between the intensity of primary emission at 495 nm and that of secondary emission at 520 nm was used to quantify the level of kinase activity. The recombinant proteins of human c-MER and AXL catalytic domains, Fluorescein-labeled poly-GT substrate, Tb-labeled anti-phosphorylated tyrosine antibodies, the kinase assay buffer, and 0.5M EDTA solution were purchased (Life technologies, USA). The TR-FRET assays were carried out in the white low volume 384-well plate (Corning, USA). To measure the compound mediated inhibition of kinase activity, the recombinant kinases were pre-incubated with test compounds for 20 minutes prior to the addition of 200 nM fluorescein labeled poly-GT substrates and 10 uM ATP, and then the reaction was carried out for 1 hour at room temperature. 10 mM EDTA was added to terminate the enzyme reaction, and the level of phosphorylation of poly-GT substrate was determined following 30 min incubation with 2 nM Tb-labeled antibody. The fluorescence intensity was measured with Envision™ plate reader (PerkinElmer, USA).

In Cell MER Kinase Assay Using BaF3 Cellular System

CD8-MerTK is a chimeric fusion protein consisting of the extracellular and transmembrane domains of the human CD8α (amino acids 1 to 209) at its N-terminus and the kinase domain and intracellular parts of MerTK (amino acids 521-994) at its C-terminus. To establish an in cell kinase assay for MerTK kinase, the IL-3 dependent Ba/F3 cells of murine lymphoid origin was transfected with CD8-MerTK. The resulting Ba/F3-CDM line was then validated that Ba/F3-CDM cell proliferation is completely dependent on the activity of MerTK kinase activity when growing in the absence of IL-3. For a routine cellular assay, Ba/F3-CDM cells were seeded at 2,000 cells per well in 384-well cell culture plate containing DMEM/10% FBS culture media and incubated for 24 hours before addition of compounds pre-diluted in culture media. Following compound treatment, cells were further incubated for 48 hours and the proliferation was measured. To discriminate a Ba/F3 growth inhibition by a specific inhibition of MerTK kinase following compound treatment vs growth inhibition due to a non-specific unintended cytotoxicity of compounds, we routinely carried out control sets of Ba/F3 cells in parallel that grown in L3-supplemented growth media. In the presence of IL-3, the proliferation of Ba/F3 is no longer dependent on the MerTK activity. Cell growth and proliferation was measured with Celltiter-Glo™ system (Promega, USA) according to the manufacturer's instruction. The half-maximal growth inhibitory concentration ($GI_{50}$) value was calculated with Prism6.0 software (GraphPad, USA).

TABLE 1

Biochemical IC50 and cell growth inhibitory GI50 values.

| Compound No. | Mer TK inhibition (IC50) | Cell growth inhibition (GI50) |
|---|---|---|
| 1 | +++ | + |
| 2 | ++ | |
| 3 | ++ | |
| 4 | + | |
| 5 | + | |
| 6 | +++ | |
| 7 | +++ | |
| 8 | +++ | |
| 9 | +++ | |
| 10 | ++ | |
| 11 | +++ | |
| 12 | ++ | |
| 13 | +++ | |
| 14 | +++ | |
| 15 | + | + |
| 16 | +++ | |
| 17 | +++ | |
| 18 | +++ | |
| 19 | +++ | |
| 20 | +++ | |
| 21 | ++++ | + |
| 22 | +++ | |
| 23 | ++ | + |
| 24 | +++ | |
| 25 | +++ | |
| 26 | ++ | |
| 27 | ++ | |
| 28 | ++ | |
| 29 | ++ | |
| 30 | + | |
| 31 | + | |
| 32 | + | |
| 33 | ++ | |
| 34 | ++ | |
| 35 | + | |
| 36 | + | |
| 37 | ++ | |
| 38 | ++ | |
| 39 | ++ | |
| 40 | ++ | |
| 41 | +++ | |
| 42 | + | |
| 43 | ++ | |
| 44 | ++ | + |
| 45 | ++ | |
| 46 | ++ | |
| 47 | ++ | |
| 48 | ++ | |
| 49 | ++ | |
| 50 | + | |
| 51 | + | |
| 52 | ++ | |
| 53 | + | |
| 54 | ++ | |
| 55 | + | |
| 56 | + | |
| 57 | + | |
| 58 | + | |
| 59 | + | |
| 60 | ++ | |
| 61 | ++ | |
| 62 | + | |
| 63 | +++ | + |
| 64 | ++ | |
| 65 | +++ | ++ |
| 66 | + | |
| 67 | ++ | |
| 68 | +++ | + |
| 69 | + | |
| 70 | + | |
| 71 | + | |
| 72 | + | |
| 73 | + | |
| 74 | + | |
| 75 | + | |
| 76 | + | |
| 77 | ++ | |
| 78 | +++ | + |
| 79 | + | |
| 80 | ++ | |
| 81 | +++ | + |
| 82 | ++ | |
| 83 | + | |
| 84 | ++ | |

TABLE 1-continued

Biochemical IC50 and cell growth inhibitory GI50 values.

| Compound No. | Mer TK inhibition (IC50) | Cell growth inhibition (GI50) |
|---|---|---|
| 85 | ++ | |
| 86 | ++++ | +++ |
| 87 | ++ | |
| 88 | ++ | |
| 89 | ++ | |
| 90 | + | |
| 91 | + | |
| 92 | + | |
| 93 | ++ | + |
| 94 | + | |
| 95 | + | |
| 96 | + | |
| 97 | + | |
| 98 | + | |
| 99 | + | |
| 100 | + | |
| 101 | ++ | |
| 102 | + | |
| 103 | + | |
| 104 | + | |
| 105 | + | |
| 106 | + | |
| 107 | + | |
| 108 | + | |
| 109 | + | |
| 110 | + | |
| 111 | + | |
| 112 | + | |
| 113 | + | |
| 114 | + | |
| 115 | + | |
| 116 | + | |
| 117 | + | |
| 118 | + | |
| 119 | + | |
| 120 | + | |
| 121 | + | |
| 122 | + | |
| 123 | + | |
| 124 | + | |
| 125 | + | |
| 126 | + | |
| 127 | + | |
| 128 | + | |
| 129 | + | |
| 130 | +++ | + |
| 131 | + | |
| 132 | ++ | |
| 133 | + | |
| 134 | +++ | |
| 135 | +++ | + |
| 136 | ++++ | +++ |
| 137 | ++++ | ++++ |
| 138 | ++++ | + |
| 139 | + | |
| 140 | +++ | |
| 141 | +++ | |
| 142 | ++++ | +++ |
| 143 | + | |
| 144 | ++++ | ++ |
| 145 | ++++ | + |
| 146 | ++++ | ++++ |
| 147 | ++++ | +++ |
| 148 | ++++ | + |
| 149 | +++ | + |
| 150 | +++ | + |
| 151 | +++ | |
| 152 | +++ | |
| 153 | ++++ | ++ |
| 154 | ++ | + |
| 155 | +++ | + |
| 156 | ++++ | ++++ |
| 157 | ++++ | +++ |
| 158 | ++ | + |
| 159 | ++++ | +++ |
| 160 | +++ | +++ |
| 161 | ++++ | ++++ |
| 162 | +++ | |
| 163 | ++ | |
| 164 | + | + |
| 165 | + | |
| 166 | + | |
| 167 | ++++ | |
| 168 | ++ | + |
| 169 | + | |
| 170 | + | |
| 171 | + | |
| 172 | ++++ | ++++ |
| 173 | +++ | + |
| 174 | ++++ | +++ |
| 175 | +++ | + |
| 176 | +++ | + |
| 177 | ++++ | +++ |
| 178 | ++ | + |
| 179 | ++++ | +++ |
| 180 | ++++ | + |
| 181 | ++++ | ++++ |
| 182 | ++++ | ++++ |
| 183 | ++++ | ++++ |
| 184 | ++++ | ++++ |
| 185 | ++++ | +++ |
| 186 | ++++ | ++++ |
| 187 | ++++ | ++++ |
| 188 | ++++ | ++++ |
| 189 | ++++ | +++ |
| 190 | ++++ | ++++ |
| 191 | ++++ | +++ |
| 192 | ++++ | ++++ |
| 193 | ++++ | ++++ |
| 194 | ++++ | ++++ |
| 195 | ++++ | ++++ |
| 196 | ++++ | +++ |
| 197 | ++++ | ++++ |
| 198 | ++++ | ++++ |
| 199 | ++++ | ++++ |
| 200 | ++++ | +++ |
| 201 | +++ | +++ |
| 202 | ++++ | +++ |
| 203 | ++++ | +++ |
| 204 | ++++ | |
| 205 | ++++ | ++++ |
| 206 | ++++ | +++ |
| 207 | ++++ | |
| 208 | ++++ | ++++ |
| 209 | ++++ | ++++ |
| 210 | ++++ | ++++ |
| 211 | ++++ | ++++ |
| 212 | ++++ | + |
| 213 | ++++ | +++ |
| 214 | ++++ | ++++ |
| 215 | ++++ | ++++ |
| 216 | ++++ | ++++ |
| 217 | ++++ | ++++ |
| 218 | ++++ | ++++ |
| 219 | ++++ | ++++ |
| 220 | ++++ | ++++ |
| 221 | ++++ | ++++ |
| 222 | ++++ | ++++ |
| 223 | ++++ | +++ |
| 224 | ++++ | +++ |
| 225 | ++++ | +++ |
| 226 | ++++ | ++++ |
| 227 | ++++ | ++++ |
| 228 | ++++ | +++ |
| 229 | ++++ | ++++ |
| 230 | ++++ | ++++ |
| 231 | ++++ | |
| 232 | ++++ | ++ |
| 233 | ++++ | +++ |
| 234 | ++ | |

TABLE 1-continued

Biochemical IC50 and cell growth inhibitory GI50 values.

| Compound No. | Mer TK inhibition (IC50) | Cell growth inhibition (GI50) |
|---|---|---|
| 235 | ++++ | ++ |
| 236 | ++++ | ++++ |
| 237 | ++++ | ++++ |
| 238 | ++++ | ++++ |
| 239 | ++++ | ++++ |
| 240 | ++++ | ++++ |
| 241 | ++++ | ++ |
| 242 | ++++ | ++++ |
| 243 | ++ | + |
| 244 | + | |
| 245 | ++++ | ++ |
| 246 | ++++ | +++ |
| 247 | ++++ | +++ |
| 248 | +++ | + |
| 249 | ++++ | + |
| 250 | ++++ | +++ |
| 251 | ++++ | + |
| 252 | +++ | + |
| 253 | +++ | + |
| 254 | +++ | + |
| 255 | +++ | ++ |
| 256 | +++ | |
| 257 | +++ | + |
| 258 | +++ | |
| 259 | ++ | |
| 260 | +++ | |
| 261 | ++ | |
| 262 | + | |
| 263 | + | |
| 264 | + | |
| 265 | ++ | |
| 266 | ++ | |
| 267 | + | |
| 268 | ++ | |
| 269 | ++ | |
| 270 | +++ | |
| 271 | +++ | |
| 272 | +++ | |
| 273 | +++ | + |
| 274 | +++ | |
| 275 | +++ | ++ |
| 276 | +++ | |
| 277 | +++ | |
| 278 | +++ | |
| 279 | +++ | |
| 280 | +++ | |
| 281 | +++ | |
| 282 | +++ | |
| 283 | +++ | |
| 284 | +++ | |
| 285 | +++ | |
| 286 | +++ | |
| 287 | ++ | + |
| 288 | ++ | |
| 289 | +++ | |
| 290 | +++ | |
| 291 | +++ | |
| 292 | +++ | |
| 293 | +++ | + |
| 294 | ++ | |
| 295 | ++ | |
| 296 | ++ | |
| 297 | +++ | + |
| 298 | ++ | |
| 299 | +++ | |
| 300 | +++ | |
| 301 | +++ | |
| 302 | +++ | + |
| 303 | +++ | |
| 304 | +++ | |
| 305 | ++ | |
| 306 | +++ | |
| 307 | +++ | |
| 308 | ++ | |
| 309 | ++ | |
| 310 | ++ | |
| 311 | +++ | |
| 312 | +++ | |
| 313 | +++ | + |
| 314 | +++ | |
| 315 | +++ | |
| 316 | +++ | |
| 317 | ++ | |
| 318 | ++++ | ++ |
| 319 | +++ | |
| 320 | +++ | |
| 321 | +++ | + |
| 322 | +++ | |
| 323 | +++ | |
| 324 | +++ | |
| 325 | ++++ | + |
| 326 | +++ | |
| 327 | ++++ | + |
| 328 | ++++ | ++ |
| 329 | ++++ | |
| 330 | ++++ | |
| 331 | +++ | + |
| 332 | +++ | |
| 333 | +++ | + |
| 334 | ++ | |
| 335 | ++ | |
| 336 | ++ | |
| 337 | ++++ | ++ |
| 338 | +++ | + |
| 339 | +++ | |
| 340 | +++ | + |
| 341 | +++ | |
| 342 | ++++ | |
| 343 | +++ | |
| 344 | +++ | |
| 345 | +++ | |
| 346 | +++ | + |
| 347 | ++++ | + |
| 348 | ++++ | + |
| 349 | +++ | + |
| 350 | +++ | |
| 351 | +++ | |
| 352 | +++ | + |
| 353 | +++ | |
| 354 | ++ | |
| 355 | +++ | + |
| 356 | +++ | + |
| 357 | +++ | + |
| 358 | +++ | + |
| 359 | +++ | + |
| 360 | ++++ | + |
| 361 | +++ | + |
| 362 | + | |
| 363 | ++++ | +++ |
| 364 | ++++ | ++++ |
| 365 | +++ | + |
| 366 | ++++ | ++++ |
| 367 | ++++ | ++++ |
| 368 | ++++ | ++++ |
| 369 | ++++ | ++++ |
| 370 | ++++ | ++++ |
| 371 | ++++ | ++++ |
| 372 | ++++ | ++++ |
| 373 | ++++ | +++ |
| 374 | ++++ | +++ |
| 375 | ++++ | ++++ |
| 376 | ++++ | ++++ |
| 377 | ++++ | ++++ |
| 378 | ++++ | ++++ |
| 379 | ++++ | ++++ |
| 380 | ++++ | ++++ |
| 381 | ++++ | ++++ |
| 382 | ++++ | |
| 383 | ++++ | ++++ |
| 384 | ++++ | ++++ |

TABLE 1-continued

Biochemical IC50 and cell growth inhibitory GI50 values.

| Compound No. | Mer TK inhibition (IC50) | Cell growth inhibition (GI50) |
|---|---|---|
| 385 | ++++ | +++ |
| 386 | ++++ | ++++ |
| 387 | ++++ | ++++ |
| 388 | ++++ | +++ |
| 389 | ++++ | +++ |
| 390 | ++++ | +++ |
| 391 | ++++ | + |
| 392 | +++ | + |
| 393 | ++ | + |
| 394 | ++++ | ++ |
| 395 | ++++ | ++ |
| 396 | ++++ | + |
| 397 | +++ | + |
| 398 | +++ | ++ |
| 399 | ++++ | ++ |
| 400 | ++++ | ++ |
| 401 | ++++ | + |
| 402 | ++ | + |
| 403 | ++ | ++ |
| 404 | ++ | + |
| 405 | ++++ | +++ |
| 406 | +++ | + |
| 407 | +++ | ++ |
| 408 | +++ | + |
| 409 | +++ | + |
| 410 | +++ | + |
| 411 | ++++ | +++ |
| 412 | ++++ | + |
| 413 | ++++ | ++ |
| 414 | +++ | + |
| 415 | ++++ | + |
| 416 | ++++ | +++ |
| 417 | +++ | ++ |
| 418 | +++ | ++ |
| 419 | ++++ | + |
| 420 | +++ | + |
| 421 | +++ | + |
| 422 | +++ | + |
| 423 | +++ | ++ |
| 424 | +++ | + |
| 425 | +++ | ++ |
| 426 | ++++ | ++ |
| 427 | +++ | + |
| 428 | +++ | + |
| 429 | ++ | + |
| 430 | +++ | + |
| 431 | +++ | + |
| 432 | +++ | |
| 433 | ++++ | +++ |
| 434 | ++++ | ++ |
| 435 | ++++ | +++ |
| 436 | ++++ | ++ |
| 437 | ++++ | ++++ |
| 438 | ++++ | ++ |
| 439 | ++++ | +++ |
| 440 | ++++ | + |
| 441 | ++++ | +++ |
| 442 | ++++ | + |
| 443 | ++++ | ++++ |
| 444 | ++++ | + |
| 445 | ++++ | ++++ |
| 446 | ++++ | + |
| 447 | ++++ | ++++ |
| 448 | ++++ | ++++ |
| 449 | ++++ | ++++ |
| 450 | ++++ | ++++ |
| 451 | ++++ | ++++ |
| 452 | ++++ | ++++ |
| 453 | ++++ | +++ |
| 454 | ++++ | |
| 455 | +++ | |
| 456 | + | |
| 457 | + | |
| 458 | + | |

++++: IC50 < 10,
+++: 10 ≤ IC50 < 100,
++: 100 ≤ IC50 < 1000,
+: IC50 ≥ 1000 nM
++++: GI50 < 100,
+++: 100 ≤ GI50 < 500,
++: 500 ≤ GI50 < 1000,
+: GI50 ≥ 1000 nM

As can be seen in Table 1 above, the heterocyclic compounds of the present invention showed the activity of Mer, which compounds are useful for the prevention and/or the treatment of cancer.

The invention claimed is:

1. A method of treating a cancer influenced by inhibition of Mer kinase, the method comprising administering to a mammal in need thereof a composition comprising, as an active ingredient, a heterocyclic compound represented by the following Formula Ib, a stereoisomer thereof, an enantiomer thereof, or a pharmaceutically acceptable salt thereof:

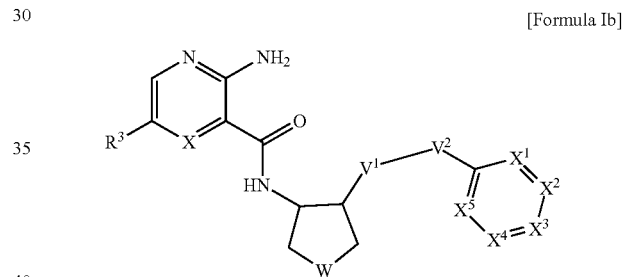

[Formula Ib]

wherein
X is CH, or N;
W is $CH_2$, $NR^{11}$, or O;
$V^1$ and $V^2$ each independently is $CR^{13}R^{13'}$, $NR^{13}$, or O;
at least one of $V_1$ and $V_2$ is $CR^{13}R^{13'}$;
$X^1$ to $X^5$ are the same as or different from each other, and are each independently $CR^{14}$ or N;
at least one of $X^1$ to $X^5$ is $CR^{14}$;
$R^3$ is H, halogen, CN, $C_{1-3}$ alkyl, 6-membered cycloalkenyl, $C_{2-6}$ alkenyl, 6-membered aryl, 10-membered biaryl, 5- to 6-membered heteroaryl comprising 1 or 2 heteroatoms selected from N and S, or 9- to 10-membered heterobiaryl comprising 1 heteroatom selected from N and O, which aryl, biaryl, heteroaryl, or heterobiaryl may optionally be substituted with one or more $R^9$;
$R^8$ is H, $C_{1-6}$ alkyl, $C_{1-4}$ fluoroalkyl, $C_{1-4}$ hydroxyalkyl, $C_{1-3}$ alkyl 6-membered aryl, or $C(=O)R^{10}$ which $C_{1-6}$ alkyl or $C_{1-3}$ alkylaryl is unsubstituted or substituted with one or more $R^9$;
$R^9$ is halogen, hydroxyl, —CN, —$NO_2$, —COOH, —(C=O)H, $C_{1-6}$ alkyl, $C_{2-6}$ alkenyl, $C_{2-6}$ alkynyl, $C_{3-10}$ cycloalkyl, $C_{1-4}$ hydroxyalkyl, $C_{1-6}$ alkoxy, 6-membered aryl, 5- to 6-membered heterocyclyl comprising 1 or 2 heteroatoms selected from N and O, —$NR^{15}R^{16}$, -L-$NR^{15}R^{16}$, -L-$COOR^{17}$, -L-alkyl, -L-C$_{3-10}$ cycloalkyl, -L-4- to 6-membered heterocyclyl comprising 1 or 2 heteroatoms selected from N and O, or -L-6-membered aryl which C$_{1-6}$ alkyl, C$_{2-6}$ alkenyl, C$_{2-6}$ alkynyl, C$_{3-10}$ cycloalkyl, C$_{1-4}$ hydroxyalkyl, C$_{1-6}$ alkoxy, aryl, heterocyclyl, -L-alkyl, -L-C$_{3-10}$ cycloalkyl, -L-heterocyclyl, or -L-aryl may substituted with halogen, hydroxyl, —CN, —NR$^{15}$R$^{16}$, C$_{1-6}$ alkyl, C$_{3-10}$ cycloalkyl, C$_{1-4}$ hydroxyalkyl, C$_{2-6}$ alkenyl, 6-membered aryl, 5- to 6-membered heterocyclyl comprising 1 or 2 heteroatoms selected from N and O, -L-5-membered heterocyclyl comprising 1 heteroatom of N, —(CH$_2$)—C(=O)—O—CH$_3$, or —(CH$_2$)$_l$—C(=O)—NR$^{15}$R$^{16}$;

R$^{10}$ is C$_{1-3}$ alkyl or C$_{1-3}$ alkylaryl;

R$^{11}$ is H, C$_{1-6}$ alkyl, C$_{1-4}$ fluoroalkyl, C$_{1-4}$ hydroxyalkyl, C$_{1-3}$ alkylaryl or C(=O)R$^{10}$ which C$_{1-6}$ alkyl or C$_{1-3}$ alkylaryl may optionally be substituted with one or more R$^9$;

R$^{13}$ and R$^{13'}$ each independently is H, C$_{1-3}$ alkyl, C$_{2-3}$ hydroxyalkyl;

each R$^{14}$ is independently selected from H, halogen, hydroxyl, —CN, —NO$_2$, C$_{1-6}$ alkyl, C$_{2-6}$ alkenyl, C$_{2-6}$ alkynyl, C$_{3-10}$ cycloalkyl, cycloalkenyl, aryl, heterocyclyl, heteroaryl, —NR$^{15}$R$^{16}$, -L-alkyl, -L-heterocyclyl, -L-heteroaryl, or -L-aryl which C$_{1-6}$ alkyl, aryl, heteroaryl, heterocyclyl may optionally be substituted with one or more R$^9$; or adjacent groups among a plurality of R$^{14}$s are bonded to each other to form a 3-7 membered cyclic ring or heterocyclic ring containing 1 or 2 of NR$^{11}$ O or S, and the cyclic or heterocyclic ring may optionally be substituted with 1 or 2 halogen(s), C$_{1-4}$ alkyl or C$_{1-4}$ alkoxy;

R$^{15}$ and R$^{16}$ each independently is H, C$_{1-6}$ alkyl, C$_{3-10}$ cycloalkyl or SO$_2$R$^{17}$;

R$^{17}$ is H, C$_{1-3}$alkyl or C$_{1-3}$ alkylaryl;

L is C$_{1-3}$ alkyl, C$_{1-3}$ alkylO, C$_{2-6}$ alkynyl, C$_{3-10}$ cycloalkyl, —(CH$_2$)$_l$—C(=O)—(CH$_2$)$_m$—, C(=O)O, —(CH$_2$)$_l$—C(=O)NH—(CH$_2$)$_m$—, —(CH$_2$)$_l$—NHC(=O)—(CH$_2$)$_m$—, —(CH$_2$)$_l$—NH—(CH$_2$)$_m$—, NR$^8$, —NH—C(=O)—CR$^{15}$R$^{16}$—NH—C(=O)—, NHC(=O), O, O(C=O)S, S, S(=O), or SO$_2$; and l and m each independently is an integer of 0 to 2, wherein the cancer is selected from the group consisting of: anaplastic astrocytoma, lung cancer, cervical carcinoma, colon cancer, ovarian cancer, breast cancer, prostate cancer, renal cell carcinoma, bladder carcinoma, melanoma, rhabdomyosarcoma, neuroblastoma, leukemia and metastatic lesions secondary therefrom.

2. A method of treating a cancer influenced by inhibition of Mer kinase, the method comprising administering to a mammal in need thereof a composition comprising, as an active ingredient, a heterocyclic compound represented by any one of the following compounds, a stereoisomer thereof, an enantiomer thereof, or a pharmaceutically acceptable salt thereof:

| | |
|---|---|
| Example 1 | 2-amino-N-((1S,2S)-2-(benzyloxy)cyclopentyl)-5-(1-methyl-1H-pyrazol-4-yl)nicotinamide |
| Example 2 | 2-amino-N-((1R,2R)-2-(benzyloxy)cyclopentyl)-5-(1-methyl-1H-pyrazol-4-yl)nicotinamide |
| Example 3 | 2-amino-N-(trans-2-(benzyloxy)cyclopentyl)-5-(1-methyl-1H-pyrazol-4-yl)nicotinamide |
| Example 4 | 2-amino-N-((1R,2S)-2-(benzyloxy)cyclopentyl)-5-(1-methyl-1H-pyrazol-4-yl)nicotinamide |
| Example 5 | 2-amino-N-(cis-2-(benzyloxy)cyclopentyl)-5-(1-methyl-1H-pyrazol-4-yl)nicotinamide |
| Example 6 | 2-amino-5-(1-methyl-1H-pyrazol-4-yl)-N-((1S,2S)-2-((2-methylbenzyl)oxy)cyclopentyl)nicotinamide |
| Example 7 | 2-amino-N-((1S,2S)-2-((3-ethylbenzyl)oxy)cyclopentyl)-5-(1-methyl-1H-pyrazol-4-yl)nicotinamide |
| Example 8 | 2-amino-N-((1S,2S)-2-((4-ethylbenzyl)oxy)cyclopentyl)-5-(1-methyl-1H-pyrazol-4-yl)nicotinamide |
| Example 9 | 2-amino-N-(trans-2-((4-ethylbenzyl)oxy)cyclopentyl)-5-(1-methyl-1H-pyrazol-4-yl)nicotinamide |
| Example 10 | 2-amino-N-((1S,2S)-2-((4-isopropylbenzyl)oxy)cyclopentyl)-5-(1-methyl-1H-pyrazol-4-yl)nicotinamide |
| Example 11 | 2-amino-N-((1S,2S)-2-((3,4-dimethylbenzyl)oxy)cyclopentyl)-5-(1-methyl-1H-pyrazol-4-yl)nicotinamide |
| Example 12 | 2-amino-N-((1R,2R)-2-((3,4-dimethylbenzyl)oxy)cyclopentyl)-5-(1-methyl-1H-pyrazol-4-yl)nicotinamide |
| Example 13 | 2-amino-N-(trans-2-((3,4-dimethylbenzyl)oxy)cyclopentyl)-5-(1-methyl-1H-pyrazol-4-yl)nicotinamide |
| Example 14 | 2-amino-N-((1S,2S)-2-((2,3-dimethylbenzyl)oxy)cyclopentyl)-5-(1-methyl-1H-pyrazol-4-yl)nicotinamide |
| Example 15 | 2-amino-N-((1S,2S)-2-((2,6-dimethylbenzyl)oxy)cyclopentyl)-5-(1-methyl-1H-pyrazol-4-yl)nicotinamide |
| Example 16 | 2-amino-N-((1S,2S)-2-((2,5-dimethylbenzyl)oxy)cyclopentyl)-5-(1-methyl-1H-pyrazol-4-yl)nicotinamide |
| Example 17 | 2-amino-N-((1S,2S)-2-((3,5-dimethylbenzyl)oxy)cyclopentyl)-5-(1-methyl-1H-pyrazol-4-yl)nicotinamide |
| Example 18 | 2-amino-N-((1S,2S)-2-((2,4-dimethylbenzyl)oxy)cyclopentyl)-5-(1-methyl-1H-pyrazol-4-yl)nicotinamide |
| Example 19 | 2-amino-N-((1S,2S)-2-((4-ethyl-3-methylbenzyl)oxy)cyclopentyl)-5-(1-methyl-1H-pyrazol-4-yl)nicotinamide |
| Example 20 | 2-amino-N-((1S,2S)-2-((3,4-diethylbenzyl)oxy)cyclopentyl)-5-(1-methyl-1H-pyrazol-4-yl)nicotinamide |
| Example 21 | 2-amino-N-((1S,2S)-2-((3-ethyl-4-methylbenzyl)oxy)cyclopentyl)-5-(1-methyl-1H-pyrazol-4-yl)nicotinamide |
| Example 22 | 2-amino-5-(1-methyl-1H-pyrazol-4-yl)-N-((1S,2S)-2-((3-propylbenzyl)oxy)cyclopentyl)nicotinamide |
| Example 23 | 2-amino-N-((1S,2S)-2-((3-cyclopentylbenzyl)oxy)cyclopentyl)-5-(1-methyl-1H-pyrazol-4-yl)nicotinamide |
| Example 24 | 2-amino-N-((1S,2S)-2-((3-isopropylbenzyl)oxy)cyclopentyl)-5-(1-methyl-1H-pyrazol-4-yl)nicotinamide |
| Example 25 | 2-amino-5-(1-methyl-1H-pyrazol-4-yl)-N-((1S,2S)-2-((3-(prop-1-en-2-yl)benzyl)oxy)cyclopentyl)nicotinamide |
| Example 26 | 2-amino-N-((1S,2S)-2-((3-cyclopropylbenzyl)oxy)cyclopentyl)-5-(1-methyl-1H-pyrazol-4-yl)nicotinamide |
| Example 27 | 2-amino-N-((1S,2S)-2-((3-cyclobutylbenzyl)oxy)cyclopentyl)-5-(1-methyl-1H-pyrazol-4-yl)nicotinamide |
| Example 28 | 2-amino-N-((1S,2S)-2-((3-ethynylbenzyl)oxy)cyclopentyl)-5-(1-methyl-1H-pyrazol-4-yl)nicotinamide |
| Example 29 | 2-amino-5-(1-methyl-1H-pyrazol-4-yl)-N-((1S,2S)-2-((4-(trifluoromethyl)benzyl)oxy)cyclopentyl)nicotinamide |
| Example 30 | 2-amino-5-(1-methyl-1H-pyrazol-4-yl)-N-((1S,2S)-2-((3-nitrobenzyl)oxy)cyclopentyl)nicotinamide |
| Example 31 | 2-amino-N-((1S,2S)-2-((3-cyanobenzyl)oxy)cyclopentyl)-5-(1-methyl-1H-pyrazol-4-yl)nicotinamide |
| Example 32 | 2-amino-N-((1S,2S)-2-((3-hydroxybenzyl)oxy)cyclopentyl)-5-(1-methyl-1H-pyrazol-4-yl)nicotinamide |

| | |
|---|---|
| Example 33 | 2-amino-N-((1S,2S)-2-((3-methyloxybenzyl)oxy)cyclopentyl)-5-(1-methyl-1H-pyrazol-4-yl)nicotinamide |
| Example 34 | 2-amino-N-((1R,2R)-2-((3-methoxybenzyl)oxy)cyclopentyl)-5-(1-methyl-1H-pyrazol-4-yl)nicotinamide |
| Example 35 | 2-amino-N-((1S,2S)-2-((4-methoxybenzyl)oxy)cyclopentyl)-5-(1-methyl-1H-pyrazol-4-yl)nicotinamide |
| Example 36 | 2-amino-N-((1R,2R)-2-((4-methoxybenzyl)oxy)cyclopentyl)-5-(1-methyl-1H-pyrazol-4-yl)nicotinamide |
| Example 37 | 2-amino-N-(trans-2-((3,5-dimethoxybenzyl)oxy)cyclopentyl)-5-(1-methyl-1H-pyrazol-4-yl)nicotinamide |
| Example 38 | 2-amino-N-((1S,2S)-2-((2,3-dimethoxybenzyl)oxy)cyclopentyl)-5-(1-methyl-1H-pyrazol-4-yl)nicotinamide |
| Example 39 | 2-amino-5-(1-methyl-1H-pyrazol-4-yl)-N-(1S,2S)-2-((3-phenoxybenzyl)oxy)cyclopentyl)nicotinamide |
| Example 40 | 2-amino-N-((1S,2S)-2-(benzo[d][1,3]dioxol-5-ylmethoxy)cyclopentyl)-5-(1-methyl-1H-pyrazol-4-yl)nicotinamide |
| Example 41 | 2-amino-5-(1-methyl-1H-pyrazol-4-yl)-N-((1S,2S)-2-((4-(methylthio)benzyl)oxy)cyclopentyl)nicotinamide |
| Example 42 | methyl 3-((((1S,2S)-2-(2-amino-5-(1-methyl-1H-pyrazol-4-yl)nicotinamido)cyclopentyl)oxy)methyl)benzoate |
| Example 43 | 2-amino-N-((1S,2S)-2-((3-chlorobenzyl)oxy)cyclopentyl)-5-(1-methyl-1H-pyrazol-4-yl)nicotinamide |
| Example 44 | 2-amino-N-(trans-2-((3-chlorobenzyl)oxy)cyclopentyl)-5-(1-methyl-1H-pyrazol-4-yl)nicotinamide |
| Example 45 | 2-amino-N-(trans-2-((4-chlorobenzyl)oxy)cyclopentyl)-5-(1-methyl-1H-pyrazol-4-yl)nicotinamide |
| Example 46 | 2-amino-N-(trans-2-((3,4-dichlorobenzyl)oxy)cyclopentyl)-5-(1-methyl-1H-pyrazol-4-yl)nicotinamid |
| Example 47 | 2-amino-N-(trans-2-((2-fluorobenzyl)oxy)cyclopentyl)-5-(1-methyl-1H-pyrazol-4-yl)nicotinamide |
| Example 48 | 2-amino-N-((1S,2S)-2-((3-fluorobenzyl)oxy)cyclopentyl)-5-(1-methyl-1H-pyrazol-4-yl)nicotinamide |
| Example 49 | 2-amino-N-(trans-2-((4-bromo-2-fluorobenzyl)oxy)cyclopentyl)-5-(1-methyl-1H-pyrazol-4-yl)nicotinamide |
| Example 50 | 2-amino-5-(1-methyl-1H-pyrazol-4-yl)-N-(trans-2-((2,4,5-trifluorobenzyl)oxy)cyclopentyl)nicotinamide |
| Example 51 | 2-amino-N-((1S,2S)-2-((3-bromobenzyl)oxy)cyclopentyl)-5-(1-methyl-1H-pyrazol-4-yl)nicotinamide |
| Example 52 | 2-amino-N-(trans-2-((3-bromo-4-fluorobenzyl)oxy)cyclopentyl)-5-(1-methyl-1H-pyrazol-4-yl)nicotinamide |
| Example 53 | 2-amino-N-((1R,2R)-2-((3-bromo-4-fluorobenzyl)oxy)cyclopentyl)-5-(1-methyl-1H-pyrazol-4-yl)nicotinamide |
| Example 54 | 2-amino-N-((1S,2S)-2-(1-(4-bromophenyl)ethoxy)cyclopentyl)-5-(1-methyl-1H-pyrazol-4-yl)nicotinamide |
| Example 55 | methyl (3-((((1S,2S)-2-(2-amino-5-(1-methyl-1H-pyrazol-4-yl)nicotinamido)cyclopentyl)oxy)methyl)benzoyl)glycinate |
| Example 56 | 2-amino-N-((1S,2S)-2-((3-((2-hydroxyethyl)carbamoyl)benzyl)-oxy)cyclopentyl)-5-(1-methyl-1H-pyrazol-4-yl)nicotinamide |
| Example 57 | 2-amino-5-(1-methyl-1H-pyrazol-4-yl)-N-((1S,2S)-2-((3-(piperidine-4-carboxamido)benzyl)oxy)cyclopentyl)nicotinamide |
| Example 58 | 2-amino-N-((1S,2S)-2-((3-((S)-2-aminopropanamido)benzyl)oxy)-cyclopentyl)-5-(1-methyl-1H-pyrazol-4-yl)nicotinamide |
| Example 59 | N-((1S,2S)-2-((3-((S)-2-acetamidopropanamido)benzyl)oxy)-cyclopentyl)-2-amino-5-(1-methyl-1H-pyrazol-4-yl)nicotinamide |
| Example 60 | 2-amino-N-((1S,2S)-2-((3-(3-aminopropanamido)benzyl)oxy)-cyclopentyl)-5-(1-methyl-1H-pyrazol-4-yl)nicotinamide |
| Example 61 | N-((1S,2S)-2-((3-(2H-1,2,3-triazol-2-yl)benzyl)oxy)cyclopentyl)-2-amino-5-(1-methyl-1H-pyrazol-4-yl)nicotinamide |
| Example 62 | N-((1S,2S)-2-((4-(2H-1,2,3-triazol-2-yl)benzyl)oxy)cyclopentyl)-2-amino-5-(1-methyl-1H-pyrazol-4-yl)nicotinamide |
| Example 63 | 2-amino-5-(1-methyl-1H-pyrazol-4-yl)-N-((1S,2S)-2-(naphthalen-2-ylmethoxy)cyclopentyl)nicotinamide |
| Example 64 | 2-amino-5-(1-methyl-1H-pyrazol-4-yl)-N-((1S,2S)-2-(quinolin-8-ylmethoxy)cyclopentyl)nicotinamide |
| Example 65 | 2-amino-5-(1-methyl-1H-pyrazol-4-yl)-N-((1S,2S)-2-((2',3',4',5'-tetrahydro-[1,1'-biphenyl]-4-yl)methoxy)cyclopentyl)nicotinamide |
| Example 66 | N-(trans-2-(([1,1'-biphenyl]-2-ylmethoxy)cyclopentyl)-2-amino-5-(1-methyl-1H-pyrazol-4-yl)nicotinamide |
| Example 67 | N-((1S,2S)-2-(([1,1'-biphenyl]-3-ylmethoxy)cyclopentyl)-2-amino-5-(1-methyl-1H-pyrazol-4-yl)nicotinamide |
| Example 68 | N-((1S,2S)-2-(([1,1'-biphenyl]-4-ylmethoxy)cyclopentyl)-2-amino-5-(1-methyl-1H-pyrazol-4-yl)nicotinamide |
| Example 69 | 2-amino-N-((1S,2S)-2-hydroxycyclopentyl)-5-(1-methyl-1H-pyrazol-4-yl)nicotinamide |
| Example 70 | 2-amino-N-(cis-2-hydroxycyclopentyl)-5-(1-methyl-1H-pyrazol-4-yl)-nicotinamide |
| Example 71 | N-((1S,2S)-2-(benzyloxy)cyclopentyl)-2-(ethylamino)-5-(1-methyl-1H-pyrazol-4-yl)nicotinamide |
| Example 72 | N-((1S,2S)-2-(benzyloxy)cyclopentyl)-2-((3,4-dimethylbenzyl)amino)-5-(1-methyl-1H-pyrazol-4-yl)nicotinamide |
| Example 73 | 2-amino-N-((6R,7S)-6-(benzyloxy)-1,4-dioxaspiro[4.4]nonan-7-yl)-5-(1-methyl-1H-pyrazol-4-yl)nicotinamide |
| Example 74 | 2-amino-N-(trans-2-(benzyloxy)cyclohexyl)-5-(1-methyl-1H-pyrazol-4-yl)nicotinamide |
| Example 75 | 2-amino-N-((1S,2S)-2-(benzyloxy)cyclohexyl)-5-(1-methyl-1H-pyrazol-4-yl)nicotinamide |
| Example 76 | 2-amino-N-(trans-2-(benzyl(methyl)amino)cyclopentyl)-5-(1-methyl-1H-pyrazol-4-yl)nicotinamide |
| Example 77 | 2-amino-5-(1-methyl-1H-pyrazol-4-yl)-N-((1S,2S)-2-(phenoxymethyl)cyclopentyl)nicotinamide |
| Example 78 | 2-amino-N-((1S,2S)-2-((3,4-dimethylphenoxy)methyl)cyclopentyl)-5-(1-methyl-1H-pyrazol-4-yl)nicotinamide |
| Example 79 | 2-amino-N-(trans-2,2-difluoro-5-(phenoxymethyl)cyclopentyl)-5-(1-methyl-1H-pyrazol-4-yl)nicotinamide |
| Example 80 | 2-amino-N-((1S,2S)-2-(((2,3-dihydro-1H-inden-5-yl)oxy)methyl)cyclopentyl)-5-(1-methyl-1H-pyrazol-4-yl)nicotinamide |
| Example 81 | 2-amino-5-(1-methyl-1H-pyrazol-4-yl)-N-((1S,2S)-2-((3,4,5-trimethylphenoxy)methyl)cyclopentyl)nicotinamide |
| Example 82 | 2-amino-N-((1S,2S)-2-((3-(dimethylamino)phenoxy)methyl)-cyclopentyl)-5-(1-methyl-1H-pyrazol-4-yl)nicotinamide |
| Example 83 | 2-amino-5-(1-methyl-1H-pyrazol-4-yl)-N-((1S,2S)-2-((3-(piperidine-1-carboxyl)phenoxy)methyl)cyclopentyl)nicotinamide |
| Example 84 | 2-amino-5-(1-methyl-1H-pyrazol-4-yl)-N-((1S,2S)-2-((4-phenoxyphenoxy)methyl)cyclopentyl)nicotinamide |
| Example 85 | 2-amino-N-((1S,2S)-2-((benzyloxy)methyl)cyclopentyl)-5-(1-methyl-1H-pyrazol-4-yl)nicotinamide |
| Example 86 | 2-amino-5-(1-methyl-1H-pyrazol-4-yl)-N-((1S,2S)-2-((4'-((4-methyl-piperazin-1-yl)methyl)-[1,1'-biphenyl]-4-yl)oxy)methyl)cyclopentyl)-nicotinamide |

| | |
|---|---|
| Example 87 | (1S,2S)-2-(benzyloxy)cyclopentyl 2-amino-5-(1-methyl-1H-pyrazol-4-yl)nicotinate |
| Example 88 | 2-amino-5-(1-methyl-1H-pyrazol-4-yl)-N-((1S,2R)-2-phenethylcyclopentyl)nicotinamide |
| Example 89 | 2-amino-N-(trans-4-(benzyloxy)tetrahydrofuran-3-yl)-5-(1-methyl-1H-pyrazol-4-yl)nicotinamide |
| Example 90 | 2-amino-5-(1-methyl-1H-pyrazol-4-yl)-N-(trans-4-morpholinotetrahydrofuran-3-yl)nicotinamide |
| Example 91 | 2-amino-5-(1-methyl-1H-pyrazol-4-yl)-N-(trans-4-(pyrrolidin-1-yl)tetrahydrofuran-3-yl)nicotinamide |
| Example 92 | 2-amino-N-(cis-4-hydroxytetrahydrofuran-3-yl)-5-(1-methyl-1H-pyrazol-4-yl)nicotinamide |
| Example 93 | 2-amino-N-(4-(benzyloxy)-1-methylpyrrolidin-3-yl)-5-(1-methyl-1H-pyrazol-4-yl)nicotinamide |
| Example 94 | 2-amino-N-(trans-4-(benzyloxy)-1-isopropylpyrrolidin-3-yl)-5-(1-methyl-1H-pyrazol-4-yl)nicotinamide |
| Example 95 | (R)-2-amino-N-(2-(benzyloxy)propyl)-5-(1-methyl-1H-pyrazol-4-yl)nicotinamide |
| Example 96 | (S)-2-amino-N-(2-(benzyloxy)propyl)-5-(1-methyl-1H-pyrazol-4-yl)nicotinamide |
| Example 97 | (S)-2-amino-N-(1-(benzyloxy)propan-2-yl)-5-(1-methyl-1H-pyrazol-4-yl)nicotinamide |
| Example 98 | (R)-2-amino-N-(1-(benzyloxy)propan-2-yl)-5-(1-methyl-1H-pyrazol-4-yl)nicotinamide |
| Example 99 | 2-amino-N-(1-(benzyloxy)-2-methylpropan-2-yl)-5-(1-methyl-1H-pyrazol-4-yl)nicotinamide |
| Example 100 | (R)-2-amino-N-(1-((3,4-dimethylbenzyl)oxy)propan-2-yl)-5-(1-methyl-1H-pyrazol-4-yl)nicotinamide |
| Example 101 | (S)-2-amino-N-(2-((3,4-dimethylbenzyl)oxy)propyl)-5-(1-methyl-1H-pyrazol-4-yl)nicotinamide |
| Example 102 | (R)-2-amino-N-(1-((4-chlorobenzyl)oxy)propan-2-yl)-5-(1-methyl-1H-pyrazol-4-yl)nicotinamide |
| Example 103 | (S)-2-amino-N-(2-((4-chlorobenzyl)oxy)propyl)-5-(1-methyl-1H-pyrazol-4-yl)nicotinamide |
| Example 104 | (R)-2-amino-N-(1-((3,4-dichlorobenzyl)oxy)propan-2-yl)-5-(1-methyl-1H-pyrazol-4-yl)nicotinamide |
| Example 105 | (S)-2-amino-N-(2-((3,4-dichlorobenzyl)oxy)propyl)-5-(1-methyl-1H-pyrazol-4-yl)nicotinamide |
| Example 106 | (R)-2-amino-N-(1-((3-methoxybenzyl)oxy)propan-2-yl)-5-(1-methyl-1H-pyrazol-4-yl)nicotinamide |
| Example 107 | (S)-2-amino-N-(2-((3-methoxybenzyl)oxy)propyl)-5-(1-methyl-1H-pyrazol-4-yl)nicotinamide |
| Example 108 | (R)-2-amino-N-(1-(benzyloxy)butan-2-yl)-5-(1-methyl-1H-pyrazol-4-yl)nicotinamide |
| Example 109 | (S)-2-amino-N-(1-(benzyloxy)-3-methylbutan-2-yl)-5-(1-methyl-1H-pyrazol-4-yl)nicotinamide |
| Example 110 | (R)-2-amino-N-(1-(benzyloxy)-3-methylbutan-2-yl)-5-(1-methyl-1H-pyrazol-4-yl)nicotinamide |
| Example 111 | (S)-2-amino-N-(1-(benzyloxy)-4-methylpentan-2-yl)-5-(1-methyl-1H-pyrazol-4-yl)nicotinamide |
| Example 112 | (R)-2-amino-N-(1-(benzyloxy)-4-methylpentan-2-yl)-5-(1-methyl-1H-pyrazol-4-yl)nicotinamide |
| Example 113 | (R)-2-amino-N-(2-(benzyloxy)-1-cyclohexylethyl)-5-(1-methyl-1H-pyrazol-4-yl)nicotinamide |
| Example 114 | (R)-2-amino-N-(1-cyclohexyl-2-hydroxyethyl)-5-(1-methyl-1H-pyrazol-4-yl)nicotinamide |
| Example 115 | (S)-2-amino-N-(2-(benzyloxy)-1-phenylethyl)-5-(1-methyl-1H-pyrazol-4-yl)nicotinamide |
| Example 116 | (R)-2-amino-N-(2-(benzyloxy)-1-phenylethyl)-5-(1-methyl-1H-pyrazol-4-yl)nicotinamide |
| Example 117 | (S)-2-amino-N-(1-(benzyloxy)-3-phenylpropan-2-yl)-5-(1-methyl-1H-pyrazol-4-yl)nicotinamide |
| Example 118 | (R)-2-amino-N-(1-(benzyloxy)-3-phenylpropan-2-yl)-5-(1-methyl-1H-pyrazol-4-yl)nicotinamide |
| Example 119 | (R)-2-amino-N-(1-(cyclobutylmethoxy)propan-2-yl)-5-(1-methyl-1H-pyrazol-4-yl)nicotinamide |
| Example 120 | methyl N-(2-amino-5-(1-methyl-1H-pyrazol-4-yl)nicotinoyl)-O-benzyl-L-serinate |
| Example 121 | methyl N-(2-amino-5-(1-methyl-1H-pyrazol-4-yl)nicotinoyl)-O-benzyl-L-threoninate |
| Example 122 | 2-amino-N-((2S,3R)-3-(benzyloxy)-1-(methylamino)-1-oxobutan-2-yl)-5-(1-methyl-1H-pyrazol-4-yl)nicotinamide |
| Example 123 | 2-amino-N-((2S,3R)-3-(benzyloxy)-1-oxo-1-(propylamino)butan-2-yl)-5-(1-methyl-1H-pyrazol-4-yl)nicotinamide |
| Example 124 | 2-amino-N-((2S,3R)-3-(benzyloxy)-1-(cyclopentylamino)-1-oxobutan-2-yl)-5-(1-methyl-1H-pyrazol-4-yl)nicotinamide |
| Example 125 | 2-amino-N-((2S,3R)-3-(benzyloxy)-1-oxo-1-(pyrrolidin-1-yl)butan-2-yl)-5-(1-methyl-1H-pyrazol-4-yl)nicotinamide |
| Example 126 | benzyl (2-amino-5-(1-methyl-1H-pyrazol-4-yl)nicotinoyl)-L-alaninate |
| Example 127 | benzyl (2-amino-5-(1-methyl-1H-pyrazol-4-yl)nicotinoyl)-L-valinate |
| Example 128 | benzyl (2-amino-5-(1-methyl-1H-pyrazol-4-yl)nicotinoyl)-L-serinate |
| Example 129 | 3-amino-N-((1S,2S)-2-(benzyloxy)cyclopentyl)-6-(1-methyl-1H-pyrazol-4-yl)pyrazine-2-carboxamide |
| Example 130 | 3-amino-N-((1S,2S)-2-((3,4-dimethylbenzyl)oxy)cyclopentyl)-6-(1-methyl-1H-pyrazol-4-yl)pyrazine-2-carboxamide |
| Example 131 | (S)-3-amino-6-(1-methyl-1H-pyrazol-4-yl)-N-(1,2,3,4-tetrahydronaphthalen-1-yl)pyrazine-2-carboxamide |
| Example 132 | 3-amino-N-(trans-4-(benzyloxy)tetrahydrofuran-3-yl)-6-(1-methyl-1H-pyrazol-4-yl)pyrazine-2-carboxamide |
| Example 133 | 3-amino-N-(cis-4-(benzyloxy)tetrahydrofuran-3-yl)-6-(1-methyl-1H-pyrazol-4-yl)pyrazine-2-carboxamide |
| Example 134 | 2-amino-N-((1S,2S)-2-((3'-amino-[1,1-biphenyl]-4-yl)methoxy)cyclopentyl)-5-(1-methyl-1H-pyrazol-4-yl)nicotinamide |
| Example 135 | 2-amino-N-((1S,2S)-2-((4'-amino-[1,1-biphenyl]-4-yl)methoxy)cyclopentyl)-5-(1-methyl-1H-pyrazol-4-yl)nicotinamide |
| Example 136 | 2-amino-5-(1-methyl-1H-pyrazol-4-yl)-N-((1S,2S)-2-((4'-(methylamino)-[1,1'-biphenyl]-4-yl)methoxy)cyclopentyl)nicotinamide |
| Example 137 | 2-amino-N-((1S,2S)-2-((4'-(dimethylamino)-[1,1'-biphenyl]-4-yl)methoxy)cyclopentyl)-5-(1-methyl-1H-pyrazol-4-yl)nicotinamide |
| Example 138 | 2-amino-N-((1S,2S)-2-((4'-((dimethylamino)methyl)-[1,1'-biphenyl]-4-yl)methoxy)cyclopentyl)-5-(1-methyl-1H-pyrazol-4-yl)nicotinamide |
| Example 139 | 2-amino-N-((1S,2S)-2-((3'-amino-2'-methyl-[1,1'-biphenyl]-4-yl)methoxy)cyclopentyl)-5-(1-methyl-1H-pyrazol-4-yl)nicotinamide |
| Example 140 | 2-amino-N-((1S,2S)-2-((3'-hydroxy-[1,1'-biphenyl]-4-yl)methoxy)cyclopentyl)-5-(1-methyl-1H-pyrazol-4-yl)nicotinamide |
| Example 141 | 2-amino-N-((1S,2S)-2-((3'-(hydroxymethyl)-[1,1'-biphenyl]-4-yl)methoxy)cyclopentyl)-5-(1-methyl-1H-pyrazol-4-yl)nicotinamide |
| Example 142 | 2-amino-N-((1S,2S)-2-((4'-(hydroxymethyl)-[1,1'-biphenyl)-4-yl)methoxy)cyclopentyl)-5-(1-methyl-1H-pyrazol-4-yl)nicotinamide |
| Example 143 | 2-amino-N-((1S,2S)-2-((3'-(aminomethyl)-[1,1'-biphenyl]-4-yl)methoxy)cyclopentyl)-5-(1-methyl-1H-pyrazol-4-yl)nicotinamide |
| Example 144 | 2-amino-N-((1S,2S)-2-((4'-(aminomethyl)-[1,1'-biphenyl]-4-yl)methoxy)cyclopentyl)-5-(1-methyl-1H-pyrazol-4-yl)nicotinamide |
| Example 145 | 2-amino-N-((1S,2S)-2-((4'-(2-aminoethyl)-[1,1'-biphenyl]-4-yl)methoxy)cyclopentyl)-5-(1-methyl-1H-pyrazol-4-yl)nicotinamide |
| Example 146 | 2-amino-5-(1-methyl-1H-pyrazol-4-yl)-N-((1S,2S)-2-((4'-(4-methylpiperazin-1-yl)-[1,1'-biphenyl]-4-yl)methoxy)cyclopentyl)nicotinamide |
| Example 147 | 2-amino-5-(1-methyl-1H-pyrazol-4-yl)-N-((1S,2S)-2-((4-(6-(piperazin-1-yl)pyridin-3-yl)benzyl)oxy)cyclopentyl)nicotinamide |
| Example 148 | 2-amino-5-(1-methyl-1H-pyrazol-4-yl)-N-((1S,2S)-2-((4-(6-(4-methylpiperazin-1-yl)pyridin-3-yl)benzyl)oxy)cyclopentyl)nicotinamide |
| Example 149 | 2-amino-5-(1-methyl-1H-pyrazol-4-yl)-N-((1S,2S)-2-((3'-(piperazin-1-yl)-[1,1'-biphenyl]-4-yl)methoxy)cyclopentyl)nicotinamide |
| Example 150 | 2-amino-5-(1-methyl-1H-pyrazol-4-yl)-N-((1S,2S)-2-((3'-(4-methylpiperazin-1-yl)-[1,1'-biphenyl]-4-yl)methoxy)cyclopentyl)nicotinamide |

| | |
|---|---|
| Example 151 | 2-amino-5-(1-methyl-1H-pyrazol-4-yl)-N-((1S,2S)-2-((3'-((4-methylpiperazin-1-yl)methyl)-[1,1'-biphenyl]-4-yl)methoxy)cyclopentyl)nicotinamide |
| Example 152 | 2-amino-5-(1-methyl-1H-pyrazol-4-yl)-N-((1S,2S)-2-((4'-(morpholine-4-carbonyl)-[1,1'-biphenyl]-4-yl)methoxy)cyclopentyl)nicotinamide |
| Example 153 | 2-amino-N-((1S,2S)-2-((4'-ethyl-[1,1'-biphenyl]-4-yl)methoxy)cyclopentyl)-5-(1-methyl-1H-pyrazol-4-yl)nicotinamide |
| Example 154 | 2-amino-N-((1S,2S)-2-[1,1'-(cyanomethyl)-[1,1'-biphenyl]-4-yl)methoxy)cyclopentyl)-5-(1-methyl-1H-pyrazol-4-yl)nicotinamide |
| Example 155 | 2-amino-N-((1S,2S)-2-((4'-carbamoyl-[1,1'-biphenyl]-4-yl)methoxy)cyclopentyl)-5-(1-methyl-1H-pyrazol-4-yl)nicotinamide |
| Example 156 | 2-amino-N-((1S,2S)-2-((3-fluoro-4'-((4-methylpiperazin-1-yl)methyl)-[1,1'-biphenyl]-4-yl)methoxy)cyclopentyl)-5-(1-methyl-1H-pyrazol-4-yl)nicotinamide |
| Example 157 | 2-amino-N-((1S,2S)-2-((3-fluoro-4'-(cis-3,4,5-trimethylpiperazin-1-yl)methyl)-[1,1'-biphenyl]-4-yl)methoxy)cyclopentyl)-5-(1-methyl-1H-pyrazol-4-yl)nicotinamide |
| Example 158 | 2-amino-5-(1-methyl-1H-pyrazol-4-yl)-N-((1S,2S)-2-((4'-((4-methylpiperazin-1-yl)methyl)-3-(trifluoromethyl)-[1,1'-biphenyl]-4-yl)methoxy)cyclopentyl)nicotinamide |
| Example 159 | 2-amino-N-((1S,2S)-2-((2-chloro-4'-((4-methylpiperazin-1-yl)methyl)-[1,1'-biphenyl]-4-yl)methoxy)cyclopentyl)-5-(1-methyl-1H-pyrazol-4-yl)nicotinamide |
| Example 160 | 2-amino-N-((1S,2S)-2-((3-fluoro-4'-(cis-4-(2-hydroxyethyl)-3,5-dimethylpiperazin-1-yl)methyl)-[1,1'-biphenyl]-4-yl)methoxy)cyclopentyl)-5-(1-methyl-1H-pyrazol-4-yl)nicotinamide |
| Example 161 | 2-amino-5-(1-methyl-1H-pyrazol-4-yl)-N-((1S,2S)-2-((4'-(2-(4-methylpiperazin-1-yl)ethyl)-[1,1'-biphenyl]-4-yl)methoxy)cyclopentyl)nicotinamide |
| Example 162 | 2-amino-5-(1-methyl-1H-pyrazol-4-yl)-N-((1S,2S)-2-((4-(1-(piperidin-4-yl)-1H-pyrazol-4-yl)benzyl)oxy)cyclopentyl)nicotinamide |
| Example 163 | 2-amino-5-(1-methyl-1H-pyrazol-4-yl)-N-((1S,2S)-2-((4-(1-(1-methylpiperidin-4-yl)-1H-pyrazol-4-yl)benzyl)oxy)cyclopentyl)nicotinamide |
| Example 164 | 2-amino-5-(1-methyl-1H-pyrazol-4-yl)-N-((1S,2R)-2-((4'-((4-methylpiperazin-1-yl)methyl)-[1,1'-biphenyl]-4-yl)methoxy)cyclopentyl)nicotinamide |
| Example 165 | 2-amino-5-(1-methyl-1H-pyrazol-4-yl)-N-((1R,2S)-2-((4'-((4-methylpiperazin-1-yl)methyl)-[1,1'-biphenyl]-4-yl)methoxy)cyclopentyl)nicotinamide |
| Example 166 | 2-amino-5-(1-methyl-1H-pyrazol-4-yl)-N-((1S,2S)-2-((4'((4-methylpiperazin-1-yl)methyl)-[1,1'-biphenyl]-4-yl)methoxy)cyclohexyl)nicotinamide |
| Example 167 | 2-amino-N-((1S,2S)-2-((4'-(2-(4-methylpiperazin-1-yl)propan-2-yl)-[1,1'-biphenyl]-4-yl)methoxy)cyclopentyl)nicotinamide |
| Example 168 | 2-amino-N-((1S,2S)-2-((4'-((4-methylpiperazin-1-yl)methyl)-3-(trifluoromethyl)-[1,1'-biphenyl]-4-yl)methoxy)cyclopentyl)nicotinamide |
| Example 169 | 2-amino-N-((1S,2S)-2-((3'-hydroxy-[1,1'-biphenyl]-3-yl)methoxy)cyclopentyl)-5-(1-methyl-1H-pyrazol-4-yl)nicotinamide |
| Example 170 | 2-amino-N-((1S,2S)-2-((3'-amino-[1,1'-biphenyl]-3-yl)methoxy)cyclopentyl)-5-(1-methyl-1H-pyrazol-4-yl)nicotinamide |
| Example 171 | 2-amino-N-((1S,2S)-2-((3'-(hydroxymethyl)-[1,1'-biphenyl]-3-yl)methoxy)cyclopentyl)-5-(1-methyl-1H-pyrazol-4-yl)nicotinamide |
| Example 172 | 2-amino-5-(1-methyl-1H-pyrazol-4-yl)-N-((1S,2S)-2-((4'-((4-methylpiperazin-1-yl)methyl)-[1,1'-biphenyl]-4-yl)methoxy)cyclopentyl)nicotinamide |
| Example 173 | 2-amino-N-((1S,2S)-2-((4'-(((2-hydroxyethyl)amino)methyl)-[1,1'-biphenyl]-4-yl)methoxy)cyclopentyl)-5-(1-methyl-1H-pyrazol-4-yl)nicotinamide |
| Example 174 | 2-amino-5-(1-methyl-1H-pyrazol-4-yl)-N-((1S,2S)-2-((4'-(morpholinomethyl)-[1,1'-biphenyl]-4-yl)methoxy)cyclopentyl)nicotinamide |
| Example 175 | 2-amino-N-((1S,2S)-2-((4'-((3,3-difluoropiperidin-1-yl)methyl)-[1,1'-biphenyl]-4-yl)methoxy)cyclopentyl)-5-(1-methyl-1H-pyrazol-4-yl)nicotinamide |
| Example 176 | 2-amino-5-(1-methyl-1H-pyrazol-4-yl)-N-((1S,2S)-2-((4'-((4-methyl-piperidin-1-yl)methyl)-[1,1'-biphenyl]-4-yl)methoxy)cyclopentyl)-nicotinamide |
| Example 177 | 2-amino-5-(1-methyl-1H-pyrazol-4-yl)-N-((1S,2S)-2-((4'(piperazin-1-ylmethyl)-[1,1'-biphenyl]-4-yl)methoxy)cyclopentyl)nicotinamide |
| Example 178 | 2-amino-5-(1-methyl-1H-pyrazol-4-yl)-N-((1S,2S)-2-((4'-((4-phenyl-piperazin-1-yl)methyl)-[1,1'-biphenyl]-4-yl)methoxy)cyclopentyl)-nicotinamide |
| Example 179 | 2-amino-5-(1-methyl-1H-pyrazol-4-yl)-N-((1S,2S)-2-((4'-((4-(pyrrolidin-1-yl)piperidin-1-yl)methyl)-[1,1'-biphenyl]-4-yl)methoxy)cyclopentyl)-nicotinamide |
| Example 180 | 2-amino-N-((1S,2S)-2-((4'-((4-hydroxypiperidin-1-yl)methyl)-[1,1'-biphenyl]-4-yl)methoxy)cyclopentyl)-5-(1-methyl-1H-pyrazol-4-yl)nicotinamide |
| Example 181 | 2-amino-N-((1S,2S)-2-((4'-((4-(2-hydroxyethyl)piperazin-1-yl)methyl)-[1,1'-biphenyl]-4-yl)methoxy)cyclopentyl)-5-(1-methyl-1H-pyrazol-4-yl)-nicotinamide |
| Example 182 | 2-amino-N-((1S,2S)-2-((4'-((4-(2-hydroxy-2-methylpropyl)piperazin-1-yl)methyl)-[1,1'-biphenyl]-4-yl)methoxy)cyclopentyl)-5-(1-methyl-1H-pyrazol-4-yl)nicotinamide |
| Example 183 | 2-amino-N-((1S,2S)-2-((4'-((4-ethylpiperazin-1-yl)methyl)-[1,1'-biphenyl]-4-yl)methoxy)cyclopentyl)-5-(1-methyl-1H-pyrazol-4-yl)nicotinamide |
| Example 184 | 2-amino-N-((1S,2S)-2-((4'-((4-cyclopropylpiperazin-1-yl)methyl)-[1,1'-biphenyl]-4-yl)methoxy)cyclopentyl)-5-(1-methyl-1H-pyrazol-4-yl)-nicotinamide |
| Example 185 | 2-amino-5-(1-methyl-1H-pyrazol-4-yl)-N-((1S,2S)-2-((4'-(((R)-3-methyl-piperazin-1-yl)methyl)-[1,1'-biphenyl]-4-y])methoxy)cyclopentyl)-nicotinamide |
| Example 186 | 2-amino-N-((1S,2S)-2-((4'-(((R)-3,4-dimethylpiperazin-1-yl)methyl)-[1,1'-biphenyl]-4-yl)methoxy)cyclopentyl)-5-(1-methyl-1H-pyrazol-4-yl)nicotinamide |
| Example 187 | 2-amino-N-((1S,2S)-2-((4'-(((R)-2,4-dimethylpiperazin-1-yl)methyl)-[1,1'-biphenyl]-4-yl)methoxy)cyclopentyl)-5-(1-methyl-1H-pyrazol-4-yl)-nicotinamide |
| Example 188 | 2-amino-N-((1S,2S)-2-((4'-((3-ethyl-4-methylpiperazin-1-yl)methyl)-[1,1'-biphenyl]-4-yl)methoxy)cyclopentyl)-5-(1-methyl-1H-pyrazol-4-yl)-nicotinamide |
| Example 189 | 2-amino-N-((1S,2S)-2-((4'-((cis-3,5-dimethylpiperazin-1-yl)methyl)-[1,1'-biphenyl]-4-yl)methoxy)cyclopentyl)-5-(1-methyl-1H-pyrazol-4-yl)-nicotinamide |
| Example 190 | 2-amino-5-(1-methyl-1H-pyrazol-4-yl)-N-((1S,2S)-2-((4'-((cis-3,4,5-trimethylpiperazin-1-yl)methyl)-[1,1'-biphenyl]-4-yl)methoxy)cyclopentyl)nicotinamide |
| Example 191 | 2-amino-N-((1S,2S)-2-((4'-((trans-2,5-dimethylpiperazin-1-yl)methyl)-[1,1'-biphenyl]-4-yl)methoxy)cyclopentyl)-5-(1-methyl-1H-pyrazol-4-yl)-nicotinamide |
| Example 192 | 2-amino-5-(1-methyl-1H-pyrazol-4-yl)-N-((1S,2S)-2-((4'-(((2R,5S)-2,4,5-trimethylpiperazin-1-yl)methyl)-[1,1'-biphenyl]-4-yl)methoxy)cyclopentyl)-nicotinamide |
| Example 193 | 2-amino-N-((1S,2S)-2-((4'-((3-(dimethylamino)pyrrolidin-1-yl)methyl)-[1,1'-biphenyl]-4-yl)methoxy)cyclopentyl)-5-(1-methyl-1H-pyrazol-4-yl)-nicotinamide |
| Example 194 | 3-amino-6-(1-methyl-1H-pyrazol-4-yl)-N-((1S,2S)-2-((4'-((4-methylpiperazin-1-yl)methyl)-[1,1'-biphenyl]-4-yl)methoxy)cyclopentyl)-pyrazine-2-carboxamide |

| | |
|---|---|
| Example 195 | 2-amino-N-((1S,2S)-2-((3'-fluoro-4'-((4-methylpiperazin-1-yl)methyl)-[1,1'-biphenyl]-4-yl)methoxy)cyclopentyl)-5-(1-methyl-1H-pyrazol-4-yl)-nicotinamide |
| Example 196 | 2-amino-N-((1S,2S)-2-((3',5'-difluoro-4'-((4-methylpiperazin-1-yl)methyl)-[1,1'-biphenyl]-4-yl)methoxy)cyclopentyl)-5-(1-methyl-1H-pyrazol-4-yl)-nicotinamide |
| Example 197 | 2-amino-5-(1-methyl-1H-pyrazol-4-yl)-N-((1S,2S)-2-((4'-((4-methylpiperazin-1-yl)methyl)-3'-(trifluoromethyl)-[1,1'-biphenyl]-4-yl)-methoxy)cyclopentyl)nicotinamide |
| Example 198 | 2-amino-5-(1-methyl-1H-pyrazol-4-yl)-N-((1S,2S)-2-((3'-methyl-4'-((4-methylpiperazin-1-yl)methyl)-[1,1'-biphenyl]-4-yl)-methoxy)cyclopentyl)nicotinamide |
| Example 199 | 2-amino-N-((1S,2S)-2-((3'-hydroxy-4'-((4-methylpiperazin-1-yl)methyl)-[1,1'-biphenyl]-4-yl)methoxy)cyclopentyl)-5-(1-methyl-1H-pyrazol-4-yl)-nicotinamide |
| Example 200 | 2-amino-N-((1S,2S)-2-((4'-((4-methylpiperazin-1-yl)methyl)-3'-nitro-[1,1'-biphenyl]-4-yl)methoxy)cyclopentyl)-5-(1-methyl-1H-pyrazol-4-yl)-nicotinamide |
| Example 201 | 2-amino-N-((1S,2S)-2-((3'-methoxy-4'-((4-methylpiperazin-1-yl)methyl)-[1,1'-biphenyl]-4-yl)methoxy)cyclopentyl)-5-(1-methyl-1H-pyrazol-4-yl)-nicotinamide |
| Example 202 | 2-amino-N-((1S,2S)-2-((2'-chloro-4'-((4-methylpiperazin-1-yl)methyl)-[1,1'-biphenyl]-4-yl)methoxy)cyclopentyl)-5-(1-methyl-1H-pyrazol-4-yl)-nicotinamide |
| Example 203 | 2-amino-5-(1-methyl-1H-pyrazol-4-yl)-N-((1S,2S)-2-((4-(6-((4-methyl-piperazin-1-yl)methyl)pyridin-3-yl)benzyl)oxy)cyclopentyl)nicotinamide |
| Example 204 | 2-amino-5-(1-methyl-1H-pyrazol-4-yl)-N-((1S,2S)-2-((4-(5-((4-methyl-piperazin-1-yl)methyl)pyridin-2-yl)benzyl)oxy)cyclopentyl)nicotinamide |
| Example 205 | 2-amino-N-((1S,2S)-2-((4'-((4-(2-hydroxyethyl)piperazin-1-yl)methyl)-3'-(trifluoromethyl)-[1,1'-biphenyl]-4-yl)methoxy)cyclopentyl)-5-(1-methyl-1H-pyrazol-4-yl)nicotinamide |
| Example 206 | 2-amino-N-((1S,2S)-2-((2'-chloro-4'-((4-(2-hydroxyethyl)piperazin-1-yl)-methyl)-[1,1'-biphenyl]-4-yl)methoxy)cyclopentyl)-5-(1-methyl-1H-pyrazol-4-yl)nicotinamide |
| Example 207 | 2-amino-N-((1S,2S)-2-((4'-((4-methylpiperazin-1-yl)methyl)-3'-(trifluoro-methyl)-[1,1'-biphenyl]-4-yl)methoxy)cyclopentyl)nicotinamide |
| Example 208 | 2-amino-5-(1-methyl-1H-pyrazol-4-yl)-N-((1S,2S)-2-((4'-(1-(4-methyl-piperazin-1-yl)ethyl)-[1,1'-biphenyl]-4-yl)methoxy)cyclopentyl)nicotinamide |
| Example 209 | 2-amino-5-(1-methyl-1H-pyrazol-4-yl)-N-((1S,2S)-2-((4'-(1-((3S,5R)-3,4,5-trimethylpiperazin-1-yl)ethyl)-[1,1'-biphenyl]-4-yl)methoxy)cyclopentyl)-nicotinamide |
| Example 210 | 2-amino-N-((1S,2S)-2-((4'-(1-(4-(2-hydroxyethyl)piperazin-1-yl)ethyl)-[1,1'-biphenyl]-4-yl)methoxy)cyclopentyl)-5-(1-methyl-1H-pyrazol-4-yl)-nicotinamide |
| Example 211 | 2-amino-N-((1S,2S)-2-((4'-(1-((3S,5R)-4-(2-hydroxyethyl)-3,5-dimethyl-piperazin-1-yl)ethyl)-[1,1'-biphenyl]-4-yl)methoxy)cyclopentyl)-5-(1-methyl-1H-pyrazol-4-yl)nicotinamide |
| Example 212 | 2-amino-N-((1S,2S)-2-((3',5'-difluoro-4'-(1-(4-(2-hydroxyethyl)piperazin-1-yl)ethyl)-[1,1'-biphenyl]-4-yl)methoxy)cyclopentyl)-5-(1-methyl-1H-pyrazol-4-yl)nicotinamide |
| Example 213 | 2-amino-5-(1-methyl-1H-pyrazol-4-yl)-N-((1S,2S)-2-((4'-((R)-1-(piperazin-1-yl)ethyl)-[1,1'-biphenyl]-4-yl)methoxy)cyclopentyl)nicotinamide |
| Example 214 | 2-amino-5-(1-methyl-1H-pyrazol-4-yl)-N-((1S,2S)-2-((4'-((R)-1-(4-methyl-piperazin-1-yl)ethyl)-[1,1'-biphenyl]-4-yl)methoxy)cyclopentyl)nicotinamide |
| Example 215 | 2-amino-5-(1-methyl-1H-pyrazol-4-yl)-N-((1S,2S)-2-((4'-((4S)-1-(4-methyl-piperazin-1-yl)ethyl)-[1,1'-biphenyl]-4-yl)methoxy)cyclopentyl)nicotinamide |
| Example 216 | 2-amino-5-(1-methyl-1H-pyrazol-4-yl)-N-((1S,2S)-2-((4'-(1-(4-methyl-piperazin-1-yl)cyclopropyl)-[1,1'-biphenyl]-4-yl)methoxy)cyclopentyl)-nicotinamide |
| Example 217 | 2-amino-5-(1-methyl-1H-pyrazol-4-yl)-N-((1S,2S)-2-((4'-(2-(4-methyl-piperazin-1-yl)propan-2-yl)-[1,1'-biphenyl]-4-yl)methoxy)cyclopentyl)-nicodnamide |
| Example 218 | 2-amino-N-((1S,2S)-2-((4'-((R)-1-(4-(2-hydroxyethyl)piperazin-1-yl)ethyl)-[1,1'-biphenyl]-4-yl)methoxy)cyclopentyl)-5-(1-methyl-1H-pyrazol-4-yl)-nicotinamide |
| Example 219 | 2-amino-N-((1S,2S)-2-((4'-((S)-1-(4-(2-hydroxyethyl)piperazin-1-yl)ethyl)-[1,1'-biphenyl]-4-yl)methoxy)cyclopentyl)-5-(1-methyl-1H-pyrazol-4-yl)-nicotinamide |
| Example 220 | 2-amino-N-((1S,2S)-2-((4'-(1-(4-(2-hydroxyethyl)piperazin-1-yl)-cyclopropyl)-[1,1'-biphenyl]-4-yl)methoxy)cyclopentyl)-5-(1-methyl-1H-pyrazol-4-yl)nicotinamide |
| Example 221 | 2-amino-N-((1S,2S)-2-((4'-(2-(4-(2-hydroxyethyl)piperazin-1-yl)propan-2-yl)-[1,1'-biphenyl]-4-yl)methoxy)cyclopentyl)-5-(1-methyl-1H-pyrazol-4-yl)-nicotinamide |
| Example 222 | 6-amino-6'-fluoro-N-((1S,2S)-2-((4'-((S)-1-(4-methylpiperazin-1-yl)ethyl)-[1,1'-biphenyl]-4-yl)methoxy)cyclopentyl)-[3,3'-bipyridine]-5-carboxamide |
| Example 223 | 6-amino-6'-fluoro-N-((1S,2S)-2-((4'-((4R)-1-(4-methylpiperazin-1-yl)ethyl)-[1,1'-biphenyl]-4-yl)methoxy)cyclopentyl)-[3,3'-bipyridine]-5-carboxamide |
| Example 224 | 6-amino-6'-fluoro-N-((1S,2S)-2-((4'-(1-(4-methylpiperazin-1-yl)cyclopropyl)-[1,1'-biphenyl]-4-yl)methoxy)cyclopentyl)-[3,3'-bipyridine]-5-carboxamide |
| Example 225 | 6-amino-6'-fluoro-N-((1S,2S)-2-((4'-(2-(4-methylpiperazin-1-yl)propan-2-yl)-[1,1'-biphenyl]-4-yl)methoxy)cyclopentyl)-[3,3'-bipyridine]-5-carboxamide |
| Example 226 | 6-amino-6'-fluoro-N-((1S,2S)-2-((4'-((S)-1-(4-(2-hydroxyethyl)piperazin-1-yl)ethyl)-[1,1'-biphenyl]-4-yl)methoxy)cyclopentyl)-[3,3'-bipyridine]-5-carboxamide |
| Example 227 | 6-amino-6'-fluoro-N-((1S,2S)-2-((4'-((R)-1-(4-(2-hydroxyethyl)piperazin-1-yl)ethyl)-[1,1'-biphenyl]-4-yl)methoxy)cyclopentyl)-[3,3'-bipyridine]-5-carboxamide |
| Example 228 | 6-amino-6'-fluoro-N-((1S,2S)-2-((4'-(1-(4-(2-hydroxyethyl)piperazin-1-yl)cyclopropyl)-[1,1'-biphenyl]-4-yl)methoxy)cyclopentyl)-[3,3'-bipyridine]-5-carboxamide |
| Example 229 | 6-amino-6'-fluoro-N-((1S,2S)-2-((4'-(2-(4-(2-hydroxyethyl)piperazin-1-yl)-propan-2-yl)-[1,1'-biphenyl]-4-yl)methoxy)cyclopentyl)-[3,3'-bipyridine]-5-carboxamide |
| Example 230 | 6-amino-5'-fluoro-N-((1S,2S)-2-((4'-(1-(4-methylpiperazin-1-yl)ethyl)-[1,1'-biphenyl]-4-yl)methoxy)cyclopentyl)-[3,3'-bipyridine]-5-carboxamide |
| Example 231 | 2-amino-5-chloro-N-((1S,2S)-2-((4'-(1-(4-methylpiperazin-1-yl)ethyl)-[1,1'-biphenyl]-4-yl)methoxy)cyclopentyl)nicotinamide |
| Example 232 | 2-amino-5-fluoro-N-((1S,2S)-2-((4'-(1-(4-methylpiperazin-1-yl)ethyl)-[1,1'-biphenyl]-4-yl)methoxy)cyclopentyl)nicotinamide |
| Example 233 | 2-amino-5-cyano-N-((1S,2S)-2-((4'-(1-(4-methylpiperazin-1-yl)ethyl)-[1,1'-biphenyl]-4-yl)methoxy)cyclopentyl)nicotinamide |
| Example 234 | 2-amino-6-chloro-N-((1S,2S)-2-((4'-(1-(4-methylpiperazin-1-yl)ethyl)-[1,1'-biphenyl]-4-yl)methoxy)cyclopentyl)nicotinamide |
| Example 235 | 2-amino-N-((1S,2S)-2-((4'-(1-(4-methylpiperazin-1-yl)ethyl)-[1,1'-biphenyl]-4-yl)methoxy)cyclopentyl)nicotinamide |
| Example 236 | 6-amino-5'-fluoro-N-((1S,2S)-2-((4'-(1-(4-(2-hydroxyethyl)piperazin-1-yl)-ethyl)-[1,1'-biphenyl]-4-yl)methoxy)cyclopentyl)-((3,3'-bipyridine]-5-carboxamide |

| Example | Name |
|---|---|
| Example 237 | 6-amino-6'-fluoro-N-((1S,2S)-2-((4'-(1-(4-(2-hydroxyethyl)piperazin-1-yl)-ethyl)-[1,1'-biphenyl]-4-yl)methoxy)cyclopentyl)-[3,3'-bipyridine]-5-carboxamide |
| Example 238 | 6-amino-2'-fluoro-N-(1S,2S)-2-((4'-(1-(4-(2-hydroxyethyl)piperazin-1-yl)-ethyl)-[1,1'-biphenyl]-4-yl)methoxy)cyclopentyl)-[3,3'-bipyridine]-5-carboxamide |
| Example 239 | 2-amino-5-(1-methyl-1H-pyrazol-4-yl)-N-((1S,2S)-2-((4'-((1-methyl-piperidin-4-yl)methyl)-[1,1'-biphenyl]-4-yl)methoxy)cyclopentyl)-nicotinamide |
| Example 240 | 2-amino-N-((1S,2S)-2-((4'-((1-(2-hydroxyethyl)piperidin-4-yl)methyl)-[1,1'-biphenyl]-4-yl)methoxy)cyclopentyl)-5-(1-methyl-1H-pyrazol-4-yl)-nicotinamide |
| Example 241 | methyl 2-(4-((4'-(((((1S,2S)-2-(2-amino-5-(1-methyl-1H-pyrazol-4-yl)-nicotinamido)cyclopentyl)oxy)methyl)-[1,1'-biphenyl]-4-yl)methyl)piperidin-1-yl)acetate |
| Example 242 | 2-amino-N-((1S,2S)-2-((4'-((1-(2-amino-2-oxoethyl)piperidin-4-yl)methyl)-[1,1'-biphenyl]-4-yl)methoxy)cyclopentyl)-5-(1-methyl-1H-pyrazol-4-yl)-nicotinamide |
| Example 243 | 2-amino-5-(1-methyl-1H-pyrazol-4-yl)-N-((1S,2S)-2-((4-(3-(4-methyl-piperazin-1-yl)propyl)benzyl)oxy)cyclopentyl)nicotinamide |
| Example 244 | 2-amino-N-(1S,2S)-2-((4-(3-(dimethylamino)propyl)benzyl)oxy)-cyclopentyl)-5-(1-methyl-1H-pyrazol-4-yl)nicotinamide |
| Example 245 | 2-amino-N-((1S,2S)-2-((4'-(2-(dimethylamino)ethoxy)-[1,1'-biphenyl]-4-yl)-methoxy)cyclopentyl)-5-(1-methyl-1H-pyrazol-4-yl)nicotinamide |
| Example 246 | 2-amino-N-((1S,2S)-2-((4'-(3-(dimethylamino)propoxy)-[1,1'-biphenyl]-4-yl)methoxy)cyclopentyl)-5-(1-methyl-1H-pyrazol-4-yl)nicotinamide |
| Example 247 | 2-amino-5-(1-methyl-1H-pyrazol-4-yl)-N-((1S,2S)-2-((4'-((1-methyl-piperidin-4-yl)oxy)-[1,1'-biphenyl]-4-yl)methoxy)cyclopentyl)nicotinamide |
| Example 248 | 2-amino-N-((1S,2S)-2-((4-(3-(dimethylamino)prop-1-yn-1-yl)benzyl)-oxy)cyclopentyl)-5-(1-methyl-1H-pyrazol-4-yl)nicotinamide |
| Example 249 | 2-amino-N-((1S,2S)-2-((4-(4-hydroxybut-1-yn-1-yl)benzyl)oxy)cyclopentyl)-5-(1-methyl-1H-pyrazol-4-yl)nicotinamide |
| Example 250 | 2-amino-N-((1S,2S)-2-((4-(5-hydroxypent-1-yn-1-yl)benzyl)oxy)-cyclopentyl)-5-(1-methyl-1H-pyrazol-4-yl)nicotinamide |
| Example 251 | 2-amino-N-((1S,2S)-2-((4-(6-hydroxyhex-1-yn-1-yl)benzyl)oxy)cyclopentyl)-5-(1-methyl-1H-pyrazol-4-yl)nicotinamide |
| Example 252 | 2-amino-5-(1-methyl-1H-pyrazol-4-yl)-N-(1S,2S)-2-((4-(4-(4-methyl-piperazin-1-yl)but-1-yl)-1-yl)benzyl)oxy)cyclopentyl)nicotinamide |
| Example 253 | 2-amino-N-((1S,2S)-2-(benzyloxy)cyclopentyl)-5-(4-((4-methylpiperazin-1-yl)methyl)phenyl)nicotinamide |
| Example 254 | 2-amino-N-((1S,2S)-2-(benzyloxy)cyclopentyl)-5-(1-(piperidin-4-yl)-1H-pyrazol-4-yl)nicotinamide |
| Example 255 | 2-amino-N-((1S,2S)-2-(benzyloxy)cyclopentyl)-5-(1-(1-methylpiperidin-4-yl)-1H-pyrazol-4-yl)nicotinamide |
| Example 256 | 2-amino-N-((1S,2S)-2-(benzyloxy)cyclopentyl)-5-(1-(1-ethylpiperidin-4-yl)-1H-pyrazol-4-yl)nicotinamide |
| Example 257 | 2-amino-N-((1S,2S)-2-(benzyloxy)cyclopentyl)-5-(1-(1-isopropylpiperidin-4-yl)-1H-pyrazol-4-yl)nicotinamide |
| Example 258 | 2-amino-N-((1S,2S)-2-(benzyloxy)cyclopentyl)-5-(1-(1-(pyrrolidin-3-yl-methyl)piperidin-4-yl)-1H-pyrazol-4-yl)nicotinamide |
| Example 259 | 2-amino-N-((1R,2R)-2-(benzyloxy)cyclopentyl)-5-(1-(piperidin-4-yl)-1H-pyrazol-4-yl)nicotinamide |
| Example 260 | 2-amino-N-((1S,2S)-2-((3,4-dichlorobenzyl)oxy)cyclopentyl)-5-(1-(piperidin-4-yl)-1H-pyrazol-4-yl)nicotinamide |
| Example 261 | 2-amino-N-((1S,2S)-2-(benzyloxy)cyclopentyl)-5-(3-(hydroxymethyl)-1-methyl-1H-pyrazol-4-yl)nicotinamide |
| Example 262 | 2-amino-N-((1S,2S)-2-(benzyloxy)cyclopentyl)-5-(3-(((2-hydroxyethyl)-amino)methyl)-1-methyl-1H-pyrazol-4-yl)nicotinamide |
| Example 263 | 2-amino-N-((1S,2S)-2-(benzyloxy)cyclopentyl)-5-(3-((3-hydroxypiperidin-1-yl)methyl)-1-methyl-1H-pyrazol-4-yl)nicotinamide |
| Example 264 | 2-amino-N-((1S,2S)-2-(benzyloxy)cyclopentyl)-5-(4-cyanophenyl)-nicotinamide |
| Example 265 | 2-amino-N-((1S,2S)-2-(benzyloxy)cyclopentyl)-5-(3-cyanophenyl)-nicotinamide |
| Example 266 | 2-amino-N-((1S,2S)-2-(benzyloxy)cyclopentyl)-5-(4-(cyanomethyl)-phenyl)nicotinamide |
| Example 267 | 2-amino-N-((1S,2S)-2-(benzyloxy)cyclopentyl)-5-(4-phenoxyphenyl)-nicotinamide |
| Example 268 | 2-amino-N-((1S,2S)-2-(benzyloxy)cyclopentyl)-5-(3-((1-methylpiperidin-4-yl)carbamoyl)phenyl)nicotinamide |
| Example 269 | 6-amino-N-((1S,2S)-2-(benzyloxy)cyclopentyl)-6'-(hydroxymethyl)-[3,3'-bipyridine]-5-carboxamide |
| Example 270 | 2-amino-N-((1S,2S)-2-((3-methylbenzyl)oxy)cyclopentyl)-5-(4-((4-methyl-piperazin-1-yl)methyl)phenyl)nicotinamide |
| Example 271 | 2-amino-N-((1S,2S)-2-((3-methylbenzyl)oxy)cyclopentyl)-5-(3-(4-methyl-piperazine-1-carbonyl)phenyl)nicotinamide |
| Example 272 | 2-amino-N-((1S,2S)-2-((3-methylbenzyl)oxy)cyclopentyl)-5-(3-(4-(pyrrolidin-1-yl)piperidine-1-carbonyl)phenyl)nicotinamide |
| Example 273 | 2-amino-N-((1S,2S)-2-((3-methylbenzyl)oxy)cyclopentyl)-5-(3-(4-methyl-piperazin-1-yl)methyl)phenyl)nicotinamide |
| Example 274 | 2-amino-5-(3-fluoro-4-((4-methylpiperazin-1-yl)methyl)phenyl)-N-((1S,2S)-2-((3-methylbenzyl)oxy)cyclopentyl)nicotinamide |
| Example 275 | 2-amino-N-((1S,2S)-2-((3-methylbenzyl)oxy)cyclopentyl)-5-(4-((4-(pyrrolidin-1-yl)piperidin-1-yl)methyl)phenyl)nicotinamide |
| Example 276 | 2-amino-N-((1S,2S)-2-((3-methylbenzyl)oxy)cyclopentyl)-5-(4-(4-methyl-piperazine-1-carbonyl)phenyl)nicotinamide |
| Example 277 | 2-amino-N-((1S,2S)-2-((3-methylbenzyl)oxy)cyclopentyl)-5-(4-(4-(pyrrolidin-1-yl)piperidine-1-carbonyl)phenyl)nicotinamide |
| Example 278 | 2-amino-N-((1S,2S)-2-((3-methylbenzyl)oxy)cyclopentyl)-5-(4-(2-((1-methylpiperidin-4-yl)amino)-2-oxoethyl)phenyl)nicotinamide |
| Example 279 | 2-amino-N-((1S,2S)-2-((3-methylbenzyl)oxy)cyclopentyl)-5-(4-(2-(4-methylpiperazin-1-yl)acetyl)phenyl)nicotinamide |
| Example 280 | 2-amino-5-(3-fluoro-4-((4-(pyrrolidin-1-yl)piperidin-1-yl)methyl)phenyl)-N-((1S,2S)-2-((3-methylbenzyl)oxy)cyclopentyl)nicotinamide |
| Example 281 | 2-amino-N-((1S,2S)-2-((3-methylbenzyl)oxy)cyclopentyl)-5-(4-(4-(4-methylpiperazin-1-yl)piperidine-1-carbonyl)phenyl)nicotinamide |
| Example 282 | 2-amino-N-((1S,2S)-2-((3-methylbenzyl)oxy)cyclopentyl)-5-(4-(piperazin-ylmethyl)phenyl)nicotinamide |
| Example 283 | 2-amino-N-((1S,2S)-2-((4-methylbenzyl)oxy)-cyclopentyl)-5-(4-methylpiperazine-1-carbonyl)phenyl)nicotinamide |
| Example 284 | 2-amino-N-((1S,2S)-2-((4-methylbenzyl)oxy)cyclopentyl)-5-(4-(4-(pyrrolidin-1-yl)piperidine-1-carbonyl)phenyl)nicotinamide |
| Example 285 | 2-amino-5-(1,5-dimethyl-1H-pyrazol-4-yl)-N-((1S,2S)-2-((3,4-dimethyl-benzyl)oxy)cyclopentyl)nicotinamide |
| Example 286 | 2-amino-5-(1,3-dimethyl-1H-pyrazol-4-yl)-N-((1S,2S)-2-((3,4-dimethyl-benzyl)oxy)cyclopentyl)nicotinamide |
| Example 287 | 2-amino-N-((1S,2S)-2-((3,4-dimethylbenzyl)oxy)cyclopentyl)-5-(2-(2-hydroxypropan-2-yl)-4-methylthiazol-5-yl)nicotinamide |
| Example 288 | 2-amino-N-((1S,2S)-2-((3,4-dimethylbenzyl)oxy)cyclopentyl)-5-(2-(3-hydroxytetrahydrofuran-3-yl)-4-methylthiazol-5-yl)nicotinamide |
| Example 289 | 2-amino-N-((1S,2S)-2-((3,4-dimethylbenzyl)oxy)cyclopentyl)-5-(4-((4-methylpiperazin-1-yl)methyl)phenyl)nicotinamide |

| | |
|---|---|
| Example 290 | 2-amino-N-((1S,2S)-2-((3,4-dimethylbenzyl)oxy)cyclopentyl)-5-(4-(2-(4-methylpiperazin-1-yl)-2-oxoethyl)phenyl)nicotinamide |
| Example 291 | 2-amino-N-((1S,2S)-2-((3,4-dimethylbenzyl)oxy)cyclopentyl)-5-(4-(morpholinomethyl)phenyl)nicotinamide |
| Example 292 | 2-amino-5-(4-((dimethylamino)methyl)phenyl)-N-((1S,2S)-2-((3,4-dimethylbenzyl)oxy)cyclopentyl)nicotinamide |
| Example 293 | 2-amino-N-((1S,2S)-2-((3,4-dimethylbenzyl)oxy)cyclopentyl)-5-(4-((4-(2-hydroxyethyl)piperazin-1-yl)methyl)phenyl)nicotinamide |
| Example 294 | 6-amino-N-((1S,2S)-2-((3,4-dimethylbenzyl)oxy)cyclopentyl)-2'-methoxy-[3,3'-bipyridine]-5-carboxamide |
| Example 295 | 2-amino-5-(4-(dimethylamino)phenyl)-N-((1S,2S)-2-((3,4-dimethylbenzyl)-oxy)cyclopentyl)nicotinamide |
| Example 296 | 2-amino-N-((1S,2S)-2-((3,4-dimethylbenzyl)oxy)cyclopentyl)-5-(3-hydroxy-phenyl)nicotinamide |
| Example 297 | 2-amino-5-(3-aminophenyl)-N-((1S,2S)-2-((3,4-dimethylbenzyl)oxy)-cyclopentyl)nicotinamide |
| Example 298 | 2-amino-N-((1S,2S)-2-((3,4-dimethylbenzyl)oxy)cyclopentyl)-5-(3-(methyl-sulfonamido)phenyl)nicotinamide |
| Example 299 | 2-amino-N-((1S,2S)-2-((3,4-dimethylbenzyl)oxy)cyclopentyl)-5-(3-(hydroxy-methyl)phenyl)nicotinamide |
| Example 300 | 2-amino-5-(3-(aminomethyl)phenyl)-N-((1S,2S)-2-((3,4-dimethylbenzyl)-oxy)cyclopentyl)nicotinamide |
| Example 301 | 2-amino-N-((1S,2S)-2-((3,4-dimethylbenzyl)oxy)cyclopentyl)-5-(3-(3-hydroxypropyl)phenyl)nicotinamide |
| Example 302 | 2-amino-N-((1S,2S)-2-((3,4-dimethylbenzyl)oxy)cyclopentyl)-5-(3-((((1r,4S)-4-hydroxycyclohexyl)amino)methyl)phenyl)nicotinamide |
| Example 303 | 2-amino-N-((1S,2S)-2-((3,4-dimethylbenzyl)oxy)cyclopentyl)-5-((3-(((1-methylpiperidin-4-yl)amino)methyl)phenyl)nicotinamide |
| Example 304 | 2-amino-N-((1S,2S)-2-((3,4-dimethylbenzyl)oxy)cyclopentyl)-5-(3-((((S)-piperidin-3-yl)amino)methyl)phenyl)nicotinamide |
| Example 305 | 3-(6-amino-5-(((1S,2S)-2-((3,4-dimethylbenzyl)oxy)cyclopentyl)-carbamoyl)pyridin-3-yl)-5-hydroxybenzoic acid |
| Example 306 | 4-(6-amino-5-(((1S,2S)-2-((3,4-dimethylbenzyl)oxy)cyclopentyl)carbamoyl)-pyridin-3-yl)-2-methylbenzoic acid |
| Example 307 | 2-amino-5-(4-aminophenyl)-N-((1S,2S)-2-((3,4-dimethylbenzyl)oxy-cyclopentyl)nicotinamide |
| Example 308 | 3-(6-amino-5-(((1S,2S)-2-((3,4-dimethylbenzyl)oxy)cyclopentyl)-carbamoyl)pyridin-3-yl)benzoic acid |
| Example 309 | 3-amino-5-(6-amino-5-(((1S,2S)-2-((3,4-dimethylbenzyl)oxy)cyclopentyl)-carbamoyl)pyridin-3-yl)benzoic acid |
| Example 310 | 2-amino-N-((1S,2S)-2-((3,4-dimethylbenzyl)oxy)cyclopentyl)-5-(2-methyl-5-(4-(pyrrolidin-1-yl)piperidine-1-carbonyl)phenyl)nicotinamide |
| Example 311 | 2-amino-N-((1S,2S)-2-((3,4-dimethylbenzyl)oxy)cyclopentyl)-5-((3-methyl-4-(4-methylpiperazine-1-carbonyl)phenyl)nicotinamide |
| Example 312 | 2-amino-5-(3-amino-5-(4-(pyrrolidin-1-yl)piperidine-1-carbonyl)phenyl)-N-((1S,2S)-2-((3,4-dimethylbenzyl)oxy)cyclopentyl)nicotinamide |
| Example 313 | 2-amino-N-((1S,2S)-2-((3,4-dimethylbenzyl)oxy)cyclopentyl)-5-((4-(hydroxy-methyl)phenyl)nicotinamide |
| Example 314 | 2-amino-N-((1S,2S)-2-((3,4-dimethylbenzyl)oxy)cyclopentyl)-5-((4-formyl-phenyl)nicotinamide |
| Example 315 | 4-(6-amino-5-(((1S,2S)-2-((3,4-dimethylbenzyl)oxy)cyclopentyl)carbamoyl)pyridin-3-yl)benzoic acid |
| Example 316 | 3-(4-(6-amino-5-(((1S,2S)-2-((3,4-dimethylbenzyl)oxy)cyclopentyl)-carbamoyl)pyridin-3-yl)phenyl)propanoic acid |
| Example 317 | 2-amino-N-((1S,2S)-2-((3,4-dimethylbenzyl)oxy)cyclopentyl)-5-(2-hydroxy-phenyl)nicotinamide |
| Example 318 | 2-amino-N-((1S,2S)-2-((3,4-dimethylbenzyl)oxy)cyclopentyl)-5-(4-((1-methylpiperidin-4-yl)carbamoyl)phenyl)nicotinamide |
| Example 319 | 2-amino-N-((1S,2S)-2-((3,4-dimethylbenzyl)oxy)cyclopentyl)-5-(4-(dimethylcarbamoyl)phenyl)nicotinamide |
| Example 320 | 2-amino-N-((1S,2S)-2-((3,4-dimethylbenzyl)oxy)cyclopentyl)-5-(4-(((1-methylpiperidin-4-yl)amino)methyl)phenyl)nicotinamide |
| Example 321 | 6-amino-N-((1S,2S)-2-((3,4-dimethylbenzyl)oxy)cyclopentyl)-6'-(hydroxymethyl)-[3,3'-bipyridine]-5-carboxamide |
| Example 322 | 2-amino-4-(6-amino-5-(((1S,2S)-2-((3,4-dimethylbenzyl)oxy)cyclopentyl)carbamoyl)pyridin-3-yl)benzoic acid |
| Example 323 | 2-amino-N-((1S,2S)-2-((3,4-dimethylbenzyl)oxy)cyclopentyl)-5-(4-(hydroxymethyl)-3-methoxyphenyl)nicotinamide |
| Example 324 | 2-amino-N-((1S,2S)-2-((3,4-dimethylbenzyl)oxy)cyclopentyl)-5-(3-fluoro-4-(hydroxymethyl)phenyl)nicotinamide |
| Example 325 | 2-amino-N-((1S,2S)-2-((3,4-dimethylbenzyl)oxy)cyclopentyl)-5-(3-fluoro-4-((4-(pyrrolidin-1-yl)piperidin-1-yl)methyl)phenyl)nicotinamide |
| Example 326 | 2-amino-N-((1S,2S)-2-((3,4-dimethylbenzyl)oxy)cyclopentyl)-5-(4-(1-hydroxyethyl)phenyl)nicotinamide |
| Example 327 | 2-amino-5-(4-((3-(dimethylamino)pyrrolidin-1-yl)methyl)phenyl)-N-((1S,2S)-2-((3,4-dimethylbenzyl)oxy)cyclopentyl)nicotinamide |
| Example 328 | 2-amino-N-((1S,2S)-2-((3,4-dimethylbenzyl)oxy)cyclopentyl)-5-(4-((4-hydroxypiperidin-1-yl)methyl)phenyl)nicotinamide |
| Example 329 | 2-amino-N-((1S,2S)-2-((3,4-dimethylbenzyl)oxy)cyclopentyl)-5-(4-((((1-methylpiperidin-4-yl)methyl)amino)methyl)phenyl)nicotinamide |
| Example 330 | 2-amino-N-((1S,2S)-2-((3,4-dimethylbenzyl)oxy)cyclopentyl)-5-(3-methyl-4-(4-(pyrrolidin-1-yl)piperidine-1-carbonyl)phenyl)nicotinamide |
| Example 331 | 2-amino-5-(3-amino-4-(4-(pyrrolidin-1-yl)piperidine-1-carbonyl)phenyl)-N-((1S,2S)-2-((3,4-dimethylbenzyl)oxy)cyclopentyl)nicotinamide |
| Example 332 | 2-amino-5-(3-amino-4-((4-(pyrrolidin-1-yl)piperidin-1-yl)methyl)phenyl)-N-((1S,2S)-2-((3,4-dimethylbenzyl)oxy)cyclopentyl)nicotinamide |
| Example 333 | 2-amino-N-((1S,2S)-2-((3,4-dimethylbenzyl)oxy)cyclopentyl)-5-(4-(hydroxymethyl)-3-methylphenyl)nicotinamide |
| Example 334 | 2-amino-5-(3-chlorophenyl)-N-((1S,2S)-2-((3,4-dimethylbenzyl)oxy)-cyclopentyl)nicotinamide |
| Example 335 | 2-amino-N-((1S,2S)-2-((3,4-dimethylbenzyl)oxy)cyclopentyl)-5-(m-tolyl)-nicotinamide |
| Example 336 | 2-amino-N-((1S,2S)-2-((3,4-dimethylbenzyl)oxy)cyclopentyl)-5-(3,5-dimethylphenyl)nicotinamide |
| Example 337 | 2-amino-N-((1S,2S)-2-((3,4-dimethylbenzyl)oxy)cyclopentyl)-5-(4-((3-morpholinopyrrolidin-1-yl)methyl)phenyl)nicotinamide |
| Example 338 | 2-amino-5-(4-((4-aminopiperidin-1-yl)methyl)phenyl)-N-((1S,2S)-2-((3,4-dimethylbenzyl)oxy)cyclopentyl)nicotinamide |
| Example 339 | 2-amino-5-(4-((3-aminopiperidin-1-yl)methyl)phenyl)-N-((1S,2S)-2-((3,4-dimethylbenzyl)oxy)cyclopentyl)nicotinamide |
| Example 340 | 2-amino-5-(4-((3-aminopyrrolidin-1-yl)methyl)phenyl)-N-((1S,2S)-2-((3,4-dimethylbenzyl)oxy)cyclopentyl)nicotinamide |
| Example 341 | 2-amino-5-(4-((3-aminopyrrolidin-1-yl)methyl)-3-fluorophenyl)-N-((1S,2S)-2-((3,4-dimethylbenzyl)oxy)cyclopentyl)nicotinamide |
| Example 342 | 2-amino-5-(4-((3-aminopyrrolidin-1-yl)methyl)-3-fluorophenyl)-N-((1S,2S)-2-((3,4-dimethylbenzyl)oxy)cyclopentyl)nicotinamide |
| Example 343 | 2-amino-5-(3-((3-(dimethylamino)pyrrolidin-1-yl)methyl)phenyl)-N-((1S,2S)-2-((3,4-dimethylbenzyl)oxy)cyclopentyl)nicotinamide |
| Example 344 | 2-amino-5-(3-((3-(dimethylamino)pyrrolidin-1-yl)methyl)-4-methoxyphenyl)-N-((1S,2S)-2-((3,4-dimethylbenzyl)oxy)cyclopentyl)nicotinamide |

| Example | Name |
|---|---|
| Example 345 | 2-amino-N-((1S,2S)-2-((3,4-dimethylbenzyl)oxy)cyclopentyl)-5-(4-((3-hydroxyazetidin-1-yl)methyl)phenyl)nicotinamide |
| Example 346 | 2-amino-5-(4-(((R)-3-(dimethylamino)pyrrolidin-1-yl)methyl)phenyl)-N-((1S,2S)-2-((3,4-dimethylbenzyl)oxy)cyclopentyl)nicotinamide |
| Example 347 | 2-amino-5-(4-(((S)-3-(dimethylamino)pyrrolidin-1-yl)methyl)phenyl)-N-((1S,2S)-2-((3,4-dimethylbenzyl)oxy)cyclopentyl)nicotinamide |
| Example 348 | 2-amino-N-((1S,2S)-2-((3,4-dimethylbenzyl)oxy)cyclopentyl)-5-(4-(((R)-3-hydroxypyrrolidin-1-yl)methyl)phenyl)nicotinamide |
| Example 349 | 2-amino-N-((1S,2S)-2-((3,4-dimethylbenzyl)oxy)cyclopentyl)-5-(4-(((S)-3-hydroxypyrrolidin-1-yl)methyl)phenyl)nicotinamide |
| Example 350 | 2-amino-N-((1S,2S)-2-((3,4-dimethylbenzyl)oxy)cyclopentyl)-5-(4-((3-hydroxypiperidin-1-yl)methyl)phenyl)nicotinamide |
| Example 351 | 2-amino-N-((1S,2S)-2-((3,4-dimethylbenzyl)oxy)cyclopentyl)-5-((4-hydroxyphenyl)nicotinamide |
| Example 352 | 2-amino-N-((1S,2S)-2-((3,4-dimethylbenzyl)oxy)cyclopentyl)-5-(4-hydroxy-3-methoxyphenyl)nicotinamide |
| Example 353 | 2-amino-5-(3,4-dimethoxyphenyl)-N-((1S,2S)-2-((3,4-dimethylbenzyl)oxy)-cyclopentyl)nicotinamide |
| Example 354 | amino-N-((1S,2S)-2-((3,4-dimethylbenzyl)oxy)cyclopentyl)-5-((3-(pyrrolidin-1-yl)phenyl)nicotinamide |
| Example 355 | 2-amino-5-(5-amino-1-methyl-1H-pyrazol-4-yl)-N-((1S,2S)-2-((3,4-dimethylbenzyl)oxy)cyclopentyl)nicotinamide |
| Example 356 | 2-amino-N-((1S,2S)-2-((3-ethyl-4-methylbenzyl)oxy)cyclopentyl)-5-((4-(hydroxymethyl)phenyl)nicotinamide |
| Example 357 | 2-amino-5-(4-((3-(dimethylamino)pyrrolidin-1-yl)methyl)phenyl)-N-((1S,2S)-2-((3-ethyl-4-methylbenzyl)oxy)cyclopentyl)nicotinamide |
| Example 358 | 2-amino-N-((1S,2S)-2-((3-ethyl-4-methylbenzyl)oxy)cyclopentyl)-5-(4-((3-hydroxypyrrolidin-1-yl)methyl)phenyl)nicotinamide |
| Example 359 | 2-amino-N-((1S,2S)-2-((3-ethyl-4-methylbenzyl)oxy)cyclopentyl)-5-(4-(2-(piperazin-1-yl)propan-2-yl)phenyl)nicotinamide |
| Example 360 | 2-amino-N-((1S,2S)-2-((3-ethyl-4-methylbenzyl)oxy)cyclopentyl)-5-(4-(2-(4-(2-hydroxyethyl)piperazin-1-yl)propan-2-yl)phenyl)nicotinamide |
| Example 361 | 3-amino-N-((1S,2S)-2-(benzyloxy)cyclopentyl)-6-(1-(piperidin-4-yl)-1H-pyrazol-4-yl)pyrazine-2-carboxamide |
| Example 362 | (S)-3-amino-6-(1-(piperidin-4-yl)-1H-pyrazol-4-yl)-N-((1,2,3,4-tetrahydronaphthalen-1-yl)pyrazine-2-carboxamide |
| Example 363 | 2-amino-5-(4-fluorophenyl)-N-((1S,2S)-2-((4'-((4-methylpiperazin-1-yl)methyl)-[1,1'-biphenyl]-4-yl)methoxy)cyclopentyl)nicotinamide |
| Example 364 | 2-amino-5-(3,4-difluorophenyl)-N-((1S,2S)-2-((4'-((4-methylpiperazin-1-yl)methyl)-[1,1'-biphenyl]-4-yl)methoxy)cyclopentyl)nicotinamide |
| Example 365 | 2-amino-N-((1S,2S)-2-((4'-((4-methylpiperazin-1-yl)methyl)-[1,1'-biphenyl]-4-yl)methoxy)cyclopentyl)-5-(4-(trifluoromethyl)phenyl)nicotinamide |
| Example 366 | 2-amino-N-((1S,2S)-2-((4'-((4-methylpiperazin-1-yl)methyl)-[1,1'-biphenyl]-4-yl)methoxy)cyclopentyl)-5-(1-(1-methylpiperidin-4-yl)-1H-pyrazol-4-yl)-nicotinamide |
| Example 367 | 2-amino-N-((1S,2S)-2-((4'-((4-methylpiperazin-1-yl)methyl)-[1,1'-biphenyl]-4-yl)methoxy)cyclopentyl)-5-(4-(4-methylpiperazin-1-yl)phenyl)nicotinamide |
| Example 368 | 2-amino-N-((1S,2S)-2-((4'-((4-methylpiperazin-1-yl)methyl)-[1,1'-biphenyl]-4-yl)methoxy)cyclopentyl)-5-(4-((methylpiperazin-1-yl)methyl)phenyl)-nicotinamide |
| Example 369 | 2-amino-5-(4-(hydroxymethyl)phenyl)-N-((1S,2S)-2-((4'-((4-methyl-piperazin-1-yl)methyl)-[1,1'-biphenyl]-4-yl)methoxy)cyclopentyl)-nicotinamide |
| Example 370 | 2-amino-N-((1S,2S)-2-((4'-((4-methylpiperazin-1-yl)methyl)-[1,1'-biphenyl]-4-yl)methoxy)cyclopentyl)-5-(m-tolyl)nicotinamide |
| Example 371 | 2-amino-N-((1S,2S)-2-((4'-((4-methylpiperazin-1-yl)methyl)-[1,1'-biphenyl]-4-yl)methoxy)cyclopentyl)-5-phenylnicotinamide |
| Example 372 | 2-amino-5-(4-hydroxyphenyl)-N-((1S,2S)-2-((4'-((4-methylpiperazin-1-yl)methyl)-[1,1'-biphenyl]-4-yl)methoxy)cyclopentyl)nicotinamide |
| Example 373 | 2-amino-5-(4-chloro-3-fluorophenyl)-N-((1S,2S)-2-((4'-((4-methylpiperazin-1-yl)methyl)-[1,1'-biphenyl]-4-yl)methoxy)cyclopentyl)nicotinamide |
| Example 374 | 2-amino-5-methyl-N-((1S,2S)-2-((4'-((4-methylpiperazin-1-yl)methyl)-[1,1'-biphenyl]-4-yl)methoxy)cyclopentyl)nicotinamide |
| Example 375 | 6-amino-N-((1S,2S)-2-((4'-((4-methylpiperazin-1-yl)methyl)-[1,1'-biphenyl]-4-yl)methoxy)cyclopentyl)-[3,3'-bipyridine]-5-carboxamide |
| Example 376 | 2-amino-5-(4-methoxyphenyl)-N-((1S,2S)-2-((4'-((4-methylpiperazin-1-yl)methyl)-[1,1'-biphenyl]-4-yl)methoxy)cyclopentyl)nicotinamide |
| Example 377 | 6-amino-N-((1S,2S)-2-((4'-((4-methylpiperazin-1-yl)methyl)-[1,1'-biphenyl]-4-yl)methoxy)cyclopentyl)-[3,4'-bipyridine]-5-carboxamide |
| Example 378 | 2-amino-N-((1S,2S)-2-((4'-((4-methylpiperazin-1-yl)methyl)-[1,1'-biphenyl]-4-yl)methoxy)cyclopentyl)-5-(4-((4-methylpiperidin-1-yl)methyl)phenyl)-nicotinamide |
| Example 379 | 2-amino-N-((1S,2S)-2-((4'-((4-methylpiperazin-1-yl)methyl)-[1,1'-biphenyl]-4-yl)methoxy)cyclopentyl)-5-(4-(morpholinomethyl)phenyl)nicotinamide |
| Example 380 | 2-amino-N-((1S,2S)-2-((4'-((4-methylpiperazin-1-yl)methyl)-[1,1'-biphenyl]-4-yl)methoxy)cyclopentyl)-5-(1-(tetrahydro-2H-pyran-4-yl)-1H-pyrazol-4-yl)nicotinamide |
| Example 381 | 2-amino-N-((1S,2S)-2-((4'-((4-methylpiperazin-1-yl)methyl)-[1,1'-biphenyl]-4-yl)methoxy)cyclopentyl)-5-(4-morpholinophenyl)nicotinamide |
| Example 382 | 2-amino-5-(cyclohex-1-en-1-yl)-N-((1S,2S)-2-((4'-((4-methylpiperazin-1-yl)methyl)-[1,1'-biphenyl]-4-yl)methoxy)cyclopentyl)nicotinamide |
| Example 383 | 2-amino-5-(3,4-dimethoxyphenyl)-N-((1S,2S)-2-((4'-((4-methylpiperazin-1-yl)methyl)-[1,1'-biphenyl]-4-yl)methoxy)cyclopentyl)nicotinamide |
| Example 384 | 6-amino-2',6'-difluoro-N-((1S,2S)-2-((4'-((4-methylpiperazin-1-yl)methyl)-[1,1'-biphenyl]-4-yl)methoxy)cyclopentyl)-[3,4'-bipyridine]-5-carboxamide |
| Example 385 | 2-amino-N-((1S,2S)-2-((4'-((4-methylpiperazin-1-yl)methyl)-[1,1'-biphenyl]-4-yl)methoxy)cyclopentyl)-5-(4-methylthiophen-3-yl)nicotinamide |
| Example 386 | 6-amino-6'-fluoro-N-((1S,2S)-2-(('4-((4-methylpiperazin-1-yl)methyl)-[1,1'-biphenyl]-4-yl)methoxy)cyclopentyl)-[3,3'-bipyridine]-5-carboxamide |
| Example 387 | 2-amino-N-((1S,2S)-2-((4'-((4-methylpiperazin-1-yl)methyl)-[1,1'-biphenyl]-4-yl)methoxy)cyclopentyl)-5-(1-(1,1,2,2-tetrafluoroethyl)-1H-pyrazol-4-yl)-nicotinamide |
| Example 388 | 2-amino-N-((3S,4S)-4-((3-ethyl-4-methylbenzyl)oxy)pyrrolidin-3-yl)-5-(1-methyl-1H-pyrazol-4-yl)nicotinamide |
| Example 389 | 2-amino-N-((3S,4S)-4-((3-ethyl-4-methylbenzyl)oxy)pyrrolidin-3-yl)-5-(4-(hydroxymethyl)phenyl)nicotinamide |
| Example 390 | 2-amino-N-((3S,4S)-4-((3-ethyl-4-methylbenzyl)oxy)pyrrolidin-3-yl)-5-(4-((4-methylpiperazin-1-yl)methyl)phenyl)nicotinamide |
| Example 391 | 2-amino-5-(4-carbamoylphenyl)-N-((3S,4S)-4-((3-ethyl-4-methylbenzyl)oxy)pyrrolidin-3-yl)nicotinamide |
| Example 392 | 2-amino-N-((3S,4S)-4-((3-ethyl-4-methylbenzyl)oxy)pyrrolidin-3-yl)-5-(m-tolyl)nicotinamide |
| Example 393 | 4-(6-amino-5-(((3S,4S)-4-((3-ethyl-4-methylbenzyl)oxy)pyrrolidin-3-yl)carbamoyl)pyridin-3-yl)benzoic acid |
| Example 394 | 2-amino-N-((3S,4S)-4-((3-ethyl-4-methylbenzyl)oxy)pyrrolidin-3-yl)-5-phenylnicotinamide |

| | |
|---|---|
| Example 395 | 6-amino-N-((3S,4S)-4-((3-ethyl-4-methylbenzyl)oxy)pyrrolidin-3-yl)-[3,4'-bipyridine]-5-carboxamide |
| Example 396 | 6-amino-N-((3S,4S)-4-((3-ethyl-4-methylbenzyl)oxy)pyrrolidin-3-yl)-[3,3'-bipyridine]-5-carboxamide |
| Example 397 | 2-amino-N-((3S,4S)-4-((3-ethyl-4-methylbenzyl)oxy)pyrrolidin-3-yl)-5-vinylnicotinamide |
| Example 398 | 2-amino-N-((3S,4S)-4-((3-ethyl-4-methylbenzyl)oxy)pyrrolidin-3-yl)-5-(4-fluorophenyl)nicotinamide |
| Example 399 | 2-amino-N-((3S,4S)-4-((3-ethyl-4-methylbenzyl)oxy)pyrrolidin-3-yl)-5-(4-formylphenyl)nicotinamide |
| Example 400 | 2-amino-5-(4-cyanophenyl)-N-((3S,4S)-4-((3-ethyl-4-methylbenzyl)oxy)pyrrolidin-3-yl)nicotinamide |
| Example 401 | 2-amino-N-((3S,4S)-4-((3-ethyl-4-methylbenzyl)oxy)pyrrolidin-3-yl)-5-(4-(methylsulfonamido)phenyl)nicotinamide |
| Example 402 | 2-amino-N-((3S,4S)-4-((3-ethyl-4-methylbenzyl)oxy)pyrrolidin-3-yl)-5-(4-phenoxyphenyl)nicotinamide |
| Example 403 | 5-([1,1'-biphenyl]-4-yl)-2-amino-N-((3S,4S)-4-((3-ethyl-4-methylbenzyl)oxy)pyrrolidin-3-yl)nicotinamide |
| Example 404 | 2-amino-5-(4-(benzyloxy)phenyl)-N-((3S,4S)-4-((3-ethyl-4-methylbenzyl)oxy)pyrrolidin-3-yl)nicotinamide |
| Example 405 | 2-amino-5-(4-(dimethylamino)phenyl)-N-((3S,4S)-4-((3-ethyl-4-methylbenzyl)oxy)pyrrolidin-3-yl)nicotinamide |
| Example 406 | 2-amino-N-((3S,4S)-4-((3-ethyl-4-methylbenzyl)oxy)pyrrolidin-3-yl)-5-(quinolin-3-yl)nicotinamide |
| Example 407 | 2-amino-5-(benzofuran-2-yl)-N-((3S,4S)-4-((3-ethyl-4-methylbenzyl)oxy)pyrrolidin-3-yl)nicotinamide |
| Example 408 | 2-amino-N-((3S,4S)-4-((3-ethyl-4-methylbenzyl)oxy)pyrrolidin-3-yl)-5-(naphthalen-1-yl)nicotinamide |
| Example 409 | 2-amino-N-((3S,4S)-4-((3-ethyl-4-methylbenzyl)oxy)pyrrolidin-3-yl)-5-(4-(trifluoromethyl)phenyl)nicotinamide |
| Example 410 | 2-amino-N-((3S,4S)-4-((3-ethyl-4-methylbenzyl)oxy)pyrrolidin-3-yl)-5-(2,4,5-trifluorophenyl)nicotinamide |
| Example 411 | 2-amino-5-(4-(cyanomethyl)phenyl)-N-((3S,4S)-4-((3-ethyl-4-methylbenzyl)oxy)pyrrolidin-3-yl)nicotinamide |
| Example 412 | 2-amino-N-((3S,4S)-4-((3-ethyl-4-methylbenzyl)oxy)pyrrolidin-3-yl)-5-(1-(piperidin-4-yl)-1H-pyrazol-4-yl)nicotinamide |
| Example 413 | 2-amino-N-((3S,4S)-4-((3-ethyl-4-methylbenzyl)oxy)pyrrolidin-3-yl)-5-(1-(1-methylpiperidin-4-yl)-1H-pyrazol-4-yl)nicotinamide |
| Example 414 | 2-amino-N-((3S,4S)-4-(benzyloxy)pyrrolidin-3-yl)-5-(1-methyl-1H-pyrazol-4-yl)nicotinamide |
| Example 415 | 2-amino-5-(1-methyl-1H-pyrazol-4-yl)-N-((3S,4S)-4-((4-methylbenzyl)oxy)pyrrolidin-3-yl)nicotinamide |
| Example 416 | 2-amino-N-((3S,4S)-4-((3-ethylbenzyl)oxy)pyrrolidin-3-yl)-5-(1-methyl-1H-pyrazol-4-yl)nicotinamide |
| Example 417 | 2-amino-N-((3S,4S)-4-((3-ethyl-4-fluorobenzyl)oxy)pyrrolidin-3-yl)-5-(1-methyl-1H-pyrazol-4-yl)nicotinamide |
| Example 418 | 2-amino-N-((3S,4S)-4-((4-chloro-3-ethylbenzyl)oxy)pyrrolidin-3-yl)-5-(1-methyl-1H-pyrazol-4-yl)nicotinamide |
| Example 419 | 2-amino-N-((3S,4S)-4-((3-ethyl-4-methylbenzyl)oxy)pyrrolidin-3-yl)-5-(4-((1-methylpiperidin-4-yl)carbamoyl)phenyl)nicotinamide |
| Example 420 | 2-amino-N-((3S,4S)-4-((3-ethyl-4-methylbenzyl)oxy)pyrrolidin-3-yl)-5-(4-((4-methylcyclohexyl)carbamoyl)phenyl)nicotinamide |
| Example 421 | 2-amino-N-((3S,4S)-4-((3-ethyl-4-methylbenzyl)oxy)pyrrolidin-3-yl)-5-(4-(4-methylpiperidine-1-carbonyl)phenyl)nicotinamide |
| Example 422 | 2-amino-5-(4-(dimethylcarbamoyl)phenyl)-N-((3S,4S)-4-((3-ethyl-4-methylbenzyl)oxy)pyrrolidin-3-yl)nicotinamide |
| Example 423 | 2-amino-N-((3S,4S)-4-((3-ethyl-4-methylbenzyl)oxy)pyrrolidin-3-yl)-5-(4-((4-methylpiperidin-1-yl)methyl)phenyl)nicotinamide |
| Example 424 | 2-amino-N-((3S,4S)-4-((3-ethyl-4-methylbenzyl)oxy)pyrrolidin-3-yl)-5-(4-(morpholinomethyl)phenyl)nicotinamide |
| Example 425 | 2-amino-5-(4-((3,3-difluoropiperidin-1-yl)methyl)phenyl)-N-((3S,4S)-4-((3-ethyl-4-methylbenzyl)oxy)pyrrolidin-3-yl)nicotinamide |
| Example 426 | 2-amino-N-((3S,4S)-4-((3-ethyl-4-methylbenzyl)oxy)-1-methylpyrrolidin-3-yl)-5-(1-methyl-1H-pyrazol-4-yl)nicotinamide |
| Example 427 | 2-amino-N-((3S,4S)-1-benzyl-4-((3-ethyl-4-methylbenzyl)oxy)pyrrolidin-3-yl)-5-(1-methyl-1H-pyrazol-4-yl)nicotinamide |
| Example 428 | 2-amino-N-((3S,4S)-4-((3-ethyl-4-methylbenzyl)oxy)-1-(3-phenylpropyl)pyrrolidin-3-yl)-5-(1-methyl-1H-pyrazol-4-yl)nicotinamide |
| Example 429 | 2-amino-N-((3S,4S)-4-((3-ethyl-4-methylbenzyl)oxy)-1-phenethylpyrrolidin-3-yl)-5-(1-methyl-1H-pyrazol-4-yl)nicotinamide |
| Example 430 | 2-amino-N-((3S,4S)-4-((3-ethyl-4-methylbenzyl)oxy)-1-isobutylpyrrolidin-3-yl)-5-(1-methyl-1H-pyrazol-4-yl)nicotinamide |
| Example 431 | 2-amino-N-((3S,4S)-1-butyl-4-((3-ethyl-4-methylbenzyl)oxy)pyrrolidin-3-yl)-5-(1-methyl-1H-pyrazol-4-yl)nicotinamide |
| Example 432 | 2-amino-N-((3S,4S)-1-ethyl-4-((3-ethyl-4-methylbenzyl)oxy)pyrrolidin-3-yl)-5-(1-methyl-1H-pyrazol-4-yl)nicotinamide |
| Example 433 | 2-amino-N-((3S,4S)-4-((3-ethyl-4-methylbenzyl)oxy)-1-methylpyrrolidin-3-yl)-5-(1-(1-methylpiperidin-4-yl)-1H-pyrazol-4-yl)nicotinamide |
| Example 434 | 2-amino-5-(1-methyl-1H-pyrazol-4-yl)-N-((3S,4S)-4-((4'-((4-methyl-piperazin-1-yl)methyl)-[1,1'-biphenyl]-4-yl)methoxy)pyrrolidin-3-yl)-nicotinamide |
| Example 435 | 2-amino-5-(1-methyl-1H-pyrazol-4-yl)-N-((3S,4S)-1-methyl-4-((4'-((4-methylpiperazin-1-yl)methyl)-[1,1'-biphenyl]-4-yl)methoxy)pyrrolidin-3-yl)nicotinamide |
| Example 436 | 2-amino-5-(1-methyl-1H-pyrazol-4-yl)-N-((3S,4S)-4-((4'-((4-methylpiperazin-1-yl)methyl)-3'-(trifluoromethyl)-[1,1'-biphenyl]-4-yl)methoxy)pyrrolidin-3-yl)nicotinamid |
| Example 437 | 2-amino-5-(1-methyl-1H-pyrazol-4-yl)-N-((3S,4S)-1-methyl-4-((4'-((4-methylpiperazin-1-yl)methyl)-3'-(trifluoromethyl)-[1,1'-biphenyl]-4-yl)methoxy)pyrrolidin-3-yl)nicotinamide |
| Example 438 | 2-amino-5-(1-methyl-1H-pyrazol-4-yl)-N-((3S,4S)-4-((4'-(1-(4-methyl-piperazin-1-yl)ethyl)-[1,1'-biphenyl]-4-yl)methoxy)pyrrolidin-3-yl)-nicotinamide |
| Example 439 | 2-amino-5-(1-methyl-1H-pyrazol-4-yl)-N-((3S,4S)-1-methyl-4-((4'-(1-(4-methylpiperazin-1-yl)ethyl)-[1,1'-biphenyl]-4-yl)methoxy)pyrrolidin-3-yl)-nicotinamide |
| Example 440 | 2-amino-N-((3S,4S)-4-((4'-(2-(4-(2-hydroxyethyl)piperazin-1-yl)propan-2-yl)-[1,1'-biphenyl]-4-yl)methoxy)pyrrolidin-3-yl)-5-(1-methyl-1H-pyrazol-4-yl)nicotinamide |
| Example 441 | 2-amino-N-((3S,4S)-4-((4'-(2-(4-(2-hydroxyethyl)piperazin-1-yl)propan-2-yl)-[1,1'-biphenyl]-4-yl)methoxy)-1-methylpyrrolidin-3-yl)-5-(1-methyl-1H-pyrazol-4-yl)nicotinamide |
| Example 442 | 2-amino-N-((3S,4S)-4-((4'-(1-(4-(2-hydroxyethyl)piperazin-1-yl)ethyl)-[1,1'-biphenyl]-4-yl)methoxy)pyrrolidin-3-yl)-5-(1-methyl-1H-pyrazol-4-yl)-nicotinamide |
| Example 443 | 2-amino-N-((3S,4S)-4-((4'-(1-(4-(2-hydroxyethyl)piperazin-1-yl)ethyl)-[1,1'-biphenyl]-4-yl)methoxy)-1-methylpyrrolidin-3-yl)-5-(1-methyl-1H-pyrazol-4-yl)nicotinamide |

-continued

| | |
|---|---|
| Example 444 | 2-amino-N-((3S,4S)-4-((4'-((4-(2-hydroxyethyl)piperazin-1-yl)methyl)-3'-(trifluoromethyl)-[1,1'-biphenyl]-4-yl)methoxy)pyrrolidin-3-yl)-5-(1-methyl-1H-pyrazol-4-yl)nicotinamide |
| Example 445 | 2-amino-N-((3S,4S)-4-((4'-((4-(2-hydroxyethyl)piperazin-1-yl)methyl)-3'-(trifluoromethyl)-[1,1'-biphenyl]-4-yl)methoxy)-1-methylpyrrolidin-3-yl)-5-(1-methyl-1H-pyrazol-4-yl)nicotinamide |
| Example 446 | 2-amino-N-((3S,4S)-4-((4'-((4-(2-hydroxyethyl)piperazin-1-yl)methyl)-[1,1'-biphenyl]-4-yl)methoxy)pyrrolidin-3-yl)-5-(1-methyl-1H-pyrazol-4-yl)nicotinamide |
| Example 447 | 2-amino-N-((3S,4S)-4-((4'-((4-(2-hydroxyethyl)piperazin-1-yl)methyl)-[1,1'-biphenyl]-4-yl)methoxy)-1-methylpyrrolidin-3-yl)-5-(1-methyl-1H-pyrazol-4-yl)nicotinamide |
| Example 448 | 2-amino-5-(1-methyl-1H-pyrazol-4-yl)-N-((3S,4R)-4-((4'-((4-methylpiperazin-1-yl)methyl)-[1,1-biphenyl]-4-yl)methoxy)tetrahydrofuran-3-yl)nicotinamide |
| Example 449 | 2-amino-5-(1-methyl-1H-pyrazol-4-yl)-N-((3S,4R)-4-((4'-((4-methyl-piperazin-1-yl)methyl)-3'-(trifluoromethyl)-[1,1'-biphenyl]-4-yl)methoxy)-tetrahydrofuran-3-yl)nicotinamide |
| Example 450 | 2-amino-5-(1-methyl-1H-pyrazol-4-yl)-N-((3S,4R)-4-((4'-(2-(4-methyl-piperazin-1-yl)propan-2-yl)-[1,1'-biphenyl]-4-yl)methoxy)tetrahydrofuran-3-yl)nicotinamide |
| Example 451 | 2-amino-N-((3S,4R)-4-((4'-((4-(2-hydroxyethyl)piperazin-1-yl)methyl)-[1,1'-biphenyl]-4-yl)methoxy)tetrahydrofuran-3-yl)-5-(1-methyl-1H-pyrazol-4-yl)-nicotinamide |
| Example 452 | 2-amino-N-((3S,4R)-4-((4'-((4-(2-hydroxyethyl)piperazin-1-yl)methyl)-3'-(trifluoromethyl)-[1,1'-biphenyl]-4-yl)methoxy)tetrahydrofuran-3-yl)-5-(1-methyl-1H-pyrazol-4-yl)nicotinamide |
| Example 453 | 2-amino-N-((3S,4R)-4-((4'-(2-(4-(2-hydroxyethyl)piperazin-1-yl)propan-2-yl)-[1,1'-biphenyl]-4-yl)methoxy)tetrahydrofuran-3-yl)-5-(1-methyl-1H-pyrazol-4-yl)nicotinamide |
| Example 454 | 2-amino-5-(1-methyl-1H-pyrazol-4-yl)-N-(trans-4-((4'-((4-methylpiperazin-1-yl)methyl)-[1,1'-biphenyl]-4-yl)methoxy)tetrahydrofuran-3-yl)nicotinamide |
| Example 455 | 2-amino-N-(trans-4-((4'-((4-methylpiperazin-1-yl)methyl)-[1,1'-biphenyl]-4-yl)methoxy)tetrahydrofuran-3-yl)nicotinamide |
| Example 456 | 2-amino-N-((1S,2S)-2-(benzyloxy)cyclopentyl)-6-((4-((4-methylpiperazin-1-yl)methyl)phenyl)amino)nicotinamide |
| Example 457 | 2-amino-N-((1S,2S)-2-(benzyloxy)cyclopentyl)-6-(phenylamino)nicotinamide; and |
| Example 458 | 2-amino-N-((1S,2S)-2-(benzyloxy)cyclopentyl)-6-((4-(4-methylpiperazin-1-yl)phenyl)amino)nicotinamide. | wherein the cancer is selected from the group consisting of: anaplastic astrocytoma, lung cancer, cervical carcinoma, colon cancer, ovarian cancer, breast cancer, prostate cancer, renal cell carcinoma, bladder carcinoma, melanoma, rhabdomyosarcoma, neuroblastoma, leukemia and metastatic lesions secondary therefrom.

3. The method of claim 1, wherein the mammal is a human.

4. The method of claim 2, wherein the mammal is a human.

* * * * *